US011136296B2

(12) United States Patent
Beck et al.

(10) Patent No.: US 11,136,296 B2
(45) Date of Patent: Oct. 5, 2021

(54) SUBSTITUTED
N-ARYLETHYL-2-ARYLQUINOLINE-4-
CARBOXAMIDES AND USE THEREOF

(71) Applicants: Bayer Aktiengesellschaft, Leverkusen
(DE); **Bayer Pharma
Aktiengesellschaft**, Berlin (DE)

(72) Inventors: Hartmut Beck, Wuppertal (DE);
Raimund Kast, Wuppertal (DE); **Mark
Meininghaus, Wuppertal (DE); Lisa
Dietz, Wuppertal (DE); Chantal
Fuerstner, Muelheim/Ruhr (DE); Timo
Stellfeld, Berlin (DE); Sonja Anlauf**,
Wermelskirchen (DE);
Clemens-Jeremias Von Buehler, Neuss
(DE); Michaela Bairlein, Wuppertal
(DE); Johanna Anlahr, Dortmund
(DE); Uwe Muenster, Wuppertal (DE);
Carsten Terjung, Bochum (DE);
Hannah Joerissen, Heiligenhaus (DE);
Peter Hauff, Berlin (DE); **Joerg
Mueller, Berlin (DE); Karoline
Droebner, Velbert (DE); Jens Nagel**,
Daxweiler (DE)

(73) Assignees: Bayer Aktiengesellschaft, Leverkusen
(DE); **Bayer Pharma
Aktiengesellschaft**, Berlin (DE)

( * ) Notice: Subject to any disclaimer, the term of this patent is extended or adjusted under 35 U.S.C. 154(b) by 99 days.

(21) Appl. No.: 16/603,719

(22) PCT Filed: Apr. 4, 2018

(86) PCT No.: PCT/EP2018/058611
§ 371 (c)(1),
(2) Date: Oct. 8, 2019

(87) PCT Pub. No.: WO2018/189011
PCT Pub. Date: Oct. 18, 2018

(65) Prior Publication Data
US 2020/0031775 A1 Jan. 30, 2020

(30) Foreign Application Priority Data
Apr. 10, 2017 (EP) .................................... 17165673

(51) Int. Cl.
*C07D 215/50* (2006.01)
(52) U.S. Cl.
CPC ................................ *C07D 215/50* (2013.01)
(58) Field of Classification Search
CPC .................................................. C07D 215/50
See application file for complete search history.

(56) References Cited

U.S. PATENT DOCUMENTS 8,058,300 B2 * 11/2011 Hutchinson ............. A61P 13/12
514/380

FOREIGN PATENT DOCUMENTS

| EP | 2415755 A1 | 2/2012 |
| WO | 95/32948 A1 | 12/1995 |
| WO | 96/02509 A1 | 2/1996 |
| WO | 97/19926 A1 | 6/1997 |
| WO | 2000/031038 A1 | 6/2000 |
| WO | 00/64877 A1 | 11/2000 |
| WO | 2004/045614 A1 | 6/2004 |
| WO | 2006/094237 A2 | 9/2006 |
| WO | 2011/153553 A2 | 12/2011 |
| WO | 2012/122370 A2 | 9/2012 |
| WO | 2013/074059 A2 | 5/2013 |
| WO | 2013/164326 A1 | 11/2013 |
| WO | 2014/117090 A1 | 7/2014 |
| WO | 2015/094912 A1 | 6/2015 |
| WO | 2016/004035 A1 | 1/2016 |
| WO | 2016/061280 A1 | 4/2016 |

OTHER PUBLICATIONS

Giardina et al Journal of Medicinal Chemistry 1999, 42, 1053-1065. (Year: 1999).*
Zhang et al Frontiers in Pharmacology Oct. 2010, vol. 1, pp. 1-7. (Year: 2010).*
Abramovitz, Mark, et al. "Cloning and Expression of a cDNA for the Human Prostanoid FP Receptor," The Journal of Biological Chemistry, (1994), vol. 269, No. 4: 2632-2636.
Agas, Dimitrios, et al. "Prostaglandin F2α: A Bone Remodeling Mediator," Journal of Cellular Physiology, (2013), vol. 228: 25-29.
Aihara, Kensaku, et al. "Clinical Relevance of Plasma Prostaglandin F2α Metabolite Concentrations in Patients with Idiopathic Pulmonary Fibrosis," PLOS One, (2013), vol. 8, No. 6: 1-7.
Barnes, Peter J. "Chronic Obstructive Pulmonary Disease," New England Journal of Medicine, (2000), vol. 343, No. 4: 269-280.
Bastiaansen-Jenniskens, Yvonne M., et al. "Stimulation of Fibrotic Processes by the Infrapatellar Fat Pad in Cultured Synoviocytes From Patients with Osteoarthritis," Arthritis & Rheumatism, (2013), vol. 65, No. 8: 2070-2080.
Basu, Samar, et al. "Type 1 Diabetes is Associated with Increased Cyclooxyenase- and Cytokine-Mediated Inflammation," Diabetes Care, (2005), vol. 28, No. 6: 1371-1375.
Basu, Samar, et al. "Presence of a 15-Ketoprostaglandin Delta13-Reductase in Porcine Cornea," Acta Chemica Scandinavica, (1992), vol. 46: 108-110.

(Continued)

*Primary Examiner* — John Mabry
(74) *Attorney, Agent, or Firm* — McBee Moore & Vanik IP, LLC

(57) ABSTRACT

The present application relates to novel substituted N-arylethyl-2-arylquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and inflammatory disorders.

13 Claims, No Drawings

(56) References Cited

OTHER PUBLICATIONS

Basu, Samar. "Bioactive Eicosanoids: Role of Prostaglandin F2α and F2-Isoprostanes in Inflammation and Oxidative Stress Related Pathology," Mol. Cells, (2010), vol. 30: 383-391.
Behr, J. et al. "Pulmonary hypertension in interstitial lung disease," Eur Respir J, (2008), vol. 31: 1357-1367.
Blanco, Isabel, et al. "Hemodynamic and Gas Exchange Effects of Sildenafil in Patients with Chronic Obstructive Pulmonary Disease and Pulmonary Hypertension," American Journal of Respiratory and Critical Care Medicine, (2010), vol. 181: 270-278.
Carlson, N. G., et al. "Vulnerability of oligodendrocyte precursor cells to death is modulated by key prostaglandins," Multiple Sclerosis Journal, (2015), vol. 21 (S11): 467-468.
Catrina, Anca I., et al. "Lungs, joints and immunity against citrullinated proteins in rheumatoid arthritis," Nat. Rev. Rheumatol., (2014), vol. 10: 645-653.
Dawood, M. Yusoff, et al. "Clinical efficacy and differential inhibition of menstrual fluid prostaglandin F2α in a randomized, double-blind, crossover treatment with placebo, acetaminophen, and ibuprofen in primary dysmenorrhea," American Journal of Obstetrics & Gynecology, (2007), vol. 196: 35.e1-35.e5.
Ding, Wen-yuan, et al. "Prostaglandin F2α facilitates collagen synthesis in cardiac fibroblasts via an F-prostanoid receptor/protein kinase C/ Rho kinase pathway independent of transforming growth factor β1," International Journal of Biochemistry & Cell Biology, (2012), vol. 44: 1031-1039.
Ding, Wen-yuan, et al. "FP-receptor gene silencing ameliorates myocardial fibrosis and protects from diabetic cardiomyopathy," J. Mol. Med., (2014), vol. 92: 629-640.
Doyle, Tracy J., et al. "A Roadmap to Promote Clinical and Translational Research in Rheumatoid Arthritis-Associated Interstitial Lung Disease," Chest, (2014), vol. 145, No. 3: 454-463.
Rosenzweig, Erika B. "Emerging treatments for pulmonary arterial hypertension," Expert Opinion on Emerging Drugs, (2006), vol. 11, No. 4: 609-619.
Estenne, Marc, et al. "Bronchiolitis Obliterans after Human Lung Transplantation," Am. J. Respir. Crit. Care Med., (2002), vol. 166: 440-444.
Ghofrani, Hossein Ardeschir, et al. "Neue Therapieoptionen in der Behandlung der pulmonalarteriellen Hypertonie," Herz, (2005), vol. 30: 296-302.
Helmersson, J., et al. "Active smoking and a history of smoking are associated with enhanced prostaglandin F2α, interleukin-6 and F2-isoprostane formation in elderly men," Atherosclerosis, (2005), vol. 181: 201-207.
Helmersson, J., et al. "Association of Type 2 Diabetes With Cyclooxygenase-Mediated Inflammation and Oxidative Stress in an Elderly Population," Circulation, (2004), vol. 109: 1729-1734.
Helmersson-Karlqvist, Johanna, et al. "Prostaglandin F2α formation is associated with mortality in a Swedish community-based cohort of older males," European Heart Journal, (2015), vol. 36: 238-243.
Montani, David, et al. "Updated clinical classification of pulmonary hypertension," Pulmonary Circulation: Diseases and their treatment, Hodder Arnold Publishing (2011), Third Edition, 197-206.
Hoeper, Marius M., et al. "Diagnosis, Assessment, and Treatment of Non-Pulmonary Arterial Hypertension Pulmonary Hypertension," Journal of the American College of Cardiology, (2009), vol. 54, No. 1: S85-96.
Hsia, Shih-Min, et al. "Effects of Resveratrol, a Grape Polyphenol, on Uterine Contraction and Ca2+ Mobilization in Rats in Vivo and in Vitro," Endocrinology, (2011), vol. 152: 2090-2099.
Kanno, Yosuke, et al. "Alpha 2-Antiplasmin Regulates the Development of Dermal Fibrosis in Mice by Prostaglandin F2α Synthesis Through Adipose Triglyceride Lipase/Calcium-Independent Phospholipase A2," Arthritis & Rheumatism, (2013), vol. 65, No. 2: 492-502.
Khidhir, K.G., et al. "Human scalp hair follicles express the genes for prostanoid FP receptor (Abstract 607)," J. Invest. Dermatol., (2009), vol. 129: S102.
Kim, Yun Tai, et al. "Prostaglandin FP receptor inhibitor reduces ischemic brain damage and neurotoxicity," Neurobiology of Disease, (2012), vol. 48: 58-65.
Kim, Joohwee, et al. "Prostaglandin F2α receptor (FP) signaling regulates BMP signaling and promotes chondrocyte differentiation," Biochimica et Biophysica Act, (2015), vol. 1853: 500-512.
Kitanaka, Jun-ichi, et al. "Cloning and Expression of a cDNA for Rat Prostaglandin F2α Receptor," Prostaglandins, (1994), vol. 48: 31-41.
Lettieri, Christopher J., et al. "Prevalence and Outcomes of Pulmonary Arterial Hypertension in Advanced Idiopathic Pulmonary Fibrosis," Chest, (2006), vol. 129: 746-752.
Ley, Brett, et al. "Clinical Course and Prediction of Survival in Idiopathic Pulmonary Fibrosis," Am. J. Respir. Crit. Care Med., (2011), vol. 183: 431-440.
Humbert, Marc, et al. "Cellular and Molecular Pathobiology of Pulmonary Arterial Hypertension," Journal of the American College of Cardiology, (2004), vol. 43, No. 12: 13S-24S.
Naeije, Robert in: A. J. Peacock et al. "Pulmonary vascular function," Pulmonary Circulation. Diseases and their treatment, 3rd Edition, Hodder Arnold Publishing, (2011), 3-15.
Oga, Toru, et al. "Prostaglandin F2α receptor signaling facilitates bleomycin-induced pulmonary fibrosis independently of transforming growth factor-β," Nature Medicine, (2009), vol. 15, No. 12: 1426-1431.
Olman, Mitchell A. "Beyond TGF-β: a prostaglandin promotes fibrosis," Nature Medicine, (2009), vol. 15, No. 12: 1360-1361.
Olson, Amy L., et al. "Rheumatoid Arthritis-Interstitial Lung Disease-associated Mortality," Am. J. Respir. Crit. Care Med., (2011), vol. 183: 372-378.
O'Reilly, Katherine M.A., et al. "Crystalline and amorphous silica differentially regulate the cyclooxygenase-prostaglandin pathway in pulmonary fibroblasts: implications for pulmonary fibrosis," Am. J. Physiol. Lung Cell Mol. Physiol., (2005), vol. 288: L1010-L1016.
Powell, Andrea M., et al. "Menstrual-PGF2α, PGE2 and TXA2 in Normal and Dysmenorrheic Women and Their Temporal Relationship to Dysmenorrhea," Prostaglandins, (1985), vol. 29, No. 2: 273-289.
Sales, Kurt J., et al. "F-Prostanoid Receptor Regulation of Fibroblast Growth Factor 2 Signaling in Endometrial Adenocarcinoma Cells," Endocrinology, (2007), vol. 148, No. 8: 3635-3644.
Sinaiko, Alan R., et al. "Relation of Body Mass Index and Insulin Resistance to Cardiovascular Risk Factors, Inflammatory Factors, and Oxidative Stress During Adolescence," Circulation, (2005), vol. 111: 1985-1991.
Soldan, M. Mateo Paz, et al. "Relapses and disability accumulation in progressive multiple sclerosis," Neurology, (2015), vol. 84: 81-88.
Stolz, D., et al. "A randomised, controlled trial of bosentan in severe COPD," Eur. Respir. J., (2008), vol. 32: 619-628.
Strieter, Robert M., et al. "New Mechanisms of Pulmonary Fibrosis," Chest, (2009), vol. 136: 1364-1370.
Sugimoto, Yukihiko, et al. "Cloning and Expression of a cDNA for Mouse Prostaglandin F Receptor," The Journal of Biological Chemistry, (1994), vol. 269, No. 2: 1356-1360.
Ito, Takayuki, et al. "Current Drug Targets and Future Therapy of Pulmonary Arterial Hypertension," Current Medical Chemistry, (2007), vol. 14: 719-733.
Von Der Beck, D., et al. "Die Therapie der idiopathischen pulmonalen Fibrose," Pneumologe, (2013), vol. 10: 105-111.
Watanabe, Kikuko, et al. "Enzymatic Formation of Prostaglandin F2α from Prostaglandin H2 and D2," The Journal of Biological Chemistry, (1985), vol. 260, No. 11: 7035-7041.
Wells, Athol U., et al. "Interstitial lung disease in connective tissue disease—mechanisms and management," Nature Reviews: Rheumatology, (2014), vol. 10: 728-739.
Woodward, D.F., et al. "International Union of Basic and Clinical Pharmacology. LXXXIII: Classification of Prostanoid Receptors, Updating 15 Years of Progress," Pharmacological Reviews, (2011), vol. 63, No. 3: 471-538.
Xiao, Bing, et al. "Rare SNP rs12731181 in the miR-590-3p Target Site of the Prostaglandin F2α Receptor Gene Confers Risk for

(56) References Cited

OTHER PUBLICATIONS

Essential Hypertension in the Han Chinese Population," Arterioscler Thromb Vasc. Biol., (2015), vol. 35: 1687-1695.
Yang, Yang, et al. "Prostanoids receptors signaling in different diseases/cancers progression," Journal of Receptors and Signal Transduction, (2013), vol. 33, No. 1: 14-27.
Zhang, Jian, et al. "PG F2α receptor: a promising therapeutic target for cardiovascular disease," Frontiers in Pharmacology, (2010), vol. 1: 1-7.
International Search Report of International Patent Application No. PCT/EP2018/058611 dated Jun. 25, 2018.

* cited by examiner

SUBSTITUTED N-ARYLETHYL-2-ARYLQUINOLINE-4-CARBOXAMIDES AND USE THEREOF

CROSS-REFERENCE TO RELATED APPLICATIONS

This application is a National Stage entry of International Application No. PCT/EP2018/058611, filed 4 Apr. 2019, which claims priority to European Patent Application No. 17165673.9, filed 10 Apr. 2017.

BACKGROUND

Field

The present application relates to novel substituted N-arylethyl-2-arylquinoline-4-carboxamide derivatives, to processes for preparation thereof, to the use thereof alone or in combinations for treatment and/or prevention of diseases, and to the use thereof for production of medicaments for treatment and/or prevention of diseases, especially for treatment and/or prevention of fibrotic and inflammatory disorders.

Description of Related Art

Prostaglandin F2alpha (PGF2α) is part of the family of bioactive prostaglandins, which are derivatives of arachidonic acid. After release from membrane phospholipids by A2 phospholipases, arachidonic acid is oxidized by cyclooxygenases to prostaglandin H2 (PGH2), which is converted further by PGF synthase to PGF2α. PGF2α can also be formed enzymatically in a much smaller proportion from other prostaglandins such as PGE2 or PGD2 [Watanabe et al., *J. Biol. Chem.* 1985, 260, 7035-7041]. PGF2α is not stored, but is released immediately after synthesis, as a result of which it displays its effects locally. PGF2α is an unstable molecule ($t_{1/2} < 1$ minute), which is rearranged rapidly by enzymatic means in the lung, liver and kidney to give an inactive metabolite, 15-ketodihydro-PGF2α [Basu et al., *Acta Chem. Scand.* 1992, 46, 108-110]. 15-Ketodihydro-PGF2α is detectable in relatively large amounts in the plasma and later also in the urine, both under physiological and pathophysiological conditions.

The biological effects of PGF2α come about through the binding and activation of a receptor on the membrane, of the PGF2α receptor or else of what is called the FP receptor. The FP receptor is one of the G protein-coupled receptors characterized by seven transmembrane domains. As well as the human FP receptor, it is also possible to clone the FP receptors of mice and rats [Abramovitz et al., *J. Biol. Chem.* 1994, 269, 2632-2636; Sugimoto et al., *J. Biol. Chem.* 1994, 269, 1356-1360; Kitanaka et al., *Prostaglandins* 1994, 48, 31-41]. In humans there exist two isoforms of the FP receptor, FPA and FPB. The FP receptor is the least selective of the prostanoid receptors, since not only PGF2α but also PGD2 and PGE2 bind to it with nanomolar affinities [Woodward et al., *Pharmacol. Rev.* 2011, 63, 471-538]. Stimulation of the FP receptor leads primarily to Gq-dependent activation of phospholipase C, which results in release of calcium and activation of the diacylglycerol-dependent protein kinase C (PKC). The elevated intracellular calcium level leads to calmodulin-mediated stimulation of myosin light-chain kinase (MLCK). As well as coupling to the G protein Gq, the FP receptor, via G12/G13, can also stimulate the Rho/Rho kinase signal transduction cascade and, via Gi coupling, can alternatively stimulate the Raf/MEK/MAP signaling pathway [Woodward et al., *Pharmacol. Rev.* 2011, 63, 471-538].

PGF2α is involved in the regulation of numerous physiological functions, for example ovarian functions, embryonal development, changes in the endometrium, uterine contraction and luteolysis, and in the induction of contractions and birth. PGF2α is also synthesized in epithelial cells in the endometrium, where it stimulates cellular proliferation [Woodward et al., *Pharmacol. Rev.* 2011, 63, 471-538]. In addition, PGF2α is a potent stimulator of smooth muscle constriction, vascular constriction and bronchoconstriction, and is involved in acute and chronic inflammatory processes [Basu, *Mol. Cells* 2010, 30, 383-391]. It has thus been shown that 15-keto-dihydro-PGF2α, a stable metabolite of PGF2α, was systemically detectable in patients having rheumatoid arthritis, psoriatic arthrosis and osteoarthrosis. In the kidney, PGF2α is involved in water absorption, natriuresis and diuresis. In the eyes, PGF2α regulates intraocular pressure. PGF2α also plays an important role in bone metabolism: Prostaglandin stimulates the sodium-dependent transport of inorganic phosphate into osteoblasts and it promotes the release of interleukin-6 and vascular endothelial growth factor (VEGF) in osteoblasts; in addition, PGF2α is a strong mitogen and a survival factor for osteoblasts [Agas et al., *J. Cell Physiol.* 2013, 228, 25-29].

Elevated PGF2α/FP receptor activity also led to upregulation of tumorigenic and angiogenic genes such as COX-2 [Sales et al., 2007, *Endocrinology* 148:3635-44], FGF-2 and VEGF [Sales et al., 2010 *Am J Pathol* 176:431], which indicates that the FP receptor stimulates endometrial tumor growth by regulation of vascular functions. In addition, the FP receptor is involved in the regulation of the proliferation of endometrial epithelial cells and can affect their adhesion to the extracellular matrix and motility. The findings suggest that PGF2α/FP receptor plays a multifactorial role in endometrial adenocarcinomas [Yang et al., 2013 *J Recept Signal Transduct*, 33(1): 14-27].

Elevated expression of the FP receptor in precursor cells of oligodendrocytes (OPCs) could be a marker for damage to oligodendrocytes and active myelin [Soldan et al., *Neurology* 2015, 84]. After autopsy, the expression of the FP receptor on OPCs in the vicinity of the edges of MS plaques was observed in tissue from patients having multiple sclerosis (MS). No FP receptor expression was found in control samples of white brain matter. This indicates that the FP receptor plays a role in the etiology of multiple sclerosis [Carlson et al., 2015, *Mult. Sclerosis.* 23 (11) 467-468].

Brain injuries lead to upregulation of prostaglandins, in particular of the proinflammatory PGF2α, and to overactivation of the FP receptor. For instance, with FP receptor-deficient mice, and by treatment with the FP antagonist AL-8810, significant neuroprotective effects were shown after occlusion of the cerebral artery [Kim et al., 2012, *Neurobiol Disease* 48, 58-65].

In addition, it was shown that PGF2α-FP receptor activation is involved in various cardiovascular dysfunctions such as myocardial fibrosis, myocardial infarction and hypertension [Zhang et al., *Frontiers in Pharmacol.* 2010, 1, 1-7; Ding et al., *Int. J. Biochem. Cell. Biol.,* 2012, 44, 1031-1039; Ding et al., *J. Mol. Med.,* 2014, 6, 629-640].

Thus, the main metabolite of PGF2α, 15-keto-dihydro-PGF2α, is elevated in humans with living conditions having elevated cardiovascular risk [Helmersson-Karlquist et al., Eur Heart J 2015, 36, 238-243], for example also in the case of smokers [Helmersson et al., 2005 *Atherosclerosis* 181, 201-207), obesity [Sinaiko et al., 2005 *Circulation* 111, 1985-1991], type I diabetes [Basu et al., 2005, 28, 1371-1375] and type II diabetes [Helmersson et al., 2004, *Circulation* 109, 1729-1734]. [Zhang et al., *Frontiers in Pharmacol* 2010, 1:1-7]. It has also been shown that genetic polymorphism in a Chinese subpopulation leads to elevated transcription of the FP gene and elevated vasocontractility [Xiao et al., 2015, *Arterioscler Thromb Vasc Biol.* 35:1687-1695].

Moreover, the PGF2α receptor (FP) is involved in joint disorders and the regulation of the signal cascade of the bone morphogenetic protein (BMP) and promotes differentiation of chondrocytes [Kim et al., *Biochim. Biophys. Acta,* 2015, 1853, 500-512]. More stable analogues of PGF2α have been developed for estrus synchronization and for influencing human reproductive functions, and also for reduction of intraocular pressure for treatment of glaucoma [Basu, *Mol. Cells* 2010, 30, 383-391]. In the latter application, a side-effect that was observed was the stimulation of hair growth, for example of eyelashes, by the more chemically stable PGF2α analogues, for example latanoprost. [Johnston et al., *Am J Ophthalmol* 1997, 124-544-547]. The genes of the FP receptor are also expressed in human hair follicles on the scalp [Khidhir et al., J Invest Dermatol, 2009, Abstr 607]. These findings suggest that the FP receptor is involved in the regulation of hair growth and may also be involved in disorders such as hirsutism, for example.

There is also a good description of the role of the FP receptor in the signal cascade in the etiology of visceral pain (dysmenorrhea). Thus, dysmenorrheic pain best correlates with the rate of PGF release during menstruation (cf. Powell et al., *Prostaglandins* 1985, 29, 273-290; Dawood and Khan-Dawood, *Am. J. Obstet. Gynecol.* 2007, 196, 35.e1-35.e5; Hsia et al., *Endocrinology* 2011, 152, 2090-2099). There has been no description of a connection of the FP receptor signaling pathway in peripheral mediated inflammatory pain to date. The data submitted herewith show this surprising connection for the first time.

In patients having idiopathic pulmonary fibrosis (IPF), it has been shown that the stable PGF2α metabolite 15-ketodihydro-PGF2α is significantly elevated in the plasma and that the level of 15-ketodihydro-PGF2α correlates with functional parameters, for example forced vital capacity (FVC), the diffusion distance of carbon monoxide in the lung (DLCO) and the 6-minute walk test. In addition, a relationship between elevated plasma 15-ketodihydro-PGF2α and the mortality of patients has been detected [Aihara et al., *PLoS One* 2013, 8, 1-6]. In accordance with this, it has also been shown that stimulation of human lung fibroblasts with naturally occurring silica dusts, which in humans can lead to silicosis in the event of chronic inhalation and as a result to pulmonary fibrosis, brings about significant upregulation of PGF2α synthesis [O'Reilly et al., *Am. J. Physiol. Lung Cell. Mol. Physiol.* 2005, 288, L1010-L1016]. In bleomycin-induced pulmonary fibrosis in mice, the elimination of the FP receptor by knockdown (FP –/–) led to a distinct reduction in pulmonary fibrosis compared to wild-type mice [Oga et al., *Nat. Med.* 2009, 15, 1426-1430]. In FP –/– mice, after administration of bleomycin, a significant reduction in the hydroxyproline content and reduced induction of profibrotic genes in the pulmonary tissue was observed. Moreover, lung function was distinctly improved in FP –/– mice compared to the wild-type mice. In human pulmonary fibroblasts, PGF2α stimulates proliferation and collagen production via the FP receptor. Since this occurs independently of the profibrotic mediator TGFβ, the PGF2α/FP receptor signaling cascade constitutes an independent route in the onset of pulmonary fibrosis [Oga et al., *Nat. Med.* 2009, 15, 1426-1430]. These findings show that the FP receptor is a therapeutic target protein for treatment of IPF [Olman, *Nat. Med.* 2009, 15, 1360-1361]. The involvement of PGF2α in the induction of fibrotic lesions has also been shown in cardiac mouse fibroblasts [Ding et al., *Int. J. Biochem. & Cell Biol.* 2012, 44, 1031-1039], in an animal model of scleroderma [Kanno et al., *Arthritis Rheum.* 2013, 65, 492-502] and in synoviocytes from patients with gonioarthrosis [Bastiaansen et al. *Arthritis Rheum.* 2013, 65, 2070-2080].

It is therefore assumed that the FP receptor plays an important role in many disorders, injuries and pathological lesions whose etiology and/or progression is associated with inflammatory events and/or proliferative and fibroproliferative tissue and vessel remodeling. These may especially be disorders of and/or damage to the lung, the cardiovascular system or the kidney, or the disorder may be a blood disorder, a neoplastic disease or another inflammatory disorder.

Inflammatory and fibrotic disorders of and damage to the lung which should be mentioned in this context are in particular idiopathic pulmonary fibrosis, interstitial pulmonary disorders associated with rheumatoid arthritis, pulmonary hypertension, bronchiolitis obliterans syndrome (BOS), chronic-obstructive pulmonary disease (COPD), asthma and cystic fibrosis. Disorders of and damage to the cardiovascular system in which the FP receptor is involved are, for example, tissue lesions following myocardial infarction and associated with heart failure. Renal disorders are, for example, renal insufficiency and kidney failure. An example of a blood disorder is sickle cell anemia. Examples of tissue degradation and remodeling in the event of neoplastic processes are the invasion of cancer cells into healthy tissue (formation of metastases) and neovascularization (neoangiogenesis). Other inflammatory diseases where the FP receptor plays a role are, for example, arthrosis and multiple sclerosis.

Idiopathic fibrosis of the lung or idiopathic pulmonary fibrosis (IPF) is a progressive lung disease which, left untreated, results in death within an average of 2.5 to 3.5 years after diagnosis. At the time of diagnosis, patients are usually more than 60 years old, men being slightly more frequently affected than women. Onset of IPF is insidious and characterized by increasing shortness of breath and a dry tickly cough. IPF is one of the group of idiopathic interstitial pneumonias (IIP), a heterogeneous group of pulmonary disorders which are characterized by fibrosis and inflammation of varying severity which can be distinguished using clinical, imaging and fine tissue criteria. Within this group, idiopathic pulmonary fibrosis is of particular significance owing to its frequency and aggressive progression [Ley et al., *Am. J. Respir. Crit. Care Med.* 2011, 183, 431-440]. IPF may either occur sporadically or be hereditary. As yet, the causes are unknown. However, in recent years there have been numerous indications that chronic damage of the alveolar epithelium leads to the release of profibrotic cytokines/mediators followed by increased fibroblast proliferation and increased collagen fiber formation, resulting in a patchy fibrosis and the typical honeycomb structure of the lung [Strieter et al., *Chest* 2009, 136, 1364-1370]. The clinical sequelae of fibrotization are a decrease in the elasticity of the pulmonary tissue, a reduced diffusing capacity and the development of severe hypoxia. With regard to lung function, a corresponding worsening of the forced vital capacity (FVC) and the diffusing capacity (DLCO) can be detected. Essential and prognostically important comorbidities of IPF are acute exacerbation and pulmonary hypertension [von der Beck et al., *Der Pneumologe* 2013, 10(2), 105-111]. The prevalence of pulmonary hypertension in interstitial pulmonary disorders is 10-40% [Lettieri et al., *Chest* 2006, 129, 746-752; Behr et al., *Eur. Respir. J.* 2008, 31, 1357-1367]. Currently, there is no curative treatment for IPF—except for lung transplantation.

Rheumatoid arthritis (RA) is a progressive systemic autoimmune disorder which is characterized by chronic erosive synovitis. Interstitial lung disorder (ILD) is one of the most common extra-articular manifestations of RA [Wells et al. *Nat Rev Rheumatol* 2014, 10, 728-739]. About 10% of patients having RA have a clinically proven interstitial pulmonary disorder (RA-ILD); a further third show subclinical ILD in CT scans of the chest. The mortality rate for patients with RA-ILD is three times as high as for patients with RA without ILD, with an average life expectation of only 2.6 years after diagnosis of ILD [Olson et al. *Am J Respir Crit Care Med* 2011 183, 372-378; Doyle et al. *Chest* 2014, 145(3), 454-463].

The inflammatory and autoimmune disorders of the lung together with various environmental triggers (e.g. smoke, fine dust, chemical irritants) and a genetic disposition play an important role in the development and progression of RA-ILD [Catrina et al. *Nat Rev Rheumatol* 2014, 10(11), 645-653].

Pulmonary hypertension (PH) is a progressive lung disease which, left untreated, results in death within an average of 2.8 years after diagnosis. By definition, the mean pulmonary arterial pressure (mPAP) in case of chronic pulmonary hypertension is >25 mmHg at rest or >30 mmHg under exertion (normal value<20 mmHg). The pathophysiology of pulmonary hypertension is characterized by vasoconstriction and remodeling of the pulmonary vessels. In chronic PH, there is a neomuscularization of primarily unmuscularized lung vessels, and the circumference of the vascular musculature of the vessels already muscularized increases. This increasing obliteration of the pulmonary circulation results in progressive stress on the right heart, which leads to a reduced output from the right heart and eventually ends in right heart failure [M. Humbert et al., *J. Am. Coll. Cardiol.* 2004, 43, 13S-24S]. Idiopathic (or primary) pulmonary arterial hypertension (IPAH) is a very rare disorder, whereas secondary pulmonary hypertension (non-PAH PH, NPAHPH) is very common, and it is thought that the latter is currently the third most common group of cardiovascular disorders after coronary heart disease and systemic hypertension [Naeije, in: A. J. Peacock et al. (Eds.), Pulmonary Circulation. *Diseases and their treatment*, 3$^{rd}$ edition, Hodder Arnold Publ., 2011, 3]. Since 2008, pulmonary hypertension is classified in accordance with the Dana Point classification into various sub-groups according to the respective etiology [D. Montana and G. Simonneau, in: A. J. Peacock et al. (Eds.), *Pulmonary Circulation. Diseases and their treatment*, 3$^{rd}$ edition, Hodder Arnold Publ., 2011, 197-206].

Despite all the advances in the therapy of PH there is as yet no prospect of cure of this serious disorder. Standard therapies available on the market (for example prostacyclin analogues, endothelin receptor antagonists, phosphodiesterase inhibitors) are able to improve the quality of life, the exercise tolerance and the prognosis of the patients. These are therapeutic principles which are administered systemically and act primarily hemodynamically by modulating vessel tone. The applicability of these medicaments is limited owing to side effects, some of which are serious, and/or complicated administration forms. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently. Currently, these standard therapeutics are approved only for the treatment of pulmonary arterial hypertension (PAH). In the case of secondary forms of PH such as PH-COPD, these therapeutic principles (for example sildenafil, bosentan) fail in clinical studies since, as a result of non-selective vasodilation, they lead to a reduction (desaturation) of the arterial oxygen content in the patients. The probable reason for this is an unfavorable effect on the ventilation-perfusion adaptation in the lung in heterogeneous lung disorders owing to the systemic administration of non-selective vasodilators [I. Blanco et al., *Am. J. Respir. Crit. Care Med.* 2010, 181, 270-278; D. Stolz et al., *Eur. Respir. J.* 2008, 32, 619-628].

Novel combination therapies are one of the most promising future therapeutic options for the treatment of pulmonary hypertension. In this connection, the finding of novel pharmacological mechanisms for the treatment of PH is of particular interest [Ghofrani et al., *Herz* 2005, 30, 296-302; E. B. Rosenzweig, *Expert Opin. Emerging Drugs* 2006, 11, 609-619; T. Ito et al., *Curr. Med. Chem.* 2007, 14, 719-733]. In particular, such novel therapeutic approaches which can be combined with the therapy concepts already on the market may form the basis of a more efficient treatment and thus be of great advantage for the patients.

In the context of the present invention, the term "pulmonary hypertension" includes both primary and secondary sub-forms (NPAHPH) as defined according to the Dana Point classification in accordance with their respective etiology [D. Montana and G. Simonneau, in: A. J. Peacock et al. (Eds.), *Pulmonary Circulation. Diseases and their treatment*, 3$^{rd}$ edition, Hodder Arnold Publ., 2011, 197-206; Hoeper et al., *J. Am. Coll. Cardiol.*, 2009, 54 (1), Suppl. S, p 85-p 96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite suppressants), with disorders having a significant venous/capillary component such as pulmonary venoocclusive disorder and pulmonary capillary hemangiomatosis, or with other disorders such as disorders of the thyroid, glycogen storage diseases, Gaucher disease, hereditary teleangiectasia, hemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxemia (e.g. sleep apnea syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumor disorders, parasites, foreign bodies). Less common forms of pulmonary hypertension, such as in patients suffering from sarcoidosis, histiocytosis X or lymphangiomatosis, are summarized in group 5.

Bronchiolitis obliterans syndrome (BOS) is a chronic rejection reaction after a lung transplant. Within the first five years after a lung transplant about 50-60% of all patients are affected, and within the first nine years more than 90% of patients [Estenne et al., *Am. J. Respir. Crit. Care Med.* 2003, 166, 440-444]. The cause of the disease has not been elucidated. In spite of numerous improvements in the treatment of transplantation patients, the number of BOS cases has hardly changed over the last years. BOS is the most important long-term complication in lung transplantations and is considered to be the main reason for the fact that survival rates are still markedly below those for other organ transplantations. BOS is an inflammatory event which is associated with changes in the lung tissue affecting primarily the small respiratory passages. Damage and inflammatory changes of the epithelial cells and the subepithelial structures of the smaller respiratory passages lead, owing to ineffective regeneration of the epithelium and aberrant tissue repair, to excessive fibroproliferation. There is scarring and finally destruction of the bronchi and also clots of granulation tissue in the small respiratory passages and alveolae, occasionally with vascular involvement. The diagnosis is based on the lung function. In BOS, there is a worsening of the FEV1 compared to the average of the two best values measured postoperatively. Currently, there is no curative treatment of BOS. Some of the patients show improvements under intensified immunosuppression; patients not showing any response experience persistent deterioration, such that retransplantation is indicated.

Chronic obstructive pulmonary disease (COPD) is a slowly progressing pulmonary disease characterized by an obstruction of respiratory flow which is caused by pulmonary emphysema and/or chronic bronchitis. The first symptoms of the disease generally manifest themselves during the fourth or fifth decade of life. In the subsequent years of life, shortness of breath frequently becomes worse, and there are instances of coughing combined with copious and purulent sputum, and stenotic respiration extending as far as breathlessness (dyspnea). COPD is primarily a smokers' disease: smoking is the cause of 90% of all cases of COPD and of 80-90% of all COPD-related deaths. COPD is a big medical problem and constitutes the sixth most frequent cause of death worldwide. Of people over the age of 45, about 4-6% are affected. Although the obstruction of the respiratory flow may only be partial and temporal, COPD cannot be cured. Accordingly, the aim of treatment is to improve the quality of life, to alleviate the symptoms, to prevent acute worsening and to slow the progressive impairment of lung function. Existing pharmacotherapies, which have hardly changed over the last two to three decades, are the use of bronchodilators to open blocked respiratory passages, and in certain situations corticosteroids to control the inflammation of the lung [P. J. Barnes, *N. Engl. J. Med.* 2000, 343, 269-280]. The chronic inflammation of the lung, caused by cigarette smoke or other irritants, is the driving force of the development of the disease. The basic mechanism comprises immune cells which, during the inflammatory reaction of the lung, release proteases and various cytokines which cause pulmonary emphysema and remodeling of the bronchi.

It is an object of the present invention to identify and provide novel substances that are potent, chemically and metabolically stable, non-prostanoid antagonists of the FP receptor, and are suitable as such for treatment and/or prevention particularly of fibrotic and inflammatory disorders.

WO 95/32948-A1, WO 96/02509-A1, WO 97/19926-A1 and WO 2000/031038-A1, inter alia, disclose 2-arylquinoline-4-carboxamides as $NK_3$ or dual $NK_2/NK_3$ antagonists suitable for treatment of disorders of the lung and central nervous system. WO 2016/004035 discloses 2-arylquinoline-4-carboxamides as TSH receptor agonists which can serve for treatment of functional disorders and malignant thyroid lesions. WO 2000/064877 claims quinoline-4-carboxamide derivatives which can be used as $NK_3$ antagonists for the treatment of various disorders, inter alia of the lung and the central nervous system. WO 2004/045614-A1 describes particular quinoline-carboxamides as glucokinase ligands for the treatment of diabetes. WO 2006/094237-A2 discloses quinoline derivatives as sirtuin modulators which can be used for treatment of various kinds of disorders. WO 2011/153553-A2 claims various bicyclic heteroaryl compounds as kinase inhibitors for the treatment of neoplastic disorders in particular. EP 2 415 755-A1 describes, inter alia, quinoline derivatives suitable for treatment of disorders associated with the activity of plasminogen activator inhibitor 1 (PAI-1). WO 2013/074059-A2 details various quinoline-4-carboxamide derivatives which can serve as inhibitors of cytosine deaminases for boosting DNA transfection of cells. WO 2013/164326-A1 discloses N,3-diphenylnaphthalene-1-carboxamides as agonists of the EP2 prostaglandin receptor for treatment of respiratory pathway disorders. WO 2014/117090-A1 describes various 2-arylquinoline derivatives as inhibitors of metalloenzymes. WO 2012/122370-A2 discloses quinoline-4-carboxamide derivatives which can be used for the treatment of autoimmune and neoplastic disorders. WO 2015/094912-A1 discloses, inter alia, substituted N,2-diphenylquinoline-4-carboxamide derivatives that are suitable as antagonists of the prostaglandin EP4 receptor for treatment of arthritis and associated states of pain. WO 2016/061280 discloses protein tyrosine phosphatase modulators having a 4-amino-2-arylquinoline base structure, which can be used inter alia for treatment of metabolic disorders, diabetes and cardiovascular disorders.

SUMMARY

The present invention relates to compounds of the general formula (I)

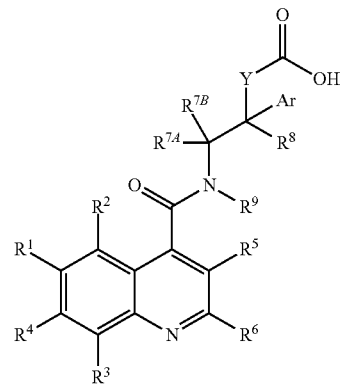

in which

Ar represents phenyl or represents pyridyl,
  where phenyl may be up to tetrasubstituted and pyridyl up to disubstituted, in each case identically or differently, by fluorine, chlorine, by up to tri-fluorine-substituted ($C_1$-$C_4$)-alkyl, up to tetra-fluorine-substituted ($C_3$-$C_4$)-cycloalkyl, up to tri-fluorine-substituted ($C_1$-$C_2$) alkoxy, or up to tri-fluorine-substituted ($C_1$-$C_2$)-alkylsulfanyl, or where two substituents of the phenyl or pyridyl group, if they are attached to adjacent ring atoms, are optionally attached to one another in such a way that they together form a methylenedioxy or ethylenedioxy group,
  or
  where phenyl may be up to pentasubstituted by fluorine, Y represents a bond or a group of the formula

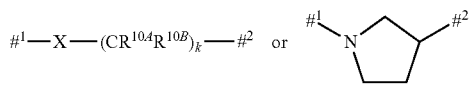

where
  #$^1$ represents the attachment site to the carbon atom,
  #$^2$ represents the attachment site to the carboxyl group,
  X represents a bond, —$CH_2$—, —O—, —$S(=O)_m$— or —$N(R^{11})$—, in which
    m represents 0, 1 or 2 and
    $R^{11}$ represents hydrogen or methyl,
  $R^{10A}$ and $R^{10B}$ independently of one another represent hydrogen, fluorine or methyl, or
  $R^{10A}$ and $R^{10B}$ together with the carbon atom to which they are attached form a cyclopropyl group,
  k represents 1, 2, 3 or 4, $R^1$ represents halogen, up to penta-fluorine-substituted ($C_1$-$C_4$)-alkyl, up to tri-fluorine-substituted methoxy, (trifluoromethyl)sulfanyl, pentafluorosulfanyl, trimethylsilyl, ethynyl, cyclopropyl or cyclobutyl,
  where cyclopropyl and cyclobutyl may be up to tetrasubstituted by fluorine, $R^2$, $R^3$ and $R^4$ independently of one another represent hydrogen, halogen or up to tri-fluorine-substituted methyl, $R^5$ represents halogen, up to penta-fluorine-substituted ($C_1$-$C_4$)-alkyl, up to tri-fluorine-substituted methoxy, hydroxyl, methylsulfanyl, (trifluoromethyl)sulfanyl, cyano, ethenyl, cyclopropyl or cyclobutyl,
  where cyclopropyl and cyclobutyl may be up to tetrasubstituted by fluorine, $R^6$ represents phenyl which may be up to trisubstituted by identical or different substituents from the group consisting of fluorine, chlorine, methyl, which is up to trisubstituted by fluorine, and methoxy, which is up to trisubstituted by fluorine, or represents thienyl which may be mono- or disubstituted by methyl or monosubstituted by chlorine or bromine, or represents thiazolyl or pyridyl, $R^{7A}$ and $R^{7B}$ independently of one another represent hydrogen or methyl,
  or
$R^{7A}$ and $R^{7B}$ together with the carbon atom to which they are attached form a cyclopropyl group, $R^8$ represents hydrogen, fluorine, methyl, trifluoromethyl, ethyl or hydroxyl, $R^9$ represents hydrogen or methyl, and the N-oxides, salts, solvates, salts of the N-oxides and solvates of the N-oxides and salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Compounds of the invention are likewise N-oxides of the compounds of the formula (I) and the salts, solvates and solvates of the salts thereof.

DETAILED DESCRIPTION OF A PREFERRED EMBODIMENT

Preferred salts in the context of the present invention are physiologically acceptable salts of the compounds of the invention. Also encompassed are salts which are not themselves suitable for pharmaceutical applications but can be used, for example, for the isolation, purification or storage of the compounds of the invention.

Physiologically acceptable salts of the compounds of the invention especially include the salts derived from conventional bases, by way of example and with preference alkali metal salts (e.g. sodium and potassium salts), alkaline earth metal salts (e.g. calcium and magnesium salts), zinc salts and ammonium salts derived from ammonia or organic amines having 1 to 16 carbon atoms, by way of example and with preference ethylamine, diethylamine, triethylamine, DIPEA, monoethanolamine, diethanolamine, triethanolamine, dimethylaminoethanol, diethylaminoethanol, tris (hydroxymethyl)aminomethane, choline (2-hydroxy-N,N,N-trimethylethanaminium), procaine, dicyclohexylamine, dibenzylamine, N-methylmorpholine, N-methylpiperidine, arginine, lysine and 1,2-ethylenediamine.

In addition, physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner. Preference is given to employing chromatographic methods for this purpose, especially HPLC chromatography on achiral or chiral separation phases. In the case of carboxylic acids as intermediates or end products, separation is alternatively also possible via diastereomeric salts using chiral amine bases.

In the context of the present invention, the term "enantiomerically pure" is understood to the effect that the compound in question with respect to the absolute configuration of the chiral centers is present in an enantiomeric excess of more than 95%, preferably more than 98%. The enantiomeric excess, ee, is calculated here by evaluating an HPLC analysis chromatogram on a chiral phase using the formula below:

$$ee = \left|\frac{\text{Enantiomer 1 (area percent)} - \text{Enantiomer 2 (area percent)}}{\text{Enantiomer 1 (area percent)} + \text{Enantiomer 2 (area percent)}}\right| \times 100\%.$$

If the compounds of the invention can occur in tautomeric forms, the present invention encompasses all the tautomeric forms.

The present invention also encompasses all suitable isotopic variants of the compounds of the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labeled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds according to the invention. The term "prodrugs" refers here to compounds which may themselves be biologically active or inactive, but are converted while present in the body, for example by a metabolic or hydrolytic route, to compounds of the invention.

The present invention comprises as prodrugs in particular hydrolyzable ester derivatives of the inventive carboxylic acids of the formula (I). These are understood to mean esters which can be hydrolyzed to the free carboxylic acids, as the main biologically active compounds, in physiological media under the conditions of the biological tests described hereinbelow and in particular in vivo by an enzymatic or chemical route. Preferred esters of this kind are ($C_1$-$C_4$)-alkyl esters of the formula (IV) in which the alkyl group may be straight-chain or branched. Particular preference is given to methyl, ethyl or tert-butyl esters.

In the context of the present invention, unless specified otherwise, the substituents are defined as follows:

The expression "halogen" or "halogen atom" denotes, for example, a fluorine, chlorine, bromine or iodine atom.

The expression "$C_1$-$C_4$-alkyl" denotes a straight-chain or branched saturated monovalent hydrocarbyl group having 1, 2, 3 or 4 carbon atoms, for example a methyl, ethyl, propyl, isopropyl, butyl, sec-butyl, isobutyl or tert-butyl group or an isomer thereof.

The expression "$C_3$-$C_4$-cycloalkyl" relates to a saturated monovalent mono- or bicyclic hydrocarbyl ring having 3 or 4 carbon atoms. The $C_3$-$C_4$-cycloalkyl group is, for example, a monocyclic hydrocarbyl ring, for example a cyclopropyl or cyclobutyl group.

The expression "$C_1$-$C_2$-alkoxy" denotes a straight-chain or branched saturated monovalent group of the formula ($C_1$-$C_2$-alkyl)-O—, in which the expression "$C_1$-$C_2$-alkyl" is as defined above, e.g. a methoxy or ethoxy group, or an isomer thereof.

The expression "$C_1$-$C_2$-alkylsulfanyl" denotes a straight-chain or branched saturated monovalent group of the formula ($C_1$-$C_2$-alkyl)-S— in which the expression "$C_1$-$C_2$-alkyl" is as defined above, e.g. a methylsulfanyl or ethylsulfanyl group.

An oxo substituent in the context of the invention is an oxygen atom bonded to a carbon atom via a double bond.

The term "$C_1$-$C_4$", as it is used in this text, e.g. in the context of the definition of "$C_1$-$C_4$-alkyl", refers to an alkyl group having a number of carbon atoms limited to 1 to 3, i.e. 1, 2, 3 or 4 carbon atoms.

If a range of values is listed, this includes every individual value and subranges within the range. "$C_1$-$C_4$" includes, for example, $C_1$, $C_2$, $C_3$, $C_4$, $C_1$-$C_4$, $C_1$-$C_3$, $C_1$-$C_2$, $C_2$-$C_4$, $C_2$-$C_3$ and $C_3$-$C_4$.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

Preference is given in the context of the present invention to compounds of the formula (I) in which Ar represents phenyl or represents 2-pyridyl,
  where phenyl may be up to tetrasubstituted by fluorine or up to trisubstituted by identical or different fluorine, chlorine, methyl, trifluoromethyl, difluoromethyl, methoxy, difluoromethoxy, trifluoromethoxy or ethoxy substituents, or where two substituents of the phenyl group, if they are attached to adjacent ring atoms, are optionally attached to one another in such a way that they together form a methylenedioxy group, and
  where 2-pyridyl may be up to disubstituted by identical or different substituents from the group consisting of chlorine and methoxy, Y represents a bond or a group of the formula

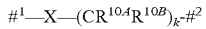

where
$^1$ represents the attachment site to the carbon atom,
$^2$ represents the attachment site to the carboxyl group,
X represents —CH$_2$—, —O—, —S(=O)$_m$— or —N(R$^{11}$)—, in which m represents 0 or 2 and $R^{11}$ represents hydrogen or methyl, $R^{10A}$ and $R^{10B}$ independently of one another represent hydrogen, fluorine or methyl, k represents 1, 2 or 3, $R^1$ represents chlorine, bromine, iodine, methyl, isopropyl, tert-butyl, difluoromethyl, trifluoromethyl, trifluoromethoxy, (trifluoromethyl)sulfanyl, trimethylsilyl, ethynyl, cyclopropyl or cyclobutyl, $R^2$ represents hydrogen, $R^3$ and $R^4$ independently of one another represent hydrogen, chlorine or methyl, $R^5$ represents fluorine, chlorine, bromine, iodine, methyl, ethyl, propyl, monofluoromethyl, difluoromethyl, trifluoromethyl, methoxy, trifluoromethoxy, hydroxy, methylsulfanyl or cyclopropyl, and $R^6$ represents phenyl which may be mono- or disubstituted by identical or different fluorine or chlorine substituents or monosubstituted by methyl, trifluoromethyl, methoxy or trifluoromethoxy, or represents thienyl which may be mono- or disubstituted by methyl or monosubstituted by chlorine or bromine, $R^{7A}$ represents hydrogen or methyl, $R^{7B}$ represents hydrogen, $R^8$ represents hydrogen, fluorine, methyl, ethyl or hydroxy, $R^9$ represents hydrogen, and the salts, solvates and solvates of the salts thereof.

Preference is given in the context of the present invention to compounds of the formula (I) in which Ar represents phenyl, where phenyl may be up to tetrasubstituted by fluorine or up to trisubstituted by identical or different fluorine, chlorine, methyl, trifluoromethyl, difluoromethyl, methoxy, difluoromethoxy or trifluoromethoxy substituents, Y represents a group of the formula $\#^1$—$(CH_2)_n$-$\#^2$ where $\#^1$ represents the attachment site to the carbon atom, $\#^2$ represents the attachment site to the carboxyl group, n represents 1, 2 or 3, $R^1$ represents bromine or ethynyl, $R^2$, $R^3$ and $R^4$ each represent hydrogen, $R^5$ represents chlorine or methyl, and $R^6$ represents phenyl which may be monosubstituted by fluorine, $R^{7A}$ and $R^{7B}$ each represent hydrogen, $R^8$ represents hydrogen or methyl, $R^9$ represents hydrogen, and the salts, solvates and solvates of the salts thereof.

In the context of the present invention, particular preference is given to compounds of the formula (I) in which Ar represents phenyl, where phenyl may be up to tetrasubstituted by fluorine or up to trisubstituted by identical or different fluorine, chlorine, methyl, trifluoromethyl, difluoromethoxy or trifluoromethoxy substituents, Y represents a group of the formula $\#^1$—$CH_2CH_2$-$\#^2$ where $\#^1$ represents the attachment site to the carbon atom, $\#^2$ represents the attachment site to the carboxyl group, $R^1$ represents bromine or ethynyl, $R^2$, $R^3$, $R^4$ each represent hydrogen, $R^5$ represents methyl or chlorine, $R^6$ represents phenyl, $R^{7A}$, $R^{7B}$, $R^8$ and $R^9$ are each hydrogen, and the salts, solvates and solvates of the salts thereof.

A particular embodiment of the present invention comprises compounds of the formula (I) in which $R^1$ is bromine, and $R^2$, $R^3$ and $R^4$ are each hydrogen, and the N-oxides, salts, solvates, salts of the N-oxides and solvates of the N-oxides and salts thereof.

A further particular embodiment of the present invention encompasses compounds of the formula (I) in which $R^1$ represents ethynyl, and $R^2$, $R^3$ and $R^4$ each represent hydrogen, and the N-oxides, salts, solvates, salts of the N-oxides and solvates of the N-oxides and salts thereof.

A further particular embodiment of the present invention encompasses compounds of the formula (I) in which $R^5$ represents methyl or chlorine, and the N-oxides, salts, solvates, salts of the N-oxides and solvates of the N-oxides and salts thereof.

A further particular embodiment of the present invention encompasses compounds of the formula (I) in which $R^5$ represents methyl, and the N-oxides, salts, solvates, salts of the N-oxides and solvates of the N-oxides and salts thereof.

A further particular embodiment of the present invention encompasses compounds of the formula (I) in which $R^6$ represents phenyl which may be monosubstituted by fluorine, a the N-oxides, salts, solvates, salts of the N-oxides and solvates of the N-oxides and salts thereof.

A further particular embodiment of the present invention encompasses compounds of the formula (I) in which $R^6$ represents phenyl, and the N-oxides, salts, solvates, salts of the N-oxides and solvates of the N-oxides and salts thereof.

A further particular embodiment of the present invention encompasses compounds of the formula (I) in which Y represents a bond, and the N-oxides, salts, solvates, salts of the N-oxides and solvates of the N-oxides and salts thereof.

A further particular embodiment of the present invention encompasses compounds of the formula (I) in which Y represents a group of the formula $\#^1$—$CH_2$-$\#^2$ where $\#^1$ represents the attachment site to the carbon atom, $\#^2$ represents the attachment site to the carboxyl group, and the N-oxides, salts, solvates, salts of the N-oxides and solvates of the N-oxides and salts thereof.

A further particular embodiment of the present invention encompasses compounds of the formula (I) in which Y represents a group of the formula $\#^1$—$CH_2CH_2$-$\#^2$ where $\#^1$ represents the attachment site to the carbon atom, $\#^2$ represents the attachment site to the carboxyl group, and the N-oxides, salts, solvates, salts of the N-oxides and solvates of the N-oxides and salts thereof.

A further particular embodiment of the present invention encompasses compounds of the formula (I) in which X represents —O—, and the N-oxides, salts, solvates, salts of the N-oxides and solvates of the N-oxides and salts thereof.

A further particular embodiment of the present invention encompasses compounds of the formula (I) in which
$R^8$ represents hydrogen or methyl,
and the N-oxides, salts, solvates, salts of the N-oxides and solvates of the N-oxides and salts thereof.

A further particular embodiment of the present invention encompasses compounds of the formula (I) in which
$R^{7A}$ represents methyl,
$R^{7B}$ represents hydrogen,
and the N-oxides, salts, solvates, salts of the N-oxides and solvates of the N-oxides and salts thereof.

A further particular embodiment of the present invention encompasses compounds of the formula (I) in which
Ar is phenyl,
where phenyl may be up to tetrasubstituted by fluorine or up to trisubstituted by identical or different fluorine, chlorine, methyl, trifluoromethyl, difluoromethyl, methoxy, difluoromethoxy, trifluoromethoxy or ethoxy substituents, or where two substituents of the phenyl group, if they are attached to adjacent ring atoms, are optionally attached to one another in such a way that they together form a methylenedioxy group,
and the N-oxides, salts, solvates, salts of the N-oxides and solvates of the N-oxides and salts thereof.

A further particular embodiment of the present invention encompasses compounds of the formula (I) in which
Ar represents phenyl,
where phenyl may be up to tetrasubstituted by fluorine or up to trisubstituted by identical or different fluorine, chlorine, methyl, trifluoromethyl, difluoromethoxy or trifluoromethoxy substituents,
and the N-oxides, salts, solvates, salts of the N-oxides and solvates of the N-oxides and salts thereof.

A further particular embodiment of the present invention encompasses compounds of the formula (I) in which
Ar represents 2-pyridyl,
where 2-pyridyl may be up to disubstituted by identical or different substituents from the group consisting of chlorine and methoxy,
and the N-oxides, salts, solvates, salts of the N-oxides and solvates of the N-oxides and salts thereof.

A further particular embodiment of the present invention encompasses compounds of the formula (I) in which
$R^2$, $R^3$ and $R^4$ independently of one another represent hydrogen,
and the N-oxides, salts, solvates, salts of the N-oxides and solvates of the N-oxides and salts thereof.

A further particular embodiment of the present invention encompasses compounds of the formula (I) in which
$R^1$ represents bromine,
$R^2$, $R^3$, $R^4$ each represent hydrogen,
$R^5$ represents methyl,
$R^6$ represents phenyl,
and the N-oxides, salts, solvates, salts of the N-oxides and solvates of the N-oxides and salts thereof.

A further particular embodiment of the present invention encompasses compounds of the formula (I) in which
$R^1$ represents ethynyl,
$R^2$, $R^3$, $R^4$ each represent hydrogen,
$R^5$ represents methyl,
$R^6$ represents phenyl,
and the N-oxides, salts, solvates, salts of the N-oxides and solvates of the N-oxides and salts thereof.

The individual radical definitions specified in the respective combinations or preferred combinations of radicals are, independently of the respective combinations of the radicals specified, also replaced as desired by radical definitions of other combinations.

Very particular preference is given to combinations of two or more of the abovementioned preferred ranges.

The radical definitions specified as preferred, particularly preferred and very particularly preferred apply both to the compounds of the formula (I) and correspondingly toward all intermediates.

The invention furthermore provides a process for preparing the compounds of the formula (I) according to the invention, characterized in that a compound of the formula (II)

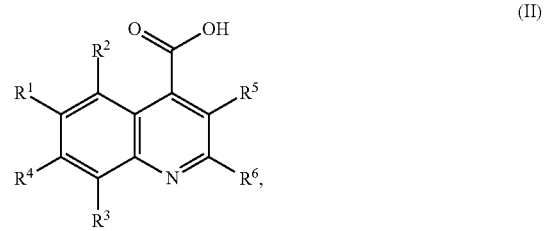

in which $R^1$, $R^2$, $R^3$, $R^4$, $R^5$ and $R^6$ have the meanings given above, is, in a first step,

[A] with activation of the carboxylic acid function reacted with an amine compound of the formula (III-A) or (III-B)

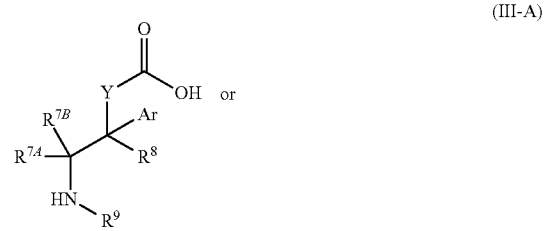

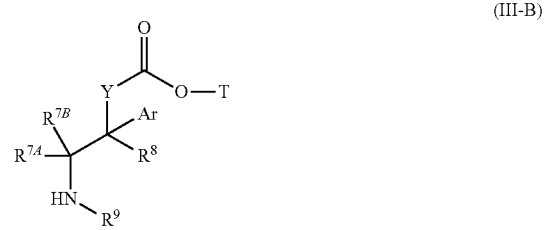

in which $R^{7A}$, $R^{7B}$, $R^8$, $R^9$ and Ar have the meanings given above and T represents an ester protecting group, in particular $(C_1-C_4)$-alkyl, and optionally in a subsequent step

[B] the ester radical T of a compound of the formula (IV) obtained from step [A] after reaction with an amine compound (III-B)

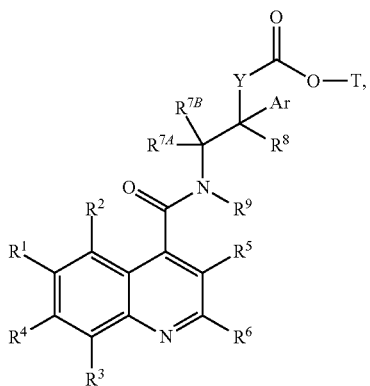

(IV)

in which $R^1$, $R^2$, $R^3$, $R^4$, $R^5$, $R^6$, $R^{7A}$, $R^{7B}$, $R^8$, $R^9$ and Ar have the meanings given above,
and
T represents an ester protecting group, in particular $(C_1-C_4)$-alkyl,
is detached,
and the compounds of the formula (I) thus obtained

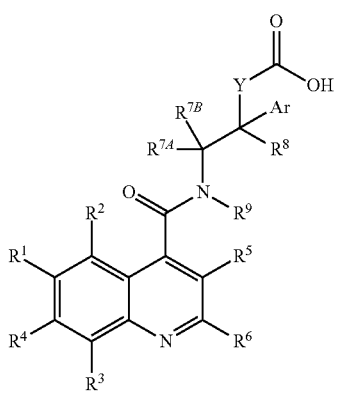

(I)

in which $R^1$, $R^2$, $R^3$, $R^4$, $R^5$, $R^6$, $R^{7A}$, $R^{7B}$, $R^8$, $R^9$ and Ar have the meanings given above,
are optionally separated into their enantiomers and/or diastereomers and/or converted with the appropriate (i) solvents and/or (ii) acids or bases to the solvates, salts and/or solvates of the salts thereof.

The coupling reaction (II)+(III-A)→(I) and (II)+(III-B)→(IV) [amide formation] can be effected either by a direct route with the aid of a condensing or activating agent or via the intermediate stage of a carbonyl chloride or carbonyl imidazolide obtainable from (II).

Suitable such condensing or activating agents are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chloroenamines such as 1-chloro-N,N,2-trimethylprop-1-ene-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), O-(1H-6-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and suitable bases are alkali metal carbonates, for example sodium carbonate or potassium carbonate, or tertiary amine bases such as triethylamine, N-methylmorpholine (NMM), N-methylpiperidine (NMP), DIPEA, pyridine or 4-N,N-dimethylaminopyridine (DMAP). The condensing agent or activating agent preferably used is O-(7-azabenzotriazol-1-yl)-N,N,N',N'-tetramethyluronium hexafluorophosphate (HATU) in combination with DIPEA.

In the case of a two-stage reaction regime via the carbonyl chlorides or carbonyl imidazolides obtainable from (II), the coupling with the amine component (III-A)/(III-B) is conducted in the presence of a customary base, for example sodium carbonate or potassium carbonate, triethylamine, DIPEA, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU), 1,5-diazabicyclo[4.3.0]non-5-ene (DBN), sodium methoxide or potassium methoxide, sodium ethoxide or potassium ethoxide, sodium tert-butoxide or potassium tert-butoxide, or sodium hydride or potassium hydride. Preference is given to using triethylamine or DIPEA as base.

The preferred coupling method is the direct reaction of (II) with the amine compound (III) with the aid of a condensing or activating agent.

Inert solvents for the coupling reactions mentioned are—according to the method used—for example ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP). It is also possible to use mixtures of such solvents. Preference is given to using N,N-dimethylformamide. The couplings are generally conducted within a temperature range from 0° C. to +130° C., preferably at +20° C. to +80° C.

The carbonyl imidazolides themselves are obtainable by known methods by reaction of (II) with N,N'-carbonyldiimidazole (CDI) at elevated temperature (+60° C. to +150° C.) in a correspondingly relatively high-boiling solvent such as N,N-dimethylformamide (DMF). The preparation of the carbonyl chlorides is accomplished in a customary manner by treating (II) with thionyl chloride or oxalyl chloride in an inert solvent such as dichloromethane.

Suitable ester protecting groups T are, in general, all protecting groups known to the person skilled in the art, for example suitably substituted methyl, such as methylthiomethyl (MTM), tetrahydropyranyl (THP), 2-(trimethylsilyl)ethoxymethyl (SEM), benzyloxymethyl (BOM), phenacyl and N-phthalimidomethyl, suitably 2-substituted ethyl, such as 4-methylphenylsulfonylethyl (TSE), 2,2,2-trichloroethyl, 2-(trimethylsilyl)ethyl and 2-(2'-pyridyl)ethyl (PET), allyl, benzyl, suitably substituted benzyl, such as diphenylmethyl (DPM), bis(ortho-nitrophenyl)methyl, 9-anthrylmethyl, 2,4,6-trimethylbenzyl, 4-bromobenzyl, 4-methoxybenzyl (PMB), piperonyl and suitably substituted silyl, such as triethylsilyl (TES), tert-butyldimethylsilyl (TBDMS) and di-tert-butylmethylsilyl (DTBMS); the ester protecting group T used in the process according to the invention is especially and with preference $(C_1-C_4)$-alkyl.

The detachment of the ester protecting group T in process step (IV)→(I) is conducted by customary methods, by treating the ester in an inert solvent with an acid or a base, with conversion of the salt of the carboxylic acid initially formed in the latter variant to the free carboxylic acid by subsequent treatment with acid. In the case of the tert-butyl esters, the ester cleavage is preferably effected with an acid. Methyl and ethyl ester are preferably cleaved using a base. Benzyl esters can alternatively also be cleaved by hydrogenation (hydrogenolysis) in the presence of a suitable catalyst, for example palladium on activated carbon. Silyl esters can be cleaved by treatment with acids or fluorides, e.g. tetrabutylammonium fluoride.

Suitable inert solvents for these reactions are water and the organic solvents customary for ester cleavage. These include in particular alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulfoxide. It is equally possible to use mixtures of these solvents. In the case of a basic ester hydrolysis, preference is given to using mixtures of water with tetrahydrofuran, 1,4-dioxane, methanol and/or ethanol. Preference is given to using dichloromethane in the case of the reaction with trifluoroacetic acid, and 1,4-dioxane in the case of the reaction with hydrogen chloride, in each case under anhydrous conditions.

Suitable bases for a hydrolysis reaction are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to using aqueous lithium hydroxide solution or sodium hydroxide solution.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, optionally with addition of water. Preference is given to using hydrogen chloride or trifluoroacetic acid.

The ester cleavage is generally conducted within a temperature range from −200 to +100° C., preferably at 0° C. to +80° C.

Compounds of the formula (I) can be converted by customary methods to their corresponding salts, derived from bases.

Salts of compounds of the formula (I) that have been derived from customary bases can be prepared, for example, by addition of bases, such as alkali metal and alkaline earth metal hydroxide solutions, to compounds of the formula (I). Preference is given to using aqueous hydroxide solutions (e.g. sodium hydroxide solution). The aqueous hydroxide solutions (e.g. potassium hydroxide solution) can also be generated in situ, by mixing an organometallic compound dissolved in an organic solvent (e.g. potassium tert-butoxide solution in THF) with water or an aqueous solution. The base-derived salts in question can also be prepared by addition of bases, such as alkali metal and alkaline earth metal hydroxide solutions, to ester compounds of the formula (IV), by first detaching the ester group T and directly forming the salt in question in situ, i.e. without isolation of the free carboxylic acid. Preferred ester groups T with regard to detachment by bases are the methyl and ethyl group.

Depending on their respective substitution pattern, the compounds of the formula (II) can be prepared by, in analogy to processes known from the literature (see WO 2016/146602 A1, p. 26 to 32), reacting either an isatin derivative of the formula (V) in an acid or base-mediated condensation reaction with a ketomethylene compound of the formula (VI) to give the compound of the formula (VII) (Scheme 1) or ortho-aminophenylacetate of the formula (VIII) in an acid-induced condensation reaction with a diketo compound of the formula (IX) to give a compound of the formula (VII-A) (Scheme 2).

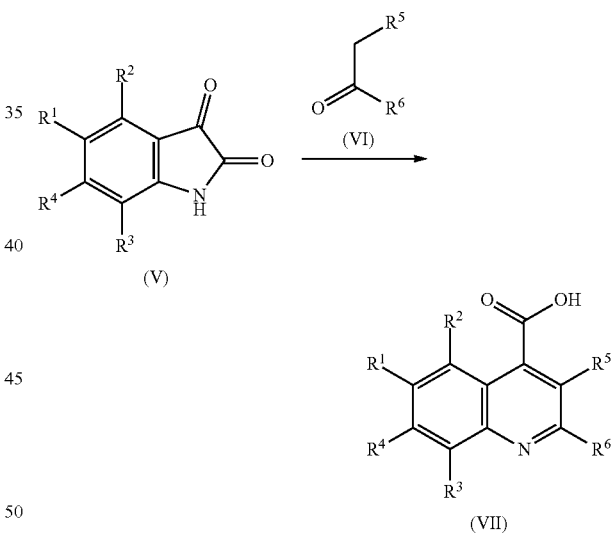

Scheme 1

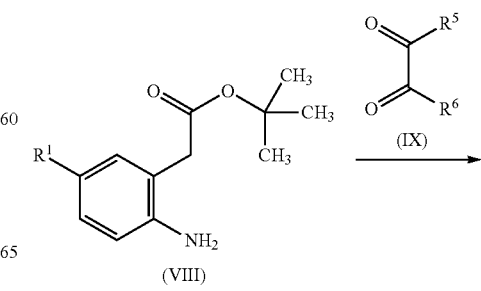

Scheme 2

-continued

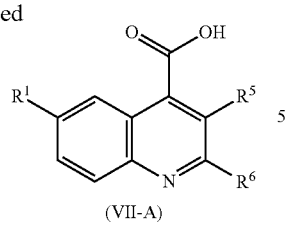

(VII-A)

The condensation of the isatin derivative of the formula (V) with the ketomethylene compound of the formula (VI) to give the quinoline-4-carboxylic acid of the formula (VII) (Scheme 1) can be achieved by heating the reactants in the presence of an aqueous acid, such as sulfuric acid or concentrated hydrochloric acid, or in the presence of an aqueous base, such as aqueous sodium hydroxide or potassium hydroxide solution. In the case of use of an acid, preference is given to using acetic acid as solvent for the reaction; in the case of a basic reaction regime, preference is given to using an alcoholic solvent such as methanol or ethanol. The condensation is generally conducted within a temperature range from +70° C. to +120° C. [cf., for example, K. Lackey and D. D. Sternbach, *Synthesis,* 1993, 993-997; A. N. Boa et al., *Bioorg. Med. Chem.* 2005, 13 (6), 1945-1967].

The condensation reaction to give the quinoline-4-carboxylic acid of the formula (VII-A) (Scheme 2) is carried out analogously by heating the ortho-aminophenylacetic ester of the formula (VIII) and the diketone of the formula (IX) with aqueous acid, in particular concentrated hydrochloric acid. The inert solvent used for the reaction here too is preferably acetic acid.

For its part, the ortho-aminophenylacetic ester of the formula (VIII) can be converted following a process described in the literature by base-mediated reaction of the α-chloroacetic ester of the formula (XX) with a nitrophenyl derivative of the formula (XXI) into an ortho-nitrophenylacetic ester of the formula (XXII) (Scheme 3). Subsequent reduction of the nitro group to give a compound of the formula (XXI) can be achieved, for example, by catalytic hydrogenation [cf. P. Beier et al., *J. Org. Chem.* 2011, 76, 4781-4786].

-continued

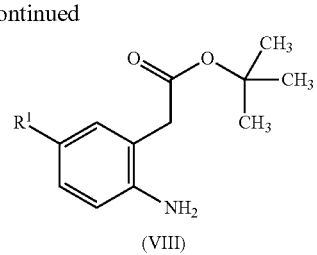

(VIII)

The compounds of the formulae (III-A) and (III-B), depending on the respective substitution pattern, can be prepared, for example, by the synthesis routes described in Schemes 4 to 10 below and in the experimental section in the respective examples, and in analogy to synthesis methods known from the literature:

Scheme 4

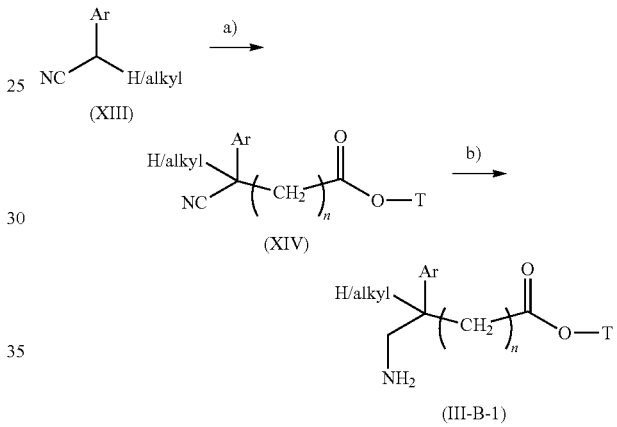

(when Y = #¹—(CH₂)ₙ—#² with n = 0, 1, 2, 3 (III-B-1)).

[alkyl = methyl, ethyl; Ar = subst. phenyl, subst. pyridyl; T = ester protecting group, e.g. methyl, ethyl, tert-butyl; n = 0, 1, 2, 3; a): when n = 0: di-tert-butyl dicarbonate, LDA, -78° C.; when n = 1: tert-butyl bromoacetate, LDA or LiHMDS, -78° C.; when n = 2: tert-butyl 3-bromopropanoate, LDA or LiHMDS, -78° C.; or tert-butyl acrylate, potassium carbonate or sodium hydride; when n = 3: tert-butyl 4-bromobutanoate, LDA, -78° C. b): H₂, Raney nickel or PtO₂. LDA = lithium diisoprop-ylamide; LiHMDS = lithium bis(trimethylsilyl)amide].

Scheme 3

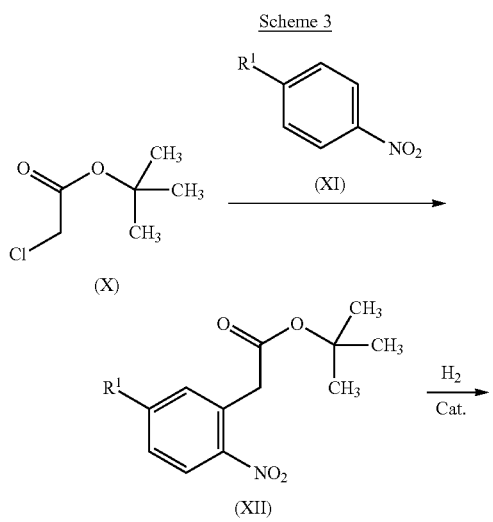

Scheme 5

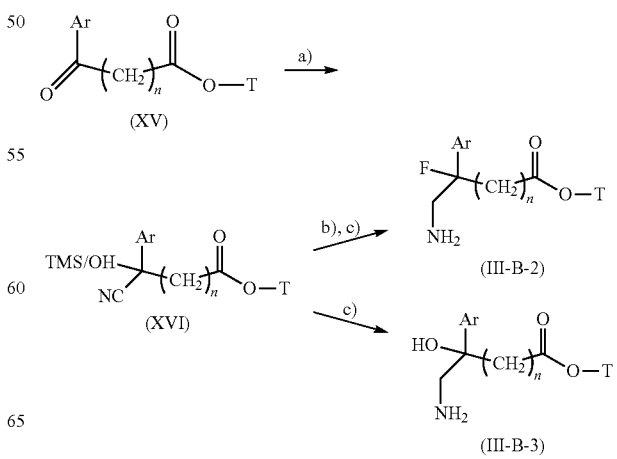

-continued

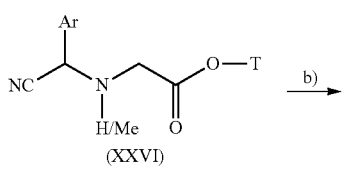

(XXVI)

-continued

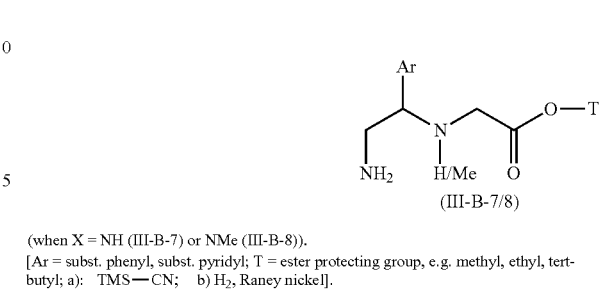

(III-B-7/8)

(when X = NH (III-B-7) or NMe (III-B-8)).
[Ar = subst. phenyl, subst. pyridyl; T = ester protecting group, e.g. methyl, ethyl, tert-butyl; a): TMS—CN; b) H₂, Raney nickel].

(when R8 = fluorine (III-B-2), hydroxyl (III-B-3)).

[Ar = subst. phenyl, subst. pyridyl; T = ester protecting group, e.g. methyl, ethyl, tert-butyl; n = 0, 1, 2, 3; a): e.g. KCN or TMSCN; b) DAST; c): H₂, catalyst, e.g. Raney nickel or PtO₂. DAST = diethylaminosulfur trifluoride].

Scheme 6

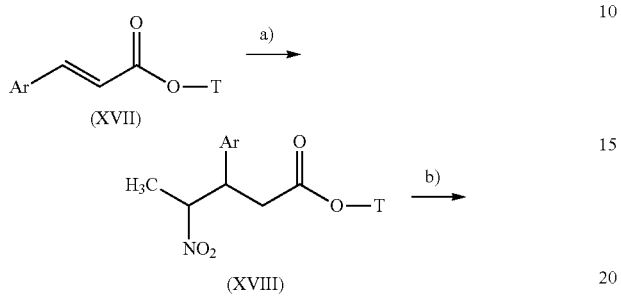

(when $R^{7A}/R^{7B}$ = H, Me (III-B-4)).

[Ar = subst. phenyl, subst. pyridyl; T = ester protecting group, e.g. methyl, ethyl, tert-butyl; a): nitroethane, base, e.g. 2-tert-butyl-1,1,3,3-tetramethylguanidine; b) zinc dust, hydrochloric acid].

Scheme 9

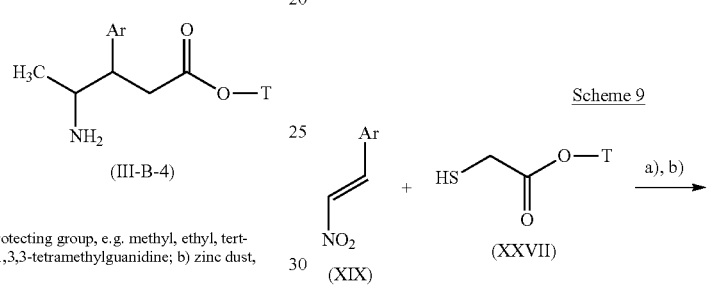

Scheme 7

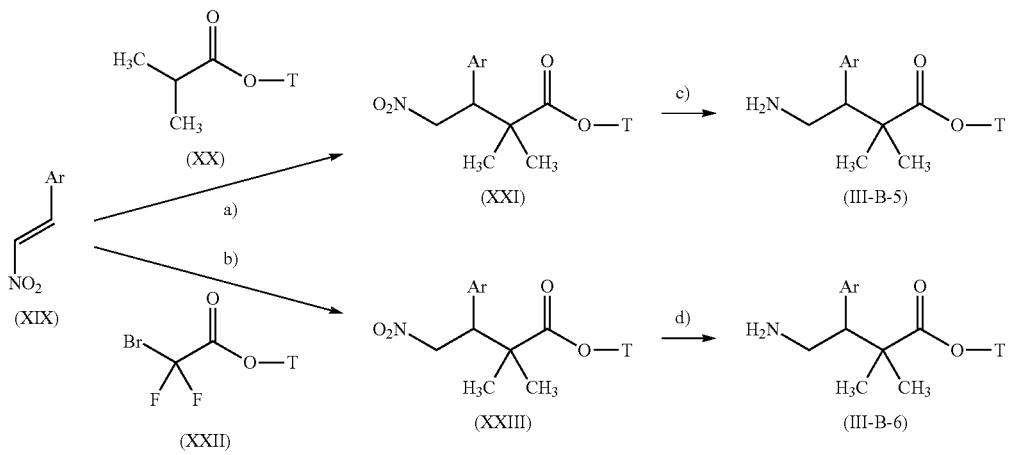

(when $R^{10A}/R^{10B}$ = Me, Me (III-B-5) or F, F (III-B-6)).

[Ar = subst. phenyl, subst. pyridyl; T = ester protecting group, e.g. methyl, ethyl, tert-butyl; a): LDA, -78° C.; b) zinc; c) H₂, Raney nickel; d) H₂, PtO₂. LDA = lithium diisopropylamide].

Scheme 8

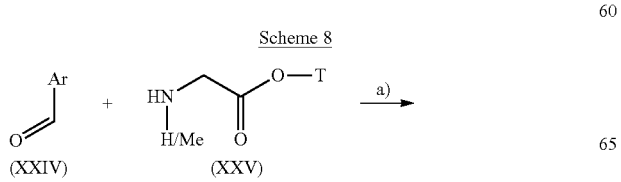

-continued

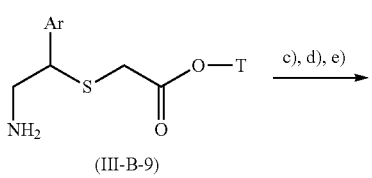

(III-B-9)

-continued

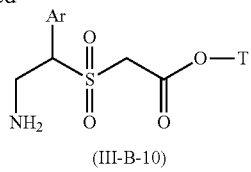

(III-B-10)

(when X = S (III-B-9) or SO₂ (III-B-10)).

[Ar = subst. phenyl, subst. pyridyl; T = ester protecting group, e.g. methyl, ethyl, tert-butyl; a) e.g. in DCM; b) SnCl₂; c) protection of amino functionality, e.g. as NH—Boc: di-tert-butyl dicar-bonate, triethylamine; d) mCPBA; e) deprotection of amino functionality, e.g. HCl/dioxane. Boc = tert-butyloxycarbonyl; DCM = dichloromethane].

Scheme 10

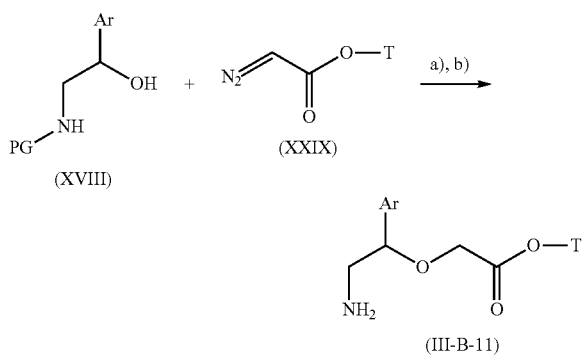

(when X = O (III-B-11)).

[Ar = subst. phenyl, subst. pyridyl; T = ester protecting group, e.g. methyl, ethyl, tert-butyl; PG = protecting group, e.g. Boc; a) Rh₂(OAc)₄; b) deprotection of amino functionality, e.g. HCl/di-oxane. Boc = tert-butyloxycarbonyl].

Separation of the compounds according to the invention into the corresponding enantiomers and/or diastereomers can, if appropriate, also be conducted at the early stage of the intermediates (III-A), (III-B) or (IV), which are then reacted further in separated form in accordance with the reaction sequence described above. It may be appropriate to provide the amine functionality of the intermediates (III-A) and (III-B) with a protecting group, e.g. Boc, prior to such a separation and then to deprotect it again after the separation. For such a separation of the stereoisomers of intermediates, preference is likewise given to employing chromatographic methods on achiral or chiral separation phases.

The compounds of the formulae (V), (VI), (VIII), (IX), (X), (XI), (XIII), (XV), (XVII), (XIX), (XX), (XXII), (XXIV), (XXV), (XXVII), (XVIII) and (XXIX) are likewise commercially available or described as such in the literature, or they can be prepared in a simple manner proceeding from other commercially available compounds in analogy to methods known from the literature.

Detailed procedures and further literature references can also be found in the experimental section, in the section on the preparation of the starting compounds and intermediates.

Further compounds of the formula (I) according to the invention can, if expedient, also be prepared by transformations of functional groups of individual radicals and substituents, in particular those listed under $R^1$ and $R^5$, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, bromination), dehalogenation, amination, alkylation and acylation, the formation of carboxylic esters, carboxamides and sulfonamides, ester cleavage and hydrolysis, and the introduction and removal of temporary protecting groups.

The compounds of the invention have valuable pharmacological properties and can be used for treatment and/or prophylaxis of disorders in humans and animals.

The compounds of the invention are potent, chemically and metabolically stable antagonists of the FP receptor ("FP antagonists") and are therefore suitable for treatment and/or prevention of disorders and pathological processes, especially those where the FP receptor is involved in the course of an inflammatory event and/or tissue or vessel reconstruction.

In the context of the present invention, these especially include disorders such as the group of the interstitial idiopathic pneumonias which includes idiopathic pulmonary fibrosis (IPF), acute interstitial pneumonia, non-specific interstitial pneumonias, lymphoid interstitial pneumonias, respiratory bronchiolitis with interstitial lung disease, cryptogenic organizing pneumonias, desquamative interstitial pneumonias and non-classifiable idiopathic interstitial pneumonias, and also granulomatous interstitial lung diseases, rheumatoid arthritis with interstitial pulmonary disease, interstitial lung diseases of known etiology and other interstitial lung diseases of unknown etiology, pulmonary arterial hypertension (PAH) and other forms of pulmonary hypertension (PH), bronchiolitis obliterans syndrome (BOS), chronic-obstructive pulmonary disease (COPD), pulmonary sarcoidosis, acute respiratory distress syndrome (ARDS), acute lung injury (ALI), alpha-1-antitrypsin deficiency (AATD), pulmonary emphysema (for example pulmonary emphysema induced by cigarette smoke), cystic fibrosis (CF), inflammatory and fibrotic disorders of the kidney, chronic intestinal inflammations (IBD, Crohn's disease, ulcerative colitis), peritonitis, peritoneal fibrosis, rheumatoid disorders, multiple sclerosis, inflammatory and fibrotic skin disorders, sickle cell anemia and inflammatory and fibrotic eye disorders.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds according to the invention can additionally be used for the treatment and/or prevention of cardiovascular disorders such as, for example, high blood pressure (hypertension), heart failure, coronary heart disease, stable and unstable angina pectoris, renal hypertension, peripheral and cardial vascular disorders, arrhythmias, atrial and ventricular arrhythmias and impaired conduction such as, for example, atrioventricular blocks degrees I-III, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-ParkinsonWhite syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prevention of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation such as, for example, pulmonary edema, cerebral edema, renal edema or edema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischemic cardiomyopathy, dilatative cardiomyopathy, hypertrophic cardiomyopathy, idiopathic cardiomyopathy, diabetic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for treatment and/or prevention of sequelae of renal insufficiency, for example hypertension, pulmonary edema, heart failure, uremia, anemia, electrolyte disturbances (for example hyperkalemia, hyponatremia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention can also be used for treatment of disorders of the female reproductive system, such as uterine myoma, endometriosis, dysmenorrhea and premature contractions, and also periphally mediated inflammatory pain (for example in the case of symptomatic endometriosis). In addition, they are suitable for prophylaxis or treatment of hirsutism or hypertrichosis.

In addition, the compounds of the invention have antiinflammatory action and can therefore be used as antiinflammatory agents for the treatment and/or prevention of sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis, vulvovaginitis, rheumatoid disorders, osteoarthritis, inflammatory disorders of the central nervous system, multiple sclerosis, inflammatory skin disorders and inflammatory eye disorders.

The compounds of the invention are also suitable for treatment and/or prevention of fibrotic disorders of the internal organs, for example the lung, the heart, the kidney, the bone marrow and in particular the liver, and also dermatological fibroses and fibrotic eye disorders. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphea, keloids, hypertrophic scarring, nevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for aging or keratinized skin.

The compounds of the invention can also be used for treatment and/or prevention of anemias such as hemolytic anemias, in particular hemoglobinopathies such as sickle cell anemia and thalassamias, megaloblastic anemias, iron deficiency anemias, anemias owing to acute blood loss, displacement anemias and aplastic anemias.

Moreover, the compounds of the invention are suitable for treatment of cancers, for example skin cancer, brain tumors, breast cancer, bone marrow tumors, leukemias, liposarcomas, carcinomas of the gastrointestinal tract, of the liver, the pancreas, the lung, the kidney, the ureter, the prostate and the genital tract and also of malignant tumors of the lymphoproliferative system, for example Hodgkin's and non-Hodgkin's lymphoma.

In addition, the compounds according to the invention can be used for the treatment and/or prevention of arteriosclerosis, impaired lipid metabolism and dyslipidemias (hypolipoproteinemia, hypertriglyceridemias, hyperlipidemia, combined hyperlipidemias, hypercholesterolemia, abetalipoproteinemia, sitosterolemia), xanthomatosis, Tangier disease, adiposity, obesity, metabolic disorders (metabolic syndrome, hyperglycemia, insulin-dependent diabetes, non-insulin-dependent diabetes, gestation diabetes, hyperinsulinemia, insulin resistance, glucose intolerance and diabetic sequelae, such as retinopathy, nephropathy and neuropathy), of disorders of the gastrointestinal tract and the abdomen (glossitis, gingivitis, periodontitis, esophagitis, eosinophilic gastroenteritis, mastocytosis, Crohn's disease, colitis, proctitis, anus pruritis, diarrhea, celiac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, such as, for example, dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrheic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, such as, for example, HPV, HCMV, HIV, SARS), of disorders of the skeletal bone and the joints and also the skeletal muscle (multifarious forms of arthritis, such as, for example, arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, hemophilic arthritis, juvenile chronic arthritis, rheumatoid arthritis and metastatic arthritis, furthermore Still syndrome, Felty syndrome, Sjörgen syndrome, Clutton syndrome, Poncet syndrome, Pott syndrome and Reiter syndrome, multifarious forms of arthropathies, such as, for example, arthropathia deformans, arthropathia neuropathica, arthropathia ovaripriva, arthropathia psoriatica and arthropathia tabica, systemic scleroses, multifarious forms of inflammatory myopathies, such as, for example, myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Günther syndrome and the Münchmeyer syndrome), of inflammatory changes of the arteries (multifarious forms of arteritis, such as, for example, endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, such as, for example, cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

Owing to their profile of biochemical and pharmacological properties, the compounds of the invention are particularly suitable for treatment and/or prevention of interstitial lung diseases, especially idiopathic pulmonary fibrosis (IPF), and also of pulmonary hypertension (PH), bronchiolitis obliterans syndrome (BOS), inflammatory and fibrotic skin and eye disorders and fibrotic disorders of the internal organs.

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method of treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further active ingredients, especially for treatment and/or prevention of the aforementioned disorders. Preferred examples of combination active ingredients suitable for this purpose include:

- organic nitrates and NO donors, for example sodium nitroprusside, nitroglycerin, isosorbide mononitrate, isosorbide dinitrate, molsidomine or SIN-1, and inhaled NO;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;
- NO- and heme-independent activators of soluble guanylate cyclase (sGC), such as in particular the compounds described in WO 01/19355, WO 01/19776, WO 01/19778, WO 01/19780, WO 02/070462 and WO 02/070510;
- NO-independent but heme-dependent stimulators of soluble guanylate cyclase (sGC), such as in particular riociguat and the compounds described in WO 00/06568, WO 00/06569, WO 02/42301, WO 03/095451, WO 2011/147809, WO 2012/004258, WO 2012/028647 and WO 2012/059549;
- prostacyclin analogs and IP receptor agonists, by way of example and with preference iloprost, beraprost, treprostinil, epoprostenol or selexipag;
- endothelin receptor antagonists, by way of example and with preference bosentan, darusentan, ambrisentan or sitaxsentan;
- compounds which inhibit human neutrophile elastase (HNE), by way of example and with preference sivelestat or DX-890 (reltran);
- compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;
- compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);
- compounds which block the binding of serotonin to its receptors, by way of example and with preference antagonists of the 5-HT$_{2B}$ receptor such as PRX-08066;
- antagonists of growth factors, cytokines and chemokines, by way of example and with preference antagonists of TGF-β, CTGF, IL-1, IL-4, IL-5, IL-6, IL-8, IL-13 and integrins;
- Rho kinase-inhibiting compounds, by way of example and with preference fasudil, Y-27632, SLx-2119, BF-66851, BF-66852, BF-66853, KI-23095 or BA-1049;
- compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;
- compounds which influence the energy metabolism of the heart, by way of example and with preference etomoxir, dichloroacetate, ranolazine or trimetazidine;
- anti-obstructive agents as used, for example, for treatment of chronic obstructive pulmonary disease (COPD) or bronchial asthma, by way of example and with preference from the group of the inhalatively or systemically administered agonists of the β-adrenergic receptor (β-mimetics) and the inhalatively administered antimuscaringergic substances;
- antiinflammatory, immunomodulating, immunosuppressive and/or cytotoxic agents, by way of example and with preference from the group of the systemically or inhalatively administered corticosteroids and also acetylcysteine, montelukast, azathioprine, cyclophosphamide, hydroxycarbamide, azithromycin, pirfenidone or etanercept;
- antifibrotic agents, byway of example and with preference the multikinase inhibitor nintedanib, adenosine A2b receptor antagonists, sphingosine-1-phosphate receptor 3 (S1P3) antagonists, autotaxin inhibitors, lysophosphatidic acid receptor 1 (LPA-1) and lysophosphatidic acid receptor 2 (LPA-2) antagonists, lysyl oxidase (LOX) inhibitors, lysyl oxidase-like 2 inhibitors, CTGF inhibitors, IL-4 antagonists, IL-13 antagonists, $\alpha_v\beta_6$-integrin antagonists, TGF-β antagonists, inhibitors of the Wnt signaling pathway or CCR2 antagonists;
- antithrombotic agents, by way of example and with preference from the group of platelet aggregation inhibitors, the anticoagulants and the profibrinolytic substances;
- hypotensive active compounds, by way of example and with preference from the group of the calcium antagonists, angiotensin AII antagonists, ACE inhibitors, vasopeptidase inhibitors, endothelin antagonists, renin inhibitors, α-receptor blockers, β-receptor blockers, mineralocorticoid receptor antagonists and also the diuretics;
- lipid metabolism modifiers, by way of example and with preference from the group of the thyroid receptor agonists, cholesterol synthesis inhibitors, by way of example and with preference HMG-CoA reductase or squalene synthesis inhibitors, of the ACAT inhibitors, CETP inhibitors, MTP inhibitors, PPAR-α, PPAR-γ and/or PPAR-δ agonists, cholesterol absorption inhibitors, lipase inhibitors, polymeric bile acid adsorbents, bile acid reabsorption inhibitors and lipoprotein (a) antagonists; and/or
- chemotherapeutics like those employed, for example, for the therapy of neoplasms in the lung or other organs.

In a preferred embodiment of the invention, the compounds of the invention are administered in combination with a β-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscaringergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, beclomethasone, betamethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin. Hypotensive agents are preferably understood to mean compounds from the group of the calcium antagonists, angiotensin AII antagonists, ACE inhibitors, endothelin antagonists, renin inhibitors, α-receptor blockers, β-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an $α_1$-receptor blocker, by way of example and with preference prazosin.

In a preferred embodiment of the invention, the compounds of the invention are administered in combination with a β-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with an angiotensin AII antagonist, by way of example and with preference losartan, candesartan, valsartan, telmisartan or embursatan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-α, PPAR-γ and/or PPAR-δ agonists, cholesterol absorption inhibitors, polymeric bile acid adsorbers, bile acid reabsorption inhibitors, lipase inhibitors and the lipoprotein (a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS201038, R-103757 or JTT-130.

In a preferred embodiment of the invention, the compounds of the invention are administered in combination with a PPAR-γ agonist, by way of example and with preference pioglitazone or rosiglitazone.

In a preferred embodiment of the invention, the compounds of the invention are administered in combination with a PPAR-δ agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein (a) antagonist, by way of example and with preference gemcabene calcium (Cl-1027) or nicotinic acid.

Particular preference is given to combinations of the compounds of the invention with one or more further active ingredients selected from the group consisting of PDE 5 inhibitors, sGC activators, sGC stimulators, prostacyclin analogues, IP receptor agonists, endothelin antagonists, compounds that inhibit the signal transduction cascade and pirfenidone.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, vaginal, dermal, transdermal, conjunctival or otic route, or as an implant or stent.

The compounds according to the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous, intravitreal or intraperitoneal route). Administration forms suitable for parenteral administration include inter alia preparations for injection and infusion in the form of solutions, suspensions, emulsions, lyophilizates or sterile powders.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, eye drops, eye ointments, eyewashes, ocular inserts, ear drops, sprays, powders, washes or tampons, vaginal capsules, aqueous suspensions (lotions, shaking mixtures), lipophilic suspensions, emulsions, microemulsions, ointments, creams, transdermal therapeutic systems (for example patches), milk, pastes, foams, dusting powders, implants or stents.

Oral and parenteral administration are preferred, especially oral, intravenous and intrapulmonary (inhalative) administration.

The compounds according to the invention can be converted to the administration forms mentioned. This can be accomplished in a manner known per se by mixing with pharmaceutically suitable excipients. These excipients include fillers and carriers (for example cellulose, microcrystalline cellulose, for example Avicel®, lactose, mannitol, starch, calcium phosphates, for example Di-Cafos®), ointment bases (for example vaseline, paraffins, triglycerides, waxes, wool wax, wool wax alcohols, lanolin, hydrophilic ointment, polyethylene glycols), suppository bases (for example polyethylene glycols, cocoa butter, hard fat), solvents (e.g. water, ethanol, isopropanol, glycerol, propylene glycol, mid-chain triglycerides fatty oils, liquid polyethylene glycols, paraffins), surfactants, emulsifiers, dispersants or wetting agents (for example sodium dodecylsulfate, lecithin, phospholipids, fatty alcohols, for example Lanette®, sorbitan fatty acid esters, for example Span®, polyoxyethylene sorbitan fatty acid esters, for example Tween®, polyoxyethylene fatty acid glycerides, for example Cremophor®, polyoxyethylene fatty acid esters, polyoxyethylene fatty alcohol ethers, glycerol fatty acid esters, poloxamers, for example Pluronic®), buffer substances, and also acids and bases (for example phosphates, carbonates, citric acid, acetic acid, hydrochloric acid, sodium hydroxide, ammonium carbonate, trometamol, triethanolamine), isotonizing agents (for example glucose, sodium chloride), adsorbents (for example finely divided silicas), viscosity-increasing agents, gel formers, thickeners or binders (for example polyvinylpyrrolidone, methyl cellulose, hydroxypropyl methyl cellulose, hydroxypropyl cellulose, carboxymethyl cellulose-sodium, starch, carbomers, polyacrylic acids, for example Carbopol®, alginates, gelatins), disintegrants (for example modified starch, carboxymethyl cellulose-sodium, sodium starch glycolate, for example Explotab®, crosslinked polyvinylpyrrolidone, croscarmellose-sodium, for example AcDiSol®), flow regulators, lubricants, glidants and mold release agents (for example magnesium stearate, stearic acid, talc, finely divided silicas, for example Aerosil®), coating agents (for example sugar, shellac) and film formers for films or diffusion membranes with fast or modified dissolution (for example by polyvinylpyrrolidones, for example Kollidon®, polyvinyl alcohol, hydroxypropyl methyl cellulose, hydroxypropyl cellulose, ethyl cellulose, hydroxypropyl methyl cellulose phthalate, cellulose acetate, cellulose acetate phthalate, polyacrylates, polymethacrylates, for example Eudragit®), capsule materials (e.g. gelatins, hydroxypropyl methyl cellulose), synthetic polymers (for example polylactides, polyglycolides, polyacrylates, polymethacrylates, for example Eudragit®, polyvinylpyrrolidones, for example Kollidon®, polyvinyl alcohols, polyvinyl acetate, polyethylene oxides, polyethylene glycols and the copolymers and block copolymers thereof), plasticizers (for example polyethylene glycols, propylene glycol, glycerol, triacetin, triacetyl citrate, dibutyl phthalate), penetration enhancers, stabilizers (e.g. antioxidants, for example ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), dyes (e.g. inorganic pigments, for example iron oxides, titanium dioxide), aromas, sweeteners, flavor and/or odor correctors.

In general, it has been found to be advantageous in the case of parenteral administration to administer amounts of about 0.001 to 1 mg/kg, preferably about 0.01 to 0.5 mg/kg body weight to achieve effective results. In the case of oral administration the dosage is about 0.01 to 100 mg/kg, preferably about 0.01 to 20 mg/kg and most preferably 0.1 to 10 mg/kg body weight. In the case of intrapulmonary administration, the amount is generally about 0.1 to 50 mg per inhalation.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The present invention further provides pharmaceutical compositions comprising at least one compound according to the invention, typically together with one or more pharmaceutically suitable excipients, and the use thereof according to the present invention.

The working examples which follow illustrate the invention. The invention is not restricted to the examples.

A. EXAMPLES

Abbreviations and Acronyms $[\alpha]_D^{20}$ specific angle of rotation (in polarimetry)
br. broad (in NMR)
d doublet (in NMR)
dd doublet of doublets (in NMR)
DIPEA N,N-diisopropylethylamine
DMF N,N-dimethylformamide
DMSO dimethyl sulfoxide
ΔT heating, temperature increase (in reaction schemes)
ee enantiomeric excess
EI electron impact ionization (in MS)
ESI electrospray ionization (in MS)
Et ethyl
h hour(s)
HATU O-(7-azabenzotriazol-1-yl)-N,N,N',N'-tetramethyluronium hexafluorophosphate (CAS RN 148893-10-1)
HPLC high-pressure, high-performance liquid chromatography
IPr isopropyl
LC liquid chromatography
LC-MS liquid chromatography-coupled mass spectrometry
LDA lithium diisopropylamide
LiHMDS lithium bis(trimethylsilyl)amide
m multiplet (in NMR)
M molar
Me methyl
min minute(s)
MS mass spectrometry
NMR Nuclear magnetic resonance spectrometry
q quartet (in NMR)
qd quartet of doublets (in NMR)
RP reverse phase (in HPLC)
RT room temperature
$R_t$ retention time (in HPLC, LC/MS)
s singlet (in NMR)
SFC supercritical fluid chromatography
t triplet (in NMR)
td triplet of doublets (in NMR)
TFA trifluoroacetic acid
tert tertiary
THF tetrahydrofuran
TosMIC para-toluenesulfonylmethyl isocyanide
UPLC ultra-performance liquid chromatography
UV ultraviolet spectrometry Other abbreviations have their meanings as familiar to the person skilled in the art.

HPLC and LC-MS Methods:

Method 1 (LC-MS):

MS instrument type: Thermo Scientific FT-MS; instrument type UHPLC+: Thermo Scientific UltiMate 3000; column: Waters, HSST3, 2.1×75 mm, C18 1.8 µm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 2 (LC-MS):

Instrument: Waters ACQUITY SQD UPLC System; column: Waters Acquity UPLC HSS T3 1.8 µm 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 3 (LC-MS):

Instrument: Waters ACQUITY SQD UPLC System; column: Waters Acquity UPLC HSS T3 1.8 µm 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 4 (LC-MS):

Instrument: Waters Single Quad MS System; instrument Waters UPLC Acquity; column: Waters BEH C18 1.7 µm 50×2.1 mm; mobile phase A: 1 l of water+1.0 ml of (25% strength ammonia)/l, mobile phase B: 1 l of acetonitrile; gradient: 0.0 min 92% A→0.1 min 92% A→1.8 min 5%

A→3.5 min 5% A; oven: 50° C.; flow rate: 0.45 ml/min; UV detection: 210 nm (208-400 nm)

Method 5 (LC-MS):
Instrument: Waters Acquity UPLCMS SingleQuad; column: Acquity UPLC BEH C18 1.7 µm, 50×2.1 mm; mobile phase A: water+0.1% by volume formic acid (99%), mobile phase B: acetonitrile; gradient: 0.0 min 1% B→1.6 min 99% B→2.0 min 99% B; flow rate 0.8 ml/min; temperature: 60° C.; DAD scan: 210-400 nm.

Method 6 (LC-MS):
Instrument: Waters Acquity UPLCMS SingleQuad; column: Acquity UPLC BEH C18 1.7 µm, 50×2.1 mm; mobile phase A: water+0.2% by volume aqueous ammonia (32%), mobile phase B: acetonitrile; gradient: 0.0 min 1% B→1.6 min 99% B→2.0 min 99% B; flow rate 0.8 ml/min; temperature: 60° C.; DAD scan: 210-400 nm.

Method 7 (LC-MS):
Instrument: Agilent MS Quad 6150; HPLC: Agilent 1290; column: Waters Acquity UPLC HSS T3 1.8 µm 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 8 (LC-MS):
MS instrument type: ThermoFisherScientific LTQ-Orbitrap-XL; HPLC instrument type: Agilent 1200SL; column: Agilent, POROSHELL 120, 3×150 mm, SB—C18 2.7 µm; mobile phase A: 1 l of water+0.1% trifluoroacetic acid; mobile phase B: 1 l of acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV detection: 210 nm Method 9 (LC-MS):
Detection: MSD ESI pos/neg; column: Waters XSelect CSH C18, 30×2.1 mm, 3.5 µm; mobile phase A: 0.1% formic acid in acetonitrile; eluent B: 0.1% formic acid in water; gradient: 0.0 min 5% A→1.6 min 98% A→3.0 min 98% A; oven: 35° C.; flow rate: 1.0 ml/min; UV detection: 220-320 nm Method 10 (LC-MS):
Detection: MSD ES pos; column: Waters XSelect CSH C18, 30×2.1 mm, 3.5 µm; mobile phase A: 95% acetonitrile+5% 10 mM ammonium bicarbonate in water; mobile phase B: 10 mM ammonium bicarbonate in water; gradient: 0.0 min 5% A→1.6 min 98% A→3.0 min 98% A; oven: 25° C.; flow rate: 1.0 ml/min; UV detection: 220 nm Method 11 (LC-MS):
Detection: MSD ESI pos/neg; column: Waters XSelect CSH C18, 50×2.1 mm, 3.5 µm; mobile phase A: 0.1% formic acid in acetonitrile; eluent B: 0.1% formic acid in water; gradient: 0.0 min 5% A→3.5 min 98% A→6.0 min 98% A; oven: 35° C.; flow rate: 0.8 ml/min; UV detection: 270 nm Method 12 (GC-MS):
Instrument: Thermo Scientific DSQII, Thermo Scientific Trace GC Ultra; column: Restek RTX35MS, 15 m×200 µm×0.33 µm; constant helium flow rate: 1.20 ml/min; oven: 60° C.; inlet: 220° C.; gradient: 60° C., 30° C./min→300° C. (maintain for 3.33 min).

Method 13 (GC-MS):
Instrument: Agilent 6890N; detection: MSD EI pos; column: RXi-5MS 20 µm, ID 180 µm; df 0.18 am; detection temperature: 280° C.; mass range 50-550; carrier gas: helium; average flow rate: 50 cm/s; initial temperature: 100° C., initial time: 1.5 min; solvent delay: 1.0 min; final temperature: 250° C., final time: 250° C.; injection volume 1 µl; slit ratio 100:1.

Method 14 (Preparative HPLC):
Column: Chromatorex C18 10 µm, 250×40 mm; mobile phase A: water, mobile phase B: acetonitrile; injection at 3 min; gradient: 0.0 min 30% B→6.0 min 30% B→27 min 95% B→38 min 95% B→39 min 30% B→40.2 min 30% B; flow rate: 50 ml/min. UV detection: 210 nm Method 15 (Preparative HPLC):
Column: Chromatorex C18 10 µm, 125×30 mm; mobile phase A: water+0.1% TFA, mobile phase B: acetonitrile; injection at 3 min; gradient: 0.0 min 30% B→5.5 min 30% B→17.65 min 95% B→19.48 min 95% B→19.66 min 30% B→20.51 min 30% B; flow rate: 75 ml/min. UV detection: 210 nm Method 16 (Preparative HPLC):
Column: Chromatorex C18 10 µm, 250×40 mm; mobile phase A: water+0.1% TFA, mobile phase B: acetonitrile; injection at 3 min; gradient: 0.0 min 30% B→6.0 min 30% B→27 min 95% B→38 min 95% B→39 min 30% B→40.2 min 30% B; flow rate: 50 ml/min. UV detection: 210 nm Method 17 (Preparative HPLC):
Column: Chromatorex C18 10 µm, 125×30 mm; mobile phase A: water, mobile phase B: acetonitrile; injection at 3 min; gradient: 0.0 min 30% B→5.5 min 30% B→17.65 min 95% B→19.48 min 95% B→19.66 min 30% B→20.51 min 30% B; flow rate: 75 ml/min. UV detection: 210 nm Method 18 (Preparative HPLC):
Column: Chromatorex C18 10 µm, 125×30 mm; mobile phase A: water, mobile phase B: acetonitrile; injection at 3 min; gradient: 0.0 min 10% B→5.5 min 10% B→17.65 min 95% B→19.48 min 95% B→19.66 min 10% B→20.51 min 10% B; flow rate: 75 ml/min. UV detection: 210 nm Method 19 (Preparative HPLC):
Column: Chromatorex C18 10 µm, 250×40 mm; mobile phase A: water, mobile phase B: acetonitrile; injection at 3 min; gradient: 0.0 min 10% B→6.0 min 10% B→27 min 95% B→38 min 95% B→39 min 10% B→40.2 min 10% B; flow rate: 50 ml/min. UV detection: 210 nm Method 20 (Preparative HPLC):
Column: Chromatorex C18 10 µm, 250×40 mm; mobile phase A: water+0.1% TFA, mobile phase B: acetonitrile; injection at 3 min; gradient: 0.0 min 10% B→6.0 min 10% B→27 min 95% B→38 min 95% B→39 min 10% B→40.2 min 10% B; flow rate: 50 ml/min. UV detection: 210 nm Method 21 (Preparative HPLC):
Column: Reprosil C18 10 µm, 250×40 mm; mobile phase A: water+0.1% TFA, mobile phase B: acetonitrile; injection at 3 min; gradient: 0.0 min 10% B→6.0 min 10% B→27 min 95% B→38 min 95% B→39 min 10% B→40.2 min 10% B; flow rate: 50 ml/min. UV detection: 210 nm.

Method 22 (Preparative HPLC):
Column: Reprosil C18 10 µm, 125×30 mm; mobile phase A: water+0.1% TFA, mobile phase B: acetonitrile; injection at 3 min; gradient: 0.0 min 10% B→5.5 min 10% B→17.65 min 95% B→19.48 min 95% B→19.66 min 10% B→20.51 min 10% B; flow rate: 75 ml/min. UV detection: 210 nm.

Method 23 (Preparative HPLC):
Chromatorex C18 10 µm, 125×30 mm; mobile phase A: water+0.1% TFA, mobile phase B: acetonitrile; injection at 3 min; gradient: 0.0 min 10% B→5.5 min 10% B→17.65 min 95% B 19.48 min 95% B→19.66 min 10% B→20.51 min 10% B; flow rate: 75 ml/min. UV detection: 210 nm Method 24 (Preparative HPLC):
Column: Reprosil C18 10 µm, 125×30 mm; mobile phase A: water+0.1% TFA, mobile phase B: acetonitrile; injection at 3 min; gradient: 0.0 min 30% B→5.5 min 30% B→17.65 min 95% B→19.48 min 95% B→19.66 min 30% B→20.51 min 30% B; flow rate: 75 ml/min. UV detection: 210 nm Method 25 (Preparative HPLC):

Instrument: Waters Acquity SQD UPLC System; column: Waters Acquity UPLC HSS T3 1.8μ, 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 26 (Preparative HPLC):

Instrument: Waters Prep LC/MS System, column: Phenomenex Kinetex C18, 5 μm 100×30 mm; At-column injection (complete injection); mobile phase A: water, mobile phase B: acetonitrile, mobile phase C: 2% formic acid in water; flow rate for mobile phase (A+B): 65 ml/min, flow rate for mobile phase C: constant 5 ml/min; gradient (A/B): 0.0 min 30% B→2 min 30% B→2.2 min 50% B→7 min 90% B→7.5 min 92% B→9 min 92% B→30% B; UV detection: 210 nm.

Method 27 (Preparative HPLC):

Column: Chromatorex, C18 10 μm, 125 mm×30 mm; mobile phase A: water, mobile phase B: acetonitrile; injection at 3 min; gradient: 0.0 min 10% B→6 min 10% B→27 min 95% B→38 min 95% B→39 min 10% B→40 min 10% B; flow rate: 75 ml/min, UV detection: 210 nm.

Method 28 (Preparative HPLC):

Column: Reprosil C18 10 μm, 250 mm×40 mm; mobile phase A: water+0.1% formic acid, mobile phase B: acetonitrile+0.1% formic acid; gradient: 0.0 min 10% B→6 min 10% B→27 min 95% B→38 min 95% B→39 min 10% B→40 min 10% B; flow rate: 75 ml/min, UV detection: 210 nm.

Method 29 (Preparative HPLC):

Column: Chromatorex C18, 10 μm, 250 mm×40 mm; mobile phase A: water+0.1% formic acid, mobile phase B: methanol+formic acid; gradient: 0.0 min 20% B→6.2 min 20% B→6.5 min 40% B→15.5 min 60% B→16 min 100% B→23 min 100% B→23.6 min 20% B→25.8 min 20% B; flow rate: 75 ml/min, UV detection: 210 nm.

Method 30 (Preparative HPLC):

Column: Chromatorex C18, 10 μm, 125 mm×30 mm; mobile phase A: water+0.1% formic acid, mobile phase B: acetonitrile+0.1% formic acid; injection at 3 min; gradient: 0.0 min 10% B→6.0 min 10% B→27 min 95% B→38 min 95% B→39 min 10% B→40 min 10% B; flow rate: 75 ml/min, UV detection: 210 nm.

Method 31 (Preparative HPLC):

Column: Chromatorex C18 10 μm, 250 mm×40 mm; mobile phase A: water+0.1% formic acid, mobile phase B: acetonitrile+0.1% formic acid; gradient: 0.0 min 10% B→6.0 min 10% B→27 min 95% B→38 min 95% B→39 min 10% B→40 min 10% B; flow rate: 75 ml/min, UV detection: 210 nm.

Method 32 (Preparative HPLC):

Column: Reprosil C18 10 μm, 250 mm×40 mm; mobile phase A: water+0.1% formic acid, mobile phase B: methanol+formic acid; gradient: 0.0 min 5% B→5.0 min 5% B→5.5 min 20% B→10.4 min 40% B→10.9 min 100% B→18.9 min 100% B→19.2 min 5% B→22.4 min 5% B; flow rate: 75 ml/min, UV detection: 210 nm.

Further Details:

The percentages in the example and test descriptions which follow are, unless indicated otherwise, percentages by weight; parts are parts by weight. Solvent ratios, dilution ratios and concentration data for liquid/liquid solutions are based in each case on volume.

In the case of purifications of compounds of the invention by preparative HPLC by the described methods in which the mobile phases contain additives, for example trifluoroacetic acid, formic acid or ammonia, the compounds of the invention can be obtained in salt form, for example as trifluoroacetate, formate or ammonium salt, if the compounds of the invention contain a sufficiently basic or acidic functionality. Such a salt can be converted to the corresponding free base or acid by various methods known to the person skilled in the art.

Purity figures are generally based on corresponding peak integrations in the LC/MS chromatogram, but may additionally also have been determined with the aid of the $^1$H NMR spectrum. Compounds may still contain residues of solvent which have not normally been taken into account in the reporting of the purity. If no purity is indicated, either the purity is 100% according to automated peak integration in the LC/MS chromatogram or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of $^1$H NMR signals which follow have in some cases been taken directly from the suggestions of the ACD SpecManager (ACD/Labs Release 12.00, Product version 12.5) or ACD/Spectrus Processor 2014 (File Version S20S41, Build 72444, 21 Aug. 2014) or ACD/Spektrus Processor 2015 Pack 2 (File Version S40S41, Build 79720, 30 Jul. 2015) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the center of the signal in question. In the case of broad multiplets, an interval is given. Signals obscured or partly obscured by solvent or water were either tentatively assigned or have not been listed. Significantly broadened signals—caused, for example, by rapid rotation of molecular moieties or because of exchanging protons—were likewise assigned tentatively (often referred to as a broad multiplet or broad singlet) or are not listed.

The $^1$H NMR data of selected examples are in some cases stated in the form of $^1$H NMR peak lists. For each signal peak, first the δ value in ppm and then the signal intensity in round brackets are listed. The δ value/signal intensity number pairs for different signal peaks are listed with separation from one another by commas. The peak list for an example therefore takes the following form: $δ_1$ (intensity$_1$), $δ_2$ (intensity$_2$), . . . , $δ_i$ (intensity$_i$), . . . , $δ_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H NMR printouts and thus usually contain all peaks listed in a conventional NMR interpretation. In addition, like conventional $^1$H NMR printouts, they may show solvent signals, signals of stereoisomers of the target compounds which are likewise provided by the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "by-product fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional $^1$H NMR interpretation.

A detailed description of the presentation of NMR data in the form of peak lists can be found in the publication "Citation of NMR Peaklist Data within Patent Applications" (cf. Research Disclosure Database Number 605005, 2014, Aug. 1, 2014 or http://www.researchdisclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analyzed, it may be advisable to set the parameters "MinimumHeight" to values of <1%.

Melting points and melting ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Materials and Intermediates

Example 1A

6-Bromo-3-methyl-2-phenylquinoline-4-carbonyl chloride

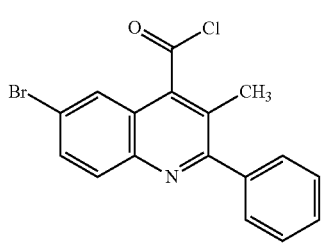 [SMILES: Cc1c(-c2ccccc2)nc2ccc(Br)cc2c1C(=O)Cl]

A few drops of DMF were added to a suspension of 6-bromo-3-methyl-2-phenylquinoline-4-carboxylic acid (10.0 g, 29.2 mmol, preparable according to WO 2016 146602 A1, p. 51, Example 3A) in dichloromethane (100 ml). Oxalyl chloride (5.1 ml, 58 mmol) was then slowly added dropwise. Stirring was continued until the evolution of gas had ceased and the mixture was then concentrated and dried under reduced pressure. The residue obtained was used directly (without further work-up) for subsequent reactions.

Example 2A (6-Chloro-2,3-difluorophenyl)methanol

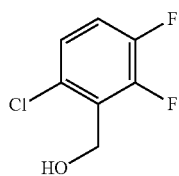 [SMILES: OCc1c(Cl)ccc(F)c1F]

To a solution of 6-chloro-2,3-difluorobenzaldehyde (5.00 g, 28.3 mmol) in THF (20 ml) was added in portions, at RT, sodium borohydride (1.39 g, 36.8 mmol) (evolution of gas). Subsequently, a further 20 ml of THF were added, and the mixture was stirred at RT for 45 min. Thereafter, dichloromethane (100 ml), water (100 ml) and saturated ammonium chloride solution (50 ml) were added to the mixture, which was agitated. The aqueous phase was acidified inbetween with concentrated acetic acid. After phase separation, the organic phase was washed once with saturated aqueous sodium chloride solution, dried over sodium sulfate, filtered and concentrated, and the residue was dried briefly under reduced pressure. This gave 5.35 g (100% purity, ">106% of theory", not entirely dry) of the title compound.

GC-MS (Method 12): $R_t$=3.23 min, MS (EIpos): m/z=178 [M]$^+$ $^1$H-NMR (400 MHz, DMSO-d6) δ [ppm]: 7.45 (dd, 1H), 7.36 (ddd, 1H), 5.36 (t, 1H), 4.59 (dd, 3H).

Example 3A

[2-(Difluoromethoxy)-6-fluorophenyl]methanol

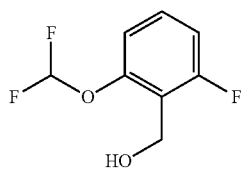

With ice cooling, sodium borohydride (995 mg, 26.3 mmol) was added to a solution of 2-(difluoromethoxy)-6-fluorobenzaldehyde (10.0 g, 52.6 mmol) in ethanol (100 ml), with the internal temperature increasing to about 20° C. Subsequently, the mixture was stirred without cooling for a further 2 h. Thereafter, dichloromethane (100 ml), water (150 ml) and saturated ammonium chloride solution (50 ml) were added to the mixture, which was agitated. The mixture was acidified with concentrated acetic acid (about 1 ml). After phase separation, the aqueous phase was extracted once with dichloromethane (100 ml), and the combined organic phases were washed once with saturated aqueous sodium chloride solution, dried over sodium sulfate, filtered and concentrated, and the residue was briefly dried under reduced pressure. This gave 9.90 g (99% purity, 97% of theory) of the title compound.

GC-MS (Method 12): $R_t$=3.04 min, MS (EIpos): m/z=192 [M]$^+$ $^1$H-NMR (400 MHz, DMSO-d6) δ [ppm]: −0.008 (0.53), 0.008 (0.55), 0.918 (0.70), 1.909 (1.97), 4.488 (14.37), 4.492 (15.14), 4.501 (15.42), 4.505 (15.39), 5.105 (7.08), 5.119 (14.11), 5.133 (6.48), 7.017 (8.05), 7.035 (6.81), 7.056 (7.70), 7.099 (4.02), 7.121 (8.26), 7.142 (4.75), 7.202 (16.00), 7.386 (11.15), 7.403 (4.54), 7.407 (7.33), 7.423 (7.21), 7.428 (3.89), 7.444 (3.19).

$^1$H-NMR (400 MHz, DMSO-d6) δ [ppm]: 7.50-6.97 (m, 4H), 5.12 (t, 1H), 4.50 (dd, 2H).

Example 4A 2-(Bromomethyl)-1-chloro-3,4-difluorobenzene

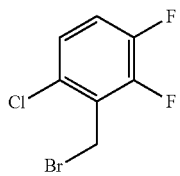 [SMILES: Fc1ccc(Cl)c(CBr)c1F]

To a solution of (6-chloro-2,3-difluorophenyl)methanol (5.34 g, 29.9 mmol, Example 2A) in dichloromethane (30 ml) were added dropwise while stirring, at −15° C., phosphorus tribromide (1.6 ml, 16 mmol). Subsequently, the cooling bath was removed and the mixture was stirred at RT for a further 2 h. Thereafter, saturated sodium bicarbonate solution, water and dichloromethane (50 ml each) were added gradually to the mixture, which was agitated. After phase separation, the organic phase was washed with saturated aqueous sodium chloride solution (100 ml), dried over sodium sulfate, filtered and concentrated, and the residue was dried briefly under reduced pressure. This gave 3.88 g (94% purity by GC-MS, 51% of theory) of the title compound.

GC-MS (Method 12): $R_t$=3.57 min, MS (EIpos): m/z=240 [M]$^+$ $^1$H-NMR (400 MHz, DMSO-d6) δ [ppm]: 7.55 (dd, 1H), 7.45 (ddd, 1H), 4.71 (d, 3H).

Example 5A (+/−)-2-(3-Chloropyridin-2-yl)propanenitrile (Racemate)

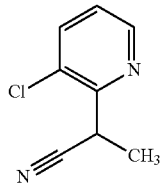

Under argon and at RT, a 1 M solution of LiHMDS in THF/ethylbenzene (100 ml, 100 mmol) was added dropwise to a solution of 2,3-dichloropyridine (4.00 g, 27.0 mmol) and propionitrile (2.68 g, 48.7 mmol) in THF (50 ml), and the mixture was stirred at RT for 20 h. Water was then added, and the mixture was extracted with ethyl acetate. The organic phase was dried over sodium sulfate, filtered and concentrated, and the residue was initially prepurified by flash column chromatography (100 g silica gel Biotage Snap-Cartridge KP-Sil, dichloromethane/methanol 95:5, Isolera One) and then repurified by preparative HPLC (Method 15). This gave 2.23 g (80% purity, 40% of theory) of the title compound.

LC-MS (Method 1): $R_t$=1.29 min; MS (ESIpos): m/z=167 [M+H]$^+$

From an experiment carried out analogously, the following H-NMR of the title compound was obtained:

$^1$H-NMR (400 MHz, DMSO-d6): δ [ppm]=8.59 (dd, 1H), 8.03 (dd, 1H), 7.48 (dd, 1H), 4.73 (q, 1H), 1.59 (d, 3H).

Example 6A (+/−)-2-(5-Fluoro-2-methoxyphenyl)propanenitrile (Racemate)

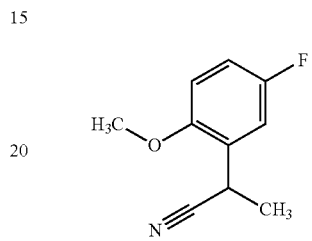

At −78° C., a 1.6 M butyllithium solution in hexane (15 ml, 23 mmol) was added dropwise to a solution of diisopropylamine (3.3 ml, 23 mmol) in THF (110 ml), and the mixture was stirred at −78° C. for 45 min. A solution of (5-fluoro-2-methoxyphenyl)acetonitrile (3.50 g, 21.2 mmol, CAS-RN 501008-41-9, commercially available) in THF (110 ml) was then added dropwise at −78° C., and the mixture was stirred at −78° C. for a further hour. A solution of iodomethane (1.4 ml, 22 mmol) in THF (15 ml) was then added slowly, and the mixture was stirred at −78° C. for a further 10 min. Subsequently, the cooling bath was removed and the mixture was stirred at RT for 1.5 h. Saturated ammonium chloride solution was added and the mixture was agitated. After addition of ethyl acetate, the phases were separated and the aqueous phase was extracted twice with ethyl acetate. The combined organic phases were washed with saturated aqueous sodium chloride solution, dried over sodium sulfate, filtered and concentrated, and the residue was purified by flash column chromatography (120 g silica gel Reveleris, flow rate 80 ml/min, heptane/ethyl acetate gradient 1:0→6:4, run time 38 min). This gave 2.40 g (97% purity, 61% of theory) of the title compound.

GC-MS (Method 13): $R_t$=2.99 min; MS (ESIpos): m/z=179 [M]$^+$ $^1$H-NMR (400 MHz, CDCl$_3$): δ [ppm]=7.20-7.10 (m, 1H), 7.05-6.96 (m, 1H), 6.85-6.81 (m, 1H), 2.22 (q, 1H), 3.84 (s, 3H), 1.57 (d, 3H).

Example 7A (+/−)-2-(3,5-Difluoro-2-methoxyphenyl)propanenitrile (Racemate)

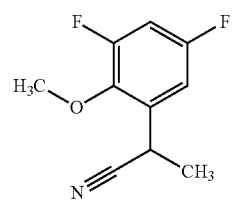

At −78° C., a 1.6 M butyllithium solution in hexane (8.2 ml, 13 mmol) was added dropwise to a solution of diisopropylamine (1.9 ml, 14 mmol) in THF (25 ml), and the mixture was stirred at −78° C. for 30 min. A solution of (3,5-difluoro-2-methoxyphenyl)acetonitrile (2.00 g, 10.9 mmol, CAS-RN 886761-64-4, commercially available) in THF (5.5 ml) was then added dropwise at −78° C., and the mixture was stirred at −78° C. for a further 30 min. A solution of iodomethane (710 µl, 11 mmol) in THF (25 ml) was then added slowly, and the mixture was stirred at −78° C. for a further 30 min. Saturated ammonium chloride solution was then added and the mixture was agitated. The cooling bath was removed and the mixture was allowed to warm to RT. By addition of 1 M hydrochloric acid, the aqueous phase was adjusted to about pH 3. After addition of saturated sodium chloride solution, the mixture was extracted three times with ethyl acetate, and the combined organic phases were dried over sodium sulfate, filtered and concentrated. The residue was purified by flash column chromatography (40 g of silica gel, mobile phase dichloromethane). The combined target fractions were concentrated and the residue was dried under reduced pressure. This gave 1.99 g (88% purity, 81% of theory) of the title compound.

GC-MS (Method 13): $R_t$=2.97 min; MS (ESIpos): m/z=179 [M]$^+$

Example 8A (+/−)-2-(4-Fluoro-2-methoxyphenyl)propanenitrile (Racemate)

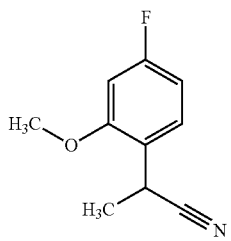

Under nitrogen, TosMIC (6.39 g, 32.7 mmol) was added to a solution of 1-(4-fluoro-2-methoxyphenyl)ethanone (5.00 g, 29.7 mmol, CAS-RN 51788-80-8, commercially available) in 1,2-dimethoxyethane (30 ml), and the mixture was cooled to −10° C. A solution of potassium tert-butoxide (6.67 g, 59.5 mmol) in tert-butanol (75 ml) was added slowly, keeping the temperature below 5° C. After 2 h of stirring at 0° C. and 1 h at RT, the resulting suspension was concentrated until a sludge had been obtained, and water (60 ml) was added. After three extractions with diethyl ether (50 ml each), the combined organic phases were dried over sodium sulfate, filtered and concentrated. The residue was purified by flash column chromatography (120 g of silica gel, mobile phase dichloromethane, flow rate 40 ml/min). The combined target fractions were concentrated and the residue was dried under reduced pressure. This gave 3.77 g (99% purity, 70% of theory) of the title compound.

GC-MS (Method 13): $R_t$=2.97 min; MS (ESIpos): m/z=179 [M]$^+$

Example 9A (+/−)-2-(2-Fluoro-6-methoxyphenyl)propanenitrile (Racemate)

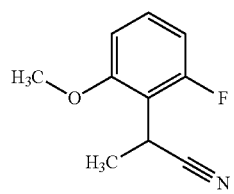

Under argon and at −78° C., a mixture of 2.5 M butyllithium solution in hexane (13 ml, 33 mmol) and THF (50 ml) was added slowly to a solution of N,N-diisopropylethylamine (5.8 ml, 33 mmol) in THF (75 ml). The reaction mixture was allowed to warm to 0° C., stirred at 0° C. for 5 min and cooled back down again to −78° C. A solution of (2-fluoro-6-methoxyphenyl)acetonitrile (5.00 g, 30.3 mmol, CAS-RN 500912-18-5, commercially available) in THF (25 ml) was then added slowly. The reaction mixture was once more allowed to warm to 0° C., stirred at 0° C. for 5 min and cooled back down again to −78° C. A solution of iodomethane (2.0 ml, 31.79 mmol) in THF (25 ml) was then added slowly. The mixture was stirred overnight, with the temperature gradually rising to RT. At 0° C., saturated ammonium chloride solution and water (50 ml each) were then added and the mixture was shaken and extracted twice with ethyl acetate (150 ml each). The combined organic phases were washed once with saturated aqueous sodium chloride solution (200 ml), dried over sodium sulfate, filtered and concentrated, and the residue was taken up in dichloromethane and purified by flash column chromatography (400 g of silica gel Buchi Snap-Cartridge KP-Sil, cyclohexane/ethyl acetate 9:1). The combined target fractions were concentrated, and the residue was (briefly) dried under reduced pressure. This gave 3.33 g (100% purity, 61% of theory) of the title compound.

GC-MS (Method 12): $R_t$=4.31 min; MS (ESIpos): m/z=179 [M]$^+$ $^1$H-NMR (400 MHz, DMSO-d6) δ [ppm]: 1.492 (15.85), 1.509 (16.00), 3.314 (9.13), 3.887 (0.90), 4.452 (0.69), 4.455 (0.70), 4.470 (2.12), 4.473 (2.10), 4.488 (2.11), 4.491 (2.05), 4.505 (0.69), 4.508 (0.65), 6.861 (1.62), 6.863 (1.60), 6.884 (2.45), 6.907 (1.81), 6.909 (1.81), 6.943 (3.36), 6.964 (3.72), 7.353 (1.56), 7.370 (1.87), 7.374 (2.99), 7.391 (3.02), 7.395 (1.60), 7.412 (1.36).

$^1$H-NMR (400 MHz, DMSO-d6): δ [ppm]=7.44-7.30 (m, 1H), 6.95 (d, 1H), 6.92-6.85 (m, 1H), 4.48 (qd, 1H), 3.88 (s, 3H), 1.50 (d, 3H).

Example 10A (+/−)-2-(2-Chloro-5-fluorophenyl)propanenitrile (Racemate)

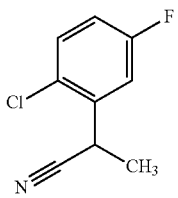

Under argon and at −78° C., a mixture of 2.5 M butyllithium solution in hexane (6.5 ml, 16 mmol), diluted with THF (20 ml), was slowly added dropwise to a solution of N,N-diisopropylethylamine (2.8 ml, 16 mmol) in THF (40 ml). With stirring, the mixture was then allowed to warm to 0° C. and, after 5 min, cooled back down again to −78° C. Subsequently, a solution of (2-chloro-5-fluorophenyl)acetonitrile (2.50 g, 14.7 mmol, CAS-RN 395675-23-7, commercially available) in THF (20 ml) was slowly added dropwise. With stirring, the mixture was then allowed to warm to 0° C. and, after 5 min, cooled back down again to −78° C. Subsequently, a solution of iodomethane (960 μl, 15 mmol) in THF (20 ml) was slowly added dropwise. Stirring of the mixture was continued overnight, in the course of which the cooling bath (dry ice/isopropanol) was allowed to come gradually to RT. Subsequently, saturated ammonium chloride solution and water (50 ml of each) were slowly added at 0° C., and the mixture was agitated. After phase separation, the aqueous phase was extracted twice with ethyl acetate (150 ml each time). The combined organic phases were washed once with saturated aqueous sodium chloride solution (200 ml), dried over sodium sulfate, filtered and concentrated, and the residue was taken up in dichloromethane and purified by flash column chromatography (100 g silica gel Biotage Snap-Cartridge KP-Sil, cyclohexane/ethyl acetate gradient 93:7→7:3, Isolera One). The combined target fractions were concentrated and the residue was dried under reduced pressure. This gave 2.54 g (97% purity, 91% of theory) of the title compound.

LC-MS (Method 1): $R_t$=1.78 min; MS (ESIpos): m/z=184 [M+H]$^+$ $^1$H-NMR (400 MHz, DMSO-d6) δ [ppm]: 7.60 (dd, 1H), 7.48 (dd, 1H), 7.31 (td, 1H), 4.52 (q, 1H), 1.59 (d, 3H).

Example 11A (2-Chloro-3,6-difluorophenyl)acetonitrile

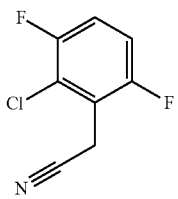 [SMILES: N#CCc1c(F)ccc(F)c1Cl]

To a solution of 2-(bromomethyl)-3-chloro-1,4-difluorobenzene (4.80 g, 19.9 mmol, CAS-RN 90292-67-4, commercially available) in dichloromethane (40 ml) were added, while stirring, water (40 ml) and tetrabutylammonium bromide (641 mg, 1.99 mmol). Subsequently, a solution of potassium cyanide (3.88 g, 59.6 mmol) in water (40 ml) was added, and the mixture was stirred at RT for 2.5 h. Subsequently, the phases were separated, and the organic phase was washed three times with saturated sodium bicarbonate solution, dried over sodium sulfate, filtered and concentrated, and the residue was dried briefly under reduced pressure. This gave 3.80 g (94% purity, 96% of theory) of the title compound.

LC-MS (Method 1): $R_t$=1.59 min; MS (ESIneg): m/z=186 [M−H]$^-$ $^1$H-NMR (400 MHz, DMSO-d6) δ [ppm]: 7.57 (td, 1H), 7.44 (td, 1H), 4.15 (d, 2H).

Example 12A (2-Chloro-3-fluorophenyl)acetonitrile

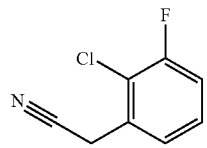 [SMILES: N#CCc1cccc(F)c1Cl]

To a solution of 1-(bromomethyl)-2-chloro-3-fluorobenzene (6.96 g, 31.1 mmol) in dichloromethane (60 ml) were added, while stirring, water (60 ml) and tetrabutylammonium bromide (1.00 g, 3.11 mmol). Subsequently, a solution of potassium cyanide (6.08 g, 93.4 mmol) in water (60 ml) was added, and the mixture was stirred at RT for 2.5 h. Subsequently, the phases were separated, and the organic phase was washed three times with saturated sodium bicarbonate solution, dried over sodium sulfate, filtered and concentrated, and the residue was dried briefly under reduced pressure. This gave 4.98 g (100% purity, 94% of theory) of the title compound.

GC-MS (Method 12): $R_t$=4.03 min, MS (EIpos): m/z=169 [M]$^+$ $^1$H-NMR (400 MHz, DMSO-d6) δ [ppm]: 4.175 (16.00), 7.400 (0.90), 7.408 (1.10), 7.414 (1.15), 7.417 (1.13), 7.424 (2.60), 7.440 (2.84), 7.443 (2.99), 7.459 (5.37), 7.468 (1.52), 7.474 (1.39).

$^1$H-NMR (400 MHz, DMSO-d6) δ [ppm]: 7.50-7.37 (m, 3H), 4.18 (s, 2H).

Example 13A (6-Chloro-2,3-difluorophenyl)acetonitrile

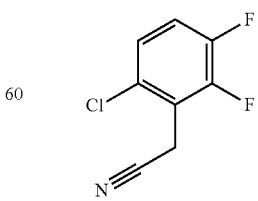

To a solution of 2-(bromomethyl)-1-chloro-3,4-difluorobenzene (3.87 g, 16.0 mmol, Example 4A) in acetonitrile (48 ml) were added, while stirring, trimethylsilyl cyanide (2.5 ml, 18 mmol) and a 1 M solution of tetrabutylammonium fluoride in THF (19 ml, 19 mmol), and the mixture was stirred at 80° C. for 30 min. After cooling to RT, the solvent was removed on a rotary evaporator. The residue was taken up in ethyl acetate (80 ml), and the solution was washed with water and saturated sodium chloride solution (80 ml each time), dried over sodium sulfate, filtered and concentrated. The residue was taken up in dichloromethane and purified by flash column chromatography (100 g silica gel Biotage Snap-Cartridge KP-Sil, cyclohexane/ethyl acetate gradient 93:7→7:3, Isolera One). The combined target fractions were concentrated and the residue was dried under reduced pressure. This gave 2.24 g (71% purity by GC-MS, 96% of theory) of the title compound.

GC-MS (Method 12): $R_t$=3.92 min, MS (EIpos): m/z=187 [M]$^+$

LC-MS (Method 1): $R_t$=1.57 min; MS (ESIneg): m/z=186 [M-H]$^-$ $^1$H-NMR (400 MHz, DMSO-d6) δ [ppm]: 7.58 (dd, 1H), 7.49 (ddd, 1H), 4.16 (d, 2H).

Example 14A (2,3,5,6-Tetrafluorophenyl)acetonitrile

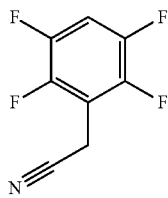 [SMILES: N#CCc1c(F)c(F)cc(F)c1F]

Potassium cyanide (1.34 g, 20.6 mmol) was initially charged in acetonitrile (64 ml) and water (13 ml) at RT. 3-(Bromomethyl)-1,2,4,5-tetrafluorobenzene (5.00 g, 20.6 mmol) was added and the mixture was subsequently stirred at 40° C. for 5 h and then further at RT overnight. For work-up, the reaction mixture was diluted with 150 ml of water, adjusted to pH 13 with about 10 ml of 1 M aqueous sodium hydroxide solution and extracted twice with tert-butyl methyl ether. The combined organic phases were washed twice with saturated aqueous sodium chloride solution, dried over sodium sulfate and concentrated on a rotary evaporator at a reduced pressure of 80 mbar and at most 40° C. The residue was dissolved in a little dichloromethane and purified by flash column chromatography (Isolera, 100 g Ultra Snap column, cyclohexane/ethyl acetate gradient). The combined target fractions were concentrated on a rotary evaporator at a reduced pressure of 80 mbar and at most 40° C. This gave 2.47 g (100% purity, 63% of theory) of the title compound.

LC-MS (Method 2): $R_t$=0.77 min; hardly any ionization $^1$H-NMR (400 MHz, DMSO-d6) δ [ppm]: −0.008 (2.92), 0.008 (1.75), 2.524 (1.31), 4.221 (16.00), 7.924 (0.58), 7.943 (1.16), 7.951 (1.18), 7.963 (0.79), 7.970 (2.15), 7.977 (0.73), 7.989 (1.16), 7.997 (1.11), 8.016 (0.53).

Example 15A (+/−)-Ethyl (2-chlorophenyl)(cyano)acetate (Racemate)

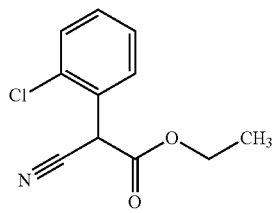

Under argon, sodium hydride (21.8 g, 544 mmol, 60% in mineral oil) and diethyl carbonate (60 ml, 490 mmol) were added to a solution of (2-chlorophenyl)acetonitrile (75.0 g, 495 mmol) in toluene (2.0 l), and the mixture was stirred at 80° C. overnight. After cooling to RT, 1 liter of 1 M hydrochloric acid was added, and the mixture was stirred for 5 min and extracted three times with ethyl acetate. The combined organic phases were dried over sodium sulfate, filtered and concentrated and the residue was purified by flash column chromatography (silica gel, cyclohexane/ethyl acetate 10:1). The combined target fractions were concentrated and the residue was dried under reduced pressure. This gave 100 g (90% of theory) of the title compound. An alternative preparation method is described in *Journal of the American Chemical Society* 1965, 87 (5), 1115-1120.

Example 16A (+/−)-tert-Butyl 2-(3-chloropyridin-2-yl)-2-cyanopropanoate (Racemate)

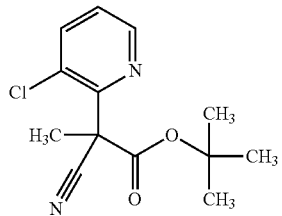 [SMILES: CC(C)(C)OC(=O)C(C)(C#N)c1ncccc1Cl]

Under argon and at −78° C., a 2 M solution of LDA in THF (4.5 ml, 9.0 mmol) was added slowly to a solution of (+/−)-2-(3-chloropyridin-2-yl)propanenitrile (1.00 g, 6.00 mmol, Example 5A) in THF (8.8 ml), and the mixture was allowed to warm to 0° C. and, after 15 min, once more cooled to −78° C. Subsequently, di-tert-butyl dicarbonate (1.96 ml, 9.00 mmol) was slowly added dropwise at −78° C., the cooling bath was removed and the reaction mixture was stirred at RT overnight. Subsequently, with stirring, water was slowly added to the mixture, which was agitated and extracted twice with ethyl acetate. The combined organic phases were washed with saturated aqueous sodium chloride solution, dried over sodium sulfate, filtered and concentrated, and the residue was purified by preparative HPLC (Method 22). The combined target fractions were concentrated and the residue was dried under reduced pressure. This gave 921 mg (86% purity, 49% of theory) of the title compound.

LC-MS (Method 1): $R_t$=1.95 min

Example 17A (+/−)-tert-Butyl 2-cyano-2-(2,6-difluorophenyl)propanoate (Racemate)

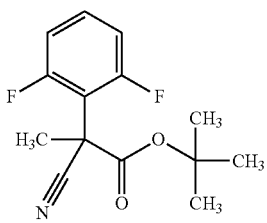 [SMILES: CC(C)(C)OC(=O)C(C)(C#N)c1c(F)cccc1F]

Under argon and at −78° C., a 2 M solution of LDA in THF (24 ml, 49 mmol) was added slowly to a solution of (+/−)-2-(2,6-difluorophenyl)propanenitrile (5.00 g, 29.91 mmol, preparable according to *Russian Journal of Organic Chemistry* 2009, 45, 1531-1534) in THF (38 ml), and the mixture was allowed to warm to 0° C. and, after 15 min, once more cooled to −78° C. Subsequently, ditert-butyl dicarbonate (10.7 g, 49.0 mmol) was slowly added dropwise at −78° C., and the mixture was then stirred at 0° C. for 3 h. Subsequently, with stirring, water was slowly added to the mixture, which was agitated and extracted twice with ethyl acetate. The combined organic phases were washed with saturated aqueous sodium chloride solution, dried over sodium sulfate, filtered and concentrated, and the residue was dried under reduced pressure. This gave 6.80 g (79% purity, 66% of theory) of the title compound.

LC-MS (Method 1): $R_t$=2.08 min; MS (ESIpos): m/z=268 [M+H]$^+$ $^1$H-NMR (400 MHz, DMSO-d6) δ [ppm]: 1.116 (2.15), 1.132 (2.17), 1.385 (1.30), 1.403 (13.17), 1.437 (16.00), 1.468 (5.97), 1.945 (1.50), 1.949 (2.52), 1.953 (1.48), 7.223 (0.50), 7.245 (0.67), 7.248 (0.58), 7.269 (0.62), 7.563 (0.41).

Example 18A (+/−)-tert-Butyl cyano(3-methoxyphenyl)acetate (Racemate)

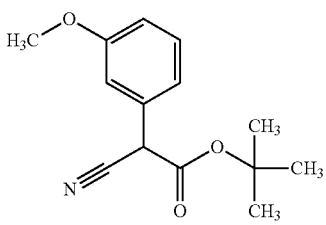

Under argon and at −78° C., a 2 M solution of LDA in THF (15 ml, 31 mmol) was added slowly to a solution of (3-methoxyphenyl)acetonitrile (3.00 g, 20.4 mmol) in THF (16 ml), and the mixture was allowed to warm to 0° C. and, after 15 min, once more cooled to −78° C. Subsequently, ditert-butyl dicarbonate (6.67 g, 30.6 mmol), dissolved in THF (15 ml), was slowly added dropwise at −78° C., and the mixture was allowed to warm to RT and stirred at RT overnight. Subsequently, with stirring, water was slowly added to the mixture, which was agitated and extracted twice with ethyl acetate (60 ml and 45 ml). The combined organic phases were washed with saturated aqueous sodium chloride solution, dried over sodium sulfate, filtered and concentrated, and the residue was dried under reduced pressure. The residue was purified by flash column chromatography (100 g silica gel Biotage Snap-Cartridge KP-Sil, cyclohexane/ethyl acetate 100:0→9:1). The combined target fractions were concentrated and the residue was dried under reduced pressure. This gave 4.00 g (78% purity, 62% of theory) of the title compound.

LC-MS (Method 2): $R_t$=1.01 min; MS (ESIpos): m/z=248 [M+H]$^+$

Example 19A (+/−)-tert-Butyl (3-chlorophenyl)(cyano)acetate (Racemate)

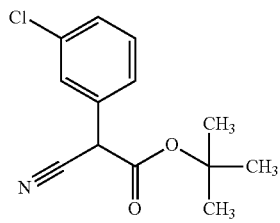 [SMILES: CC(C)(C)OC(=O)C(C#N)c1cccc(Cl)c1]

Under argon and at −78° C., a 2 M solution of LDA in THF (15 ml, 30 mmol) was added slowly to a solution of (3-chlorophenyl)acetonitrile (3.00 g, 19.8 mmol) in THF (16 ml), and the mixture was allowed to warm to 0° C. and, after 15 min, once more cooled to −78° C. Subsequently, ditert-butyl dicarbonate (6.48 g, 29.7 mmol), dissolved in THF (15 ml), was slowly added dropwise at −78° C., and the mixture was allowed to warm to RT and stirred at RT overnight. Subsequently, with stirring, water was slowly added to the mixture, which was agitated and extracted twice with ethyl acetate (60 ml and 40 ml). The combined organic phases were washed with saturated aqueous sodium chloride solution, dried over sodium sulfate, filtered and concentrated, and the residue was dried under reduced pressure. The residue was purified by flash column chromatography (120 g silica gel Biotage Snap-Cartridge KP-Sil, cyclohexane/ethyl acetate 100:0→9:1). The combined target fractions were concentrated and the residue was dried under reduced pressure. This gave 400 mg (55% purity, 4% of theory) of a first batch of the title compound and 2.6 g (80% purity, 42% of theory, see analysis) of a second batch of the title compound and 2.5 g (70% purity, 35% of theory) of a third charge of the title compound. The three charges were combined and used in the next reaction (see Example 86A).

LC-MS (Method 1): $R_t$=2.07 min; MS (ESIneg): m/z=250 [M−H]$^-$

Example 20A (+/−)-tert-Butyl cyano(3-methylphenyl)acetate (Racemate)

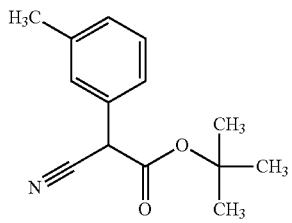

Under argon and at −78° C., a 2 M solution of LDA in THF (17 ml, 34 mmol) was added slowly to a solution of (3-methylphenyl)acetonitrile (3.00 g, 22.9 mmol) in THF (35 ml), and the mixture was allowed to warm to 0° C. and, after 15 min, once more cooled to −78° C. Subsequently, ditert-butyl dicarbonate (7.49 g, 34.3 mmol) was slowly added dropwise at −78° C., and the mixture was stirred at 0° C. for 3 h. Subsequently, with stirring, water (50 ml) was slowly added to the mixture, which was agitated and extracted twice with ethyl acetate (70 ml and 50 ml). The combined organic phases were washed with saturated aqueous sodium chloride solution, dried over sodium sulfate, filtered and concentrated, and the residue was dried under reduced pressure. The residue was purified by flash column chromatography (100 g silica gel Biotage Snap-Cartridge KP-Sil, cyclohexane/ethyl acetate 100:0→9:1). The combined target fractions were concentrated and the residue was dried under reduced pressure. This gave 3.20 g (82% purity, 50% of theory) of the title compound.

LC-MS (Method 2): $R_t$=1.07 min; MS (ESIneg): m/z=230 [M−H]$^-$

Example 21A (+/−)-tert-Butyl cyano(2-fluoro-6-methoxyphenyl) acetate (Racemate)

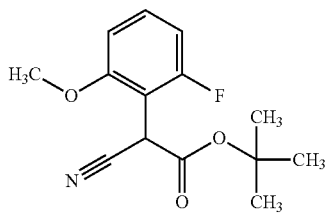 [SMILES: COc1cccc(F)c1C(C#N)C(=O)OC(C)(C)C]

Under argon and at −65° C., a 2 M solution of LDA in THF (23 ml, 45 mmol) was added slowly to a solution of (2-fluoro-6-methoxyphenyl)acetonitrile (5.00 g, 30.3 mmol, CAS-RN 500912-18-5) in THF (25 ml), and the mixture was allowed to warm to 0° C. and, after 15 min, once more cooled to −65° C. Subsequently, a solution of di-tert-butyl dicarbonate (10 ml, 45 mmol) in THF (11 ml) was slowly added dropwise, keeping the internal temperature below −40° C. The mixture was stirred overnight, with the temperature gradually rising to RT. With ice cooling and stirring, 1 M hydrochloric acid (45.4 ml, 45.4 mmol) was then slowly added to the mixture, followed by water (30 ml) and ethyl acetate (80 ml). After agitation and phase separation, the aqueous phase was extracted once with ethyl acetate (80 ml). The combined organic phases were dried over sodium sulfate, filtered and concentrated, and the residue was taken up in dichloromethane and purified by flash column chromatography (500 g of silica gel, cyclohexane/ethyl acetate 10:1). The combined target fractions were concentrated, and the residue was dried under reduced pressure. This gave 10.4 g (62% purity, 80% of theory) of the title compound.

LC-MS (Method 1): $R_t$=1.89 min; MS (ESIpos): m/z=266 [M+H]$^+$

Example 22A (+/−)-tert-Butyl 2-cyano-2-(2-methoxyphenyl)propanoate (Racemate)

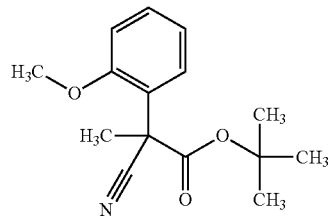 [SMILES: COc1ccccc1C(C)(C#N)C(=O)OC(C)(C)C]

Under argon and at −78° C., a 2 M solution of LDA in THF (9.3 ml, 19 mmol) was added slowly to a solution of 2-(2-methoxyphenyl)propanenitrile (2.00 g, 12.4 mmol, CAS-RN 62115-71-3, commercially available) in THF (18 ml), and the mixture was allowed to warm to 0° C. and, after 15 min, once more cooled to −78° C. Subsequently, di-tert-butyl dicarbonate (4.06 g, 18.6 mmol) was added slowly. The mixture was stirred overnight, with the temperature gradually rising to RT. Subsequently, with stirring, water was slowly added to the mixture, which was extracted twice with ethyl acetate. The combined organic phases were washed with saturated aqueous sodium chloride solution, dried over sodium sulfate, filtered and concentrated, and the residue was taken up in dichloromethane and prepurified by flash column chromatography (100 g of silica gel, cyclohexane/ethyl acetate 85:15). The combined target fractions were concentrated, and the residue was lyophilized in acetonitrile/water. The prepurified product was then repurified by preparative HPLC (column: XBridge C18, 5 μm, 100 mm×30 mm; flow rate: 75 ml/min; detection: 210 nm; temperature: 40° C.; injection: 0.30 ml; mobile phase: 40% acetonitrile/55% water/5% (water+1% ammonia)→70% acetonitrile/25% water/5% (water+1% ammonia; run time 5 min). The combined target fractions were concentrated, and the residue was lyophilized in acetonitrile/water. This gave 1.44 g (100% purity, 44% of theory) of the title compound.

LC-MS (Method 1): $R_t$=1.97 min; MS (ESIpos): m/z=262 [M+H]$^+$

Example 23A (+/−)-tert-Butyl 2-(2-chloro-6-fluorophenyl)-2-cyanopropanoate (Racemate)

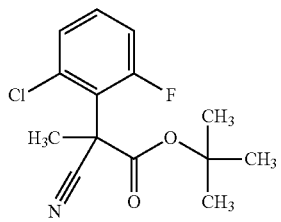 [SMILES: CC(C)(C)OC(=O)C(C)(C#N)c1c(F)cccc1Cl]

Under argon and at −78° C., a 2 M solution of LDA in THF (20 ml, 41 mmol) was added slowly to a solution of 2-(2-chloro-6-fluorophenyl)propanenitrile (5.00 g, 27.2 mmol, CAS-RN 1260829-70-6, commercially available) in THF (22 ml), and the mixture was allowed to warm to 0° C. and, after 15 min, once more cooled to −78° C. Subsequently, di-tert-butyl dicarbonate (9.4 ml, 41 mmol) was added slowly. The mixture was stirred overnight, with the temperature gradually rising to RT. Subsequently, with stirring, water was slowly added to the mixture, which was extracted twice with ethyl acetate. The combined organic phases were washed with saturated aqueous sodium chloride solution, dried over sodium sulfate, filtered and concentrated, and the residue was twice purified by preparative HPLC (Method 14). The combined target fractions were concentrated, and the residue was lyophilized in acetonitrile/water. This gave 1.33 g (98% purity, 17% of theory) of the title compound.

LC-MS (Method 3): $R_t$=3.49 min; MS (ESIpos): m/z=284 [M+H]$^+$ $^1$H-NMR (400 MHz, DMSO-d6) δ [ppm]: 7.59-7.43 (m, 2H), 7.37 (ddd, 1H), 2.04 (d, 3H), 1.44 (s, 9H).

Example 24A (+/−)-tert-Butyl 3-(2-chlorophenyl)-3-cyanopropanoate (Racemate)

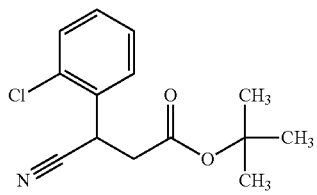 [SMILES: CC(C)(C)OC(=O)CC(C#N)c1ccccc1Cl]

To a solution of (2-chlorophenyl)acetonitrile (5.00 g, 33.0 mmol) in THF (50 ml) under argon was added gradually while stirring, at −78° C., a 2 M solution of LDA in THF (25 ml, 49 mmol). The mixture was allowed to come to 0° C. and, after 15 min, cooled back down again to −78° C. Subsequently, tert-butyl bromoacetate (5.8 ml, 40 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated, and the residue was purified by preparative HPLC [column: Kinetix C18, 5 μm, 100×21.2 mm; flow rate: 30 ml/min; detection: 210 nm; injection volume: 0.4 ml; mobile phase: 50% water/45% acetonitrile/5% formic acid (1% in water)→5% water/90% acetonitrile/5% formic acid (1% in water), run time: 6.0 min]. This gave 6.98 g (purity 100%, 78% of theory) of the title compound.

LC-MS (Method 1): $R_t$=2.10 min; MS (ESIpos): m/z=266 [M+H]$^+$

Example 25A (+/−)-tert-Butyl 3-(3-chlorophenyl)-3-cyanopropanoate (Racemate)

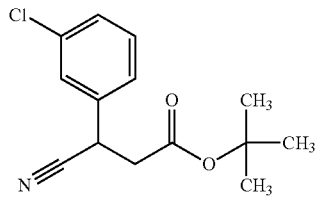 [SMILES: CC(C)(C)OC(=O)CC(C#N)c1cccc(Cl)c1]

To a solution of (3-chlorophenyl)acetonitrile (1.00 g, 6.60 mmol) in THF (10 ml) under argon was added gradually while stirring, at −78° C., a 2 M solution of LDA in THF (4.9 ml, 9.9 mmol). The mixture was allowed to come to 0° C. and, after 15 min, cooled back down again to −78° C. Subsequently, tert-butyl bromoacetate (1.5 ml, 9.9 mmol) was slowly added dropwise with stirring. The cooling bath was removed and, with stirring, the mixture was allowed to warm to RT overnight. Subsequently, water was slowly added to the mixture, which was extracted twice with ethyl acetate. The combined organic phases were washed with saturated aqueous sodium chloride solution, dried over magnesium sulfate, filtered and concentrated. The crude product was combined with the crude product of an analogous preliminary experiment (amount of (3-chlorophenyl) acetonitrile employed: 100 mg (0.66 mmol)), taken up in dichloromethane and purified by flash column chromatography (100 g of silica gel Biotage Snap-Cartridge KP-Sil, cyclohexane/ethyl acetate 97:3 and 8:2, Isolera One). This gave 710 mg (purity 95%, 35% of theory) of the title compound.

LC-MS (Method 1): $R_t$=2.10 min; MS (ESIpos): m/z=266 [M+H]$^+$ $^1$H-NMR (500 MHz, DMSO-d6) δ [ppm]: 1.215 (0.55), 1.365 (16.00), 1.399 (0.56), 1.418 (1.40), 1.430 (0.66), 2.927 (0.56), 2.940 (0.56), 3.024 (0.54), 3.040 (0.55), 4.538 (0.40), 7.430 (0.56), 7.434 (0.78), 7.440 (1.60), 7.451 (0.49), 7.556 (0.75).

Example 26A (+/−)-tert-Butyl 3-cyano-3-(2-methylphenyl)propanoate (Racemate)

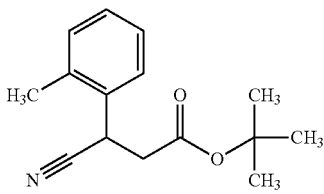

To a solution of (2-methylphenyl)acetonitrile (1.00 g, 7.62 mmol) in THF (11 ml) under argon was added gradually while stirring, at −78° C., a 2 M solution of LDA in THF (5.7 ml, 11 mmol). The mixture was allowed to come to 0° C. and, after 15 min, cooled back down again to −78° C. Subsequently, tert-butyl bromoacetate (1.7 ml, 11 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 97:3→8:2, Isolera One). This gave 880 mg (purity 98%, 47% of theory) of the title compound.

LC-MS (Method 1): $R_t$=2.10 min; MS (ESIpos): m/z=246 [M+H]$^+$ $^1$H-NMR (400 MHz, DMSO-d6): δ [ppm]=7.47-7.39 (m, 1H), 7.29-7.20 (m, 3H), 4.50 (dd, 1H), 3.01-2.81 (m, 2H), 2.36 (s, 3H), 1.37 (s, 9H).

Example 27A (+/−)-tert-Butyl 3-cyano-3-(2,6-dichlorophenyl)propanoate (Racemate)

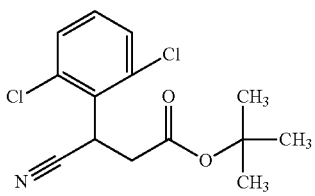 [SMILES: CC(C)(C)OC(=O)CC(C#N)c1c(Cl)cccc1Cl]

To a solution of (2,6-dichlorophenyl)acetonitrile (1.00 g, 5.38 mmol) in THF (8 ml) under argon was added gradually while stirring, at −78° C., a 2 M solution of LDA in THF (4.0 ml, 8.1 mmol). The mixture was allowed to come to 0° C. and, after 15 min, cooled back down again to −78° C. Subsequently, tert-butyl bromoacetate (1.2 ml, 8.1 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 97:3→8:2, Isolera One). This gave 682 mg (98% purity, 41% of theory) of the title compound.

LC-MS (Method 1): $R_t$=2.17 min; MS (ESIpos): m/z=300 [M+H]$^+$ $^1$H-NMR (500 MHz, DMSO-d6) δ [ppm]: 0.933 (1.68), 0.946 (1.79), 1.363 (16.00), 1.392 (2.64), 1.401 (1.37), 3.025 (0.58), 3.038 (0.57), 3.181 (0.57), 3.198 (0.58), 3.315 (0.99), 7.461 (0.61), 7.463 (0.68), 7.478 (0.76), 7.582 (2.03), 7.598 (1.35).

Example 28A (+/−)-tert-Butyl 3-cyano-3-(3-methoxyphenyl)propanoate (Racemate)

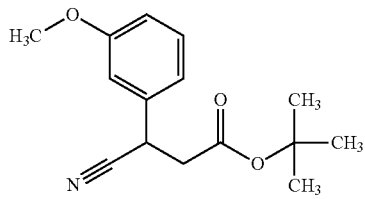 [SMILES: COc1cccc(C(C#N)CC(=O)OC(C)(C)C)c1]

To a solution of (3-methoxyphenyl)acetonitrile (1.00 g, 6.79 mmol) in THF (10 ml) under argon were added gradually while stirring, at −78° C., a 2 M solution of LDA in THF (5.1 ml, 10 mmol). The mixture was allowed to come to 0° C. and, after 15 min, cooled back down again to −78° C. Subsequently, tert-butyl bromoacetate (1.5 ml, 10 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 97:3→8:2, Isolera One). This gave 389 mg (90% purity, 20% of theory) of the title compound.

LC-MS (Method 1): $R_t$=1.96 min; MS (ESIpos): m/z=262 [M+H]$^+$ $^1$H-NMR (400 MHz, DMSO-d6): δ [ppm]=7.36-7.27 (m, 1H), 7.05-6.98 (m, 2H), 6.94-6.87 (m, 1H), 4.43 (dd, 1H), 3.76 (s, 3H), 3.00 (dd, 1H), 2.87 (dd, 1H), 1.38 (s, 9H).

Example 29A (+/−)-tert-Butyl 3-(3-chloropyridin-2-yl)-3-cyanobutanoate (Racemate)

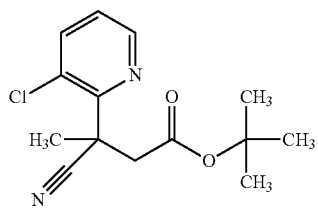 [SMILES: CC(C)(C)OC(=O)CC(C)(C#N)c1ncccc1Cl]

Under argon and at −78° C., a 2 M solution of LDA in THF (5.4 ml, 11 mmol) was added slowly with stirring to a solution of (+/−)-2-(3-chloropyridin-2-yl)propanenitrile (1.20 g, 7.20 mmol, Example 5A) in THF (10 ml). The mixture was allowed to come to 0° C. and, after 15 min, cooled back down again to −78° C. Subsequently, tert-butyl bromoacetate (1.3 ml, 8.6 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was purified by preparative HPLC (Method 22). This gave 1.08 g (100% purity, 53% of theory) of the title compound.

LC-MS (Method 1): $R_t$=1.93 min; MS (ESIpos): m/z=225 [M-$^t$Bu+H]$^+$

Example 30A (+/−)-tert-Butyl 3-(2-chloro-6-fluorophenyl)-3-cyanopropanoate (Racemate)

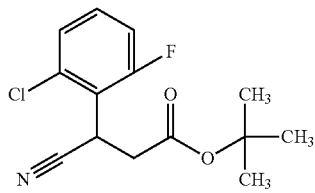 [SMILES: CC(C)(C)OC(=O)CC(C#N)c1c(F)cccc1Cl]

To a solution of (2-chloro-6-fluorophenyl)acetonitrile (1.00 g, 5.90 mmol) in THF (8.7 ml) under argon was added gradually while stirring, at −78° C., a 2 M solution of LDA in THF (4.4 ml, 8.8 mmol). The mixture was allowed to come to 0° C. and, after 15 min, cooled back down again to −78° C. Subsequently, tert-butyl bromoacetate (1.3 ml, 8.8 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 97:3→8:2, Isolera One). This gave 878 mg (98% purity, 51% of theory) of the title compound.

LC-MS (Method 1): $R_t$=2.07 min; MS (ESIpos): m/z=284 [M+H]$^+$ $^1$H-NMR (500 MHz, DMSO-d6): δ [ppm]=7.54-7.47 (m, 1H), 7.47-7.42 (m, 1H), 7.37 (ddd, 1H), 4.88-4.82 (m, 1H), 3.14-3.07 (m, 1H), 3.02-2.93 (m, 1H), 1.34 (s, 9H).

Example 31A (+/−)-tert-Butyl 3-cyano-3-(4-methylphenyl)propanoate (Racemate)

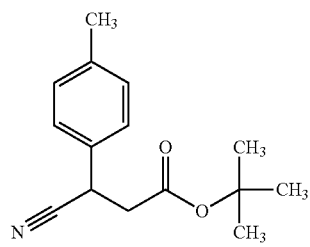

To a solution of (4-methylphenyl)acetonitrile (1.00 g, 7.62 mmol) in THF (11 ml) under argon was added gradually while stirring, at −78° C., a 2 M solution of LDA in THF (5.7 ml, 11 mmol). The mixture was allowed to come to 0° C. and, after 15 min, cooled back down again to −78° C. Subsequently, tert-butyl bromoacetate (1.7 ml, 11 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 97:3→8:2, Isolera One). This gave 288 mg (90% purity, 14% of theory) of the title compound.

LC-MS (Method 1): $R_t$=2.09 min; MS (ESIpos): m/z=246 [M+H]$^+$ $^1$H-NMR (400 MHz, DMSO-d6): δ [ppm]=7.32 (d, 2H), 7.21 (d, 2H), 4.40 (dd, 1H), 2.95 (dd, 1H), 2.83 (dd, 1H), 2.29 (s, 3H), 1.37 (s, 9H).

Example 32A (+/−)-tert-Butyl 3-cyano-3-(3-methylphenyl)propanoate (Racemate)

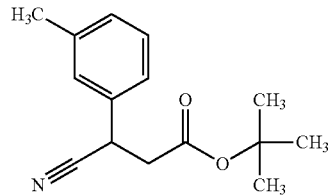 [SMILES: Cc1cccc(C(C#N)CC(=O)OC(C)(C)C)c1]

To a solution of (3-methylphenyl)acetonitrile (1.00 g, 7.62 mmol) in THF (11 ml) under argon was added gradually while stirring, at −78° C., a 2 M solution of LDA in THF (5.7 ml, 11 mmol). The mixture was allowed to come to 0° C. and, after 15 min, cooled back down again to −78° C. Subsequently, tert-butyl bromoacetate (1.7 ml, 11 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 97:3→8:2, Isolera One). This gave 174 mg (90% purity, 8% of theory) of the title compound.

LC-MS (Method 1): $R_t$=2.09 min; MS (ESIpos): m/z=246 [M+H]$^+$ $^1$H-NMR (400 MHz, DMSO-d6): δ [ppm]=7.34-7.08 (m, 4H), 4.41 (dd, 1H), 2.96 (dd, 1H), 2.85 (dd, 1H), 2.31 (s, 3H), 1.37 (s, 9H).

Example 33A (+/−)-tert-Butyl 3-cyano-3-(2-methoxyphenyl)propanoate (Racemate)

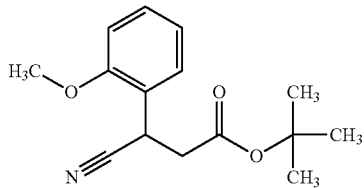

To a solution of (2-methoxyphenyl)acetonitrile (5.00 g, 34.0 mmol) in THF (50 ml) under argon were added gradually while stirring, at −78° C., a 2 M solution of LDA in THF (25 ml, 51 mmol). The mixture was allowed to come to 0° C. and, after 15 min, cooled back down again to −78° C. Subsequently, tert-butyl bromoacetate (7.5 ml, 51 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was dissolved in a mixture of acetonitrile and methanol (64 ml) and purified by preparative HPLC [column: Kinetix C18, 5 μm, 150×21.2 mm; flow rate: 30 ml/min; detection: 210 nm; injection volume: 0.5 ml; mobile phase: 65% water/30% acetonitrile/5% formic acid (1% in water)→15% water/80% acetonitrile/5% formic acid (1% in water), run time: 6.0 min]. This gave 4.90 g (96% purity, 53% of theory) of the title compound.

LC-MS (Method 1): $R_t$=2.00 min; MS (ESIpos): m/z=262 [M+H]$^+$

Example 34A (+/−)-tert-Butyl 3-cyano-3-[2-(trifluoromethoxy)phenyl]propanoate (Racemate)

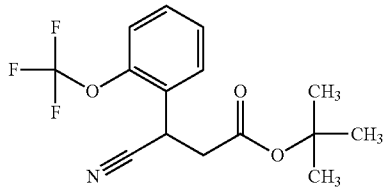 [SMILES: CC(C)(C)OC(=O)CC(C#N)c1ccccc1OC(F)(F)F]

To a solution of [2-(trifluoromethoxy)phenyl]acetonitrile (5.00 g, 24.9 mmol) in THF (37 ml) under argon was added gradually while stirring, at −78° C., a 2 M solution of LDA in THF (19 ml, 37 mmol). The mixture was allowed to come to 0° C. and, after 15 min, cooled back down again to −78° C. Subsequently, tert-butyl bromoacetate (5.5 ml, 37 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was purified by flash column chromatography (150 g of silica gel, cyclohexane→cyclohexane/ethyl acetate 95:5). This gave 6.70 g (65% purity, 56% of theory) of the title compound.

LC-MS (Method 1): $R_t$=2.19 min; MS (ESIpos): m/z=316 [M+H]$^+$

Example 35A (+/−)-tert-Butyl 3-cyano-3-(pyridin-2-yl)propanoate (Racemate)

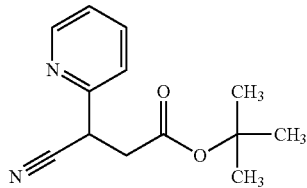 [SMILES: CC(C)(C)OC(=O)CC(C#N)c1ccccn1]

To a solution of pyridin-2-ylacetonitrile (5.00 g, 42.3 mmol) in THF (62 ml) under argon was added gradually while stirring, at −78° C., a 2 M solution of LDA in THF (32 ml, 63 mmol). The mixture was allowed to come to 0° C. and, after 15 min, cooled back down again to −78° C. Subsequently, tert-butyl bromoacetate (9.4 ml, 63 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was purified by preparative HPLC [column: Kinetix C18, 5 μm, 150×21.2 mm; flow rate: 30 ml/min; detection: 210 nm; injection volume: 0.75 ml; mobile phase: 65% water/30% acetonitrile/5% formic acid (1% in water)→15% water/80% acetonitrile/5% formic acid (1% in water), run time: 6.0 min]. This gave 1.94 g (98% purity, 19% of theory) of the title compound.

LC-MS (Method 1): $R_t$=1.59 min; MS (ESIpos): m/z=231 [M−H]$^−$

Example 36A (+/−)-tert-Butyl 3-cyano-3-[2-(trifluoromethyl)phenyl]propanoate (Racemate)

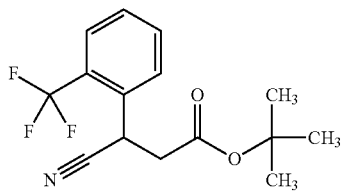

To a solution of (trifluoromethyl)phenyl]acetonitrile (2.50 g, 13.5 mmol) in THF (22 ml) under argon was added gradually while stirring, at −78, a 2 M solution of LDA in THF (10 ml, 20 mmol). The mixture was allowed to come to 0° C. and, after 15 min, cooled back down again to −78° C. Subsequently, tert-butyl bromoacetate (3.0 ml, 20 mmol) was slowly added dropwise thereto at −78° C. while stirring. Stirring of the mixture was continued overnight, in the course of which the cooling bath (dry ice/acetone) was allowed to come gradually to RT. Subsequently, at 0° C., water and ethyl acetate (50 ml each) were added, and the mixture was agitated and allowed to warm to RT. After phase separation, the aqueous phase was extracted once with ethyl acetate (50 ml). The combined organic phases were washed once with saturated aqueous sodium chloride solution (100 ml), dried over sodium sulfate, filtered and concentrated, and the residue was taken up in dichloromethane and purified by flash column chromatography (50 g silica gel Biotage Snap-Cartridge KP-Sil, cyclohexane/ethyl acetate gradient 93:7→7:3, Isolera One). The combined target fractions were concentrated and the residue was dried under reduced pressure. This gave 2.7 g (98% purity, 66% of theory) of the title compound.

LC-MS (Method 2): $R_t$=1.14 min; MS (ESIpos): m/z=300 [M+H]$^+$

Example 37A (+/−)-tert-Butyl 3-cyano-3-(3-methoxypyridin-2-yl)propanoate (Racemate)

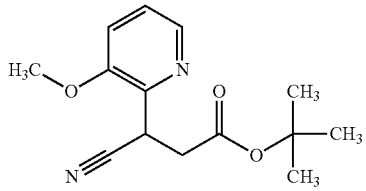 [SMILES: COc1cccnc1C(C#N)CC(=O)OC(C)(C)C]

To a solution of (3-methoxypyridin-2-yl)acetonitrile (2.00 g, 13.5 mmol), preparable according to US2003/220368 A1, p. 30) in THF (20 ml) under argon was added gradually while stirring, at −78° C., a 2 M solution of LDA in THF (10 ml, 20 mmol). The mixture was allowed to come to 0° C. and, after 15 min, cooled back down again to −78° C. Subsequently, tert-butyl bromoacetate (3.0 ml, 20 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was purified by preparative HPLC [column: Chromatorex C18, 10 μm, 290×100 mm; flow rate: 250 ml/min; detection: 210 nm; injection volume: 18 ml; mobile phase: 70% water/30% acetonitrile→10% water/90% acetonitrile; run time: 40 min]. This gave 2.32 g (99% purity, 65% of theory) of the title compound.

LC-MS (Method 1): $R_t$=1.69 min; MS (ESIneg): m/z=261 [M−H]$^-$

Example 38A (+/−)-tert-Butyl 3-(2-chlorophenyl)-3-cyanobutanoate (Racemate)

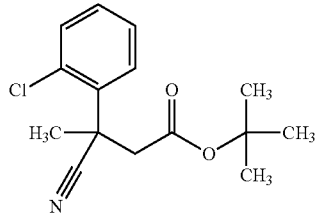 [SMILES: CC(C)(C)OC(=O)CC(C)(C#N)c1ccccc1Cl]

To a solution of (+/−)-2-(2-chlorophenyl)propanenitrile (5.00 g, 30.2 mmol), preparable according to ChemCatChem 2014, 6 (8), 2425-2431) in THF (42 ml) under argon was added gradually while stirring, at −78° C., a 2 M solution of LDA in THF (23 ml, 45 mmol). The mixture was allowed to come to 0° C. and, after 15 min, cooled back down again to −78° C. Subsequently, tert-butyl bromoacetate (5.3 ml, 36 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 8:2). This gave 6.30 g (97% purity, 72% of theory) of the title compound.

LC-MS (Method 1): $R_t$=2.11 min; MS (ESIpos): m/z=280 [M+H]$^+$ $^1$H-NMR (400 MHz, DMSO-d6) δ [ppm]: 1.256 (16.00), 1.390 (0.79), 1.397 (4.13), 1.889 (4.42), 3.116 (0.68), 3.155 (1.02), 3.297 (1.02), 3.313 (0.96), 3.336 (0.68), 7.406 (0.44), 7.410 (0.66), 7.420 (0.95), 7.429 (0.88), 7.434 (0.57), 7.525 (0.55), 7.564 (0.55).

Example 39A (+/−)-tert-Butyl 3-(2-chloro-6-fluorophenyl)-3-cyanobutanoate (Racemate)

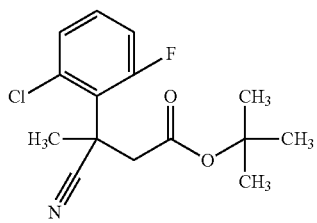 [SMILES: CC(C)(C)OC(=O)CC(C)(C#N)c1c(F)cccc1Cl]

To a solution of (+/−)-2-(2-chloro-6-fluorophenyl)propanenitrile (5.00 g, 27.2 mmol), preparable from (2-chloro-6-fluorophenyl)acetonitrile by methylation with tetrabutylammonium iodide and potassium carbonate in toluene at 80° C. (analogously to ChemCatChem 2014, 6 (8), 2425-2431) in THF (38 ml) under argon was added gradually while stirring, at −78° C., a 2 M solution of LDA in THF (20 ml, 41 mmol). The mixture was allowed to come to 0° C. and, after 15 min, cooled back down again to −78° C. Subsequently, tert-butyl bromoacetate (4.8 ml, 33 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was taken up in dichloromethane and purified by flash column chromatography (100 g silica gel Biotage Snap-Cartridge KP-Sil, cyclohexane/ethyl acetate 8:2). This gave 5.26 g (98% purity, 64% of theory) of the title compound.

LC-MS (Method 2): $R_t$=1.12 min; MS (ESIpos): m/z=298 [M+H]$^+$ $^1$H-NMR (400 MHz, DMSO-d6) δ [ppm]: 1.298 (16.00), 1.862 (2.46), 1.868 (2.44), 3.246 (0.50), 3.259 (0.51), 3.311 (0.83), 3.406 (0.53), 3.415 (0.52), 7.412 (1.35), 7.419 (0.70), 7.422 (0.55), 7.429 (0.41).

Example 40A (+/−)-tert-Butyl 3-cyano-3-(2-methoxyphenyl)butanoate (Racemate)

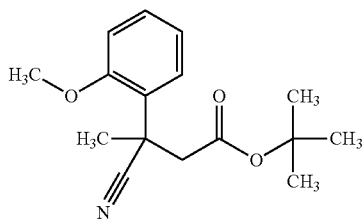 [SMILES: COc1ccccc1C(C)(C#N)CC(=O)OC(C)(C)C]

To a solution of 2-(2-methoxyphenyl)propanenitrile (8.00 g, 49.6 mmol, preparable according to *Organic Letters* 2008, 10 (20), 4573-4576) in THF (73 ml) under argon was added gradually while stirring, at −78° C., a 2 M solution of LDA in THF (37 ml, 74 mmol). The mixture was allowed to come to 0° C. and, after 15 min, cooled back down again to −78° C. Subsequently, tert-butyl bromoacetate (11 ml, 74 mmol) was slowly added dropwise with stirring. The cooling bath was removed and, with stirring, the mixture was allowed to warm to RT overnight. Subsequently, water was added gradually to the mixture, which was extracted twice with ethyl acetate. The combined organic phases were washed with saturated aqueous sodium chloride solution, dried over magnesium sulfate, filtered and concentrated. The residue was purified by preparative HPLC [column: Chromatorex C18, 10 μm, 370×100 mm; flow rate: 250 ml/min; detection: 210 nm; temperature: 22° C.; injection volume: 18 ml; mobile phase: 30% water/70% acetonitrile→10% water/90% acetonitrile; run time: 31 min]. This gave 7.93 g (95% purity, 55% of theory) of the title compound.

LC-MS (Method 1): $R_t$=2.05 min; MS (ESIpos): m/z=276 [M+H]$^+$ $^1$H-NMR (400 MHz, DMSO-d6) δ [ppm]: 1.215 (16.00), 1.782 (4.55), 2.949 (0.80), 2.987 (1.16), 3.131 (1.14), 3.169 (0.78), 3.312 (0.57), 6.989 (0.56), 6.992 (0.59), 7.098 (0.52), 7.117 (0.61), 7.360 (0.49), 7.370 (0.67), 7.375 (0.63), 7.390 (0.59), 7.394 (0.43).

$^1$H-NMR (400 MHz, DMSO-d6): 5 [ppm]=7.41-7.31 (m, 2H), 7.11 (d, 1H), 6.99 (td, 1H), 3.86 (s, 3H), 3.15 (d, 1H), 2.97 (d, 1H), 1.78 (s, 3H), 1.21 (s, 9H).

Example 41A (+/−)-tert-Butyl 3-cyano-3-(5-fluoro-2-methoxyphenyl)propanoate (Racemate)

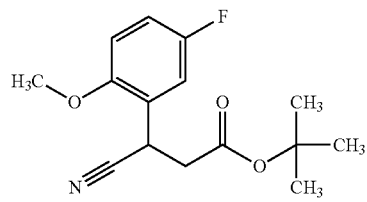 [SMILES: COc1ccc(F)cc1C(C#N)CC(=O)OC(C)(C)C]

Under nitrogen and at −78° C., a solution of (5-fluoro-2-methoxyphenyl)acetonitrile (1.00 g, 6.05 mmol) in THF (22 ml) was added dropwise to a solution of lithium bis(trimethylsilyl)amide (6.36 ml, 1 M, 6.36 mmol) in THF (22 ml). After 45 min of stirring at −78° C., a solution of tert-butyl bromoacetate (1.18 g, 6.05 mmol) in THF (22 ml) was added and the reaction mixture was stirred at −78° C. for a further hour, followed by 2 h at RT. Subsequently, ethyl acetate and water were added, the mixture was agitated and the phases were separated. The aqueous phase was extracted twice with ethyl acetate. The combined organic phases were washed with saturated aqueous sodium chloride solution, dried over sodium sulfate, filtered and concentrated, and the residue was prepurified by flash column chromatography (40 g of silica gel Reveleris, heptane/ethyl acetate gradient). The prepurified product was then repurified by flash column chromatography (40 g Reversed Phase C18 Reveleris, flow rate 40 ml/min, (water+0.1% formic acid)/(acetonitrile+0.1% formic acid) gradient). This gave 941 mg (purity 98%, 55% of theory) of the title compound.

LC-MS (Method 10): $R_t$=2.28 min; MS (ESpos): m/z=297 [M]$^+$ $^1$H-NMR (400 MHz, DMSO-d6): δ [ppm]=7.15 (d, 1H), 7.02 (dd, 1H), 6.84 (dd, 1H), 4.47 (dd, 1H), 3.86 (s, 3H), 2.90-2.70 (m, 2H), 1.45 (s, 9H).

Example 42A (+/−)-tert-Butyl 3-cyano-3-(2-fluoro-6-methoxyphenyl)propanoate (Racemate)

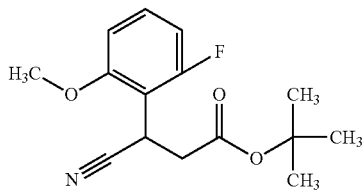 [SMILES: COc1cccc(F)c1C(C#N)CC(=O)OC(C)(C)C]

To a solution of (2-fluoro-6-methoxyphenyl)acetonitrile (5.00 g, 30.3 mmol) in THF (50 ml) under argon was added gradually while stirring, at −78 to −60° C., a 2 M solution of LDA in THF (23 ml, 45 mmol). The mixture was allowed to come to 0° C. and, after 15 min, cooled back down again to −78° C. Subsequently, tert-butyl bromoacetate (6.7 ml, 45 mmol) was slowly added dropwise thereto at −78 to −60° C. while stirring. The cooling bath was removed and, with stirring, the mixture was allowed to slowly warm to RT. After 4 h, at 0° C., water and ethyl acetate (50 ml each) were added, the mixture was agitated and the phases were separated. The aqueous phase was extracted once with ethyl acetate (50 ml). The combined organic phases were washed once with saturated aqueous sodium chloride solution (100 ml), dried over sodium sulfate, filtered and concentrated, and the residue was dried under reduced pressure. This gave 11.4 g ("93% purity", ">100% of theory", comprises further impurities) of the title compound.

LC-MS (Method 1): $R_t$=2.00 min; MS (ESIpos): m/z=280 [M+H]$^+$ $^1$H-NMR (400 MHz, DMSO-d6) δ [ppm]: 1.334 (16.00), 1.397 (0.78), 1.425 (3.42), 2.844 (0.47), 2.862 (0.47), 2.999 (0.42), 3.020 (0.42), 3.309 (3.17), 4.017 (0.76), 4.635 (0.44), 6.894 (0.43), 6.958 (0.53), 6.980 (0.58), 7.402 (0.46), 7.419 (0.45).

$^1$H-NMR (400 MHz, DMSO-d6): δ [ppm]=7.41 (dd, 1H), 6.97 (d, 1H), 6.89 (t, 1H), 4.63 (dd, 1H), 3.89 (s, 3H), 3.03 (dd, 1H), 2.83 (dd, 1H), 1.33 (s, 9H).

Example 43A (+/−)-tert-Butyl 3-cyano-3-(2-ethoxyphenyl)propanoate (Racemate)

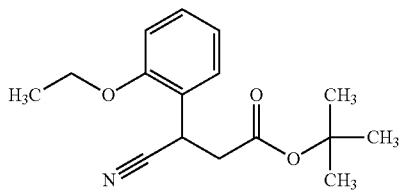 [SMILES: CCOc1ccccc1C(C#N)CC(=O)OC(C)(C)C]

At −78° C., a solution of 1.6 M butyllithium in hexane (13 ml, 20 mmol) was added dropwise to a solution of diisopropylamine (2.9 ml, 20 mmol) in THF (110 ml), and the mixture was stirred at −78° C. for 45 min. Subsequently, a solution of (2-ethoxyphenyl)acetonitrile (3.00 g, 18.6 mmol) in THF (110 ml) was added dropwise. After one hour of stirring at −78° C., a solution of tert-butyl bromoacetate (2.8 ml, 20 mmol) in THF (15 ml) was added and the reaction mixture was stirred at −78° C. for a further 45 min. Subsequently, the cooling bath was removed and the mixture was stirred at RT for a further 2 h. The mixture was once more cooled to −78° C., saturated ammonium chloride solution was added, the mixture was allowed to warm to RT, ethyl acetate was added and the mixture was agitated. After phase separation, the aqueous phase was extracted twice with ethyl acetate. The combined organic phases were washed with saturated aqueous sodium chloride solution, dried over sodium sulfate, filtered and concentrated, and the residue was purified by flash column chromatography (40 g Reversed Phase C18 Reveleris, flow rate 100 ml/min, (water+0.1% formic acid)/(acetonitrile+0.1% formic acid) gradient). The combined target fractions were concentrated and the residue was dried under reduced pressure. This gave 1.96 g (99% purity, 38% of theory) of the title compound.

LC-MS (Method 10): $R_t$=2.22 min; MS (ESpos): m/z=293 [M+18]$^+$ $^1$H-NMR (400 MHz, CDCl$_3$): δ [ppm]=7.39 (d, 1H), 7.38-7.25 (m, partially obscured, 1H), 7.00-6.90 (m, 1H), 6.88 (d, 1H), 4.50 (dd, 1H), 4.10 (dd, 2H), 2.90-2.70 (m, 2H), 1.50-1.43 (m, 12H).

Example 44A (+/−)-tert-Butyl 3-cyano-3-(5-fluoro-2-methoxyphenyl)butanoate (Racemate)

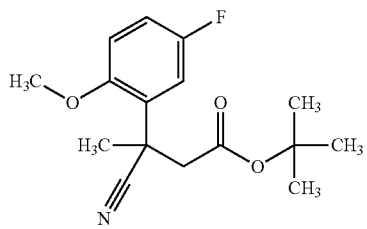 [SMILES: COc1ccc(F)cc1C(C)(C#N)CC(=O)OC(C)(C)C]

Under nitrogen and at −78° C., a solution of 1.6 M butyllithium in hexane (10 ml, 16 mmol) was added dropwise to a solution of diisopropylamine (2.3 ml, 16 mmol) in THF (80 ml), and the mixture was stirred at −78° C. for 45 min. Subsequently, a solution of (+/−)-2-(5-fluoro-2-methoxyphenyl)propanenitrile (2.40 g, 13.4 mmol, Example 6A) in THF (80 ml) was added dropwise. After 50 min of stirring at −78° C., a solution of tert-butyl bromoacetate (2.3 ml, 16 mmol) in THF (10 ml) was added and the reaction mixture was stirred at −78° C. for a further 30 min. Subsequently, the cooling bath was removed and the mixture was stirred at RT for a further 2 h. Saturated ammonium chloride solution was added and the mixture was agitated. After addition of ethyl acetate, the phases were separated and the aqueous phase was extracted twice with ethyl acetate. The combined organic phases were washed with saturated aqueous sodium chloride solution, dried over sodium sulfate, filtered and concentrated, and the residue was prepurified by flash column chromatography (120 g silica gel Reveleris, flow rate 80 ml/min, heptane/dichloromethane gradient 1:0→0:1, run time 38 min)). This gave two prepurified product fractions which were repurified by flash column chromatography (40 g and 80 g of silica gel Reveleris, flow rate 40 ml/min and 55 ml/min, respectively, heptane/ethyl acetate gradient 1:0→7: and 31:0→6:4, respectively, run time 32 min and 25 min, respectively). This gave 486 mg (97% purity, 12% of theory, see analysis) of a first batch and 890 mg (96% purity, 22% of theory) of a second batch of the title compound.

LC-MS (Method 10): $R_t$=2.27 min; MS (ESpos): m/z=294 [M+1]$^+$

GC-MS (Method 13): $R_t$=3.84 min; MS (ESIpos): m/z=293 [M]$^+$ $^1$H-NMR (400 MHz, CDCl$_3$): δ [ppm]=7.24 (d, 1H), 7.05-6.93 (m 1H), 7.90-7.81 (m, 1H), 3.89 (s, 3H), 3.18 (d, 1H), 2.96 (d, 1H), 1.86 (s, 3H), 1.31 (s, 9H).

Example 45A (+/−)-tert-Butyl 3-cyano-3-(3,5-difluoro-2-methoxyphenyl)butanoate (Racemate)

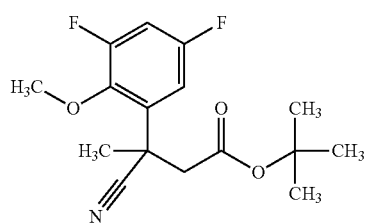 [SMILES: COc1c(F)cc(F)cc1C(C)(C#N)CC(=O)OC(C)(C)C]

Under nitrogen and at −78° C., a solution of 1.6 M butyllithium in hexane (7.6 ml, 12 mmol) was added dropwise to a solution of diisopropylamine (1.8 ml, 13 mmol) in THF (25 ml), and the mixture was stirred at −78° C. for 30 min. Subsequently, a solution of (+/−)-2-(3,5-difluoro-2-methoxyphenyl)propanenitrile (1.99 g, 10.1 mmol, Example 7A) in THF (10 ml) was added dropwise. After 30 min of stirring at −78° C., a solution of tert-butyl bromoacetate (2.56 g, 13.1 mmol) in THF (25 ml) was added and the mixture was stirred at −78° C. for a further 30 min. Saturated ammonium chloride solution was then added, and the mixture was agitated and allowed to warm to RT. By addition of 1 M hydrochloric acid, the aqueous phase was adjusted to about pH 3. After addition of saturated sodium chloride solution, the mixture was extracted three times with ethyl acetate, and the combined organic phases were dried over sodium sulfate, filtered and concentrated. The residue was purified by flash column chromatography (120 g of silica gel Reveleris, flow rate 40 ml/min, mobile phase dichloromethane). The combined target fractions were concentrated and the residue was dried under reduced pressure. This gave 1.54 g (99% purity, 49% of theory) of the title compound.

LC-MS (Method 9): $R_t$=2.26 min; MS (ESpos): m/z=312 [M+1]$^+$

GC-MS (Method 13): $R_t$=3.64 min; MS (ESIpos): m/z=311 [M]$^+$

Example 46A (+/−)-tert-Butyl 3-cyano-3-(4-fluoro-2-methoxyphenyl)butanoate (Racemate)

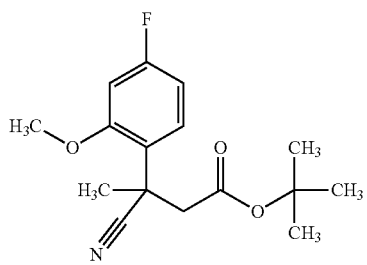 [SMILES: COc1cc(F)ccc1C(C)(C#N)CC(=O)OC(C)(C)C]

Under nitrogen and at −78° C., a solution of 1.6 M butyllithium in hexane (16 ml, 25 mmol) was added dropwise to a solution of diisopropylamine (3.7 ml, 27 mmol) in THF (50 ml), and the mixture was stirred at −78° C. for 30 min. Subsequently, a solution of (+/−)-2-(4-fluoro-2-methoxyphenyl)propanenitrile (3.77 g, 21.0 mmol, Example 8A) in THF (20 ml) was added dropwise. After 30 min of stirring at −78° C., a solution of tert-butyl bromoacetate (5.33 g, 27.3 mmol) in THF (50 ml) was added and the mixture was stirred at −78° C. for a further 30 min. Water was then added, and the mixture was agitated and allowed to warm to RT. By addition of 1 M hydrochloric acid, the aqueous phase was adjusted to about pH 3. After addition of saturated sodium chloride solution, the mixture was extracted three times with ethyl acetate, and the combined organic phases were dried over sodium sulfate, filtered and concentrated. The residue was purified by flash column chromatography (220 g of silica gel, mobile phase dichloromethane, flow rate 80 ml/min). The combined target fractions were concentrated and the residue was dried under reduced pressure. This gave 3.02 g (99% purity, 49% of theory) of the title compound.

GC-MS (Method 13): $R_t$=3.81 min; MS (ESIpos): m/z=293 [M]$^+$ $^1$H-NMR (400 MHz, CDCl$_3$): δ [ppm]=7.50-7.40 (m, 1H), 6.70-6.65 (m, 2H), 3.89 (s, 3H), 3.14 (d, 1H), 2.95 (d, 1H), 1.86 (s, 3H), 1.30 (s, 9H).

Example 47A (+/−)-tert-Butyl 3-cyano-3-(2-fluoro-6-methoxyphenyl)butanoate (Racemate)

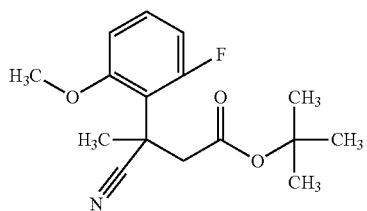 [SMILES: COc1cccc(F)c1C(C)(C#N)CC(=O)OC(C)(C)C]

To a solution of (+/−)-2-(2-fluoro-6-methoxyphenyl)propanenitrile (578 mg, 3.22 mmol, Example 9A) in THF (6.0 ml) under argon was added gradually while stirring, at −78° C., a 2 M solution of LDA in THF (2.4 ml, 4.8 mmol). The mixture was allowed to come to 0° C. and, after 15 min, cooled back down again to −78° C. Subsequently, tert-butyl bromoacetate (943 mg, 4.84 mmol) was slowly added dropwise thereto at −78° C. while stirring. After 3 h of stirring at −78° C., water and ethyl acetate (50 ml each) were added, and the mixture was agitated and allowed to warm to RT. After phase separation, the aqueous phase was extracted once with ethyl acetate (50 ml). The combined organic phases were washed once with saturated aqueous sodium chloride solution (100 ml), dried over sodium sulfate, filtered and concentrated, and the residue was taken up in dichloromethane and purified by flash column chromatography (50 g silica gel Biotage Snap-Cartridge KP-Sil, cyclohexane/ethyl acetate gradient 93:7→7:3, Isolera One). The combined target fractions were concentrated and the residue was dried under reduced pressure. This gave 809 mg (80% purity, 68% of theory) of the title compound.

LC-MS (Method 1): $R_t$=2.01 min; MS (ESIpos): m/z=294 [M+H]$^+$ $^1$H-NMR (400 MHz, DMSO-d6): δ [ppm]=7.39-7.30 (m, 1H), 6.98-6.93 (m, 1H), 6.85-6.74 (m, 1H), 3.85 (s, 3H), 3.27 (dd, 1H), 3.05 (dd, 1H), 1.76 (d, 3H), 1.27 (s, 9H).

Example 48A tert-Butyl 3-(2-chlorophenyl)-4-nitropentanoate (Diastereomer Mixture)

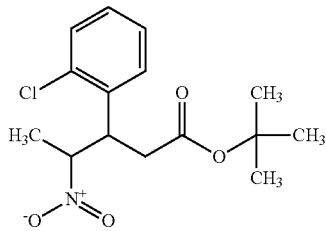

2-tert-Butyl 1,1,3,3-tetramethylguanidine (210 µl, 1.0 mmol) was added to a solution of tert-butyl (2E)-3-(2-chlorophenyl)acrylate (1.00 g, 4.19 mmol, preparable according to *Beilstein Journal of Organic Chemistry* 2012, 8, 1747-1752) in nitroethane (8.0 ml, 92 mmol), and the mixture was stirred under reflux overnight. After cooling to RT, the mixture was filtered and purified by preparative HPLC (Method 16). This gave 1.10 g (purity about 90% according to $^1$H NMR, 75% of theory) of the title compound.

$^1$H-NMR (400 MHz, DMSO-d6) δ [ppm]: 1.153 (16.00), 1.180 (12.81), 1.266 (2.26), 1.283 (2.28), 1.302 (0.50), 1.308 (1.93), 1.504 (1.82), 1.520 (1.84), 2.030 (0.60), 2.644 (0.50), 2.656 (0.49), 2.720 (0.45), 2.745 (0.52), 2.751 (0.51), 2.766 (0.56), 2.771 (0.51), 2.798 (0.47), 7.290 (0.42), 7.294 (0.44), 7.309 (0.44), 7.314 (0.59), 7.328 (0.52), 7.333 (0.73), 7.338 (0.64), 7.344 (0.43), 7.358 (0.50), 7.362 (0.50), 7.410 (0.42), 7.414 (0.41), 7.480 (0.56), 7.483 (0.59), 7.492 (0.82), 7.498 (0.86), 7.502 (0.47), 7.511 (0.49), 7.516 (0.41).

$^1$H-NMR (400 MHz, DMSO-d6) δ [ppm]: 7.70-6.93 (m, 4H), 5.22-4.81 (m, 1H), 4.27-3.94 (m, 1H), 2.87-2.57 (m, 2H), 1.51 & 1.27 (2×d, 3H), 1.18 & 1.15 (2×d, 9H).

Example 49A (+/−)-tert-Butyl 4-(2-chlorophenyl)-4-cyanobutanoate (Racemate)

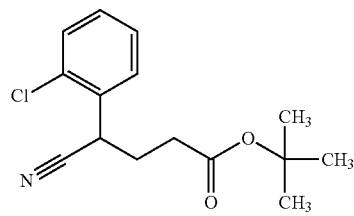 [SMILES: CC(C)(C)OC(=O)CCC(C#N)c1ccccc1Cl]

To a solution of (2-chlorophenyl)acetonitrile (5.00 g, 33.0 mmol) in THF (46 ml) under argon was added gradually while stirring, at −78° C., a 2 M solution of LDA in THF (25 ml, 49 mmol). The mixture was allowed to come to 0° C. and, after 15 min, cooled back down again to −78° C. Subsequently, tert-butyl 3-bromopropanoate (8.28 g, 39.6 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was purified by preparative HPLC (Method 19). The combined target fractions were concentrated and the residue was dried under reduced pressure. This gave 5.20 g (75% purity, 42% of theory) of the title compound.

LC-MS (Method 1): $R_t$=2.22 min; MS (ESIpos): m/z=280 [M+H]$^+$

Example 50A (+/−)-tert-Butyl 4-(2-chlorophenyl)-4-cyanopentanoate (Racemate)

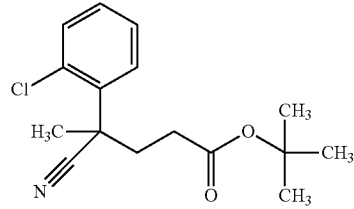 [SMILES: CC(C)(C)OC(=O)CCC(C)(C#N)c1ccccc1Cl]

Under argon and at −78° C., a 2 M solution of LDA in THF (23 ml, 45 mmol) was added slowly, with stirring, to a solution of 2-(2-chlorophenyl)propanenitrile (5.00 g, 30.2 mmol, preparable by methylation of 2-(2-chlorophenyl)acetonitrile according to WO2011/123419 A1, p. 386-387) in THF (42 ml). The mixture was allowed to warm to 0° C. and, after 15 min, cooled back down again to −78° C. Subsequently, tert-butyl 3-bromopropanoate (7.57 g, 36.2 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was purified by preparative HPLC (Method 16). The combined target fractions were concentrated and the residue was dried under reduced pressure. This gave 2.21 g (81% purity, 20% of theory) of the title compound.

LC-MS (Method 1): $R_t$=2.27 min; MS (ESIpos): m/z=294 [M+H]$^+$

Example 51A (+/−)-tert-Butyl 4-(2-chloro-6-fluorophenyl)-4-cyanobutanoate (Racemate)

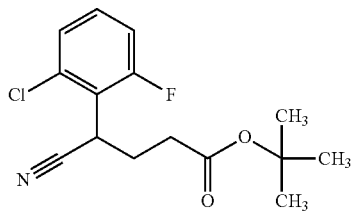 [SMILES: CC(C)(C)OC(=O)CCC(C#N)c1c(F)cccc1Cl]

To a solution of (2-chloro-6-fluorophenyl)acetonitrile (2.00 g, 11.8 mmol) in THF (15 ml) under argon was added gradually while stirring, at −78° C., a 2 M solution of LDA in THF (8.8 ml, 18 mmol). The mixture was allowed to come to 0° C. and, after 15 min, cooled back down again to −78° C. Subsequently, tert-butyl 3-bromopropanoate (2.2 ml, 14 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was prepurified by flash column chromatography (50 g silica gel Biotage Snap-Cartridge KP-Sil, cyclohexane/ethyl acetate gradient 93:7→6:4, Isolera One). This was followed by repurification by preparative HPLC (Method 16). The combined target fractions were concentrated and the residue was dried under reduced pressure. This gave 1.45 g (100% purity, 41% of theory) of the title compound.

LC-MS (Method 1): $R_t$=2.16 min; MS (ESIpos): m/z=298 [M+H]$^+$

Example 52A (+/−)-tert-Butyl 4-cyano-4-(2-methylphenyl)butanoate (Racemate)

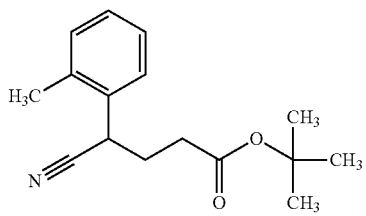

To a solution of (2-methylphenyl)acetonitrile (2.00 g, 15.2 mmol) in THF (17 ml) under argon was added gradually while stirring, at −78° C., a 2 M solution of LDA in THF (11 ml, 23 mmol). The mixture was allowed to come to 0° C. and, after 15 min, cooled back down again to −78° C. Subsequently, tert-butyl 3-bromopropanoate (2.9 ml, 18 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was prepurified by flash column chromatography (100 g silica gel Biotage Snap-Cartridge KP-Sil, cyclohexane/ethyl acetate 85:15, Isolera One). This was followed by repurification by preparative HPLC (Method 16). The combined target fractions were concentrated and the residue was dried under reduced pressure. This gave 534 mg (98% purity, 13% of theory) of the title compound.

LC-MS (Method 1): $R_t$=2.17 min; MS (ESIpos): m/z=260 [M+H]$^+$

Example 53A (+/−)-tert-Butyl 4-(2-chloro-5-fluorophenyl)-4-cyanobutanoate (Racemate)

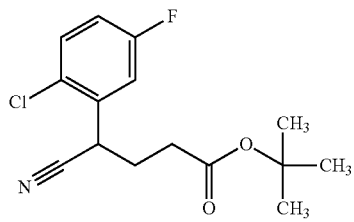 [SMILES: CC(C)(C)OC(=O)CCC(C#N)c1cc(F)ccc1Cl]

To a solution of (2-chloro-5-fluorophenyl)acetonitrile (10.0 g, 59.0 mmol) in THF (75 ml) under argon was added gradually while stirring, at −78° C., a 2 M solution of LDA in THF (44 ml, 88 mmol). The mixture was allowed to come to 0° C. and, after 15 min, cooled back down again to −78° C. Subsequently, tert-butyl 3-bromopropanoate (11 ml, 71 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was purified by flash column chromatography (340 g silica gel Biotage Snap-Cartridge KP-Sil, cyclohexane/ethyl acetate gradient 93:7→3:7, Isolera One). The combined target fractions were concentrated and the residue was dried under reduced pressure. This gave 14.8 g (93% purity, 78% of theory) of the title compound.

LC-MS (Method 1): $R_t$=2.22 min; MS (ESIpos): m/z=298 [M+H]$^+$

Example 54A (+/−)-tert-Butyl 4-cyano-4-(2-methoxyphenyl)butanoate (Racemate)

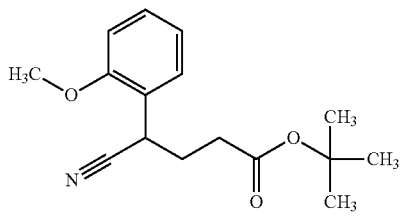 [SMILES: COc1ccccc1C(C#N)CCC(=O)OC(C)(C)C]

To a solution of (2-methoxyphenyl)acetonitrile (2.00 g, 13.6 mmol) in THF (17 ml) under argon were added gradually while stirring, at −78° C., a 2 M solution of LDA in THF (10 ml, 20 mmol). The mixture was allowed to come to 0° C. and, after 15 min, cooled back down again to −78° C. Subsequently, tert-butyl 3-bromopropanoate (2.6 ml, 16 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was prepurified by flash column chromatography (100 g silica gel Biotage Snap-Cartridge KP-Sil, cyclohexane/ethyl acetate gradient 93:7→6:4, Isolera One). This was followed by repurification by preparative HPLC (Method 16). The combined target fractions were concentrated and the residue was dried under reduced pressure. This gave 495 mg (98% purity, 13% of theory) of the title compound.

LC-MS (Method 1): $R_t$=2.13 min; MS (ESIpos): m/z=276 [M+H]$^+$

Example 55A (+/−)-tert-Butyl 4-(2-chloro-5-fluorophenyl)-4-cyanopentanoate (Racemate)

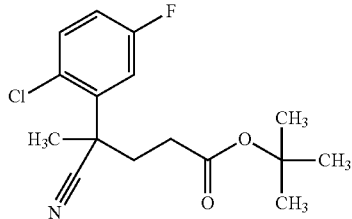 [SMILES: CC(C)(C)OC(=O)CCC(C)(C#N)c1cc(F)ccc1Cl]

To a solution of (+/−)-2-(2-chloro-5-fluorophenyl)propanenitrile (2.50 g, 13.6 mmol, Example 10A) in THF (17 ml) under argon was added gradually while stirring, at −78° C., a 2 M solution of LDA in THF (10 ml, 20 mmol). The mixture was allowed to come to 0° C. and, after 15 min, cooled back down to −78° C. Subsequently, tert-butyl 3-bromopropanoate (2.6 ml, 16 mmol) was slowly added dropwise thereto at −78° C. while stirring. Stirring of the mixture was continued overnight, in the course of which the cooling bath (dry ice/acetone) was allowed to come gradually to RT. Subsequently, water was added gradually to the mixture, which was extracted twice with ethyl acetate. The combined organic phases were washed once with saturated aqueous sodium chloride solution, dried over sodium sulfate, filtered and concentrated, and the residue was purified by flash column chromatography (340 g silica gel Biotage Snap-Cartridge KP-Sil, cyclohexane/ethyl acetate gradient 93:7→3:7, Isolera One). The combined target fractions were concentrated and the residue was dried under reduced pressure. This gave 1.20 g (75% purity, 21% of theory) of the title compound.

LC-MS (Method 1): $R_t$=2.29 min; MS (ESIpos): m/z=312 [M+H]$^+$

Example 56A (+/−)-tert-Butyl 4-(2-chloro-3,6-difluorophenyl)-4-cyanobutanoate (Racemate)

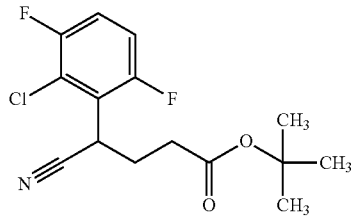 [SMILES: CC(C)(C)OC(=O)CCC(C#N)c1c(F)ccc(F)c1Cl]

To a solution of (2-chloro-3,6-difluorophenyl)acetonitrile (3.84 g, 20.5 mmol, Example 11A) in THF (15 ml) under argon was added gradually while stirring, at −78° C., a 2 M solution of LDA in THF (12 ml, 25 mmol). The mixture was allowed to come to 0° C. and, after 15 min, cooled back down again to −78° C. Subsequently, a solution of tert-butyl 3-bromopropanoate (2.6 ml, 16 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 4.14 g (95% purity, 61% of theory) of the title compound.

LC-MS (Method 1): $R_t$=2.17 min; MS (ESIpos): m/z=338 [M+Na]$^+$ $^1$H-NMR (400 MHz, DMSO-d6) δ [ppm]: 7.58 (td, 1H), 7.45 (td, 1H), 4.68 (t, 1H), 2.39-2.32 (m, 2H), 2.29-2.17 (m, 1H), 2.17-2.05 (m, 1H), 1.37 (s, 9H).

Example 57A (+/−)-tert-Butyl 4-cyano-4-(2-fluorophenyl)butanoate (Racemate)

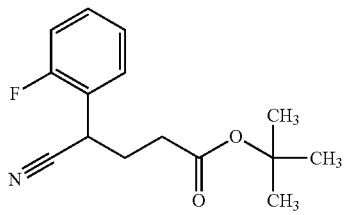 [SMILES: CC(C)(C)OC(=O)CCC(C#N)c1ccccc1F]

To a solution of (2-fluorophenyl)acetonitrile (5.00 g, 37.0 mmol) in THF (35 ml) under argon was added gradually while stirring, at −78° C., a 2 M solution of LDA in THF (22 ml, 44 mmol). The mixture was allowed to come to 0° C. and, after 15 min, cooled back down again to −78° C. Subsequently, a solution of tert-butyl 3-bromopropanoate (7.0 ml, 44 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 4.22 g (69% purity, 29% of theory) of the title compound.

LC-MS (Method 1): $R_t$=2.08 min; MS (ESIpos): m/z=264 [M+H]$^+$

Example 58A (+/−)-tert-Butyl 4-cyano-4-[2-(difluoromethoxy)phenyl]butanoate (Racemate)

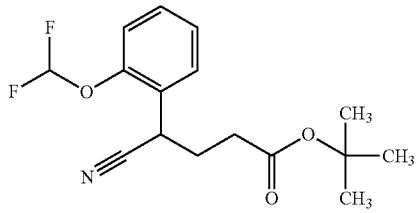

To a solution of [2-(difluoromethoxy)phenyl]acetonitrile (5.00 g, 27.3 mmol) in THF (25 ml) under argon was added gradually while stirring, at −78° C., a 2 M solution of LDA in THF (16 ml, 33 mmol). The mixture was allowed to come to 0° C. and, after 15 min, cooled back down again to −78° C. Subsequently, a solution of tert-butyl 3-bromopropanoate (5.2 ml, 33 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 3.85 g (83% purity, 38% of theory) of the title compound.

LC-MS (Method 1): $R_t$=2.10 min; MS (ESIpos): m/z=312 [M+H]$^+$

Example 59A (+/−)-tert-Butyl 4-cyano-4-(2,6-difluorophenyl)butanoate (Racemate)

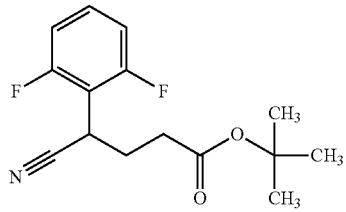 [SMILES: CC(C)(C)OC(=O)CCC(C#N)c1c(F)cccc1F]

To a solution of (2,6-difluorophenyl)acetonitrile (5.00 g, 32.7 mmol) in THF (30 ml) under argon were added gradually while stirring, at −78° C., a 2 M solution of LDA in THF (20 ml, 39 mmol). The mixture was allowed to come to 0° C. and, after 15 min, cooled back down again to −78° C. Subsequently, a solution of tert-butyl 3-bromopropanoate (6.2 ml, 39 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 4.87 g (76% purity, 40% of theory) of the title compound.

LC-MS (Method 1): $R_t$=2.06 min; MS (ESIpos): m/z=282 [M+H]$^+$

Example 60A (+/−)-tert-Butyl 4-(2-chloro-3-fluorophenyl)-4-cyanobutanoate (Racemate)

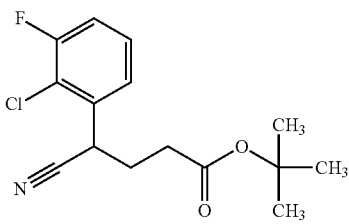 [SMILES: CC(C)(C)OC(=O)CCC(C#N)c1cccc(F)c1Cl]

To a solution of (2-chloro-3-fluorophenyl)acetonitrile (4.00 g, 23.6 mmol, Example 12A) in THF (30 ml) under argon was added gradually while stirring, at −78° C., a 2 M solution of LDA in THF (14 ml, 28 mmol). The mixture was allowed to come to 0° C. and, after 15 min, cooled back down again to −78° C. Subsequently, a solution of tert-butyl 3-bromopropanoate (4.5 ml, 28 mmol) in THF (20 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 4.36 g (95% purity, 59% of theory) of the title compound.

LC-MS (Method 1): $R_t$=2.24 min; MS (ESIpos): m/z=298 [M+H]$^+$ $^1$H-NMR (400 MHz, DMSO-d6) δ [ppm]: 0.007 (0.14), 1.174 (0.02), 1.222 (0.06), 1.342 (0.84), 1.346 (0.35), 1.382 (16.00), 1.429 (0.05), 1.539 (0.06), 1.987 (0.03), 2.071 (0.04), 2.090 (0.09), 2.106 (0.20), 2.125 (0.45), 2.142 (0.53), 2.162 (0.44), 2.182 (0.23), 2.196 (0.08), 2.217 (0.06), 2.252 (0.02), 2.302 (0.07), 2.317 (0.08), 2.343 (0.38), 2.358 (0.60), 2.362 (0.45), 2.376 (0.75), 2.395 (0.29), 2.417 (0.12), 2.436 (0.04), 2.669 (0.03), 2.709 (0.02), 3.730 (0.02), 4.174 (0.10), 4.566 (0.34), 4.586 (0.43), 4.603 (0.33), 7.426 (0.24), 7.431 (0.29), 7.444 (0.48), 7.449 (0.60), 7.460 (0.54), 7.466 (0.30), 7.476 (0.47), 7.482 (0.52), 7.491 (0.55), 7.508 (0.28), 7.529 (0.09).

$^1$H-NMR (400 MHz, DMSO-d6) δ [ppm]: 7.55-7.40 (m, 3H), 4.59 (dd, 1H), 2.45-2.29 (m, 2H), 2.23-2.06 (m, 2H), 1.38 (s, 9H).

Example 61A (+/−)-tert-Butyl N-[(2-chlorophenyl)(cyano)methyl]-N-methylglycinate (Racemate)

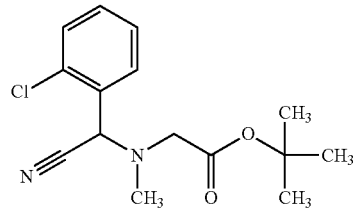 [SMILES: CN(CC(=O)OC(C)(C)C)C(C#N)c1ccccc1Cl]

Saturated sodium carbonate solution was added to a solution of tert-butyl N-methylglycinate hydrochloride (1.03 g, 7.11 mmol) in ethyl acetate (10 ml), and the mixture was agitated. After phase separation, the organic phase was dried over sodium sulfate, filtered and concentrated. The residue was dissolved in dichloromethane (50 ml), and 2-chlorobenzaldehyde (1.00 g, 7.11 mmol) was added dropwise at RT. After stirring at RT for 15 min, trimethylsilanecarbonitrile (706 mg, 7.11 mmol) was added dropwise, and the mixture was stirred at RT overnight. Subsequently, the mixture was concentrated, and the residue was taken up in ethyl acetate and washed with saturated aqueous sodium chloride solution. The organic phase was dried over sodium sulfate, filtered and concentrated, and the residue was purified by preparative HPLC (Method 16). The combined target fractions were concentrated, and the residue was dried under reduced pressure. This gave 1.47 g (90% purity, 63% of theory) of the title compound.

LC-MS (Method 1): $R_t$=2.19 min; MS (ESIpos): m/z=295 [M+H]$^+$

Example 62A (+/−)-tert-Butyl N-[(2-chlorophenyl)(cyano)methyl] glycinate (Racemate)

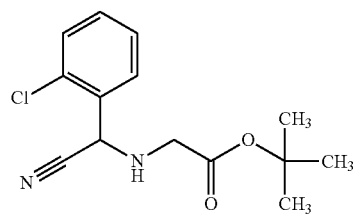 [SMILES: CC(C)(C)OC(=O)CNC(C#N)c1ccccc1Cl]

At RT, 2-chlorobenzaldehyde (1.00 g, 7.11 mmol) was added dropwise to a solution of tert-butyl glycinate (933 mg, 7.11 mmol) in dichloromethane (50 ml). After stirring at RT for 15 min, trimethylsilanecarbonitrile (706 mg, 7.11 mmol) was added dropwise, and the mixture was stirred at RT overnight. Subsequently, the mixture was concentrated, and the residue was taken up in ethyl acetate and washed with saturated aqueous sodium chloride solution. The organic phase was dried over sodium sulfate, filtered and concentrated, and the residue was purified by preparative HPLC (Method 16). The combined target fractions were concentrated, and the residue was dried under reduced pressure. This gave 1.47 g (purity 33%, 24% of theory) of the title compound.

LC-MS (Method 1): R$_t$=2.01 min; MS (ESIpos): m/z=225 [M-C$_4$H$_8$+H]$^+$

Example 63A (+/−)-Methyl {[1-(2-chlorophenyl)-2-nitroethyl]sulfanyl}acetate (Racemate)

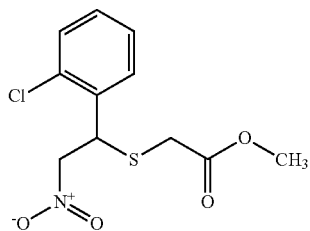

Under argon and at −30° C., a solution of methylsulfanyl acetate (578 mg, 5.45 mmol) in dichloromethane (25 ml) was added to a solution of 1-chloro-2-[(E)-2-nitrovinyl]benzene (1.00 g, 5.45 mmol) in dichloromethane (50 ml), and the mixture was stirred at −30° C. for 2 h and at RT for 16 h. Subsequently, the mixture was concentrated and the residue was dissolved in acetonitrile and purified by preparative HPLC (Method 16). The combined target fractions were concentrated and the residue was dried under reduced pressure. This gave 1.52 g (100% purity, 97% of theory) of the title compound.

LC-MS (Method 2): R$_t$=0.96 min; MS (ESIpos): m/z=307

$^1$H-NMR (400 MHz, DMSO-d6) δ [ppm]: 7.62-7.59 (m, 1H), 7.52-7.48 (m, 1H), 7.40-7.32 (m, 2H), 5.35 (dd, 1H), 5.29 (dd, 1H), 5.13 (dd, 1H), 3.60 (s, 3H), 3.59 (d, 1H), 3.43 (d, 1H).

Example 64A (+/−)-tert-Butyl 4-(6-chloro-2,3-difluorophenyl)-4-cyanobutanoate (Racemate)

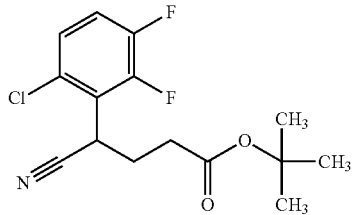 [SMILES: CC(C)(C)OC(=O)CCC(C#N)c1c(Cl)ccc(F)c1F]

To a solution of (6-chloro-2,3-difluorophenyl)acetonitrile (2.23 g, 11.9 mmol, not corrected for purity, Example 13A) in THF (15 ml) under argon was added gradually while stirring, at −78° C., a 2 M solution of LDA in THF (7.1 ml, 14 mmol). The mixture was allowed to come to 0° C. and, after 15 min, cooled back down again to −78° C. Subsequently, a solution of tert-butyl 3-bromopropanoate (4.5 ml, 28 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water (50 ml) and ethyl acetate (100 ml) were gradually added at about 0° C. to the mixture, which was agitated. After phase separation, the aqueous phase was extracted once with ethyl acetate (50 ml). The combined organic phases were washed once with saturated aqueous sodium chloride solution (80 ml), dried over sodium sulfate, filtered and concentrated, and the residue was taken up in dichloromethane and purified by flash column chromatography (50 g silica gel Biotage Snap-Cartridge Ultra, cyclohexane/ethyl acetate gradient 93:7→7:3, Isolera One). The combined target fractions were concentrated and the residue was dried under reduced pressure. This gave 2.29 g (83% purity, 51% of theory) of the title compound.

LC-MS (Method 1): R$_t$=2.17 min; MS (ESIpos): m/z=316 [M+H]$^+$ $^1$H-NMR (400 MHz, DMSO-d6) δ [ppm]: 7.73-7.53 (m, 1H), 7.52-7.41 (m, 1H), 4.68 (t, 1H), 2.43-2.32 (m, 2H), 2.32-2.18 (m, 1H), 2.18-2.04 (m, 1H), 1.37 (s, 9H).

Example 65A (+/−)-Methyl 4-cyano-4-[2-(trifluoromethyl)phenyl]butanoate (Racemate)

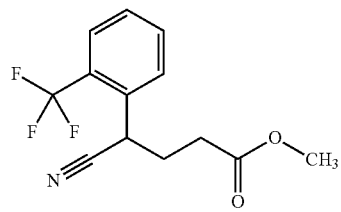 [SMILES: COC(=O)CCC(C#N)c1ccccc1C(F)(F)F]

To a solution of [2-(trifluoromethyl)phenyl]acetonitrile (5.00 g, 27.0 mmol) in THF (15 ml) under argon was added gradually while stirring, at −78° C., a 2 M solution of LDA in THF (16 ml, 32 mmol). The mixture was allowed to come to 0° C. and, after 15 min, cooled back down again to −78° C. Subsequently, a solution of methyl 3-bromopropanoate (5.41 g, 32.4 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (50 g silica gel Biotage Snap-Cartridge Ultra, cyclohexane/ethyl acetate gradient 93:7→7:3, Isolera One). The combined target fractions were concentrated and the residue was dried under reduced pressure. This gave 4.97 g (98% purity, 66% of theory) of the title compound.

LC-MS (Method 1): R$_t$=1.82 min $^1$H-NMR (400 MHz, DMSO-d6) δ [ppm]: 7.92-7.75 (m, 3H), 7.67-7.56 (m, 1H), 4.39 (dd, 1H), 3.59 (s, 3H), 2.57-2.43 (m, 2H, partially obscured), 2.37-2.23 (m, 1H), 2.22-2.09 (m, 1H).

Example 66A (+/−)-tert-Butyl 4-cyano-4-(5-fluoro-2-methylphenyl)butanoate (Racemate)

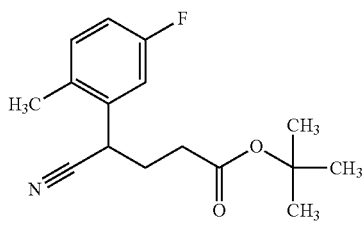 [SMILES: Cc1ccc(F)cc1C(C#N)CCC(=O)OC(C)(C)C]

To a solution of (5-fluoro-2-methylphenyl)acetonitrile (4.00 g, 26.8 mmol) in THF (30 ml) under argon was added gradually while stirring, at −78° C., a 2 M solution of LDA in THF (16 ml, 32 mmol). The mixture was allowed to come to 0° C. and, after 15 min, cooled back down again to −78° C. Subsequently, a solution of tert-butyl 3-bromopropanoate (5.1 ml, 32 mmol) in THF (20 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 4.94 g (100% purity, 66% of theory) of the title compound.

LC-MS (Method 1): $R_t$=2.18 min; MS (ESIpos): m/z=278 [M+H]$^+$ $^1$H-NMR (400 MHz, DMSO-d6) δ [ppm]: 7.29 (dd, 1H), 7.23 (dd, 1H), 7.11 (td, 1H), 4.34 (dd, 1H), 2.42-2.34 (m, 2H), 2.30 (s, 3H), 2.17-1.96 (m, 2H), 1.40 (s, 9H).

Example 67A (+/−)-tert-Butyl 4-cyano-4-[2-(trifluoromethoxy)phenyl]butanoate (Racemate)

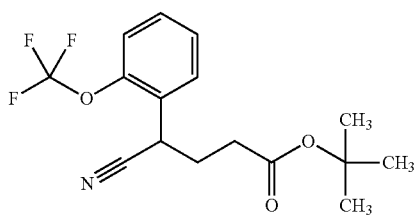 [SMILES: CC(C)(C)OC(=O)CCC(C#N)c1ccccc1OC(F)(F)F]

To a solution of [2-(trifluoromethoxy)phenyl]acetonitrile (5.00 g, 24.9 mmol) in THF (65 ml) under argon was added gradually while stirring, at −78° C., a 2 M solution of LDA in THF (15 ml, 30 mmol). The mixture was allowed to come to 0° C. and, after 15 min, cooled back down again to −78° C. Subsequently, a solution of tert-butyl 3-bromopropanoate (4.7 ml, 30 mmol) in THF (45 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 3.13 g (80% purity, 31% of theory) of the title compound.

LC-MS (Method 1): $R_t$=2.27 min; MS (ESIpos): m/z=330 [M+H]$^+$

Example 68A (+/−)-tert-Butyl 4-cyano-4-(pyridin-2-yl)butanoate (Racemate)

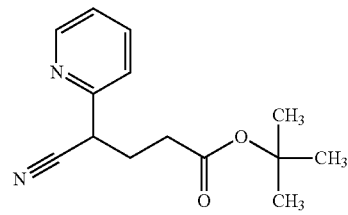

Reaction A: Pyridin-2-ylacetonitrile (27 mg, 229 μmol), tert-butyl acrylate (50 μl, 340 μmol) and potassium carbonate (63 mg, 457 μmol) were taken up in DMF (0.3 ml) and heated in a microwave (100° C.) for 1 h. The reaction mixture was concentrated under reduced pressure. The LC-MS spectrum of the crude product showed about 10% (UV) of a product having the desired mass.

Reaction B: Pyridin-2-ylacetonitrile (988 mg, 8.36 mmol) was taken up in DMF (10 ml), and sodium hydride (401 mg, 60% purity, 10.0 mmol) was added slowly (evolution of gas). After 10 min at RT, tert-butyl acrylate (1.2 ml, 8.4 mmol) was added slowly, and the reaction mixture was stirred at RT for 3 h. The reaction mixture was added to water, extracted with dichloromethane, dried (sodium sulfate) and concentrated. The LC-MS spectrum of the crude product showed about 8% (UV) of a product having the desired mass.

Reaction C: In a flask that had been dried by heating, tetrahydrofuran (10 ml) was initially charged under nitrogen, pyridin-2-ylacetonitrile (1.09 g, 9.23 mmol) was added and, at −78° C., a 2 M solution of LDA in THF (6.9 ml, 14 mmol) was slowly added dropwise. The mixture was stirred at −78° C. for 10 min and at 0° C. for 20 min and then once more cooled to −78° C. Subsequently, tert-butyl 3-bromopropanoate (2.32 g, 11.1 mmol) was added very slowly, and after complete addition the mixture was stirred at −78° C. for 1 h. The cooling bath was removed, and the reaction mixture was stirred for a further 20 h while warming to RT. The mixture was added to water and extracted with ethyl acetate, and the organic phase was washed with saturated sodium chloride solution, dried (sodium sulfate) and concentrated. The LC-MS spectrum of the crude product showed about 17% (UV) of a product having the desired mass.

The combined crude products from Reaction A, Reaction B and Reaction C were purified chromatographically (Biotage Isolera Four, LiChroprep RP-18 (40-63 μm); gradient 5%-45% acetonitrile in 0.1% aqueous ammonia solution). This gave 799 mg (48% purity, 9% of theory) of the title compound.

LC-MS (Method 6): $R_t$=1.09 min; MS (ESIpos): m/z=247 [M+H]$^+$

Example 69A (+/−)-tert-Butyl 4-cyano-4-[2-fluoro-6-(trifluoromethyl)phenyl]butanoate (Racemate)

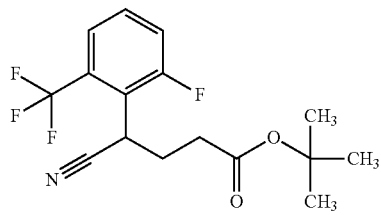 [SMILES: CC(C)(C)OC(=O)CCC(C#N)c1c(F)cccc1C(F)(F)F]

The reaction was conducted under argon. To prepare an LDA solution, butyllithium (1.6 M solution in hexane, 27 ml, 43 mmol) was added gradually at −15° C. to a solution of diisopropylamine (6.2 ml, 44 mmol) in THF (27 ml), and the mixture was stirred at 0° C. for a further 10 min. This solution was slowly added dropwise to a solution, cooled to −78° C., of [2-fluoro-6-(trifluoromethyl)phenyl]acetonitrile (8.01 g, 98% purity, 38.7 mmol, CAS-RN 179946-34-0, commercially available) in 74 ml of THF. On completion of addition, the cooling bath was removed, the mixture was allowed to come to 0° C. and, after 15 min, was cooled again to −78° C. Subsequently, a solution of tert-butyl 3-bromopropanoate (8.0 ml, 97% purity, 46 mmol) in 27 ml of THF was slowly added dropwise and the mixture was stirred at −78° C. for a further 1 h. The cooling bath was removed, and stirring of the reaction mixture at RT was continued overnight. For workup, an ammonium chloride solution (10% in water, 300 ml) was added, and the mixture was stirred vigorously for 5 min and then extracted twice with ethyl acetate. The combined organic phases were washed successively, twice each time, with 1 M hydrochloric acid, a saturated sodium bicarbonate solution and a saturated sodium chloride solution, then dried over sodium sulfate and concentrated under reduced pressure. The residue was dissolved in a mixture of cyclohexane, a little ethyl acetate and dichloromethane, and purified by flash column chromatography on silica gel (cyclohexane/ethyl acetate gradient 100:0 to 70:30). The combined target fractions were concentrated, and the residue was dried under reduced pressure and then purified further by preparative HPLC (Method 27). The product-containing fractions were concentrated, and the residue was dried under reduced pressure. This gave 4.52 g (100% purity, 35% of theory) of the title compound.

LC-MS (Method 1): $R_t$=2.23 min; MS (ESIpos): m/z=332 [M+H]$^+$ $^1$H-NMR (400 MHz, DMSO-d6) δ [ppm]: 1.219 (0.06), 1.379 (16.00), 1.536 (0.07), 2.073 (0.16), 2.091 (0.22), 2.107 (0.28), 2.125 (0.26), 2.144 (0.10), 2.213 (0.07), 2.231 (0.19), 2.250 (0.22), 2.267 (0.18), 2.285 (0.13), 2.302 (0.08), 2.327 (0.07), 2.365 (0.07), 2.384 (0.36), 2.393 (0.38), 2.402 (0.59), 2.410 (0.56), 2.420 (0.29), 2.428 (0.27), 2.452 (0.06), 2.669 (0.06), 4.373 (0.20), 4.390 (0.39), 4.407 (0.19), 7.698 (0.31), 7.711 (1.11), 7.722 (0.54), 7.748 (0.35), 7.766 (0.11).

Example 70A (+/−)-tert-Butyl 4-cyano-4-(2,3,5,6-tetrafluorophenyl)butanoate (Racemate)

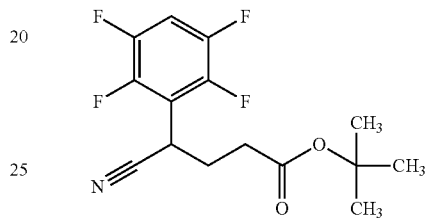

The reaction was conducted under argon. To prepare an LDA solution, butyllithium (1.6 M solution in hexane, 9 ml, 14 mmol) was added gradually at −15° C. to a solution of diisopropylamine (2.1 ml, 15 mmol) in THF (9 ml), and the mixture was stirred at 0° C. for a further 10 min. This solution was slowly added dropwise to a solution, cooled to −78° C., of (2,3,5,6-tetrafluorophenyl)acetonitrile (2.47 g, 13.1 mmol, Example 14A) in THF (25 ml). On completion of addition, the cooling bath was removed, the mixture was allowed to come to 0° C. and, after 15 min, was cooled again to −78° C. Subsequently, a solution of tert-butyl 3-bromopropanoate (2.5 ml, 16 mmol) in THF (9 ml) was slowly added dropwise and the mixture was stirred at −78° C. for a further 1 h. The cooling bath was removed, and stirring of the reaction mixture at RT was continued overnight. For workup, an ammonium chloride solution (10% in 100 ml of water) was added, and the mixture was stirred vigorously for 5 min and then extracted twice with ethyl acetate. The combined organic phases were washed successively, twice each time, with 1 M hydrochloric acid, a saturated sodium bicarbonate solution and a saturated sodium chloride solution, then dried over sodium sulfate and concentrated under reduced pressure. The residue was purified by flash column chromatography on silica gel (Isolera, 50 g Ultra Snap column, cyclohexane/ethyl acetate gradient). The combined target fractions were concentrated, and the residue was dried under reduced pressure. This gave 3.43 g (100% purity, 83% of theory) of the title compound.

LC-MS (Method 1): $R_t$=2.11 min; MS (ESIpos): m/z=318 [M+H]$^+$ $^1$H-NMR (400 MHz, DMSO-d6) δ [ppm]: 1.211 (0.06), 1.347 (1.57), 1.370 (16.00), 1.397 (0.08), 1.527 (0.06), 2.058 (0.05), 2.076 (0.15), 2.095 (0.19), 2.111 (0.29), 2.129 (0.28), 2.148 (0.11), 2.167 (0.08), 2.185 (0.27), 2.202 (0.33), 2.220 (0.25), 2.236 (0.15), 2.254 (0.08), 2.283 (0.02), 2.311 (0.06), 2.356 (0.68), 2.374 (1.21), 2.392 (0.47), 2.419 (0.03), 2.444 (0.04), 2.669 (0.03), 2.709 (0.03), 4.612 (0.25), 4.631 (0.50), 4.650 (0.24), 7.944 (0.06), 7.963 (0.13), 7.970 (0.14), 7.989 (0.27), 8.009 (0.15), 8.016 (0.15), 8.035 (0.08).

Example 71A (+/−)-tert-Butyl 4-cyano-4-(2,3,5-trifluorophenyl)butanoate (Racemate)

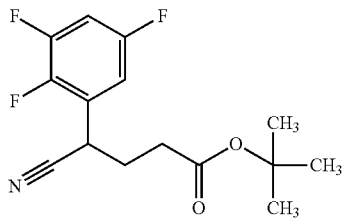 [SMILES: CC(C)(C)OC(=O)CCC(C#N)c1cc(F)cc(F)c1F]

Under argon and at −78° C. an LDA solution (2 M in THF, 7.8 ml, 16 mmol) was added slowly, with stirring, to a solution of (2,3,5-trifluorophenyl)acetonitrile (2.50 g, 97% purity, 14.2 mmol, CAS-RN 243666-14-0, commercially available) in THF (15 ml). The mixture was allowed to come to 0° C. and, after 15 min, cooled back down again to −78° C. Subsequently, a solution of tert-butyl 3-bromopropanoate (3.36 g, 97% purity, 15.6 mmol) in 5 ml of THF was slowly added dropwise with stirring at −78° C. Stirring of the mixture was continued overnight, in the course of which the cooling bath (dry ice/acetone) was allowed to come gradually to RT. Subsequently, ethyl acetate and water (100 ml each) were added to the mixture. The phases were separated. The aqueous phase was extracted twice with ethyl acetate. The combined organic phases were washed with saturated aqueous sodium chloride solution, dried over sodium sulfate and concentrated. The residue was taken up in dichloromethane and purified by flash column chromatography (Biotage 100 g silica gel cartridge, cyclohexane/ethyl acetate gradient 97:3 to 90:10). This gave two fractions that were concentrated separately under reduced pressure. After drying under reduced pressure, the second fraction gave 600 mg (100% purity, 14% of theory) of a first batch of the title compound. The contaminated first fractions were repurified by preparative HPLC (Method 28). The combined target fractions were concentrated, and the residue was dried under reduced pressure. This gave 1.30 g (100% purity, 31% of theory, see analysis) of a second batch of the title compound.

LC-MS (Method 1): $R_t$=2.15 min; MS (ESIpos): m/z=300 [M+H]$^+$ $^1$H-NMR (400 MHz, DMSO-d6) δ [ppm]: 1.220 (0.06), 1.379 (16.00), 1.536 (0.06), 2.051 (0.05), 2.070 (0.16), 2.088 (0.22), 2.104 (0.34), 2.122 (0.34), 2.141 (0.15), 2.165 (0.26), 2.182 (0.30), 2.200 (0.23), 2.216 (0.13), 2.235 (0.08), 2.329 (0.77), 2.348 (1.15), 2.366 (0.40), 2.671 (0.02), 2.711 (0.02), 4.489 (0.33), 4.508 (0.61), 4.526 (0.31), 7.253 (0.16), 7.259 (0.21), 7.267 (0.22), 7.272 (0.21), 7.281 (0.22), 7.287 (0.16), 7.293 (0.11), 7.576 (0.08), 7.583 (0.09), 7.592 (0.10), 7.599 (0.16), 7.603 (0.16), 7.612 (0.15), 7.620 (0.16), 7.625 (0.16), 7.632 (0.10), 7.639 (0.09), 7.647 (0.09).

Example 72A (+/−)-tert-Butyl 4-cyano-4-(2,3,6-trichlorophenyl)butanoate (Racemate)

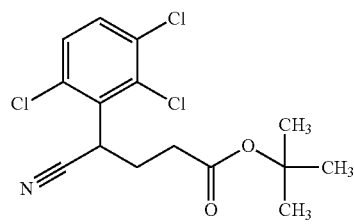 [SMILES: CC(C)(C)OC(=O)CCC(C#N)c1c(Cl)ccc(Cl)c1Cl]

The reaction was conducted under argon. To prepare an LDA solution, butyllithium (1.6 M solution in hexane, 30 ml, 48 mmol) was added gradually at −15° C. to a solution of diisopropylamine (7.1 ml, 51 mmol) in THF (30 ml), and the mixture was stirred at 0° C. for a further 10 min. This solution was slowly added dropwise to a solution, cooled to −78° C., of (2,3,6-trichlorophenyl)acetonitrile (10.0 g, 97% purity, 44.0 mmol, CAS-RN 3215-65-4, commercially available) in THF (84 ml). On completion of addition, the cooling bath was removed, the mixture was allowed to come to 0° C. and, after 15 min, was cooled again to −78° C. Subsequently, a solution of tert-butyl 3-bromopropanoate (9.1 ml, 97% purity, 53 mmol) in THF (30 ml) was slowly added dropwise and the mixture was stirred at −78° C. for a further 1 h. The cooling bath was removed, and stirring of the reaction mixture at RT was continued overnight. For workup, an ammonium chloride solution (10% in 300 ml of water) was added, and the mixture was stirred vigorously for 5 min and then extracted twice with ethyl acetate. The combined organic phases were washed successively, twice each time, with 1 M hydrochloric acid, a saturated sodium bicarbonate solution and a saturated sodium chloride solution, then dried over sodium sulfate and concentrated under reduced pressure. The residue was purified by preparative HPLC (Method 27). The combined target fractions were concentrated, and the residue was dried under reduced pressure. This gave 10.2 g (95% purity, 63% of theory) of the title compound.

LC-MS (Method 1): $R_t$=2.41 min; MS (ESIpos): m/z=348 [M+H]$^+$ $^1$H-NMR (500 MHz, DMSO-d6) δ [ppm]: 1.382 (16.00), 1.997 (0.45), 2.316 (0.42), 2.367 (0.45), 2.381 (0.71), 2.403 (0.63), 3.322 (0.80), 5.002 (0.48), 7.620 (0.69), 7.637 (0.90), 7.746 (0.92), 7.763 (0.70).

Example 73A (+/−)-tert-Butyl 5-(2-chlorophenyl)-5-cyanopentanoate (Racemate)

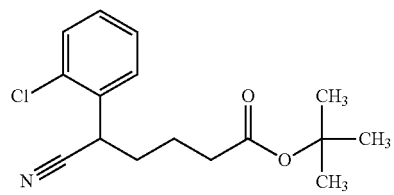 [SMILES: CC(C)(C)OC(=O)CCCC(C#N)c1ccccc1Cl]

To a solution of (2-chlorophenyl)acetonitrile (2.12 g, 14.0 mmol) in THF (20 ml) under argon was added gradually while stirring, at −78° C., a 2 M solution of LDA in THF (8.4 ml, 17 mmol). The mixture was allowed to come to 0° C. and, after 15 min, cooled back down again to −78° C. Subsequently, a solution of tert-butyl 4-bromobutanoate (3.75 g, 16.8 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (70 ml of each) were gradually added at about 0° C. to the mixture, which was agitated. After phase separation, the aqueous phase was extracted once with ethyl acetate (70 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated and the residue was dried under reduced pressure. This gave 2.70 g (96% purity, 63% of theory) of the title compound.

LC-MS (Method 1): $R_t$=2.31 min; MS (ESIpos): m/z=294 [M+H]$^+$ $^1$H-NMR (400 MHz, DMSO-d6) δ [ppm]: 7.62-7.50 (m, 2H), 7.49-7.37 (m, 2H), 4.49 (dd, 1H), 2.28 (td, 2H), 1.99-1.78 (m, 2H), 1.72-1.51 (m, 2H), 1.38 (s, 9H).

Example 74A (+/−)-tert-Butyl 5-(2-chlorophenyl)-5-cyanohexanoate (Racemate)

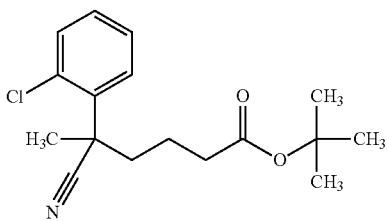 [SMILES: CC(C)(C)OC(=O)CCCC(C)(C#N)c1ccccc1Cl]

To a solution of 2-(2-chlorophenyl)propanenitrile (2.32 g, 14.0 mmol, CAS-RN 75920-46-6, commercially available) in THF (20 ml) under argon was added gradually while stirring, at −78° C., a 2 M solution of LDA in THF (11 ml, 21 mmol). The mixture was allowed to come to 0° C. and, after 15 min, cooled back down again to −78° C. Subsequently, a solution of tert-butyl 4-bromobutanoate (3.75 g, 16.8 mmol) in THF (10 ml) was slowly added dropwise thereto at −78° C. while stirring. Stirring of the mixture was continued overnight, in the course of which the cooling bath (dry ice/acetone) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated aqueous sodium chloride solution (150 ml), dried over sodium sulfate, filtered and concentrated, and the residue was taken up in dichloromethane and purified by flash column chromatography (100 g silica gel Biotage Snap-Cartridge KP-Sil, cyclohexane/ethyl acetate gradient 93:7→7:3, Isolera One). The combined target fractions were concentrated and the residue was dried under reduced pressure. This gave 2.47 g (98% purity, 56% of theory) of the title compound.

LC-MS (Method 1): $R_t$=2.34 min; MS (ESIpos): m/z=308 [M+H]$^+$ $^1$H-NMR (400 MHz, DMSO-d6) δ [ppm]: 1.217 (0.06), 1.377 (16.00), 1.429 (0.19), 1.454 (0.11), 1.476 (0.30), 1.494 (0.46), 1.514 (0.33), 1.533 (0.21), 1.808 (3.89), 1.939 (0.15), 1.960 (0.23), 1.973 (0.21), 1.982 (0.16), 1.989 (0.18), 2.000 (0.20), 2.015 (0.16), 2.212 (0.19), 2.227 (0.84), 2.244 (1.47), 2.254 (0.27), 2.262 (0.65), 2.288 (0.13), 7.392 (0.13), 7.405 (0.36), 7.410 (0.45), 7.414 (0.39), 7.421 (0.91), 7.429 (0.53), 7.433 (0.48), 7.438 (0.49), 7.451 (0.17), 7.528 (0.54), 7.534 (0.41), 7.547 (0.27), 7.552 (0.40), 7.564 (0.52), 7.569 (0.34), 7.582 (0.35), 7.588 (0.37).

$^1$H-NMR (400 MHz, DMSO-d6) δ [ppm]: 7.61-7.51 (m, 2H), 7.48-7.36 (m, 2H), 2.31-2.18 (m, 3H), 2.04-1.92 (m, 1H), 1.81 (s, 3H), 1.57-1.44 (m, 2H), 1.38 (s, 9H).

Example 75A (+/−)-Methyl 3-amino-2-phenylpropanoate hydrochloride (Racemate)

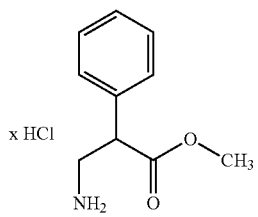

At RT, oxalyl chloride (740 μl, 8.5 mmol) was slowly added to a suspension of (+/−)-3-amino-2-phenylpropanoic acid (700 mg, 4.24 mmol) in methanol (10 ml), and the mixture was stirred at RT for 5 days. Then the mixture was concentrated. Repeatedly, dichloromethane was added to the residue and the mixture was re-concentrated. Subsequently, the residue was dried under reduced pressure. This gave 933 mg (95% purity, 97% of theory) of the title compound.

LC-MS (Method 4): $R_t$=0.93 min; MS (ESIpos): m/z=180 [M+H]$^+$

1H-NMR (400 MHz, DMSO-d6): δ [ppm]=8.20 (br. s, 3H), 7.63-7.10 (m, 5H), 4.11 (dd, 1H), 3.64 (s, 3H), 3.46 (dd, 1H), 3.07 (dd, 1H).

Example 76A (+/−)-Ethyl 3-amino-2-(2-chlorophenyl)propanoate (Racemate)

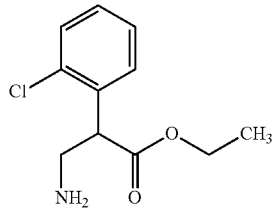

Raney nickel (1.13 g, 19.2 mmol) was added to a solution of (+/−)-ethyl (2-chlorophenyl)(cyano)acetate (8.60 g, 38.5 mmol, Example 15A) in ethanol (140 ml), and the mixture was hydrogenated at 3 bar for 20 h. Subsequently, the catalyst was filtered off through kieselguhr and washed with ethanol, and the mother liquor was concentrated. The residue was taken up in dichloromethane and purified by flash column chromatography (200 g silica gel Biotage Snap-Cartridge KP-Sil, dichloromethane/methanol 40:1). The combined target fractions were concentrated and the residue was dried under reduced pressure. This gave 869 mg (87% purity, 9% of theory) of the title compound.

LC-MS (Method 4): $R_t$=1.19 min; MS (ESIpos): m/z=228 [M+H]$^+$ $^1$H-NMR (400 MHz, DMSO-d6): δ [ppm]=7.50-7.44 (m, 1H), 7.43-7.26 (m, 3H), 4.15-4.03 (m, 3H), 3.10 (dd, 1H), 2.83 (dd, 1H), 1.54 (br. s, 2H), 1.14 (t, 3H).

Example 77A (+/−)-Methyl 3-amino-2-(2-methoxyphenyl)propanoate hydrochloride (Racemate)

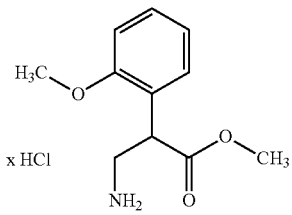

With cooling using an ice/acetone bath, oxalyl chloride (1.0 ml, 12 mmol) was slowly added dropwise to a solution of (+/−)-3-amino-2-(2-methoxyphenyl)propanoic acid hydrochloride (1.39 g, 6.00 mmol, CAS-RN 91012-74-7, commercially available) in methanol (14 ml, 350 mmol), and the mixture was stirred at RT for 24 h. Then the mixture was concentrated. Repeatedly, dichloromethane was added to the residue and the mixture was re-concentrated. Subsequently, the residue was dried under reduced pressure. This gave 1.83 g (89% purity, ">100% of theory", contains solvent) of the title compound.

LC-MS (Method 4): $R_t$=0.94 min; MS (ESIpos): m/z=210 [M+H]$^+$ $^1$H-NMR (400 MHz, DMSO-d6) δ [ppm]: 3.373 (1.52), 3.394 (1.49), 3.425 (1.14), 3.716 (5.40), 3.766 (1.44), 3.780 (16.00), 3.805 (5.37), 6.936 (0.77), 6.939 (0.84), 6.955 (1.68), 6.958 (1.78), 6.974 (0.96), 6.976 (0.99), 7.042 (1.55), 7.063 (1.84), 7.182 (1.39), 7.187 (1.54), 7.201 (1.21), 7.205 (1.25), 7.306 (0.96), 7.311 (0.89), 7.325 (1.25), 7.345 (0.73), 7.350 (0.64), 8.079 (0.97).

$^1$H-NMR (400 MHz, DMSO-d6): δ [ppm]=8.08 (br. s, 2H), 7.36-7.29 (m, 1H), 7.19 (dd, 1H), 7.05 (d, 1H), 6.99-6.92 (m, 1H), 4.30-4.22 (m, 1H), 3.81 (s, 1H), 3.78 (s, 3H), 3.72 (s, 1H), 3.62 (s, 3H), 3.45-3.35 (m, 1H, obscured), 3.02-2.93 (m, 1H).

Example 78A (+/−)-Methyl 3-amino-2-(4-fluorophenyl)propanoate hydrochloride (Racemate)

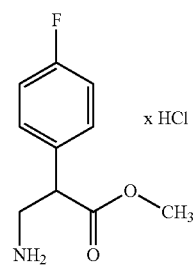

With cooling using an ice/acetone bath, oxalyl chloride (400 μl, 4.6 mmol) was slowly added dropwise to a solution of (+/−)-3-amino-2-(4-fluorophenyl)propanoic acid hydrochloride (500 mg, 2.28 mmol, CAS-No. 15032-53-8) in methanol (5.4 ml, 130 mmol), and the mixture was stirred at RT for 24 h. Then the mixture was concentrated. Repeatedly, dichloromethane was added to the residue and the mixture was re-concentrated. Subsequently, the residue was dried under reduced pressure. This gave 570 mg (100% purity, ">100% of theory", contains solvent) of the title compound.

LC-MS (Method 4): $R_t$=0.99 min; MS (ESIpos): m/z=198 [M+H]$^+$ $^1$H-NMR (400 MHz, DMSO-d6) δ [ppm]: 3.428 (0.95), 3.449 (0.95), 3.639 (16.00), 3.680 (1.34), 7.204 (1.44), 7.226 (3.36), 7.248 (1.99), 7.342 (2.08), 7.348 (0.90), 7.355 (2.25), 7.364 (1.75), 7.377 (1.52), 8.125 (1.09).

Example 79A (+/−)-Methyl 3-amino-2-hydroxy-2-phenylpropanoate hydrochloride (Racemate)

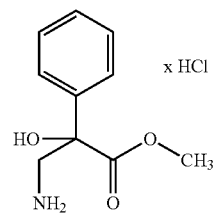

For 15 min, hydrogen chloride was passed through a suspension of (+/−)-3-amino-2-hydroxy-2-phenylpropanoic acid (4.0 g, 22.10 mmol, preparable according to *Justus Liebigs Annalen der Chemie* 1961, 639, 166-180) in methanol (600 ml). The suspension turned into a solution. The reaction mixture was then stirred under reflux for 2.5 h. After cooling to RT, the mixture was concentrated, and the residue was triturated with tert-butyl methyl ether. The solids present were filtered off and dried under reduced pressure. This gave 2.81 g (55% of theory) of the title compound.

Example 80A (+/−)-Ethyl 3-amino-2-[3-(trifluoromethyl)phenyl]propanoate (Racemate)

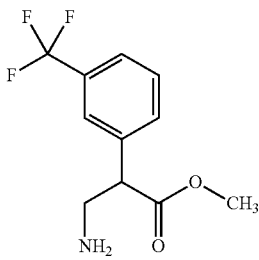 [SMILES: COC(=O)C(CN)c1cccc(C(F)(F)F)c1]

Raney nickel (288 mg, 4.90 mmol) was added to a solution of (+/−)-ethyl cyano[3-(trifluoromethyl)phenyl]acetate (1.26 g, 4.90 mmol, preparable according to U.S. Pat. No. 4,909,830, 1990 and *European Journal of Organic Chemistry* 2014, 27, 6025-6029) in tert-butanol (20 ml), and the mixture was hydrogenated at atmospheric pressure for two days. The catalyst was subsequently filtered off through kieselguhr, the mother liquor was concentrated and the residue was dried under reduced pressure. The residue was purified by preparative HPLC (Method 22). The combined target fractions were concentrated and the residue was dried under reduced pressure. This gave 63 mg (100% purity, 5% of theory) of the title compound.

LC-MS (Method 4): $R_t$=1.43 min; MS (ESIpos): m/z=262 [M+H]$^+$

Example 81A (+/−)-Ethyl 3-amino-2-(1,3-benzodioxol-5-yl)propanoate (Racemate)

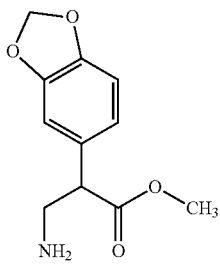 [SMILES: COC(=O)C(CN)c1ccc2c(c1)OCO2]

Raney nickel (189 mg, 3.22 mmol) was added to a solution of (+/−)-ethyl 1,3-benzodioxol-5-yl(cyano)acetate (750 mg, 3.22 mmol, preparable according to *Beilstein Journal of Organic Chemistry* 2015, 11, 875-883) in tert-butanol (13 ml), and the mixture was hydrogenated at atmospheric pressure for two days. The catalyst was subsequently filtered off through kieselguhr, the mother liquor was concentrated and the residue was dried under reduced pressure. This gave 150 mg (100% purity, 20% of theory) of the title compound.

LC-MS (Method 1): $R_t$=0.71 min; MS (ESIpos): m/z=238 [M+H]$^+$

Example 82A (+/−)-tert-Butyl 3-amino-2-(3-chloropyridin-2-yl)-2-methylpropanoate (Racemate)

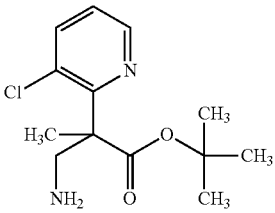 [SMILES: CC(C)(C)OC(=O)C(C)(CN)c1ncccc1Cl]

Raney nickel (198 mg, 3.37 mmol) was added to a solution of (+/−)-tert-butyl 2-(3-chloropyridin-2-yl)-2-cyanopropanoate (900 mg, not corrected for purity, "3.37 mmol", Example 16A) in tert-butanol (20 ml), and the mixture was hydrogenated at atmospheric pressure overnight. Subsequently, the catalyst was filtered off through kieselguhr and the mother liquor was concentrated. The residue was dried under reduced pressure and then purified by preparative HPLC (Method 16). The combined target fractions were concentrated and the residue was dried under reduced pressure. This gave 255 mg (100% purity, 28% of theory) of the title compound.

LC-MS (Method 1): $R_t$=1.04 min; MS (ESIpos): m/z=271 [M+H]$^+$

Example 83A (+/−)-tert-Butyl 3-amino-2-(2,6-difluorophenyl)-2-methylpropanoate (Racemate)

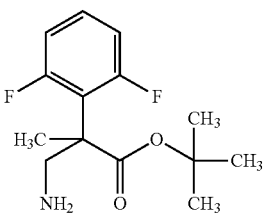 [SMILES: CC(C)(C)OC(=O)C(C)(CN)c1c(F)cccc1F]

Raney nickel (1.03 g, 17.5 mmol) was added to a solution of (+/−)-tert-butyl 2-cyano-2-(2,6-difluorophenyl)propanoate (6.80 g, 79% purity, 20.1 mmol, Example 17A) in tert-butanol (22 ml), and the mixture was hydrogenated at atmospheric pressure for three days. Subsequently, the catalyst was filtered off through kieselguhr and the mother liquor was concentrated. The residue was taken up in ethyl acetate and extracted twice with 1 M hydrochloric acid. The combined aqueous phases were made alkaline using 20% strength aqueous sodium hydroxide solution and then extracted twice with ethyl acetate. The combined organic phases were dried over magnesium sulfate, filtered and concentrated, and the residue was dried under reduced pressure. This gave 1.40 g (99% purity, 25% of theory) of the title compound.

LC-MS (Method 2): $R_t$=0.57 min; MS (ESIpos): m/z=216 [M-$^t$Bu+H]$^+$ $^1$H-NMR (400 MHz, DMSO-d6) δ [ppm]: 1.368 (16.00), 1.497 (1.28), 1.502 (2.25), 1.508 (1.24), 2.990 (0.85), 2.998 (0.74), 7.005 (0.55), 7.026 (0.72), 7.031 (0.61), 7.052 (0.67), 7.332 (0.44).

¹H-NMR (400 MHz, DMSO-d6): δ [ppm]=7.39-7.28 (m, 1H), 7.08-6.98 (m, 2H), 3.05-2.94 (m, 2H), 1.50 (t, 3H), 1.37 (s, 9H).

Example 84A (+/−)-Ethyl 3-amino-2-methyl-2-[3-(trifluoromethyl)phenyl]propanoate (Racemate)

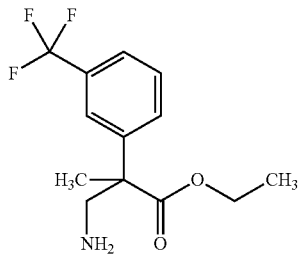 [SMILES: CCOC(=O)C(C)(CN)c1cccc(C(F)(F)F)c1]

Raney nickel (390 mg, 6.64 mmol) was added to a solution of (+/−)-ethyl 2-cyano-2-[3-(trifluoromethyl)phenyl]propanoate (1.80 g, 6.64 mmol, preparable according to WO 2016/94260 A1, p. 82, analogously to the preparation of (+/−)-ethyl 2-cyano-2-(4-fluorophenyl)propanoate) in tert-butanol (39 ml), and the mixture was hydrogenated at atmospheric pressure overnight. The catalyst was subsequently filtered off through kieselguhr, the mother liquor was concentrated and the residue was dried under reduced pressure. The residue was purified by preparative HPLC (Method 16). The combined target fractions were concentrated and the residue was dried under reduced pressure. This gave 615 mg (96% purity, 32% of theory) of the title compound.

LC-MS (Method 2): $R_t$=0.55 min; MS (ESIpos): m/z=276 [M+H]⁺

Example 85A (+/−)-tert-Butyl 3-amino-2-(3-methoxyphenyl)propanoate (Racemate)

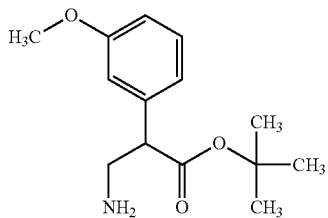

Raney nickel (1.00 g, 17.03 mmol) was added to a solution of (+/−)-tert-butyl cyano(3-methoxyphenyl)acetate (4.00 g, 16.2 mmol, Example 18A) in tert-butanol (75 ml), and the mixture was hydrogenated at atmospheric pressure for 5 days. The catalyst was subsequently filtered off through kieselguhr, the mother liquor was concentrated and the residue was dried under reduced pressure. The residue was then taken up in ethyl acetate and extracted with 1 M hydrochloric acid. The aqueous phase was subsequently made alkaline with concentrated aqueous sodium hydroxide solution and extracted with ethyl acetate. The combined organic phases were dried over sodium sulfate, filtered and concentrated, and the residue was dried under reduced pressure. This gave 750 mg (89% purity, 16% of theory) of the title compound.

LC-MS (Method 2): $R_t$=0.59 min; MS (ESIpos): m/z=252 [M+H]⁺

¹H-NMR (400 MHz, DMSO-d6): 5 [ppm]=7.24 (t, 1H), 6.86-6.76 (m, 3H), 3.73 (s, 3H), 3.48 (dd, 1H), 3.01 (dd, 1H), 2.73 (dd, 1H), 1.37 (s, 9H).

Example 86A (+/−)-tert-Butyl 3-amino-2-(3-chlorophenyl)propanoate (Racemate)

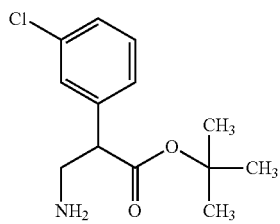 [SMILES: CC(C)(C)OC(=O)C(CN)c1cccc(Cl)c1]

Raney nickel (1.28 g, 21.9 mmol) was added to a solution of (+/−)-tert-butyl (3-chlorophenyl)(cyano)acetate (5.50 g, "21.9 mmol", not corrected for purity, Example 19A) in tert-butanol (95 ml), and the mixture was hydrogenated at atmospheric pressure for 5 days. The catalyst was subsequently filtered off through kieselguhr, the mother liquor was concentrated and the residue was dried under reduced pressure. The residue was then taken up in ethyl acetate (50 ml) and extracted with 1 M hydrochloric acid (80 ml). The aqueous phase was subsequently made alkaline with concentrated aqueous sodium hydroxide solution and extracted with ethyl acetate (70 ml). The combined organic phases were dried over sodium sulfate, filtered and concentrated, and the residue was dried under reduced pressure. This gave 500 mg (95% purity, "9%" of theory) of the title compound.

LC-MS (Method 1): $R_t$=1.11 min; MS (ESIpos): m/z=200 [M-ᵗBu+H]⁺

¹H-NMR (400 MHz, DMSO-d6): 5 [ppm]=7.42-7.29 (m, 3H), 7.26-7.20 (m, 1H), 3.60 (t, 1H), 3.08 (dd, 1H), 2.81 (dd, 1H), 1.37 (s, 9H).

Example 87A (+/−)-tert-Butyl 3-amino-2-(3-methylphenyl)propanoate (Racemate)

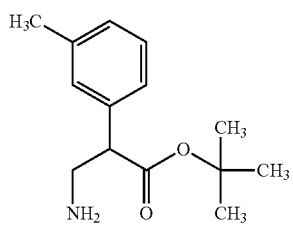 [SMILES: Cc1cccc(C(CN)C(=O)OC(C)(C)C)c1]

Raney nickel (812 mg, 13.8 mmol) was added to a solution of (+/−)-tert-butyl cyano(3-methylphenyl)acetate (3.20 g, 13.8 mmol, Example 20A) in tert-butanol (60 ml), and the mixture was hydrogenated at atmospheric pressure for 5 days. The catalyst was subsequently filtered off through kieselguhr, the mother liquor was concentrated and the residue was dried under reduced pressure. The residue was then taken up in ethyl acetate (50 ml) and extracted with 1 M hydrochloric acid (80 ml). The aqueous phase was subsequently made alkaline with concentrated aqueous sodium hydroxide solution and extracted with ethyl acetate (70 ml). The combined organic phases were dried over sodium sulfate, filtered and concentrated, and the residue was dried under reduced pressure. This gave 700 mg (90% purity, 19% of theory) of the title compound.

LC-MS (Method 2): $R_t$=0.63 min; MS (ESIpos): m/z=236 $[M+H]^+$ $^1$H-NMR (400 MHz, DMSO-d6) δ [ppm]: 1.366 (16.00), 1.384 (0.46), 1.399 (0.45), 2.282 (4.17), 3.451 (0.41), 7.019 (0.47), 7.049 (1.41), 7.068 (0.54), 7.185 (0.44), 7.203 (0.64).

$^1$H-NMR (400 MHz, DMSO-d6): δ [ppm]=7.25-7.15 (m, 1H), 7.09-6.99 (m, 3H), 3.45 (dd, 1H), 3.02 (dd, 1H), 2.71 (dd, 1H), 2.28 (s, 3H), 1.37 (s, 9H).

Example 88A (+/−)-tert-Butyl 3-amino-2-(2-fluoro-6-methoxyphenyl)propanoate (Racemate)

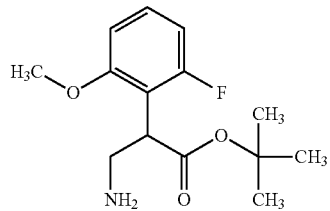

Palladium on carbon (26 mg, 10% purity, 24.3 μmol) was added to a solution of (+/−)-tert-butyl cyano(2-fluoro-6-methoxyphenyl)acetate (1.04 g, 62% purity, 2.43 mmol, Example 21A) in acetic acid (10 ml), and the mixture was hydrogenated at atmospheric pressure for 24 h. Subsequently, the catalyst was filtered off through kieselguhr and washed twice with acetic acid (2 ml each). The filtrate was diluted with water (100 ml) and extracted twice with ethyl acetate (50 ml each). Subsequently, the aqueous phase was adjusted to pH 8 with aqueous sodium hydroxide solution and extracted twice with ethyl acetate (100 ml each). The combined organic phases were dried over sodium sulfate, filtered and concentrated, and the residue was dried under reduced pressure. This gave 222 mg (71% purity, 24% of theory) of the title compound.

LC-MS (Method 1): $R_t$=0.96 min; MS (ESIpos): m/z=270 $[M+H]^+$

Example 89A (+/−)-tert-Butyl 3-amino-2-(2-methoxyphenyl)-2-methylpropanoate (Racemate)

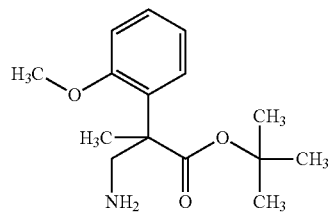

Raney nickel (292 mg, 4.97 mmol) was added to a solution of (+/−)-tert-butyl 2-cyano-2-(2-methoxyphenyl)propanoate (1.30 g, 4.97 mmol, Example 22A) in tert-butanol (25 ml), and the mixture was hydrogenated at atmospheric pressure overnight. Subsequently, the catalyst was filtered off through kieselguhr and the mother liquor was concentrated. The residue was dried under reduced pressure. This gave 1.31 g (70% purity, 69% of theory) of the title compound.

LC-MS (Method 1): $R_t$=1.02 min; MS (ESIpos): m/z=266 $[M+H]^+$

Example 90A (+/−)-tert-Butyl 3-amino-2-(2-chloro-6-fluorophenyl)-2-methylpropanoate (Racemate)

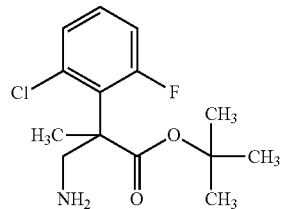 [SMILES: CC(C)(C)OC(=O)C(C)(CN)c1c(F)cccc1Cl]

Raney nickel (269 mg, 4.58 mmol) was added to a solution of (+/−)-tert-butyl 2-(2-chloro-6-fluorophenyl)-2-cyanopropanoate (1.30 g, 4.58 mmol, Example 23A) in tert-butanol (26 ml), and the mixture was hydrogenated at atmospheric pressure overnight. Subsequently, the catalyst was filtered off through kieselguhr and the mother liquor was concentrated. The residue was dried under reduced pressure. This gave 1.25 g (70% purity, 67% of theory) of the title compound.

LC-MS (Method 1): $R_t$=1.08 min; MS (ESIpos): m/z=288 $[M+H]^+$

Example 91A (+/−)-tert-Butyl 4-amino-3-(2-chlorophenyl)butanoate (Racemate)

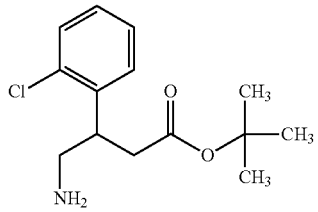 [SMILES: CC(C)(C)OC(=O)CC(CN)c1ccccc1Cl]

Raney nickel (22 mg, 376 µmol) was added to a solution of (+/−)-tert-butyl 3-(2-chlorophenyl)-3-cyanopropanoate (100 mg, 376 µmol, Example 24A) in tert-butanol (10 ml), and the mixture was hydrogenated at atmospheric pressure overnight. The catalyst was subsequently filtered off through kieselguhr and the mother liquor was purified by preparative HPLC (Method 22). This gave 87 mg (purity 100%, 86% of theory) of the title compound.

LC-MS (Method 1): $R_t$=0.99 min; MS (ESIpos): m/z=270 [M+H]$^+$ $^1$H-NMR (400 MHz, DMSO-d6) δ [ppm]: 1.200 (16.00), 1.212 (0.81), 2.683 (0.47), 2.708 (0.49), 2.811 (0.49), 2.825 (0.51), 3.053 (0.47), 7.305 (0.48), 7.308 (0.50), 7.365 (0.52), 7.460 (1.19), 7.480 (0.88), 7.483 (0.77), 7.939 (0.44).

Example 92A (+/−)-tert-Butyl 4-amino-3-(3-chlorophenyl)butanoate (Racemate)

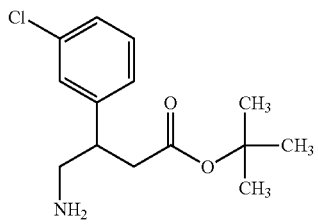 [SMILES: CC(C)(C)OC(=O)CC(CN)c1cccc(Cl)c1]

Raney nickel (157 mg, 2.67 mmol) was added to a solution of (+/−)-tert-butyl 3-(3-chlorophenyl)-3-cyanopropanoate (710 mg, 2.67 mmol, Example 25A) in tert-butanol (11.6 ml), and the mixture was hydrogenated at atmospheric pressure overnight. Subsequently, the catalyst was filtered off through kieselguhr and the mother liquor was concentrated. The residue was dried under reduced pressure. This gave 294 mg (purity 40%, 16% of theory) of the title compound.

LC-MS (Method 1): $R_t$=1.39 min; MS (ESIpos): m/z=270 [M+H]$^+$

Example 93A (+/−)-tert-Butyl 4-amino-3-(2-methylphenyl)butanoate (Racemate)

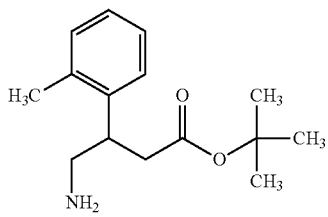 [SMILES: Cc1ccccc1C(CN)CC(=O)OC(C)(C)C]

Raney nickel (203 mg, 3.46 mmol) was added to a solution of (+/−)-tert-butyl 3-cyano-3-(2-methylphenyl)propanoate (850 mg, 3.46 mmol, Example 26A) in tert-butanol (15 ml), and the mixture was hydrogenated at atmospheric pressure overnight. Subsequently, the catalyst was filtered off through kieselguhr and the mother liquor was concentrated. This gave 724 mg (95% purity, 80% of theory) of the title compound.

LC-MS (Method 4): $R_t$=1.32 min; MS (ESIpos): m/z=250 [M+H]$^+$ $^1$H-NMR (400 MHz, DMSO-d6): δ [ppm]=7.18-7.02 (m, 4H), 3.31-3.22 (m, 1H), 2.76 (dd, 1H), 2.70-2.55 (m, 2H), 2.40 (dd, 1H), 2.32 (s, 3H), 1.18 (s, 9H)

Example 94A (+/−)-tert-Butyl 4-amino-3-(2,6-dichlorophenyl)butanoate (Racemate)

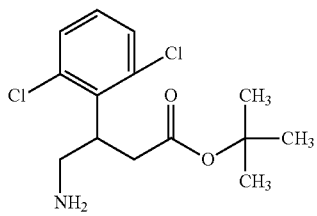

Raney nickel (133 mg, 2.27 mmol) was added to a solution of (+/−)-tert-butyl 3-cyano-3-(2,6-dichlorophenyl)propanoate (680 mg, 2.27 mmol, Example 27A) in tert-butanol (10 ml), and the mixture was hydrogenated at atmospheric pressure overnight. Subsequently, the catalyst was filtered off through kieselguhr and the mother liquor was concentrated. The residue was purified by preparative HPLC (Method 25). This gave 255 mg (94% purity, 35% of theory) of the title compound.

LC-MS (Method 4): $R_t$=1.46 min; MS (ESIpos): m/z=304 [M+H]$^+$

Example 95A (+/−)-tert-Butyl 4-amino-3-(3-methoxyphenyl)butanoate (Racemate)

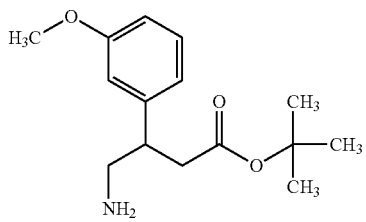 [SMILES: COc1cccc(C(CN)CC(=O)OC(C)(C)C)c1]

Raney nickel (88 mg, 1.49 mmol) was added to a solution of (+/−)-tert-butyl 3-cyano-3-(3-methoxyphenyl)propanoate (389 mg, 1.49 mmol, Example 28A) in tert-butanol (6.5 ml), and the mixture was hydrogenated at atmospheric pressure overnight. Subsequently, the catalyst was filtered off through kieselguhr and the mother liquor was concentrated and dried under reduced pressure. This gave 500 mg ("90% purity", ">100% of theory", contains solvent) of the title compound.

LC-MS (Method 4): $R_t$=1.26 min; MS (ESIpos): m/z=266 [M+H]$^+$

Example 96A (+/−)-tert-Butyl 4-amino-3-(3-chloropyridin-2-yl)-3-methylbutanoate (Racemate)

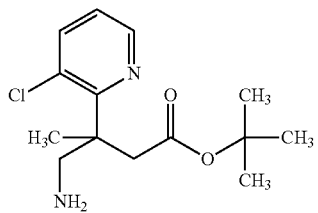

Raney nickel (209 mg, 3.56 mmol) was added to a solution of (+/−)-tert-butyl 3-(3-chloropyridin-2-yl)-3-cyanobutanoate (1.00 g, 3.56 mmol, Example 29A) in tert-butanol (21 ml), and the mixture was hydrogenated at atmospheric pressure overnight. The catalyst was subsequently filtered off through kieselguhr and the mother liquor was purified by preparative HPLC (Method 16). This gave 616 mg (100% purity, 61% of theory) of the title compound.

LC-MS (Method 2): $R_t$=0.62 min; MS (ESIpos): m/z=285 [M+H]$^+$

Example 97A (+/−)-tert-Butyl 4-amino-3-(2-chloro-6-fluorophenyl)butanoate (Racemate)

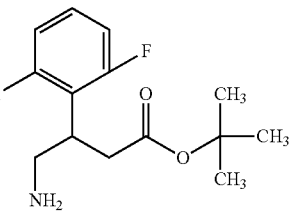

Method A:

Raney nickel (180 mg, 3.07 mmol) was added to a solution of (+/−)-tert-butyl 2-(2-chloro-6-fluorophenyl)-3-cyanopropanoate (870 mg, 3.07 mmol, Example 30A) in tert-butanol (13.4 ml), and the mixture was hydrogenated at atmospheric pressure for three days. Subsequently, the catalyst was filtered off through kieselguhr and the mother liquor was concentrated. This gave 551 mg (30% purity, 19% of theory) of the title compound.

LC-MS (Method 1): $R_t$=1.02 min; MS (ESIpos): m/z=288 [M+H]$^+$

Method B:

Raney nickel (7.15 g, 122 mmol) was added to a solution of (+/−)-tert-butyl 3-(2-chloro-6-fluorophenyl)-3-cyanopropanoate (43.9 g, 79% purity, 122 mmol, Example 30A) in tert-butanol (500 ml), and the mixture was hydrogenated at atmospheric pressure for four days. Subsequently, more Raney nickel (7.15 g, 122 mmol) was added, and the mixture was hydrogenated at atmospheric pressure for a further day. Subsequently, the catalyst was filtered off through kieselguhr and washed twice with tert-butanol (15 ml). The filtrate was concentrated and the residue was taken up in ethyl acetate (300 ml) and extracted twice with 1 M hydrochloric acid (250 ml). The combined aqueous phases were adjusted to pH 8-9 with saturated sodium carbonate solution and extracted twice with ethyl acetate (200 ml). The combined organic phases were dried over sodium sulfate, filtered and concentrated. This gave 20.11 g (98% purity, 57% of theory) of the title compound.

LC-MS (Method 2): $R_t$=0.55 min; MS (ESIpos): m/z=288 [M+H]$^+$ $^1$H-NMR (400 MHz, DMSO-$d_6$): δ [ppm]=7.36-7.22 (m, 2H), 7.21-7.07 (m, 1H), 3.73-3.54 (m, 1H), 2.87-2.72 (m, 3H), 2.70-2.56 (m, 1H), 1.20 (s, 9H).

Example 98A (+/−)-tert-Butyl 4-amino-3-(4-methylphenyl)butanoate (Racemate)

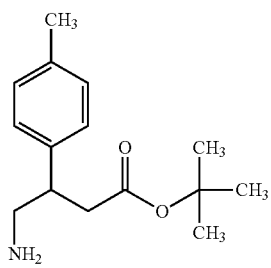 [SMILES: Cc1ccc(C(CN)CC(=O)OC(C)(C)C)cc1]

Raney nickel (60 mg, 1.03 mmol) was added to a solution of (+/−)-tert-butyl 3-cyano-3-(4-methylphenyl)propanoate (280 mg, 90% purity, 1.03 mmol, Example 31A) in tert-butanol (4.5 ml), and the mixture was hydrogenated at atmospheric pressure overnight. Subsequently, the catalyst was filtered off through kieselguhr and the mother liquor was concentrated. This gave 106 mg (97% purity, 40% of theory) of the title compound.

LC-MS (Method 2): $R_t$=0.66 min; MS (ESIpos): m/z=250 [M+H]$^+$

Example 99A (+/−)-tert-Butyl 4-amino-3-(3-methylphenyl)butanoate (Racemate)

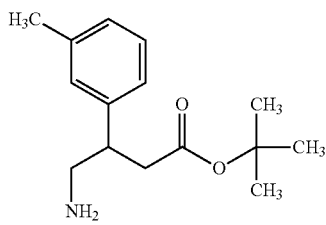

Raney nickel (42 mg, 709 μmol) was added to a solution of (+/−)-tert-butyl 3-cyano-3-(3-methylphenyl)propanoate (174 mg, 709 μmol, Example 32A) in tert-butanol (3.1 ml), and the mixture was hydrogenated at atmospheric pressure overnight. Subsequently, the catalyst was filtered off through kieselguhr and the mother liquor was concentrated. This gave 171 mg (77% purity, 74% of theory) of the title compound.

LC-MS (Method 1): $R_t$=1.02 min; MS (ESIpos): m/z=250 [M+H]$^+$

Example 100A (+/−)-tert-Butyl 4-amino-3-(2-methoxyphenyl)butanoate (Racemate)

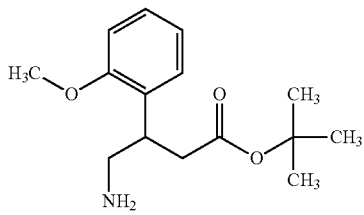

Raney nickel (1.08 g, 18.4 mmol) was added to a solution of (+/−)-tert-butyl 3-cyano-3-(2-methoxyphenyl)propanoate (4.80 g, 18.4 mmol, Example 33A) in tert-butanol (80 ml), and the mixture was hydrogenated at atmospheric pressure overnight. Subsequently, the catalyst was filtered off through kieselguhr and the mother liquor was concentrated. This gave 4.23 g (92% purity, 80% of theory) of the title compound.

LC-MS (Method 2): $R_t$=0.57 min; MS (ESIpos): m/z=266 [M+H]$^+$ $^1$H-NMR (400 MHz, DMSO-d6): δ [ppm]=7.21-7.14 (m, 1H), 7.11 (dd, 1H), 6.94 (d, 1H), 6.87 (td, 1H), 3.76 (s, 3H), 3.45-3.33 (m, 1H), 2.75-2.65 (m, 2H), 2.61 (dd, 1H), 2.43 (dd, 1H), 1.22 (s, 9H).

Example 101A (+/−)-tert-Butyl 4-amino-3-[2-(trifluoromethoxy)phenyl]butanoate (Racemate)

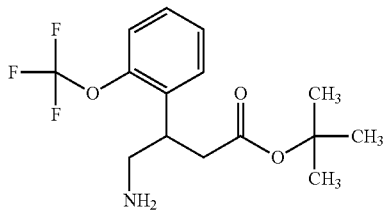 [SMILES: CC(C)(C)OC(=O)CC(CN)c1ccccc1OC(F)(F)F]

Raney nickel (669 mg, 11.4 mmol) was added to a solution of (+/−)-tert-butyl 3-cyano-3-[2-(trifluoromethoxy)phenyl]propanoate (6.70 g, 65% purity, 13.8 mmol, Example 34A) in tert-butanol (14 ml), and the mixture was hydrogenated at atmospheric pressure for 24 h. Subsequently, the catalyst was filtered off through kieselguhr and the mother liquor was concentrated. The residue was taken up in ethyl acetate and extracted twice with 1 M hydrochloric acid. The combined aqueous phases were made alkaline using 20% strength aqueous sodium hydroxide solution and then extracted twice with ethyl acetate. The combined organic phases were dried over magnesium sulfate, filtered and concentrated, and the residue was dried under reduced pressure. This gave 700 mg (100% purity, 16% of theory) of the title compound.

LC-MS (Method 2): $R_t$=0.71 min; MS (ESIpos): m/z=320 [M+H]$^+$

¹H-NMR (400 MHz, DMSO-d6): δ [ppm]=7.46-7.39 (m, 1H), 7.38-7.26 (m, 3H), 3.43-3.33 (m, 1H), 2.80 (dd, 1H), 2.75-2.59 (m, 2H), 2.42 (dd, 1H), 1.22 (s, 9H).

Example 102A (+/−)-tert-Butyl 4-amino-3-(pyridin-2-yl)butanoate (Racemate)

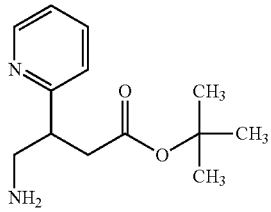 [SMILES: CC(C)(C)OC(=O)CC(CN)c1ccccn1]

Raney nickel (480 mg, 8.18 mmol) was added to a solution of (+/−)-tert-butyl 3-cyano-3-(pyridin-2-yl)propanoate (1.90 g, 8.18 mmol, Example 35A) in tert-butanol (35 ml), and the mixture was hydrogenated at atmospheric pressure overnight. Subsequently, the catalyst was filtered off through kieselguhr and the mother liquor was concentrated. The residue was purified by preparative HPLC [column: XBridge C18, 5 μm, 100 mm×30 mm; flow rate: 75 ml/min; detection: 210 nm; temperature: 40° C.; injection: 0.60 ml; mobile phase: 90% water/5% (acetonitrile/water 8:2)+1% ammonia solution/5% acetonitrile→0% water/5% (acetonitrile/water 8:2)+1% ammonia solution/95% acetonitrile; run time 8.5 min]. This gave 559 mg of a first batch of the title compound (80% purity, 23% of theory, see LC-MS) and 383 mg of a second batch of the title compound (27% purity, 5% of theory).

LC-MS (Method 4): $R_t$=1.06 min; MS (ESIpos): m/z=237 [M+H]⁺

Example 103A (+/−)-tert-Butyl 4-amino-3-[2-(trifluoromethyl)phenyl]butanoate (Racemate)

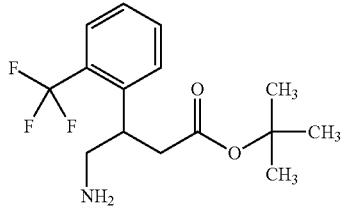 [SMILES: CC(C)(C)OC(=O)CC(CN)c1ccccc1C(F)(F)F]

Raney nickel (392 mg, 6.68 mmol) was added to a solution of (+/−)-tert-butyl 3-cyano-3-[2-(trifluoromethyl)phenyl]propanoate (2.00 g, 6.68 mmol, Example 36A) in tert-butanol (39 ml), and the mixture was hydrogenated at atmospheric pressure overnight. Subsequently, more Raney nickel (392 mg, 6.68 mmol) was added, and the mixture was hydrogenated at atmospheric pressure for a further 24 h. The catalyst was subsequently filtered off through kieselguhr, the filtrate was concentrated and the residue was dried under reduced pressure. This gave 1.90 g (purity 60%, 56% of theory) of the title compound.

LC-MS (Method 1): $R_t$=1.16 min; MS (ESIpos): m/z=304 [M+H]⁺

Example 104A (+/−)-tert-Butyl 4-amino-3-(3-methoxypyridin-2-yl)butanoate (Racemate)

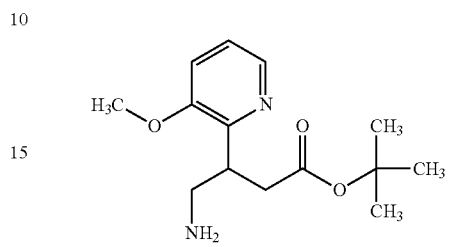

Raney nickel (492 mg, 8.39 mmol) was added to a solution of (+/−)-tert-butyl 3-cyano-3-(3-methoxypyridin-2-yl)propanoate (2.20 g, 8.39 mmol, Example 37A) in tert-butanol (37 ml), and the mixture was hydrogenated at atmospheric pressure overnight. Subsequently, the catalyst was filtered off through kieselguhr and the mother liquor was concentrated and dried under reduced pressure. This gave 2.02 g (95% purity, 86% of theory) of the title compound.

LC-MS (Method 4): $R_t$=1.12 min; MS (ESIpos): m/z=267 [M+H]⁺

Example 105A (+/−)-tert-Butyl 3-(2-chlorophenyl)-2,2-dimethyl-4-nitrobutanoate (Racemate)

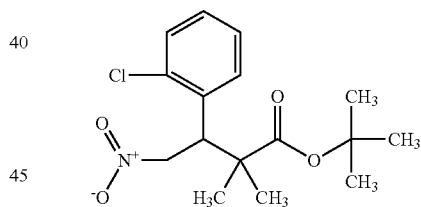

Under argon and at −78° C., a solution of tert-butyl 2-methylpropanoate (511 mg, 3.54 mmol) in THF (2 ml) was slowly added dropwise to a 2 M solution of LDA in THF/heptane/ethylbenzene, and the mixture was stirred at −78° C. for 30 min. A solution of 1-chloro-2-(2-nitrovinyl)benzene (500 mg, 2.72 mmol, CAS number 3156-34-1) in THF (2 ml) was then added dropwise, and the mixture was stirred at −78° C. for a further 30 min. Glacial acetic acid and then water were subsequently added, and the mixture was allowed to warm to RT and then extracted repeatedly with ethyl acetate. The combined organic phases were washed once with saturated sodium chloride solution, dried over magnesium sulfate, filtered and concentrated, and the residue was purified by flash column chromatography (50 g silica gel Biotage Snap-Cartridge KP-Sil, cyclohexane/ethyl acetate 80:20). This gave 590 mg (88% purity, 58% of theory) of the title compound.

LC-MS (Method 7): $R_t$=1.61 min; MS (ESIneg): m/z=326 [M−H]⁻

$^1$H-NMR (400 MHz, DMSO-d6): δ [ppm]=7.54 (dd, 1H), 7.47 (dd, 1H), 7.40-7.28 (m, 2H), 5.14 (dd, 1H), 4.91 (dd, 1H), 4.49 (dd, 1H), 1.42 (s, 9H), 1.08 (s, 3H), 1.06 (s, 3H).

Example 106A (+/−)-tert-Butyl 4-amino-3-(2-chlorophenyl)-2,2-dimethylbutanoate (Racemate)

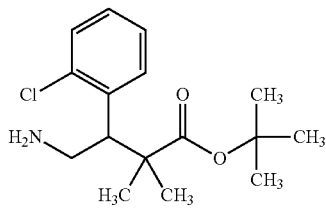 [SMILES: CC(C)(C)OC(=O)C(C)(C)C(CN)c1ccccc1Cl]

Raney nickel (an estimated 200 mg, 3.4 mmol) was added to a solution of (+/−)-tert-butyl 3-(2-chlorophenyl)-2,2-dimethyl-4-nitrobutanoate (595 mg, 1.82 mmol, Example 105A) in methanol (10 ml), and the mixture was hydrogenated at atmospheric pressure for 3 h. The catalyst was subsequently filtered off through kieselguhr and washed with methanol, and the mother liquor was purified by preparative HPLC (Method: Chromatorex C18, 10 μm, 30×125 mm, acetonitrile/(water+0.005% ammonia) gradient: acetonitrile 10%-90%). This gave 320 mg (purity 100%, 86% of theory) of the title compound.

LC-MS (Method 8): $R_t$=5.00 min; MS (ESIpos): m/z=298 [M+H]$^+$

LC-MS (Method 7): $R_t$=0.86 min; MS (ESIpos): m/z=242 [M-$^t$Bu+H]$^+$ $^1$H-NMR (400 MHz, DMSO-d6): δ [ppm]=7.45 (dd, 1H), 7.39-7.30 (m, 2H), 7.28-7.22 (m, 1H), 3.72 (dd, 1H), 2.98-2.89 (m, 1H), 2.85-2.79 (m, 1H), 1.40 (s, 9H), 1.01 (s, 3H), 0.97 (s, 3H).

Example 107A (+/−)-tert-Butyl 4-amino-3-(2-chlorophenyl)-3-methylbutanoate (Racemate)

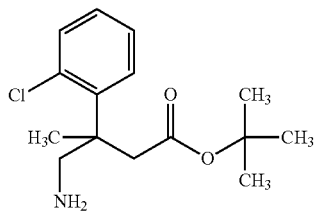 [SMILES: CC(C)(C)OC(=O)CC(C)(CN)c1ccccc1Cl]

Raney nickel (1.05 g, 17.9 mmol) was added to a solution of (+/−)-tert-butyl 3-(2-chlorophenyl)-3-cyanobutanoate (5.00 g, 17.9 mmol, Example 38A) in tert-butanol (100 ml), and the mixture was hydrogenated at atmospheric pressure for 24 h. The catalyst was subsequently filtered off through kieselguhr, the mother liquor was concentrated and the residue was dried under reduced pressure. This gave 3.58 g (70% purity, 49% of theory) of the title compound.

LC-MS (Method 1): $R_t$=1.05 min; MS (ESIpos): m/z=284 [M+H]$^+$

Example 108A (+/−)-tert-Butyl 4-amino-3-(2-fluorophenyl)-3-methylbutanoate (Racemate)

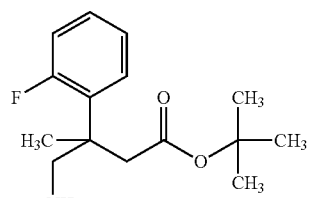

Raney nickel (789 mg, 13.4 mmol) was added to a solution of (+/−)-tert-butyl 3-(2-chloro-6-fluorophenyl)-3-cyanobutanoate (4.00 g, 13.4 mmol, Example 39A) in tert-butanol (76 ml), and the mixture was hydrogenated at atmospheric pressure overnight. Subsequently, the catalyst was filtered off through kieselguhr, the mother liquor was concentrated and the residue was purified by flash column chromatography (100 g silica gel Biotage Snap-Cartridge KP-Sil, cyclohexane/ethyl acetate 85:15). The combined target fractions were concentrated and the residue was dried under reduced pressure. This gave 2.51 g (75% purity, 51% of theory) of the title compound as a mixture with tert-butyl 4-amino-3-(2-chloro-6-fluorophenyl)-3-methylbutanoate (10% according to LC-MS).

LC-MS (Method 1): $R_t$=0.90 min; MS (ESIpos): m/z=268 [M+H]$^+$

Example 109A (+/−)-tert-Butyl 4-amino-3-methyl-3-(pyridin-2-yl)butanoate (Racemate)

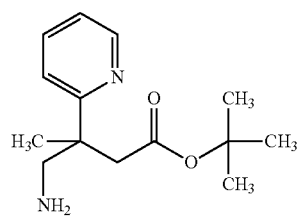

Raney nickel (3.09 g, 52.7 mmol) was added to a solution of (+/−)-tert-butyl 3-(3-chloropyridin-2-yl)-3-cyanobutanoate (14.8 g, 52.7 mmol, Example 29A) in tert-butanol (300 ml), and the mixture was hydrogenated at atmospheric pressure overnight. The catalyst was subsequently filtered off through kieselguhr, the mother liquor was concentrated and the residue was purified by preparative HPLC (Method 16). This gave 5.55 g of a fraction which mainly comprised the unreacted starting material (+/−)-tert-butyl 3-(3-chloropyridin-2-yl)-3-cyanobutanoate. This fraction was once more dissolved in tert-butanol (200 ml), Raney nickel (3.09 g, 52.7 mmol) was added and the mixture was hydrogenated at atmospheric pressure overnight. The catalyst was then filtered off through kieselguhr. The mother liquor was concentrated and the residue was dried under reduced pressure. This gave 4.0 g of the title compound (11% purity, about 3% of theory) as a mixture with tert-butyl 4-amino-3-(3-chloropyridin-2-yl)-3-methylbutanoate (75% according to LC-MS). This mixture was used directly (without further purification) for the next reaction (see Example 203A).

LC-MS (Method 2): $R_t$=0.54 min; MS (ESIpos): m/z=251 [M+H]$^+$

Example 110A (+/−)-tert-Butyl 4-amino-3-(2-methoxyphenyl)-3-methylbutanoate (Racemate)

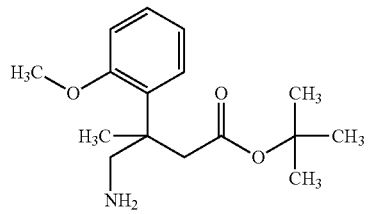

Raney nickel (1.49 g, 25.4 mmol) was added to a solution of (+/−)-tert-butyl 3-cyano-3-(2-methoxyphenyl)butanoate (7.00 g, 25.4 mmol, Example 40A) in tert-butanol (140 ml), and the mixture was hydrogenated at atmospheric pressure overnight. The catalyst was subsequently filtered off through kieselguhr, the mother liquor was concentrated and the residue was dried under reduced pressure. This gave 5.52 g (92% purity, 72% of theory) of the title compound.

LC-MS (Method 2): $R_t$=0.63 min; MS (ESIpos): m/z=280 [M+H]$^+$

Example 111A (+/−)-tert-Butyl 4-amino-3-(5-fluoro-2-methoxyphenyl)butanoate hydrochloride

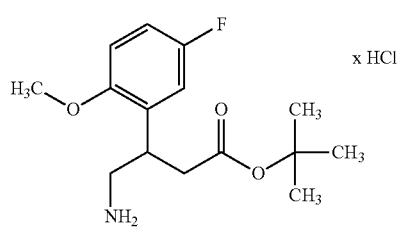 [SMILES: COc1ccc(F)cc1C(CN)CC(=O)OC(C)(C)C]

Under nitrogen, concentrated hydrochloric acid (150 μl, 12 M, 1.8 mmol) and then platinum dioxide (29 mg, 83% purity, 107 μmol) were added to a solution of (+/−)-tert-butyl 3-cyano-3-(5-fluoro-2-methoxyphenyl)propanoate (150 mg, 537 μmol, Example 41A) in methanol (10 ml), and the mixture was then hydrogenated at atmospheric pressure for 1 h. The catalyst was subsequently filtered off through kieselguhr, the mother liquor was concentrated and the residue was dried under reduced pressure. In a repeat experiment, concentrated hydrochloric acid (0.55 ml, 12 M, 6.58 mmol) and then platinum dioxide (106 mg, 83% purity, 387 μmol) were added to a solution of (+/−)-tert-butyl 3-cyano-3-(5-fluoro-2-methoxyphenyl)propanoate (775 mg, 2.78 mmol, Example 41A) in methanol (50 ml), and the mixture was hydrogenated at atmospheric pressure for 2 h. The catalyst was subsequently filtered off through kieselguhr, the mother liquor was concentrated and the residue was dried under reduced pressure. The residues from the two experiments were combined and partitioned between dichloromethane and saturated sodium bicarbonate solution. After phase separation, the aqueous phase was extracted twice with dichloromethane. The combined organic phases were dried over sodium sulfate, filtered and concentrated, and the residue was purified by means of flash column chromatography (40 g silica gel Reveleris, dichloromethane/(10% methanol in dichloromethane) 100:0→16:84). The combined target fractions were concentrated, and three times in succession tert-butyl methyl ether was added and the mixture was concentrated again. The residue was dissolved in tert-butyl methyl ether, 1 M hydrochloric acid in diethyl ether (1.94 ml, 1.94 mmol) was added and the mixture was stirred at RT for 30 min. The suspension was subsequently concentrated, then twice in succession tert-butyl methyl ether was added and the mixture was concentrated again, and the residue was dried under reduced pressure. This gave 541 mg (purity 98%, 50% of theory, based on the sum of (+/−)-tert-butyl 3-cyano-3-(5-fluoro-2-methoxyphenyl)propanoate employed) of the title compound.

LC-MS (Method 9): $R_t$=2.35 min; MS (ESIpos): m/z=284 [M−HCl+H]$^+$ $^1$H-NMR (400 MHz, DMSO-d6) δ [ppm]: 8.98 (br. s, 3H), 7.15-6.95 (m, 3H), 3.79 (s, 3H), 3.70-3.60 (m, 1H), 3.01 (br. s, 2H), 2.76 (dd, 1H), 2.62 (dd, H), 1.22 (s, 9H).

Example 112A (+/−)-tert-Butyl 4-amino-3-(2-fluoro-6-methoxyphenyl)butanoate (Racemate)

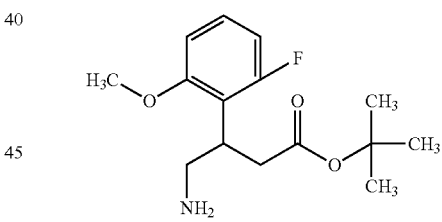

Platinum dioxide (152 mg, 667 μmol) was added to a solution of (+/−)-tert-butyl 3-cyano-3-(2-fluoro-6-methoxyphenyl)propanoate (1.00 g, 93% purity, 3.34 mmol, Example 42A) in methanol (30 ml), and the mixture was hydrogenated at atmospheric pressure for 3 h. Subsequently, 1 M hydrochloric acid (3.3 ml, 3.3 mmol) was added and the mixture was hydrogenated at atmospheric pressure for a further 17 h. The catalyst was subsequently filtered off through kieselguhr, saturated sodium bicarbonate solution and water (30 ml each) were added to the filtrate and the mixture was twice extracted with dichloromethane (50 ml each). The combined organic phases were dried over magnesium sulfate, filtered and concentrated, and the residue was dried under reduced pressure. This gave 799 mg (82% purity, 69% of theory) of the title compound.

LC-MS (Method 1): $R_t$=1.02 min; MS (ESIpos): m/z=284 [M+H]$^+$

Example 113A (+/−)-tert-Butyl 4-amino-3-(2-ethoxyphenyl)butanoate hydrochloride (Racemate)

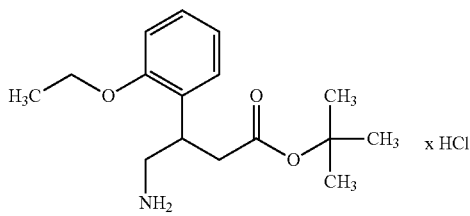 [SMILES: CCOc1ccccc1C(CN)CC(=O)OC(C)(C)C]

Under nitrogen, platinum dioxide (384 mg, 83% purity, 1.40 mmol) and concentrated hydrochloric acid (580 µl, 12 M, 7.0 mmol) were added to a solution of (+/−)-tert-butyl 3-cyano-3-(2-ethoxyphenyl)propanoate (150 mg, 537 µmol, Example 43A) in methanol (140 ml), and the mixture was then hydrogenated at atmospheric pressure for 4 h. The catalyst was then filtered off and the filtrate was partitioned between dichloromethane and saturated sodium bicarbonate solution. After phase separation, the aqueous phase was extracted twice with dichloromethane. The combined organic phases were dried over sodium sulfate and filtered. A 2 M solution of hydrogen chloride in diethyl ether (3.5 ml, 7.0 mmol) was added to the filtrate, the mixture was concentrated, dichloromethane was then added and the mixture was concentrated again. The residue was dissolved in acetonitrile, the solution was concentrated again and the residue was dried under reduced pressure. After removal of 200 mg of the residue for purification experiments, 1.80 g (90% purity, 73% of theory) of the title compound were subsequently obtained.

LC-MS (Method 10): $R_t$=2.08 min; MS (ESpos): m/z=280 [M−HCl+H]$^+$ $^1$H-NMR (400 MHz, DMSO-d6) δ [ppm]: 8.89 (br. s, 3H), 7.24 (dd, 1H), 7.18 (d, 1H), 6.95 (d, 1H), 6.91 (dd, 1H), 4.05 (q, 2H), 3.62-3.53 (m, 1H), 3.04 (d, 2H), 2.75 (dd, 1H), 2.66 (dd, 1H), 1.38 (t, 3H, partially obscured), 1.20 (s, 9H).

Example 114A (+/−)-tert-Butyl 4-amino-3-(5-fluoro-2-methoxyphenyl)-3-methylbutanoate hydrochloride (Racemate)

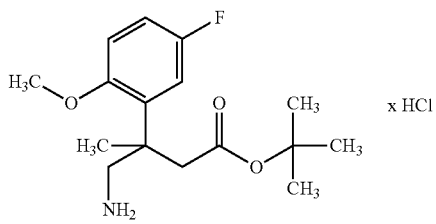 [SMILES: COc1ccc(F)cc1C(C)(CN)CC(=O)OC(C)(C)C]

Under nitrogen, concentrated hydrochloric acid (390 µl, 12 M, 4.7 mmol) and then platinum dioxide (257 mg, 83% purity, 938 µmol) were added to a solution of (+/−)-tert-butyl 3-cyano-3-(5-fluoro-2-methoxyphenyl)butanoate (1.38 g, 4.69 mmol, Example 44A) in methanol (95 ml), and the mixture was then hydrogenated at atmospheric pressure for 2.5 h. The catalyst was subsequently filtered off and the filtrate was partitioned between dichloromethane and saturated sodium bicarbonate solution. After phase separation, the aqueous phase was extracted twice with dichloromethane. The combined organic phases were dried over sodium sulfate and filtered. A 2 M solution of hydrogen chloride in diethyl ether (2.3 ml, 4.7 mmol) was then added to the filtrate, the mixture was concentrated, and twice in succession dichloromethane was added and the mixture was concentrated again. The residue was dried under reduced pressure. This gave 1.33 g (95% purity, 81% of theory) of the title compound.

LC-MS (Method 11): $R_t$=2.39 min; MS (ESpos): m/z=298 [M−HCl+H]$^+$ $^1$H-NMR (400 MHz, CDCl$_3$): δ [ppm]=7.96 (br. s, 3H), 7.10-6.90 (m, 2H), 6.88-6.80 (m, 1H), 3.86 (s, 3H), 3.48 (d, 1H), 3.14 (d, 1H), 3.03 (d, 1H), 2.58 (d, 1H), 1.62 (s, 3H), 1.22 (s, 9H).

Example 115A (+/−)-tert-Butyl 4-amino-3-(3,5-difluoro-2-methoxyphenyl)-3-methylbutanoate hydrochloride (Racemate)

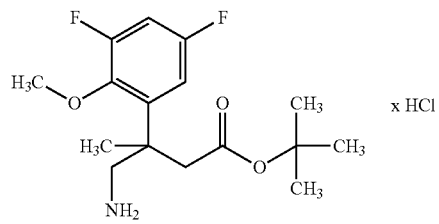 [SMILES: COc1c(F)cc(F)cc1C(C)(CN)CC(=O)OC(C)(C)C]

Under nitrogen, platinum dioxide hydrate (242 mg, 989 µmol) and then a solution of concentrated hydrochloric acid (410 µl, 12 M, 4.9 mmol) in water (4.5 ml) were added to a solution of (+/−)tert-butyl 3-cyano-3-(3,5-difluoro-2-methoxyphenyl)butanoate (1.54 g, 4.95 mmol, Example 45A) in methanol (100 ml), and the mixture was then hydrogenated at atmospheric pressure for 4 h. The catalyst was subsequently filtered off and the filtrate was divided into two portions and successively washed in each case with saturated sodium bicarbonate solution and extracted twice with dichloromethane. The combined organic phases were each dried over sodium sulfate and filtered. After addition of a 1 M solution of hydrogen chloride in diethyl ether (a total of 5 ml, divided into two equal portions), each of the mixtures obtained were concentrated and the residue was in each case dried under reduced pressure. The two residues obtained were combined. This gave 1.50 g (96% purity, 83% of theory) of the title compound.

LC-MS (Method 11): $R_t$=2.43 min; MS (ESpos): m/z=316 [M−HCl+H]$^+$ $^1$H-NMR (400 MHz, CDCl$_3$): δ [ppm]=8.11 (br. s, 3H), 6.90-6.70 (m, 2H), 4.00 (s, 3H), 3.42 (dd, 1H), 3.17 (dd, 1H), 3.00 (d, 1H), 2.60 (d, 1H), 1.62 (s, 3H), 1.27 (s, 9H).

Example 116A (+/−)-tert-Butyl 4-amino-3-(4-fluoro-2-methoxyphenyl)-3-methylbutanoate hydrochloride (Racemate)

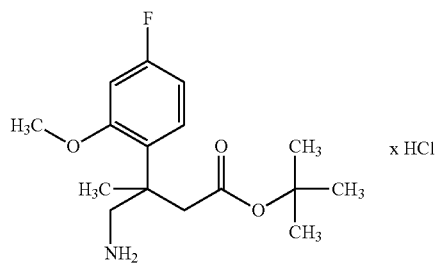 [SMILES: COc1cc(F)ccc1C(C)(CN)CC(=O)OC(C)(C)C]

Under nitrogen, platinum dioxide hydrate (563 mg, 83% purity, 2.06 mmol) and then concentrated hydrochloric acid (860 μl, 12 M, 10 mmol) were added to a solution of (+/−)-tert-butyl 3-cyano-3-(4-fluoro-2-methoxyphenyl)butanoate (3.02 g, 10.3 mmol, Example 46A) in methanol (200 ml), and the mixture was then hydrogenated at atmospheric pressure for 4 h. The catalyst was subsequently filtered off and the filtrate was washed with saturated sodium bicarbonate solution and extracted twice with dichloromethane. The combined organic phases were dried over sodium sulfate and filtered. After addition of a 2 M solution of hydrogen chloride in diethyl ether (5.2 ml), the mixture obtained was concentrated and the residue was dried under reduced pressure. This gave 3.02 g (99% purity, 87% of theory) of the title compound.

LC-MS (Method 11): $R_t$=3.01 min; MS (ESpos): m/z=298 [M−HCl+H]$^+$ $^1$H-NMR (400 MHz, CDCl$_3$): δ [ppm]=7.90 (br. s, 3H), 7.20-7.15 (m, 1H), 6.65-6.55 (m, 2H), 3.87 (s, 3H), 3.40 (m, 1H), 3.13 (m, 1H), 2.96 (d, 1H), 2.58 (d, 1H), 1.62 (s, 3H), 1.22 (s, 9H).

Example 117A (+/−)-Ethyl 2,2-difluoro-3-(2-methoxyphenyl)-4-nitrobutanoate (Racemate)

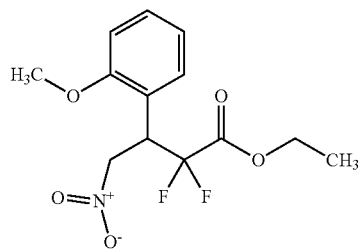 [SMILES: CCOC(=O)C(F)(F)C(C[N+](=O)[O-])c1ccccc1OC]

In a flask which had been dried by heating, and under argon, a slurried Rieke zinc suspension (about 5 ml, about 500 mg, about 7.7 mmol) was heated to 80° C., and ethyl bromo(difluoro)acetate (740 μl, 5.6 mmol) was added dropwise. After a further 5 min at 80° C., 1-methoxy-2-[(E)-2-nitrovinyl]benzene (500 mg, 2.79 mmol) was added, and the mixture was stirred at 80° C. for a further 15 min. The mixture was then allowed to warm to RT, and 1 M hydrochloric acid (about 20 ml) was added. Once residual zinc had dissolved, the mixture was extracted with ethyl acetate. The organic phase was washed with saturated aqueous sodium chloride solution, dried over sodium sulfate, filtered and concentrated. The residue was purified by flash column chromatography (50 g silica gel Biotage Snap-Cartridge KP-Sil, cyclohexane/ethyl acetate gradient 1:0→10:1). The combined target fractions were concentrated and the residue was lyophilized. This gave 105 mg (47% purity, 3% of theory) of the title compound.

LC-MS (Method 7): $R_t$=1.31 min; MS (ESIneg): m/z=302 [M−H]$^−$

Example 118A (+/−)-Ethyl 4-amino-2,2-difluoro-3-(2-methoxyphenyl)butanoate hydrochloride (Racemate)

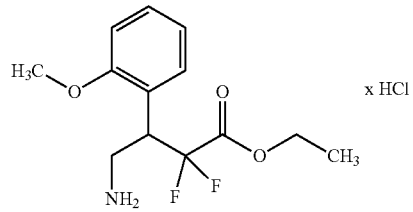

Platinum dioxide (30 mg, 132 μmol) was added to a mixture of (+/−)-ethyl 2,2-difluoro-3-(2-methoxyphenyl)-4-nitrobutanoate (95 mg, 313 μmol, not corrected for purity, Example 117A) in a mixture of methanol (3 ml) and 1 M hydrochloric acid (630 μl), and the mixture was hydrogenated overnight. Subsequently, once more, platinum dioxide (30 mg, 132 μmol) and 1 M hydrochloric acid (1 ml) were added, and the mixture was stirred at RT for a further 3 days. The mixture was then filtered through kieselguhr and concentrated. Repeatedly, dichloromethane was added to the residue and the mixture was concentrated again. Drying under reduced pressure gave 80 mg (35% purity, 33% of theory) of the title compound.

LC-MS (Method 7): $R_t$=0.72 min; MS (ESIpos): m/z=274 [M+H]$^+$

Example 119A (+/−)-tert-Butyl 4-amino-3-(2-fluoro-6-methoxyphenyl)-3-methylbutanoate (Racemate)

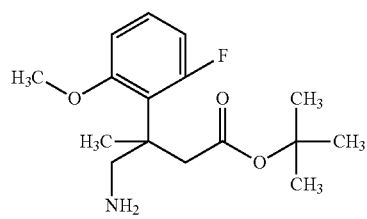 [SMILES: COc1cccc(F)c1C(C)(CN)CC(=O)OC(C)(C)C]

Platinum dioxide (97.0 mg, 427 μmol) and then 1 M hydrochloric acid (2.1 ml, 2.1 mmol) were added to a solution of (+/−)-tert-butyl 3-cyano-3-(2-fluoro-6-methoxyphenyl)butanoate (798 mg, 79% purity, 2.14 mmol, Example 47A) in methanol (19 ml), and the mixture was then hydrogenated at atmospheric pressure for 17 h. The catalyst was subsequently filtered off, saturated sodium bicarbonate solu-

Example 120A tert-Butyl 4-amino-3-(2-chlorophenyl)pentanoate (Diastereomer Mixture)

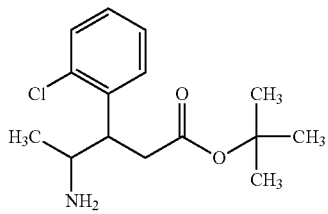

At RT, 1 M hydrochloric acid (26.1 ml, 26.1 mmol) and zinc dust (5.01 g, 76.74 mmol) were added to a solution of tert-butyl 3-(2-chlorophenyl)-4-nitropentanoate (602 mg, 1.92 mmol, Example 48A) in ethanol (30 ml), and the mixture was stirred at RT for one day. Subsequently, the mixture was, using saturated sodium bicarbonate solution (about 50 ml), adjusted to pH 9, water (50 ml) and ethyl acetate (100 ml) were added and the mixture was agitated. The solid present was filtered off through kieselguhr. The filtrate was separated into organic and aqueous phase and the aqueous phase was extracted once with ethyl acetate (50 ml). The combined organic phases were washed once with saturated aqueous sodium chloride solution (100 ml) and dried over sodium sulfate, filtered and concentrated. The residue was briefly dried under reduced pressure. This gave 493 mg (74% purity, 67% of theory) of the title compound.

LC-MS (Method 2): $R_t$=0.61 & 0.63 min; MS (ESIpos): in each case m/z=284 (M+H)

Example 121A (+/−)-tert-Butyl 5-amino-4-(2-chlorophenyl)pentanoate (Racemate)

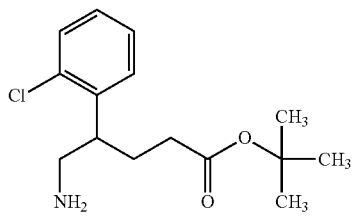 [SMILES: CC(C)(C)OC(=O)CCC(CN)c1ccccc1Cl]

Raney nickel (944 mg, 16.1 mmol) was added to a solution of (+/−)-tert-butyl 4-(2-chlorophenyl)-4-cyanobutanoate (4.50 g, 16.1 mmol, Example 49A) in tert-butanol (90 ml), and the mixture was hydrogenated at atmospheric pressure overnight. Subsequently, Raney nickel (944 mg, 16.1 mmol) was again added to the mixture and hydrogenation was effected at atmospheric pressure for a further 24 h. Thereafter, the catalyst was filtered off through kieselguhr and the mother liquor was concentrated. The residue was taken up in dichloromethane and purified by flash column chromatography (100 g silica gel Biotage Snap-Cartridge KP-Sil, cyclohexane/ethyl acetate gradient 93:7→7:3, Isolera One). The combined target fractions were concentrated and the residue was dried under reduced pressure. This gave 1.62 g (91% purity, 32% of theory) of the title compound.

LC-MS (Method 4): $R_t$=1.70 min; MS (ESIpos): m/z=284 [M+H]$^+$

Example 122A (+/−)-tert-Butyl 5-amino-4-(2-chlorophenyl)-4-methylpentanoate (Racemate)

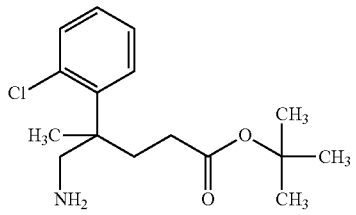 [SMILES: CC(C)(C)OC(=O)CCC(C)(CN)c1ccccc1Cl]

Raney nickel (300 mg, 5.11 mmol) was added to a solution of (+/−)-tert-butyl 4-(2-chlorophenyl)-4-cyanopentanoate (1.50 g, 5.11 mmol, Example 50A) in tert-butanol (30 ml), and the mixture was hydrogenated at atmospheric pressure overnight. Subsequently, Raney nickel (944 mg, 16.1 mmol) was again added to the mixture and hydrogenation was effected at atmospheric pressure for a further 24 h. Subsequently, Raney nickel (944 mg, 16.1 mmol) was once more added to the mixture and hydrogenation was effected at atmospheric pressure for a further 24 h. Thereafter, the catalyst was filtered off through kieselguhr and the mother liquor was concentrated. The residue was purified by preparative HPLC (Method 16). The combined target fractions were concentrated and the residue was dried under reduced pressure. This gave 840 mg (73% purity, 40% of theory) of the title compound.

LC-MS (Method 1): $R_t$=1.22 min; MS (ESIpos): m/z=298 [M+H]$^+$

Example 123A (+/−)-tert-Butyl 5-amino-4-(2-chloro-6-fluorophenyl)pentanoate (Racemate)

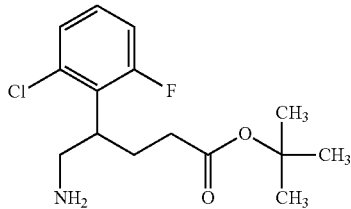 [SMILES: CC(C)(C)OC(=O)CCC(CN)c1c(F)cccc1Cl]

Raney nickel (286 mg, 4.87 mmol) was added to a solution of (+/−)-tert-butyl 4-(2-chloro-6-fluorophenyl)-4-cyanobutanoate (1.45 g, 4.87 mmol, Example 51A) in tert-butanol (30 ml), and the mixture was hydrogenated at atmospheric pressure overnight. Subsequently, Raney nickel (286 mg, 4.87 mmol) was again added to the mixture and hydrogenation was effected at atmospheric pressure for a further 24 h. Thereafter, the catalyst was filtered off through kieselguhr and the mother liquor was concentrated. This gave 1.28 g (67% purity, 58% of theory) of the title compound.

LC-MS (Method 1): $R_t$=1.19 min; MS (ESIpos): m/z=302 [M+H]$^+$

Example 124A (+/−)-tert-Butyl 5-amino-4-(2-methylphenyl)pentanoate (Racemate)

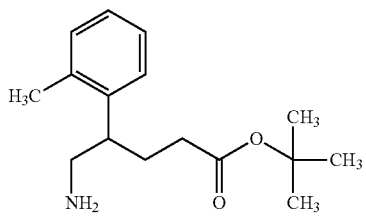

Raney nickel (121 mg, 2.06 mmol) was added to a solution of (+/−)-tert-butyl 4-cyano-4-(2-methylphenyl)butanoate (534 mg, 2.06 mmol, Example 52A) in tert-butanol (13 ml), and the mixture was hydrogenated at atmospheric pressure overnight. Subsequently, the catalyst was filtered off through kieselguhr and the mother liquor was concentrated. This gave 505 mg (95% purity, 89% of theory) of the title compound.

LC-MS (Method 1): $R_t$=1.18 min; MS (ESIpos): m/z=264 [M+H]$^+$

Example 125A (+/−)-tert-Butyl 5-amino-4-(2-chloro-5-fluorophenyl)pentanoate (Racemate)

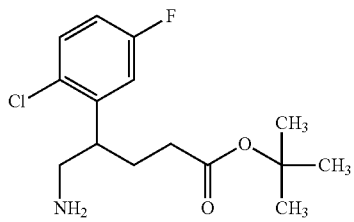 [SMILES: CC(C)(C)OC(=O)CCC(CN)c1cc(F)ccc1Cl]

Raney nickel (2.57 g, 43.7 mmol) was added to a solution of (+/−)-tert-butyl 4-(2-chloro-5-fluorophenyl)-4-cyanobutanoate (14.0 g, 93% purity, 43.7 mmol, Example 53A) in tert-butanol (260 ml), and the mixture was hydrogenated at atmospheric pressure overnight. Subsequently, Raney nickel (2.57 g, 43.7 mmol) was again added and the mixture was hydrogenated at atmospheric pressure for a further 24 h. Subsequently, Raney nickel (2.57 g, 43.7 mmol) was once more added and the mixture was hydrogenated at atmospheric pressure for a further 24 h. Thereafter, the catalyst was filtered off through kieselguhr and the mother liquor was concentrated. This gave 14.4 g (60% purity, 65% of theory) of the title compound.

LC-MS (Method 1): $R_t$=1.14 min; MS (ESIpos): m/z=302 [M+H]$^+$

Example 126A (+/−)-tert-Butyl 5-amino-4-(2-methoxyphenyl)pentanoate (Racemate)

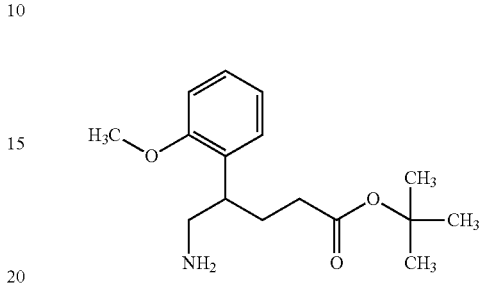

Raney nickel (106 mg, 1.80 mmol) was added to a solution of (+/−)-tert-butyl 4-cyano-4-(2-methoxyphenyl)butanoate (495 mg, 1.80 mmol, Example 54A) in tert-butanol (11 ml), and the mixture was hydrogenated at atmospheric pressure overnight. Subsequently, the catalyst was filtered off through kieselguhr and the mother liquor was concentrated. This gave 269 mg (85% purity, 46% of theory) of the title compound.

LC-MS (Method 2): $R_t$=0.68 min; MS (ESIpos): m/z=280 [M+H]

Example 127A (+/−)-tert-Butyl 5-amino-4-(2-chloro-5-fluorophenyl)-4-methylpentanoate (Racemate)

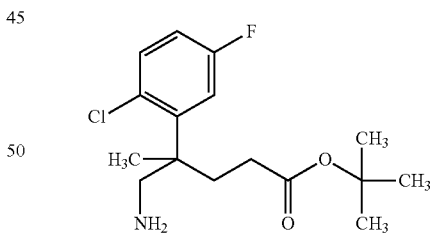

Raney nickel (226 mg, 3.85 mmol) was added to a solution of (+/−)-tert-butyl 4-(2-chloro-5-fluorophenyl)-4-cyanopentanoate (1.20 g, 3.85 mmol, Example 55A) in tert-butanol (25 ml), and the mixture was hydrogenated at atmospheric pressure overnight. Subsequently, the catalyst was filtered off through kieselguhr and the mother liquor was concentrated. This gave 1.54 g (66% purity, 84% of theory) of the title compound.

LC-MS (Method 1): $R_t$=1.24 min; MS (ESIpos): m/z=316 [M+H]$^+$

Example 128A (+/−)-tert-Butyl 5-amino-4-(2-chloro-3,6-difluorophenyl)pentanoate (Racemate)

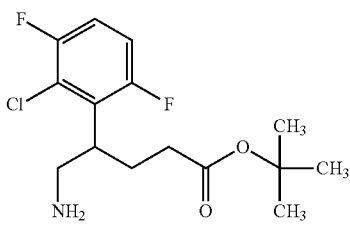

Raney nickel (762 mg, 13.0 mmol) was added to a solution of (+/−)-tert-butyl 4-(2-chloro-3,6-difluorophenyl)-4-cyanobutanoate (4.10 g, 13.0 mmol, Example 56A) in tert-butanol (75 ml), and the mixture was hydrogenated at atmospheric pressure for 24 h. Subsequently, the catalyst was filtered off through kieselguhr, which was washed through twice with tert-butanol (15 ml), and the mother liquor was concentrated. The residue was taken up in ethyl acetate (80 ml) and the solution was extracted successively with 1 M hydrochloric acid and water (80 ml each time). The combined aqueous phases were adjusted to pH 8-9 with saturated sodium bicarbonate solution and extracted twice with ethyl acetate (100 ml each). The combined organic phases were dried over sodium sulfate, filtered and concentrated, and the residue was dried under reduced pressure. This gave 1.76 g (100% purity, 42% of theory) of the title compound.

LC-MS (Method 1): $R_t$=1.21 min; MS (ESIpos): m/z=320 [M+H]$^+$

Example 129A (+/−)-tert-Butyl 5-amino-4-(2-fluorophenyl)pentanoate (Racemate)

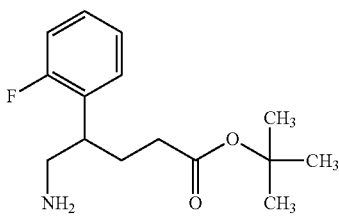 [SMILES: CC(C)(C)OC(=O)CCC(CN)c1ccccc1F]

Raney nickel (941 mg, 16.0 mmol) was added to a solution of (+/−)-tert-butyl 4-cyano-4-(2-fluorophenyl)butanoate (4.22 g, 16.0 mmol, not corrected for purity, Example 57A) in tert-butanol (100 ml), and the mixture was hydrogenated at atmospheric pressure overnight. Subsequently, Raney nickel (941 mg, 16.0 mmol) was again added and the mixture was hydrogenated at atmospheric pressure for another night. Subsequently, the catalyst was filtered off through kieselguhr and the mother liquor was concentrated. This gave 3.02 g (60% purity, 42% of theory) of the title compound.

LC-MS (Method 2): $R_t$=0.61 min; MS (ESIpos): m/z=268 [M+H]$^+$

Example 130A (+/−)-tert-Butyl 5-amino-4-[2-(difluoromethoxy)phenyl]pentanoate (Racemate)

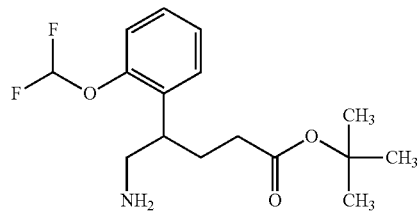 [SMILES: CC(C)(C)OC(=O)CCC(CN)c1ccccc1OC(F)F]

Raney nickel (726 mg, 12.4 mmol) was added to a solution of (+/−)-tert-butyl 4-cyano-4-[2-(difluoromethoxy)phenyl]butanoate (3.85 g, 12.4 mmol, Example 58A) in tert-butanol (75 ml), and the mixture was hydrogenated at atmospheric pressure overnight. Subsequently, the catalyst was filtered off through kieselguhr and the mother liquor was concentrated. This gave 2.92 g (80% purity, 60% of theory) of the title compound.

LC-MS (Method 2): $R_t$=0.68 min; MS (ESIpos): m/z=316 [M+H]$^+$

Example 131A (+/−)-tert-Butyl 5-amino-4-(2,6-difluorophenyl)pentanoate (Racemate)

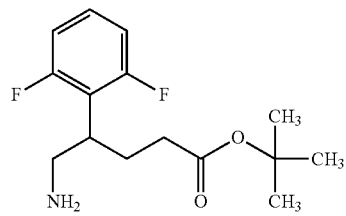

Raney nickel (1.00 g, 17.1 mmol) was added to a solution of (+/−)-tert-butyl 4-cyano-4-(2,6-difluorophenyl)butanoate (4.80 g, 17.1 mmol, Example 59A) in tert-butanol (100 ml), and the mixture was hydrogenated at atmospheric pressure overnight. Subsequently, the catalyst was filtered off through kieselguhr and the mother liquor was concentrated. This gave 4.06 g (81% purity, 67% of theory) of the title compound.

LC-MS (Method 2): $R_t$=0.64 min; MS (ESIpos): m/z=286 [M+H]$^+$

Example 132A (+/−)-tert-Butyl 5-amino-4-(2-chloro-3-fluorophenyl)pentanoate (Racemate)

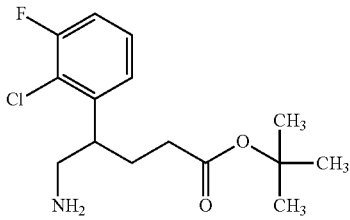 [SMILES: CC(C)(C)OC(=O)CCC(CN)c1cccc(F)c1Cl]

Raney nickel (852 mg, 14.5 mmol) was added to a solution of (+/−)-tert-butyl 4-(2-chloro-3-fluorophenyl)-4-cyanobutanoate (4.32 g, 14.5 mmol, Example 60A) in tert-butanol (85 ml), and the mixture was hydrogenated at atmospheric pressure overnight. Subsequently, the catalyst was filtered off through kieselguhr, which was washed through twice with tert-butanol (15 ml), and the mother liquor was concentrated. The residue was taken up in ethyl acetate (80 ml) and extracted successively with 1 M hydrochloric acid and water (80 ml each time). The combined aqueous phases were adjusted to pH 8-9 using saturated sodium bicarbonate solution and extracted twice with ethyl acetate (80 ml). The combined organic phases were dried over sodium sulfate, filtered and concentrated, and the residue was dried under reduced pressure. This gave 2.43 g (85% purity, 47% of theory) of the title compound.

LC-MS (Method 1): $R_t$=1.28 min; MS (ESIpos): m/z=302 [M+H]$^+$

Example 133A (+/−)-tert-Butyl N-[2-amino-1-(2-chlorophenyl)ethyl]-N-methylglycinate (Racemate)

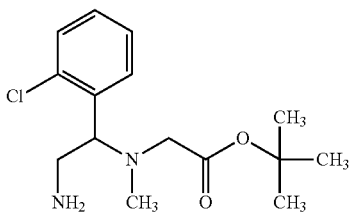 [SMILES: CN(CC(=O)OC(C)(C)C)C(CN)c1ccccc1Cl]

Raney nickel (279 mg, 4.75 mmol) was added to a solution of (+/−)-tert-butyl N-[(2-chlorophenyl)(cyano)methyl]-N-methylglycinate (1.40 g, 4.75 mmol, Example 61A) in tert-butanol (28 ml), and the mixture was hydrogenated at atmospheric pressure overnight. Subsequently, more Raney nickel (279 mg, 4.75 mmol) was added, and the mixture was hydrogenated at atmospheric pressure for a further 24 h. The catalyst was then filtered off through kieselguhr, the mother liquor was concentrated and the residue was dried under reduced pressure. This gave 800 mg (41% purity, 23% of theory) of the title compound.

LC-MS (Method 1): $R_t$=1.21 min; MS (ESIpos): m/z=299 [M+H]$^+$

Example 134A (+/−)-tert-Butyl N-[2-amino-1-(2-chlorophenyl)ethyl]glycinate (Racemate)

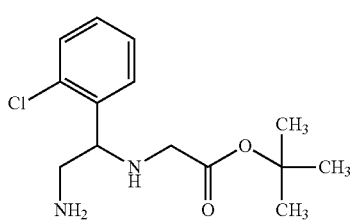

Raney nickel (293 mg, 4.99 mmol) was added to a solution of (+/−)-tert-butyl N-[(2-chlorophenyl)(cyano)methyl]glycinate (1.40 g, "4.99 mmol", not corrected for purity, Example 62A) in tert-butanol (29 ml), and the mixture was hydrogenated at atmospheric pressure overnight. The catalyst was subsequently filtered off through kieselguhr, the mother liquor was concentrated and the residue was dried under reduced pressure. This gave 1.25 g (about 50% purity, 44% of theory) of the title compound.

LC-MS (Method 2): $R_t$=0.66 min; MS (ESIpos): m/z=285 [M+H]$^+$

Example 135A (+/−)-tert-Butyl [2-(2-chlorophenyl)-2-hydroxyethyl]carbamate (Racemate)

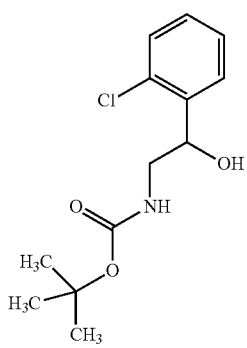 [SMILES: CC(C)(C)OC(=O)NCC(O)c1ccccc1Cl]

At RT, triethylamine (3.6 ml, 26 mmol) and di-tert-butyl dicarbonate (5.67 g, 26.0 mmol) were added to a solution of (+/−)-2-amino-1-(2-chlorophenyl)ethanol (3.98 g, 23.2 mmol) in dichloromethane (50 ml) (evolution of gas), and the mixture was stirred at RT for 18 h. The mixture was then diluted with dichloromethane (100 ml), washed with dilute sodium bicarbonate solution and saturated sodium chloride solution (100 ml each), dried over sodium sulfate, filtered and concentrated, and the residue was dried under reduced pressure. This gave 7.50 g (53% purity by GC-MS, 63% of theory) of the title compound.

GC-MS (Method 12): $R_t$=6.53 min, MS (EIpos): m/z=215 [M-C$_4$H$_8$]$^+$

Example 136A (+/−)-Ethyl [2-[(tert-butoxycarbonyl)amino]-1-(2-chlorophenyl)ethoxy]acetate (Racemate)

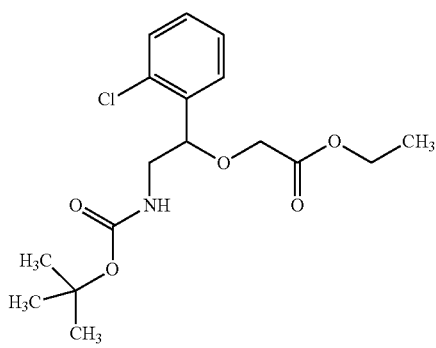 [SMILES: CCOC(=O)COC(CNC(=O)OC(C)(C)C)c1ccccc1Cl]

At RT and under argon, ethyl diazoacetate (4.6 ml, 44 mmol) and rhodium(II) acetate dimer were added to a solution of (+/−)-tert-butyl [2-(2-chlorophenyl)-2-hydroxyethyl]carbamate (7.41 g, 85% purity, 23.2 mmol, Example 135A) in dichloroethane (50 ml) (evolution of gas), and the mixture was stirred at RT for 17 h. More ethyl diazoacetate (4.6 ml, 44 mmol) was then added, and the mixture was stirred at RT for a further four days and then concentrated with formation of a residue ("residue 1"). Part of this "residue 1" (about 1.4 g) was dissolved in dichloromethane (50 ml), and the solution was washed with water (50 ml) and dilute sodium bicarbonate solution, dried over sodium sulfate, filtered and concentrated. The residue was taken up in dichloromethane and purified by flash column chromatography (50 g silica gel Biotage Snap-Cartridge Ultra, cyclohexane/ethyl acetate 97:3→7:3, Isolera One). Concentration and drying of the combined target fractions gave 300 mg (75% purity, 3% of theory) of a first batch of the title compound. The remaining amount of "residue 1" (about 12 g) was taken up in dichloromethane and purified in two portions by flash column chromatography (100 g each of silica gel Biotage Snap-Cartridge Ultra, cyclohexane/ethyl acetate 97:3→7:3, Isolera One). Concentration and drying of the combined target fractions gave 2.89 g (86% purity, 31% of theory) of a second batch of the title compound. From this second batch, 500 mg were removed, dissolved in acetonitrile and repurified by preparative HPLC (Method 16). The target fractions were combined and adjusted to pH 7-8 using saturated sodium bicarbonate solution. The acetonitrile phase was removed on a rotary evaporator and the aqueous phase was extracted twice with ethyl acetate. The combined organic phases were dried over sodium sulfate, filtered and concentrated, and the residue was dried under reduced pressure. This gave 234 mg (100% purity) of the repurified title compound (see analysis).

LC-MS (Method 1): $R_t$=2.13 min; MS (ESIpos): m/z=358 [M+H]$^+$ $^1$H-NMR (400 MHz, DMSO-d6) δ [ppm]: −0.150 (0.11), 0.007 (0.79), 1.150 (3.98), 1.168 (8.32), 1.186 (4.12), 1.254 (1.35), 1.332 (16.00), 1.987 (1.08), 2.327 (0.14), 2.365 (0.15), 2.669 (0.14), 2.709 (0.15), 3.213 (1.08), 3.223 (1.17), 3.238 (0.75), 3.911 (1.58), 3.952 (2.73), 4.020 (0.28), 4.043 (1.39), 4.067 (1.23), 4.085 (3.99), 4.102 (3.21), 4.120 (1.04), 4.905 (0.64), 4.920 (0.93), 4.934 (0.49), 6.774 (0.68), 7.310 (0.28), 7.329 (0.82), 7.348 (0.84), 7.361 (0.83), 7.379 (1.24), 7.395 (0.57), 7.418 (1.21), 7.444 (1.55), 7.463 (0.85).

$^1$H-NMR (400 MHz, DMSO-d6) δ [ppm]: 7.51-7.24 (m, 4H), 6.78 (t, 1H), 4.92 (t, 1H), 4.09 (q, 2H), 4.06-3.86 (m, 2H), 3.28-3.16 (m, 2H), 1.33 (s, 7H), 1.26 (br. s, 2H), 1.17 (t, 3H).

Example 137A (+/−)-Ethyl [2-amino-1-(2-chlorophenyl)ethoxy]acetate hydrochloride (Racemate)

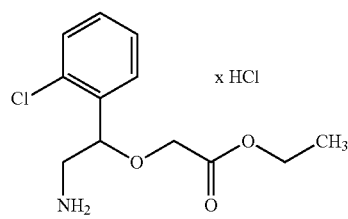 [SMILES: CCOC(=O)COC(CN)c1ccccc1Cl]

(+/−)-Ethyl [2-[(tert-butoxycarbonyl)amino]-1-(2-chlorophenyl)ethoxy]acetate (1.91 g, 5.34 mmol, Example 136A) was dissolved in a 4 M solution of hydrogen chloride in dioxane and allowed to stand at RT for 2.5 h. The mixture was then concentrated and repeatedly dichloromethane was added and the mixture was concentrated again. The residue was dried under reduced pressure. This gave 1.90 g (72% purity, 87% of theory) of the title compound.

LC-MS (Method 2): $R_t$=0.52 min; MS (ESIpos): m/z=258 [M+H]$^+$

Example 138A (+/−)-Methyl {[2-amino-1-(2-chlorophenyl)ethyl]sulfanyl}acetate (Racemate)

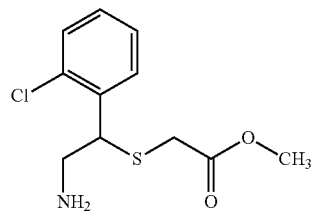 [SMILES: COC(=O)CSC(CN)c1ccccc1Cl]

At RT, tin(II) chloride was added to a solution of (+/−)-methyl {[1-(2-chlorophenyl)-2-nitroethyl]sulfanyl}acetate (1.40 g, 4.83 mmol, Example 63A) in methanol (28 ml) and acetic acid (14 ml), and the mixture was stirred under reflux for 3 h. After cooling to RT, the mixture was concentrated and the residue was dissolved in acetonitrile and purified by means of preparative HPLC (Method 16). The combined target fractions were concentrated, and the residue was dried under reduced pressure. This gave 3.80 g (50% purity by HPLC-MS, ">100% of theory", contains solvent) of the title compound.

LC-MS (Method 1): $R_t$=0.79 min; MS (ESIpos): m/z=260 [M+H]$^+$

Example 139A (+/−)-Methyl ({2-[(tert-butoxycarbonyl)amino]-1-(2-chlorophenyl)ethyl}sulfanyl)acetate (Racemate)

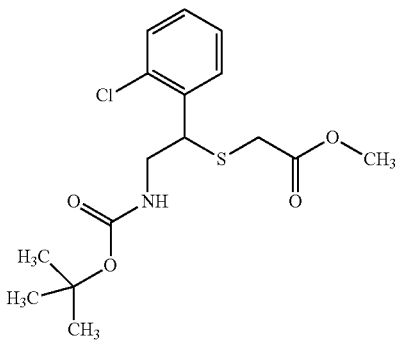 [SMILES: COC(=O)CSC(CNC(=O)OC(C)(C)C)c1ccccc1Cl]

At RT, triethylamine (420 µl, 3.0 mmol) and di-tert-butyl dicarbonate (661 mg, 3.03 mmol) were added in succession to a solution of (+/−)-methyl {[2-amino-1-(2-chlorophenyl)ethyl]sulfanyl}acetate (1.56 g, 45% purity, 2.70 mmol, Example 138A) in dichloromethane (5.8 ml) (evolution of gas), and the mixture was stirred at RT overnight. The mixture was then diluted to a volume of 100 ml with dichloromethane and washed once with semi-concentrated sodium bicarbonate solution. The resulting precipitate was filtered off and discarded. The mixture was then washed with saturated aqueous sodium chloride solution, dried over sodium sulfate, filtered and concentrated, and the residue was twice purified by preparative HPLC (Method 16). The combined target fractions were concentrated, and the residue was dried under reduced pressure. This gave 100 mg (98% purity, 10% of theory) of the title compound.

LC-MS (Method 1): $R_t$=2.00 min; MS (ESIpos): m/z=382 [M+Na]$^+$ $^1$H-NMR (400 MHz, DMSO-d6) δ [ppm]: 7.50-7.41 (m, 2H), 7.40-7.23 (m, 2H), 6.99 (t, 1H), 4.60 (t, 1H), 3.55 (s, 3H), 3.50-3.28 (m, 3H), 3.23-3.13 (m, 1H), 1.33 (s, 9H).

Example 140A (+/−)-Methyl {[2-[(tert-butoxycarbonyl)amino]-1-(2-chlorophenyl)ethyl]sulfonyl}acetate (Racemate)

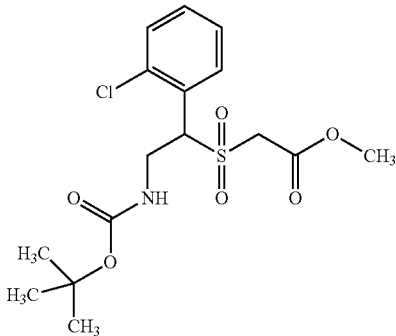 [SMILES: COC(=O)CS(=O)(=O)C(CNC(=O)OC(C)(C)C)c1ccccc1Cl]

At RT, meta-chloroperbenzoic acid (103 mg, 70% purity, 417 µmol) was added to a solution of (+/−)-methyl ({2-[(tert-butoxycarbonyl)amino]-1-(2-chlorophenyl)ethyl}sulfanyl)acetate (100 mg, 278 µmol, Example 139A) in dichloromethane (5 ml), and the mixture was stirred at RT overnight. Saturated sodium bicarbonate solution (5 ml) was then added, the mixture was stirred vigorously, dichloromethane and water were then added and the mixture was agitated. After phase separation, the aqueous phase was extracted once with dichloromethane. The combined organic phases were dried over sodium sulfate, filtered and concentrated, and the residue was dissolved in acetonitrile and purified by preparative HPLC (Method 17). The combined target fractions were concentrated, and the residue was dried under reduced pressure. This gave 75 mg (100% purity, 69% of theory) of the title compound.

LC-MS (Method 1): $R_t$=1.77 min; MS (ESIneg): m/z=390 [M−H]$^−$

Example 141A (+/−)-Methyl {[2-amino-1-(2-chlorophenyl)ethyl]sulfonyl}acetate hydrochloride

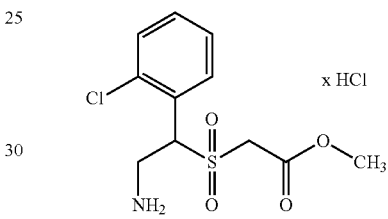

(+/−)-Methyl {[2-[(tert-butoxycarbonyl)amino]-1-(2-chlorophenyl)ethyl]sulfonyl}acetate (75 mg, 191 µmol, Example 140A) was dissolved in a 4 M solution of hydrogen chloride in dioxane (720 µl, 2.9 mmol) and the mixture was allowed to stand at RT for 3 h. The mixture was then concentrated and repeatedly dichloromethane was added and the mixture was concentrated again. This gave 60 mg (97% purity, 93% of theory) of the title compound.

LC-MS (Method 4): $R_t$=1.03 min; MS (ESIpos): m/z=292 [M−HCl+H]$^+$

Example 142A (+/−)-tert-Butyl 5-amino-4-(6-chloro-2,3-difluorophenyl)pentanoate (Racemate)

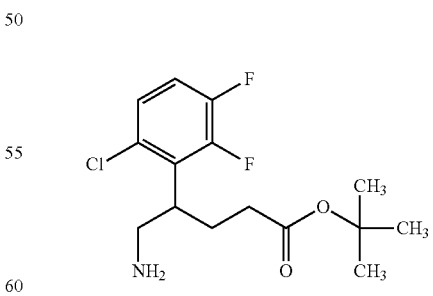

Raney nickel (349 mg, 5.95 mmol) was added to a solution of (+/−)-tert-butyl 4-(6-chloro-2,3-difluorophenyl)-4-cyanobutanoate (2.26 g, 83% purity, 5.95 mmol, Example 64A) in tert-butanol (35 ml), and the mixture was hydrogenated at atmospheric pressure overnight. Subsequently, the catalyst was filtered off through kieselguhr, which was washed through twice with tert-butanol (10 ml), and the filtrate was concentrated. The residue was taken up in ethyl acetate (50 ml) and extracted successively with 1 M hydrochloric acid and water (50 ml each time). The combined aqueous phases were adjusted to pH 8-9 using saturated sodium bicarbonate solution and extracted twice with ethyl acetate (50 ml). The combined organic phases were dried over sodium sulfate, filtered and concentrated, and the residue was dried under reduced pressure. This gave 1.05 g (97% purity, 53% of theory) of the title compound.

LC-MS (Method 4): $R_t$=1.82 min; MS (ESIpos): m/z=320 [M+H]$^+$

Example 143A (+/−)-Methyl 5-amino-4-[2-(trifluoromethyl)phenyl]pentanoate (Racemate)

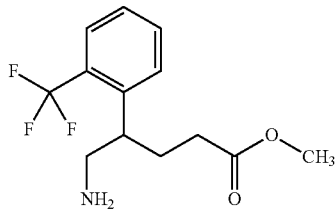 [SMILES: COC(=O)CCC(CN)c1ccccc1C(F)(F)F]

Platinum dioxide (737 mg, 3.24 mmol) and concentrated hydrochloric acid (1.4 ml, 12 M, 16 mmol) were added to a solution of (+/−)-methyl 4-cyano-4-[2-(trifluoromethyl)phenyl]butanoate (4.40 g, 16.2 mmol, Example 65A) in methanol (150 ml), and the mixture was hydrogenated at atmospheric pressure overnight. Subsequently, the catalyst was filtered off through kieselguhr and washed with methanol, and the filtrate was concentrated. The residue was combined with a residue obtained analogously in a preliminary experiment (amount of (+/−)-methyl 4-cyano-4-[2-(trifluoromethyl)phenyl]butanoate employed: 200 mg, 737 μmol). This gave 5.50 g (77% purity, 91% of theory, based on a total of 16.94 mmol (+/−)-methyl 4-cyano-4-[2-(trifluoromethyl)phenyl]butanoate employed) of the title compound.

LC-MS (Method 2): $R_t$=0.52 min; MS (ESIpos): m/z=276 [M+H]$^+$

Example 144A (+/−)-tert-Butyl 5-amino-4-(5-fluoro-2-methylphenyl)pentanoate (Racemate)

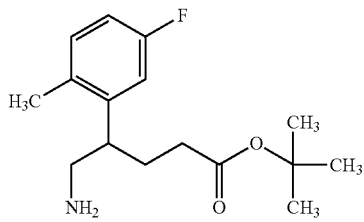 [SMILES: Cc1ccc(F)cc1C(CN)CCC(=O)OC(C)(C)C]

Raney nickel (1.04 g, 17.7 mmol) was added to a solution of (+/−)-tert-butyl 4-cyano-4-(5-fluoro-2-methylphenyl)butanoate (4.92 g, 17.7 mmol, Example 66A) in tert-butanol (100 ml), and the mixture was hydrogenated at atmospheric pressure for 24 h. Subsequently, the catalyst was filtered off through kieselguhr, which was washed through twice with tert-butanol (15 ml), and the filtrate was concentrated. The residue was taken up in ethyl acetate (80 ml) and extracted successively with 1 M hydrochloric acid and water (80 ml each time). The combined aqueous phases were adjusted to pH 8-9 using saturated sodium bicarbonate solution and extracted twice with ethyl acetate (80 ml). The combined organic phases were dried over sodium sulfate, filtered and concentrated, and the residue was dried under reduced pressure. This gave 2.04 g (92% purity, 38% of theory) of the title compound.

LC-MS (Method 4): $R_t$=1.94 min; MS (ESIpos): m/z=282 [M+H]$^+$ $^1$H-NMR (400 MHz, DMSO-d6) δ [ppm]: 1.109 (0.34), 1.197 (0.07), 1.293 (0.03), 1.357 (16.00), 1.394 (0.15), 1.513 (0.24), 1.609 (0.11), 1.621 (0.11), 1.638 (0.25), 1.648 (0.17), 1.663 (0.22), 1.681 (0.14), 1.709 (0.06), 1.927 (0.05), 1.943 (0.10), 1.950 (0.13), 1.964 (0.28), 1.986 (1.50), 1.995 (1.06), 2.011 (0.26), 2.018 (0.20), 2.072 (0.03), 2.232 (3.57), 2.303 (0.20), 2.366 (0.03), 2.641 (0.07), 2.659 (0.11), 2.672 (0.57), 2.681 (0.59), 2.690 (0.75), 2.696 (0.71), 2.711 (0.09), 2.728 (0.08), 2.851 (0.21), 2.863 (0.20), 3.172 (0.05), 3.312 (0.65), 6.866 (0.17), 6.873 (0.21), 6.887 (0.37), 6.894 (0.43), 6.909 (0.20), 6.916 (0.23), 6.968 (0.43), 6.974 (0.37), 6.994 (0.42), 7.001 (0.36), 7.105 (0.03), 7.150 (0.35), 7.166 (0.40), 7.187 (0.30).

$^1$H-NMR (400 MHz, DMSO-d6) δ [ppm]: 7.17 (dd, 1H), 6.99 (dd, 1H), 6.89 (td, 1H), 2.93-2.80 (m, 1H), 2.74-2.62 (m, 2H), 2.23 (s, 3H), 2.06-1.87 (m, 3H), 1.74-1.60 (m, 1H), 1.50 (br. s, 2H), 1.36 (s, 9H).

Example 145A (+/−)-tert-Butyl 5-amino-4-[2-(trifluoromethoxy)phenyl]pentanoate (Racemate)

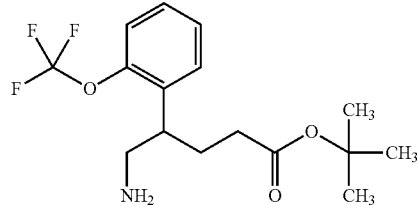 [SMILES: CC(C)(C)OC(=O)CCC(CN)c1ccccc1OC(F)(F)F]

Raney nickel (446 mg, 7.59 mmol) was added to a solution of (+/−)-tert-butyl 4-cyano-4-[2-(trifluoromethoxy)phenyl]butanoate (3.13 g, 80% purity, 7.59 mmol, Example 67A) in tert-butanol (45 ml), and the mixture was hydrogenated at atmospheric pressure overnight. Subsequently, more Raney nickel (446 mg, 7.59 mmol) was added, and the mixture was hydrogenated at atmospheric pressure for a further 24 h. Thereafter, the catalyst was filtered off through kieselguhr and the filtrate was concentrated and dried under reduced pressure. This gave 3.00 g (83% purity, 98% of theory) of the title compound.

LC-MS (Method 1): $R_t$=1.29 min; MS (ESIpos): m/z=334 [M+H]$^+$

Example 146A (+/−)-tert-Butyl 5-amino-4-(pyridin-2-yl)pentanoate (Racemate)

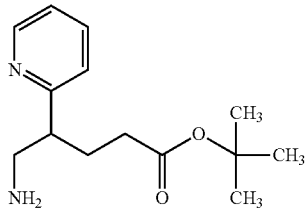 [SMILES: CC(C)(C)OC(=O)CCC(CN)c1ccccn1]

(+/−)-tert-Butyl 4-cyano-4-(pyridin-2-yl)butanoate (799 mg, 3.24 mml, Example 68A) was dissolved in tert-butanol (10 ml), Raney-Nickel (228 mg, 3.89 mmol) was added and the reaction mixture was stirred at atmospheric pressure under a hydrogen atmosphere overnight. The reaction mixture was filtered and concentrated. This gave 678 mg of the title compound as a crude product. The crude product was used directly (without further purification) in the subsequent reaction.

LC-MS (Method 6): $R_t$=1.08 min; MS (ESIpos): m/z=251 [M+H]$^+$

Example 147A (+/−)-tert-Butyl 5-amino-4-[2-fluoro-6-(trifluoromethyl)phenyl]pentanoate (Racemate)

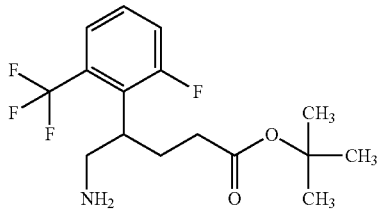 [SMILES: CC(C)(C)OC(=O)CCC(CN)c1c(F)cccc1C(F)(F)F]

Raney nickel (801 mg, 13.6 mmol) was added to a solution of (+/−)-tert-butyl 4-cyano-4-[2-fluoro-6-(trifluoromethyl)phenyl]butanoate (4.52 g, 13.6 mmol, Example 69A) in tert-butanol (100 ml) and methanol (15 ml), and the mixture was hydrogenated with stirring at atmospheric pressure overnight. Once more, Raney nickel (2 g, 34.0 mmol) was added to the reaction mixture and the mixture was stirred vigorously at atmospheric pressure under hydrogen for 40 h. Subsequently, the catalyst was filtered off through kieselguhr, which was washed through three times with methanol (30 ml each time), and the filtrate was concentrated under reduced pressure. The residue was taken up in 200 ml of ethyl acetate. This organic phase was extracted twice with 200 ml of 1 M hydrochloric acid. The combined aqueous phases were brought to pH 8-9 by gradual addition of sodium bicarbonate, then extracted twice with 200 ml each time of ethyl acetate. The combined organic phases were dried over sodium sulfate and concentrated on a rotary evaporator. The residue was dried under reduced pressure. This gave 3.32 g (92% purity, 67% of theory) of the title compound.

LC-MS (Method 1): $R_t$=1.21 min; MS (ESIpos): m/z=336 [M+H]$^+$ $^1$H-NMR (400 MHz, DMSO-d6) δ [ppm]: 1.109 (0.25), 1.156 (0.06), 1.167 (0.07), 1.174 (0.12), 1.191 (0.06), 1.327 (16.00), 1.390 (0.40), 1.484 (0.07), 1.882 (0.09), 1.905 (0.14), 1.930 (0.25), 1.946 (0.23), 1.965 (0.29), 1.979 (0.15), 1.987 (0.45), 2.006 (0.19), 2.034 (0.10), 2.055 (0.30), 2.074 (0.35), 2.093 (0.31), 2.118 (0.16), 2.129 (0.11), 2.150 (0.04), 2.310 (0.07), 2.365 (0.02), 2.669 (0.02), 2.782 (0.10), 2.799 (0.17), 2.812 (0.24), 2.828 (0.25), 2.872 (0.18), 2.876 (0.18), 2.890 (0.29), 2.895 (0.30), 2.920 (0.37), 3.494 (0.02), 3.522 (0.03), 4.019 (0.05), 4.037 (0.05), 7.476 (0.66), 7.485 (0.49), 7.489 (0.49), 7.501 (0.31), 7.509 (0.87), 7.521 (0.09), 7.550 (0.51), 7.557 (0.32), 7.564 (0.37), 7.573 (0.26), 7.614 (0.04), 7.637 (0.04).

Example 148A (+/−)-tert-Butyl 5-amino-4-(2,3,5,6-tetrafluorophenyl)pentanoate (Racemate)

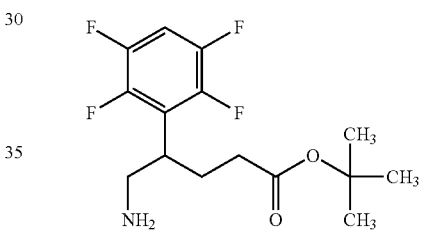

Raney nickel (157 mg, 2.68 mmol) was added to a solution of (+/−)-tert-butyl 4-cyano-4-(2,3,5,6-tetrafluorophenyl)butanoate (850 mg, 2.68 mmol, Example 70A) in tert-butanol (20 ml) and methanol (2.1 ml), and the mixture was hydrogenated with stirring at atmospheric pressure overnight. Subsequently, the catalyst was filtered off through kieselguhr, which was washed through twice with tert-butanol (10 ml) and methanol (10 ml), and the filtrate was concentrated under reduced pressure. The residue was taken up in ethyl acetate (100 ml). This organic phase was extracted twice with 1 M hydrochloric acid (100 ml). The combined aqueous phases were brought to pH 8-9 by gradual addition of sodium bicarbonate and then extracted twice with ethyl acetate (100 ml each). The combined organic phases were dried over sodium sulfate and concentrated on a rotary evaporator. This gave 586 mg (95% purity, 65% of theory) of the title compound.

LC-MS (Method 1): $R_t$=1.15 min; MS (ESIpos): m/z=322 [M+H]$^+$ $^1$H-NMR (400 MHz, DMSO-d6) δ [ppm]: 1.219 (0.06), 1.379 (16.00), 1.536 (0.07), 2.073 (0.16), 2.091 (0.22), 2.107 (0.28), 2.125 (0.26), 2.144 (0.10), 2.213 (0.07), 2.231 (0.19), 2.250 (0.22), 2.267 (0.18), 2.285 (0.13), 2.302 (0.08), 2.327 (0.07), 2.365 (0.07), 2.384 (0.36), 2.393 (0.38), 2.402 (0.59), 2.410 (0.56), 2.420 (0.29), 2.428 (0.27), 2.452 (0.06), 2.669 (0.06), 4.373 (0.20), 4.390 (0.39), 4.407 (0.19), 7.698 (0.31), 7.711 (1.11), 7.722 (0.54), 7.748 (0.35), 7.766 (0.11).

Example 149A (+/−)-tert-Butyl 5-amino-4-(2,3,5-trifluorophenyl)pentanoate (Racemate)

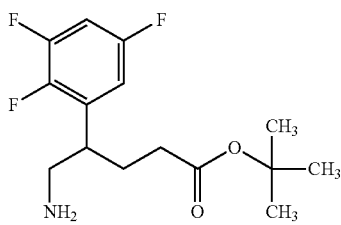 [SMILES: CC(C)(C)OC(=O)CCC(CN)c1cc(F)cc(F)c1F]

Raney nickel (118 mg, 2.00 mmol) was added to a solution of (+/−)-tert-butyl 4-cyano-4-(2,3,5-trifluorophenyl)butanoate (600 mg, 2.00 mmol, Example 71A) in tert-butanol (15 ml), and the mixture was hydrogenated at atmospheric pressure overnight. Subsequently, the catalyst was filtered off through kieselguhr, which was washed through twice with tert-butanol (5 ml each), and the filtrate was concentrated under reduced pressure. The residue was taken up in ethyl acetate (50 ml). This organic phase was extracted twice with 1 M hydrochloric acid (50 ml each). The combined aqueous phases were brought to pH 8-9 by gradual addition of sodium bicarbonate and then extracted twice with ethyl acetate (50 ml each). The combined organic phases were dried over sodium sulfate and concentrated on a rotary evaporator. This gave 200 mg (96% purity, 32% of theory) of the title compound.

LC-MS (Method 3): $R_t$=1.81 min; MS (ESIpos): m/z=304 [M+H]$^+$ $^1$H-NMR (400 MHz, DMSO-d6) δ [ppm]: 1.110 (0.34), 1.193 (0.08), 1.234 (0.08), 1.353 (16.00), 1.509 (0.17), 1.639 (0.07), 1.673 (0.16), 1.689 (0.20), 1.698 (0.17), 1.714 (0.17), 1.729 (0.09), 1.865 (0.06), 1.934 (0.06), 1.955 (0.13), 1.968 (0.17), 1.984 (0.18), 2.003 (0.18), 2.025 (0.88), 2.041 (0.91), 2.059 (0.29), 2.328 (0.05), 2.367 (0.04), 2.691 (0.14), 2.710 (0.21), 2.723 (0.39), 2.742 (0.46), 2.755 (0.40), 2.771 (0.46), 2.787 (0.14), 2.802 (0.16), 2.944 (0.18), 7.039 (0.22), 7.051 (0.22), 7.063 (0.22), 7.301 (0.08), 7.309 (0.09), 7.329 (0.18), 7.337 (0.17), 7.345 (0.17), 7.365 (0.10), 7.373 (0.09).

Example 150A (+/−)-tert-Butyl 5-amino-4-(2,3,6-trichlorophenyl)pentanoate (Racemate)

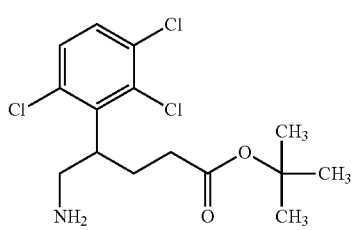 [SMILES: CC(C)(C)OC(=O)CCC(CN)c1c(Cl)ccc(Cl)c1Cl]

Raney nickel (1.64 g, 27.9 mmol) was added to a solution of (+/−)-tert-butyl 4-cyano-4-(2,3,6-trichlorophenyl)butanoate (10.2 mg, 95% purity, 27.9 mmol, Example 72A) in tert-butanol (210 ml) and methanol (9.1 ml), and the mixture was hydrogenated with stirring at atmospheric pressure overnight. An additional amount of Raney nickel (2.0 g, 34.0 mmol) was added, and the mixture was hydrogenated at atmospheric pressure while stirring for three further days. Subsequently, the catalyst was filtered off through kieselguhr, which was washed through three times with methanol (30 ml each time), and the filtrate was concentrated. The residue was taken up in ethyl acetate (400 ml). This organic phase was extracted twice with 1 M hydrochloric acid (300 ml). The combined aqueous phases were brought to pH 8-9 by gradual addition of sodium bicarbonate and then extracted twice with ethyl acetate (300 ml each time). The combined organic phases were dried over sodium sulfate and concentrated on a rotary evaporator. Drying under reduced pressure gave 2.54 g (89% purity, 23% of theory) of the title compound.

LC-MS (Method 1): $R_t$=1.30 min; MS (ESIpos): m/z=352 [M+H]$^+$ $^1$H-NMR (400 MHz, DMSO-d6) δ [ppm]: 1.336 (16.00), 1.352 (1.85), 1.492 (0.42), 2.013 (0.65), 2.022 (0.61), 2.030 (0.63), 2.042 (0.89), 2.055 (0.81), 2.070 (0.42), 2.082 (0.42), 2.097 (0.43), 3.049 (0.54), 3.069 (0.57), 7.426 (0.52), 7.506 (0.64), 7.532 (0.56), 7.544 (0.61), 7.553 (0.41).

Example 151A (+/−)-tert-Butyl 6-amino-5-(2-chlorophenyl)hexanoate (Racemate)

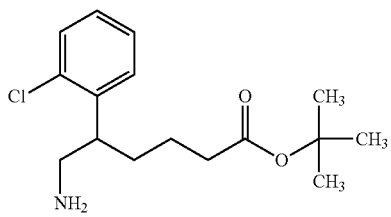 [SMILES: CC(C)(C)OC(=O)CCCC(CN)c1ccccc1Cl]

Raney nickel (540 mg, 9.19 mmol) was added to a solution of (+/−)-tert-butyl 5-(2-chlorophenyl)-5-cyanopentanoate (2.70 g, 9.19 mmol, Example 73A) in tert-butanol (54 ml), and the mixture was hydrogenated at atmospheric pressure for 24 h. Subsequently, the catalyst was filtered off through kieselguhr, which was washed through twice with tert-butanol (15 ml), and the filtrate was concentrated. The residue was taken up in ethyl acetate (60 ml) and extracted successively with 1 M hydrochloric acid and water. The combined aqueous phases were adjusted to pH 8-9 with saturated sodium bicarbonate solution and extracted twice with ethyl acetate (80 ml each). The combined organic phases were dried over sodium sulfate, filtered and concentrated, and the residue was dried under reduced pressure. This gave 1.32 g (95% purity, 46% of theory) of the title compound.

LC-MS (Method 1): $R_t$=1.33 min; MS (ESIpos): m/z=298 [M+H]$^+$ $^1$H-NMR (400 MHz, DMSO-d6) δ [ppm]: 1.111 (0.02), 1.195 (0.08), 1.271 (0.23), 1.290 (0.45), 1.315 (0.77), 1.334 (1.17), 1.356 (16.00), 1.462 (0.15), 1.477 (0.17), 1.485 (0.23), 1.496 (0.24), 1.509 (0.29), 1.519 (0.27), 1.532 (0.20), 1.542 (0.12), 1.556 (0.09), 1.697 (0.17), 1.710 (0.26), 1.724 (0.27), 1.736 (0.26), 1.744 (0.21), 1.769 (0.14), 1.784 (0.08), 1.876 (0.06), 2.074 (0.13), 2.093 (0.23), 2.113 (0.58), 2.131 (0.90), 2.144 (0.77), 2.162 (0.39), 2.183 (0.14), 2.201 (0.09), 2.367 (0.06), 2.739 (1.29), 2.756 (1.29), 3.110 (0.18), 3.127 (0.32), 3.140 (0.35), 3.150 (0.32), 3.163 (0.27), 3.180 (0.13), 7.171 (0.12), 7.196 (0.28), 7.206 (0.32), 7.211 (0.31), 7.217 (0.44), 7.227 (0.35), 7.238 (0.29), 7.248 (0.07), 7.293 (0.22), 7.315 (1.26), 7.326 (1.32), 7.405 (0.67), 7.425 (0.53).

Example 152A (+/−)-tert-Butyl 6-amino-5-(2-chlorophenyl)-5-methylhexanoate (Racemate)

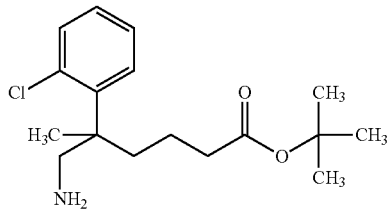 [SMILES: CC(C)(C)OC(=O)CCCC(C)(CN)c1ccccc1Cl]

Raney nickel (454 mg, 7.73 mmol) was added to a solution of (+/−)-tert-butyl 5-(2-chlorophenyl)-5-cyanohexanoate (2.38 g, 7.73 mmol, Example 74A) in tert-butanol (45 ml), and the mixture was hydrogenated at atmospheric pressure for 24 h. Subsequently, Raney nickel (454 mg, 7.73 mmol) was again added and the mixture was hydrogenated at atmospheric pressure for a further 24 h. Subsequently, Raney nickel (454 mg, 7.73 mmol) was once more added and the mixture was hydrogenated at atmospheric pressure for a further 24 h. Subsequently, the catalyst was filtered off through kieselguhr, which was washed through twice with tert-butanol (15 ml), and the filtrate was concentrated. The residue was taken up in ethyl acetate (80 ml) and extracted successively with 1 M hydrochloric acid and water (80 ml each time). The combined aqueous phases were adjusted to pH 8-9 with saturated sodium bicarbonate solution and extracted twice with ethyl acetate (100 ml each). The combined organic phases were dried over sodium sulfate, filtered and concentrated, and the residue was dried under reduced pressure. This gave 820 mg (61% purity, 21% of theory) of the title compound as a mixture with the dechlorinated product ((+/−)-tert-butyl 6-amino-5-methyl-5-phenylhexanoate).

LC-MS (Method 1): $R_t$=1.24 min; MS (ESIpos): m/z=312 [M+H]$^+$

Example 153A (+/−)-Methyl 3-{[(6-bromo-3-methyl-2-phenylquinolin-4-yl)carbonyl]amino}hydratropate (Racemate)

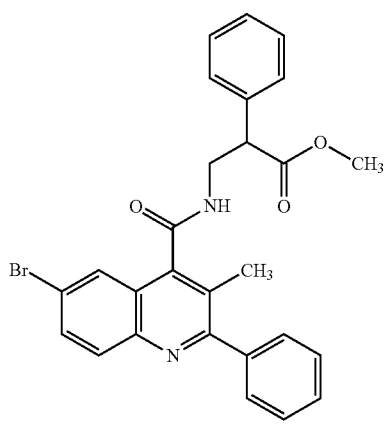 [SMILES: COC(=O)C(CNC(=O)c1c(C)c(-c2ccccc2)nc2ccc(Br)cc12)c1ccccc1]

HATU (428 mg, 1.13 mmol) and DIPEA (390 μl, 2.3 mmol) were added to a mixture of 6-bromo-3-methyl-2-phenylquinoline-4-carboxylic acid (257 mg, 750 μmol, preparable according to WO 2016 146602 A1, p. 51, Example 3A) in DMF (4 ml), and the mixture was stirred at RT for 30 min. (+/−)-Methyl 3-amino-2-phenylpropanoate hydrochloride (178 mg, 825 μmol, Example 75A) was then added, and the mixture was stirred at 60° C. for 1.5 h. After cooling to RT, 10% strength citric acid (50 ml) was added, and the precipitate formed was filtered off, washed twice with water (5 ml) and dried under reduced pressure. The precipitate was then taken up in dichloromethane and purified by flash column chromatography (50 g silica gel Biotage Snap-Cartridge KP-Sil, cyclohexane/ethyl acetate 97:3→8:2, Isolera One). This gave 175 mg (90% purity, 42% of theory) of the title compound.

LC-MS (Method 1): $R_t$=2.16 min; MS (ESIpos): m/z=547/549 [M+H]$^+$ $^1$H-NMR (400 MHz, DMSO-d6) δ [ppm]: −0.008 (1.64), 0.008 (1.20), 2.167 (2.67), 3.287 (1.39), 3.647 (16.00), 4.106 (0.90), 4.126 (1.46), 7.325 (1.12), 7.336 (1.15), 7.347 (0.78), 7.387 (12.53), 7.398 (7.56), 7.493 (0.93), 7.507 (2.84), 7.514 (2.14), 7.526 (5.17), 7.537 (5.83), 7.543 (3.52), 7.555 (1.01), 7.851 (1.24), 7.856 (1.07), 7.873 (1.92), 7.879 (1.75), 7.945 (3.66), 7.968 (2.29), 9.024 (1.33).

Example 154A (+/−)-Ethyl 3-{[(6-bromo-3-methyl-2-phenylquinolin-4-yl)carbonyl]amino}-2-(2-chlorophenyl)propanoate (Racemate)

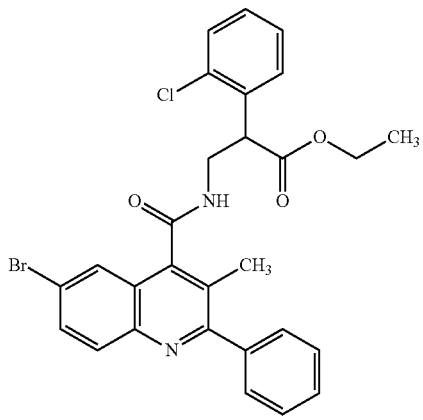 [SMILES: CCOC(=O)C(CNC(=O)c1c(C)c(-c2ccccc2)nc2ccc(Br)cc12)c1ccccc1Cl]

In succession, triethylamine (1.4 ml, 10 mmol) and a mixture of 6-bromo-3-methyl-2-phenylquinoline-4-carbonyl chloride (1.80 g, 5.00 mmol, Example 1A) in dichloromethane (25 ml) were added to a solution of (+/−)-ethyl 3-amino-2-(2-chlorophenyl)propanoate (1.25 g, 5.50 mmol, Example 76A) in dichloromethane (25 ml), and the reaction mixture was stirred at RT for 2 h. Dichloromethane (50 ml) and water (100 ml) were then added to the mixture, which was agitated. The aqueous phase was extracted twice with dichloromethane (100 ml each). The combined organic phases were dried over sodium sulfate, filtered and concentrated, and the residue was taken up in dichloromethane and purified by flash column chromatography (200 g silica gel Biotage Snap-Cartridge KP-Sil, cyclohexane/ethyl acetate 9:1). This gave 2.36 g (100% purity, 86% of theory) of the title compound.

LC-MS (Method 1): $R_t$=2.37 min; MS (ESIpos): m/z=551/553 [M+H]$^+$ $^1$H-NMR (400 MHz, DMSO-d6) δ [ppm]: −0.008 (1.26), 0.008 (1.20), 0.890 (2.24), 1.131 (7.34), 1.149 (16.00), 1.157 (1.41), 1.166 (7.62), 1.175 (1.72), 1.193 (0.77), 1.398 (7.12), 1.988 (2.67), 2.184 (11.70), 4.021 (1.07), 4.039 (1.23), 4.111 (1.87), 4.128 (5.28), 4.146 (5.04), 4.164 (1.63), 4.558 (1.60), 4.577 (3.41), 4.596 (1.41), 7.354 (1.78), 7.358 (1.84), 7.372 (1.87), 7.378 (2.92), 7.382 (1.97), 7.397 (2.15), 7.401 (2.27), 7.416 (0.98), 7.419 (0.83), 7.492 (1.87), 7.496 (3.72), 7.502 (3.99), 7.508 (6.94), 7.513 (7.28), 7.519 (4.27), 7.525 (7.98), 7.527 (9.43), 7.531 (6.54), 7.535 (8.60), 7.538 (8.48), 7.542 (5.71), 7.545 (4.27), 7.555 (1.57), 7.849 (2.18), 7.854 (1.90), 7.871 (3.29), 7.876 (3.13), 7.944 (5.62), 7.966 (3.53), 9.014 (1.17), 9.029 (2.36), 9.043 (1.14).

Example 155A (+/−)-Methyl 3-{[(6-bromo-3-methyl-2-phenylquinolin-4-yl)carbonyl]amino}-2-(2-methoxyphenyl)propanoate (Racemate)

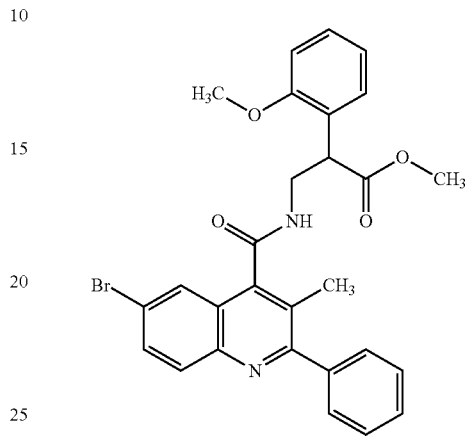

In succession, triethylamine (1.4 ml, 10 mmol) and a suspension of 6-bromo-3-methyl-2-phenylquinoline-4-carbonyl chloride (902 mg, 2.50 mmol, Example 1A) in dichloromethane (10 ml) were added to a solution of (+/−)-methyl 3-amino-2-(2-methoxyphenyl)propanoate hydrochloride (1.52 g, 89% purity, 5.50 mmol, Example 77A) in dichloromethane (15 ml), and the mixture was stirred at RT for 24 h. Subsequently, dichloromethane and water (100 ml of each) were added to the mixture, which was agitated. The aqueous phase was extracted once with dichloromethane (100 ml). The combined organic phases were dried over sodium sulfate, filtered and concentrated, and the residue was taken up in dichloromethane and purified by flash column chromatography (200 g silica gel Biotage Snap-Cartridge KP-Sil, cyclohexane/ethyl acetate 8:2). The combined target fractions were concentrated and the residue was dried under reduced pressure. This gave 1.14 g (100% purity, 85% of theory) of the title compound.

LC-MS (Method 1): $R_t$=2.14 min; MS (ESIpos): m/z=533/535 [M+H]$^+$ $^1$H-NMR (400 MHz, DMSO-d6) δ [ppm]: 1.988 (0.57), 2.194 (6.26), 3.303 (2.46), 3.324 (1.41), 3.622 (14.45), 3.799 (16.00), 4.364 (0.82), 4.383 (1.55), 4.402 (0.71), 6.945 (0.84), 6.947 (0.81), 6.964 (1.83), 6.966 (1.71), 6.983 (1.08), 7.034 (1.46), 7.053 (1.84), 7.279 (3.27), 7.297 (3.66), 7.301 (1.80), 7.315 (0.75), 7.493 (0.95), 7.504 (1.39), 7.508 (2.60), 7.514 (2.02), 7.521 (1.24), 7.527 (4.31), 7.539 (5.20), 7.541 (5.04), 7.546 (3.03), 7.549 (1.98), 7.558 (0.93), 7.850 (1.24), 7.855 (1.01), 7.872 (1.86), 7.878 (1.67), 7.943 (3.32), 7.966 (2.06), 8.929 (1.40).

Example 156A (+/−)-Methyl 3-{[(6-bromo-3-methyl-2-phenylquinolin-4-yl)carbonyl]amino}-2-(4-fluorophenyl)propanoate (Racemate)

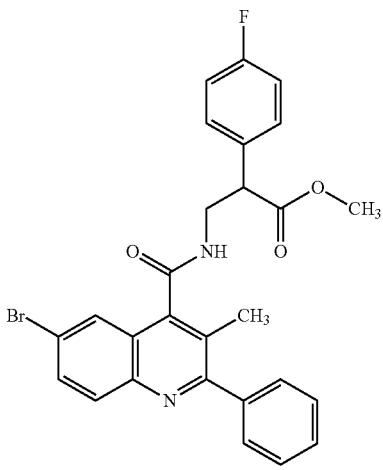 [SMILES: COC(=O)C(CNC(=O)c1c(C)c(-c2ccccc2)nc2ccc(Br)cc12)c1ccc(F)cc1]

In succession, triethylamine (140 µl, 1.0 mmol) and a suspension of 6-bromo-3-methyl-2-phenylquinoline-4-carbonyl chloride (180 mg, 500 µmol, Example 1A) in dichloromethane (2 ml) were added to a solution of (+/−)-methyl 3-amino-2-(4-fluorophenyl)propanoate hydrochloride (129 mg, 550 µmol, Example 78A) in dichloromethane (3 ml), and the mixture was stirred at RT for 18 h. More (+/−)-methyl 3-amino-2-(4-fluorophenyl)propanoate hydrochloride (129 mg, 550 µmol, Example 78A) in dichloromethane (2 ml) and triethylamine (140 µl, 1.0 mmol) were then added, and the reaction mixture was stirred at RT for a further 4 days. Subsequently, dichloromethane and water (50 ml of each) were added to the mixture, which was agitated. The aqueous phase was extracted once with dichloromethane (50 ml). The combined organic phases were dried over sodium sulfate, filtered and concentrated, and the residue was taken up in dichloromethane and purified by flash column chromatography (50 g silica gel Biotage Snap-Cartridge KP-Sil, cyclohexane/ethyl acetate 8:2). The combined target fractions were concentrated and the residue was dried under reduced pressure. This gave 213 mg (90% purity, 74% of theory) of the title compound.

LC-MS (Method 1): $R_t$=2.19 min; MS (ESIpos): m/z=521/523 $[M+H]^+$ $^1$H-NMR (400 MHz, DMSO-d6): d [ppm]=9.01 (t, 1H), 7.95 (d, 1H), 7.86 (dd, 1H), 7.71 (br. s, 1H), 7.57-7.49 (m, 5H), 7.47-7.38 (m, 2H), 7.25-7.18 (m, 2H), 4.14 (t, 1H), 4.02-3.78 (br. m, 2H), 3.65 (s, 3H), 2.18 (br. s, 3H).

Example 157A (+/−)-Ethyl 3-{[(6-bromo-3-methyl-2-phenylquinolin-4-yl)carbonyl]amino}-2-methylphenylpropanoate (Racemate)

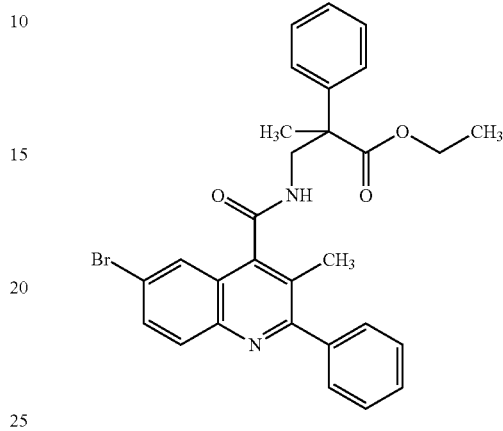

In succession, N,N-diisopropylethylamine (260 µl, 1.5 mmol) and a suspension of 6-bromo-3-methyl-2-phenylquinoline-4-carbonyl chloride (180 mg, 500 µmol, Example 1A) in dichloromethane (2 ml) were added to a suspension of (+/−)-ethyl 3-amino-2-methyl-2-phenylpropanoate hydrochloride (146 mg, 600 µmol, preparable according to *Archiv der Pharmazie* 1985, 318 (7), 593-600) in dichloromethane (3 ml), and the mixture was stirred at RT for 16 h. Subsequently, dichloromethane and water (30 ml of each) were added to the mixture, which was agitated. The aqueous phase was extracted once with dichloromethane (30 ml). The combined organic phases were dried over sodium sulfate, filtered and concentrated, and the residue was taken up in dichloromethane and purified by means of flash column chromatography (50 g silica gel Biotage Snap-Cartridge KP-Sil, cyclohexane/ethyl acetate gradient 93:7→7:3, Isolera One). The combined target fractions were concentrated and the residue was dried under reduced pressure. This gave 225 mg (100% purity, 85% of theory) of the title compound.

LC-MS (Method 1): $R_t$=2.39 min; MS (ESIpos): m/z=531/533 $[M+H]^+$ $^1$H-NMR (400 MHz, DMSO-d6) δ [ppm]: 0.890 (0.83), 1.123 (6.66), 1.141 (13.96), 1.158 (7.14), 1.175 (1.38), 1.192 (0.72), 1.397 (2.24), 1.646 (16.00), 1.988 (2.56), 2.156 (2.64), 3.980 (0.77), 4.020 (0.70), 4.038 (0.69), 4.068 (0.78), 4.077 (0.77), 4.087 (1.02), 4.095 (2.44), 4.105 (1.73), 4.113 (2.67), 4.124 (2.66), 4.142 (2.42), 4.150 (1.36), 4.168 (0.87), 7.303 (1.56), 7.318 (1.50), 7.366 (1.45), 7.387 (5.68), 7.399 (7.92), 7.403 (13.69), 7.419 (1.37), 7.480 (0.44), 7.492 (1.60), 7.507 (4.84), 7.512 (3.61), 7.525 (6.69), 7.541 (8.34), 7.560 (1.72), 7.720 (0.61), 7.841 (1.93), 7.846 (1.67), 7.864 (2.87), 7.869 (2.68), 7.941 (5.55), 7.963 (3.54), 8.721 (1.12), 8.735 (2.00), 8.751 (1.09).

Example 158A (+/−)-Methyl 2-({[(6-bromo-3-methyl-2-phenylquinolin-4-yl)carbonyl]amino}methyl)-2-phenylbutanoate (Racemate)

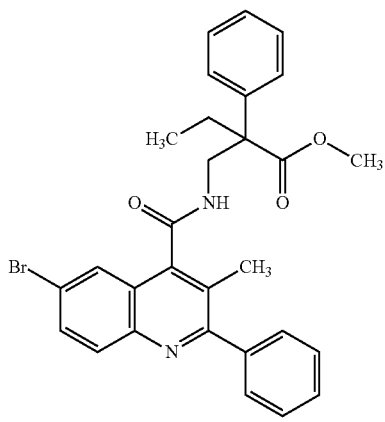 [SMILES: CCC(CNC(=O)c1c(C)c(-c2ccccc2)nc2ccc(Br)cc12)(C(=O)OC)c1ccccc1]

HATU (833 mg, 2.19 mmol) and DIPEA (760 µl, 4.4 mmol) were added to a mixture of 6-bromo-3-methyl-2-phenylquinoline-4-carboxylic acid (500 mg, 1.46 mmol, preparable according to WO 2016 146602 A1, p. 51, Example 3A) in DMF (5 ml), and the mixture was stirred at RT for 30 min. (+/−)-Methyl 2-(aminomethyl)-2-phenylbutanoate hydrochloride (562 mg, 95% purity, 2.19 mmol, preparable according to *Archiv der Pharmazie* 1985, 318 (7), 593-600), dissolved in DMF (3 ml) was then added, and the mixture was stirred at 60° C. overnight. After cooling to RT, ethyl acetate and water (20 ml of each) were added to the mixture, which was agitated. The aqueous phase was extracted twice with ethyl acetate (20 ml each). The combined organic phases were dried over sodium sulfate, filtered and concentrated, and the residue was taken up in dichloromethane and purified by flash column chromatography (100 g silica gel Biotage Snap-Cartridge KP-Sil, cyclohexane/ethyl acetate 9:1). This gave 567 mg (98% purity, 72% of theory) of the title compound.

LC-MS (Method 2): $R_t$=1.24 min; MS (ESIpos): m/z=531/533 [M+H]$^+$ $^1$H-NMR (400 MHz, DMSO-d6) δ [ppm]: −0.008 (0.63), 0.008 (0.56), 0.793 (2.77), 0.811 (6.44), 0.830 (2.94), 1.398 (0.51), 2.109 (1.08), 2.127 (3.11), 2.146 (4.00), 2.163 (2.40), 3.625 (16.00), 4.039 (0.43), 4.052 (0.47), 4.074 (0.65), 4.085 (0.60), 4.202 (0.58), 4.219 (0.62), 4.235 (0.46), 7.271 (0.56), 7.288 (1.55), 7.306 (1.12), 7.325 (2.20), 7.342 (5.33), 7.361 (3.46), 7.379 (2.92), 7.399 (0.99), 7.492 (1.16), 7.507 (3.59), 7.512 (2.64), 7.525 (4.86), 7.540 (5.95), 7.560 (1.26), 7.842 (1.41), 7.847 (1.26), 7.864 (2.14), 7.869 (2.02), 7.939 (4.01), 7.962 (2.55), 8.639 (0.83), 8.654 (1.55), 8.669 (0.80).

Example 159A (+/−)-Ethyl 3-{[(6-bromo-3-methyl-2-phenylquinolin-4-yl)carbonyl]amino}-2-[3-(trifluoromethyl)phenyl]propanoate (Racemate)

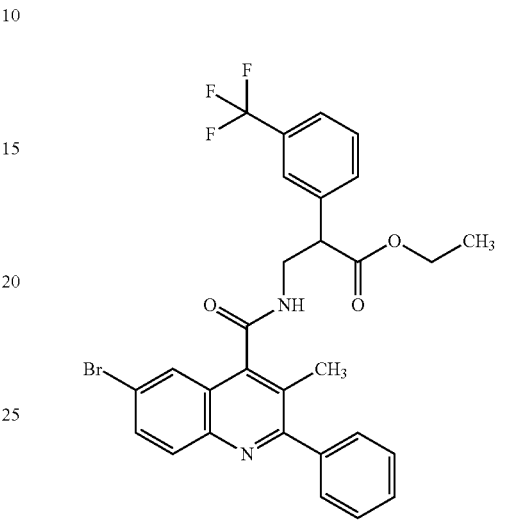

HATU (87 mg, 230 µmol) and DIPEA (80 µl, 460 µmol) were added to a mixture of 6-bromo-3-methyl-2-phenylquinoline-4-carboxylic acid (52 mg, 153 µmol, preparable according to WO 2016 146602 A1, p. 51, Example 3A) in DMF (1.5 ml), and the mixture was stirred at RT for 30 min. (+/−)-Ethyl 3-amino-2-[3-(trifluoromethyl)phenyl]propanoate (60 mg, 230 µmol, Example 80A) dissolved in DMF (1.5 ml) was then added, and the mixture was stirred at 60° C. overnight. After cooling to RT, the mixture was purified by preparative HPLC (Method 22). The combined target fractions were concentrated and dried under reduced pressure. This gave 43 mg (98% purity, 47% of theory) of the title compound.

LC-MS (Method 1): $R_t$=2.41 min; MS (ESIpos): m/z=585/587 [M+H]$^+$ $^1$H-NMR (400 MHz, DMSO-d6) δ [ppm]: 1.137 (5.86), 1.154 (11.79), 1.172 (5.88), 1.195 (3.38), 1.212 (3.46), 1.426 (11.61), 1.459 (1.63), 2.011 (3.91), 2.111 (2.10), 2.189 (0.44), 2.321 (0.63), 3.656 (0.73), 3.721 (1.10), 3.736 (1.02), 3.898 (0.66), 3.918 (0.84), 3.932 (1.58), 3.952 (2.40), 3.968 (2.49), 3.986 (1.38), 4.099 (0.63), 4.109 (1.09), 4.117 (1.61), 4.126 (2.89), 4.135 (3.04), 4.144 (3.09), 4.153 (2.68), 4.161 (1.51), 4.170 (0.92), 4.179 (0.53), 4.223 (1.36), 4.242 (2.35), 4.261 (1.04), 7.506 (3.76), 7.523 (16.00), 7.565 (0.63), 7.577 (0.56), 7.585 (0.56), 7.597 (0.53), 7.625 (1.00), 7.644 (2.61), 7.664 (2.44), 7.699 (3.02), 7.741 (5.52), 7.847 (1.72), 7.852 (1.65), 7.870 (2.67), 7.874 (2.58), 7.941 (4.43), 7.963 (2.81), 8.106 (0.43), 8.124 (0.41), 8.617 (0.41), 8.997 (1.32), 9.010 (2.41), 9.023 (1.25).

Example 160A (+/−)-Ethyl 2-(1,3-benzodioxol-5-yl)-3-{[(6-bromo-3-methyl-2-phenylquinolin-4-yl)carbonyl]amino}propanoate (Racemate)

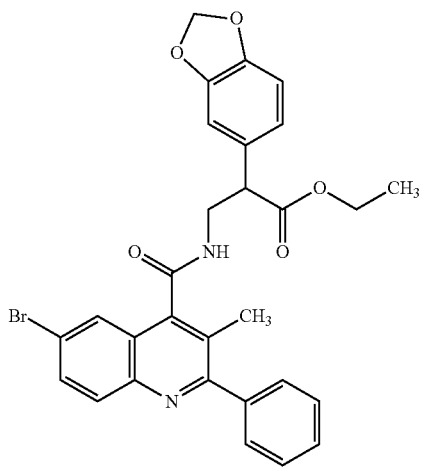 [SMILES: CCOC(=O)C(CNC(=O)c1c(C)c(-c2ccccc2)nc2ccc(Br)cc12)c1ccc2c(c1)OCO2]

HATU (240 mg, 632 μmol) and DIPEA (220 μl, 1.3 mmol) were added to a mixture of 6-bromo-3-methyl-2-phenylquinoline-4-carboxylic acid (144 mg, 421 μmol, preparable according to WO 2016 146602 A1, p. 51, Example 3A) in DMF (5 ml), and the mixture was stirred at RT for 30 min. (+/−)-Ethyl 3-amino-2-(1,3-benzodioxol-5-yl)propanoate (150 mg, 632 μmol, Example 81A) dissolved in DMF (4 ml) was then added, and the mixture was stirred at 60° C. overnight. After cooling to RT, the mixture was purified by preparative HPLC (Method 22). The combined target fractions were concentrated and dried under reduced pressure. This gave 126 mg (98% purity, 52% of theory) of the title compound.

LC-MS (Method 2): $R_t$=1.22 min; MS (ESIpos): m/z=561/563 [M+H]$^+$ $^1$H-NMR (400 MHz, DMSO-d6) δ [ppm]: 1.132 (7.84), 1.150 (16.00), 1.168 (7.82), 2.203 (8.18), 3.788 (0.91), 3.889 (0.95), 3.993 (2.51), 4.012 (4.07), 4.032 (1.55), 4.043 (0.47), 4.061 (1.04), 4.071 (1.16), 4.079 (1.28), 4.088 (3.86), 4.107 (5.28), 4.125 (3.40), 4.135 (1.13), 4.143 (0.99), 4.153 (0.87), 6.013 (15.21), 6.836 (2.25), 6.839 (2.39), 6.855 (4.06), 6.859 (4.32), 6.900 (6.60), 6.920 (3.60), 6.946 (6.37), 6.949 (6.20), 7.485 (0.65), 7.498 (1.98), 7.513 (5.89), 7.518 (4.93), 7.532 (9.29), 7.544 (12.04), 7.562 (2.49), 7.748 (0.84), 7.852 (2.40), 7.857 (2.28), 7.874 (3.60), 7.879 (3.55), 7.948 (6.49), 7.970 (4.10), 8.979 (1.64), 8.992 (3.19), 9.006 (1.64).

Example 161A (+/−)-tert-Butyl 3-{[(6-bromo-3-methyl-2-phenylquinolin-4-yl)carbonyl]amino}-2-(3-chloropyridin-2-yl)-2-methylpropanoate (Racemate)

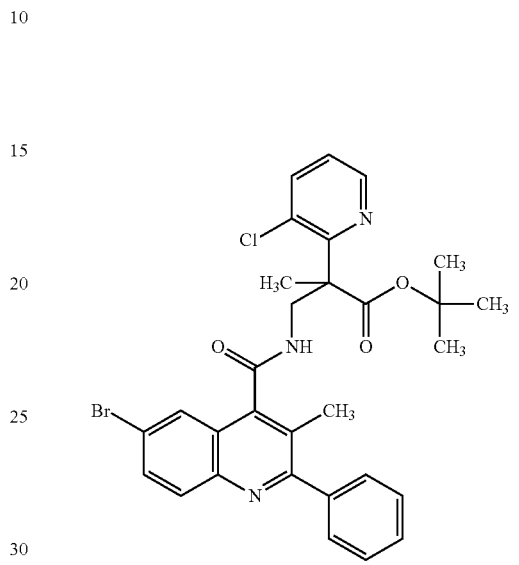

HATU (358 mg, 942 μmol) and DIPEA (330 μl, 1.9 mmol) were added to a mixture of 6-bromo-3-methyl-2-phenylquinoline-4-carboxylic acid (215 mg, 628 μmol, preparable according to WO 2016 146602 A1, p. 51, Example 3A) in DMF (2 ml), and the mixture was stirred at RT for 30 min. (+/−)-tert-Butyl 3-amino-2-(3-chloropyridin-2-yl)-2-methylpropanoate (255 mg, 942 μmol, Example 82A) dissolved in DMF (2 ml) was then added, and the mixture was stirred at 60° C. overnight. After cooling to RT, the mixture was purified by preparative HPLC (Method 15). The combined target fractions were concentrated and dried under reduced pressure. This gave 230 mg (98% purity, 60% of theory) of the title compound.

LC-MS (Method 2): $R_t$=1.36 min; MS (ESIpos): m/z=594/596 [M+H]$^+$ $^1$H-NMR (400 MHz, DMSO-d6) δ [ppm]: 1.405 (16.00), 1.677 (4.42), 2.174 (1.39), 7.369 (0.45), 7.380 (0.48), 7.388 (0.50), 7.400 (0.48), 7.504 (1.05), 7.511 (0.83), 7.522 (2.01), 7.531 (2.12), 7.839 (0.57), 7.844 (0.42), 7.861 (0.83), 7.866 (0.71), 7.906 (0.70), 7.909 (0.69), 7.926 (2.00), 7.948 (0.81), 8.519 (0.64), 8.521 (0.63), 8.530 (0.63), 8.671 (0.59).

$^1$H-NMR (400 MHz, DMSO-d6): δ [ppm]=8.67 (t, 1H), 8.53 (d, 1H), 7.98-7.89 (m, 2H), 7.85 (dd, 1H), 7.81 (br. s, 1H), 7.57-7.46 (m, 5H), 7.38 (dd, 1H), 4.48 (br. dd, 1H), 3.92 (br. d, 1H), 2.17 (br. s, 3H), 1.68 (s, 3H), 1.40 (s, 9H).

Example 162A (+/−)-Methyl 3-{[(6-bromo-3-methyl-2-phenylquinolin-4-yl)carbonyl]amino}-2-(2-fluorophenyl)-2-methylpropanoate (Racemate)

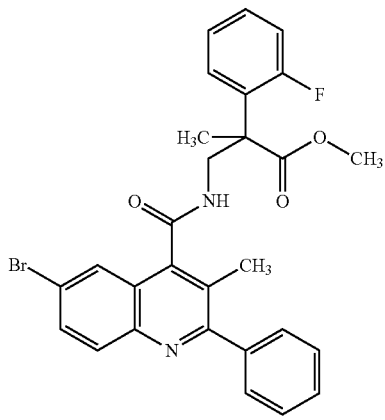 [SMILES: COC(=O)C(C)(CNC(=O)c1c(C)c(-c2ccccc2)nc2ccc(Br)cc12)c1ccccc1F]

In succession, N,N-diisopropylethylamine (260 µl, 1.5 mmol) and a suspension of 6-bromo-3-methyl-2-phenylquinoline-4-carbonyl chloride (180 mg, 500 µmol, Example 1A) in dichloromethane (2 ml) were added to a suspension of (+/−)-methyl 3-amino-2-(2-fluorophenyl)-2-methylpropanoate (127 mg, 600 µmol, CAS-RN 1803580-97-3, commercially available) in dichloromethane (3 ml), and the mixture was stirred at RT for 16 h. Subsequently, dichloromethane and water (30 ml of each) were added to the mixture, which was agitated. The aqueous phase was extracted once with dichloromethane (30 ml). The combined organic phases were dried over sodium sulfate, filtered and concentrated, and the residue was taken up in dichloromethane and purified by means of flash column chromatography (50 g silica gel Biotage Snap-Cartridge KP-Sil, cyclohexane/ethyl acetate gradient 93:7→7:3, Isolera One). The combined target fractions were concentrated and the residue was dried under reduced pressure. This gave 208 mg (100% purity, 78% of theory) of the title compound.

LC-MS (Method 1): $R_t$=2.25 min; MS (ESIpos): m/z=535/537 [M+H]$^+$ $^1$H-NMR (400 MHz, DMSO-d6) δ [ppm]: 1.157 (0.91), 1.174 (1.83), 1.192 (0.94), 1.397 (0.91), 1.614 (8.25), 1.988 (3.41), 2.149 (0.77), 3.311 (16.00), 3.931 (0.42), 4.020 (0.84), 4.038 (0.83), 4.199 (0.51), 4.216 (0.55), 4.231 (0.46), 4.250 (0.42), 7.171 (0.61), 7.192 (0.83), 7.201 (0.75), 7.209 (0.64), 7.222 (1.09), 7.227 (1.32), 7.247 (0.77), 7.371 (0.64), 7.387 (0.59), 7.447 (0.69), 7.467 (1.23), 7.492 (1.21), 7.507 (2.39), 7.513 (1.85), 7.525 (3.88), 7.538 (4.70), 7.556 (0.86), 7.840 (0.91), 7.845 (0.86), 7.863 (1.41), 7.868 (1.37), 7.934 (2.68), 7.956 (1.66), 8.762 (0.58), 8.778 (1.03), 8.793 (0.57).

Example 163A (+/−)-tert-Butyl 3-{[(6-bromo-3-methyl-2-phenylquinolin-4-yl)carbonyl]amino}-2-(2,6-difluorophenyl)-2-methylpropanoate (Racemate)

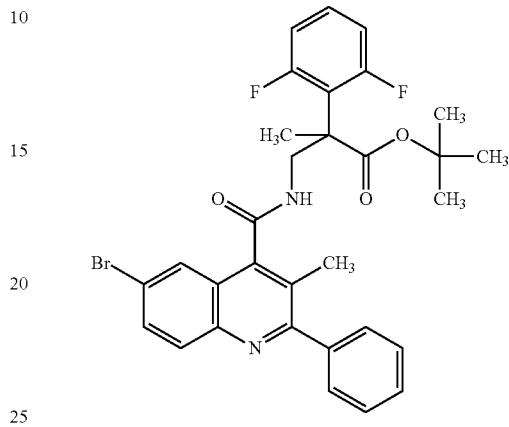

HATU (917 mg, 2.41 mmol) and DIPEA (840 µl, 4.8 mmol) were added to a mixture of 6-bromo-3-methyl-2-phenylquinoline-4-carboxylic acid (550 mg, 1.61 mmol, preparable according to WO 2016 146602 A1, p. 51, Example 3A) in DMF (5 ml), and the mixture was stirred at RT for 30 min. (+/−)-tert-Butyl 3-amino-2-(2,6-difluorophenyl)-2-methylpropanoate (689 mg, 95% purity, 2.41 mmol, Example 83A) dissolved in DMF (3.5 ml) was then added, and the mixture was stirred at 60° C. overnight. After cooling to RT, ethyl acetate and water (20 ml of each) were added to the mixture, which was agitated. The aqueous phase was extracted twice with ethyl acetate (20 ml each). The combined organic phases were washed once with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15). This gave 645 mg (98% purity, 66% of theory) of the title compound.

LC-MS (Method 1): $R_t$=2.59 min; MS (ESIpos): m/z=595/597 [M+H]$^+$ $^1$H-NMR (400 MHz, DMSO-d6) δ [ppm]: 1.401 (16.00), 1.744 (1.68), 7.072 (0.64), 7.096 (0.43), 7.506 (1.02), 7.512 (0.83), 7.524 (1.97), 7.533 (1.98), 7.838 (0.43), 7.860 (0.67), 7.865 (0.64), 7.930 (1.26), 7.953 (0.79), 8.791 (0.50).

$^1$H-NMR (400 MHz, DMSO-d6): δ [ppm]=8.79 (t, 1H), 7.94 (d, 1H), 7.85 (dd, 1H), 7.80-7.47 (m, 6H), 7.45-7.34 (m, 1H), 7.07 (br. t, 2H), 4.18 (br. dd, 1H), 3.78 (br. d, 1H), 2.16 (br. s, 3H), 1.74 (br. s, 3H), 1.40 (s, 9H).

Example 164A (+/−)-Methyl 3-{[(6-bromo-3-methyl-2-phenylquinolin-4-yl)carbonyl]amino}-2-(2-chlorophenyl)-2-methylpropanoate (Racemate)

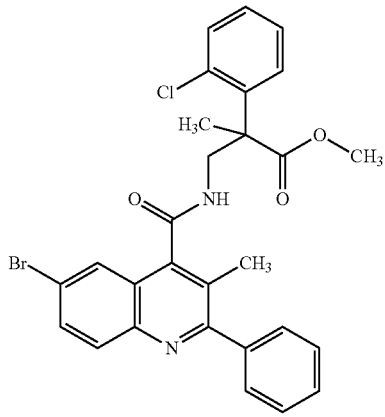 [SMILES: COC(=O)C(C)(CNC(=O)c1c(C)c(-c2ccccc2)nc2ccc(Br)cc12)c1ccccc1Cl]

HATU (833 mg, 2.19 mmol) and DIPEA (760 μl, 4.4 mmol) were added to a mixture of 6-bromo-3-methyl-2-phenylquinoline-4-carboxylic acid (500 mg, 1.46 mmol, preparable according to WO 2016 146602 A1, p. 51, Example 3A) in DMF (5 ml), and the mixture was stirred at RT for 30 min. (+/−)-Methyl 3-amino-2-(2-chlorophenyl)-2-methylpropanoate (525 mg, 95% purity, 2.19 mmol, available at Santai Labs) dissolved in DMF (3 ml) was then added, and the mixture was stirred at 60° C. overnight. After cooling to RT, ethyl acetate and water (20 ml of each) were added to the mixture, which was agitated. The aqueous phase was extracted twice with ethyl acetate (20 ml each). The combined organic phases were washed once with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15). This gave 554 mg (98% purity, 67% of theory) of the title compound.

LC-MS (Method 1): $R_t$=2.30 min; MS (ESIpos): m/z=551/553 [M+H]$^+$ $^1$H-NMR (400 MHz, DMSO-d6) δ [ppm]: 1.397 (1.34), 1.662 (9.58), 1.988 (0.59), 2.072 (0.62), 2.152 (0.72), 3.640 (16.00), 3.930 (0.48), 3.953 (0.55), 4.405 (0.60), 4.423 (0.64), 4.438 (0.58), 4.457 (0.52), 7.344 (0.97), 7.362 (1.87), 7.377 (1.41), 7.398 (0.76), 7.453 (1.58), 7.472 (1.30), 7.491 (1.10), 7.506 (3.18), 7.512 (2.71), 7.524 (6.80), 7.536 (6.85), 7.838 (1.13), 7.843 (1.11), 7.861 (1.78), 7.866 (1.77), 7.930 (3.34), 7.952 (2.02), 8.712 (0.72), 8.729 (1.22), 8.744 (0.69).

Example 165A (+/−)-Ethyl 3-{[(6-bromo-3-methyl-2-phenylquinolin-4-yl)carbonyl]amino}-2-fluorohydratropate (Racemate)

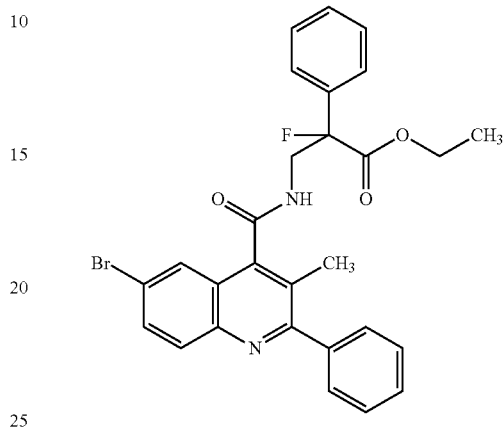

HATU (150 μl, 750 μmol) and DIPEA (260 μl, 1.5 mmol) were added to a mixture of 6-bromo-3-methyl-2-phenylquinoline-4-carboxylic acid (171 mg, 500 μmol, preparable according to WO 2016 146602 A1, p. 51, Example 3A) in DMF (5 ml), and the mixture was stirred at RT for 5 min. (+/−)-Ethyl 3-amino-2-fluoro-2-phenylpropanoate hydrochloride (186 mg, 750 μmol, CAS-RN 1909308-68-4, commercially available) was then added, and the mixture was stirred at 60° C. for 2.5 h. After cooling to RT, ethyl acetate and water (50 ml of each) were added to the mixture, which was agitated. The aqueous phase was extracted once with ethyl acetate (50 ml). The combined organic phases were washed once with saturated aqueous sodium chloride solution (80 ml), dried over sodium sulfate, filtered and concentrated, and the residue was taken up in dichloromethane and purified by flash column chromatography (50 g of silica gel Biotage Snap-Cartridge KP-Sil, cyclohexane/ethyl acetate 93:7→7:3). The combined target fractions were concentrated and the residue was dried under reduced pressure. This gave 222 mg (100% purity, 83% of theory) of the title compound.

LC-MS (Method 2): $R_t$=1.20 min; MS (ESIpos): m/z=535/537 [M+H]$^+$ $^1$H-NMR (400 MHz, DMSO-d6) δ [ppm]: −0.008 (1.50), 0.008 (1.61), 1.143 (0.70), 1.179 (7.74), 1.197 (16.00), 1.215 (8.00), 1.233 (0.88), 1.397 (1.11), 2.168 (1.34), 2.327 (0.57), 4.217 (3.02), 4.233 (3.04), 5.754 (1.29), 7.387 (0.85), 7.398 (0.54), 7.478 (5.24), 7.494 (7.07), 7.509 (9.52), 7.514 (8.51), 7.528 (12.06), 7.542 (13.27), 7.581 (9.10), 7.599 (6.45), 7.850 (2.41), 7.871 (3.52), 7.944 (7.12), 7.966 (4.46), 9.179 (1.98), 9.194 (3.94), 9.209 (1.91).

Example 166A (+/−)-Ethyl 3-{[(6-bromo-3-methyl-2-phenylquinolin-4-yl)carbonyl]amino}-2-methyl-2-[3-(trifluoromethyl)phenyl]propanoate (Racemate)

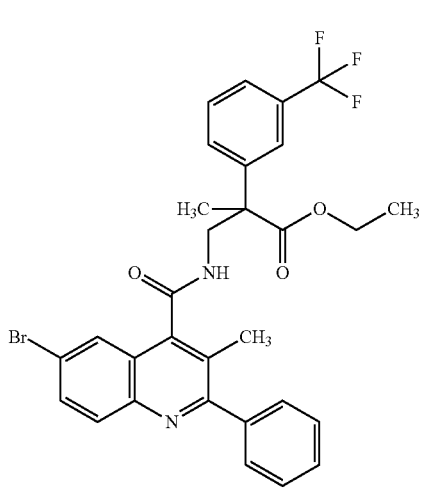 [SMILES: CCOC(=O)C(C)(CNC(=O)c1c(C)c(-c2ccccc2)nc2ccc(Br)cc12)c1cccc(C(F)(F)F)c1]

HATU (843 mg, 2.22 mmol) and DIPEA (770 µl, 4.4 mmol) were added to a mixture of 6-bromo-3-methyl-2-phenylquinoline-4-carboxylic acid (506 mg, 1.48 mmol, preparable according to WO 2016 146602 A1, p. 51, Example 3A) in DMF (6 ml), and the mixture was stirred at RT for 30 min. (+/−)-Ethyl 3-amino-2-methyl-2-[3-(trifluoromethyl)phenyl]propanoate (610 mg, 2.22 mmol, Example 84A) dissolved in DMF (3 ml) was then added, and the mixture was stirred at 60° C. overnight. After cooling to RT, the mixture was purified by preparative HPLC (Method 15). The combined target fractions were concentrated and the residue was dried under reduced pressure. This gave 577 mg (98% purity, 64% of theory) of the title compound.

LC-MS (Method 1): $R_t$=2.50 min; MS (ESIpos): m/z=599/601 [M+H]$^+$ $^1$H-NMR (400 MHz, DMSO-d6) δ [ppm]: 1.124 (6.68), 1.142 (14.17), 1.160 (6.91), 1.398 (0.94), 1.694 (16.00), 2.074 (1.16), 3.939 (1.13), 3.952 (1.23), 3.973 (1.51), 3.986 (1.41), 4.100 (0.67), 4.109 (0.82), 4.118 (0.87), 4.127 (3.00), 4.144 (4.39), 4.162 (2.88), 4.170 (0.82), 4.179 (0.79), 4.188 (0.64), 4.219 (1.62), 4.237 (1.71), 4.253 (1.39), 4.271 (1.30), 7.478 (0.48), 7.493 (1.25), 7.503 (4.16), 7.510 (3.72), 7.521 (10.32), 7.525 (9.36), 7.621 (0.97), 7.641 (2.45), 7.660 (2.39), 7.686 (2.87), 7.706 (5.92), 7.732 (2.76), 7.751 (1.95), 7.837 (1.69), 7.842 (1.63), 7.859 (2.60), 7.864 (2.57), 7.935 (5.22), 7.957 (3.35), 8.766 (1.12), 8.782 (1.97), 8.796 (1.16).

Example 167A (+/−)-tert-Butyl 3-{[(6-bromo-3-methyl-2-phenylquinolin-4-yl)carbonyl]amino}-2-(3-methoxyphenyl)propanoate (Racemate)

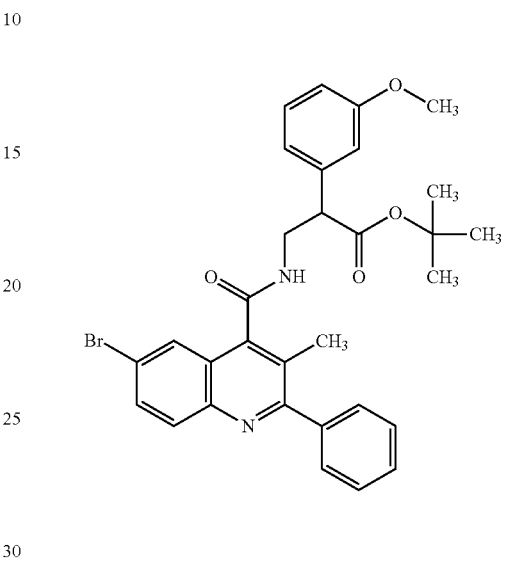

HATU (1.14 g, 2.99 mmol) and DIPEA (1.4 ml, 8.0 mmol) were added to a mixture of 6-bromo-3-methyl-2-phenylquinoline-4-carboxylic acid (681 mg, 1.99 mmol, preparable according to WO 2016 146602 A1, p. 51, Example 3A) in DMF (6.8 ml), and the mixture was stirred at RT for 30 min. (+/−)-tert-Butyl 3-amino-2-(3-methoxyphenyl)propanoate (750 mg, 2.99 mmol, Example 85A) dissolved in DMF (4.6 ml) was then added, and the mixture was stirred at 60° C. overnight. After cooling to RT, water (60 ml) was added to the mixture, which was agitated. The aqueous phase was extracted twice with ethyl acetate (100 ml and 80 ml). The combined organic phases were washed once with saturated aqueous sodium chloride solution, dried over sodium sulfate, filtered and concentrated, and the residue was purified by flash column chromatography (50 g silica gel Biotage Snap-Cartridge KP-Sil, cyclohexane/ethyl acetate 100:0→7:3, Isolera). This gave 940 mg (92% purity, 76% of theory) of the title compound.

LC-MS (Method 2): $R_t$=1.28 min; MS (ESIpos): m/z=575/577 [M+H]$^+$ $^1$H-NMR (400 MHz, DMSO-d6) δ [ppm]: −0.008 (0.84), 0.008 (0.62), 1.375 (16.00), 1.398 (7.07), 2.184 (1.00), 2.523 (0.41), 3.749 (6.57), 3.960 (0.51), 6.879 (0.43), 6.898 (1.61), 6.923 (0.54), 6.943 (0.62), 7.304 (0.59), 7.509 (0.84), 7.516 (0.75), 7.529 (1.92), 7.535 (1.86), 7.542 (1.36), 7.849 (0.46), 7.871 (0.69), 7.876 (0.65), 7.945 (1.19), 7.967 (0.76), 8.992 (0.54).

Example 168A (+/−)-tert-Butyl 3-{[(6-bromo-3-methyl-2-phenylquinolin-4-yl)carbonyl]amino}-2-(3-chlorophenyl)propanoate (Racemate)

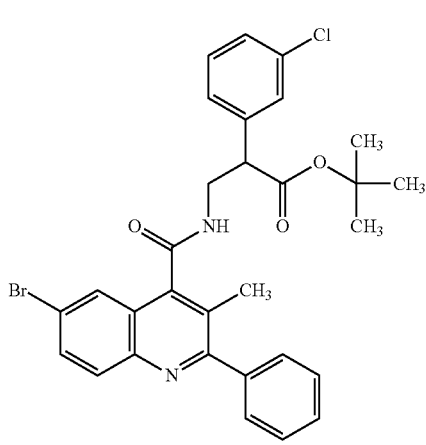 [SMILES: Cc1c(-c2ccccc2)nc2ccc(Br)cc2c1C(=O)NCC(C(=O)OC(C)(C)C)c1cccc(Cl)c1]

HATU (743 mg, 1.95 mmol) and DIPEA (910 µl, 5.2 mmol) were added to a mixture of 6-bromo-3-methyl-2-phenylquinoline-4-carboxylic acid (681 mg, 1.99 mmol, preparable according to WO 2016 146602 A1, p. 51, Example 3A) in DMF (4.5 ml), and the mixture was stirred at RT for 30 min. (+/−)-tert-Butyl 3-amino-2-(3-chlorophenyl)propanoate (500 mg, 1.95 mmol, Example 86A) dissolved in DMF (3.0 ml) was then added, and the mixture was stirred at 60° C. overnight. After cooling to RT, water (40 ml) was added to the mixture, which was agitated. The aqueous phase was extracted twice with ethyl acetate (70 ml and 50 ml). The combined organic phases were washed once with saturated aqueous sodium chloride solution, dried over sodium sulfate, filtered and concentrated, and the residue was purified by flash column chromatography (50 g silica gel Biotage Snap-Cartridge KP-Sil, cyclohexane/ethyl acetate 100:0→7:3, Isolera). This gave 430 mg (88% purity, 50% of theory) of the title compound.

LC-MS (Method 2): $R_t$=1.36 min; MS (ESIpos): m/z=579/581 [M+H]$^+$ $^1$H-NMR (400 MHz, DMSO-d6): δ [ppm]=8.98 (t, 1H), 7.95 (d, 1H), 7.86 (dd, 1H), 7.68 (br. s, 1H), 7.56-7.47 (m, 5H), 7.46-7.32 (m, 4H), 4.01 (t, 1H), 3.93-3.76 (m, 2H), 2.15 (br. s, 3H), 1.38 (s, 9H).

Example 169A (+/−)-tert-Butyl 3-{[(6-bromo-3-methyl-2-phenylquinolin-4-yl)carbonyl]amino}-2-(3-methylphenyl)propanoate (Racemate)

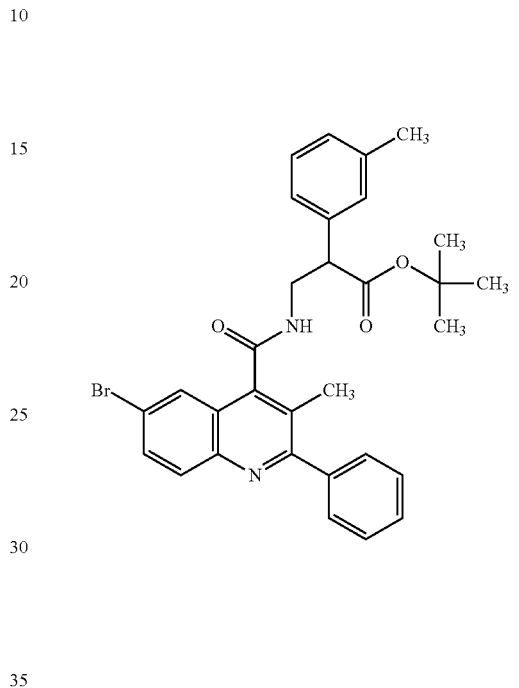

HATU (1.13 g, 2.97 mmol) and DIPEA (1.4 ml, 7.9 mmol) were added to a mixture of 6-bromo-3-methyl-2-phenylquinoline-4-carboxylic acid (678 mg, 1.98 mmol, preparable according to WO 2016 146602 A1, p. 51, Example 3A) in DMF (6.8 ml), and the mixture was stirred at RT for 30 min. (+/−)-tert-Butyl 3-amino-2-(3-methylphenyl)propanoate (699 mg, 2.97 mmol, Example 87A) dissolved in DMF (4.6 ml) was then added, and the mixture was stirred at 60° C. overnight. After cooling to RT, water (60 ml) was added to the mixture, which was agitated. The aqueous phase was extracted twice with ethyl acetate (110 ml and 80 ml). The combined organic phases were washed once with saturated aqueous sodium chloride solution (60 ml), dried over sodium sulfate, filtered and concentrated, and the residue was purified by flash column chromatography (50 g silica gel Biotage Snap-Cartridge KP-Sil, cyclohexane/ethyl acetate 100:0→7:3, Isolera). This gave 830 mg (95% purity, 71% of theory) of the title compound.

C-MS (Method 1): $R_t$=2.56 min; MS (ESIpos): m/z=559/561 [M+H]$^+$ $^1$H-NMR (400 MHz, DMSO-d6): δ [ppm]=8.99 (t, 1H), 7.95 (d, 1H), 7.87 (dd, 1H), 7.76 (br. s, 1H), 7.59-7.44 (m, 5H), 7.27 (t, 1H), 7.19-7.07 (m, 3H), 3.99-3.90 (m, 1H), 3.89-3.80 (m, 1H), 3.78-3.66 (m, 1H), 2.31 (s, 3H), 2.19 (br. s, 2H), 1.37 (s, 9H).

Example 170A (+/−)-Methyl 3-{[(6-bromo-3-methyl-2-phenylquinolin-4-yl)carbonyl]amino}-2-hydroxy-2-(2-methoxyphenyl)propanoate (Racemate)

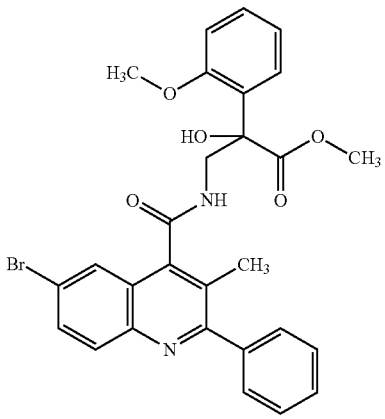 [SMILES: COC(=O)C(O)(CNC(=O)c1c(C)c(-c2ccccc2)nc2ccc(Br)cc12)c1ccccc1OC]

HATU (150 µl, 2.2 mmol) and DIPEA (770 µl, 4.4 mmol) were added to a mixture of 6-bromo-3-methyl-2-phenylquinoline-4-carboxylic acid (506 mg, 1.48 mmol, preparable according to WO 2016 146602 A1, p. 51, Example 3A) in DMF (7.5 ml), and the mixture was stirred at RT for 5 min. (+/−)-Methyl 3-amino-2-hydroxy-2-(2-methoxyphenyl)propanoate (500 mg, 2.22 mmol, available at Santai Labs, Art No. ADH-GM-15173) was then added, and the mixture was stirred at 60° C. for 8.5 h. After cooling to RT, ethyl acetate and water (100 ml of each) were added to the mixture, which was agitated. After phase separation, the aqueous phase was extracted once with ethyl acetate (100 ml). The combined organic phases were washed once with saturated aqueous sodium chloride solution (80 ml), dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 93:7→4:6, Isolera). This gave 586 mg (100% purity, 72% of theory) of the title compound.

LC-MS (Method 1): $R_t$=1.98 min; MS (ESIpos): m/z=549/551 $[M+H]^+$ $^1$H-NMR (400 MHz, DMSO-d6) δ [ppm]: −0.008 (0.91), 0.008 (0.93), 1.988 (0.67), 2.092 (1.03), 2.522 (0.43), 3.310 (16.00), 3.635 (12.16), 6.293 (3.96), 6.939 (0.57), 6.958 (1.16), 6.977 (0.66), 6.997 (1.00), 7.017 (1.16), 7.280 (0.42), 7.300 (0.67), 7.479 (0.57), 7.482 (0.55), 7.494 (1.81), 7.501 (1.68), 7.514 (4.48), 7.518 (4.24), 7.526 (2.88), 7.538 (0.56), 7.590 (0.79), 7.609 (0.74), 7.813 (0.84), 7.818 (0.78), 7.835 (1.31), 7.840 (1.30), 7.899 (2.67), 7.921 (1.57), 8.478 (0.46), 8.493 (0.78), 8.508 (0.45).

$^1$H-NMR (400 MHz, DMSO-d6) δ [ppm]: 8.49 (t, 1H), 7.91 (d, 1H), 7.83 (dd, 1H), 7.71 (br. s, 1H), 7.60 (d, 1H), 7.55-7.46 (m, 5H), 7.30 (t, 1H), 7.05-6.92 (m, 2H), 6.29 (s, 1H), 4.35-4.11 (m, 1H), 4.09-3.93 (m, 1H), 3.76 (s, 3H), 3.64 (s, 3H), 2.09 (br. s, 3H).

Separation of the Enantiomers:

The title compound (309 mg) was dissolved in a mixture of ethanol (2 ml) and dichloromethane (3 ml) and separated into the enantiomers by preparative HPLC on a chiral phase (see Examples 171A and 172A) [column: Daicel Chiralpak IA, 5 µm 250 mm×20 mm; flow rate: 15 ml/min; detection: 220 nm; temperature: 50° C.; injection: 0.15 ml; mobile phase: 100% ethanol; run time 18 min, isocratic]. The combined target fractions were concentrated, and the residue was lyophilized in acetonitrile/water.

Example 171A (−)-Methyl 3-{[(6-bromo-3-methyl-2-phenylquinolin-4-yl)carbonyl]amino}-2-hydroxy-2-(2-methoxyphenyl)propanoate (Enantiomer 1)

In the enantiomer separation described in Example 170A, 145 mg (100% purity, ee 99%) of the title compound were obtained as the enantiomer that eluted earlier.

$[α]_D^{20}$=−68.6°, 589 nm, c=0.34 g/100 ml, methanol

LC-MS (Method 1): $R_t$=2.00 min; MS (ESIpos): m/z=549/551 $[M+H]^+$ $^1$H-NMR (500 MHz, DMSO-d6) δ [ppm]: 2.095 (0.99), 3.465 (0.46), 3.473 (0.45), 3.487 (0.43), 3.636 (16.00), 6.945 (0.70), 6.960 (1.40), 6.975 (0.80), 6.999 (1.22), 7.016 (1.33), 7.285 (0.49), 7.300 (0.76), 7.314 (0.43), 7.474 (0.42), 7.482 (1.02), 7.490 (1.00), 7.494 (1.82), 7.499 (2.36), 7.514 (4.54), 7.522 (4.89), 7.526 (5.82), 7.538 (0.96), 7.596 (0.92), 7.610 (0.88), 7.818 (1.06), 7.822 (1.03), 7.836 (1.53), 7.840 (1.50), 7.903 (3.12), 7.921 (2.06), 8.485 (0.61), 8.497 (1.00), 8.508 (0.60).

$^1$H-NMR (500 MHz, DMSO-d6) δ [ppm]: 8.50 (t, 1H), 7.91 (d, 1H), 7.83 (dd, 1H), 7.67 (br. s, 1H), 7.60 (d, 1H), 7.56-7.46 (m, 5H), 7.30 (t, 1H), 7.05-6.92 (m, 2H), 6.29 (br. s, 1H), 4.22 (br. s, 1H), 4.01 (br. s, 1H), 3.76 (s, 3H), 3.64 (s, 3H), 2.09 (br. s, 3H).

Example 172A (+)-Methyl 3-{[(6-bromo-3-methyl-2-phenylquinolin-4-yl)carbonyl]amino}-2-hydroxy-2-(2-methoxyphenyl)propanoate (Enantiomer 2)

In the enantiomer separation described in Example 170A, 137 mg (100% purity, ee 99%) of the title compound were obtained as the enantiomer that eluted later.

$[α]_D^{20}$=+71.8°, 589 nm, c=0.33 g/100 ml, methanol

LC-MS (Method 1): $R_t$=2.00 min; MS (ESIpos): m/z=549/551 $[M+H]^+$ $^1$H-NMR (500 MHz, DMSO-d6) δ [ppm]: 2.095 (1.37), 3.762 (16.00), 6.946 (0.95), 6.960 (1.90), 6.975 (1.09), 7.000 (1.66), 7.016 (1.81), 7.286 (0.67), 7.300 (1.05), 7.315 (0.59), 7.475 (0.56), 7.484 (1.38), 7.492 (1.40), 7.496 (2.52), 7.501 (3.23), 7.515 (6.13), 7.524 (6.70), 7.527 (7.88), 7.539 (1.35), 7.596 (1.28), 7.611 (1.22), 7.821 (1.43), 7.824 (1.40), 7.839 (2.07), 7.842 (2.05), 7.905 (4.13), 7.923 (2.71), 8.488 (0.85), 8.499 (1.37), 8.511 (0.83).

$^1$H-NMR (500 MHz, DMSO-d6) δ [ppm]: 8.50 (t, 1H), 7.91 (d, 1H), 7.83 (dd, 1H), 7.68 (br. s, 1H), 7.60 (d, 1H), 7.55-7.44 (m, 5H), 7.30 (t, 1H), 7.07-6.91 (m, 2H), 6.28 (br. s, 1H), 4.22 (br. s, 1H), 4.01 (br. s, 1H), 3.76 (s, 3H), 3.64 (s, 3H), 2.10 (br. s, 3H).

Example 173A (+/−)-tert-Butyl 3-{[(6-bromo-3-methyl-2-phenylquinolin-4-yl)carbonyl]amino}-2-(2-fluoro-6-methoxyphenyl)propanoate (Racemate)

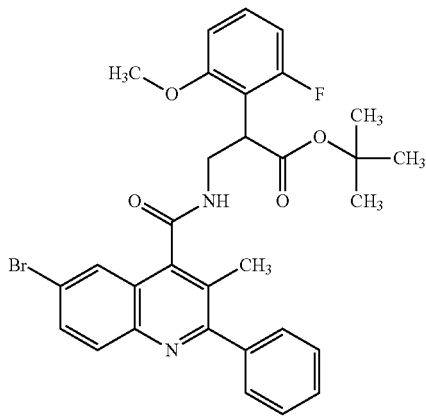 [SMILES: COc1cccc(F)c1C(CNC(=O)c1c(C)c(-c2ccccc2)nc2ccc(Br)cc12)C(=O)OC(C)(C)C]

HATU (256 mg, 673 µmol) and DIPEA (230 µl, 1.3 mmol) were added to a mixture of 6-bromo-3-methyl-2-phenylquinoline-4-carboxylic acid (192 mg, 561 µmol, preparable according to WO 2016 146602 A1, p. 51, Example 3A) in DMF (2.0 ml), and the mixture was stirred at RT for 15 min. (+/−)-tert-Butyl 3-amino-2-(2-fluoro-6-methoxyphenyl)propanoate (213 mg, 71% purity, 561 µmol, Example 88A) was then added, and the mixture was stirred at 60° C. for 2 h. After cooling to RT, ethyl acetate and water (50 ml of each) were added to the mixture, which was agitated. After phase separation, the aqueous phase was extracted once with ethyl acetate (30 ml). The combined organic phases were washed once with saturated aqueous sodium chloride solution (80 ml), dried over sodium sulfate, filtered and concentrated, and the residue was taken up in dichloromethane and prepurified by flash column chromatography (50 g of silica gel Biotage Snap-Cartridge KP-Sil, cyclohexane/ethyl acetate 93:7→7:3, Isolera One). The prepurified product was then repurified by preparative HPLC (Method 15). The combined target fractions were concentrated, and the residue was dried under reduced pressure. This gave 192 mg (100% purity, 58% of theory) of the title compound.

LC-MS (Method 2): $R_t$=1.30 min; MS (ESIpos): m/z=593/595 [M+H]$^+$ $^1$H-NMR (500 MHz, DMSO-d6) δ [ppm]: 8.80 (t, 1H), 7.94 (d, 1H), 7.86 (dd, 1H), 7.78 (br. s, 1H), 7.55-7.47 (m, 5H), 7.34-7.26 (m, 1H), 6.88 (d, 1H), 6.82 (t, 1H), 4.34 (dd, 1H), 4.14-4.05 (m, 1H), 3.80 (s, 3H), 3.71 (br. s, 1H), 2.18 (s, 3H), 1.37 (s, 9H).

Separation of the Enantiomers:

The title compound (224 mg, combined with a quantity from a preliminary experiment) was dissolved in methanol (10 ml) and separated into the enantiomers by preparative SFC on a chiral phase (see Examples 174A and 175A) [column: Chiralpak AD SFC, 5 µm, 250 mm×20 mm; flow rate: 60 ml/min; detection: 210 nm; temperature: 40° C.; injection: 0.50 ml; mobile phase: 70% carbon dioxide/30% ethanol; run time 11 min, isocratic]. The combined target fractions were concentrated, and the residue was dried under reduced pressure.

Example 174A (−)-tert-Butyl 3-{[(6-bromo-3-methyl-2-phenylquinolin-4-yl)carbonyl]amino}-2-(2-fluoro-6-methoxyphenyl)propanoate (Enantiomer 1)

In the enantiomer separation described in Example 173A, 81 mg (100% purity, ee 100%) of the title compound were obtained as the enantiomer that eluted earlier.

$[α]_D^{20}$=−62.0°, 589 nm, c=0.33 g/100 ml, chloroform

LC-MS (Method 2): $R_t$=1.30 min; MS (ESIpos): m/z=593/595 [M+H]$^+$ $^1$H-NMR (400 MHz, DMSO-d6) δ [ppm]: 1.364 (16.00), 2.181 (2.78), 3.794 (5.53), 6.818 (0.64), 6.869 (0.67), 6.890 (0.73), 7.289 (0.41), 7.307 (0.40), 7.502 (0.87), 7.510 (0.77), 7.522 (2.43), 7.526 (2.34), 7.534 (1.34), 7.840 (0.46), 7.846 (0.40), 7.863 (0.71), 7.868 (0.66), 7.930 (1.25), 7.952 (0.76), 8.795 (0.59).

$^1$H-NMR (400 MHz, DMSO-d6) δ [ppm]: 8.79 (t, 1H), 7.94 (d, 1H), 7.86 (dd, 1H), 7.77 (br. s, 1H), 7.56-7.46 (m, 5H), 7.35-7.25 (m, 1H), 6.88 (d, 1H), 6.82 (t, 1H), 4.34 (dd, 1H), 4.14-4.04 (m, 1H), 3.79 (s, 3H), 3.75-3.65 (m, 1H), 2.18 (s, 3H), 1.36 (s, 9H).

Example 175A (+)-tert-Butyl 3-{[(6-bromo-3-methyl-2-phenylquinolin-4-yl)carbonyl]amino}-2-(2-fluoro-6-methoxyphenyl)propanoate (Enantiomer 2)

In the enantiomer separation described in Example 173A, 92 mg (100% purity, ee 100%) of the title compound were obtained as the enantiomer that eluted later.

$[α]_D^{20}$=+60.9°, 589 nm, c=0.32 g/100 ml, chloroform

LC-MS (Method 2): $R_t$=1.30 min; MS (ESIpos): m/z=593/595 [M+H]$^+$ $^1$H-NMR (400 MHz, DMSO-d6) δ [ppm]: 1.364 (16.00), 2.181 (2.95), 3.795 (5.53), 6.818 (0.67), 6.841 (0.40), 6.870 (0.70), 6.891 (0.77), 7.290 (0.44), 7.308 (0.43), 7.502 (0.93), 7.510 (0.82), 7.523 (2.63), 7.526 (2.55), 7.841 (0.47), 7.846 (0.41), 7.863 (0.72), 7.868 (0.67), 7.930 (1.24), 7.953 (0.76), 8.795 (0.63).

$^1$H-NMR (400 MHz, DMSO-d6) δ [ppm]: 8.79 (t, 1H), 7.94 (d, 1H), 7.86 (dd, 1H), 7.77 (br. s, 1H), 7.56-7.46 (m, 5H), 7.35-7.24 (m, 1H), 6.88 (d, 1H), 6.82 (t, 1H), 4.34 (dd, 1H), 4.16-4.03 (m, 1H), 3.79 (s, 3H), 3.71 (br. s, 1H), 2.18 (s, 3H), 1.36 (s, 9H).

Example 176A (+/−)-tert-Butyl 3-{[(6-bromo-3-methyl-2-phenylquinolin-4-yl)carbonyl]amino}-2-(2-methoxyphenyl)-2-methylpropanoate (Racemate)

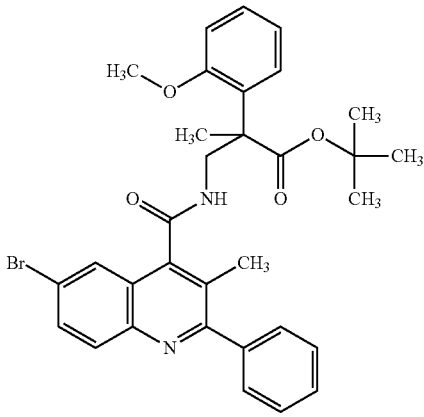 [SMILES: COc1ccccc1C(C)(CNC(=O)c1c(C)c(-c2ccccc2)nc2ccc(Br)cc12)C(=O)OC(C)(C)C]

HATU (1.30 g, 3.43 mmol) and DIPEA (1.2 ml, 6.9 mmol) were added to a mixture of 6-bromo-3-methyl-2-phenylquinoline-4-carboxylic acid (782 mg, 2.29 mmol, preparable according to WO 2016 146602 A1, p. 51, Example 3A) in DMF (10 ml), and the mixture was stirred at RT for 30 min. (+/−)-tert-Butyl 3-amino-2-(2-methoxyphenyl)-2-methylpropanoate (1.30 g, 70% purity, 3.43 mmol, Example 89A) dissolved in DMF (5 ml) was then added, and the mixture was stirred at 60° C. overnight. After cooling to RT, ethyl acetate and water (50 ml of each) were added to the mixture. After agitation and phase separation, the aqueous phase was extracted twice with ethyl acetate (50 ml each). The combined organic phases were washed once with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 93:7→6:4, Isolera One). The combined target fractions were concentrated, and the residue was lyophilized in acetonitrile/water. This gave 1.09 g (98% purity, 79% of theory) of the title compound.

LC-MS (Method 1): $R_t$=2.55 min; MS (ESIpos): m/z=589/591 [M+H]$^+$ $^1$H-NMR (400 MHz, DMSO-d6) δ [ppm]: 8.39 (dd, 1H), 7.92 (d, 1H), 7.84 (dd, 1H), 7.65 (br. s, 1H), 7.55-7.45 (m, 5H), 7.30-7.20 (m, 2H), 6.98 (d, 1H), 6.93 (t, 1H), 4.29 (dd, 1H), 3.78 (s, 3H), 3.72 (dd, 1H), 2.08 (br. s, 3H), 1.57 (s, 3H), 1.36 (s, 9H).

Separation of the Enantiomers:

The title compound (1.00 g) was dissolved in ethanol (25 ml) and separated into the enantiomers by preparative SFC on a chiral phase (see Examples 177A and 178A) [column: Daicel Chiralpak AD, 20 μm 360 mm×50 mm; flow rate: 140 ml/min; detection: 210 nm; temperature: 38° C.; injection: 2.0 ml; mobile phase: 70% carbon dioxide/30% ethanol→50% carbon dioxide/50% ethanol, run time 9 min]: The combined target fractions were concentrated, and the residue was dried under reduced pressure.

Example 177A (−)-tert-Butyl 3-{[(6-bromo-3-methyl-2-phenylquinolin-4-yl)carbonyl]amino}-2-(2-methoxyphenyl)-2-methylpropanoate (Enantiomer 1)

In the enantiomer separation described in Example 176A, the prepurified title compound was obtained as earlier-eluting enantiomer (ee 100%) and repurified by preparative HPLC (Method 20). The combined target fractions were concentrated and lyophilized. This gave 440 mg (98% purity) of the title compound.

$[α]_D^{20}$=−95.7°, 589 nm, c=0.35 g/100 ml, chloroform

LC-MS (Method 2): $R_t$=1.35 min; MS (ESIpos): m/z=589/591 [M+H]$^+$ $^1$H-NMR (600 MHz, DMSO-d6) δ [ppm]: 8.41 (dd, 1H), 7.92 (d, 1H), 7.84 (dd, 1H), 7.60 (br. s, 1H), 7.55-7.46 (m, 5H), 7.30-7.20 (m, 2H), 6.98 (d, 1H), 6.93 (t, 1H), 4.30 (dd, 1H), 3.78 (s, 3H), 3.75-3.68 (m, 1H), 2.08 (br. s, 3H), 1.57 (s, 3H), 1.36 (s, 9H).

Example 178A (+)-tert-Butyl 3-{[(6-bromo-3-methyl-2-phenylquinolin-4-yl)carbonyl]amino}-2-(2-methoxyphenyl)-2-methylpropanoate (Enantiomer 2)

In the enantiomer separation described in Example 176A, the prepurified title compound was obtained as later-eluting enantiomer (ee 100%) and repurified by preparative HPLC (Method 20). The combined target fractions were concentrated and lyophilized. This gave 450 mg (98% purity) of the title compound.

$[α]_D^{20}$=+93.1°, 589 nm, c=0.36 g/100 ml, chloroform

LC-MS (Method 2): $R_t$=1.35 min; MS (ESIpos): m/z=589/591 [M+H]$^+$ $^1$H-NMR (600 MHz, DMSO-d6) δ [ppm]: 1.364 (16.00), 1.568 (2.53), 6.988 (0.40), 7.228 (0.68), 7.241 (0.64), 7.498 (0.58), 7.503 (0.80), 7.517 (2.34), 7.524 (1.93), 7.848 (0.52), 7.850 (0.50), 7.917 (0.99), 7.931 (0.69), 8.408 (0.45).

$^1$H-NMR (600 MHz, DMSO-d6) δ [ppm]: 8.41 (dd, 1H), 7.92 (d, 1H), 7.84 (dd, 1H), 7.63 (br. s, 1H), 7.55-7.46 (m, 5H), 7.31-7.19 (m, 2H), 6.98 (d, 1H), 6.93 (t, 1H), 4.29 (dd, 1H), 3.78 (s, 3H), 3.75-3.67 (m, 1H), 2.08 (br. s, 3H), 1.57 (s, 3H), 1.36 (s, 9H).

Example 179A (+/−)-tert-Butyl 3-{[(6-bromo-3-methyl-2-phenylquinolin-4-yl)carbonyl]amino}-2-(2-chloro-6-fluorophenyl)-2-methylpropanoate (Racemate)

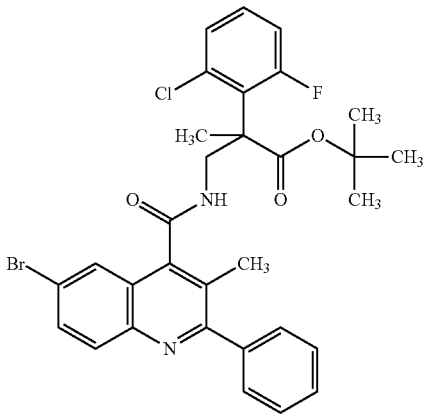

HATU (1.16 g, 3.04 mmol) and DIPEA (1.1 ml, 6.1 mmol) were added to a mixture of 6-bromo-3-methyl-2-phenylquinoline-4-carboxylic acid (694 mg, 2.03 mmol, preparable according to WO 2016 146602 A1, p. 51, Example 3A) in DMF (15 ml), and the mixture was stirred at RT for 30 min. (+/−)-tert-Butyl 3-amino-2-(2-chloro-6-fluorophenyl)-2-methylpropanoate (1.25 g, 70% purity, 3.04 mmol, Example 90A) dissolved in DMF (5 ml) was then added, and the mixture was stirred at 60° C. overnight. After cooling to RT, ethyl acetate and water (50 ml of each) were added to the mixture. After agitation and phase separation, the aqueous phase was extracted twice with ethyl acetate (50 ml each). The combined organic phases were washed once with saturated aqueous sodium chloride solution, dried over sodium sulfate, filtered and concentrated, and the residue was taken up in dichloromethane and purified by flash column chromatography (100 g of silica gel, Biotage Snap-Cartridge KP-Sil, cyclohexane/ethyl acetate 93:7→6:4, Isolera One). The combined target fractions were concentrated, and the residue was lyophilized in acetonitrile/water. This gave 960 mg (83% purity, 64% of theory) of the title compound.

LC-MS (Method 1): $R_t$=2.63 min; MS (ESIpos): m/z=611/613 [M+H]$^+$

LC-MS (Method 7): $R_t$=1.71 min

Separation of the Enantiomers:

The title compound (960 mg) was dissolved in methanol (35 ml) and separated into the enantiomers by preparative SFC on a chiral phase (see Examples 180A and 181A) [column: Daicel Chiralpak AD, 250 mm×20 mm; flow rate: 80 ml/min; detection: 210 nm; temperature: 40° C.; injection: 0.8 ml; mobile phase: 80% carbon dioxide/20% methanol; run time 7 min, isocratic]. The combined target fractions were concentrated, and the residue was dried under reduced pressure.

Example 180A (+)-tert-Butyl 3-{[(6-bromo-3-methyl-2-phenylquinolin-4-yl)carbonyl]amino}-2-(2-chloro-6-fluorophenyl)-2-methylpropanoate (Enantiomer 1)

In the enantiomer separation described in Example 179A, the prepurified title compound was obtained as earlier-eluting enantiomer (ee>99%) and repurified twice by preparative HPLC (Method 20). The combined target fractions were concentrated, and the residue was dried under reduced pressure. 205 mg (98% purity, 21% of theory) of the title compound were obtained.

$[\alpha]_D^{20}$=+65.8°, 589 nm, c=0.40 g/100 ml, methanol

LC-MS (Method 1): $R_t$=2.65 min; MS (ESIpos): m/z=611/613 [M+H]$^+$ $^1$H-NMR (500 MHz, DMSO-d6) δ [ppm]: 8.77 (t, 1H), 7.94 (d, 1H), 7.86 (dd, 1H), 7.68 (br. s, 1H), 7.58-7.47 (m, 5H), 7.42-7.28 (m, 2H), 7.23-7.13 (m, 1H), 4.47 (br. s, 1H), 3.81 (br. s, 1H), 2.16 (br. s, 3H), 1.84 (d, 3H), 1.42 (s, 9H).

Example 181A (−)-tert-Butyl 3-{[(6-bromo-3-methyl-2-phenylquinolin-4-yl)carbonyl]amino}-2-(2-chloro-6-fluorophenyl)-2-methylpropanoate (Enantiomer 2)

In the enantiomer separation described in Example 179A, the prepurified title compound was obtained as later-eluting enantiomer (ee>99%) and repurified by preparative HPLC (Method 20). The combined target fractions were concentrated, and the residue was dried under reduced pressure. 289 mg (98% purity, 30% of theory) of the title compound were obtained.

$[\alpha]_D^{20}$=−70.6°, 589 nm, c=0.36 g/100 ml, methanol

LC-MS (Method 1): $R_t$=2.67 min; MS (ESIpos): m/z=611/613 [M+H]$^+$ $^1$H-NMR (500 MHz, DMSO-d6) δ [ppm]: 8.76 (t, 1H), 7.94 (d, 1H), 7.85 (dd, 1H), 7.68 (br. s, 1H), 7.57-7.46 (m, 5H), 7.41-7.28 (m, 2H), 7.22-7.13 (m, 1H), 4.47 (br. s, 1H), 3.80 (br. s, 1H), 2.16 (br. s, 3H), 1.83 (d, 3H), 1.42 (s, 9H).

Example 182A (+/−)-tert-Butyl 4-{[(6-bromo-3-methyl-2-phenylquinolin-4-yl)carbonyl]amino}-3-(2-chlorophenyl)butanoate (Racemate)

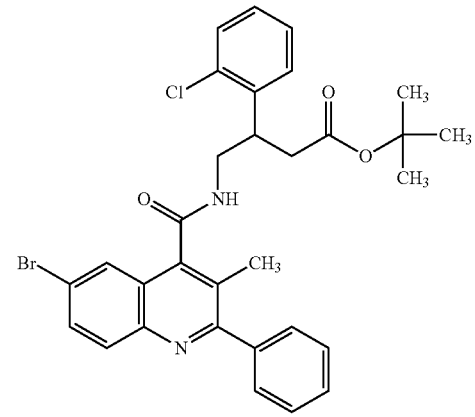 [SMILES: Cc1c(-c2ccccc2)nc2ccc(Br)cc2c1C(=O)NCC(CC(=O)OC(C)(C)C)c1ccccc1Cl]

HATU (846 mg, 2.22 mmol) and DIPEA (770 μl, 4.4 mmol) were added to a mixture of 6-bromo-3-methyl-2-phenylquinoline-4-carboxylic acid (507 mg, 1.48 mmol, preparable according to WO 2016 146602 A1, p. 51, Example 3A) in DMF (5 ml), and the mixture was stirred at RT for 30 min. (+/−)-tert-Butyl 4-amino-3-(2-chlorophenyl)butanoate (600 mg, 2.22 mmol, Example 91A) dissolved in DMF (4 ml) was then added, and the mixture was stirred at 60° C. overnight. After cooling to RT, the mixture was purified by preparative HPLC (Method 22). 527 mg (98% purity, 58% of theory) of the title compound were obtained.

LC-MS (Method 1): $R_t$=2.54 min; MS (ESIpos): m/z=593/595 [M+H]⁺

The ¹H NMR was obtained from the product batch (104 mg, 98% purity, 89% of theory) an experiment which had been carried out analogously (starting with 66 mg, 19.3 mmol of 6-bromo-3-methyl-2-phenylquinoline-4-carboxylic acid):

¹H-NMR (400 MHz, DMSO-d6) δ [ppm]: 8.86 (t, 1H), 7.95 (d, 1H), 7.86 (dd, 1H), 7.78-7.62 (m, 1H), 7.58-7.47 (m, 6H), 7.44 (dd, 1H), 7.35 (t, 1H), 7.27 (t, 1H), 4.00-3.87 (m, 1H), 3.84-3.57 (br. m, 2H, partially obscured), 2.82-2.60 (m, 2H), 2.16 (s, 3H), 1.25 (s, 9H).

Example 183A (+/−)-tert-Butyl 4-{[(6-bromo-3-methyl-2-phenylquinolin-4-yl)carbonyl]amino}-3-(3-chlorophenyl)butanoate (Racemate)

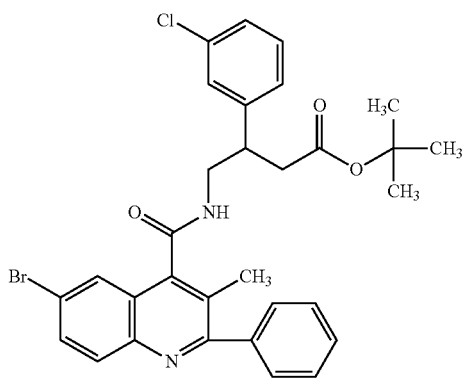 [SMILES: Cc1c(-c2ccccc2)nc2ccc(Br)cc2c1C(=O)NCC(CC(=O)OC(C)(C)C)c1cccc(Cl)c1]

HATU (166 mg, 436 μmol) and DIPEA (150 μl, 870 μmol) were added to a mixture of 6-bromo-3-methyl-2-phenylquinoline-4-carboxylic acid (99 mg, 291 μmol, preparable according to WO 2016 146602 A1, p. 51, Example 3A) in DMF (1.5 ml), and the mixture was stirred at RT for 30 min. (+/−)-tert-Butyl 4-amino-3-(3-chlorophenyl)butanoate (294 mg, 40% purity, 436 μmol, Example 92A) dissolved in DMF (1 ml) was then added, and the mixture was stirred at 60° C. overnight. After cooling to RT, the mixture was purified by preparative HPLC (Method 21). This gave 224 mg (66% purity, 86% of theory) of the title compound.

LC-MS (Method 1): $R_t$=2.53 min; MS (ESIpos): m/z=591/593 (M+H)⁺

Example 184A (+/−)-tert-Butyl 4-{[(6-bromo-3-methyl-2-phenylquinolin-4-yl)carbonyl]amino}-3-(2-methylphenyl)butanoate (Racemate)

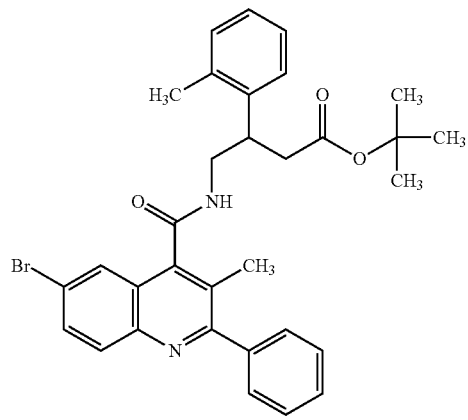 [SMILES: Cc1ccccc1C(CNC(=O)c1c(C)c(-c2ccccc2)nc2ccc(Br)cc12)CC(=O)OC(C)(C)C]

HATU (1.05 g, 2.76 mmol) and DIPEA (960 μl, 5.5 mmol) were added to a mixture of 6-bromo-3-methyl-2-phenylquinoline-4-carboxylic acid (629 mg, 1.84 mmol, preparable according to WO 2016 146602 A1, p. 51, Example 3A) in DMF (6.5 ml), and the mixture was stirred at RT for 30 min. (+/−)-tert-Butyl 4-amino-3-(2-methylphenyl)butanoate (724 mg, 95% purity, 2.76 mmol, Example 93A) dissolved in DMF (3.5 ml) was then added, and the mixture was stirred at 60° C. overnight. After cooling to RT, the mixture was purified by preparative HPLC (Method 21). This gave 778 mg (95% purity, 70% of theory) of the title compound.

LC-MS (Method 1): $R_t$=2.56 min; MS (ESIpos): m/z=573/575 (M+H)

¹H-NMR (400 MHz, DMSO-d6): δ [ppm]=8.88 (t, 1H), 7.95 (d, 1H), 7.86 (dd, 1H), 7.69 (br. s, 1H), 7.59-7.44 (m, 5H), 7.34 (d, 1H), 7.26-7.03 (m, 3H), 3.80-3.62 (m, 2H), 3.57-3.38 (m, 1H), 2.78-2.67 (m, 1H), 2.64-2.56 (m, 1H), 2.39 (s, 3H), 2.14 (br. s, 2H), 1.22 (s, 9H).

Example 185A (+/−)-tert-Butyl 4-{[(6-bromo-3-methyl-2-phenylquinolin-4-yl)carbonyl]amino}-3-(2,6-dichlorophenyl)butanoate

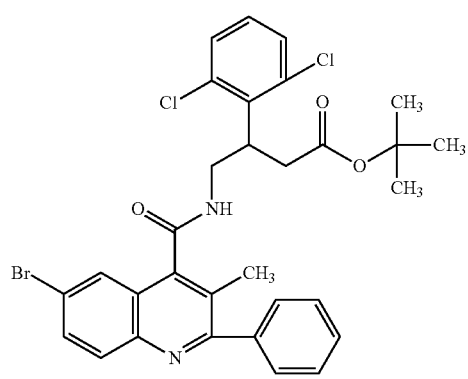 [SMILES: Cc1c(-c2ccccc2)nc2ccc(Br)cc2c1C(=O)NCC(CC(=O)OC(C)(C)C)c1c(Cl)cccc1Cl]

HATU (300 mg, 788 µmol) and DIPEA (270 µl, 1.6 mmol) were added to a mixture of 6-bromo-3-methyl-2-phenylquinoline-4-carboxylic acid (180 mg, 525 µmol, preparable according to WO 2016 146602 A1, p. 51, Example 3A) in DMF (4.5 ml), and the mixture was stirred at RT for 30 min. (+/−)-tert-Butyl 4-amino-3-(2,6-dichlorophenyl)butanoate (255 mg, 94% purity, 788 µmol, Example 94A) dissolved in DMF (2 ml) was then added, and the mixture was stirred at 60° C. overnight. After cooling to RT, the mixture was purified by preparative HPLC (Method 21). This gave 150 mg (91% purity, 41% of theory) of the title compound.

LC-MS (Method 2): $R_t$=1.41 min; MS (ESIpos): m/z=627/629/631 (M+H)

$^1$H-NMR (400 MHz, DMSO-d6): δ [ppm]=8.96 (t, 1H), 7.99-7.93 (m, 1H), 7.90-7.83 (m, 1H), 7.60-7.38 (m, 8H), 7.36-7.26 (m, 1H), 4.38 (br. s, 1H), 4.07 (br. s, 1H), 3.78 (br. s, 1H, obscured), 3.04 (dd, 1H), 2.82 (dd, 1H), 2.19 (br. s, 3H), 1.24 (s, 9H).

Example 186A (+/−)-tert-Butyl 4-{[(6-bromo-3-methyl-2-phenylquinolin-4-yl)carbonyl]amino}-3-(3-methoxyphenyl)butanoate (Racemate)

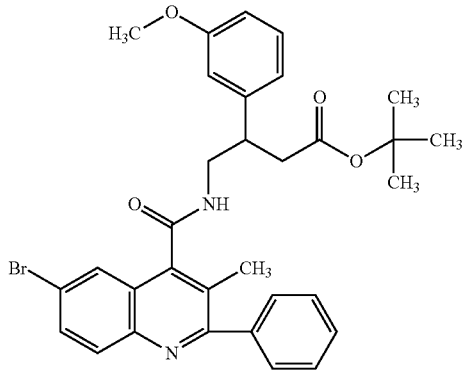 [SMILES: COc1cccc(C(CNC(=O)c2c(C)c(-c3ccccc3)nc3ccc(Br)cc23)CC(=O)OC(C)(C)C)c1]

HATU (645 mg, 1.70 mmol) and DIPEA (590 µl, 3.4 mmol) were added to a mixture of 6-bromo-3-methyl-2-phenylquinoline-4-carboxylic acid (387 mg, 1.13 mmol, preparable according to WO 2016 146602 A1, p. 51, Example 3A) in DMF (4.5 ml), and the mixture was stirred at RT for 30 min. (+/−)-tert-Butyl 4-amino-3-(3-methoxyphenyl)butanoate (500 mg, 90% purity, 1.70 mmol, Example 95A) dissolved in DMF (2 ml) was then added, and the mixture was stirred at 60° C. overnight. After cooling to RT, the mixture was purified by preparative HPLC (Method 21). This gave 225 mg (93% purity, 31% of theory) of the title compound.

LC-MS (Method 1): $R_t$=2.42 min; MS (ESIpos): m/z=589/591 [M+H]$^+$ $^1$H-NMR (400 MHz, DMSO-d6): δ [ppm]=8.81 (t, 1H), 7.94 (d, 1H), 7.86 (dd, 1H), 7.66 (br. s, 1H), 7.57-7.46 (m, 5H), 7.23 (t, 1H), 6.92-6.86 (m, 2H), 6.83-6.74 (m, 1H), 3.80-3.66 (m, 1H, partially obscured), 3.72 (s, 3H), 3.66-3.48 (m, 1H), 3.43-3.23 (m, 1H), 2.72 (dd, 1H), 2.59-2.52 (m, 1H, partially obscured), 2.11 (br. s, 3H), 1.27 (s, 9H).

Example 187A (+/−)-tert-Butyl 4-{[(6-bromo-3-methyl-2-phenylquinolin-4-yl)carbonyl]amino}-3-(3-chloropyridin-2-yl)-3-methylbutanoate (Racemate)

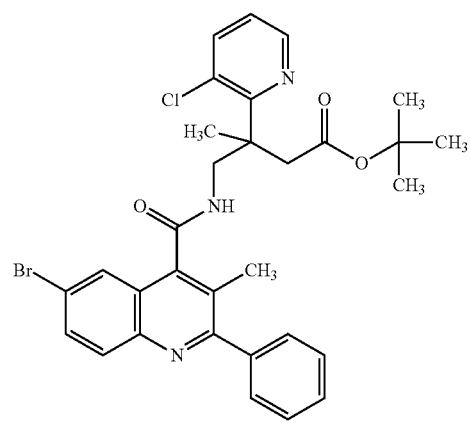 [SMILES: Cc1c(-c2ccccc2)nc2ccc(Br)cc2c1C(=O)NCC(C)(CC(=O)OC(C)(C)C)c1ncccc1Cl]

HATU (822 mg, 2.16 mmol) and DIPEA (0.75 ml, 4.33 mmol) were added to a mixture of 6-bromo-3-methyl-2-phenylquinoline-4-carboxylic acid (493 mg, 1.44 mmol, preparable according to WO 2016 146602 A1, p. 51, Example 3A) in DMF (4 ml), and the mixture was stirred at RT for 30 min. (+/−)-tert-Butyl 4-amino-3-(3-chloropyridin-2-yl)-3-methylbutanoate (616 mg, 2.16 mmol, Example 96A) dissolved in DMF (4 ml) was then added, and the mixture was stirred at 60° C. overnight. After cooling to RT, the mixture was purified by preparative HPLC (Method 21). This gave 694 mg (98% purity, 77% of theory) of the title compound.

LC-MS (Method 2): $R_t$=1.35 min; MS (ESIpos): m/z=608/610 [M+H]$^+$ $^1$H-NMR (400 MHz, DMSO-d6): δ [ppm]=8.69 (t, 1H), 8.48 (dd, 1H), 7.94 (d, 1H), 7.86 (dd, 2H), 7.71 (d, 1H), 7.58-7.44 (m, 5H), 7.32 (dd, 1H), 4.12 (br. s, 1H), 3.99 (br. s, 1H), 3.32 (d, 1H), 2.67 (d, 1H), 2.16 (s, 3H), 1.68 (s, 3H), 1.20 (s, 9H)

Example 188A (+/−)-tert-Butyl 4-{[(6-bromo-3-methyl-2-phenylquinolin-4-yl)carbonyl]amino}-3-(2-chloro-6-fluorophenyl)butanoate (Racemate)

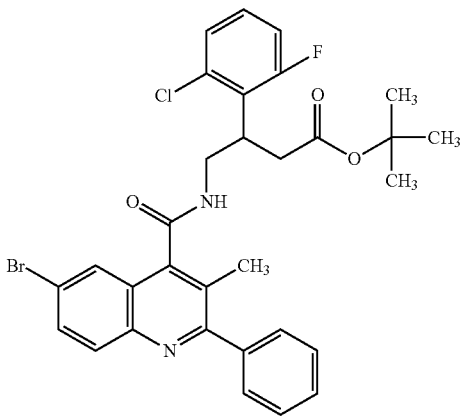 [SMILES: Cc1c(-c2ccccc2)nc2ccc(Br)cc2c1C(=O)NCC(CC(=O)OC(C)(C)C)c1c(F)cccc1Cl]

HATU (8.26 g, 21.7 mmol) and DIPEA (7.6 ml, 43 mmol) were added to a mixture of 6-bromo-3-methyl-2-phenylquinoline-4-carboxylic acid (4.95 g, 14.5 mmol, preparable according to WO 2016 146602 A1, p. 51, Example 3A) in DMF (65 ml), and the mixture was stirred at RT for 30 min. (+/−)-tert-Butyl 4-amino-3-(2-chloro-6-fluorophenyl)butanoate (5.00 g, 17.4 mmol, Example 97A) dissolved in DMF (20 ml) was then added, and the mixture was stirred at 60° C. overnight. After cooling to RT, the mixture was concentrated, and 200 ml each of ethyl acetate and water were added to the residue, which was agitated. The aqueous phase was extracted once with ethyl acetate. The combined organic phases were washed once with 200 ml of saturated aqueous sodium chloride solution, dried over sodium sulfate, filtered and concentrated, and the residue was taken up in dichloromethane and purified by flash column chromatography (500 g of silica gel Biotage Snap-Cartridge KP-Sil, cyclohexane/ethyl acetate 9:1→8:2). This gave 5.23 g (100% purity, 59% of theory) of the title compound.

LC-MS (Method 2): $R_t$=1.33 min; MS (ESIpos): m/z=611/613 [M+H]$^+$ $^1$H-NMR (400 MHz, DMSO-d6): δ [ppm]=8.97 (t, 1H), 7.95 (d, 1H), 7.86 (dd, 1H), 7.78-7.59 (br. m, 1H), 7.60-7.44 (m, 5H), 7.38-7.29 (m, 2H), 7.26-7.12 (m, 1H), 4.16-3.98 (m, 1H), 3.93-3.56 (br. m, 2H), 2.85-2.61 (m, 2H), 2.17 (br. s, 3H), 1.24 (s, 9H).

Separation of the Enantiomers:

The title compound (5.15 g) was taken up in 50 ml of methanol, filtered and separated into the enantiomers by preparative SFC on a chiral phase (see Examples 189A and 190A) [column: Daicel Chiralcel OJ-H, 5 μm, 250 mm×30 mm; flow rate: 175 ml/min; detection: 210 nm; temperature: 38° C.; injection: 0.4 ml; mobile phase: 80% carbon dioxide/20% isopropanol; run time 8 min, isocratic].

Example 189A (−)-tert-Butyl 4-{[(6-bromo-3-methyl-2-phenylquinolin-4-yl)carbonyl]amino}-3-(2-chloro-6-fluorophenyl)butanoate (Enantiomer 1)

In the enantiomer separation described in Example 188A, 1.89 g (100% purity, ee 97%) of the title compound were obtained as the enantiomer that eluted earlier.

$[α]_D^{20}$=−16.6°, 589 nm, c=0.50 g/100 ml, chloroform

LC-MS (Method 1): $R_t$=2.52 min; MS (ESIpos): m/z=611/613 [M+H]$^+$ $^1$H-NMR (400 MHz, DMSO-d6): δ [ppm]=8.97 (t, 1H), 7.95 (d, 1H), 7.86 (dd, 1H), 7.78-7.57 (m, 1H), 7.58-7.43 (m, 5H), 7.40-7.28 (m, 2H), 7.26-7.13 (m, 1H), 4.17-3.99 (m, 1H), 3.94-3.59 (br. m, 2H), 2.88-2.61 (m, 2H), 2.17 (br. s, 3H), 1.24 (s, 9H).

Example 190A (+)-tert-Butyl 4-{[(6-bromo-3-methyl-2-phenylquinolin-4-yl)carbonyl]amino}-3-(2-chloro-6-fluorophenyl)butanoate (Enantiomer 2)

In the enantiomer separation described in Example 188A, 1.85 g (98% purity, ee 95%) of the title compound were obtained as the enantiomer that eluted later.

$[α]_D^{20}$=+16.1°, 589 nm, c=0.52 g/100 ml, chloroform

LC-MS (Method 1): $R_t$=2.52 min; MS (ESIpos): m/z=611/613 [M+H]$^+$ $^1$H-NMR (400 MHz, DMSO-d6): δ [ppm]=8.97 (t, 1H), 7.95 (d, 1H), 7.86 (dd, 1H), 7.79-7.60 (br. m, 1H), 7.56-7.44 (m, 5H), 7.41-7.27 (m, 2H), 7.26-7.13 (m, 1H), 4.18-4.00 (m, 1H), 3.97-3.61 (br. m, 2H), 2.85-2.61 (m, 2H), 2.17 (br. s, 3H), 1.24 (s, 9H).

Example 191A (+/−)-tert-Butyl 4-{[(6-bromo-3-methyl-2-phenylquinolin-4-yl)carbonyl]amino}-3-(4-methylphenyl)butanoate (Racemate)

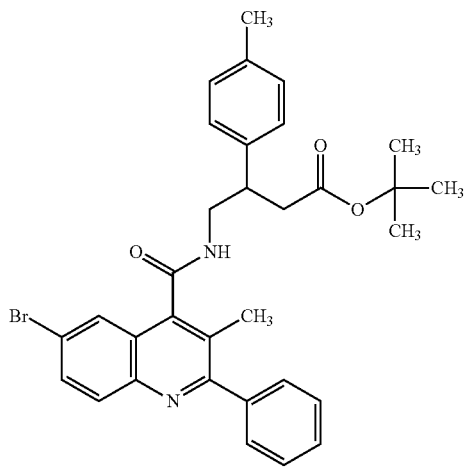 [SMILES: Cc1ccc(C(CNC(=O)c2c(C)c(-c3ccccc3)nc3ccc(Br)cc23)CC(=O)OC(C)(C)C)cc1]

HATU (244 mg, 642 μmol) and DIPEA (220 μl, 1.3 mmol) were added to a mixture of 6-bromo-3-methyl-2-phenylquinoline-4-carboxylic acid (146 mg, 428 μmol, preparable according to WO 2016 146602 A1, p. 51, Example 3A) in DMF (1.5 ml), and the mixture was stirred at RT for 30 min. (+/−)-tert-Butyl 4-amino-3-(4-methylphenyl)butanoate (160 mg, 642 μmol, Example 98A) dissolved in DMF (1 ml) was then added, and the mixture was stirred at 60° C. overnight. After cooling to RT, the mixture was purified by preparative HPLC (Method 21). This gave 138 mg (98% purity, 55% of theory) of the title compound.

LC-MS (Method 1): $R_t$=2.54 min; MS (ESIpos): m/z=573/575 [M+H]$^+$

¹H-NMR (400 MHz, DMSO-d6): δ [ppm]=8.80 (t, 1H), 7.94 (d, 1H), 7.85 (dd, 1H), 7.78-7.57 (br. s, 1H), 7.56-7.45 (m, 5H), 7.21 (d, 2H), 7.13 (d, 2H), 3.89-3.40 (br. m, 2H, obscured), 3.39-3.26 (m, 1H), 2.71 (dd, 1H), 2.50 (1H, obscured), 2.26 (s, 3H), 2.14 (br. s, 3H), 1.27 (s, 9H).

Example 192A (+/−)-tert-Butyl 4-{[(6-bromo-3-methyl-2-phenylquinolin-4-yl)carbonyl]amino}-3-(3-methylphenyl)butanoate (Racemate)

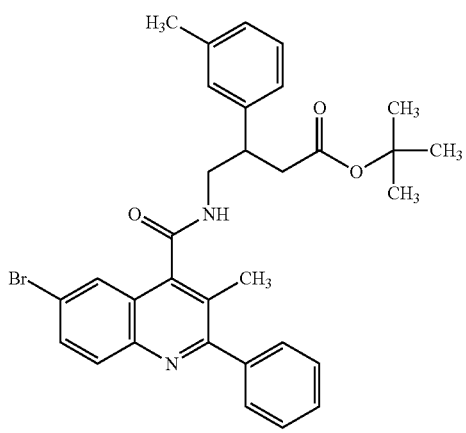 [SMILES: Cc1cccc(C(CNC(=O)c2c(C)c(-c3ccccc3)nc3ccc(Br)cc23)CC(=O)OC(C)(C)C)c1]

HATU (197 mg, 518 µmol) and DIPEA (180 µl, 1.0 mmol) were added to a mixture of 6-bromo-3-methyl-2-phenylquinoline-4-carboxylic acid (118 mg, 345 µmol, preparable according to WO 2016 146602 A1, p. 51, Example 3A) in DMF (1.0 ml), and the mixture was stirred at RT for 30 min. (+/−)-tert-Butyl 4-amino-3-(3-methylphenyl)butanoate (170 mg, 76% purity, 518 µmol, Example 99A) dissolved in DMF (1.0 ml) was then added, and the mixture was stirred at 60° C. overnight. After cooling to RT, the mixture was purified by preparative HPLC (Method 21). This gave 128 mg (98% purity, 63% of theory) of the title compound.

LC-MS (Method 1): $R_t$=2.54 min; MS (ESIpos): m/z=573/575 [M+H]⁺

¹H-NMR (400 MHz, DMSO-d6): δ [ppm]=8.81 (t, 1H), 7.94 (d, 1H), 7.85 (dd, 1H), 7.80-7.58 (br. s, 1H), 7.56-7.46 (m, 5H), 7.24-7.00 (m, 4H), 3.80-3.52 (br. m, 2H, obscured), 3.40-3.28 (m, 1H), 2.72 (dd, 1H), 2.54-2.45 (1H, obscured), 2.27 (s, 3H), 2.13 (br. s, 3H), 1.26 (s, 9H)

Example 193A (+/−)-tert-Butyl 4-{[(6-bromo-3-methyl-2-phenylquinolin-4-yl)carbonyl]amino}-3-(2-methoxyphenyl)butanoate (Racemate)

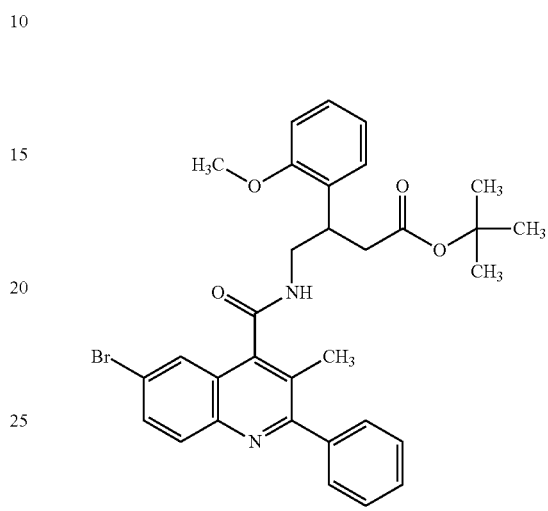

HATU (5.54 g, 14.6 mmol) and DIPEA (5.1 ml, 29 mmol) were added to a mixture of 6-bromo-3-methyl-2-phenylquinoline-4-carboxylic acid (3.32 g, 9.71 mmol, preparable according to WO 2016 146602 A1, p. 51, Example 3A) in DMF (35 ml), and the mixture was stirred at RT for 30 min. (+/−)-tert-Butyl 4-amino-3-(2-methoxyphenyl)butanoate (4.20 g, 92% purity, 14.6 mmol, Example 100A) dissolved in DMF (20 ml) was then added, and the mixture was stirred at 60° C. overnight. After cooling to RT, the mixture was concentrated, and the residue was taken up in ethyl acetate and water (200 ml each) and agitated. After phase separation, the aqueous phase was extracted once with ethyl acetate, and the combined organic phases were washed once with saturated aqueous sodium chloride solution (200 ml), dried over sodium sulfate, filtered and concentrated on a rotary evaporator. The residue was taken up in dichloromethane and purified by flash column chromatography (340 g silica gel Biotage Snap-Cartridge KP-Sil, cyclohexane/ethyl acetate 97:3→8:2, Isolera One). This gave 4.50 g (98% purity, 77% of theory) of the title compound.

LC-MS (Method 1): $R_t$=2.50 min; MS (ESIpos): m/z=589/591 [M+H]⁺

¹H-NMR (400 MHz, DMSO-d6): δ [ppm]=8.77 (t, 1H), 7.94 (d, 1H), 7.85 (dd, 1H), 7.71 (br. s, 1H), 7.57-7.45 (m, 5H), 7.27-7.17 (m, 2H), 6.98 (d, 1H), 6.91 (t, 1H), 3.80 (s, 3H), 3.78-3.61 (m, 3H), 2.71-2.58 (m, 2H), 2.15 (s, 3H), 1.25 (s, 9H).

Example 194A (+/−)-tert-Butyl 4-{[(6-bromo-3-methyl-2-phenylquinolin-4-yl)carbonyl]amino}-3-[2-(trifluoromethoxy)phenyl]butanoate (Racemate)

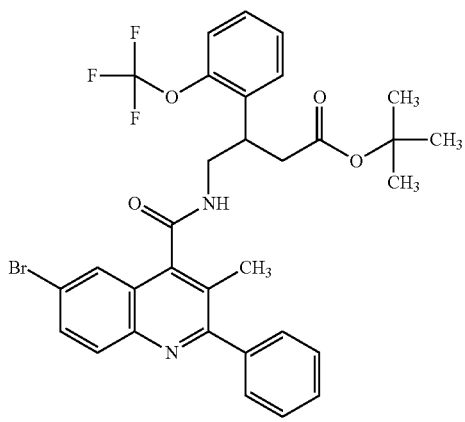 [SMILES: Cc1c(-c2ccccc2)nc2ccc(Br)cc2c1C(=O)NCC(CC(=O)OC(C)(C)C)c1ccccc1OC(F)(F)F]

HATU (792 mg, 2.08 mmol) and DIPEA (730 μl, 4.2 mmol) were added to a mixture of 6-bromo-3-methyl-2-phenylquinoline-4-carboxylic acid (475 mg, 1.39 mmol, preparable according to WO 2016 146602 A1, p. 51, Example 3A) in DMF (4.5 ml), and the mixture was stirred at RT for 30 min. (+/−)-tert-Butyl 4-amino-3-[2-(trifluoromethoxy)phenyl]butanoate (700 mg, 95% purity, 2.08 mmol, Example 101A) dissolved in DMF (3 ml) was then added, and the mixture was stirred at 60° C. overnight. After cooling to RT, ethyl acetate and water (20 ml of each) were added to the mixture, which was agitated. The aqueous phase was extracted twice with ethyl acetate (20 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15). This gave 367 mg (98% purity, 40% of theory) of the title compound.

LC-MS (Method 1): $R_t$=2.60 min; MS (ESIpos): m/z=643/645 [M+H]$^+$ $^1$H-NMR (600 MHz, DMSO-d6): δ [ppm]=8.91 (t, 1H), 7.95 (d, 1H), 7.86 (dd, 1H), 7.81-7.61 (br. m, 1H), 7.61-7.47 (m, 6H), 7.43-7.30 (m, 3H), 3.85-3.70 (m, 2H), 3.69-3.57 (m, 1H), 2.76 (dd, 1H), 2.60 (dd, 1H), 2.16 (br. s, 3H), 1.26 (s, 9H).

Example 195A (+/−)-tert-Butyl 4-{[(6-bromo-3-methyl-2-phenylquinolin-4-yl)carbonyl]amino}-3-(pyridin-2-yl)butanoate (Racemate)

HATU (708 mg, 1.86 mmol) and DIPEA (650 μl, 3.7 mmol) were added to a mixture of 6-bromo-3-methyl-2-phenylquinoline-4-carboxylic acid (425 mg, 1.24 mmol, preparable according to WO 2016 146602 A1, p. 51, Example 3A) in DMF (4.5 ml), and the mixture was stirred at RT for 30 min. (+/−)-tert-Butyl 4-amino-3-(pyridin-2-yl)butanoate (550 mg, 80% purity, 1.86 mmol, Example 102A) dissolved in DMF (2 ml) was then added, and the mixture was stirred at 60° C. overnight. After cooling to RT, the mixture was purified by preparative HPLC (Method 21). This gave 659 mg (98% purity, 93% of theory) of the title compound.

LC-MS (Method 1): $R_t$=2.16 min; MS (ESIpos): m/z=560/562 [M+H]$^+$ $^1$H-NMR (400 MHz, DMSO-d6): δ [ppm]=8.88 (t, 1H), 8.69 (d, 1H), 8.09-7.98 (m, 1H), 7.95 (d, 1H), 7.86 (dd, 1H), 7.80-7.57 (br. m, 2H), 7.57-7.46 (m, 6H), 3.91-3.78 (m, 1H), 3.75-3.58 (m, 2H), 2.89-2.72 (m, 2H), 2.14 (br. s, 3H), 1.28 (s, 9H).

Example 196A (+/−)-tert-Butyl 4-{[(6-bromo-3-methyl-2-phenylquinolin-4-yl)carbonyl]amino}-3-[2-(trifluoromethyl)phenyl]butanoate (Racemate)

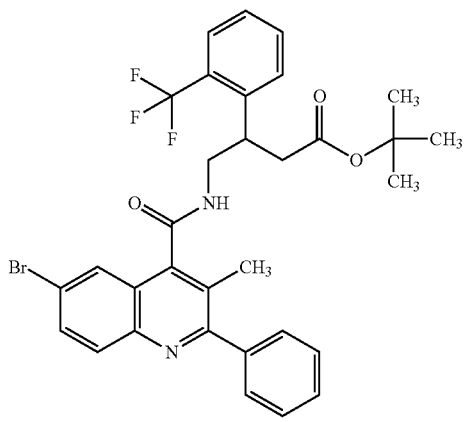 [SMILES: Cc1c(-c2ccccc2)nc2ccc(Br)cc2c1C(=O)NCC(CC(=O)OC(C)(C)C)c1ccccc1C(F)(F)F]

HATU (1.43 g, 3.76 mmol) and DIPEA (1.3 ml, 7.5 mmol) were added to a mixture of 6-bromo-3-methyl-2-phenylquinoline-4-carboxylic acid (857 mg, 2.51 mmol, preparable according to WO 2016 146602 A1, p. 51, Example 3A) in DMF (10 ml), and the mixture was stirred at RT for 30 min. (+/−)-tert-Butyl 4-amino-3-[2-(trifluoromethyl)phenyl]butanoate (1.90 g, 60% purity, 3.76 mmol, Example 103A) dissolved in DMF (3 ml) was then added, and the mixture was stirred at 60° C. overnight. Subsequently, ethyl acetate and water (20 ml of each) were added to the mixture, which was agitated. After phase separation, the aqueous phase was extracted twice with ethyl acetate (20 ml each time). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15, Isolera One). The combined target fractions were concentrated and the residue was lyophilized. This gave 1.10 g (98% purity, 68% of theory) of the title compound.

LC-MS (Method 1): $R_t$=2.58 min; MS (ESIpos): m/z=627/629 $[M+H]^+$ $^1$H-NMR (400 MHz, DMSO-d6) δ [ppm]: 1.249 (16.00), 1.397 (4.44), 2.161 (1.10), 2.687 (0.40), 2.706 (0.41), 2.735 (0.40), 2.751 (0.41), 3.314 (1.68), 7.474 (0.59), 7.492 (0.67), 7.506 (1.12), 7.525 (1.58), 7.539 (2.10), 7.558 (0.44), 7.685 (0.56), 7.718 (0.64), 7.738 (0.55), 7.760 (0.65), 7.779 (0.41), 7.838 (0.41), 7.861 (0.63), 7.865 (0.57), 7.939 (1.09), 7.962 (0.71), 8.902 (0.54).

$^1$H-NMR (400 MHz, DMSO-d6): δ [ppm]=8.90 (t, 1H), 7.95 (d, 1H), 7.85 (dd, 1H), 7.79-7.57 (m, 4H), 7.57-7.44 (m, 6H), 3.90-3.60 (m, 3H), 2.75 (dd, 1H), 2.69 (dd, 1H), 2.16 (br. s, 3H), 1.25 (s, 9H).

Example 197A (+/−)-tert-Butyl 4-{[(6-bromo-3-methyl-2-phenylquinolin-4-yl)carbonyl]amino}-3-(3-methoxypyridin-2-yl)butanoate (Racemate)

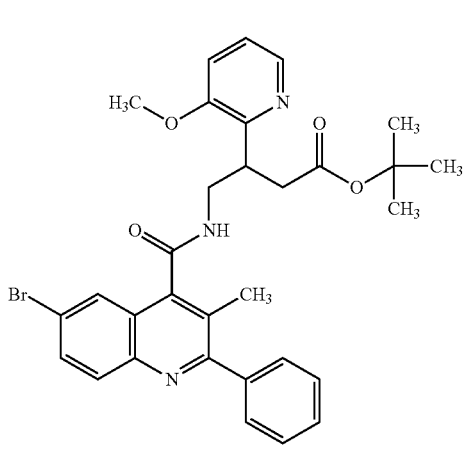 [SMILES: COc1cccnc1C(CNC(=O)c1c(C)c(-c2ccccc2)nc2ccc(Br)cc12)CC(=O)OC(C)(C)C]

HATU (2.73 g, 7.19 mmol) and DIPEA (2.5 ml, 14 mmol) were added to a mixture of 6-bromo-3-methyl-2-phenylquinoline-4-carboxylic acid (1.64 g, 4.79 mmol, preparable according to WO 2016 146602 A1, p. 51, Example 3A) in DMF (20 ml), and the mixture was stirred at RT for 30 min. (+/−)-tert-Butyl 4-amino-3-(3-methoxypyridin-2-yl)butanoate (2.02 g, 95% purity, 7.19 mmol, Example 104A) dissolved in DMF (8 ml) was then added, and the mixture was stirred at 60° C. overnight. After cooling to RT, the mixture was purified by preparative HPLC (Method 21). This gave 1.73 g (98% purity, 60% of theory) of the title compound.

LC-MS (Method 1): $R_t$=2.24 min; MS (ESIpos): m/z=590/592 $[M+H]^+$ $^1$H-NMR (400 MHz, DMSO-d6) δ [ppm]: 1.255 (16.00), 2.192 (4.16), 5.754 (0.86), 7.506 (0.89), 7.511 (0.69), 7.524 (1.44), 7.536 (1.73), 7.538 (1.71), 7.543 (1.00), 7.546 (0.66), 7.843 (0.42), 7.865 (0.65), 7.871 (0.58), 7.937 (1.13), 7.959 (0.71), 8.128 (0.53), 8.131 (0.53), 8.140 (0.54).

$^1$H-NMR (400 MHz, DMSO-d6): δ [ppm]=8.77 (t, 1H), 8.14 (dd, 1H), 7.95 (d, 1H), 7.86 (dd, 1H), 7.77 (s, 1H), 7.58-7.47 (m, 5H), 7.43 (d, 1H), 7.27 (dd, 1H), 4.02-3.90 (m, 1H), 3.84 (s, 3H), 3.79-3.62 (m, 2H), 2.87 (dd, 1H), 2.63 (dd, 1H), 2.19 (s, 3H), 1.25 (s, 9H).

Example 198A (+/−)-tert-Butyl 4-{[(6-bromo-3-methyl-2-phenylquinolin-4-yl)carbonyl]amino}-3-(2-chlorophenyl)-2,2-dimethylbutanoate (Racemate)

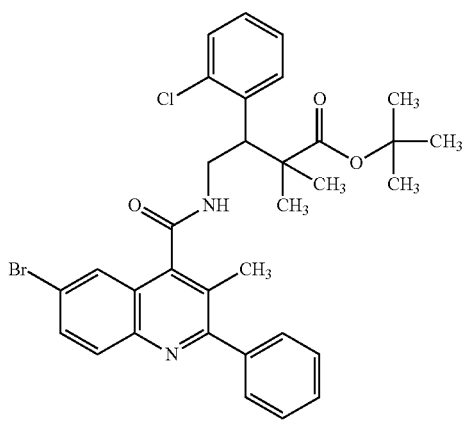 [SMILES: Cc1c(-c2ccccc2)nc2ccc(Br)cc2c1C(=O)NCC(c1ccccc1Cl)C(C)(C)C(=O)OC(C)(C)C]

HATU (443 mg, 1.16 mmol) and DIPEA (470 µl, 2.7 mmol) were added to a mixture of 6-bromo-3-methyl-2-phenylquinoline-4-carboxylic acid (306 mg, 895 µmol, preparable according to WO 2016 146602 A1, p. 51, Example 3A) in DMF (1.5 ml), and the mixture was stirred at RT for 30 min. (+/−)-tert-Butyl 4-amino-3-(2-chlorophenyl)-2,2-dimethylbutanoate (320 mg, 1.07 mmol, Example 106A) dissolved in DMF (4 ml) was then added, and the mixture was stirred at RT overnight. Subsequently, the mixture was purified by preparative HPLC (method: Chromatorex C18, 10 µm, 30×125 mm, acetonitrile/water gradient: acetonitrile 10%-90%). This gave 328 mg (99% purity, 59% of theory) of the title compound.

LC-MS (Method 2): $R_t$=1.53 min; MS (ESIpos): m/z=621/523 (M+H)

1H-NMR (400 MHz, DMSO-d6): δ [ppm]=8.69 (t, 1H), 7.90 (d, 1H), 7.82 (dd, 1H), 7.58-7.22 (m, 10H), 4.17-4.09 (m, 1H), 4.05-3.87 (m, 1H), 3.77-3.63 (m, 1H), 1.97 (br. s, 3H), 1.48 (s, 9H), 1.10 (s, 3H), 1.06 (s, 3H).

Example 199A (+/−)-tert-Butyl 4-{[(6-bromo-3-methyl-2-phenylquinolin-4-yl)carbonyl]amino}-3-(2-chlorophenyl)-3-methylbutanoate (Racemate)

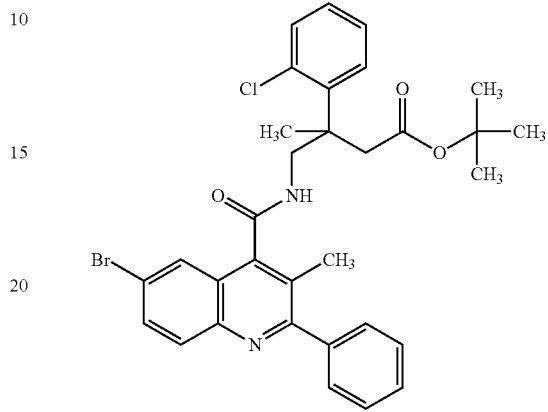

HATU (1.88 g, 4.93 mmol) and DIPEA (1.7 ml, 9.9 mmol) were added to a mixture of 6-bromo-3-methyl-2-phenylquinoline-4-carboxylic acid (1.13 g, 3.29 mmol, preparable according to WO 2016 146602 A1, p. 51, Example 3A) in DMF (12 ml), and the mixture was stirred at RT for 30 min. (+/−)-tert-Butyl 4-amino-3-(2-chlorophenyl)-3-methylbutanoate (2.00 g, 70% purity, 4.93 mmol, Example 107A) dissolved in DMF (6 ml) was then added, and the mixture was stirred at 60° C. overnight. After cooling to RT, ethyl acetate and water (50 ml of each) were added to the mixture, which was agitated. The aqueous phase was extracted twice with ethyl acetate (50 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage Snap-Cartridge KP-Sil, cyclohexane/ethyl acetate 85:15). This gave 1.94 g (87% purity, 84% of theory) of the prepurified title compound. Of these 1.94 g, 250 mg were repurified by preparative HPLC (Method 20). This gave 144 mg (98% purity) of the repurified title compound (see analysis).

LC-MS (Method 1): $R_t$=2.63 min; MS (ESIpos): m/z=607/609 (M+H)+

1H-NMR (400 MHz, DMSO-d6) δ [ppm]: 1.119 (16.00), 1.652 (2.39), 2.572 (0.66), 2.608 (0.71), 3.415 (0.53), 3.450 (0.49), 7.287 (0.59), 7.305 (0.42), 7.433 (0.75), 7.452 (0.44), 7.457 (0.42), 7.499 (0.89), 7.506 (0.75), 7.518 (1.75), 7.527 (1.66), 7.853 (0.53), 7.857 (0.52), 7.927 (0.99), 7.950 (0.63), 8.664 (0.43).

1H-NMR (400 MHz, DMSO-d6): δ [ppm]=8.66 (t, 1H), 7.94 (d, 1H), 7.85 (dd, 1H), 7.65 (br. s, 1H), 7.57-7.47 (m, 5H), 7.46-7.37 (m, 2H), 7.33-7.23 (m, 2H), 4.37 (dd, 1H), 3.75 (dd, 1H), 3.43 (d, 1H), 2.59 (d, 1H), 2.12 (br. s, 3H), 1.65 (s, 3H), 1.12 (s, 9H).

Example 200A (+/−)-tert-Butyl 4-{[(6-bromo-3-methyl-2-phenylquinolin-4-yl)carbonyl]amino}-3-(2-fluorophenyl)-3-methylbutanoate (Racemate)

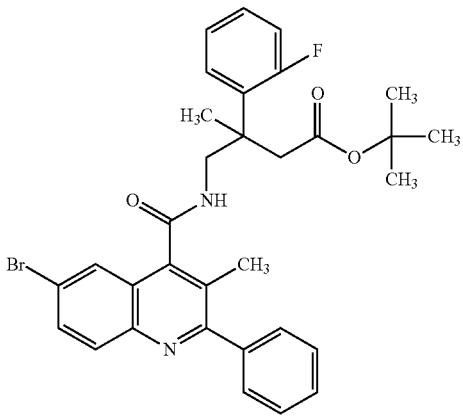 [SMILES: Cc1c(-c2ccccc2)nc2ccc(Br)cc2c1C(=O)NCC(C)(CC(=O)OC(C)(C)C)c1ccccc1F]

HATU (1.02 g, 2.68 mmol) and DIPEA (940 µl, 5.4 mmol) were added to a mixture of 6-bromo-3-methyl-2-phenylquinoline-4-carboxylic acid (612 mg, 1.79 mmol, preparable according to WO 2016 146602 A1, p. 51, Example 3A) in DMF (7 ml), and the mixture was stirred at RT for 30 min. (+/−)-tert-Butyl 4-amino-3-(2-fluorophenyl)-3-methylbutanoate (810 mg, "2.68 mmol", not corrected for purity, Example 108A) dissolved in DMF (3 ml) was then added, and the mixture was stirred at 60° C. overnight. After cooling to RT, ethyl acetate and water (50 ml of each) were added to the mixture, which was agitated. The aqueous phase was extracted twice with ethyl acetate (50 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage Snap-Cartridge KP-Sil, cyclohexane/ethyl acetate 85:15). The prepurified product was repurified by preparative HPLC (Method 20). This gave 255 mg (95% purity, "23% of theory") of the title compound.

LC-MS (Method 1): $R_t$=2.55 min; MS (ESIpos): m/z=591/593 (M+H)$^+$ $^1$H-NMR (400 MHz, DMSO-d6) δ [ppm]: 1.126 (16.00), 1.197 (0.85), 1.569 (2.52), 2.976 (0.56), 3.011 (0.50), 7.139 (0.43), 7.157 (0.47), 7.172 (0.41), 7.315 (0.52), 7.335 (0.60), 7.502 (0.97), 7.509 (0.83), 7.520 (1.94), 7.529 (1.82), 7.857 (0.57), 7.862 (0.59), 7.931 (1.10), 7.954 (0.69), 8.726 (0.42).

Separation of the Enantiomers:

The title compound (220 mg) was dissolved in a mixture of isopropanol (4 ml) and dichloromethane (2 ml) and separated into the enantiomers by preparative HPLC on a chiral phase (see Examples 201A and 202A) [column: Daicel Chiralpak IE, 5 µm 250 mm×20 mm; flow rate: 15 ml/min; detection: 220 nm; temperature: 40° C.; injection: 0.2 ml; mobile phase: 60% heptane/40% isopropanol, isocratic; run time 20 min].

Example 201A (+)-tert-Butyl 4-{[(6-bromo-3-methyl-2-phenylquinolin-4-yl)carbonyl]amino}-3-(2-fluorophenyl)-3-methylbutanoate (Enantiomer 1)

In the enantiomer separation described in Example 200A, 96 mg (98% purity, ee 99%) of the title compound were obtained as the enantiomer that eluted earlier.

$[α]_D^{20}$=+20.7°, 589 nm, c=0.25 g/100 ml, methanol

LC-MS (Method 2): $R_t$=1.35 min; MS (ESIpos): m/z=591/593 (M+H)$^+$ $^1$H-NMR (500 MHz, DMSO-d6) δ [ppm]: 1.126 (16.00), 1.197 (0.42), 1.569 (2.02), 2.979 (0.44), 3.007 (0.41), 7.335 (0.41), 7.501 (0.66), 7.505 (0.68), 7.517 (1.25), 7.529 (1.41), 7.852 (0.41), 7.856 (0.41), 7.930 (0.88), 7.948 (0.60).

$^1$H-NMR (500 MHz, DMSO-d6): δ [ppm]=8.72 (t, 1H), 7.94 (d, 1H), 7.84 (dd, 1H), 7.68 (br. s, 1H), 7.56-7.47 (m, 5H), 7.37-7.28 (m, 2H), 7.19-7.10 (m, 2H), 4.08 (dd, 1H), 3.62 (dd, 1H), 2.99 (d, 1H), −2.5 (1H, obscured), 2.08 (br. s, 3H), 1.57 (s, 3H), 1.13 (s, 9H).

Example 202A (−)-tert-Butyl 4-{[(6-bromo-3-methyl-2-phenylquinolin-4-yl)carbonyl]amino}-3-(2-fluorophenyl)-3-methylbutanoate (Enantiomer 2)

In the enantiomer separation described in Example 200A, 97 mg (98% purity, ee 99%) of the title compound were obtained as the enantiomer that eluted later.

$[α]_D^{20}$=−17.2°, 589 nm, c=0.25 g/100 ml, methanol

LC-MS (Method 2): $R_t$=1.35 min; MS (ESIpos): m/z=591/593 (M+H)

$^1$H-NMR (500 MHz, DMSO-d6) δ [ppm]: 1.126 (16.00), 1.569 (2.16), 2.979 (0.47), 3.007 (0.43), 7.335 (0.45), 7.501 (0.71), 7.504 (0.72), 7.517 (1.33), 7.528 (1.50), 7.851 (0.44), 7.855 (0.42), 7.930 (0.90), 7.948 (0.61).

$^1$H-NMR (500 MHz, DMSO-d6): δ [ppm]=8.72 (t, 1H), 7.94 (d, 1H), 7.84 (dd, 1H), 7.65 (br. s, 1H), 7.56-7.45 (m, 5H), 7.37-7.26 (m, 2H), 7.20-7.07 (m, 2H), 4.08 (dd, 1H), 3.62 (dd, 1H), 2.99 (d, 1H), −2.5 (1H, obscured), 2.10 (br. s, 3H), 1.57 (s, 3H), 1.17-1.07 (m, 9H).

Example 203A (+/−)-tert-Butyl 4-{[(6-bromo-3-methyl-2-phenylquinolin-4-yl)carbonyl]amino}-3-methyl-3-(pyridin-2-yl)butanoate (Racemate)

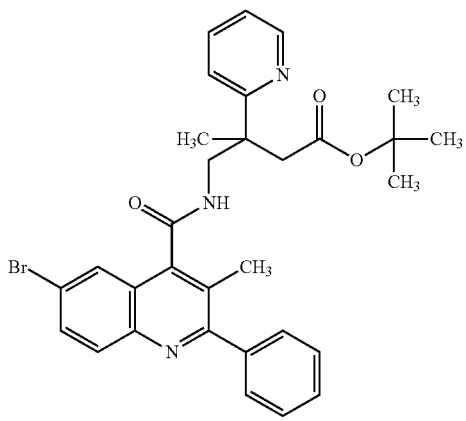 [SMILES: Cc1c(-c2ccccc2)nc2ccc(Br)cc2c1C(=O)NCC(C)(CC(=O)OC(C)(C)C)c1ccccn1]

HATU (4.01 g, 10.5 mmol) and DIPEA (3.7 ml, 21 mmol) were added to a mixture of 6-bromo-3-methyl-2-phenylquinoline-4-carboxylic acid (2.40 g, 7.02 mmol, preparable according to WO 2016 146602 A1, p. 51, Example 3A) in DMF (30 ml), and the mixture was stirred at RT for 30 min. The mixture obtained in Example 109A (4.00 g) of (+/−)-tert-butyl 4-amino-3-methyl-3-(pyridin-2-yl)butanoate and (+/−)-tert-butyl 4-amino-3-(3-chloropyridin-2-yl)-3-methylbutanoate, dissolved in DMF (10 ml), was then added, and the reaction mixture was stirred at 60° C. overnight. After cooling to RT, ethyl acetate and water (50 ml each) were added, the mixture was agitated and the phases were separated. The aqueous phase was extracted twice with ethyl acetate (50 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage Snap-Cartridge KP-Sil, cyclohexane/ethyl acetate 85:15). The combined target fractions were concentrated and the residue was lyophilized. This was followed by repurification by preparative HPLC (Method 20). This gave 1.07 g (98% purity) of the title compound and 1.56 g (98% purity) of tert-butyl 4-{[(6-bromo-3-methyl-2-phenylquinolin-4-yl)carbonyl]amino}-3-(3-chloropyridin-2-yl)-3-methylbutanoate.

LC-MS (Method 1): $R_t$=2.37 min; MS (ESIpos): m/z=574/576 [M+H]$^+$ $^1$H-NMR (400 MHz, DMSO-d6) δ [ppm]: 1.180 (1.07), 1.205 (16.00), 1.552 (2.74), 2.141 (0.81), 2.159 (0.47), 2.610 (0.47), 2.647 (0.55), 3.049 (0.44), 3.162 (0.58), 7.499 (0.90), 7.506 (0.72), 7.517 (1.45), 7.529 (1.88), 7.836 (0.42), 7.858 (0.63), 7.864 (0.59), 7.933 (1.25), 7.955 (0.91).

$^1$H-NMR (400 MHz, DMSO-d6) δ [ppm]=8.73 (br. t, 1H), 8.64 (br. d, 1H), 7.95 (d, 1H), 7.86 (dd, 1H), 7.69-7.61 (m, 2H), 7.57-7.47 (m, 6H), 7.46-7.38 (m, 1H), 3.96 (dd, 1H), 3.76 (dd, 1H), 3.08 (d, 1H), 2.64 (d, 1H), 2.16 (s, 3H), 1.56 (s, 3H), 1.21 (s, 9H).

Example 204A (+/−)-tert-Butyl 4-{[(6-bromo-3-methyl-2-phenylquinolin-4-yl)carbonyl]amino}-3-(2-methoxyphenyl)-3-methylbutanoate (Racemate)

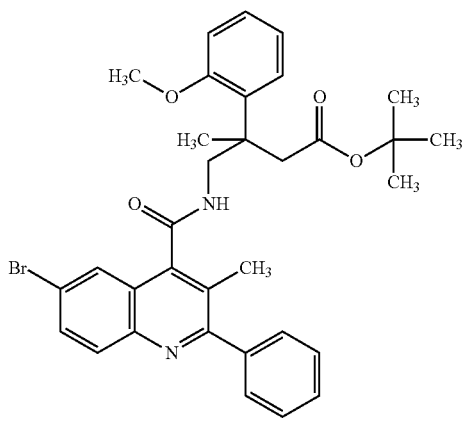 [SMILES: COc1ccccc1C(C)(CNC(=O)c1c(C)c(-c2ccccc2)nc2ccc(Br)cc12)CC(=O)OC(C)(C)C]

HATU (6.26 g, 16.5 mmol) and DIPEA (5.7 ml, 33 mmol) were added to a mixture of 6-bromo-3-methyl-2-phenylquinoline-4-carboxylic acid (3.76 g, 11.0 mmol, preparable according to WO 2016 146602 A1, p. 51, Example 3A) in DMF (45 ml), and the mixture was stirred at RT for 30 min. (+/−)-tert-Butyl 4-amino-3-(2-methoxyphenyl)-3-methylbutanoate (5.00 g, 92% purity, 16.5 mmol, Example 110A) dissolved in DMF (20 ml) was then added, and the mixture was stirred at 60° C. overnight. After cooling to RT, ethyl acetate and water (50 ml of each) were added to the mixture, which was agitated. The aqueous phase was extracted twice with ethyl acetate (50 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 93:7→6:4, Isolera One). This gave 6.00 g (98% purity, 89% of theory) of the title compound.

LC-MS (Method 7): $R_t$=1.70 min; MS (ESIpos): m/z=603/605 (M+H)$^+$ $^1$H-NMR (400 MHz, DMSO-d6) δ [ppm]: −0.008 (0.52), 0.008 (0.45), 1.095 (16.00), 1.398 (6.40), 1.553 (2.19), 2.433 (0.64), 2.466 (0.72), 3.181 (0.56), 3.214 (0.53), 3.309 (5.17), 6.889 (0.46), 6.986 (0.41), 7.006 (0.48), 7.188 (0.55), 7.208 (0.67), 7.495 (0.76), 7.503 (0.70), 7.514 (1.98), 7.518 (1.79), 7.527 (1.04), 7.848 (0.57), 7.853 (0.55), 7.921 (1.07), 7.944 (0.68).

$^1$H-NMR (400 MHz, DMSO-d6): δ [ppm]=8.54 (t, 1H), 7.93 (d, 1H), 7.84 (dd, 1H), 7.70 (br. s, 1H), 7.56-7.44 (m, 5H), 7.27-7.14 (m, 2H), 7.00 (d, 1H), 6.89 (t, 1H), 4.18 (dd, 1H), 3.68 (dd, 1H), 3.20 (d, 1H), 2.45 (d, 1H), 2.10 (br. s, 3H), 1.55 (s, 3H), 1.09 (s, 9H).

Separation of the Enantiomers:

The title compound (2.0 g) was dissolved in a mixture (100 ml) of methanol and acetonitrile and separated into the enantiomers by preparative SFC on a chiral phase (see Examples 205A and 206A) [column: Daicel Chiralpak AD-H, 5 μm, 250 mm×30 mm; flow rate: 150 ml/min; detection: 210 nm; temperature: 38° C.; injection: 0.4 ml; mobile phase: 75% carbon dioxide/25% ethanol, isocratic, run time 6.5 min]:

Example 205A (+)-tert-Butyl 4-{[(6-bromo-3-methyl-2-phenylquinolin-4-yl)carbonyl]amino}-3-(2-methoxyphenyl)-3-methylbutanoate (Enantiomer 1)

In the enantiomer separation described in Example 204A, 723 mg (98% purity, ee 94%) of the title compound were obtained as the enantiomer that eluted earlier.

$[α]_D^{20}$=+16.2°, 589 nm, c=0.50 g/100 ml, methanol

LC-MS (Method 1): $R_t$=2.60 min; MS (ESIpos): m/z=603/605 [M+H]$^+$ $^1$H-NMR (600 MHz, DMSO-d6) δ [ppm]: 1.091 (16.00), 1.555 (2.18), 2.434 (0.67), 2.456 (0.71), 3.193 (0.51), 3.215 (0.49), 3.858 (3.12), 7.191 (0.53), 7.202 (0.46), 7.204 (0.48), 7.498 (0.54), 7.502 (0.74), 7.515 (1.28), 7.525 (1.65), 7.848 (0.47), 7.851 (0.46), 7.928 (0.94), 7.942 (0.69).

$^1$H-NMR (600 MHz, DMSO-d6): δ [ppm]=8.56 (t, 1H), 7.93 (d, 1H), 7.84 (dd, 1H), 7.68 (br. s, 1H), 7.57-7.43 (m, 5H), 7.28-7.16 (m, 2H), 7.00 (d, 1H), 6.89 (t, 1H), 4.19 (dd, 1H), 3.67 (dd, 1H), 3.20 (d, 1H), 2.45 (d, 1H), 2.09 (br. s, 3H), 1.56 (s, 3H), 1.09 (s, 9H).

Example 206A (−)-tert-Butyl 4-{[(6-bromo-3-methyl-2-phenylquinolin-4-yl)carbonyl]amino}-3-(2-methoxyphenyl)-3-methylbutanoate (Enantiomer 2)

In the enantiomer separation described in Example 204A, 718 mg (98% purity, ee 100%) of the title compound were obtained as the enantiomer that eluted later.

$[\alpha]_D^{20}$=−19.2°, 589 nm, c=0.25 g/100 ml, methanol

LC-MS (Method 1): $R_t$=2.60 min; MS (ESIpos): m/z=603/605 [M+H]$^+$ $^1$H-NMR (600 MHz, DMSO-d6) δ [ppm]: 1.091 (16.00), 1.556 (2.09), 2.435 (0.66), 2.456 (0.70), 3.193 (0.49), 3.215 (0.48), 3.350 (1.37), 7.189 (0.45), 7.191 (0.51), 7.202 (0.44), 7.204 (0.47), 7.497 (0.53), 7.501 (0.72), 7.514 (1.23), 7.525 (1.56), 7.847 (0.46), 7.851 (0.44), 7.927 (0.96), 7.942 (0.69).

$^1$H-NMR (600 MHz, DMSO-d6): δ [ppm]=8.56 (t, 1H), 7.93 (d, 1H), 7.84 (dd, 1H), 7.67 (br. s, 1H), 7.56-7.43 (m, 5H), 7.28-7.15 (m, 2H), 7.00 (d, 1H), 6.89 (t, 1H), 4.19 (dd, 1H), 3.67 (dd, 1H), 3.20 (d, 1H), 2.45 (d, 1H), 2.13 (br. s, 1H), 1.56 (s, 3H), 1.09 (s, 9H).

Example 207A (+/−)-tert-Butyl 4-{[(6-bromo-3-methyl-2-phenylquinolin-4-yl)carbonyl]amino}-3-(5-fluoro-2-methoxyphenyl)butanoate (Racemate)

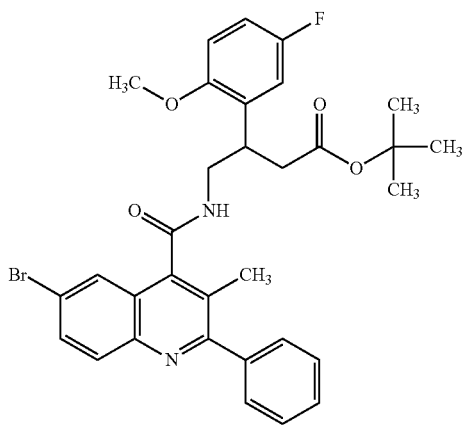 [SMILES: COc1ccc(F)cc1C(CNC(=O)c1c(C)c(-c2ccccc2)nc2ccc(Br)cc12)CC(=O)OC(C)(C)C]

HATU (143 mg, 375 µmol) and DIPEA (130 µl, 750 µmol) were added to a mixture of 6-bromo-3-methyl-2-phenylquinoline-4-carboxylic acid (86 mg, 250 µmol, preparable according to WO 2016 146602 A1, p. 51, Example 3A) in DMF (2 ml), and the mixture was stirred at RT for 30 min. (+/−)-tert-Butyl 4-amino-3-(5-fluoro-2-methoxyphenyl)butanoate hydrochloride (120 mg, 375 µmol, Example 111A) dissolved in DMF (1 ml) was then added, and the mixture was stirred at 60° C. overnight. After cooling to RT, ethyl acetate and water (50 ml of each) were added to the mixture, which was agitated. The aqueous phase was extracted twice with ethyl acetate (50 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 93:7→6:4, Isolera One). This gave 100 mg (98% purity, 64% of theory) of the title compound.

LC-MS (Method 1): $R_t$=2.49 min; MS (ESIpos): m/z=607/609 [M+H]$^+$ $^1$H-NMR (400 MHz, DMSO-d6) δ [ppm]: 1.235 (0.42), 1.266 (16.00), 2.145 (1.72), 2.621 (0.48), 2.641 (0.86), 2.654 (0.51), 3.741 (0.60), 3.753 (0.58), 3.779 (4.38), 6.990 (0.70), 7.003 (0.83), 7.084 (0.46), 7.091 (0.40), 7.108 (0.45), 7.503 (1.00), 7.510 (0.84), 7.522 (2.12), 7.529 (2.02), 7.837 (0.43), 7.859 (0.65), 7.864 (0.61), 7.933 (1.19), 7.956 (0.75), 8.783 (0.51).

Separation of the Enantiomers:

The title compound (440 mg, from a repeat experiment carried out analogously) was dissolved in a mixture of acetonitrile (2 ml) and isopropanol (2 ml) and separated into the enantiomers by preparative HPLC on a chiral phase (see Examples 208A and 209A) [column: Daicel Chiralpak ID, 5 µm 250 mm×20 mm; flow rate: 20 ml/min; detection: 220 nm; temperature: 23° C.; injection: 0.1 ml; mobile phase: 80% heptane/20% ethanol; isocratic].

Example 208A (−)-tert-Butyl 4-{[(6-bromo-3-methyl-2-phenylquinolin-4-yl)carbonyl]amino}-3-(5-fluoro-2-methoxyphenyl)butanoate (Enantiomer 1)

In the enantiomer separation described in Example 207A, 181 mg (98% purity, ee 98%) of the title compound were obtained as the enantiomer that eluted earlier.

$[\alpha]_D^{20}$=−6.4°, 589 nm, c=0.37 g/100 ml, chloroform

LC-MS (Method 1): $R_t$=2.49 min; MS (ESIpos): m/z=607/609 [M+H]$^+$ $^1$H-NMR (600 MHz, DMSO-d6) δ [ppm]: 1.265 (16.00), 2.146 (0.51), 2.688 (0.46), 6.992 (0.51), 7.000 (0.48), 7.506 (0.56), 7.511 (0.60), 7.521 (0.43), 7.524 (1.24), 7.534 (1.92), 7.537 (1.48), 7.862 (0.48), 7.865 (0.45), 7.940 (0.98), 7.955 (0.72), 8.804 (0.41).

$^1$H-NMR (600 MHz, DMSO-d6): δ [ppm]=8.80 (t, 1H), 7.95 (d, 1H), 7.86 (dd, 1H), 7.66 (br. s, 1H), 7.57-7.46 (m, 5H), 7.11 (dd, 1H), 7.03 (td, 1H), 6.99 (dd, 1H), 3.79-3.70 (m, 2H), 3.78 (s, 3H), 3.68-3.62 (m, 1H), 2.69-2.60 (m, 2H), 2.15 (br. s, 3H), 1.27 (s, 9H).

Example 209A (+)-tert-Butyl 4-{[(6-bromo-3-methyl-2-phenylquinolin-4-yl)carbonyl]amino}-3-(5-fluoro-2-methoxyphenyl)butanoate (Enantiomer 2)

In the enantiomer separation described in Example 207A, 175 mg (98% purity, ee 99%) of the title compound were obtained as the enantiomer that eluted later.

$[\alpha]_D^{20}$=+2.9°, 589 nm, c=0.38 g/100 ml, chloroform

LC-MS (Method 1): $R_t$=2.49 min; MS (ESIpos): m/z=607/609 [M+H]$^+$ $^1$H-NMR (600 MHz, DMSO-d6) δ [ppm]: 1.266 (16.00), 2.146 (0.52), 6.992 (0.51), 7.000 (0.48), 7.506 (0.55), 7.511 (0.60), 7.521 (0.40), 7.524 (1.24), 7.534 (1.92), 7.537 (1.52), 7.862 (0.48), 7.865 (0.46), 7.940 (0.97), 7.955 (0.71), 8.805 (0.42).

$^1$H-NMR (600 MHz, DMSO-d6): δ [ppm]=8.80 (t, 1H), 7.95 (d, 1H), 7.86 (dd, 1H), 7.66 (br. s, 1H), 7.56-7.47 (m, 5H), 7.11 (dd, 1H), 7.03 (td, 1H), 6.99 (dd, 1H), 3.78 (s, 3H), 3.77-3.70 (m, 2H), 3.68-3.63 (m, 1H), 2.69-2.59 (m, 2H), 2.15 (br. s, 3H), 1.27 (s, 9H).

Example 210A (+/−)-tert-Butyl 4-{[(6-bromo-3-methyl-2-phenylquinolin-4-yl)carbonyl]amino}-3-(2-fluoro-6-methoxyphenyl)butanoate (Racemate)

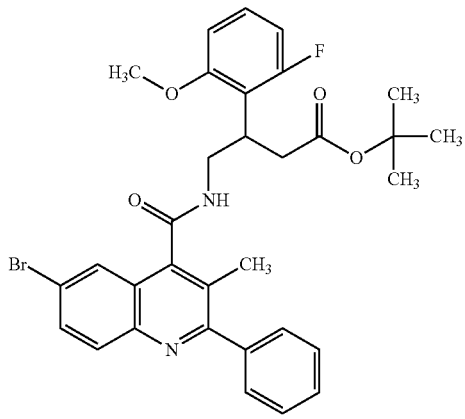 [SMILES: COc1cccc(F)c1C(CNC(=O)c1c(C)c(-c2ccccc2)nc2ccc(Br)cc12)CC(=O)OC(C)(C)C]

HATU (778 mg, 2.04 mmol) and DIPEA (710 μl, 4.1 mmol) were added to a mixture of 6-bromo-3-methyl-2-phenylquinoline-4-carboxylic acid (583 mg, 1.70 mmol, preparable according to WO 2016 146602 A1, p. 51, Example 3A) in DMF (6 ml), and the mixture was stirred at RT for 15 min. (+/−)-tert-Butyl 4-amino-3-(2-fluoro-6-methoxyphenyl)butanoate (587 mg, 82% purity, 1.70 mmol, Example 112A) dissolved in DMF (5 ml) was then added, and the mixture was stirred at 60° C. for 5 h and then at RT overnight. Subsequently, ethyl acetate and water (100 ml of each) were added to the mixture, which was agitated. The aqueous phase was extracted once with ethyl acetate (80 ml). The combined organic phases were washed with saturated aqueous sodium chloride solution (100 ml), dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 93:7→7:3, Isolera One). This gave 441 mg (100% purity, 43% of theory) of the title compound.

LC-MS (Method 1): $R_t$=2.49 min; MS (ESIpos): m/z=607/609 [M+H]$^+$ $^1$H-NMR (400 MHz, DMSO-d6) δ [ppm]: 1.175 (0.67), 1.192 (0.45), 1.225 (16.00), 1.248 (0.75), 1.988 (1.21), 2.169 (0.92), 2.683 (0.52), 2.697 (0.66), 3.815 (4.33), 6.761 (0.45), 6.835 (0.52), 6.855 (0.58), 7.503 (0.81), 7.510 (0.71), 7.522 (1.95), 7.527 (1.89), 7.535 (1.21), 7.840 (0.42), 7.863 (0.64), 7.868 (0.60), 7.933 (1.20), 7.955 (0.74), 8.860 (0.46).

1H-NMR (400 MHz, DMSO-d6): δ [ppm]=8.86 (t, 1H), 7.94 (d, 1H), 7.86 (dd, 1H), 7.72 (br. s, 1H), 7.56-7.47 (m, 5H), 7.29-7.16 (m, 1H), 6.85 (d, 1H), 6.76 (t, 1H), 3.99-3.88 (m, 1H), 3.82 (s, 3H), 3.84-3.64 (m, 2H), 2.76-2.62 (m, 2H), 2.17 (br. s, 3H), 1.23 (s, 9H).

Separation of the Enantiomers:

The title compound (437 mg) was dissolved in methanol (35 ml) and separated into the enantiomers by preparative SFC on a chiral phase (see Examples 211A and 212A) [column: Daicel Chiralpak AD SFC, 250 mm×20 mm; flow rate: 80 ml/min; detection: 210 nm; temperature: 40° C.; injection: 0.3 ml; mobile phase: 80% carbon dioxide/20% ethanol; isocratic, run time 8.0 min]:

Example 211A (+)-tert-Butyl 4-{[(6-bromo-3-methyl-2-phenylquinolin-4-yl)carbonyl]amino}-3-(2-fluoro-6-methoxyphenyl)butanoate (Enantiomer 1)

In the enantiomer separation described in Example 210A, 203 mg (100% purity, ee 100%) of the title compound were obtained as the enantiomer that eluted earlier.

$[α]_D^{20}$=+12.9°, 589 nm, c=0.39 g/100 ml, chloroform

LC-MS (Method 2): $R_t$=1.31 min; MS (ESIpos): m/z=607/609 [M+H]$^+$ $^1$H-NMR (400 MHz, DMSO-d6) δ [ppm]: 1.225 (16.00), 2.170 (1.08), 2.684 (0.57), 2.698 (0.77), 2.719 (0.41), 3.815 (4.50), 6.762 (0.50), 6.834 (0.57), 6.855 (0.63), 7.503 (0.85), 7.510 (0.73), 7.522 (2.02), 7.528 (1.96), 7.862 (0.62), 7.867 (0.60), 7.933 (1.11), 7.955 (0.69), 8.861 (0.53).

1H-NMR (400 MHz, DMSO-d6): δ [ppm]=8.86 (t, 1H), 7.94 (d, 1H), 7.86 (dd, 1H), 7.72 (br. s, 1H), 7.57-7.46 (m, 5H), 7.24 (dd, 1H), 6.85 (d, 1H), 6.76 (t, 1H), 4.01-3.87 (m, 1H), 3.82 (s, 3H), 3.83-3.65 (m, 2H), 2.77-2.61 (m, 2H), 2.17 (br. s, 3H), 1.23 (s, 9H).

Example 212A (−)-tert-Butyl 4-{[(6-bromo-3-methyl-2-phenylquinolin-4-yl)carbonyl]amino}-3-(2-fluoro-6-methoxyphenyl)butanoate (Enantiomer 2)

In the enantiomer separation described in Example 210A, 185 mg (99% purity, ee 96%) of the title compound were obtained as the enantiomer that eluted later.

$[α]_D^{20}$=−14.2°, 589 nm, c=0.44 g/100 ml, chloroform

LC-MS (Method 2): $R_t$=1.31 min; MS (ESIpos): m/z=607/609 [M+H]$^+$ $^1$H-NMR (400 MHz, DMSO-d6) δ [ppm]: 1.225 (16.00), 1.249 (0.71), 2.170 (1.46), 2.684 (0.70), 2.698 (0.99), 2.720 (0.52), 3.314 (6.09), 3.719 (0.48), 3.796 (0.41), 6.762 (0.63), 6.785 (0.40), 6.834 (0.65), 6.855 (0.72), 7.226 (0.42), 7.503 (1.06), 7.508 (0.96), 7.527 (2.63), 7.843 (0.46), 7.866 (0.74), 7.933 (1.12), 7.955 (0.70), 8.861 (0.66).

$^1$H-NMR (400 MHz, DMSO-d6): δ [ppm]=8.86 (t, 1H), 7.94 (d, 1H), 7.86 (d, 1H), 7.72 (br. s, 1H), 7.56-7.47 (m, 5H), 7.24 (dd, 1H), 6.85 (d, 1H), 6.76 (t, 1H), 4.01-3.88 (m, 1H), 3.82 (s, 3H), 3.85-3.65 (m, 2H), 2.78-2.62 (m, 2H), 2.17 (br. s, 3H), 1.23 (s, 9H).

Example 213A (+/−)-tert-Butyl 4-{[(6-bromo-3-methyl-2-phenylquinolin-4-yl)carbonyl]amino}-3-(2-ethoxyphenyl)butanoate (Racemate)

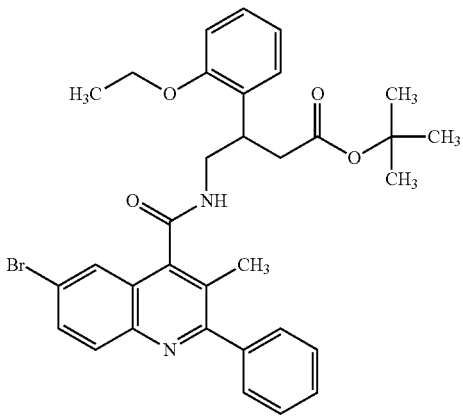 [SMILES: CCOc1ccccc1C(CNC(=O)c1c(C)c(-c2ccccc2)nc2ccc(Br)cc12)CC(=O)OC(C)(C)C]

HATU (457 mg, 1.20 mmol) and DIPEA (420 μl, 2.4 mmol) were added to a mixture of 6-bromo-3-methyl-2-phenylquinoline-4-carboxylic acid (274 mg, 802 μmol, preparable according to WO 2016 146602 A1, p. 51, Example 3A) in DMF (3 ml), and the mixture was stirred at RT for 15 min. (+/−)-tert-Butyl 4-amino-3-(2-ethoxyphenyl)butanoate hydrochloride (400 mg, 95% purity, 1.20 mmol, Example 113A) dissolved in DMF (2 ml) was then added, and the mixture was stirred at 60° C. overnight. Subsequently, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15, Isolera One). This gave 265 mg (98% purity, 54% of theory) of the title compound.

LC-MS (Method 1): $R_t$=2.62 min; MS (ESIpos): m/z=603/605 [M+H]$^+$ $^1$H-NMR (400 MHz, DMSO-d6) δ [ppm]: 1.245 (16.00), 1.356 (1.23), 1.373 (2.56), 1.391 (1.23), 2.151 (1.35), 2.661 (0.70), 2.675 (0.57), 2.682 (0.48), 3.660 (0.41), 4.040 (0.88), 4.058 (0.84), 6.884 (0.57), 6.954 (0.52), 6.974 (0.58), 7.193 (1.00), 7.212 (0.79), 7.502 (0.86), 7.509 (0.79), 7.521 (1.77), 7.527 (1.71), 7.530 (1.45), 7.534 (1.09), 7.538 (0.84), 7.836 (0.41), 7.858 (0.62), 7.864 (0.56), 7.932 (1.09), 7.955 (0.69).

$^1$H-NMR (400 MHz, DMSO-d6): δ [ppm]=8.76 (t, 1H), 7.94 (d, 1H), 7.85 (dd, 1H), 7.72 (br. s, 1H), 7.56-7.45 (m, 5H), 7.23-7.14 (m, 2H), 6.96 (d, 1H), 6.88 (td, 1H), 4.05 (q, 2H), 3.87-3.75 (m, 1H), 3.73-3.58 (m, 2H), 2.71-2.63 (m, 2H), 2.15 (br. s, 3H), 1.37 (t, 3H), 1.25 (s, 9H).

Separation of the Enantiomers:

The title compound (240 mg) was dissolved in methanol (20 ml) and separated into the enantiomers by preparative SFC on a chiral phase (see Examples 214A and 215A) [column: Daicel Chiralcel OJ-H, 250 mm×20 mm; flow rate: 80 ml/min; detection: 210 nm; temperature: 40° C.; injection: 0.5 ml; mobile phase: 83% carbon dioxide/17% ethanol; isocratic, run time 8.0 min].

Example 214A (−)-tert-Butyl 4-{[(6-bromo-3-methyl-2-phenylquinolin-4-yl)carbonyl]amino}-3-(2-ethoxyphenyl)butanoate (Enantiomer 1)

In the enantiomer separation described in Example 213A, 79 mg (98% purity, ee 100%) of the title compound were obtained as the enantiomer that eluted earlier.

$[α]_D^{20}$=−17.1°, 589 nm, c=0.35 g/100 ml, methanol

LC-MS (Method 2): $R_t$=1.39 min; MS (ESIpos): m/z=603/605 [M+H]$^+$ $^1$H-NMR (400 MHz, DMSO-d6) δ [ppm]: 1.245 (16.00), 1.356 (1.21), 1.373 (2.58), 1.391 (1.25), 2.151 (1.59), 2.661 (0.78), 2.676 (0.65), 3.660 (0.47), 4.040 (0.94), 4.057 (0.93), 6.885 (0.65), 6.954 (0.58), 6.974 (0.67), 7.193 (1.06), 7.212 (0.83), 7.502 (0.89), 7.508 (0.75), 7.521 (1.93), 7.527 (1.92), 7.836 (0.43), 7.858 (0.64), 7.863 (0.61), 7.932 (1.18), 7.955 (0.75), 8.764 (0.43).

$^1$H-NMR (400 MHz, DMSO-d6): δ [ppm]=8.77 (t, 1H), 7.94 (d, 1H), 7.85 (dd, 1H), 7.72 (br. s, 1H), 7.57-7.45 (m, 5H), 7.23-7.14 (m, 2H), 6.96 (d, 1H), 6.89 (t, 1H), 4.05 (q, 2H), 3.88-3.77 (m, 1H), 3.74-3.58 (m, 2H), 2.73-2.60 (m, 2H), 2.15 (br. s, 3H), 1.37 (t, 3H), 1.25 (s, 9H).

Example 215A (+)-tert-Butyl 4-{[(6-bromo-3-methyl-2-phenylquinolin-4-yl)carbonyl]amino}-3-(2-ethoxyphenyl)butanoate (Enantiomer 2)

In the enantiomer separation described in Example 213A, 72 mg (98% purity, ee 98%) of the title compound were obtained as the enantiomer that eluted later.

$[α]_D^{20}$=+10.9°, 589 nm, c=0.34 g/100 ml, methanol

LC-MS (Method 2): $R_t$=1.39 min; MS (ESIpos): m/z=603/605 [M+H]$^+$ $^1$H-NMR (400 MHz, DMSO-d6) δ [ppm]: 1.245 (16.00), 1.356 (1.23), 1.374 (2.59), 1.391 (1.26), 2.151 (1.65), 2.661 (0.83), 2.676 (0.69), 3.661 (0.50), 4.040 (0.98), 4.058 (0.96), 6.885 (0.67), 6.954 (0.60), 6.974 (0.70), 7.193 (1.11), 7.212 (0.86), 7.502 (0.92), 7.509 (0.79), 7.521 (2.00), 7.528 (1.96), 7.836 (0.42), 7.858 (0.64), 7.863 (0.60), 7.932 (1.11), 7.955 (0.71), 8.764 (0.46).

$^1$H-NMR (400 MHz, DMSO-d6): δ [ppm]=8.76 (t, 1H), 7.94 (d, 1H), 7.85 (dd, 1H), 7.72 (br. s, 1H), 7.58-7.46 (m, 5H), 7.27-7.12 (m, 2H), 6.96 (d, 1H), 6.89 (t, 1H), 4.05 (q, 2H), 3.88-3.75 (m, 1H), 3.71-3.59 (m, 2H), 2.72-2.62 (m, 2H), 2.15 (br. s, 3H), 1.37 (t, 3H), 1.25 (s, 9H).

185

Example 216A (+/−)-tert-Butyl 4-{[(6-bromo-3-methyl-2-phenylquinolin-4-yl)carbonyl]amino}-3-(5-fluoro-2-methoxyphenyl)-3-methylbutanoate (Racemate)

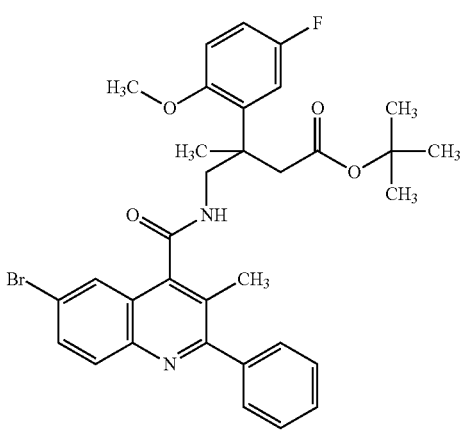 [SMILES: COc1ccc(F)cc1C(C)(CNC(=O)c1c(C)c(-c2ccccc2)nc2ccc(Br)cc12)CC(=O)OC(C)(C)C]

HATU (1.35 g, 3.56 mmol) and DIPEA (1.2 ml, 7.1 mmol) were added to a mixture of 6-bromo-3-methyl-2-phenylquinoline-4-carboxylic acid (812 mg, 2.37 mmol, preparable according to WO 2016 146602 A1, p. 51, Example 3A) in DMF (8 ml), and the mixture was stirred at RT for 15 min. (+/−)-tert-Butyl 4-amino-3-(5-fluoro-2-methoxyphenyl)-3-methylbutanoate hydrochloride (1.25 g, 95% purity, 3.56 mmol, Example 114A) dissolved in DMF (5 ml) was then added, and the mixture was stirred at 60º overnight. Subsequently, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15, Isolera One). This gave 930 mg (98% purity, 62% of theory) of the title compound.

LC-MS (Method 1): $R_t$=2.57 min; MS (ESIpos): m/z=621/623 [M+H]$^+$ $^1$H-NMR (600 MHz, DMSO-d6) δ [ppm]: 1.131 (16.00), 1.526 (2.14), 2.441 (0.62), 2.463 (0.66), 3.336 (6.15), 7.503 (0.52), 7.506 (0.69), 7.520 (1.18), 7.530 (1.38), 7.933 (0.73), 7.948 (0.54).

$^1$H-NMR (600 MHz, DMSO-d6): δ [ppm]=8.59 (t, 1H), 7.94 (d, 1H), 7.85 (dd, 1H), 7.69 (br. s, 1H), 7.56-7.47 (m, 5H), 7.09-6.99 (m, 2H), 6.97 (dd, 1H), 4.24 (br. s, 1H), 3.85 (s, 3H), 3.61 (br. d, 1H), 3.21 (d, 1H), 2.45 (d, 1H), 2.11 (br. s, 3H), 1.53 (s, 3H), 1.13 (s, 9H).

Separation of the Enantiomers:

The title compound (775 mg) was dissolved in isopropanol (30 ml), filtered and separated into the enantiomers by preparative SFC on a chiral phase (see Examples 217A and 218A) [column: Daicel Chiralpak AD, 360 mm×50 mm; flow rate: 400 ml/min; detection: 210 nm; temperature: 40° C.; injection: 2.0 ml; mobile phase: 75% carbon dioxide/

186

25% ethanol; isocratic, run time 9.0 min]: The combined target fractions were concentrated.

Example 217A (+)-tert-Butyl 4-{[(6-bromo-3-methyl-2-phenylquinolin-4-yl)carbonyl]amino}-3-(5-fluoro-2-methoxyphenyl)-3-methylbutanoate (Enantiomer 1)

In the enantiomer separation described in Example 216A, 377 mg ("98% purity", contains isopropanol, ee 96%) of the title compound were obtained as the enantiomer that eluted earlier.

$[\alpha]_D^{20}$=+11.9°, 589 nm, c=0.35 g/100 ml, methanol

LC-MS (Method 1): $R_t$=2.56 min; MS (ESIpos): m/z=621/623 [M+H]$^+$ $^1$H-NMR (400 MHz, DMSO-d6) δ [ppm]: 1.030 (5.33), 1.045 (5.34), 1.135 (16.00), 1.526 (2.20), 2.440 (0.63), 2.474 (0.74), 3.187 (0.48), 3.221 (0.45), 3.311 (4.42), 4.323 (0.65), 4.333 (0.62), 6.983 (0.48), 7.500 (0.81), 7.508 (0.72), 7.519 (1.81), 7.525 (1.58), 7.852 (0.52), 7.857 (0.51), 7.928 (1.03), 7.950 (0.65).

$^1$H-NMR (400 MHz, DMSO-d6): δ [ppm]=8.57 (t, 1H), 7.94 (d, 1H), 7.85 (dd, 1H), 7.68 (br. s, 1H), 7.56-7.46 (m, 5H), 7.10-6.99 (m, 2H), 6.97 (dd, 1H), 4.23 (dd, 1H), 3.85 (s, 3H), 3.62 (dd, 1H), 3.20 (d, 1H), 2.46 (d, 1H), 2.10 (br. s, 3H), 1.53 (s, 3H), 1.13 (s, 9H).

Example 218A (−)-tert-Butyl 4-{[(6-bromo-3-methyl-2-phenylquinolin-4-yl)carbonyl]amino}-3-(5-fluoro-2-methoxyphenyl)-3-methylbutanoate (Enantiomer 2)

In the enantiomer separation described in Example 216A, 295 mg ("98% purity", contains isopropanol, ee 99%) of the title compound were obtained as the enantiomer that eluted later.

$[\alpha]_D^{20}$=−11.5°, 589 nm, c=0.36 g/100 ml, methanol

LC-MS (Method 1): $R_t$=2.56 min; MS (ESIpos): m/z=621/623 [M+H]$^+$ $^1$H-NMR (400 MHz, DMSO-d6) δ [ppm]: 1.030 (4.50), 1.045 (4.53), 1.134 (16.00), 1.526 (2.35), 2.440 (0.64), 2.474 (0.74), 3.187 (0.51), 3.221 (0.47), 3.853 (4.12), 4.323 (0.65), 4.333 (0.62), 6.955 (0.42), 6.982 (0.50), 7.500 (0.85), 7.508 (0.76), 7.519 (1.92), 7.525 (1.68), 7.852 (0.53), 7.857 (0.52), 7.927 (1.00), 7.950 (0.64).

$^1$H-NMR (400 MHz, DMSO-d6): δ [ppm]=8.57 (t, 1H), 7.94 (d, 1H), 7.85 (dd, 1H), 7.68 (br. s, 1H), 7.56-7.46 (m, 5H), 7.10-6.99 (m, 2H), 6.96 (dd, 1H), 4.23 (dd, 1H), 3.85 (s, 3H), 3.62 (dd, 1H), 3.20 (d, 1H), 2.46 (d, 1H), 2.10 (br. s, 3H), 1.53 (s, 3H), 1.13 (s, 9H).

Example 219A (+/−)-tert-Butyl 4-{[(6-bromo-3-methyl-2-phenylquinolin-4-yl)carbonyl]amino}-3-(3,5-difluoro-2-methoxyphenyl)-3-methylbutanoate (Racemate)

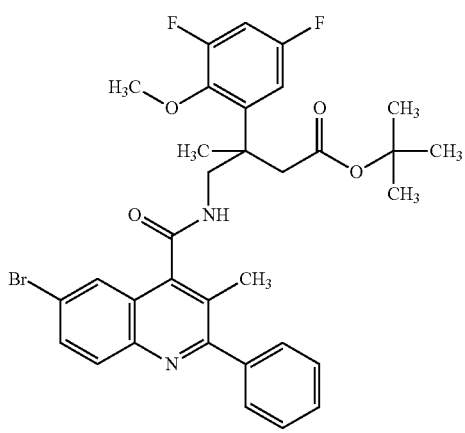 [SMILES: COc1c(F)cc(F)cc1C(C)(CNC(=O)c1c(C)c(-c2ccccc2)nc2ccc(Br)cc12)CC(=O)OC(C)(C)C]

HATU (1.37 g, 3.59 mmol) and DIPEA (1.3 ml, 7.2 mmol) were added to a mixture of 6-bromo-3-methyl-2-phenylquinoline-4-carboxylic acid (819 mg, 2.39 mmol, preparable according to WO 2016 146602 A1, p. 51, Example 3A) in DMF (8 ml), and the mixture was stirred at RT for 30 min. (+/−)-tert-Butyl 4-amino-3-(3,5-difluoro-2-methoxyphenyl)-3-methylbutanoate hydrochloride (1.33 g, 95% purity, 3.59 mmol, Example 115A) dissolved in DMF (5 ml) was then added, and the mixture was stirred at 60° C. overnight. After cooling to RT, ethyl acetate and water (20 ml of each) were added to the mixture, which was agitated. After phase separation, the aqueous phase was extracted twice with ethyl acetate (20 ml each time). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15, Isolera One). This gave 988 mg (98% purity, 63% of theory) of the title compound.

LC-MS (Method 1): $R_t$=2.64 min; MS (ESIpos): m/z=639/641 [M+H]$^+$ $^1$H-NMR (600 MHz, DMSO-d6) δ [ppm]: 1.178 (16.00), 1.520 (2.02), 2.524 (0.70), 3.985 (2.10), 3.989 (2.04), 7.496 (0.44), 7.507 (0.63), 7.511 (0.70), 7.525 (1.11), 7.536 (0.69), 7.538 (0.75), 7.542 (0.96), 7.945 (0.70), 7.960 (0.52), 8.665 (0.40).

1H-NMR (600 MHz, DMSO-d6): δ [ppm]=8.67 (t, 1H), 7.95 (d, 1H), 7.86 (d, 1H), 7.67 (br. s, 1H), 7.57-7.48 (m, 5H), 7.30-7.22 (m, 1H), 6.88 (d, 1H), 4.10 (dd, 1H), 3.99 (d, 3H), 3.64 (dd, 1H), 3.16 (d, 1H), 2.53 (obscured, 1H), 2.33-1.97 (br., 3H), 1.52 (s, 3H), 1.18 (s, 9H).

Separation of the Enantiomers:

The title compound (835 mg) was dissolved in a mixture of isopropanol (25 ml) and acetonitrile (5 ml), heated to 50° C., filtered and separated into the enantiomers by preparative SFC on a chiral phase (see Examples 220A and 221A) [column: Daicel Chiralpak IC, 250 mm×20 mm; flow rate: 100 ml/min; detection: 220 nm; temperature: 40° C.; injection: 1.0 ml; mobile phase: 70% carbon dioxide/30% ethanol; isocratic, run time 4.0 min]: The combined target fractions were concentrated and the residue was dried under reduced pressure.

Example 220A (+)-tert-Butyl 4-{[(6-bromo-3-methyl-2-phenylquinolin-4-yl)carbonyl]amino}-3-(3,5-difluoro-2-methoxyphenyl)-3-methylbutanoate (Enantiomer 1)

In the enantiomer separation described in Example 219A, 300 mg (98% purity, ee 93%) of the title compound were obtained as the enantiomer that eluted earlier.

$[α]_D^{20}$=+15.7°, 589 nm, c=0.36 g/100 ml, methanol

LC-MS (Method 1): $R_t$=2.61 min; MS (ESIpos): m/z=639/641 [M+H]$^+$ $^1$H-NMR (400 MHz, DMSO-d6) δ [ppm]: 1.181 (16.00), 1.522 (2.09), 3.140 (0.40), 3.983 (2.49), 3.988 (2.48), 7.506 (0.89), 7.512 (0.70), 7.524 (1.38), 7.537 (1.67), 7.863 (0.49), 7.868 (0.47), 7.940 (0.97), 7.962 (0.62), 8.647 (0.41).

$^1$H-NMR (400 MHz, DMSO-d6): δ [ppm]=8.65 (t, 1H), 7.95 (d, 1H), 7.86 (dd, 1H), 7.63 (br. s, 1H), 7.57-7.48 (m, 5H), 7.31-7.19 (m, 1H), 6.88 (br. d, 1H), 4.09 (dd, 1H), 3.99 (d, 3H), 3.65 (dd, 1H), 3.16 (d, 1H), 2.53 (obscured, 1H), 2.16 (br. s, 3H), 1.52 (s, 3H), 1.18 (s, 9H).

Example 221A (−)-tert-Butyl 4-{[(6-bromo-3-methyl-2-phenylquinolin-4-yl)carbonyl]amino}-3-(3,5-difluoro-2-methoxyphenyl)-3-methylbutanoate (Enantiomer 2)

In the enantiomer separation described in Example 219A, 310 mg (98% purity, ee 97%) of the title compound were obtained as the enantiomer that eluted later.

$[α]_D^{20}$=−15.6°, 589 nm, c=0.34 g/100 ml, methanol

LC-MS (Method 1): $R_t$=2.61 min; MS (ESIpos): m/z=639/641 [M+H]$^+$ $^1$H-NMR (400 MHz, DMSO-d6) δ [ppm]: 1.180 (16.00), 1.521 (2.76), 3.140 (0.52), 3.175 (0.48), 3.983 (3.03), 3.988 (2.98), 6.865 (0.41), 6.891 (0.40), 7.492 (0.44), 7.506 (1.24), 7.524 (1.86), 7.537 (2.20), 7.841 (0.42), 7.863 (0.63), 7.939 (1.04), 7.962 (0.67), 8.646 (0.56).

1H-NMR (400 MHz, DMSO-d6): δ [ppm]=8.65 (t, 1H), 7.95 (d, 1H), 7.85 (dd, 1H), 7.68 (br. s, 1H), 7.58-7.46 (m, 5H), 7.31-7.19 (m, 1H), 6.88 (d, 1H), 4.09 (dd, 1H), 3.99 (d, 3H), 3.65 (dd, 1H), 3.16 (d, 1H), 2.53 (obscured, 1H), 2.16 (br. s, 3H), 1.52 (s, 3H), 1.18 (s, 9H).

Example 222A (+/−)-tert-Butyl 4-{[(6-bromo-3-methyl-2-phenylquinolin-4-yl)carbonyl]amino}-3-(4-fluoro-2-methoxyphenyl)-3-methylbutanoate (Racemate)

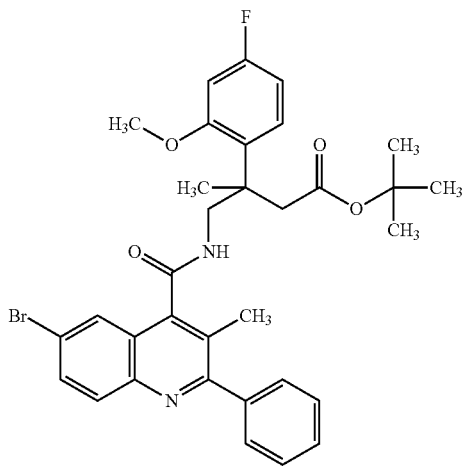 [SMILES: COc1cc(F)ccc1C(C)(CNC(=O)c1c(C)c(-c2ccccc2)nc2ccc(Br)cc12)CC(=O)OC(C)(C)C]

HATU (2.56 g, 6.74 mmol) and DIPEA (2.3 ml, 13 mmol) were added to a mixture of 6-bromo-3-methyl-2-phenylquinoline-4-carboxylic acid (1.54 g, 4.50 mmol, preparable according to WO 2016 146602 A1, p. 51, Example 3A) in DMF (15 ml), and the mixture was stirred at RT for 30 min. (+/−)-tert-Butyl 4-amino-3-(4-fluoro-2-methoxyphenyl)-3-methylbutanoate hydrochloride (2.37 g, 95% purity, 6.74 mmol, Example 116A) dissolved in DMF (9 ml) was then added, and the mixture was stirred at 60° C. overnight. After cooling to RT, ethyl acetate and water (40 ml of each) were added to the mixture, which was agitated. After phase separation, the aqueous phase was extracted twice with ethyl acetate (40 ml each time). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15, Isolera One). This gave 1.89 g (98% purity, 66% of theory) of the title compound.

LC-MS (Method 1): $R_t$=2.59 min; MS (ESIpos): m/z=621/623 [M+H]$^+$ $^1$H-NMR (600 MHz, DMSO-d6) δ [ppm]: 1.116 (16.00), 1.531 (1.67), 2.388 (0.59), 2.410 (0.60), 3.169 (0.48), 3.191 (0.48), 3.336 (6.51), 7.500 (0.53), 7.504 (0.72), 7.517 (1.18), 7.528 (1.46), 7.929 (0.79), 7.943 (0.57).

$^1$H-NMR (600 MHz, DMSO-d6): δ [ppm]=8.57 (t, 1H), 7.94 (d, 1H), 7.84 (dd, 1H), 7.67 (br. s, 1H), 7.56-7.47 (m, 5H), 7.18 (dd, 1H), 6.90 (d, 1H), 6.70 (br. t, 1H), 4.24 (dd, 1H), 3.87 (s, 3H), 3.57 (dd, 1H), 3.18 (d, 1H), 2.40 (d, 1H), 2.10 (br. s, 3H), 1.53 (s, 3H), 1.12 (s, 9H).

Separation of the Enantiomers:

The title compound (1.73 g) was dissolved in a mixture of isopropanol (95 ml) and acetonitrile (5 ml), heated to 50° C., filtered and separated into the enantiomers by preparative SFC on a chiral phase (see Examples 223A and 224A) [column: Daicel Chiralpak IC, 250 mm×20 mm; flow rate: 100 ml/min; detection: 210 nm; temperature: 40° C.; injection: 6.0 ml; mobile phase: carbon dioxide/ethanol/methanol 7:3:0→7:0:3; isocratic, run time 14.0 min]. The combined target fractions were concentrated and the residue was dried under reduced pressure.

Example 223A (+)-tert-Butyl 4-{[(6-bromo-3-methyl-2-phenylquinolin-4-yl)carbonyl]amino}-3-(4-fluoro-2-methoxyphenyl)-3-methylbutanoate (Enantiomer 1)

In the enantiomer separation described in Example 222A, 750 mg (98% purity, ee 100%) of the title compound were obtained as the enantiomer that eluted earlier.

$[\alpha]_D^{20}$=+11.1°, 589 nm, c=0.40 g/100 ml, methanol

LC-MS (Method 2): $R_t$=1.36 min; MS (ESIpos): m/z=621/623 [M+H]$^+$ $^1$H-NMR (400 MHz, DMSO-d6) δ [ppm]: 1.030 (0.95), 1.045 (0.95), 1.120 (16.00), 1.531 (2.02), 2.388 (0.61), 2.421 (0.65), 3.159 (0.56), 3.192 (0.53), 3.869 (3.82), 7.175 (0.44), 7.178 (0.42), 7.498 (0.82), 7.506 (0.74), 7.517 (1.89), 7.522 (1.69), 7.849 (0.54), 7.854 (0.51), 7.923 (1.03), 7.946 (0.64).

$^1$H-NMR (400 MHz, DMSO-d6): δ [ppm]=8.55 (t, 1H), 7.93 (d, 1H), 7.84 (dd, 1H), 7.67 (br. s, 1H), 7.55-7.47 (m, 5H), 7.18 (dd, 1H), 6.89 (dd, 1H), 6.70 (td, 1H), 4.23 (dd, 1H), 3.87 (s, 3H), 3.57 (dd, 1H), 3.18 (d, 1H), 2.41 (d, 1H), 2.11 (br. s, 3H), 1.53 (s, 3H), 1.12 (s, 9H).

Example 224A (−)-tert-Butyl 4-{[(6-bromo-3-methyl-2-phenylquinolin-4-yl)carbonyl]amino}-3-(4-fluoro-2-methoxyphenyl)-3-methylbutanoate (Enantiomer 2)

In the enantiomer separation described in Example 222A, 820 mg (98% purity, ee 99%) of the title compound were obtained as the enantiomer that eluted later.

$[\alpha]_D^{20}$=−11.5°, 589 nm, c=0.38 g/100 ml, methanol

LC-MS (Method 2): $R_t$=1.36 min; MS (ESIpos): m/z=621/623 [M+H]$^+$ $^1$H-NMR (400 MHz, DMSO-d6) δ [ppm]: 1.030 (3.00), 1.046 (3.01), 1.120 (16.00), 1.531 (1.99), 2.389 (0.60), 2.422 (0.65), 3.160 (0.56), 3.193 (0.52), 3.869 (3.80), 7.175 (0.43), 7.179 (0.42), 7.498 (0.81), 7.506 (0.71), 7.517 (1.85), 7.523 (1.67), 7.849 (0.53), 7.854 (0.51), 7.923 (1.03), 7.946 (0.65).

$^1$H-NMR (400 MHz, DMSO-d6): δ [ppm]=8.55 (t, 1H), 7.93 (d, 1H), 7.84 (dd, 1H), 7.67 (br. s, 1H), 7.56-7.46 (m, 5H), 7.18 (dd, 1H), 6.89 (dd, 1H), 6.70 (td, 1H), 4.23 (dd, 1H), 3.87 (s, 3H), 3.57 (dd, 1H), 3.18 (d, 1H), 2.41 (d, 1H), 2.11 (br. s, 3H), 1.53 (s, 3H), 1.12 (s, 9H).

Example 225A (+/−)-Ethyl 4-{[(6-bromo-3-methyl-2-phenylquinolin-4-yl)carbonyl]amino}-2,2-difluoro-3-(2-methoxyphenyl)butanoate (Racemate)

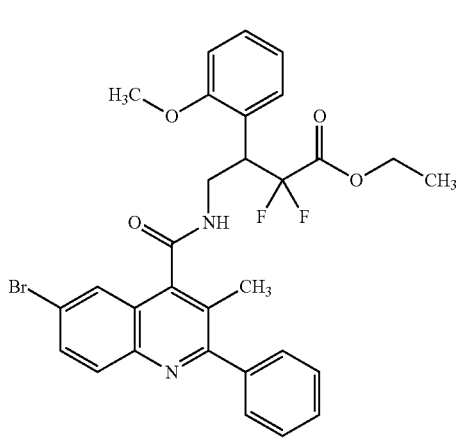 [SMILES: CCOC(=O)C(F)(F)C(CNC(=O)c1c(C)c(-c2ccccc2)nc2ccc(Br)cc12)c1ccccc1OC]

HATU (137 mg, 361 μmol) and DIPEA (120 μl, 690 μmol) were added to a mixture of 6-bromo-3-methyl-2-phenylquinoline-4-carboxylic acid (95 mg, 278 μmol, preparable according to WO 2016 146602 A1, p. 51, Example 3A) in DMF (1.5 ml), and the mixture was stirred at RT for 30 min. (+/−)-Ethyl 4-amino-2,2-difluoro-3-(2-methoxyphenyl)butanoate hydrochloride (86 mg, 278 μmol, Example 118A) was then added, and the mixture was stirred at RT overnight. The mixture was then purified by preparative HPLC (Chromatorex C18, 10 μm, 125×30 mm, acetonitrile/water gradient with 0.01% TFA). Two separate fractions were collected and concentrated and the two residues were lyophilized. One residue gave 46 mg (60% purity, 17% of theory, see analysis) of the title compound. The other residue gave, after re-purification by preparative HPLC (Chromatorex C18, 10 μm, 125×30 mm, acetonitrile/water gradient with 0.01% TFA), 8.8 mg (96% purity, 5% of theory) of the corresponding carboxylic acid (+/−)-4-{[(6-bromo-3-methyl-2-phenylquinolin-4-yl)carbonyl]amino}-2,2-difluoro-3-(2-methoxyphenyl)butanoic acid.

LC-MS (Method 7): $R_t$=1.56 min; MS (ESIpos): m/z=597/599 [M+H]$^+$

Example 226A (+/−)-tert-Butyl 4-{[(6-bromo-3-methyl-2-phenylquinolin-4-yl)carbonyl]amino}-3-(5-fluoro-6-methoxyphenyl)-3-methylbutanoate (Racemate)

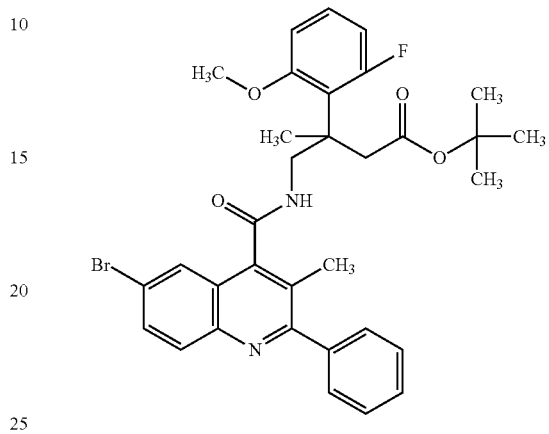

HATU (456 mg, 1.20 mmol) and DIPEA (420 μl, 2.4 mmol) were added to a mixture of 6-bromo-3-methyl-2-phenylquinoline-4-carboxylic acid (342 mg, 1.00 mmol, preparable according to WO 2016 146602 A1, p. 51, Example 3A) in DMF (4 ml), and the mixture was stirred at RT for 15 min. (+/−)-tert-Butyl 4-amino-3-(2-fluoro-6-methoxyphenyl)-3-methylbutanoate (363 mg, 82% purity, 1.00 mmol, Example 119A) dissolved in DMF (3 ml) was then added, and the mixture was stirred at 60° C. for 3 h and then at RT overnight. Subsequently, ethyl acetate and water (100 ml of each) were added to the mixture, which was agitated. After phase separation, the aqueous phase was extracted once with ethyl acetate (80 ml). The combined organic phases were washed with saturated aqueous sodium chloride solution (100 ml), dried over sodium sulfate, filtered and concentrated, and the residue was taken up in dichloromethane and purified by flash column chromatography (50 g of silica gel Biotage Snap-Cartridge KP-Sil, cyclohexane/ethyl acetate 97:3→7:3, Isolera One). The combined target fractions were concentrated and the residue was dried under reduced pressure. This gave 288 mg (84% purity, 39% of theory) of the title compound.

LC-MS (Method 1): $R_t$=2.57 min; MS (ESIpos): m/z=621/623 [M+H]$^+$ $^1$H-NMR (500 MHz, DMSO-d6): δ [ppm]=8.68 (t, 1H), 7.94 (d, 1H), 7.84 (dd, 1H), 7.66 (br. s, 1H), 7.55-7.47 (m, 5H), 7.25-7.18 (m, 1H), 6.84 (d, 1H), 6.68 (dd, 1H), 4.24 (br. dd, 1H), 3.84 (s, 3H), 3.57 (br. dd, 1H), 3.34 (d, 1H), 2.35 (d, 1H), 2.12 (br. s, 3H), 1.69 (d, 3H), 1.17 (s, 9H).

Separation of the Enantiomers:

The title compound (215 mg) was separated into the enantiomers by preparative HPLC on a chiral phase (see Examples 227A and 228A) [column: Daicel Chiralpak ID, 5 μm 250 mm×20 mm; flow rate: 15 ml/min; detection: 220 nm; temperature: 25° C.; injection: 0.15 ml; mobile phase: 50% heptane/50% ethanol; run time 10 min, isocratic].

Example 227A (−)-tert-Butyl 4-{[(6-bromo-3-methyl-2-phenylquinolin-4-yl)carbonyl]amino}-3-(2-fluoro-6-methoxyphenyl)-3-methylbutanoate (Enantiomer 1)

In the enantiomer separation described in Example 226A, 76 mg (87% purity, ee 97%) of the title compound were obtained as the enantiomer that eluted earlier.

$[\alpha]_D^{20}$=−8.0°, 436 nm, c=0.34 g/100 ml, chloroform

LC-MS (Method 1): $R_t$=2.57 min; MS (ESIpos): m/z=621/623 $[M+H]^+$ $^1$H-NMR (400 MHz, DMSO-d6): δ [ppm]=8.67 (t, 1H), 7.94 (d, 1H), 7.84 (dd, 1H), 7.64 (br. s, 1H), 7.55-7.47 (m, 5H), 7.26-7.17 (m, 1H), 6.84 (d, 1H), 6.68 (dd, 1H), 4.24 (br. dd, 1H), 3.84 (s, 3H), 3.57 (br. dd, 1H), 3.34 (d, 1H, partially obscured), 2.35 (d, 1H), 2.11 (br. s, 3H), 1.69 (d, 3H), 1.17 (s, 9H).

Example 228A (+)-tert-Butyl 4-{[(6-bromo-3-methyl-2-phenylquinolin-4-yl)carbonyl]amino}-3-(2-fluoro-6-methoxyphenyl)-3-methylbutanoate (Enantiomer 2)

In the enantiomer separation described in Example 226A, 61 mg (100% purity, ee 94%) of the title compound were obtained as the enantiomer that eluted later.

$[\alpha]_D^{20}$=+3.7°, 436 nm, c=0.31 g/100 ml, chloroform

LC-MS (Method 1): $R_t$=2.57 min; MS (ESIpos): m/z=621/623 $[M+H]^+$ $^1$H-NMR (400 MHz, DMSO-d6): δ [ppm]=8.68 (t, 1H), 7.94 (d, 1H), 7.85 (dd, 1H), 7.64 (br. s, 1H), 7.56-7.46 (m, 5H), 7.26-7.17 (m, 1H), 6.84 (d, 1H), 6.68 (dd, 1H), 4.24 (dd, 1H), 3.84 (s, 3H), 3.57 (dd, 1H), 3.34 (d, 1H, partially obscured), 2.35 (d, 1H), 2.11 (br. s, 3H), 1.69 (d, 3H), 1.17 (s, 9H).

Example 229A tert-Butyl 4-{[(6-bromo-3-methyl-2-phenylquinolin-4-yl)carbonyl]amino}-3-(2-chlorophenyl)pentanoate (Diastereomer Mixture)

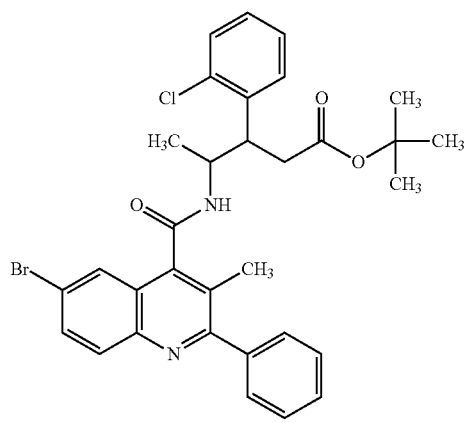 [SMILES: Cc1c(-c2ccccc2)nc2ccc(Br)cc2c1C(=O)NC(C)C(CC(=O)OC(C)(C)C)c1ccccc1Cl]

HATU (552 mg, 1.45 mmol) and DIPEA (510 μl, 2.9 mmol) were added to a mixture of 6-bromo-3-methyl-2-phenylquinoline-4-carboxylic acid (414 mg, 1.21 mmol, preparable according to WO 2016 146602 A1, p. 51, Example 3A) in DMF (5 ml), and the mixture was stirred at RT for 15 min. tert-Butyl 4-amino-3-(2-chlorophenyl)pentanoate (462 mg, 74% purity, 1.21 mmol, Example 120A) dissolved in DMF (3 ml) was then added, and the mixture was stirred at 60° C. for 22 h. After cooling to RT, the mixture was purified directly (without further workup) by preparative HPLC on an achiral phase (Method 14). The combined target fractions were each concentrated and the respective residues were dried under reduced pressure (see Examples 230A and 231A).

Example 230A (+/−)-tert-Butyl 4-{[(6-bromo-3-methyl-2-phenylquinolin-4-yl)carbonyl]amino}-3-(2-chlorophenyl)pentanoate (Racemate 1)

In the diastereomer separation described in Example 229A, 123 mg (100% purity) of the title compound were obtained as the racemate that eluted earlier.

LC-MS (Method 1): $R_t$=2.61 min; MS (ESIpos): m/z=607/609 $[M+H]^+$ $^1$H-NMR (400 MHz, DMSO-d6) δ [ppm]: 1.200 (16.00), 1.234 (1.15), 1.245 (1.94), 1.262 (1.83), 2.710 (0.58), 2.734 (0.56), 2.760 (0.63), 2.773 (0.67), 3.747 (0.40), 3.759 (0.42), 7.490 (0.69), 7.505 (2.14), 7.511 (1.76), 7.523 (3.09), 7.536 (1.81), 7.831 (0.42), 7.853 (0.59), 7.929 (0.98), 7.951 (0.63).

$^1$H-NMR (400 MHz, DMSO-d6) δ [ppm]: 8.72 (br. s, 1H), 7.94 (d, 1H), 7.84 (d, 1H), 7.78-7.15 (m, 10H), 4.72-4.57 (m, 1H), 3.81-3.69 (m, 1H), 2.86-2.63 (m, 2H), 2.39-1.69 (br. m, 3H), 1.25 (d, 3H), 1.20 (s, 9H).

Example 231A (+/−)-tert-Butyl 4-{[(6-bromo-3-methyl-2-phenylquinolin-4-yl)carbonyl]amino}-3-(2-chlorophenyl)pentanoate (Racemate 2)

In the diastereomer separation described in Example 229A, 148 mg (75% purity) of a first batch, 56 mg (89% purity, see analysis) of a second batch and 57 mg (40% purity) of a third batch of the title compound were obtained as the racemate that eluted later. The byproduct present was in each case the compound from Example 230A (racemate 1) in different proportions.

LC-MS (Method 1): $R_t$=2.66 min; MS (ESIpos): m/z=607/609 $[M+H]^+$ $^1$H-NMR (400 MHz, DMSO-d6) δ [ppm]: 8.89 (br. s, 1H), 7.99 (d, 1H), 7.89 (dd, 1H), 7.74 (br. s, 1H), 7.72-7.24 (m, 10H), 4.52-4.39 (m, 1H), 3.82-3.71 (m, 1H), 2.95-2.75 (m, 2H), 2.30 (br. s, 3H), 1.21 (d, 3H), 1.15 (s, 9H).

Example 232A (+/−)-tert-Butyl 5-{[(6-bromo-3-methyl-2-phenylquinolin-4-yl)carbonyl]amino}-4-(2-chlorophenyl)pentanoate (Racemate)

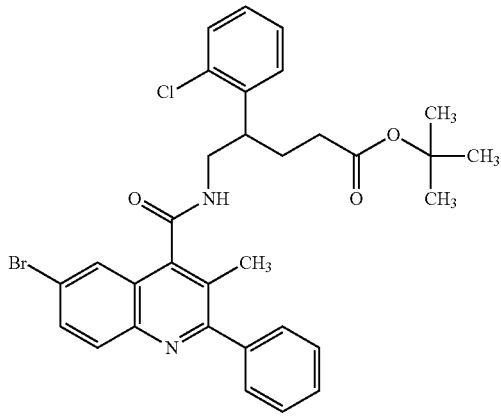 [SMILES: Cc1c(-c2ccccc2)nc2ccc(Br)cc2c1C(=O)NCC(CCC(=O)OC(C)(C)C)c1ccccc1Cl]

HATU (1.93 g, 5.07 mmol) and DIPEA (1.8 ml, 10 mmol) were added to a mixture of 6-bromo-3-methyl-2-phenylquinoline-4-carboxylic acid (1.16 g, 3.38 mmol, preparable according to WO 2016 146602 A1, p. 51, Example 3A) in DMF (15 ml), and the mixture was stirred at RT for 30 min. (+/−)-tert-Butyl 5-amino-4-(2-chlorophenyl)pentanoate (1.58 g, 91% purity, 5.07 mmol, Example 121A) dissolved in DMF (5 ml) was then added, and the mixture was stirred at 60° C. overnight. After cooling to RT, ethyl acetate and water (30 ml of each) were added to the mixture, which was agitated. After phase separation, the aqueous phase was extracted twice with ethyl acetate (30 ml each time). The combined organic phases were washed with saturated aqueous sodium chloride solution, dried over sodium sulfate, filtered and concentrated, and the residue was taken up in dichloromethane and prepurified by flash column chromatography (100 g of silica gel Biotage Snap-Cartridge KP-Sil, cyclohexane/ethyl acetate 85:15, Isolera One). This was followed by repurification by preparative HPLC (Method 16). The combined target fractions were concentrated and the residue was dried under reduced pressure. This gave 1.43 g (98% purity, 68% of theory) of the title compound.

LC-MS (Method 1): $R_t$=2.63 min; MS (ESIpos): m/z=607/609 [M+H]$^+$ $^1$H-NMR (400 MHz, DMSO-d6) δ [ppm]: 1.152 (0.02), 1.206 (0.07), 1.290 (0.09), 1.311 (0.17), 1.334 (0.13), 1.367 (16.00), 1.393 (0.24), 1.523 (0.07), 1.772 (0.06), 1.804 (0.16), 1.823 (0.21), 1.846 (0.12), 2.011 (0.07), 2.031 (0.17), 2.043 (0.19), 2.060 (0.23), 2.082 (1.29), 2.094 (0.71), 2.111 (0.40), 2.119 (0.45), 2.139 (0.78), 2.253 (0.04), 2.327 (0.03), 2.366 (0.02), 2.670 (0.03), 2.710 (0.02), 3.611 (0.23), 3.718 (0.32), 7.246 (0.17), 7.264 (0.37), 7.283 (0.26), 7.354 (0.23), 7.373 (0.41), 7.391 (0.21), 7.436 (0.63), 7.456 (0.51), 7.499 (1.28), 7.507 (0.85), 7.518 (3.11), 7.696 (0.09), 7.830 (0.40), 7.835 (0.37), 7.853 (0.61), 7.858 (0.59), 7.928 (1.12), 7.950 (0.71), 8.837 (0.24), 8.851 (0.47), 8.865 (0.23).

$^1$H-NMR (400 MHz, DMSO-d6) δ [ppm]: 8.85 (t, 1H), 7.94 (d, 1H), 7.85 (dd, 1H), 7.68 (br. s, 1H), 7.55-7.48 (m, 6H), 7.45 (d, 1H), 7.37 (br. t, 1H), 7.27 (br. t, 1H), 3.81-3.53 (m, 3H), 2.20-1.98 (m, 6H), 1.89-1.75 (m, 1H), 1.37 (s, 9H).

Example 233A (+/−)-tert-Butyl 5-{[(6-bromo-3-methyl-2-phenylquinolin-4-yl)carbonyl]amino}-4-(2-chlorophenyl)-4-methylpentanoate (Racemate)

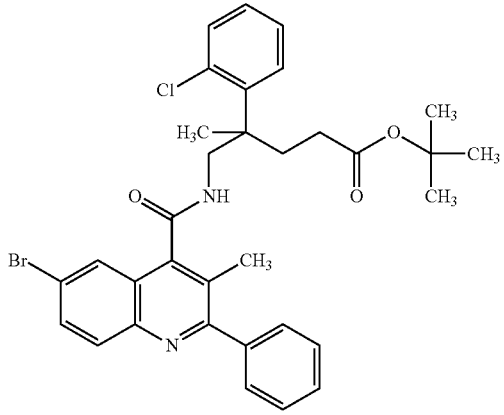 [SMILES: Cc1c(-c2ccccc2)nc2ccc(Br)cc2c1C(=O)NCC(C)(CCC(=O)OC(C)(C)C)c1ccccc1Cl]

HATU (783 mg, 2.06 mmol) and DIPEA (720 μl, 4.1 mmol) were added to a mixture of 6-bromo-3-methyl-2-phenylquinoline-4-carboxylic acid (470 mg, 1.37 mmol, preparable according to WO 2016 146602 A1, p. 51, Example 3A) in DMF (6.0 ml), and the mixture was stirred at RT for 30 min. (+/−)-tert-Butyl 5-amino-4-(2-chlorophenyl)-4-methylpentanoate (840 mg, 73% purity, 2.06 mmol, Example 122A) dissolved in DMF (2 ml) was then added, and the mixture was stirred at 60° C. overnight. After cooling to RT, ethyl acetate and water (30 ml of each) were added to the mixture, which was agitated. After phase separation, the aqueous phase was extracted twice with ethyl acetate (30 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage Snap-Cartridge KP-Sil, cyclohexane/ethyl acetate 85:15, Isolera One). This was followed by repurification by preparative HPLC (Method 16). The combined target fractions were concentrated and the residue was dried under reduced pressure. This gave 309 mg (98% purity, 35% of theory) of the title compound.

LC-MS (Method 1): $R_t$=2.70 min; MS (ESIpos): m/z=621/623 [M+H]$^+$ $^1$H-NMR (400 MHz, DMSO-d6) δ [ppm]: 1.188 (0.07), 1.233 (0.04), 1.280 (0.14), 1.297 (0.08), 1.348 (16.00), 1.375 (0.18), 1.512 (2.18), 1.717 (0.11), 1.729 (0.13), 1.745 (0.17), 1.756 (0.28), 1.767 (0.15), 1.783 (0.21), 1.796 (0.20), 1.872 (0.19), 1.885 (0.21), 1.907 (0.24), 1.919 (0.23), 1.934 (0.12), 1.947 (0.19), 1.986 (0.23), 1.999 (0.19), 2.015 (0.27), 2.026 (0.35), 2.037 (0.22), 2.053 (0.26), 2.065 (0.24), 2.317 (0.06), 2.365 (0.04), 2.634 (0.12), 2.647 (0.13), 2.668 (0.22), 2.696 (0.12), 2.708 (0.12), 3.666 (0.28), 3.679 (0.31), 3.699 (0.33), 3.713 (0.31), 3.922 (0.27), 4.339 (0.22), 4.357 (0.24), 4.373 (0.22), 4.390 (0.20), 7.257 (0.12), 7.275 (0.32), 7.298 (0.40), 7.320 (0.41), 7.337 (0.21), 7.356 (0.06), 7.375 (0.04), 7.408 (0.57), 7.425 (0.69), 7.445 (0.29), 7.473 (0.11), 7.498 (0.83), 7.506 (0.76), 7.517 (2.01), 7.668 (0.07), 7.828 (0.36), 7.833 (0.33), 7.850 (0.55), 7.855 (0.52), 7.924 (1.00), 7.946 (0.64), 8.614 (0.25), 8.629 (0.41), 8.644 (0.25).

Separation of the Enantiomers:

The title compound (220 mg) was dissolved in a hot mixture of ethanol (7 ml) and acetonitrile (3 ml) and separated into the enantiomers by preparative HPLC on a chiral phase (see Examples 234A and 235A) [column: Daicel Chiralpak IC, 5 μm 250 mm×20 mm; flow rate: 15 ml/min; detection: 210 nm; temperature: 25° C.; injection: 0.5 ml; mobile phase: 20% ethanol/80% heptane; run time 20 min, isocratic]. The combined target fractions were concentrated and the residue was lyophilized.

Example 234A (−)-tert-Butyl 5-{[(6-bromo-3-methyl-2-phenylquinolin-4-yl)carbonyl]amino}-4-(2-chlorophenyl)-4-methylpentanoate (Enantiomer 1)

In the enantiomer separation described in Example 233A, 91 mg (98% purity, ee 99%) of the title compound were obtained as the enantiomer that eluted earlier.

$[\alpha]_D^{20}$=−33.9°, 589 nm, c=0.25 g/100 ml, methanol

LC-MS (Method 1): $R_t$=2.68 min; MS (ESIpos): m/z=621/623 [M+H]$^+$ $^1$H-NMR (400 MHz, DMSO-d6) δ [ppm]: 0.007 (0.49), 1.280 (0.15), 1.348 (16.00), 1.512 (1.93), 1.728 (0.12), 1.756 (0.24), 1.783 (0.19), 1.795 (0.18), 1.872 (0.16), 1.884 (0.17), 1.919 (0.20), 1.946 (0.16), 1.986 (0.20), 2.026 (0.29), 2.053 (0.22), 2.669 (0.23), 2.708 (0.13), 3.665 (0.23), 3.679 (0.25), 3.699 (0.27), 3.713 (0.25), 4.338 (0.19), 4.356 (0.20), 4.372 (0.19), 4.389 (0.18), 7.276 (0.28), 7.298 (0.36), 7.322 (0.36), 7.337 (0.17), 7.405 (0.48), 7.428 (0.60), 7.446 (0.27), 7.497 (0.74), 7.505 (0.68), 7.516 (1.81), 7.826 (0.34), 7.831 (0.30), 7.848 (0.52), 7.853 (0.49), 7.922 (1.01), 7.945 (0.63), 8.612 (0.22), 8.627 (0.35), 8.643 (0.21).

Example 235A (+)-tert-Butyl 5-{[(6-bromo-3-methyl-2-phenylquinolin-4-yl)carbonyl]amino}-4-(2-chlorophenyl)-4-methylpentanoate (Enantiomer 2)

In the enantiomer separation described in Example 233A, 96 mg (98% purity, ee 99%) of the title compound were obtained as the enantiomer that eluted later.

$[\alpha]_D^{20}$=+35.1°, 589 nm, c=0.26 g/100 ml, methanol

LC-MS (Method 1): $R_t$=2.68 min; MS (ESIpos): m/z=621/623 [M+H]$^+$ $^1$H-NMR (400 MHz, DMSO-d6) δ [ppm]: 0.007 (0.35), 1.188 (0.07), 1.280 (0.15), 1.297 (0.08), 1.348 (16.00), 1.512 (2.03), 1.717 (0.10), 1.728 (0.12), 1.745 (0.16), 1.756 (0.26), 1.783 (0.20), 1.795 (0.19), 1.872 (0.16), 1.885 (0.19), 1.919 (0.22), 1.947 (0.17), 1.986 (0.21), 1.999 (0.17), 2.015 (0.24), 2.025 (0.30), 2.053 (0.24), 2.065 (0.21), 2.327 (0.07), 2.669 (0.22), 2.709 (0.13), 3.665 (0.24), 3.679 (0.26), 3.699 (0.29), 3.712 (0.27), 4.338 (0.20), 4.356 (0.22), 4.372 (0.20), 4.389 (0.18), 7.275 (0.30), 7.298 (0.38), 7.319 (0.38), 7.337 (0.18), 7.405 (0.51), 7.424 (0.63), 7.445 (0.28), 7.497 (0.77), 7.505 (0.71), 7.516 (1.87), 7.826 (0.34), 7.831 (0.31), 7.848 (0.52), 7.853 (0.49), 7.922 (1.02), 7.944 (0.64), 8.612 (0.23), 8.627 (0.37), 8.642 (0.22).

Example 236A (+/−)-tert-Butyl 5-{[(6-bromo-3-methyl-2-phenylquinolin-4-yl)carbonyl]amino}-4-(2-chloro-6-fluorophenyl)pentanoate (Racemate)

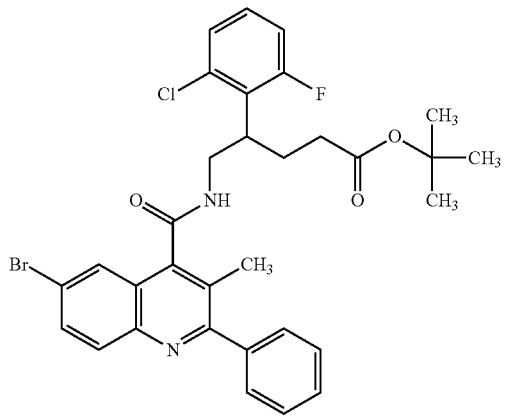 [SMILES: Cc1c(-c2ccccc2)nc2ccc(Br)cc2c1C(=O)NCC(CCC(=O)OC(C)(C)C)c1c(F)cccc1Cl]

HATU (1.01 g, 2.66 mmol) and DIPEA (930 μl, 5.3 mmol) were added to a mixture of 6-bromo-3-methyl-2-phenylquinoline-4-carboxylic acid (608 mg, 1.78 mmol, preparable according to WO 2016 146602 A1, p. 51, Example 3A) in DMF (8.0 ml), and the mixture was stirred at RT for 30 min. (+/−)-tert-Butyl 5-amino-4-(2-chloro-6-fluorophenyl)pentanoate (1.20 g, 67% purity, 2.66 mmol, Example 123A) dissolved in DMF (2 ml) was then added, and the mixture was stirred at 60° C. overnight. After cooling to RT, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage Snap-Cartridge KP-Sil, cyclohexane/ethyl acetate 85:15, Isolera One). This was followed by repurification by preparative HPLC (Method 16). The combined target fractions were concentrated and the residue was dried under reduced pressure. This gave 604 mg (98% purity, 53% of theory) of the title compound.

LC-MS (Method 1): $R_t$=2.60 min; MS (ESIpos): m/z=625/627 [M+H]$^+$ $^1$H-NMR (400 MHz, DMSO-d6) δ [ppm]: 1.361 (16.00), 2.119 (0.88), 2.135 (0.88), 2.158 (1.67), 7.330 (0.95), 7.501 (0.94), 7.509 (0.86), 7.521 (3.11), 7.838 (0.48), 7.843 (0.44), 7.860 (0.72), 7.865 (0.69), 7.933 (1.26), 7.955 (0.78), 8.938 (0.47).

$^1$H-NMR (400 MHz, DMSO-d6) δ [ppm]: 8.94 (t, 1H), 7.94 (d, 1H), 7.85 (dd, 1H), 7.72 (br. s, 1H), 7.56-7.45 (m, 5H), 7.37-7.28 (m, 2H), 7.27-7.16 (m, 1H), 3.89-3.53 (m, 3H), 2.21-1.90 (m, 7H), 1.36 (s, 9H).

Example 237A (+/−)-tert-Butyl 5-{[(6-bromo-3-methyl-2-phe-nylquinolin-4-yl)carbonyl]amino}-4-(2-methylphe-nyl)pentanoate (Racemate)

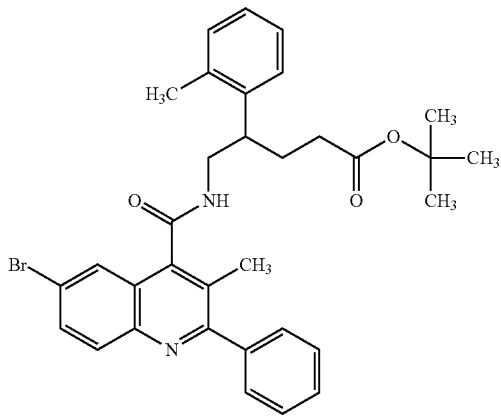 [SMILES: Cc1ccccc1C(CCC(=O)OC(C)(C)C)CNC(=O)c1c(C)c(-c2ccccc2)nc2ccc(Br)cc12]

HATU (667 mg, 1.75 mmol) and DIPEA (610 µl, 3.5 mmol) were added to a mixture of 6-bromo-3-methyl-2-phenylquinoline-4-carboxylic acid (400 mg, 1.17 mmol, preparable according to WO 2016 146602 A1, p. 51, Example 3A) in DMF (4.0 ml), and the mixture was stirred at RT for 30 min. (+/−)-tert-Butyl 5-amino-4-(2-methylphenyl)pentanoate (486 mg, 95% purity, 1.75 mmol, Example 124A) dissolved in DMF (2.5 ml) was then added, and the mixture was stirred at 60° C. overnight. After cooling to RT, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15, Isolera One). The combined target fractions were concentrated and the residue was lyophilized. This gave 429 mg (98% purity, 61% of theory) of the title compound.

LC-MS (Method 1): $R_t$=2.61 min; MS (ESIpos): m/z=587/589 [M+H]$^+$ $^1$H-NMR (400 MHz, DMSO-d6) δ [ppm]: −0.009 (0.21), 0.007 (0.23), 1.202 (0.07), 1.304 (0.08), 1.336 (0.13), 1.362 (16.00), 1.397 (0.14), 1.518 (0.06), 1.747 (0.05), 1.779 (0.15), 1.804 (0.19), 1.821 (0.13), 2.029 (0.20), 2.041 (0.22), 2.060 (1.22), 2.072 (0.80), 2.093 (0.46), 2.109 (0.40), 2.328 (3.10), 2.365 (0.05), 2.669 (0.05), 2.709 (0.04), 3.483 (0.10), 3.496 (0.14), 3.515 (0.18), 3.530 (0.18), 3.545 (0.11), 3.698 (0.14), 3.716 (0.22), 3.734 (0.20), 3.749 (0.17), 3.768 (0.10), 7.094 (0.13), 7.112 (0.34), 7.130 (0.30), 7.165 (0.56), 7.183 (0.32), 7.211 (0.34), 7.229 (0.18), 7.301 (0.55), 7.321 (0.38), 7.490 (0.23), 7.500 (0.69), 7.508 (0.67), 7.519 (2.17), 7.530 (0.94), 7.694 (0.12), 7.835 (0.37), 7.840 (0.34), 7.857 (0.56), 7.863 (0.55), 7.933 (1.02), 7.955 (0.65), 8.820 (0.21), 8.835 (0.34), 8.848 (0.21).

Separation of the Enantiomers:

The title compound (390 mg) was dissolved in isopropanol (4 ml) and separated into the enantiomers by preparative HPLC on a chiral phase (see Examples 238A and 239A) [column: Daicel Chiralpak AD-H, 5 µm, 250 mm×20 mm; flow rate: 20 ml/min; detection: 210 nm; temperature: 23° C.; injection: 0.25 ml; mobile phase: 20% isopropanol/80% heptane; run time 10 min, isocratic]. The combined target fractions were concentrated and the residue was lyophilized.

Example 238A (−)-tert-Butyl 5-{[(6-bromo-3-methyl-2-phenylqui-nolin-4-yl)carbonyl]amino}-4-(2-methylphenyl)pen-tanoate (Enantiomer 1)

In the enantiomer separation described in Example 237A, 128 mg (98% purity, ee 99%) of the title compound were obtained as the enantiomer that eluted earlier.

$[α]_D^{20}$=−11.1°, 589 nm, c=0.35 g/100 ml, methanol

LC-MS (Method 1): $R_t$=2.63 min; MS (ESIpos): m/z=587/589 [M+H]$^+$ $^1$H-NMR (400 MHz, DMSO-d6) δ [ppm]: 1.201 (0.07), 1.304 (0.09), 1.336 (0.15), 1.362 (16.00), 1.518 (0.06), 1.748 (0.06), 1.779 (0.16), 1.804 (0.20), 1.822 (0.14), 1.853 (0.04), 2.014 (0.16), 2.029 (0.22), 2.041 (0.25), 2.060 (1.31), 2.072 (0.85), 2.093 (0.49), 2.108 (0.42), 2.328 (3.28), 2.365 (0.04), 2.669 (0.03), 2.709 (0.03), 3.304 (0.19), 3.321 (0.20), 3.483 (0.12), 3.496 (0.16), 3.515 (0.20), 3.530 (0.20), 3.545 (0.13), 3.698 (0.18), 3.716 (0.28), 3.734 (0.25), 3.750 (0.23), 3.768 (0.17), 3.876 (0.18), 7.093 (0.14), 7.111 (0.36), 7.130 (0.32), 7.164 (0.60), 7.182 (0.34), 7.211 (0.36), 7.229 (0.19), 7.301 (0.59), 7.320 (0.41), 7.490 (0.25), 7.501 (0.75), 7.508 (0.71), 7.520 (2.27), 7.531 (0.97), 7.695 (0.13), 7.836 (0.38), 7.841 (0.34), 7.859 (0.59), 7.864 (0.56), 7.934 (1.07), 7.956 (0.68), 8.821 (0.23), 8.836 (0.36), 8.850 (0.22).

Example 239A (+)-tert-Butyl 5-{[(6-bromo-3-methyl-2-phenylqui-nolin-4-yl)carbonyl]amino}-4-(2-methylphenyl)pen-tanoate (Enantiomer 2)

In the enantiomer separation described in Example 237A, 128 mg (98% purity, ee 99%) of the title compound were obtained as the enantiomer that eluted later.

$[α]_D^{20}$=+16.8°, 589 nm, c=0.37 g/100 ml, methanol

LC-MS (Method 2): $R_t$=1.40 min; MS (ESIpos): m/z=587/589 [M+H]$^+$ $^1$H-NMR (400 MHz, DMSO-d6) δ [ppm]: −0.009 (0.32), 0.008 (0.27), 1.078 (0.08), 1.093 (0.08), 1.202 (0.06), 1.261 (0.17), 1.304 (0.08), 1.336 (0.13), 1.362 (16.00), 1.518 (0.06), 1.779 (0.14), 1.804 (0.18), 2.029 (0.18), 2.060 (1.12), 2.072 (0.73), 2.094 (0.42), 2.328 (2.92), 3.496 (0.13), 3.515 (0.16), 3.530 (0.17), 3.697 (0.14), 3.716 (0.21), 3.733 (0.18), 3.749 (0.16), 3.768 (0.09), 7.093 (0.12), 7.112 (0.31), 7.130 (0.28), 7.165 (0.53), 7.182 (0.29), 7.211 (0.31), 7.229 (0.17), 7.302 (0.51), 7.320 (0.35), 7.490 (0.22), 7.500 (0.67), 7.508 (0.64), 7.519 (2.04), 7.531 (0.90), 7.695 (0.12), 7.835 (0.38), 7.840 (0.34), 7.857 (0.57), 7.863 (0.55), 7.933 (1.05), 7.955 (0.66), 8.820 (0.19), 8.835 (0.31), 8.849 (0.19).

Example 240A (+/−)-tert-Butyl 5-{[(6-bromo-3-methyl-2-phenylquinolin-4-yl)carbonyl]amino}-4-(2-chloro-5-fluorophenyl)pentanoate (Racemate)

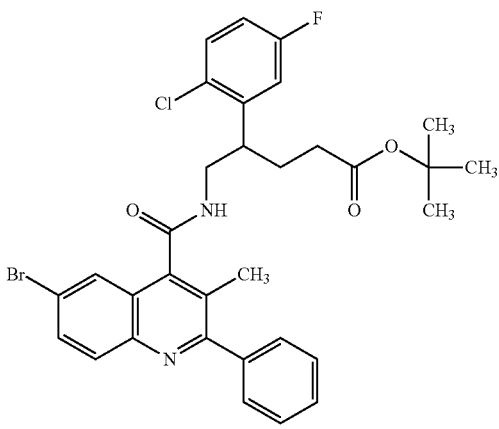

HATU (5.29 g, 13.9 mmol) and DIPEA (4.8 ml, 28 mmol) were added to a mixture of 6-bromo-3-methyl-2-phenylquinoline-4-carboxylic acid (3.17 g, 9.28 mmol, preparable according to WO 2016 146602 A1, p. 51, Example 3A) in DMF (30 ml), and the mixture was stirred at RT for 30 min. (+/−)-tert-Butyl 5-amino-4-(2-chloro-5-fluorophenyl)pentanoate (7.00 g, 60% purity, 13.9 mmol, Example 125A) dissolved in DMF (20 ml) was then added, and the mixture was stirred at 60° C. overnight. After cooling to RT, ethyl acetate and water (150 ml of each) were added to the mixture, which was agitated. After phase separation, the aqueous phase was extracted twice with ethyl acetate (150 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge Ultra, cyclohexane/ethyl acetate 85:15, Isolera One). The combined target fractions were concentrated and the residue was lyophilized. This gave 4.03 g (91% purity, 63% of theory) of the title compound.

LC-MS (Method 1): $R_t$=2.61 min; MS (ESIpos): m/z=625/627 [M+H]$^+$ $^1$H-NMR (400 MHz, DMSO-d6) δ [ppm]: −0.008 (0.22), 0.008 (0.21), 0.018 (0.08), 0.838 (0.09), 0.863 (0.04), 1.211 (0.07), 1.283 (0.08), 1.313 (0.11), 1.344 (4.94), 1.359 (0.72), 1.371 (16.00), 1.397 (0.20), 1.499 (0.04), 1.528 (0.07), 1.663 (0.06), 1.785 (0.14), 1.801 (0.16), 1.820 (0.18), 1.842 (0.14), 1.928 (0.06), 1.947 (0.07), 1.971 (0.19), 1.988 (0.26), 2.009 (0.25), 2.022 (0.23), 2.041 (0.26), 2.059 (0.24), 2.074 (0.21), 2.093 (0.72), 2.110 (0.92), 2.139 (1.05), 2.328 (0.05), 2.366 (0.05), 2.690 (0.17), 2.710 (0.12), 3.223 (0.06), 3.607 (0.19), 3.735 (0.37), 7.035 (0.07), 7.056 (0.12), 7.077 (0.09), 7.116 (0.18), 7.140 (0.30), 7.155 (0.21), 7.181 (0.08), 7.188 (0.07), 7.394 (0.10), 7.411 (0.36), 7.418 (0.38), 7.436 (0.38), 7.444 (0.32), 7.478 (0.47), 7.491 (0.59), 7.500 (1.12), 7.508 (0.83), 7.518 (2.77), 7.530 (1.02), 7.664 (0.06), 7.832 (0.42), 7.837 (0.37), 7.854 (0.64), 7.859 (0.60), 7.929 (1.10), 7.951 (0.71), 8.842 (0.20), 8.856 (0.39), 8.870 (0.19).

Separation of the Enantiomers:

The title compound (4.00 g) was dissolved in ethanol (40 ml) and separated into the enantiomers by preparative HPLC on a chiral phase (see Examples 241A and 242A) [column: Daicel Chiralcel OX-H, 5 μm, 250 mm×20 mm; flow rate: 40 ml/min; injection: 0.13 ml; mobile phase: 20% ethanol/ 80% heptane; run time 9 min, isocratic]. The combined target fractions were concentrated and the residue was lyophilized.

Example 241A (−)-tert-Butyl 5-{[(6-bromo-3-methyl-2-phenylquinolin-4-yl)carbonyl]amino}-4-(2-chloro-5-fluorophenyl)pentanoate (Enantiomer 1)

In the enantiomer separation described in Example 240A, 1.57 g (86% purity, ee 99%) of the title compound were obtained as the enantiomer that eluted earlier.

$[α]_D^{20}$=−15.8°, 589 nm, c=0.34 g/100 ml, methanol

LC-MS (Method 1): $R_t$=2.60 min; MS (ESIpos): m/z=625/627 [M+H]$^+$ $^1$H-NMR (400 MHz, DMSO-d6) δ [ppm]: 1.312 (0.15), 1.344 (1.32), 1.370 (16.00), 1.819 (0.18), 2.021 (0.25), 2.043 (0.26), 2.059 (0.27), 2.073 (0.28), 2.092 (0.75), 2.109 (0.94), 2.139 (1.11), 3.607 (0.20), 3.734 (0.39), 7.136 (0.32), 7.410 (0.34), 7.417 (0.34), 7.435 (0.33), 7.477 (0.49), 7.490 (0.63), 7.499 (1.20), 7.507 (0.89), 7.517 (3.06), 7.831 (0.45), 7.836 (0.40), 7.853 (0.69), 7.858 (0.64), 7.928 (1.16), 7.951 (0.73), 8.856 (0.39).

Example 242A (+)-tert-Butyl 5-{[(6-bromo-3-methyl-2-phenylquinolin-4-yl)carbonyl]amino}-4-(2-chloro-5-fluorophenyl)pentanoate (Enantiomer 2)

In the enantiomer separation described in Example 240A, 1.28 g (98% purity, ee 95%) of the title compound were obtained as the enantiomer that eluted later.

$[α]_D^{20}$=+15.1°, 589 nm, c=0.36 g/100 ml, methanol

LC-MS (Method 1): $R_t$=2.60 min; MS (ESIpos): m/z=625/627 [M+H]$^+$ $^1$H-NMR (400 MHz, DMSO-d6) δ [ppm]: −0.009 (0.20), 0.007 (0.19), 0.857 (0.07), 1.027 (0.03), 1.044 (0.04), 1.086 (0.04), 1.101 (0.04), 1.210 (0.07), 1.282 (0.09), 1.331 (0.14), 1.344 (1.33), 1.370 (16.00), 1.526 (0.07), 1.784 (0.13), 1.800 (0.15), 1.818 (0.17), 1.841 (0.13), 2.008 (0.20), 2.021 (0.22), 2.039 (0.22), 2.059 (0.19), 2.073 (0.16), 2.092 (0.70), 2.109 (0.92), 2.138 (1.04), 2.327 (0.05), 2.365 (0.04), 2.669 (0.05), 2.709 (0.05), 3.607 (0.18), 3.733 (0.37), 7.136 (0.24), 7.409 (0.33), 7.417 (0.34), 7.435 (0.34), 7.442 (0.32), 7.477 (0.47), 7.490 (0.59), 7.499 (1.11), 7.507 (0.79), 7.517 (2.61), 7.529 (0.96), 7.532 (0.87), 7.664 (0.06), 7.831 (0.42), 7.836 (0.38), 7.853 (0.64), 7.858 (0.61), 7.928 (1.12), 7.950 (0.71), 8.841 (0.20), 8.855 (0.39), 8.869 (0.19).

Example 243A (+/−)-tert-Butyl 5-{[(6-bromo-3-methyl-2-phenylquinolin-4-yl)carbonyl]amino}-4-(2-methoxyphenyl)pentanoate (Racemate)

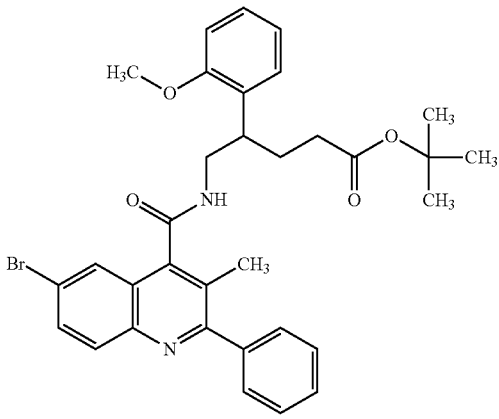 [SMILES: COc1ccccc1C(CCC(=O)OC(C)(C)C)CNC(=O)c1c(C)c(-c2ccccc2)nc2ccc(Br)cc12]

HATU (308 mg, 811 µmol) and DIPEA (280 µl, 1.6 mmol) were added to a mixture of 6-bromo-3-methyl-2-phenylquinoline-4-carboxylic acid (185 mg, 541 µmol, preparable according to WO 2016 146602 A1, p. 51, Example 3A) in DMF (3 ml), and the mixture was stirred at RT for 30 min. (+/−)-tert-Butyl 5-amino-4-(2-methoxyphenyl)pentanoate (267 mg, 85% purity, 811 µmol, Example 126A) dissolved in DMF (1.5 ml) was then added, and the mixture was stirred at 60° C. overnight. After cooling to RT, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 85:15, Isolera One). The combined target fractions were concentrated and the residue was lyophilized. This gave 213 mg (98% purity, 64% of theory) of the title compound.

LC-MS (Method 1): $R_t$=2.57 min; MS (ESIpos): m/z=603/605 [M+H]$^+$ $^1$H-NMR (400 MHz, DMSO-d6) δ [ppm]: −0.009 (0.16), 0.007 (0.13), 1.200 (0.07), 1.300 (0.10), 1.325 (0.17), 1.360 (16.00), 1.516 (0.06), 1.788 (0.12), 1.806 (0.16), 1.841 (0.08), 1.948 (0.06), 1.969 (0.15), 1.981 (0.17), 1.988 (0.17), 1.999 (0.19), 2.004 (0.19), 2.028 (0.97), 2.044 (0.74), 2.062 (0.26), 2.143 (0.93), 2.263 (0.03), 2.327 (0.03), 2.365 (0.02), 2.669 (0.03), 2.709 (0.02), 3.233 (0.02), 3.393 (0.17), 3.591 (0.02), 3.618 (0.08), 3.633 (0.14), 3.651 (0.25), 3.666 (0.31), 3.688 (0.23), 3.704 (0.25), 3.724 (0.23), 3.737 (0.12), 3.749 (0.18), 3.773 (4.01), 6.922 (0.24), 6.941 (0.52), 6.959 (0.32), 6.976 (0.54), 6.997 (0.63), 7.197 (0.27), 7.217 (0.50), 7.223 (0.64), 7.241 (0.53), 7.488 (0.24), 7.498 (0.72), 7.507 (0.67), 7.518 (2.34), 7.529 (0.96), 7.714 (0.21), 7.829 (0.39), 7.834 (0.34), 7.852 (0.59), 7.857 (0.55), 7.926 (1.07), 7.948 (0.68), 8.752 (0.22), 8.767 (0.44), 8.781 (0.22).

Separation of the Enantiomers:

The title compound (160 mg) was dissolved in isopropanol (3 ml) and separated into the enantiomers by preparative HPLC on a chiral phase (see Examples 244A and 245A) [column: Daicel Chiralcel AD-H, 5 µm, 250 mm×20 mm; flow rate: 25 ml/min; injection: 0.10 ml; mobile phase: 40% isopropanol/60% heptane; run time 14 min, isocratic]. The combined target fractions were concentrated and the residue was lyophilized.

Example 244A (−)-tert-Butyl 5-{[(6-bromo-3-methyl-2-phenylquinolin-4-yl)carbonyl]amino}-4-(2-methoxyphenyl)pentanoate (Enantiomer 1)

In the enantiomer separation described in Example 243A, 63 mg (98% purity, ee 99%) of the title compound were obtained as the enantiomer that eluted earlier.

$[\alpha]_D^{20}$=−9.6°, 589 nm, c=0.32 g/100 ml, methanol

LC-MS (Method 1): $R_t$=2.57 min; MS (ESIpos): m/z=603/605 [M+H]$^+$ $^1$H-NMR (400 MHz, DMSO-d6) δ [ppm]: −0.154 (0.03), 0.141 (0.03), 1.100 (0.05), 1.116 (0.05), 1.195 (0.06), 1.296 (0.11), 1.321 (0.16), 1.356 (16.00), 1.512 (0.06), 1.801 (0.16), 1.964 (0.14), 1.976 (0.16), 1.994 (0.18), 2.023 (0.95), 2.039 (0.73), 2.057 (0.25), 2.138 (0.92), 2.258 (0.03), 2.322 (0.04), 2.361 (0.05), 2.664 (0.05), 2.705 (0.05), 3.614 (0.08), 3.629 (0.14), 3.646 (0.24), 3.662 (0.31), 3.683 (0.22), 3.699 (0.25), 3.719 (0.23), 3.732 (0.12), 3.769 (4.00), 6.918 (0.24), 6.936 (0.52), 6.955 (0.30), 6.972 (0.54), 6.992 (0.62), 7.193 (0.27), 7.213 (0.50), 7.218 (0.64), 7.236 (0.53), 7.484 (0.22), 7.494 (0.69), 7.502 (0.66), 7.514 (2.37), 7.525 (0.97), 7.710 (0.21), 7.826 (0.38), 7.831 (0.34), 7.848 (0.59), 7.853 (0.56), 7.922 (1.07), 7.944 (0.68), 8.748 (0.22), 8.762 (0.43), 8.777 (0.21).

Example 245A (+)-tert-Butyl 5-{[(6-bromo-3-methyl-2-phenylquinolin-4-yl)carbonyl]amino}-4-(2-methoxyphenyl)pentanoate (Enantiomer 2)

In the enantiomer separation described in Example 243A, 59 mg (98% purity, ee 98%) of the title compound were obtained as the enantiomer that eluted later.

$[\alpha]_D^{20}$=+11.3°, 589 nm, c=0.36 g/100 ml, methanol

LC-MS (Method 1): $R_t$=2.57 min; MS (ESIpos): m/z=603/605 [M+H]$^+$ $^1$H-NMR (400 MHz, DMSO-d6) δ [ppm]: 1.029 (0.07), 1.045 (0.07), 1.105 (0.15), 1.120 (0.15), 1.200 (0.07), 1.300 (0.10), 1.325 (0.15), 1.360 (16.00), 1.516 (0.07), 1.805 (0.17), 1.968 (0.15), 1.980 (0.18), 1.999 (0.19), 2.028 (1.00), 2.044 (0.78), 2.062 (0.27), 2.143 (1.00), 2.327 (0.06), 2.668 (0.05), 3.394 (0.20), 3.618 (0.13), 3.633 (0.18), 3.651 (0.28), 3.667 (0.35), 3.688 (0.25), 3.704 (0.27), 3.724 (0.25), 3.738 (0.14), 3.773 (4.12), 6.923 (0.25), 6.941 (0.56), 6.959 (0.33), 6.977 (0.58), 6.997 (0.67), 7.197 (0.29), 7.222 (0.67), 7.241 (0.56), 7.489 (0.24), 7.500 (0.73), 7.508 (0.69), 7.520 (2.58), 7.716 (0.24), 7.831 (0.39), 7.837 (0.36), 7.854 (0.60), 7.859 (0.59), 7.927 (1.11), 7.949 (0.70), 8.753 (0.23), 8.768 (0.46), 8.782 (0.23).

Example 246A (+/−)-tert-Butyl 5-{[(6-bromo-3-methyl-2-phenylquinolin-4-yl)carbonyl]amino}-4-(2-chloro-5-fluorophenyl)-4-methylpentanoate (Racemate)

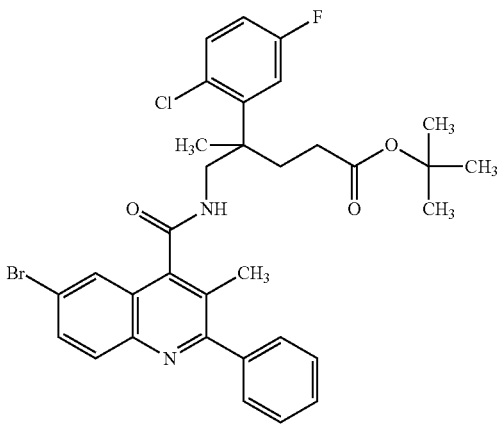 [SMILES: Cc1c(-c2ccccc2)nc2ccc(Br)cc2c1C(=O)NCC(C)(CCC(=O)OC(C)(C)C)c1cc(F)ccc1Cl]

HATU (1.22 g, 3.22 mmol) and DIPEA (1.1 ml, 6.4 mmol) were added to a mixture of 6-bromo-3-methyl-2-phenylquinoline-4-carboxylic acid (734 mg, 2.15 mmol, preparable according to WO 2016 146602 A1, p. 51, Example 3A) in DMF (8 ml), and the mixture was stirred at RT for 30 min. (+/−)-tert-Butyl 5-amino-4-(2-chloro-5-fluorophenyl)-4-methylpentanoate (1.54 g, 66% purity, 3.22 mmol, Example 127A) dissolved in DMF (4 ml) was then added, and the mixture was stirred at 60° C. overnight. After cooling to RT, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage Snap-Cartridge KP-Sil, cyclohexane/ethyl acetate 85:15, Isolera One). This was followed by repurification by preparative HPLC (Method 16). The combined target fractions were concentrated and the residue was dried under reduced pressure. This gave 377 mg (98% purity, 27% of theory) of the title compound.

LC-MS (Method 1): $R_t$=2.69 min; MS (ESIpos): m/z=639 [M+H]$^+$ $^1$H-NMR (400 MHz, DMSO-d6) δ [ppm]: −0.151 (0.01), 1.192 (0.07), 1.280 (0.14), 1.306 (0.08), 1.352 (16.00), 1.500 (2.15), 1.740 (0.11), 1.753 (0.13), 1.768 (0.17), 1.780 (0.27), 1.791 (0.14), 1.807 (0.22), 1.819 (0.21), 1.874 (0.19), 1.885 (0.20), 1.908 (0.23), 1.914 (0.22), 1.919 (0.23), 1.936 (0.13), 1.948 (0.17), 2.029 (0.24), 2.042 (0.24), 2.058 (0.29), 2.069 (0.37), 2.080 (0.23), 2.096 (0.26), 2.108 (0.23), 2.324 (0.06), 2.365 (0.03), 2.618 (0.11), 2.630 (0.12), 2.659 (0.18), 2.680 (0.11), 2.692 (0.09), 3.634 (0.20), 3.647 (0.21), 3.668 (0.23), 3.680 (0.21), 4.384 (0.18), 4.401 (0.20), 4.417 (0.19), 4.434 (0.16), 4.863 (0.04), 7.148 (0.15), 7.176 (0.57), 7.183 (0.42), 7.204 (0.43), 7.211 (0.30), 7.248 (0.02), 7.489 (0.48), 7.503 (0.99), 7.509 (0.84), 7.521 (1.70), 7.530 (1.54), 7.833 (0.32), 7.838 (0.30), 7.856 (0.49), 7.860 (0.47), 7.931 (0.97), 7.953 (0.62), 8.629 (0.23), 8.644 (0.37), 8.658 (0.23).

$^1$H-NMR (400 MHz, DMSO-d6) δ [ppm]: 8.65 (t, 1H), 7.94 (d, 1H), 7.85 (dd, 1H), 7.63 (br. s, 1H), 7.56-7.46 (m, 6H), 7.23-7.13 (m, 2H), 4.41 (dd, 1H), 3.66 (dd, 1H), 2.73-2.59 (m, 1H), 2.15 (br. s, 3H), 2.13-2.01 (m, 1H), 1.97-1.86 (m, 1H), 1.84-1.72 (m, 1H), 1.50 (s, 3H), 1.35 (s, 9H).

Separation of the Enantiomers:

The title compound (330 mg) was dissolved in methanol (25 ml) and separated into the enantiomers by preparative SFC on a chiral phase (see Examples 247A and 248A) [column: Daicel Chiralpak AD-H, 5 µm, 250 mm×20 mm; flow rate: 80 ml/min; detection: 210 nm; temperature: 40° C.; injection: 0.5 ml; mobile phase: 88% carbon dioxide/ 12% methanol; run time 18 min, isocratic]. The combined target fractions were concentrated, and the residue was in each case dried under reduced pressure.

Example 247A (−)-tert-Butyl 5-{[(6-bromo-3-methyl-2-phenylquinolin-4-yl)carbonyl]amino}-4-(2-chloro-5-fluorophenyl)-4-methylpentanoate (Enantiomer 1)

In the enantiomer separation described in Example 246A, 146 mg (98% purity, ee 99%) of the title compound were obtained as the enantiomer that eluted earlier.

$[α]_D^{20}$=−29.3°, 589 nm, c=0.34 g/100 ml, methanol

LC-MS (Method 1): $R_t$=2.69 min; MS (ESIpos): m/z=639/671 [M+H]$^+$ $^1$H-NMR (400 MHz, DMSO-d6) δ [ppm]: 1.352 (16.00), 1.499 (2.16), 1.778 (0.27), 1.805 (0.23), 1.884 (0.21), 1.906 (0.23), 2.068 (0.37), 2.655 (0.19), 3.644 (0.21), 3.665 (0.23), 4.399 (0.19), 7.175 (0.59), 7.203 (0.43), 7.501 (1.00), 7.508 (0.90), 7.520 (1.86), 7.831 (0.33), 7.853 (0.51), 7.929 (0.99), 7.951 (0.63), 8.641 (0.36).

$^1$H-NMR (400 MHz, DMSO-d6) δ [ppm]: 8.64 (t, 1H), 7.94 (d, 1H), 7.85 (dd, 1H), 7.68 (br. s, 1H), 7.57-7.45 (m, 6H), 7.24-7.13 (m, 2H), 4.41 (dd, 1H), 3.66 (dd, 1H), 2.71-2.60 (m, 1H), 2.15 (br. s, 3H), 2.12-2.01 (m, 1H), 1.97-1.86 (m, 1H), 1.83-1.73 (m, 1H), 1.50 (s, 3H), 1.35 (s, 9H).

Example 248A (+)-tert-Butyl 5-{[(6-bromo-3-methyl-2-phenylquinolin-4-yl)carbonyl]amino}-4-(2-chloro-5-fluorophenyl)-4-methylpentanoate (Enantiomer 2)

In the enantiomer separation described in Example 246A, 139 mg (98% purity, ee 99%) of the title compound were obtained as the enantiomer that eluted later.

$[α]_D^{20}$=+26.7°, 589 nm, c=0.32 g/100 ml, methanol

LC-MS (Method 1): $R_t$=2.69 min; MS (ESIpos): m/z=639/641 [M+H]$^+$ $^1$H-NMR (400 MHz, DMSO-d6) δ [ppm]: 1.192 (0.07), 1.233 (0.06), 1.280 (0.16), 1.307 (0.07), 1.352 (16.00), 1.499 (1.97), 1.738 (0.10), 1.750 (0.12), 1.766 (0.16), 1.778 (0.25), 1.789 (0.13), 1.805 (0.21), 1.817 (0.20), 1.871 (0.17), 1.883 (0.19), 1.905 (0.21), 1.918 (0.21), 1.933 (0.12), 1.946 (0.16), 2.028 (0.23), 2.040 (0.22), 2.057 (0.26), 2.068 (0.33), 2.095 (0.24), 2.107 (0.21), 2.322 (0.09), 2.365 (0.05), 2.627 (0.12), 2.659 (0.17), 2.709 (0.05), 3.632 (0.18), 3.644 (0.19), 3.665 (0.21), 3.678 (0.19), 4.382 (0.16), 4.399 (0.17), 4.415 (0.16), 4.432 (0.14), 7.175 (0.53), 7.203 (0.40), 7.210 (0.27), 7.487 (0.43), 7.501 (0.88), 7.508 (0.79), 7.519 (1.62), 7.527

(1.39), 7.831 (0.30), 7.836 (0.27), 7.853 (0.45), 7.858 (0.43), 7.929 (0.89), 7.951 (0.57), 8.625 (0.20), 8.640 (0.33), 8.655 (0.20).

$^1$H-NMR (400 MHz, DMSO-d6) δ [ppm]: 8.64 (t, 1H), 7.94 (d, 1H), 7.85 (dd, 1H), 7.66 (br. s, 1H), 7.57-7.44 (m, 6H), 7.23-7.13 (m, 2H), 4.41 (dd, 1H), 3.66 (dd, 1H), 2.72-2.59 (m, 1H), 2.15 (br. s, 3H), 2.13-2.02 (m, 1H), 1.96-1.86 (m, 1H), 1.84-1.72 (m, 1H), 1.50 (s, 3H), 1.35 (s, 9H).

Example 249A (+/−)-tert-Butyl 5-{[(6-bromo-3-methyl-2-phenylquinolin-4-yl)carbonyl]amino}-4-(2-chloro-3,6-difluorophenyl)pentanoate (Racemate)

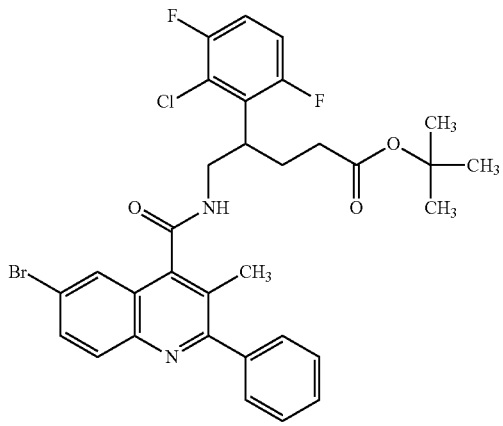 [SMILES: Cc1c(-c2ccccc2)nc2ccc(Br)cc2c1C(=O)NCC(CCC(=O)OC(C)(C)C)c1c(F)ccc(F)c1Cl]

HATU (1.28 g, 3.38 mmol) and DIPEA (1.2 ml, 6.8 mmol) were added to a mixture of 6-bromo-3-methyl-2-phenylquinoline-4-carboxylic acid (963 mg, 2.81 mmol, preparable according to WO 2016 146602 A1, p. 51, Example 3A) in DMF (10 ml), and the mixture was stirred at RT for 15 min. (+/−)-tert-Butyl 5-amino-4-(2-chloro-3,6-difluorophenyl)pentanoate (900 mg, 2.81 mmol, Example 128A) dissolved in DMF (8 ml) was then added, and the mixture was stirred at 60° C. for 2 h and then allowed to warm to RT with stirring overnight. Subsequently, ethyl acetate and water (150 ml of each) were added to the mixture, which was agitated. After phase separation, the aqueous phase was extracted once with ethyl acetate (80 ml). The combined organic phases were washed with saturated aqueous sodium chloride solution (200 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 97:3→7: 3, Isolera One). The combined target fractions were concentrated and the residue was dried under reduced pressure. This gave 1.06 g (95% purity, 56% of theory) of the title compound.

LC-MS (Method 1): $R_t$=2.60 min; MS (ESIpos): m/z=643/645 [M+H]$^+$ $^1$H-NMR (400 MHz, DMSO-d6) δ [ppm]: −0.150 (0.03), −0.009 (0.28), 0.007 (0.25), 0.145 (0.03), 0.888 (0.03), 1.156 (0.13), 1.174 (0.26), 1.192 (0.14), 1.198 (0.07), 1.255 (0.06), 1.311 (0.14), 1.358 (16.00), 1.396 (2.64), 1.514 (0.07), 1.988 (0.58), 2.059 (0.18), 2.073 (0.22), 2.089 (0.23), 2.109 (0.21), 2.156 (1.59), 2.320 (0.10), 2.365 (0.04), 2.669 (0.04), 2.709 (0.04), 2.727 (0.17), 3.721 (0.22), 3.805 (0.22), 4.002 (0.05), 4.020 (0.12), 4.038 (0.12), 4.056 (0.05), 7.268 (0.11), 7.279 (0.13), 7.292 (0.23), 7.303 (0.24), 7.317 (0.19), 7.328 (0.16), 7.402 (0.22), 7.492 (0.28), 7.502 (0.83), 7.510 (0.79), 7.521 (2.70), 7.532 (1.11), 7.568 (0.08), 7.586 (0.06), 7.733 (0.08), 7.751 (0.08), 7.841 (0.43), 7.846 (0.38), 7.863 (0.66), 7.869 (0.62), 7.936 (1.19), 7.958 (0.76), 8.215 (0.03), 8.935 (0.21), 8.949 (0.39), 8.962 (0.21).

$^1$H-NMR (400 MHz, DMSO-d6) δ [ppm]: 8.95 (t, 1H), 7.95 (d, 1H), 7.86 (dd, 1H), 7.70 (br. s, 1H), 7.56-7.47 (m, 5H), 7.45-7.36 (m, 1H), 7.35-7.25 (m, 1H), 3.88-3.66 (m, 3H), 2.21-1.91 (m, 7H), 1.36 (s, 9H).

Separation of the Enantiomers:

The title compound (925 mg) was dissolved in isopropanol (20 ml) and separated into the enantiomers by preparative HPLC on a chiral phase (see Examples 250A and 251A) [column: Daicel Chiralpak AD-H, 5 μm, 250 mm×20 mm; flow rate: 20 ml/min; detection: 220 nm; temperature: 23° C.; injection: 0.2 ml; mobile phase: 70% heptane/30% isopropanol; isocratic]. The combined target fractions were concentrated, and the respective residue was lyophilized in acetonitrile/water.

Example 250A (−)-tert-Butyl 5-{[(6-bromo-3-methyl-2-phenylquinolin-4-yl)carbonyl]amino}-4-(2-chloro-3,6-difluorophenyl)pentanoate (Enantiomer 1)

In the enantiomer separation described in Example 249A, 289 mg (100% purity, ee 99%) of the title compound were obtained as the enantiomer that eluted earlier.

$R_t$=1.40 min (chiral analytical HPLC; Daicel Chiralpak AD-3, 3 μm, 50 mm×4.6 mm, mobile phase heptane/isopropanol 80:20; flow rate 1 ml/min; detection 220 nm)

$[α]_D^{20}$=−20.2°, 589 nm, c=0.35 g/100 ml, chloroform

LC-MS (Method 1): $R_t$=2.63 min; MS (ESIpos): m/z=643/645 [M+H]$^+$ $^1$H-NMR (400 MHz, DMSO-d6) δ [ppm]: 1.310 (0.15), 1.358 (16.00), 1.979 (0.12), 2.072 (0.24), 2.088 (0.24), 2.155 (1.70), 3.719 (0.24), 3.805 (0.25), 7.302 (0.26), 7.317 (0.20), 7.400 (0.24), 7.502 (0.87), 7.510 (0.83), 7.521 (3.00), 7.841 (0.45), 7.846 (0.39), 7.863 (0.68), 7.868 (0.64), 7.935 (1.27), 7.958 (0.78), 8.948 (0.41).

$^1$H-NMR (400 MHz, DMSO-d6) δ [ppm]: 8.95 (t, 1H), 7.94 (d, 1H), 7.86 (dd, 1H), 7.71 (br. s, 1H), 7.56-7.48 (m, 5H), 7.45-7.36 (m, 1H), 7.35-7.26 (m, 1H), 3.90-3.66 (m, 3H), 2.23-1.89 (m, 7H), 1.36 (s, 9H).

Example 251A (+)-tert-Butyl 5-{[(6-bromo-3-methyl-2-phenylquinolin-4-yl)carbonyl]amino}-4-(2-chloro-3,6-difluorophenyl)pentanoate (Enantiomer 2)

In the enantiomer separation described in Example 249A, 298 mg (97% purity, ee 98%) of the title compound were obtained as the enantiomer that eluted later.

$R_t$=1.51 min (chiral analytical HPLC; Daicel Chiralpak AD-3, 3 μm, 50 mm×4.6 mm, mobile phase heptane/isopropanol 80:20; flow rate 1 ml/min; detection 220 nm)

$[α]_D^{20}$=+19.1°, 589 nm, c=0.38 g/100 ml, chloroform

LC-MS (Method 1): $R_t$=2.63 min; MS (ESIpos): m/z=643/645 [M+H]$^+$ $^1$H-NMR (400 MHz, DMSO-d6) δ [ppm]: 0.846 (0.07), 0.859 (0.09), 1.087 (0.05), 1.103 (0.06), 1.199 (0.08), 1.256 (0.09), 1.312 (0.15), 1.359 (16.00), 1.515 (0.08), 1.984

(0.14), 2.074 (0.28), 2.090 (0.28), 2.110 (0.26), 2.157 (2.02), 2.323 (0.07), 2.671 (0.04), 3.723 (0.27), 3.806 (0.29), 7.293 (0.28), 7.304 (0.30), 7.318 (0.22), 7.329 (0.20), 7.403 (0.27), 7.493 (0.32), 7.503 (0.92), 7.511 (0.88), 7.523 (3.28), 7.722 (0.07), 7.843 (0.44), 7.865 (0.68), 7.869 (0.67), 7.937 (1.19), 7.959 (0.74), 8.951 (0.47).

$^1$H-NMR (400 MHz, DMSO-d6) δ [ppm]: 8.95 (t, 1H), 7.95 (d, 1H), 7.86 (dd, 1H), 7.72 (br. s, 1H), 7.57-7.47 (m, 5H), 7.45-7.36 (m, 1H), 7.34-7.24 (m, 1H), 3.90-3.65 (m, 3H), 2.22-1.89 (m, 7H), 1.36 (s, 9H).

Example 252A (+/−)-tert-Butyl 5-{[(6-bromo-3-methyl-2-phenylquinolin-4-yl)carbonyl]amino}-4-(2-fluorophenyl)pentanoate (Racemate)

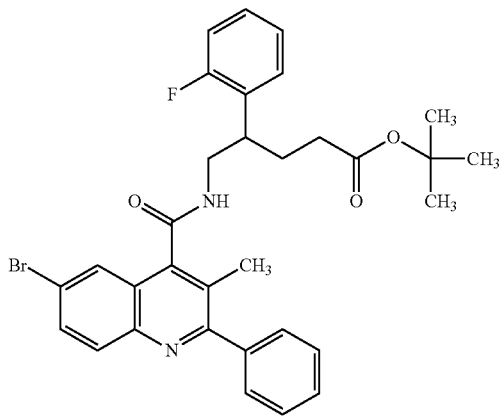 [SMILES: Cc1c(-c2ccccc2)nc2ccc(Br)cc2c1C(=O)NCC(CCC(=O)OC(C)(C)C)c1ccccc1F]

HATU (3.07 g, 8.08 mmol) and DIPEA (2.8 ml, 16 mmol) were added to a mixture of 6-bromo-3-methyl-2-phenylquinoline-4-carboxylic acid (2.30 g, 6.73 mmol, preparable according to WO 2016 146602 A1, p. 51, Example 3A) in DMF (25 ml), and the mixture was stirred at RT for 30 min. (+/−)-tert-Butyl 5-amino-4-(2-fluorophenyl)pentanoate (3.00 g, 60% purity, 6.73 mmol, Example 129A) dissolved in DMF (15 ml) was then added, and the mixture was stirred at 60° C. overnight. Subsequently, ethyl acetate and water (150 ml of each) were added to the mixture, which was agitated. After phase separation, the aqueous phase was extracted once with ethyl acetate (80 ml). The combined organic phases were washed with saturated aqueous sodium chloride solution (200 ml), dried over sodium sulfate, filtered and concentrated, and the residue was taken up in dichloromethane and prepurified by flash column chromatography (100 g silica gel Biotage Snap-Cartridge Ultra, cyclohexane/ethyl acetate gradient 97:3→7:3, Isolera One). The combined target fractions were concentrated and the residue was dissolved in acetonitrile (40 ml) and repurified by preparative HPLC [column: Chromatorex Spring Column C18, 5 μm, 370 mm×100 mm; flow rate: 250 ml/min; detection: 210 nm; temperature: 22° C.; injection: 18 ml, acetonitrile/water gradient 1:1→9:1; run time 45 min]. The combined target fractions were concentrated and the residue was dried under reduced pressure. This gave 2.49 g (98% purity, 61% of theory) of the title compound.

LC-MS (Method 2): $R_t$=1.33 min; MS (ESIpos): m/z=591/593 [M+H]$^+$ $^1$H-NMR (400 MHz, DMSO-d6) δ [ppm]: −0.022 (0.16), 0.007 (0.06), 0.851 (0.03), 1.205 (0.07), 1.230 (0.37), 1.291 (0.07), 1.321 (0.08), 1.366 (16.00), 1.522 (0.07), 1.654 (0.02), 1.679 (0.02), 1.685 (0.03), 1.691 (0.04), 1.704 (0.03), 1.711 (0.04), 1.741 (0.09), 1.749 (0.11), 1.757 (0.24), 1.766 (0.12), 1.774 (0.15), 1.793 (0.16), 1.810 (0.21), 1.818 (0.19), 1.835 (0.15), 1.869 (0.04), 1.910 (0.03), 1.925 (0.03), 1.949 (0.03), 1.957 (0.04), 1.964 (0.03), 1.999 (0.08), 2.021 (0.17), 2.037 (0.25), 2.049 (0.25), 2.074 (1.23), 2.088 (0.95), 2.110 (0.59), 2.297 (0.02), 2.327 (0.02), 2.365 (0.02), 2.669 (0.01), 2.709 (0.01), 3.314 (3.22), 3.339 (0.19), 3.352 (0.19), 3.361 (0.18), 3.387 (0.07), 3.584 (0.08), 3.600 (0.17), 3.616 (0.08), 3.633 (0.08), 3.647 (0.15), 3.665 (0.20), 3.680 (0.25), 3.693 (0.14), 3.724 (0.12), 3.742 (0.18), 3.761 (0.18), 3.779 (0.15), 3.797 (0.11), 3.805 (0.06), 3.817 (0.04), 5.210 (0.02), 5.308 (0.01), 5.364 (0.03), 5.369 (0.03), 5.379 (0.03), 5.384 (0.03), 5.840 (0.02), 5.851 (0.02), 7.142 (0.23), 7.163 (0.37), 7.188 (0.45), 7.203 (0.42), 7.222 (0.30), 7.283 (0.24), 7.298 (0.24), 7.320 (0.10), 7.340 (0.05), 7.396 (0.25), 7.399 (0.25), 7.415 (0.45), 7.433 (0.22), 7.486 (0.24), 7.498 (0.71), 7.505 (0.76), 7.516 (2.97), 7.527 (0.95), 7.679 (0.06), 7.829 (0.36), 7.834 (0.32), 7.851 (0.56), 7.856 (0.52), 7.926 (1.08), 7.948 (0.69), 8.850 (0.24), 8.864 (0.42), 8.878 (0.23), 11.682 (0.15).

$^1$H-NMR (400 MHz, DMSO-d6) δ [ppm]: 8.86 (t, 1H), 7.93 (d, 1H), 7.84 (dd, 1H), 7.68 (br. s, 1H), 7.55-7.47 (m, 5H), 7.44-7.38 (m, 1H), 7.36-7.25 (m, 1H), 7.24-7.12 (m, 2H), 3.84-3.71 (m, 1H), 3.70-3.57 (m, 1H), 3.41-3.32 (m, 1H), 2.21-1.96 (m, 6H), 1.86-1.72 (m, 1H), 1.37 (s, 9H).

Example 253A (+/−)-tert-Butyl 5-{[(6-bromo-3-methyl-2-phenylquinolin-4-yl)carbonyl]amino}-4-[2-(difluoromethoxy)phenyl]pentanoate (Racemate)

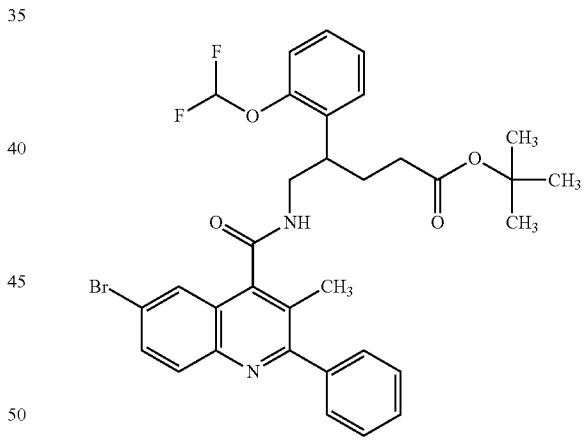

HATU (3.36 g, 8.83 mmol) and DIPEA (3.1 ml, 18 mmol) were added to a mixture of 6-bromo-3-methyl-2-phenylquinoline-4-carboxylic acid (2.52 g, 7.36 mmol, preparable according to WO 2016 146602 A1, p. 51, Example 3A) in DMF (25 ml), and the mixture was stirred at RT for 30 min. (+/−)-tert-Butyl 5-amino-4-[2-(difluoromethoxy)phenyl]pentanoate (2.90 g, 80% purity, 7.36 mmol, Example 130A) dissolved in DMF (15 ml) was then added, and the mixture was stirred at 60° C. overnight. Subsequently, ethyl acetate and water (150 ml of each) were added to the mixture, which was agitated. After phase separation, the aqueous phase was extracted once with ethyl acetate (80 ml). The combined organic phases were washed with saturated aqueous sodium chloride solution (200 ml), dried over sodium sulfate, filtered and concentrated, and the residue was dissolved in hot acetonitrile (100 ml) and purified by preparative HPLC [column: Chromatorex Spring Column C18, 5 μm, 370 mm×100 mm; flow rate: 250 ml/min; detection: 210 nm; temperature: 22° C.; injection: 18 ml, acetonitrile/water gradient 6:4→95:5; run time 37 min]. The combined target fractions were concentrated and the residue was dried under reduced pressure. This gave 4.03 g (98% purity, 84% of theory) of the title compound.

LC-MS (Method 1): R$_t$=2.56 min; MS (ESIpos): m/z=639/641 [M+H]$^+$ $^1$H-NMR (400 MHz, DMSO-d6) δ [ppm]: 1.333 (1.41), 1.356 (16.00), 1.759 (0.42), 2.060 (1.16), 2.070 (0.62), 2.076 (0.47), 2.124 (0.42), 6.998 (0.43), 7.156 (0.47), 7.176 (0.61), 7.183 (0.92), 7.257 (0.45), 7.368 (0.42), 7.423 (0.47), 7.427 (0.46), 7.501 (0.72), 7.508 (0.71), 7.520 (2.29), 7.531 (0.99), 7.534 (0.88), 7.857 (0.56), 7.862 (0.54), 7.931 (1.04), 7.953 (0.66), 8.840 (0.43).

$^1$H-NMR (400 MHz, DMSO-d6) δ [ppm]: 8.84 (t, 1H), 7.94 (d, 1H), 7.85 (dd, 1H), 7.68 (br. s, 1H), 7.56-7.47 (m, 5H), 7.43 (dd, 1H), 7.36-7.22 (m, 2H), 7.20-6.97 (m, 2H), 3.81-3.62 (m, 2H), 3.43-3.34 (m, 1H), 2.18-1.98 (m, 6H), 1.92-1.79 (m, 1H), 1.36 (s, 9H).

Example 254A (+/−)-tert-Butyl 5-{[(6-bromo-3-methyl-2-phenylquinolin-4-yl)carbonyl]amino}-4-(2,6-difluorophenyl)pentanoate (Racemate)

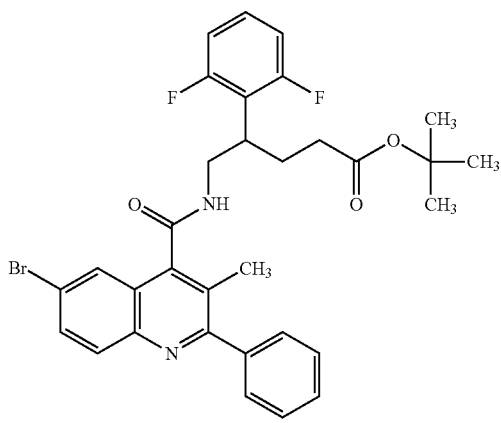 [SMILES: Cc1c(-c2ccccc2)nc2ccc(Br)cc2c1C(=O)NCC(CCC(=O)OC(C)(C)C)c1c(F)cccc1F]

HATU (5.12 g, 13.5 mmol) and DIPEA (4.7 ml, 27 mmol) were added to a mixture of 6-bromo-3-methyl-2-phenylquinoline-4-carboxylic acid (3.84 g, 11.2 mmol, preparable according to WO 2016 146602 A1, p. 51, Example 3A) in DMF (40 ml), and the mixture was stirred at RT for 30 min. (+/−)-tert-Butyl 5-amino-4-(2,6-difluorophenyl)pentanoate (4.00 g, 80% purity, 11.2 mmol, Example 131A) dissolved in DMF (20 ml) was then added, and the mixture was stirred at 60° C. overnight. Subsequently, ethyl acetate and water (150 ml of each) were added to the mixture, which was agitated. After phase separation, the aqueous phase was extracted once with ethyl acetate (80 ml). The combined organic phases were washed with saturated aqueous sodium chloride solution (200 ml), dried over sodium sulfate, filtered and concentrated, and the residue was dissolved in acetonitrile (100 ml) and purified by preparative HPLC [column: Chromatorex Spring Column C18, 5 μm, 370 mm×100 mm; flow rate: 250 ml/min; detection: 210 nm; temperature: 22° C.; injection: 18 ml, acetonitrile/water gradient 6:4→95:5; run time 37 min]. The combined target fractions were concentrated and the residue was dried under reduced pressure. This gave 5.91 g (98% purity, 85% of theory) of the title compound.

LC-MS (Method 1): R$_t$=2.55 min; MS (ESIpos): m/z=609/611 [M+H]$^+$ $^1$H-NMR (400 MHz, DMSO-d6) δ [ppm]: 1.201 (0.08), 1.231 (0.03), 1.272 (0.06), 1.297 (0.04), 1.312 (0.10), 1.361 (16.00), 1.518 (0.07), 1.711 (0.04), 1.742 (0.16), 1.758 (0.40), 1.765 (0.20), 1.774 (0.16), 1.897 (0.21), 1.912 (0.26), 1.936 (0.23), 1.957 (0.11), 2.026 (0.09), 2.044 (0.23), 2.058 (0.29), 2.079 (0.50), 2.105 (0.62), 2.121 (1.21), 2.141 (1.42), 2.326 (0.04), 2.365 (0.02), 2.670 (0.02), 3.509 (0.23), 3.584 (0.16), 3.600 (0.36), 3.615 (0.15), 3.647 (0.03), 3.663 (0.03), 3.701 (0.08), 3.715 (0.15), 3.733 (0.32), 3.749 (0.50), 3.761 (0.38), 3.795 (0.23), 5.314 (0.02), 5.363 (0.02), 5.378 (0.02), 7.053 (0.56), 7.075 (1.05), 7.099 (0.65), 7.329 (0.22), 7.347 (0.28), 7.365 (0.19), 7.488 (0.30), 7.499 (0.85), 7.508 (0.85), 7.518 (3.58), 7.718 (0.08), 7.836 (0.43), 7.859 (0.68), 7.930 (1.14), 7.952 (0.72), 8.934 (0.31), 8.949 (0.60), 8.963 (0.30), 11.681 (0.05).

$^1$H-NMR (400 MHz, DMSO-d6) δ [ppm]: 8.95 (t, 1H), 7.94 (d, 1H), 7.85 (dd, 1H), 7.72 (br. s, 1H), 7.55-7.46 (m, 5H), 7.39-7.29 (m, 1H), 7.08 (t, 2H), 3.85-3.67 (m, 2H), 3.57-3.45 (m, 1H), 2.22-2.01 (m, 6H), 1.98-1.85 (m, 1H), 1.36 (s, 9H).

Example 255A (+/−)-tert-Butyl 5-{[(6-bromo-3-methyl-2-phenylquinolin-4-yl)carbonyl]amino}-4-(2-chloro-3-fluorophenyl)pentanoate (Racemate)

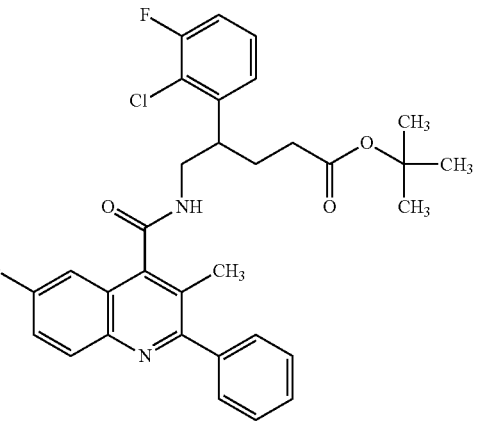

HATU (1.37 g, 3.60 mmol) and DIPEA (1.3 ml, 7.2 mmol) were added to a mixture of 6-bromo-3-methyl-2-phenylquinoline-4-carboxylic acid (1.03 g, 3.00 mmol, preparable according to WO 2016 146602 A1, p. 51, Example 3A) in DMF (12 ml), and the mixture was stirred at RT for 15 min. (+/−)-tert-Butyl 5-amino-4-(2-chloro-3-fluorophenyl)pentanoate (905 mg, 3.00 mmol, not corrected for purity, Example 132A) dissolved in DMF (9 ml) was then added, and the mixture was stirred at 60° C. for 3 h. Subsequently, ethyl acetate and water (100 ml of each) were added to the mixture, which was agitated. After phase separation, the aqueous phase was extracted once with ethyl acetate (80 ml). The combined organic phases were washed with saturated aqueous sodium chloride solution (100 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 98:2→8:2, Isolera One). The combined target fractions were concentrated and the residue was dried under reduced pressure. This gave 855 mg (97% purity, 44% of theory) of the title compound.

LC-MS (Method 1): $R_t$=2.59 min; MS (ESIpos): m/z=625/627 [M+H]$^+$ $^1$H-NMR (400 MHz, DMSO-d6) δ [ppm]: −0.151 (0.02), 0.007 (0.14), 0.144 (0.02), 0.887 (0.03), 1.156 (0.19), 1.174 (0.37), 1.192 (0.19), 1.206 (0.07), 1.232 (0.04), 1.284 (0.08), 1.308 (0.04), 1.328 (0.12), 1.366 (16.00), 1.395 (0.14), 1.522 (0.07), 1.786 (0.05), 1.805 (0.11), 1.820 (0.15), 1.837 (0.19), 1.987 (0.69), 2.018 (0.08), 2.039 (0.17), 2.052 (0.21), 2.068 (0.21), 2.095 (1.18), 2.110 (0.92), 2.131 (0.68), 2.143 (0.72), 2.265 (0.04), 2.320 (0.06), 2.365 (0.02), 2.669 (0.02), 2.709 (0.02), 3.630 (0.22), 3.661 (0.10), 3.743 (0.27), 4.002 (0.05), 4.020 (0.16), 4.038 (0.16), 4.055 (0.05), 7.142 (0.03), 7.279 (0.16), 7.299 (0.32), 7.320 (0.21), 7.362 (0.26), 7.380 (0.55), 7.396 (0.23), 7.415 (0.26), 7.430 (0.23), 7.449 (0.08), 7.476 (0.10), 7.490 (0.27), 7.499 (0.80), 7.508 (0.75), 7.519 (2.46), 7.530 (1.09), 7.646 (0.06), 7.830 (0.39), 7.836 (0.35), 7.853 (0.59), 7.858 (0.56), 7.929 (1.11), 7.951 (0.72), 8.849 (0.24), 8.863 (0.47), 8.878 (0.23).

$^1$H-NMR (400 MHz, DMSO-d6) δ [ppm]: 8.87 (t, 1H), 7.94 (d, 1H), 7.85 (dd, 1H), 7.65 (br. s, 1H), 7.56-7.47 (m, 5H), 7.46-7.35 (m, 2H), 7.34-7.26 (m, 1H), 3.74 (br. s, 2H), 3.67-3.58 (m, 1H), 2.21-2.00 (m, 6H), 1.89-1.77 (m, 1H), 1.37 (s, 9H).

Separation of the Enantiomers:

The title compound (715 mg) was dissolved in methanol (30 ml) and separated into the enantiomers by preparative SFC on a chiral phase (see Examples 256A and 257A) [column: Daicel Chiralcel OZ-H, 5 μm, 250 mm×30 mm; flow rate: 80 ml/min; detection: 210 nm; temperature: 40° C.; injection: 0.5 ml; mobile phase: 85% carbon dioxide/15% methanol; run time 12 min, isocratic]. The combined target fractions were concentrated and the residue was dried under reduced pressure.

Example 256A (−)-tert-Butyl 5-{[(6-bromo-3-methyl-2-phenylquinolin-4-yl)carbonyl]amino}-4-(2-chloro-3-fluorophenyl)pentanoate (Enantiomer 1)

In the enantiomer separation described in Example 255A, 298 mg (100% purity, ee 96%) of the title compound were obtained as the enantiomer that eluted earlier.

$[α]_D^{20}$=−5.1°, 436 nm, c=0.46 g/100 ml, chloroform

LC-MS (Method 1): $R_t$=2.60 min; MS (ESIpos): m/z=625/627 [M+H]$^+$ $^1$H-NMR (400 MHz, DMSO-d6) δ [ppm]: 1.208 (0.07), 1.286 (0.07), 1.329 (0.13), 1.368 (16.00), 1.524 (0.07), 1.821 (0.18), 1.839 (0.23), 2.040 (0.19), 2.054 (0.23), 2.074 (0.29), 2.097 (1.32), 2.111 (1.07), 2.133 (0.84), 2.145 (0.88), 2.266 (0.04), 2.329 (0.03), 2.670 (0.03), 3.632 (0.26), 3.746 (0.33), 7.281 (0.19), 7.301 (0.38), 7.323 (0.26), 7.364 (0.31), 7.382 (0.64), 7.398 (0.28), 7.416 (0.32), 7.431 (0.27), 7.491 (0.32), 7.502 (0.89), 7.509 (0.88), 7.521 (2.85), 7.650 (0.07), 7.833 (0.40), 7.838 (0.39), 7.855 (0.62), 7.860 (0.61), 7.931 (1.12), 7.953 (0.72), 8.852 (0.28), 8.866 (0.53), 8.880 (0.27).

$^1$H-NMR (400 MHz, DMSO-d6) δ [ppm]: 8.87 (t, 1H), 7.94 (d, 1H), 7.85 (dd, 1H), 7.65 (br. s, 1H), 7.56-7.47 (m, 5H), 7.46-7.35 (m, 2H), 7.34-7.26 (m, 1H), 3.75 (br. s, 2H), 3.67-3.58 (m, 1H), 2.22-2.00 (m, 6H), 1.89-1.76 (m, 1H), 1.37 (s, 9H).

Example 257A (+)-tert-Butyl 5-{[(6-bromo-3-methyl-2-phenylquinolin-4-yl)carbonyl]amino}-4-(2-chloro-3-fluorophenyl)pentanoate In the enantiomer separation described in Example 255A, 310 mg (100% purity, ee 96%) of the title compound were obtained as the enantiomer that eluted later.

$[α]_D^{20}$=+8.40, 436 nm, c=0.47 g/100 ml, chloroform

LC-MS (Method 1): $R_t$=2.60 min; MS (ESIpos): m/z=625/627 [M+H]$^+$ $^1$H-NMR (400 MHz, DMSO-d6) δ [ppm]: 1.208 (0.07), 1.285 (0.08), 1.329 (0.15), 1.367 (16.00), 1.524 (0.07), 1.837 (0.24), 2.053 (0.25), 2.074 (0.30), 2.096 (1.35), 2.110 (1.11), 2.132 (0.89), 2.143 (0.92), 2.328 (0.04), 2.367 (0.04), 2.671 (0.04), 3.630 (0.28), 3.743 (0.35), 7.281 (0.20), 7.301 (0.39), 7.322 (0.27), 7.363 (0.33), 7.381 (0.66), 7.398 (0.29), 7.416 (0.33), 7.431 (0.28), 7.502 (0.93), 7.509 (0.95), 7.521 (3.01), 7.651 (0.08), 7.833 (0.42), 7.837 (0.39), 7.855 (0.64), 7.860 (0.61), 7.930 (1.10), 7.953 (0.70), 8.851 (0.29), 8.865 (0.54), 8.879 (0.27).

$^1$H-NMR (400 MHz, DMSO-d6) δ [ppm]: 8.86 (t, 1H), 7.94 (d, 1H), 7.85 (dd, 1H), 7.65 (br. s, 1H), 7.56-7.47 (m, 5H), 7.46-7.35 (m, 2H), 7.34-7.26 (m, 1H), 3.74 (br. s, 2H), 3.68-3.55 (m, 1H), 2.19-2.00 (m, 6H), 1.89-1.76 (m, 1H), 1.37 (s, 9H).

Example 258A (+/−)-tert-Butyl N-[2-{[(6-bromo-3-methyl-2-phenylquinolin-4-yl)carbonyl]amino}-1-(2-chlorophenyl)ethyl]-N-methylglycinate (Racemate)

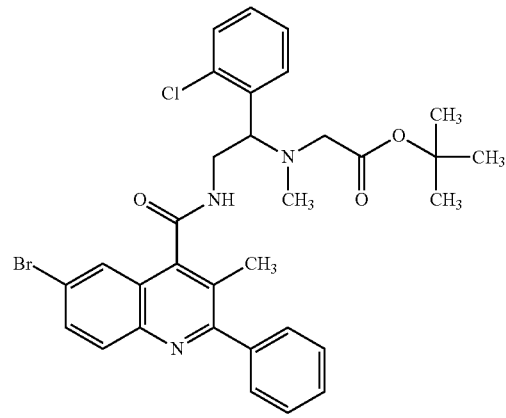 [SMILES: Cc1c(-c2ccccc2)nc2ccc(Br)cc2c1C(=O)NCC(c1ccccc1Cl)N(C)CC(=O)OC(C)(C)C]

HATU (713 mg, 1.87 mmol) and DIPEA (650 μl, 3.7 mmol) were added to a mixture of 6-bromo-3-methyl-2-phenylquinoline-4-carboxylic acid (428 mg, 1.25 mmol, preparable according to WO 2016 146602 A1, p. 51, Example 3A) in DMF (5 ml), and the mixture was stirred at RT for 30 min. (+/−)-tert-Butyl N-[2-amino-1-(2-chlorophenyl)ethyl]-N-methylglycinate (800 mg, 41% purity, 1.01 mmol, Example 133A) dissolved in DMF (3 ml) was then added, and the mixture was stirred at 60° C. overnight. Subsequently, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage, cyclohexane/ethyl acetate 85:15, Isolera One). This was followed by repurification by preparative HPLC (Method 16). The combined target fractions were concentrated and the residue was lyophilized. This gave 150 mg (98% purity, 19% of theory) of the title compound.

LC-MS (Method 1): $R_t$=2.68 min; MS (ESIpos): m/z=622/624 [M+H]$^+$ $^1$H-NMR (400 MHz, DMSO-d6) δ [ppm]: 8.85 (br. s, 1H), 7.94 (d, 1H), 7.85 (dd, 1H), 7.72 (br. d, 2H), 7.58-7.37 (m, 9H), 4.99 (br. s, 1H), 4.14 (br. s, 1H), 4.00 (br. s, 1H), 3.72 (br. s, 1H), 3.53 (br. s, 1H), 2.59 (br. s, 3H), 2.10 (s, 3H), 1.43 (s, 9H).

Example 259A (+/−)-tert-Butyl N-[2-{[(6-bromo-3-methyl-2-phenylquinolin-4-yl)carbonyl]amino}-1-(2-chlorophenyl)ethyl]glycinate (Racemate)

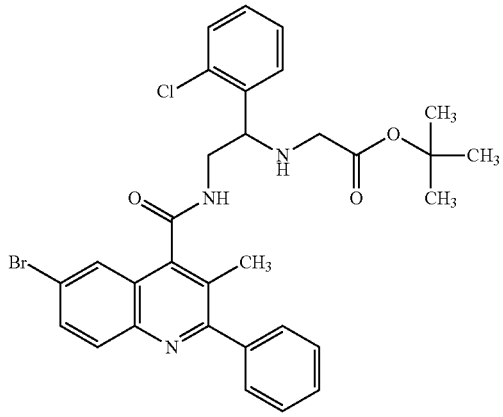 [SMILES: Cc1c(-c2ccccc2)nc2ccc(Br)cc2c1C(=O)NCC(NCC(=O)OC(C)(C)C)c1ccccc1Cl]

HATU (1.10 g, 2.89 mmol) and DIPEA (1.0 ml, 5.8 mmol) were added to a mixture of 6-bromo-3-methyl-2-phenylquinoline-4-carboxylic acid (428 mg, 1.25 mmol, preparable according to WO 2016 146602 A1, p. 51, Example 3A) in DMF (8 ml), and the mixture was stirred at RT for 30 min. (+/−)-tert-Butyl N-[2-amino-1-(2-chlorophenyl)ethyl]glycinate (1.64 mg, 50% purity, 2.89 mmol, Example 134A) dissolved in DMF (4 ml) was then added, and the mixture was stirred at 60° C. overnight. Subsequently, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was taken up in dichloromethane and prepurified by flash column chromatography (100 g of silica gel Biotage, cyclohexane/ethyl acetate 85:15, Isolera One). This was followed by repurification by preparative HPLC (Method 16). The combined target fractions were concentrated and the residue was lyophilized. This gave 300 mg (98% purity, 25% of theory) of the title compound.

LC-MS (Method 1): $R_t$=2.45 min; MS (ESIpos): m/z=608/610 [M+H]$^+$ $^1$H-NMR (400 MHz, DMSO-d6) δ [ppm]: 8.99 (t, 1H), 8.03-7.80 (m, 3H), 7.77-7.42 (m, 9H), 4.99 (br. s, 1H), 4.18-3.99 (br. m, 2H), 3.78-3.64 (br. s, 2H), 2.09 (br. s, 3H), 1.44 (s, 9H).

Example 260A (+/−)-Ethyl [2-{[(6-bromo-3-methyl-2-phenylquinolin-4-yl)carbonyl]amino}-1-(2-chlorophenyl)ethoxy]acetate (Racemate)

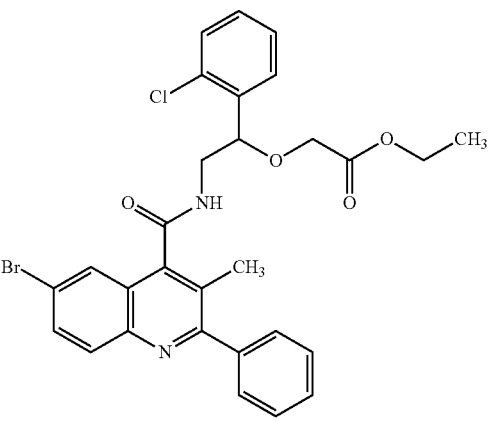 [SMILES: CCOC(=O)COC(CNC(=O)c1c(C)c(-c2ccccc2)nc2ccc(Br)cc12)c1ccccc1Cl]

HATU (2.11 g, 5.55 mmol) and DIPEA (2.7 ml, 16 mmol) were added to a mixture of 6-bromo-3-methyl-2-phenylquinoline-4-carboxylic acid (1.58 g, 4.63 mmol, preparable according to WO 2016 146602 A1, p. 51, Example 3A) in DMF (15 ml), and the mixture was stirred at RT for 15 min. (+/−)-Ethyl [2-amino-1-(2-chlorophenyl)ethoxy]acetate hydrochloride (1.89 g, 72% purity, 4.63 mmol, Example 137A) dissolved in DMF (10 ml) was then added, and the mixture was stirred at 60° C. for 1 h and then allowed to stand at RT for 16 h. Subsequently, the mixture was concentrated, ethyl acetate and water (80 ml each) were added and the mixture was agitated. After phase separation, the aqueous phase was extracted twice with ethyl acetate (80 ml). The combined organic phases were washed with saturated aqueous sodium chloride solution (100 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 93:7→7:3, Isolera One). The combined target fractions were concentrated, and the residue was dried under reduced pressure. This gave 1.11 g (92% purity, 38% of theory) of the title compound.

LC-MS (Method 1): $R_t$=2.41 min; MS (ESIpos): m/z=581/583 [M+H]$^+$ $^1$H-NMR (400 MHz, DMSO-d6) δ [ppm]: 8.97 (t, 1H), 7.96 (d, 1H), 7.90-7.84 (m, 2H), 7.62-7.47 (m, 7H), 7.47-7.36 (m, 2H), 5.20 (t, 1H), 4.21-3.99 (m, 4H), 3.78 (br. s, 2H), 2.26 (s, 3H), 1.13 (t, 3H).

Separation of the Enantiomers:

The title compound (1.10 g) was dissolved in an ethanol/acetonitrile mixture (60 ml) and separated into the enantiomers by preparative SFC on a chiral phase (see Examples 261A and 262A) [column: Daicel Chiralpak AD-H, 5 µm, 250 mm×30 mm; flow rate: 125 ml/min; detection: 210 nm;

Example 261A (+)-Ethyl [2-{[(6-bromo-3-methyl-2-phenylquinolin-4-yl)carbonyl]amino}-1-(2-chlorophenyl)ethoxy]acetate (Enantiomer 1)

In the enantiomer separation described in Example 260A, 440 mg (94% purity, ee 100%) of the title compound were obtained as the enantiomer that eluted earlier.

$[\alpha]_D^{20}$=+24.9°, 489 nm, c=1.00 g/100 ml, methanol

LC-MS (Method 2): $R_t$=1.25 min; MS (ESIpos): m/z=581/583 [M+H]$^+$ $^1$H-NMR (400 MHz, DMSO-d6) δ [ppm]: 1.117 (6.52), 1.135 (13.59), 1.152 (6.76), 2.239 (0.40), 2.261 (16.00), 2.321 (0.41), 3.782 (1.32), 4.001 (2.96), 4.042 (5.07), 4.050 (2.37), 4.068 (6.37), 4.085 (6.28), 4.103 (2.07), 4.137 (4.91), 4.178 (2.81), 5.188 (1.29), 5.203 (2.36), 5.217 (1.26), 7.372 (0.70), 7.376 (0.76), 7.390 (2.05), 7.394 (2.03), 7.409 (2.14), 7.414 (2.18), 7.419 (1.71), 7.422 (1.81), 7.438 (2.33), 7.440 (2.37), 7.456 (1.05), 7.491 (3.36), 7.495 (3.57), 7.513 (7.07), 7.533 (5.81), 7.556 (6.72), 7.575 (2.46), 7.583 (3.18), 7.588 (2.62), 7.603 (2.30), 7.607 (2.01), 7.854 (2.78), 7.873 (4.22), 7.948 (4.77), 7.971 (2.98), 8.951 (1.24), 8.965 (2.55), 8.979 (1.23).

$^1$H-NMR (400 MHz, DMSO-d6) δ [ppm]: 8.97 (t, 1H), 7.96 (d, 1H), 7.89-7.83 (m, 2H), 7.64-7.47 (m, 7H), 7.47-7.35 (m, 2H), 5.20 (t, 1H), 4.19-3.98 (m, 4H), 3.78 (br. s, 2H), 2.26 (s, 3H), 1.13 (t, 3H).

Example 262A (−)-Ethyl [2-{[(6-bromo-3-methyl-2-phenylquinolin-4-yl)carbonyl]amino}-1-(2-chlorophenyl)ethoxy]acetate (Enantiomer 2)

In the enantiomer separation described in Example 260A, 415 mg (100% purity, ee 100%) of the title compound were obtained as the enantiomer that eluted later.

$[\alpha]_D^{20}$=−28.3°, 489 nm, c=1.00 g/100 ml, methanol

LC-MS (Method 2): $R_t$=1.25 min; MS (ESIpos): m/z=581/583 [M−H]$^+$ $^1$H-NMR (400 MHz, DMSO-d6) δ [ppm]: 0.008 (0.63), 1.056 (0.45), 1.117 (7.22), 1.135 (15.06), 1.153 (7.43), 1.235 (0.42), 2.261 (16.00), 2.524 (0.66), 3.781 (1.35), 4.001 (2.99), 4.041 (5.13), 4.050 (2.50), 4.068 (6.74), 4.086 (6.66), 4.103 (2.18), 4.137 (5.01), 4.177 (2.86), 5.188 (1.31), 5.202 (2.36), 5.216 (1.26), 7.372 (0.74), 7.376 (0.87), 7.391 (2.15), 7.395 (2.25), 7.409 (2.27), 7.414 (2.40), 7.419 (1.79), 7.423 (1.97), 7.438 (2.31), 7.441 (2.57), 7.457 (1.07), 7.491 (3.48), 7.495 (3.85), 7.514 (7.54), 7.534 (5.99), 7.555 (6.98), 7.559 (5.88), 7.575 (2.51), 7.583 (3.31), 7.588 (2.71), 7.602 (2.27), 7.606 (2.08), 7.855 (3.17), 7.873 (4.31), 7.948 (5.06), 7.971 (3.14), 8.951 (1.27), 8.965 (2.55), 8.980 (1.20).

$^1$H-NMR (400 MHz, DMSO-d6) δ [ppm]: 8.97 (t, 1H), 7.96 (d, 1H), 7.89-7.83 (m, 2H), 7.62-7.47 (m, 7H), 7.47-7.36 (m, 2H), 5.20 (t, 1H), 4.19-3.98 (m, 4H), 3.78 (br. s, 2H), 2.26 (s, 3H), 1.13 (t, 3H).

Example 263A (+/−)-Methyl {[2-{[(6-bromo-3-methyl-2-phenylquinolin-4-yl)carbonyl]amino}-1-(2-chlorophenyl)ethyl]sulfanyl}acetate (Racemate)

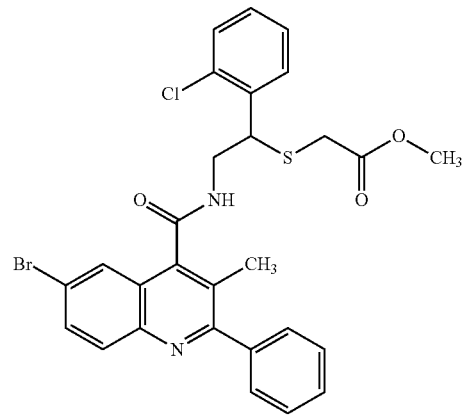 [SMILES: COC(=O)CSC(CNC(=O)c1c(C)c(-c2ccccc2)nc2ccc(Br)cc12)c1ccccc1Cl]

HATU (2.39 g, 6.29 mmol) and DIPEA (2.2 ml, 13 mmol) were added to a mixture of 6-bromo-3-methyl-2-phenylquinoline-4-carboxylic acid (1.44 g, 4.20 mmol, preparable according to WO 2016 146602 A1, p. 51, Example 3A) in DMF (8 ml), and the mixture was stirred at RT for 30 min. (+/−)-Methyl {[2-amino-1-(2-chlorophenyl)ethyl]sulfanyl}acetate (3.27 g, 50% purity, 6.29 mmol, Example 138A) dissolved in DMF (4 ml) was then added, and the mixture was stirred at 60° C. overnight. After cooling to RT, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated, and the residue was dissolved in acetonitrile and prepurified by preparative HPLC (Method 16). The residue was then repurified by flash column chromatography (340 g silica gel Biotage Snap-Cartridge KP-Sil, cyclohexane/ethyl acetate gradient 93:7→6:4, Isolera One). The combined target fractions were concentrated, and the residue was lyophilized. This gave 388 mg (87% purity, 14% of theory) of the title compound.

LC-MS (Method 2): $R_t$=1.20 min; MS (ESIpos): m/z=583/585 [M+H]$^+$

Example 264A (+/−)-Methyl {[2-{[(6-bromo-3-methyl-2-phenylquinolin-4-yl)carbonyl]amino}-1-(2-chlorophenyl)ethyl]sulfonyl}acetate (Racemate)

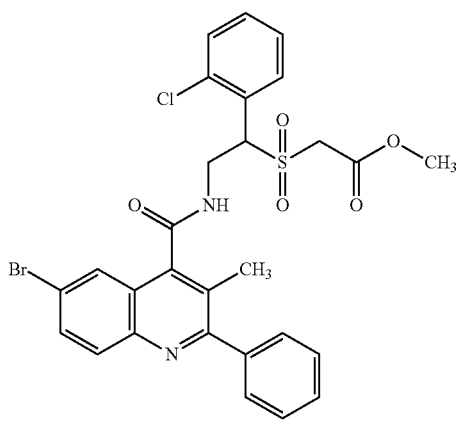 [SMILES: COC(=O)CS(=O)(=O)C(CNC(=O)c1c(C)c(-c2ccccc2)nc2ccc(Br)cc12)c1ccccc1Cl]

HATU (83 mg, 219 μmol) and DIPEA (76 μl, 440 μmol) were added to a mixture of 6-bromo-3-methyl-2-phenylquinoline-4-carboxylic acid (63 mg, 183 μmol, preparable according to WO 2016 146602 A1, p. 51, Example 3A) in DMF (1.5 ml), and the mixture was stirred at RT for 30 min. (+/−)-Methyl {[2-amino-1-(2-chlorophenyl)ethyl]sulfonyl}acetate hydrochloride (60 mg, 183 μmol, Example 141A) dissolved in DMF (0.5 ml) was then added, and the mixture was stirred at 60° C. overnight. After cooling to RT, ethyl acetate and water (150 ml of each) were added to the mixture, which was agitated. After phase separation, the aqueous phase was extracted once with ethyl acetate (80 ml). The combined organic phases were washed with saturated aqueous sodium chloride solution (200 ml), dried over sodium sulfate, filtered and concentrated, and the residue was taken up in dichloromethane and purified by preparative HPLC (Method 17). The combined target fractions were concentrated, and the residue was lyophilized. This gave 66 mg (93% purity, 55% of theory) of the title compound.

LC-MS (Method 1): $R_t$=2.04 min; MS (ESIpos): m/z=615/617 [M+H]$^+$ $^1$H-NMR (400 MHz, DMSO-d6) δ [ppm]: 9.14 (t, 1H), 7.93 (d, 1H), 7.84 (dd, 1H), 7.75-7.56 (m, 3H), 7.55-7.41 (m, 7H), 5.75 (dd, 1H), 4.81 (d, 1H), 4.49 (d, 1H), 4.41 (td, 1H), 4.26-4.10 (m, 1H), 3.75 (s, 3H), 2.02 (br. s, 3H).

Example 265A (+/−)-tert-Butyl 5-{[(6-bromo-3-methyl-2-phenylquinolin-4-yl)carbonyl]amino}-4-(6-chloro-2,3-difluorophenyl)pentanoate (Racemate)

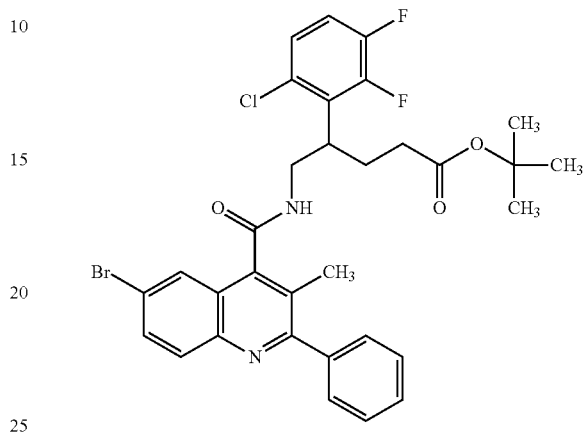

HATU (829 mg, 2.18 mmol) and DIPEA (760 μl, 4.4 mmol) were added to a mixture of 6-bromo-3-methyl-2-phenylquinoline-4-carboxylic acid (621 mg, 1.82 mmol, preparable according to WO 2016 146602 A1, p. 51, Example 3A) in DMF (8 ml), and the mixture was stirred at RT for 15 min. (+/−)-tert-Butyl 5-amino-4-(6-chloro-2,3-difluorophenyl)pentanoate (600 mg, 97% purity, 1.82 mmol, Example 142A) dissolved in DMF (4 ml) was then added, and the mixture was stirred at 60° C. for 3 h, followed by 2 h at RT. Subsequently, ethyl acetate and water (100 ml of each) were added to the mixture, which was agitated. After phase separation, the aqueous phase was extracted once with ethyl acetate (80 ml). The combined organic phases were washed with saturated aqueous sodium chloride solution (100 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 97:3→7:3, Isolera One). The combined target fractions were concentrated and the residue was dried under reduced pressure. This gave 154 mg (100% purity, 13% of theory) of a first batch of the title compound. In addition, a prepurified fraction was obtained, which was taken up in acetonitrile and repurified by preparative HPLC (Method 15). This gave 497 mg (100% purity, 42% of theory, see analysis) of a second batch of the title compound.

LC-MS (Method 2): $R_t$=1.37 min; MS (ESIpos): m/z=643/645 [M+H]$^+$ $^1$H-NMR (400 MHz, DMSO-d6) δ [ppm]: 8.95 (t, 1H), 7.94 (d, 1H), 7.86 (dd, 1H), 7.69 (br. s, 1H), 7.59-7.47 (m, 5H), 7.46-7.32 (m, 2H), 3.81 (br. s, 2H), 3.72 (br. s, 1H), 2.22-1.93 (m, 7H), 1.36 (s, 9H).

Separation of the Enantiomers:

The title compound (480 mg) was dissolved in methanol (25 ml) and separated into the enantiomers by preparative SFC on a chiral phase (see Examples 266A and 267A) [column: Daicel Chiralpak AD SFC, 5 μm, 250 mm×20 mm; flow rate: 80 ml/min; detection: 210 nm; temperature: 40° C.; injection: 0.2 ml; mobile phase: 75% carbon dioxide/

25% methanol; run time 4 min, isocratic]. The combined target fractions were concentrated, and the residue was lyophilized.

Example 266A (−)-tert-Butyl 5-{[(6-bromo-3-methyl-2-phenylquinolin-4-yl)carbonyl]amino}-4-(6-chloro-2,3-difluorophenyl)pentanoate (Enantiomer 1)

In the enantiomer separation described in Example 265A, 154 mg (100% purity, ee 100%) of the title compound were obtained as the enantiomer that eluted earlier.
$[\alpha]_D^{20}$=−32.8°, 589 nm, c=0.29 g/100 ml, methanol
LC-MS (Method 1): $R_t$=2.61 min; MS (ESIpos): m/z=643/645 [M+H]$^+$
$^1$H-NMR (400 MHz, DMSO-d6) δ [ppm]: 8.95 (t, 1H), 7.94 (d, 1H), 7.86 (dd, 1H), 7.72 (br. s, 1H), 7.57-7.46 (m, 5H), 7.46-7.32 (m, 2H), 3.91-3.63 (m, 3H), 2.25-1.86 (m, 7H), 1.36 (s, 9H).

Example 267A (+)-tert-Butyl 5-{[(6-bromo-3-methyl-2-phenylquinolin-4-yl)carbonyl]amino}-4-(6-chloro-2,3-difluorophenyl)pentanoate (Enantiomer 2)

In the enantiomer separation described in Example 265A, 162 mg (97% purity, ee 93%) of the title compound were obtained as the enantiomer that eluted later.
$[\alpha]_D^{20}$=+28.7°, 589 nm, c=0.39 g/100 ml, methanol
LC-MS (Method 1): $R_t$=2.60 min; MS (ESIpos): m/z=643/645 [M+H]$^+$
$^1$H-NMR (400 MHz, DMSO-d6) δ [ppm]: 8.95 (t, 1H), 7.94 (d, 1H), 7.86 (dd, 1H), 7.72 (br. s, 1H), 7.55-7.46 (m, 5H), 7.46-7.33 (m, 2H), 3.89-3.65 (m, 3H), 2.25-1.86 (m, 7H), 1.36 (s, 9H).

Example 268A (+/−)-Methyl 5-{[(6-bromo-3-methyl-2-phenylquinolin-4-yl)carbonyl]amino}-4-[2-(trifluoromethyl)phenyl]pentanoate (Racemate)

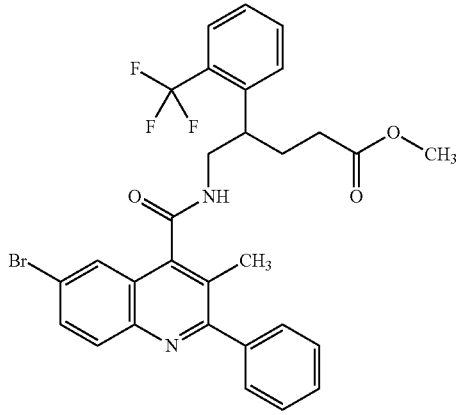 [SMILES: COC(=O)CCC(CNC(=O)c1c(C)c(-c2ccccc2)nc2ccc(Br)cc12)c1ccccc1C(F)(F)F]

HATU (7.02 g, 18.5 mmol) and DIPEA (6.4 ml, 37 mmol) were added to a mixture of 6-bromo-3-methyl-2-phenylquinoline-4-carboxylic acid (5.26 g, 15.4 mmol, preparable according to WO 2016 146602 A1, p. 51, Example 3A) in DMF (60 ml), and the mixture was stirred at RT for 30 min. (+/−)-Methyl 5-amino-4-[2-(trifluoromethyl)phenyl]pentanoate (5.50 g, 77% purity, 15.4 mmol, Example 143A) dissolved in DMF (30 ml) was then added, and the mixture was stirred at 60° C. overnight. After cooling to RT, ethyl acetate and water (150 ml of each) were added to the mixture, which was agitated. After phase separation, the aqueous phase was extracted once with ethyl acetate (80 ml). The combined organic phases were washed with saturated aqueous sodium chloride solution (200 ml), dried over sodium sulfate, filtered and concentrated, and the residue was taken up in dichloromethane and purified by flash column chromatography (340 g of silica gel Biotage Snap-Cartridge KP-Sil, cyclohexane/ethyl acetate gradient 97:3→7:3, Isolera One). The combined target fractions were concentrated and the residue was dried under reduced pressure. This gave 4.31 g (96% purity, 45% of theory) of the title compound.
LC-MS (Method 1): $R_t$=2.33 min; MS (ESIpos): m/z=599/601 [M+H]$^+$
$^1$H-NMR (400 MHz, DMSO-d6) δ [ppm]: 8.92 (t, 1H), 7.95 (d, 1H), 7.85 (dd, 1H), 7.80-7.60 (m, 4H), 7.58-7.45 (m, 6H), 3.85-3.72 (m, 1H), 3.72-3.62 (m, 1H), 3.52 (s, 3H), 3.40-3.30 (m, 1H), 2.26-2.04 (m, 6H), 2.02-1.89 (m, 1H).

Example 269A (+/−)-tert-Butyl 5-{[(6-bromo-3-methyl-2-phenylquinolin-4-yl)carbonyl]amino}-4-(5-fluoro-2-methylphenyl)pentanoate (Racemate)

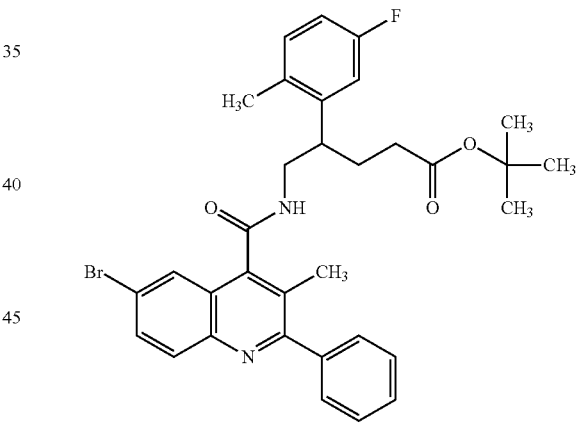

HATU (899 mg, 2.37 mmol) and DIPEA (820 µl, 4.7 mmol) were added to a mixture of 6-bromo-3-methyl-2-phenylquinoline-4-carboxylic acid (675 mg, 1.97 mmol, preparable according to WO 2016 146602 A1, p. 51, Example 3A) in DMF (9 ml), and the mixture was stirred at RT for 15 min. (+/−)-tert-Butyl 5-amino-4-(5-fluoro-2-methylphenyl)pentanoate (600 mg, 92% purity, 1.97 mmol, Example 144A) dissolved in DMF (4.8 ml) was then added, and the mixture was stirred at 60° C. for 3 h, followed by two days at RT. Subsequently, ethyl acetate and water (100 ml of each) were added to the mixture, which was agitated. After phase separation, the aqueous phase was extracted once with ethyl acetate (80 ml). The combined organic phases were washed with saturated aqueous sodium chloride solution (100 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate gradient 97:3→7:3, Isolera One). The combined target fractions were concentrated, and the residue was dried under reduced pressure. This gave 625 mg (100% purity, 52% of theory) of the title compound.

LC-MS (Method 1): $R_t$=2.61 min; MS (ESIpos): m/z=605/607 [M+H]$^+$ $^1$H-NMR (400 MHz, DMSO-d6) δ [ppm]: 0.889 (0.03), 1.156 (0.17), 1.174 (0.34), 1.192 (0.17), 1.207 (0.07), 1.233 (0.06), 1.303 (0.07), 1.336 (0.11), 1.367 (16.00), 1.396 (0.60), 1.524 (0.07), 1.744 (0.05), 1.761 (0.12), 1.778 (0.15), 1.786 (0.15), 1.795 (0.19), 1.819 (0.16), 1.834 (0.08), 1.988 (0.79), 2.001 (0.21), 2.018 (0.22), 2.038 (0.21), 2.051 (0.22), 2.069 (0.82), 2.086 (1.18), 2.104 (0.81), 2.292 (2.47), 2.669 (0.03), 2.730 (0.08), 2.889 (0.07), 3.510 (0.11), 3.523 (0.17), 3.543 (0.19), 3.557 (0.22), 3.570 (0.13), 3.708 (0.15), 3.725 (0.22), 3.745 (0.19), 3.759 (0.16), 3.779 (0.10), 4.002 (0.05), 4.020 (0.15), 4.038 (0.15), 4.056 (0.05), 6.918 (0.14), 6.938 (0.27), 6.954 (0.15), 7.155 (0.34), 7.162 (0.35), 7.189 (0.63), 7.204 (0.37), 7.225 (0.27), 7.489 (0.25), 7.499 (0.76), 7.507 (0.72), 7.518 (2.36), 7.529 (1.05), 7.647 (0.10), 7.834 (0.40), 7.839 (0.37), 7.856 (0.60), 7.861 (0.59), 7.932 (1.08), 7.955 (0.69), 8.829 (0.23), 8.843 (0.35), 8.858 (0.22).

$^1$H-NMR (400 MHz, DMSO-d6) δ [ppm]: 8.84 (t, 1H), 7.94 (d, 1H), 7.85 (dd, 1H), 7.65 (br. s, 1H), 7.56-7.45 (m, 5H), 7.25-7.13 (m, 2H), 6.94 (td, 1H), 3.81-3.68 (m, 1H), 3.59-3.47 (m, 1H), 3.38-3.29 (m, 1H, partially obscured), 2.29 (s, 3H), 2.18-1.94 (m, 6H), 1.86-1.72 (m, 1H), 1.37 (s, 9H).

Separation of the Enantiomers:

The title compound (400 mg) was dissolved in methanol (18 ml) and separated into the enantiomers by preparative SFC on a chiral phase (see Examples 270A and 271A) [column: Daicel Chiralcel OX-H, 5 μm, 250 mm×20 mm; flow rate: 80 ml/min; detection: 210 nm; temperature: 40° C.; injection: 0.3 ml; mobile phase: 80% carbon dioxide/20% ethanol; run time 6 min, isocratic]. The combined target fractions were concentrated and the residue was lyophilized.

Example 270A (−)-tert-Butyl 5-{[(6-bromo-3-methyl-2-phenylquinolin-4-yl)carbonyl]amino}-4-(5-fluoro-2-methylphenyl)pentanoate (Enantiomer 1)

In the enantiomer separation described in Example 269A, 152 mg (100% purity, ee 100%) of the title compound were obtained as the enantiomer that eluted earlier.

$[α]_D^{20}$=−13.7°, 589 nm, c=0.38 g/100 ml, methanol

LC-MS (Method 1): $R_t$=2.73 min; MS (ESIpos): m/z=605/607 [M+H]$^+$ $^1$H-NMR (400 MHz, DMSO-d6) δ [ppm]: 1.368 (16.00), 2.070 (0.80), 2.087 (1.16), 2.105 (0.78), 2.293 (2.42), 7.190 (0.62), 7.500 (0.72), 7.508 (0.68), 7.519 (2.28), 7.530 (1.02), 7.534 (0.89), 7.857 (0.58), 7.862 (0.57), 7.933 (1.05), 7.955 (0.68).

$^1$H-NMR (400 MHz, DMSO-d6) δ [ppm]: 8.84 (t, 1H), 7.94 (d, 1H), 7.85 (dd, 1H), 7.65 (br. s, 1H), 7.56-7.46 (m, 5H), 7.25-7.14 (m, 2H), 6.94 (td, 1H), 3.81-3.68 (m, 1H), 3.59-3.49 (m, 1H), 3.37-3.30 (1H, obscured), 2.29 (s, 3H), 2.18-1.95 (m, 6H), 1.85-1.73 (m, 1H), 1.37 (s, 9H).

Example 271A (+)-tert-Butyl 5-{[(6-bromo-3-methyl-2-phenylquinolin-4-yl)carbonyl]amino}-4-(5-fluoro-2-methylphenyl)pentanoate (Enantiomer 2)

In the enantiomer separation described in Example 269A, 150 mg (100% purity, ee 97%) of the title compound were obtained as the enantiomer that eluted later.

$[α]_D^{20}$=+16.9°, 589 nm, c=0.37 g/100 ml, methanol

LC-MS (Method 1): $R_t$=2.73 min; MS (ESIpos): m/z=605/507 [M+H]$^+$ $^1$H-NMR (400 MHz, DMSO-d6) δ [ppm]: 8.84 (t, 1H), 7.94 (d, 1H), 7.85 (dd, 1H), 7.65 (br. s, 1H), 7.56-7.45 (m, 5H), 7.25-7.13 (m, 2H), 6.94 (td, 1H), 3.81-3.68 (m, 1H), 3.59-3.48 (m, 1H), 3.37-3.30 (1H, obscured), 2.29 (s, 3H), 2.17-1.95 (m, 6H), 1.85-1.72 (m, 1H), 1.37 (s, 9H).

Example 272A (+/−)-tert-Butyl 5-{[(6-bromo-3-methyl-2-phenylquinolin-4-yl)carbonyl]amino}-4-[2-(trifluoromethoxy)phenyl]pentanoate (Racemate)

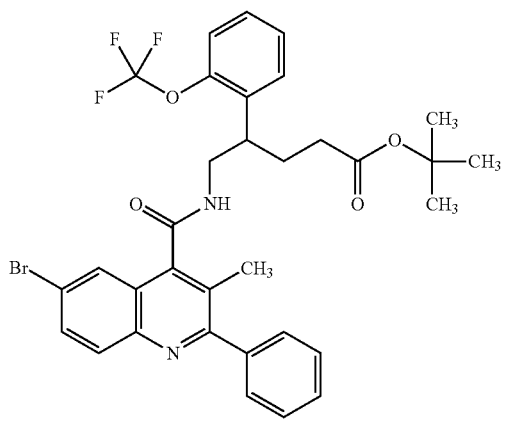 [SMILES: Cc1c(-c2ccccc2)nc2ccc(Br)cc2c1C(=O)NCC(CCC(=O)OC(C)(C)C)c1ccccc1OC(F)(F)F]

HATU (3.41 g, 8.96 mmol) and DIPEA (3.1 ml, 18 mmol) were added to a mixture of 6-bromo-3-methyl-2-phenylquinoline-4-carboxylic acid (2.56 g, 7.47 mmol, preparable according to WO 2016 146602 A1, p. 51, Example 3A) in DMF (30 ml), and the mixture was stirred at RT for 30 min. (+/−)-tert-Butyl 5-amino-4-[2-(trifluoromethoxy)phenyl]pentanoate (3.00 g, 83% purity, 7.47 mmol, Example 145A) dissolved in DMF (10 ml) was then added, and the mixture was stirred at 60° C. overnight. Subsequently, ethyl acetate and water (150 ml of each) were added to the mixture, which was agitated. After phase separation, the aqueous phase was extracted once with ethyl acetate (80 ml). The combined organic phases were washed with saturated aqueous sodium chloride solution (200 ml), dried over sodium sulfate, filtered and concentrated, and the residue was taken up in dichloromethane and purified by flash column chromatography (100 g of silica gel Biotage Snap-Cartridge KP-Sil, cyclohexane/ethyl acetate gradient 97:3→7:3, Isolera One). The combined target fractions were concentrated, and the residue was dried under reduced pressure. This gave 3.79 g (98% purity, 76% of theory) of the title compound.

LC-MS (Method 2): $R_t$=1.40 min; MS (ESIpos): m/z=657/659 [M+H]$^+$ $^1$H-NMR (400 MHz, DMSO-d6) δ [ppm]: 1.357 (16.00), 1.371 (0.55), 1.397 (3.24), 2.060 (0.44), 2.075 (1.67), 2.148 (0.51), 7.359 (0.52), 7.398 (0.71), 7.408 (0.54), 7.417 (0.67), 7.504 (0.92), 7.511 (0.82), 7.523 (2.03), 7.530 (1.95), 7.562 (0.55), 7.838 (0.42), 7.861 (0.65), 7.865 (0.54), 7.937 (1.07), 7.959 (0.70), 8.875 (0.47).

$^1$H-NMR (400 MHz, DMSO-d6) δ [ppm]: 8.87 (t, 1H), 7.95 (d, 1H), 7.85 (dd, 1H), 7.67 (br s, 1H), 7.60-7.47 (m, 6H), 7.46-7.31 (m, 3H), 3.81-3.58 (m, 2H), 3.46-3.34 (m, 1H), 2.21-2.02 (m, 6H), 1.89-1.76 (m, 1H), 1.36 (s, 9H).

Separation of the Enantiomers:

The title compound (3.50 g) was taken up in hot isopropanol (55 ml), filtered and separated into the enantiomers by preparative SFC on a chiral phase (see Examples 273A and 274A) [column: Daicel Chiralpak OD, 20 µm 360 mm×50 mm; flow rate: 300 ml/min; detection: 210 nm; temperature: 40° C.; injection: 1.0 ml; mobile phase: 80% carbon dioxide/20% isopropanol; run time 7.8 min, isocratic]. The combined target fractions were concentrated and the residue was dried under reduced pressure.

Example 273A (+)-tert-Butyl 5-{[(6-bromo-3-methyl-2-phenylquinolin-4-yl)carbonyl]amino}-4-[2-(trifluoromethoxy)phenyl]pentanoate (Enantiomer 1)

In the enantiomer separation described in Example 272A, 1.10 g (98% purity, ee 100%) of the title compound were obtained as the enantiomer that eluted earlier.

$[\alpha]_D^{20}$=+17.0°, 589 nm, c=0.50 g/100 ml, methanol

LC-MS (Method 1): $R_t$=2.67 min; MS (ESIpos): m/z=657/659 [M+H]$^+$ $^1$H-NMR (400 MHz, DMSO-d6) δ [ppm]: 8.88 (t, 1H), 7.95 (d, 1H), 7.85 (dd, 1H), 7.68 (br. s, 1H), 7.60-7.47 (m, 6H), 7.45-7.33 (m, 3H), 3.83-3.59 (m, 2H), 3.46-3.36 (m, 1H), 2.24-2.00 (m, 6H), 1.91-1.76 (m, 1H), 1.36 (s, 9H).

Example 274A (−)-tert-Butyl 5-{[(6-bromo-3-methyl-2-phenylquinolin-4-yl)carbonyl]amino}-4-[2-(trifluoromethoxy)phenyl]pentanoate (Enantiomer 2)

In the enantiomer separation described in Example 272A, 1.10 g (95% purity, ee 98%) of the title compound were obtained as the enantiomer that eluted later.

$[\alpha]_D^{20}$=−19.7°, 589 nm, c=0.31 g/100 ml, methanol

LC-MS (Method 1): $R_t$=2.67 min; MS (ESIpos): m/z=657/659 [M+H]$^+$ $^1$H-NMR (400 MHz, DMSO-d6) δ [ppm]: 8.88 (t, 1H), 7.95 (d, 1H), 7.85 (dd, 1H), 7.67 (br. s, 1H), 7.60-7.47 (m, 6H), 7.45-7.32 (m, 3H), 3.83-3.60 (m, 2H), 3.46-3.35 (m, 1H), 2.26-1.99 (m, 6H), 1.90-1.76 (m, 1H), 1.36 (s, 9H).

Example 275A (+/−)-tert-Butyl 5-{[(6-bromo-3-chloro-2-phenylquinolin-4-yl)carbonyl]amino}-4-(2-chlorophenyl)pentanoate (Racemate)

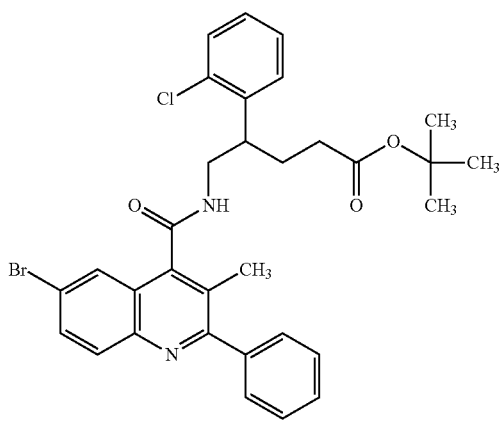 [SMILES: Cc1c(-c2ccccc2)nc2ccc(Br)cc2c1C(=O)NCC(CCC(=O)OC(C)(C)C)c1ccccc1Cl]

HATU (3.14 g, 8.25 mmol) and DIPEA (2.9 ml, 16 mmol) were added to a mixture of 6-bromo-3-chloro-2-phenylquinoline-4-carboxylic acid (1.99 g, 5.50 mmol, not corrected for purity, preparable according to WO 2016 146602 A1, p. 70, Example 37A) in DMF (30 ml), and the mixture was stirred at RT for 20 min. (+/−)-tert-Butyl 5-amino-4-(2-chlorophenyl)pentanoate (2.34 g, 8.25 mmol, Example 121A) dissolved in DMF (10 ml) was then added, and the mixture was stirred at 60° C. overnight. After cooling to RT, ethyl acetate and water (75 ml of each) were added to the mixture, which was agitated. After phase separation, the aqueous phase was extracted once with ethyl acetate. The combined organic phases were washed with saturated aqueous sodium chloride solution, dried over sodium sulfate, filtered and concentrated, and the residue was purified by flash column chromatography (100 g silica gel Biotage Snap-Cartridge KP-Sil, cyclohexane/ethyl acetate gradient 97:3→85:15, Isolera One). The combined target fractions were concentrated, and the residue was dried under reduced pressure. This gave 2.17 g (98% purity, 62% of theory) of the title compound.

LC-MS (Method 1): $R_t$=2.68 min; MS (ESIpos): m/z=627/629/631 [M+H]$^+$ $^1$H-NMR (400 MHz, DMSO-d6) δ [ppm]: 9.00 (t, 1H), 8.01 (d, 1H), 7.96 (dd, 1H), 7.71-7.64 (m, 3H), 7.58-7.43 (m, 5H), 7.41-7.34 (m, 1H), 7.31-7.24 (m, 1H), 3.77-3.67 (m, 2H), 3.66-3.56 (m, 1H), 2.17-1.99 (m, 3H), 1.90-1.76 (m, 1H), 1.36 (s, 9H).

Separation of the Enantiomers:

The title compound (2.0 g) was dissolved in ethanol (15 ml) and separated into the enantiomers by preparative HPLC on a chiral phase (see Examples 276A and 277A) [column: Daicel Chiralpak IA, 5 µm 250 mm×30 mm; flow rate: 60 ml/min; detection: 240 nm; temperature: 30° C.; injection: 0.1 ml; mobile phase: 80% heptane/20% isopropanol; run time 7.5 min, isocratic]. The combined target fractions were concentrated and the residue was dried under reduced pressure.

Example 276A (−)-tert-Butyl 5-{[(6-bromo-3-chloro-2-phenylquinolin-4-yl)carbonyl]amino}-4-(2-chlorophenyl)pentanoate (Enantiomer 1)

In the enantiomer separation described in Example 275A, 734 mg (100% purity, ee 99%) of the title compound were obtained as the enantiomer that eluted earlier.

$R_t$=1.45 min (chiral analytical HPLC; Daicel Chiralpak IA-3, 3 µm, 50 mm×4.6 mm, mobile phase heptane/isopropanol 80:20; flow rate 1 ml/min; detection 220 nm)

$[\alpha]_D^{20}$=−6.5°, 589 nm, c=0.38 g/100 ml, methanol

LC-MS (Method 1): $R_t$=2.66 min; MS (ESIpos): m/z=627/629/631 [M+H]$^+$ $^1$H-NMR (400 MHz, DMSO-d6) δ [ppm]: 9.00 (t, 1H), 8.01 (d, 1H), 7.96 (dd, 1H), 7.71-7.63 (m, 3H), 7.58-7.42 (m, 5H), 7.38 (t, 1H), 7.31-7.22 (m, 1H), 3.79-3.67 (m, 2H), 3.65-3.54 (m, 1H), 2.15-2.00 (m, 3H), 1.92-1.75 (m, 1H), 1.36 (s, 9H).

Example 277A (+)-tert-Butyl 5-{[(6-bromo-3-chloro-2-phenylquinolin-4-yl)carbonyl]amino}-4-(2-chlorophenyl)pentanoate (Enantiomer 2)

In the enantiomer separation described in Example 275A, 751 mg (100% purity, ee 99%) of the title compound were obtained as the enantiomer that eluted later.

$R_t$=1.92 min (chiral analytical HPLC; Daicel Chiralpak IA-3, 3 µm, 50 mm×4.6 mm, mobile phase heptane/isopropanol 80:20; flow rate 1 ml/min; detection 220 nm)

$[\alpha]_D^{20}$=+7.4°, 589 nm, c=0.38 g/100 ml, methanol

LC-MS (Method 1): $R_t$=2.67 min; MS (ESIpos): m/z=627/629/631 $[M+H]^+$ $^1$H-NMR (400 MHz, DMSO-d6) δ [ppm]: 9.00 (t, 1H), 8.01 (d, 1H), 7.96 (dd, 1H), 7.71-7.63 (m, 3H), 7.58-7.43 (m, 5H), 7.38 (t, 1H), 7.31-7.23 (m, 1H), 3.78-3.66 (m, 2H), 3.65-3.56 (m, 1H), 2.17-2.00 (m, 3H), 1.91-1.75 (m, 1H), 1.36 (s, 9H).

Example 278A (+/−)-tert-Butyl 4-cyano-4-[2-(trifluoromethyl)phenyl]butanoate (Racemate)

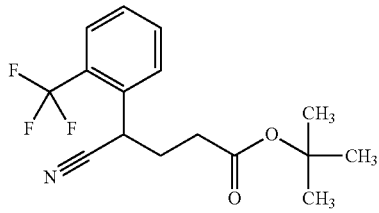 [SMILES: CC(C)(C)OC(=O)CCC(C#N)c1ccccc1C(F)(F)F]

To a solution of [2-(trifluoromethyl)phenyl]acetonitrile (14.8 g, 79.8 mmol, CAS-RN 3038-47-9, commercially available) in THF (100 ml) under argon was slowly added while stirring a 2 M solution of LDA in THF (48 ml, 96 mmol), in the course of which the internal temperature was kept between −70° C. and −60° C. The mixture was allowed to come to 0° C. and, after 15 min, cooled back down again to −70° C. Subsequently, a solution of tert-butyl 3-bromopropanoate (15 ml, 96 mmol) in THF (70 ml) was slowly added dropwise thereto at −70° C. while stirring. Stirring of the mixture was continued overnight, in the course of which the cooling bath (dry ice/acetone) was allowed to come gradually to RT. Subsequently, water (200 ml) and ethyl acetate (250 ml) were gradually added at about 0° C. to the mixture, which was agitated. After phase separation, the aqueous phase was extracted once with ethyl acetate (150 ml). The combined organic phases were washed once with saturated aqueous sodium chloride solution (250 ml), dried over sodium sulfate, filtered and concentrated, and the residue was taken up in dichloromethane and purified by flash column chromatography (400 g of silica gel, cyclohexane/ethyl acetate 9:1). The combined target fractions were concentrated, and the residue was dried under reduced pressure. This gave 18.7 g (100% purity, 75% of theory) of the title compound.

LC-MS (Method 1): $R_t$=2.26 min; MS (ESIpos): m/z=314 $[M+H]^+$ $^1$H-NMR (400 MHz, DMSO-d6) δ [ppm]: 7.91-7.75 (m, 3H), 7.62 (t, 1H), 4.35 (dd, 1H), 2.44-2.33 (m, 2H), 2.31-2.19 (m, 1H), 2.18-2.06 (m, 1H), 1.39 (s, 9H).

Example 279A (+/−)-tert-Butyl 5-amino-4-[2-(trifluoromethyl)phenyl]pentanoate (Racemate)

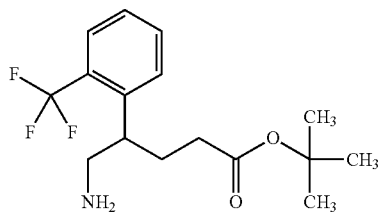 [SMILES: CC(C)(C)OC(=O)CCC(CN)c1ccccc1C(F)(F)F]

To a solution of (+/−)-tert-butyl 4-cyano-4-[2-(trifluoromethyl)phenyl]butanoate (18.6 g, 59.5 mmol, Example 278A) in tert-butanol (200 ml) was added Raney nickel (3.49 g, 59.5 mmol), and hydrogenation was effected at standard pressure for 24 h. Thereafter, the catalyst was filtered off through kieselguhr, which was washed through twice with tert-butanol (50 ml each time). The filtrate was concentrated, and the residue was dried under reduced pressure. This gave 17.8 g (82% purity, 77% of theory) of the title compound.

LC-MS (Method 1): $R_t$=1.23 min; MS (ESIpos): m/z=318 $[M+H]^+$

Example 280A (+/−)-tert-Butyl 5-{[(6-bromo-3-chloro-2-phenylquinolin-4-yl)carbonyl]amino}-4-[2-(trifluoromethyl)phenyl]pentanoate (Racemate)

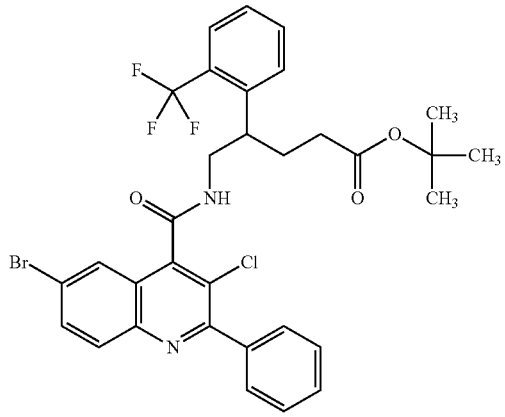 [SMILES: CC(C)(C)OC(=O)CCC(CNC(=O)c1c(Cl)c(-c2ccccc2)nc2ccc(Br)cc12)c1ccccc1C(F)(F)F]

HATU (629 mg, 1.65 mmol) and DIPEA (580 µl, 3.3 mmol) were added to a mixture of 6-bromo-3-chloro-2-phenylquinoline-4-carboxylic acid (500 mg, 1.38 mmol, not corrected for purity, preparable according to WO 2016 146602 A1, p. 70, Example 37A) in DMF (6.0 ml), and the mixture was stirred at RT for 15 min. (+/−)-tert-Butyl 5-amino-4-[2-(trifluoromethyl)phenyl]pentanoate (535 mg, 82% purity, 1.38 mmol, Example 279A) dissolved in DMF (3 ml) was then added, and the mixture was stirred at 60° C. for 18 h. Subsequently, ethyl acetate and water (100 ml of each) were added to the mixture, which was agitated. After phase separation, the aqueous phase was extracted once with ethyl acetate (80 ml). The combined organic phases were washed once with saturated aqueous sodium chloride solution (100 ml), dried over sodium sulfate, filtered and concentrated, and the residue was purified by flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. This gave 324 mg (100% purity, 36% of theory) of the title compound.

LC-MS (Method 1): $R_t$=2.69 min; MS (ESIpos): m/z=661/663 [M+H]$^+$ $^1$H-NMR (400 MHz, DMSO-d6) δ [ppm]: 9.06 (t, 1H), 8.03 (d, 1H), 7.97 (dd, 1H), 7.81-7.60 (m, 6H), 7.59-7.44 (m, 4H), 3.82-3.59 (m, 2H), 3.40-3.32 (m, 1H), 2.26-1.84 (m, 4H), 1.34 (s, 9H).

Separation of the Enantiomers:

The title compound (228 mg) was dissolved in isopropanol (6.7 ml) and separated into the enantiomers by preparative HPLC on a chiral phase (see Examples 281A and 282A) [column: Daicel Chiralcel OZ-H, 5 μm, 250 mm×20 mm; flow rate: 20 ml/min; detection: 220 nm; injection: 0.17 ml; mobile phase: 80% heptane/20% isopropanol; run time 20 min, isocratic]. The combined target fractions were concentrated and the residue was dried under reduced pressure.

Example 281A (−)-tert-Butyl 5-{[(6-bromo-3-chloro-2-phenylquinolin-4-yl)carbonyl]amino}-4-[2-(trifluoromethyl)phenyl]pentanoate (Enantiomer 1)

In the enantiomer separation described in Example 280A, 108 mg (100% purity, ee 97%) of the title compound were obtained as the enantiomer that eluted earlier.

$R_t$=1.52 min (chiral analytical HPLC; Daicel Chiralpak OZ-3, 3 μm, 50 mm×4.6 mm, mobile phase heptane/isopropanol 80:20; flow rate 1 ml/min; detection 220 nm)

[α]$_D^{20}$=−8.9°, 589 nm, c=0.45 g/100 ml, methanol

LC-MS (Method 1): $R_t$=2.68 min; MS (ESIpos): m/z=661/663 [M+H]$^+$ $^1$H-NMR (400 MHz, DMSO-d6) δ [ppm]: 9.06 (t, 1H), 8.03 (d, 1H), 7.97 (dd, 1H), 7.80-7.60 (m, 6H), 7.59-7.52 (m, 3H), 7.49 (t, 1H), 3.81-3.60 (m, 2H), 3.4-3.3 (1H, obscured), 2.26-1.81 (m, 4H), 1.37-1.30 (m, 9H).

Example 282A (+)-tert-Butyl 5-{[(6-bromo-3-chloro-2-phenylquinolin-4-yl)carbonyl]amino}-4-[2-(trifluoromethyl)phenyl]pentanoate (Enantiomer 2)

In the enantiomer separation described in Example 280A, 102 mg (100% purity, ee 97%) of the title compound were obtained as the enantiomer that eluted later.

$R_t$=2.57 min (chiral analytical HPLC; Daicel Chiralpak OZ-3, 3 μm, 50 mm×4.6 mm, mobile phase heptane/isopropanol 80:20; flow rate 1 ml/min; detection 220 nm)

[α]$_D^{20}$=+10.0°, 589 nm, c=0.37 g/100 ml, methanol

LC-MS (Method 1): $R_t$=2.68 min; MS (ESIpos): m/z=661/663 [M+H]$^+$ $^1$H-NMR (400 MHz, DMSO-d6) δ [ppm]: 9.06 (t, 1H), 8.03 (d, 1H), 7.97 (dd, 1H), 7.80-7.60 (m, 6H), 7.59-7.51 (m, 3H), 7.49 (t, 1H), 3.80-3.61 (m, 2H), 3.4-3.3 (m, 1H, partially obscured), 2.25-1.82 (m, 4H), 1.37-1.30 (m, 9H).

Example 283A (+/−)-tert-Butyl 4-(2-chlorophenyl)-5-{[(6-ethynyl-3-methyl-2-phenylquinolin-4-yl)carbonyl]amino}pentanoate (Racemate)

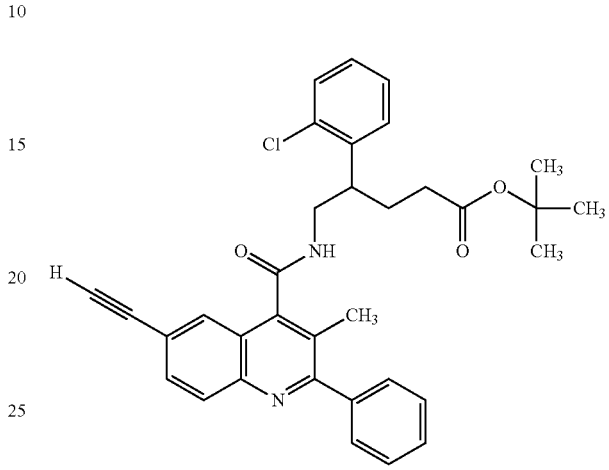

HATU (810 mg, 2.13 mmol) and DIPEA (740 μl, 4.3 mmol) were added to a mixture of 6-ethynyl-3-methyl-2-phenylquinoline-4-carboxylic acid (540 mg, 95% purity, 1.77 mmol, preparable according to WO 2016 146602 A1, p. 109, Example 97A) in DMF (8 ml), and the mixture was stirred at RT for 15 min. (+/−)-tert-Butyl 5-amino-4-(2-chlorophenyl)pentanoate (603 mg, 83% purity, 1.77 mmol, Example 121A) dissolved in DMF (4 ml) was then added, and the mixture was stirred at 60° C. overnight. After cooling to RT, ethyl acetate and water (150 ml of each) were added to the mixture, which was agitated. After phase separation, the aqueous phase was extracted once with ethyl acetate (100 ml). The combined organic phases were washed with saturated aqueous sodium chloride solution (200 ml), dried over sodium sulfate, filtered and concentrated, and the residue was purified by flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. This gave 626 mg (100% purity, 64% of theory) of the title compound.

LC-MS (Method 1): $R_t$=2.50 min; MS (ESIpos): m/z=553 [M+H]$^+$ $^1$H-NMR (400 MHz, DMSO-d6) δ [ppm]: 8.83 (t, 1H), 7.97 (d, 1H), 7.72 (dd, 1H), 7.7-7.4 (br. m, 1H), 7.56-7.48 (m, 6H), 7.44 (d, 1H), 7.37 (t, 1H), 7.26 (t, 1H), 4.42 (s, 1H), 3.86-3.50 (m, 3H), 2.26-1.97 (m, 6H), 1.91-1.72 (m, 1H), 1.35 (s, 9H).

Separation of the Enantiomers:

The title compound (481 mg) was dissolved in a mixture of ethanol (3.5 ml) and heptane (3.5 ml) and separated into the enantiomers by preparative HPLC on a chiral phase (see Examples 284A and 285A) [column: Daicel Chiralcel OX-H, 5 μm, 250 mm×20 mm; flow rate: 15 ml/min; detection: 220 nm; injection: 0.13 ml; mobile phase: 80% heptane/20% ethanol; run time 10 min, isocratic]. The combined target fractions were concentrated, and the residue was lyophilized.

Example 284A (−)-tert-Butyl 4-(2-chlorophenyl)-5-{[(6-ethynyl-3-methyl-2-phenylquinolin-4-yl)carbonyl]amino}pentanoate (Enantiomer 1)

In the enantiomer separation described in Example 283A, 205 mg (98% purity, ee 99%) of the title compound were obtained as the enantiomer that eluted earlier.
$[\alpha]_D^{20}$=−17.9°, 589 nm, c=0.44 g/100 ml, methanol
LC-MS (Method 1): $R_t$=2.48 min; MS (ESIpos): m/z=553 [M+H]$^+$
$^1$H-NMR (400 MHz, DMSO-d6) δ [ppm]: 8.83 (t, 1H), 7.97 (d, 1H), 7.72 (dd, 1H), 7.7-7.4 (br. m, 1H), 7.56-7.47 (m, 6H), 7.44 (d, 1H), 7.37 (t, 1H), 7.26 (t, 1H), 4.42 (s, 1H), 3.84-3.51 (m, 3H), 2.23-1.94 (m, 6H), 1.89-1.71 (m, 1H), 1.37 (s, 9H).

Example 285A (+)-tert-Butyl 4-(2-chlorophenyl)-5-{[(6-ethynyl-3-methyl-2-phenylquinolin-4-yl)carbonyl]amino}pentanoate (Enantiomer 2)

In the enantiomer separation described in Example 283A, 217 mg (100% purity, ee 99%) of the title compound were obtained as the enantiomer that eluted later.
$[\alpha]_D^{20}$=+15.9°, 589 nm, c=0.44 g/100 ml, methanol
LC-MS (Method 1): $R_t$=2.48 min; MS (ESIpos): m/z=553 [M+H]$^+$
$^1$H-NMR (400 MHz, DMSO-d6) δ [ppm]: 8.83 (t, 1H), 7.97 (d, 1H), 7.72 (dd, 1H), 7.7-7.4 (br. m, 1H), 7.56-7.48 (m, 6H), 7.44 (d, 1H), 7.37 (t, 1H), 7.26 (t, 1H), 4.41 (s, 1H), 3.84-3.52 (m, 3H), 2.24-1.98 (m, 6H), 1.90-1.74 (m, 1H), 1.37 (s, 9H).

Example 286A (+/−)-tert-Butyl 5-{[(6-bromo-3-chloro-2-phenylquinolin-4-yl)carbonyl]amino}-4-(2-chloro-3,6-difluorophenyl)pentanoate (Racemate)

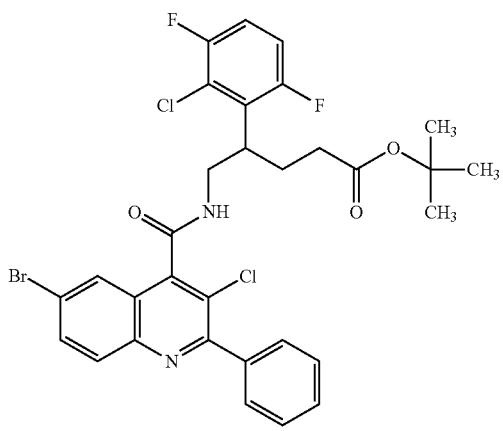 [SMILES: CC(C)(C)OC(=O)CCC(CNC(=O)c1c(Cl)c(-c2ccccc2)nc2ccc(Br)cc12)c1c(F)ccc(F)c1Cl]

HATU (629 mg, 1.65 mmol) and DIPEA (580 μl, 3.3 mmol) were added to a mixture of 6-bromo-3-chloro-2-phenylquinoline-4-carboxylic acid (500 mg, 1.38 mmol, not corrected for purity, preparable according to WO 2016 146602 A1, p. 70, Example 37A) in DMF (6.0 ml), and the mixture was stirred at RT for 15 min. (+/−)-tert-Butyl 5-amino-4-(2-chloro-3,6-difluorophenyl)pentanoate (548 mg, 81% purity, 1.38 mmol, Example 128A) dissolved in DMF (3 ml) was then added, and the mixture was stirred at 60° C. for 3 h at RT. After cooling to RT, ethyl acetate and water (100 ml of each) were added to the mixture, which was agitated. After phase separation, the aqueous phase was extracted once with ethyl acetate (80 ml). The combined organic phases were washed once with saturated aqueous sodium chloride solution (100 ml), dried over sodium sulfate, filtered and concentrated, and the residue was purified by flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. This gave 296 mg (100% purity, 32% of theory) of the title compound.
LC-MS (Method 1): $R_t$=2.67 min; MS (ESIpos): m/z=663/665/667 [M+H]$^+$
$^1$H-NMR (400 MHz, DMSO-d6) δ [ppm]: 9.10 (t, 1H), 8.02 (d, 1H), 7.98 (dd, 1H), 7.75-7.63 (m, 3H), 7.59-7.50 (m, 3H), 7.41 (td, 1H), 7.30 (td, 1H), 3.91-3.63 (m, 3H), 2.23-1.86 (m, 4H), 1.36 (s, 9H).
Separation of the Enantiomers:
The title compound (215 mg) was dissolved in ethanol (6 ml) and separated into the enantiomers by preparative HPLC on a chiral phase (see Examples 287A and 288A) [column: Daicel Chiralpak AD-H, 5 μm, 250 mm×30 mm; flow rate: 40 ml/min; detection: 240 nm; temperature: 30° C.; injection: 0.35 ml; mobile phase: 80% heptane/20% isopropanol; isocratic]. The combined target fractions were concentrated and the residue was lyophilized from acetonitrile/water.

Example 287A (−)-tert-Butyl 5-{[(6-bromo-3-chloro-2-phenylquinolin-4-yl)carbonyl]amino}-4-(2-chloro-3,6-difluorophenyl)pentanoate (Enantiomer 1)

In the enantiomer separation described in Example 286A, 66 mg (96% purity, ee 99%) of the title compound were obtained as the enantiomer that eluted earlier.
$R_t$=1.28 min (chiral analytical HPLC; Daicel Chiralpak AD 3 μm, 50 mm×4.6 mm, mobile phase heptane/isopropanol 80:20; flow rate 1 ml/min; detection 220 nm)
$[\alpha]_D^{20}$=−27.1°, 589 nm, c=0.38 g/100 ml, methanol
LC-MS (Method 1): $R_t$=2.64 min; MS (ESIpos): m/z=663/665/667 [M+H]$^+$
$^1$H-NMR (400 MHz, DMSO-d6) δ [ppm]: 9.10 (t, 1H), 8.02 (d, 1H), 7.98 (dd, 1H), 7.77-7.61 (m, 3H), 7.59-7.50 (m, 3H), 7.41 (td, 1H), 7.30 (td, 1H), 3.91-3.65 (m, 3H), 2.22-2.04 (m, 3H), 1.98 (br. s, 1H), 1.36 (s, 9H).

Example 288A (+)-tert-Butyl 5-{[(6-bromo-3-chloro-2-phenylquinolin-4-yl)carbonyl]amino}-4-(2-chloro-3,6-difluorophenyl)pentanoate (Enantiomer 2)

In the enantiomer separation described in Example 286A, 64 mg (92% purity, ee 98%) of the title compound were obtained as the enantiomer that eluted later.
$R_t$=1.42 min (chiral analytical HPLC; Daicel Chiralpak AD 3 μm, 50 mm×4.6 mm, mobile phase heptane/isopropanol 80:20; flow rate 1 ml/min; detection 220 nm)
$[\alpha]_D^{20}$=+24.9°, 589 nm, c=0.38 g/100 ml, methanol
LC-MS (Method 1): $R_t$=2.65 min; MS (ESIpos): m/z=663/665/667 [M+H]$^+$ ¹H-NMR (400 MHz, DMSO-d6) δ [ppm]: 9.10 (t, 1H), 8.02 (d, 1H), 7.98 (dd, 1H), 7.75-7.62 (m, 3H), 7.59-7.50 (m, 3H), 7.41 (td, 1H), 7.30 (td, 1H), 4.17-3.64 (m, 3H, partially obscured), 2.24-2.03 (m, 3H), 1.98 (br. s, 1H), 1.36 (s, 9H).

Example 289A (+/−)-tert-Butyl 5-{[(6-bromo-3-methyl-2-phenylquinolin-4-yl)carbonyl]amino}-4-(pyridin-2-yl)pentanoate (Racemate)

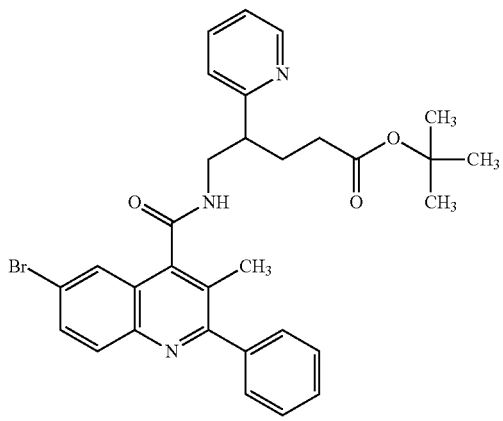 [SMILES: Cc1c(-c2ccccc2)nc2ccc(Br)cc2c1C(=O)NCC(CCC(=O)OC(C)(C)C)c1ccccn1]

6-Bromo-3-methyl-2-phenylquinoline-4-carboxylic acid (213 mg, 622 μmol, preparable according to WO 2016 146602 A1, p. 70, Example 37A) was taken up in DMF (7 ml), and HATU (284 mg, 747 μmol) was added. After stirring at RT and under nitrogen for 5 min, DIPEA (330 μl, 1.9 mmol) was added, and the mixture was stirred at RT for another 30 min. Subsequently, (+/−)tert-butyl 5-amino-4-(pyridin-2-yl)pentanoate (187 mg, 747 μmol, Example 146A, not corrected for purity) was dissolved in 20 ml of DMF and added to the reaction mixture. Stirring at RT was continued for 2 h. The reaction mixture was directly (without further work-up) purified chromatographically (Biotage Isolera Four, LiChroprep RP-18 (40-63 μm); gradient 30%-90% acetonitrile in 0.1% aqueous ammonia solution). This gave 100 mg (80% purity, 1% of theory over three steps) of the title compound.

LC-MS (Method 6): R$_t$=1.43 min; MS (ESIpos): m/z=574/576 [M+H]⁺

Example 290A (+/−)-tert-Butyl 5-{[(6-bromo-3-methyl-2-phenylquinolin-4-yl)carbonyl]amino}-4-[2-fluoro-6-(trifluoromethyl)phenyl]pentanoate (Racemate)

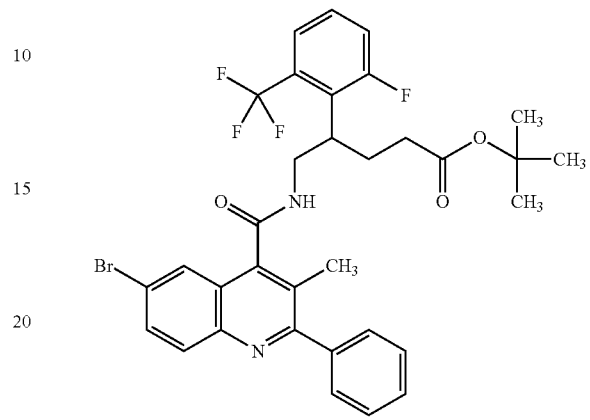

HATU (1.25 g, 3.29 mmol) and DIPEA (1.1 ml, 6.6 mmol) were added to a solution of 6-bromo-3-methyl-2-phenylquinoline-4-carboxylic acid (939 mg, 2.74 mmol, preparable according to WO 2016 146602 A1, p. 51, Example 3A) in DMF (32 ml). The mixture was stirred at RT for 15 min. A solution of (+/−)-tert-butyl 5-amino-4-[2-fluoro-6-(trifluoromethyl)phenyl]pentanoate (1.00 mg, 92% purity, 2.74 mmol, Example 147A) in a little DMF was added, and the reaction mixture was stirred at 60° C. for 1 h, and then at RT for another 30 min. 200 ml each of water and ethyl acetate were added to the mixture. The phases were separated. The organic phase was washed with 200 ml of water and then 200 ml of a saturated sodium chloride solution, dried over sodium sulfate and concentrated under reduced pressure. The residue was dissolved in a little DMSO and purified by preparative HPLC (Method 28). Suitable fractions were concentrated together and dried under reduced pressure. This gave 1.29 g (93% purity, 66% of theory) of the title compound.

LC-MS (Method 1): R$_t$=2.64 min; MS (ESIpos): m/z=659/661 [M+H]⁺

¹H-NMR (400 MHz, DMSO-d6) δ [ppm]: 8.95 (t, 1H), 7.95 (d, 1H), 7.85 (dd, 1H), 7.80-7.45 (m, 9H), 3.93 (br. s, 1H), 3.74 (br. s, 1H), 3.33 (1H, obscured, tentative), 2.28-2.00 (m, 7H), 1.34 (s, 9H).

Separation of the Enantiomers:

The resulting racemate (1.2 g) was dissolved in 140 ml of acetonitrile and a little methanol and, in portions, separated into the enantiomers (see Examples 291A and 292A) by preparative SFC on a chiral phase [method: column Daicel Chiralpak AD-H 5 μm, 250 mm×20 mm; mobile phase carbon dioxide/isopropanol 80:20 isocratic; flow rate 80 ml/min; temperature 40° C.; detection 210 nm]. The combined target fractions were concentrated, and the residue was lyophilized in acetonitrile/water.

Example 291A tert-Butyl 5-{[(6-bromo-3-methyl-2-phenylquinolin-4-yl)carbonyl]amino}-4-[2-fluoro-6-(trifluoromethyl)phenyl]pentanoate (Enantiomer 1)

In the enantiomer separation described in Example 290A, 444 mg (97% purity, ee 100%) of the title compound were obtained as the enantiomer that eluted earlier.

R$_t$=1.41 min (chiral analytical HPLC; Daicel Chiralpak AD 3 μm, 100 mm×4 mm, mobile phase carbon dioxide/isopropanol 80:20; flow rate 3 ml/min; temperature 40° C.; detection 210 nm)

LC-MS (Method 1): R$_t$=2.62 min; MS (ESIpos): m/z=659/661 [M+H]$^+$ $^1$H-NMR (400 MHz, DMSO-d6) δ [ppm]: −0.008 (0.41), 1.030 (1.89), 1.046 (1.90), 1.336 (16.00), 2.086 (0.51), 2.107 (0.49), 2.125 (0.65), 2.152 (0.53), 2.167 (0.49), 7.507 (0.85), 7.513 (0.68), 7.525 (1.40), 7.538 (1.61), 7.555 (0.43), 7.562 (0.47), 7.573 (0.50), 7.595 (0.46), 7.861 (0.58), 7.867 (0.57), 7.939 (1.06), 7.961 (0.69).

Example 292A tert-Butyl 5-{[(6-bromo-3-methyl-2-phenylquinolin-4-yl)carbonyl]amino}-4-[2-fluoro-6-(trifluoromethyl)phenyl]pentanoate (Enantiomer 2)

In the enantiomer separation described in Example 290A, 416 mg (97% purity, ee 100%) of the title compound were obtained as the enantiomer that eluted later.

R$_t$=2.01 min (chiral analytical HPLC; Daicel Chiralpak AD 3 μm, 100 mm×4 mm, mobile phase carbon dioxide/isopropanol 80:20; flow rate 3 ml/min; temperature 40° C.; detection 210 nm)

LC-MS (Method 1): R$_t$=2.62 min; MS (ESIpos): m/z=659 [M+H]$^+$ $^1$H-NMR (400 MHz, DMSO-d6) δ [ppm]: −0.008 (0.56), 0.008 (0.56), 1.030 (1.54), 1.045 (1.55), 1.336 (16.00), 2.085 (0.51), 2.107 (0.48), 2.124 (0.65), 2.152 (0.53), 2.167 (0.49), 7.506 (0.83), 7.513 (0.67), 7.524 (1.38), 7.537 (1.60), 7.555 (0.43), 7.562 (0.46), 7.573 (0.51), 7.594 (0.46), 7.861 (0.58), 7.867 (0.58), 7.938 (1.06), 7.961 (0.68).

Example 293A (+/−)-tert-Butyl 5-{[(6-bromo-3-methyl-2-phenylquinolin-4-yl)carbonyl]amino}-4-(2,3,5,6-tetrafluorophenyl)pentanoate (Racemate)

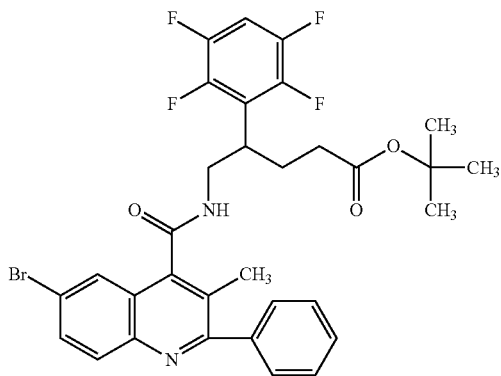 [SMILES: Cc1c(-c2ccccc2)nc2ccc(Br)cc2c1C(=O)NCC(CCC(=O)OC(C)(C)C)c1c(F)c(F)cc(F)c1F]

HATU (791 mg, 2.08 mmol) and DIPEA (720 μl, 4.2 mmol) were added to a solution of 6-bromo-3-methyl-2-phenylquinoline-4-carboxylic acid (593 mg, 1.73 mmol, preparable according to WO 2016 146602 A1, p. 51, Example 3A) in DMF (20 ml). The mixture was stirred at RT for 15 min. A solution of (+/−)-tert-butyl 5-amino-4-(2,3,5,6-tetrafluorophenyl)pentanoate (586 mg, 95% purity, 1.73 mmol, Example 148A) in a little DMF was added, and the mixture was stirred at 60° C. for 1 h, and then at RT overnight. 100 ml each of water and ethyl acetate were added to the mixture. The phases were separated. The aqueous phase was extracted with 100 ml of ethyl acetate. The combined organic phases were washed with 200 ml of a saturated aqueous sodium chloride solution, dried over sodium sulfate and concentrated under reduced pressure. The residue was dissolved in a little DMSO and purified by preparative HPLC (Method 28). The combined target fractions were concentrated, and the residue was dried under reduced pressure. This gave 700 mg (100% purity, 63% of theory) of the title compound.

LC-MS (Method 1): R$_t$=2.56 min; MS (ESIpos): m/z=645/647 [M+H]$^+$ $^1$H-NMR (400 MHz, DMSO-d6) δ [ppm]: −0.008 (0.52), 0.008 (0.56), 1.366 (16.00), 2.073 (0.62), 2.156 (1.15), 2.178 (0.49), 2.196 (0.50), 2.212 (0.40), 2.228 (0.44), 3.789 (0.44), 3.805 (0.64), 7.506 (0.79), 7.513 (0.77), 7.524 (2.69), 7.535 (1.15), 7.539 (1.01), 7.849 (0.47), 7.854 (0.43), 7.871 (0.67), 7.877 (0.67), 7.941 (1.24), 7.964 (0.76), 8.981 (0.50).

Separation of the Enantiomers:

The title compound (658 mg) was dissolved in methanol (30 ml) and separated into the enantiomers by preparative SFC on a chiral phase (see Examples 294A and 295A) [column: column Daicel Chiralpak AD-H 5 μm, 250 mm×20 mm; mobile phase carbon dioxide/isopropanol 80:20 isocratic; flow rate 80 ml/min; temperature 40° C.; detection 210 nm; isocratic]. The combined target fractions were concentrated, and the residue was lyophilized in acetonitrile/water.

Example 294A tert-Butyl 5-{[(6-bromo-3-methyl-2-phenylquinolin-4-yl)carbonyl]amino}-4-(2,3,5,6-tetrafluorophenyl)pentanoate (Enantiomer 1)

In the enantiomer separation described in Example 293A, 266 mg (100% purity, ee 100%) of the title compound were obtained as the enantiomer that eluted earlier.

R$_t$=1.37 min (chiral analytical HPLC; Daicel Chiralpak AD 3 μm, 100 mm×4 mm, mobile phase carbon dioxide/isopropanol 80:20; flow rate 3 ml/min; temperature 40° C.; detection 210 nm)

Example 295A tert-Butyl 5-{[(6-bromo-3-methyl-2-phenylquinolin-4-yl)carbonyl]amino}-4-(2,3,5,6-tetrafluorophenyl)pentanoate (Enantiomer 2)

In the enantiomer separation described in Example 293A, 275 mg (99% purity, ee 99%) of the title compound were obtained as the enantiomer that eluted later.

R$_t$=1.67 min (chiral analytical HPLC; Daicel Chiralpak AD 3 μm, 100 mm×4 mm, mobile phase carbon dioxide/isopropanol 80:20; flow rate 3 ml/min; temperature 40° C.; detection 210 nm)

Example 296A (+/−)-tert-Butyl 5-{[(6-bromo-3-methyl-2-phenylquinolin-4-yl)carbonyl]amino}-4-(2,3,5-trifluorophenyl)pentanoate (Racemate)

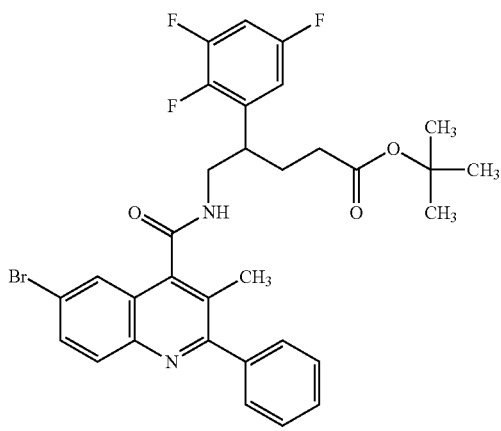

HATU (289 mg, 760 µmol) and DIPEA (260 µl, 1.5 mmol) were added to a solution of 6-bromo-3-methyl-2-phenylquinoline-4-carboxylic acid (217 mg, 633 µmol, preparable according to WO 2016 146602 A1, p. 51, Example 3A) in DMF (8.6 ml). The mixture was stirred at RT for 15 min. A solution of (+/−)-tert-butyl 5-amino-4-(2,3,5-trifluorophenyl)pentanoate (200 mg, 96% purity, 633 µmol, Example 149A) in a little DMF was added, and the mixture was stirred at 60° C. for 3 h. Water and ethyl acetate (100 ml each) were added to the mixture. The phases were separated. The aqueous phase was extracted with ethyl acetate (50 ml). The combined organic phases were washed with saturated sodium chloride solution (100 ml), dried over sodium sulfate and concentrated under reduced pressure. The residue was dissolved in a little dichloromethane and purified by flash column chromatography (Biotage 50 g silica gel, cyclohexane/ethyl acetate gradient 100:0→80:20). The clean (according to TLC) fractions were concentrated and the residue was dried under reduced pressure. This gave 115 mg (100% purity, 29% of theory, see analysis) of a first batch of the title compound. A contaminated fraction obtained was concentrated and the residue was purified by preparative HPLC (Method 32). The combined target fractions were concentrated, and the residue was dried under reduced pressure. This gave 25 mg (100% purity, 6% of theory) of a second batch of the title compound.

LC-MS (Method 1): $R_t$=2.56 min; MS (ESIpos): m/z=627/629 $[M+H]^+$ $^1$H-NMR (400 MHz, DMSO-d6) δ [ppm]: 1.371 (16.00), 1.398 (9.99), 1.826 (0.18), 2.038 (0.21), 2.127 (0.89), 3.413 (0.18), 3.714 (0.27), 7.233 (0.22), 7.413 (0.17), 7.504 (0.77), 7.512 (0.75), 7.523 (2.51), 7.839 (0.38), 7.844 (0.35), 7.861 (0.58), 7.866 (0.56), 7.935 (1.13), 7.957 (0.72), 8.889 (0.46).

$^1$H-NMR (400 MHz, DMSO-d6) δ [ppm]: 8.89 (t, 1H), 7.94 (d, 1H), 7.85 (dd, 1H), 7.66 (br. s, 1H), 7.55-7.48 (m, 5H), 7.46-7.34 (m, 1H), 7.30-7.17 (m, 1H), 3.86-3.63 (m, 2H), 3.48-3.37 (m, 1H), 2.23-1.93 (m, 6H), 1.90-1.75 (m, 1H), 1.37 (s, 9H).

Separation of the Enantiomers:

The title compound (108 mg) was dissolved in methanol (12 ml) and separated into the enantiomers by preparative SFC on a chiral phase (see Examples 297A and 298A) [column: column Daicel Chiralpak AD-H 5 µm, 250 mm×20 mm; mobile phase carbon dioxide/isopropanol 80:20 isocratic; flow rate 80 ml/min; temperature 40° C.; detection 210 nm; isocratic]. The combined target fractions were concentrated, and the residue was lyophilized in acetonitrile/water.

Example 297A tert-Butyl 5-{[(6-bromo-3-methyl-2-phenylquinolin-4-yl)carbonyl]amino}-4-(2,3,5-trifluorophenyl)pentanoate (Enantiomer 1)

In the enantiomer separation described in Example 296A, 39 mg (97% purity, ee 100%) of the title compound were obtained as the enantiomer that eluted earlier.

$R_t$=0.82 min (chiral analytical HPLC; Daicel Chiralpak AD 3 µm, 100 mm×4 mm, mobile phase carbon dioxide/isopropanol 75:25; flow rate 3 ml/min; temperature 40° C.; detection 210 nm)

Example 298A tert-Butyl 5-{[(6-bromo-3-methyl-2-phenylquinolin-4-yl)carbonyl]amino}-4-(2,3,5-trifluorophenyl)pentanoate (Enantiomer 2)

In the enantiomer separation described in Example 296A, 41 mg (99% purity, ee 99%) of the title compound were obtained as the enantiomer that eluted later.

$R_t$=1.03 min (chiral analytical HPLC; Daicel Chiralpak AD 3 µm, 100 mm×4 mm, mobile phase carbon dioxide/isopropanol 75:25; flow rate 3 ml/min; temperature 40° C.; detection 210 nm)

Example 299A (+/−)-tert-Butyl 5-{[(6-bromo-3-methyl-2-phenylquinolin-4-yl)carbonyl]amino}-4-(2,3,6-trichlorophenyl)pentanoate (Racemate)

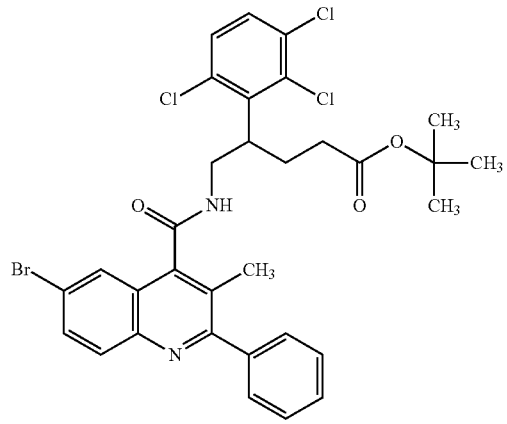 [SMILES: Cc1c(-c2ccccc2)nc2ccc(Br)cc2c1C(=O)NCC(CCC(=O)OC(C)(C)C)c1c(Cl)ccc(Cl)c1Cl]

HATU (806 mg, 2.12 mmol) and DIPEA (740 µl, 4.2 mmol) were added to a solution of 6-bromo-3-methyl-2-phenylquinoline-4-carboxylic acid (604 mg, 1.77 mmol, preparable according to WO 2016 146602 A1, p. 51, Example 3A) in DMF (20 ml). The mixture was stirred at RT for 15 min. A solution of (+/−)-tert-butyl 5-amino-4-(2,3,6- trichlorophenyl)pentanoate (700 mg, 89% purity, 1.77 mmol, Example 150A) in a little DMF was added, and the mixture was stirred at 60° C. for 1 h, followed by 30 min at RT. Water and ethyl acetate (100 ml each) were added to the mixture. The phases were separated. The organic phase was washed with water (200 ml) and then with saturated aqueous sodium chloride solution (200 ml), dried over sodium sulfate and concentrated under reduced pressure. The residue was dissolved in a little DMSO and purified by preparative HPLC (Method 28). The combined target fractions were concentrated under reduced pressure, and the residue was dried under reduced pressure. This gave 745 mg (100% purity, 62% of theory) of the title compound.

LC-MS (Method 1): $R_t$=2.78 min; MS (ESIpos): m/z=675/677/679 [M+H]$^+$ $^1$H-NMR (400 MHz, DMSO-d6) δ [ppm]: −0.008 (1.61), 0.008 (1.78), 1.331 (0.43), 1.349 (15.88), 1.353 (16.00), 2.073 (1.05), 2.092 (0.49), 2.106 (0.54), 2.120 (0.68), 2.133 (1.11), 2.146 (1.43), 2.163 (1.36), 2.179 (3.06), 2.523 (0.43), 4.067 (0.43), 4.090 (0.45), 7.472 (0.45), 7.494 (0.94), 7.504 (1.43), 7.509 (1.14), 7.512 (1.16), 7.528 (4.20), 7.550 (1.61), 7.582 (0.54), 7.591 (0.58), 7.604 (0.41), 7.841 (0.50), 7.847 (0.60), 7.864 (0.75), 7.869 (0.95), 7.876 (0.57), 7.935 (1.21), 7.942 (1.11), 7.958 (0.77), 7.964 (0.67), 8.920 (0.47), 8.935 (0.54).

Separation of the Enantiomers:

The title compound (604 mg) was dissolved in isopropanol (12 ml) and separated into the enantiomers by preparative HPLC on a chiral phase (see Examples 300A and 301A) [column: Daicel Chiralpak IE, 5 μm, 250 mm×20 mm; mobile phase heptane/isopropanol 80:20 isocratic; flow rate 15 ml/min; temperature 40° C.; detection 220 nm, run time 18 min]. The combined target fractions were concentrated, and the residue was in each case lyophilized in acetonitrile/water.

Example 300A tert-Butyl 5-{[(6-bromo-3-methyl-2-phenylquinolin-4-yl)carbonyl]amino}-4-(2,3,6-trichlorophenyl)pentanoate (Enantiomer 1)

In the enantiomer separation described in Example 299A, 321 mg (93% purity, ee 96%) of the title compound were obtained as the enantiomer that eluted earlier.

$R_t$=7.19 min (chiral analytical HPLC; Daicel Chiralpak IE 5 μm, 250 mm×4.6 mm, mobile phase heptane/0.2% diethylamine in isopropanol 50:50, isocratic; flow rate 1 ml/min; temperature 40° C.; detection 210 nm)

Example 301 tert-Butyl 5-{[(6-bromo-3-methyl-2-phenylquinolin-4-yl)carbonyl]amino}-4-(2,3,6-trichlorophenyl)pentanoate (Enantiomer 1)

In the enantiomer separation described in Example 299A, 291 mg (99% purity, ee 100%) of the title compound were obtained as the enantiomer that eluted later.

$R_t$=8.98 min (chiral analytical HPLC; Daicel Chiralpak IE 5 μm, 250 mm×4.6 mm, mobile phase heptane/0.2% diethylamine in isopropanol 50:50, isocratic; flow rate 1 ml/min; temperature 40° C.; detection 210 nm)

Example 302A (+/−)-tert-Butyl 6-{[(6-bromo-3-methyl-2-phenylquinolin-4-yl)carbonyl]amino}-5-(2-chlorophenyl)hexanoate (Racemate)

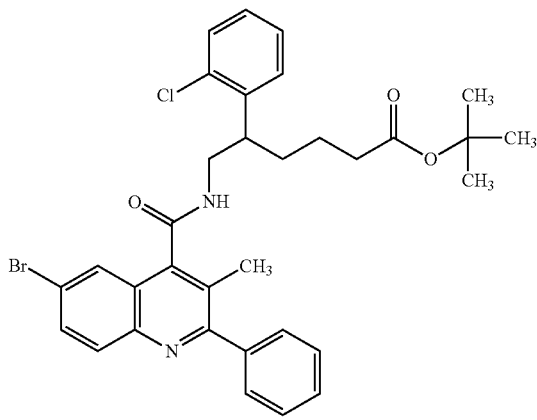 [SMILES: Cc1c(-c2ccccc2)nc2ccc(Br)cc2c1C(=O)NCC(CCCC(=O)OC(C)(C)C)c1ccccc1Cl]

HATU (1.37 g, 3.60 mmol) and DIPEA (1.3 ml, 7.2 mmol) were added to a mixture of 6-bromo-3-methyl-2-phenylquinoline-4-carboxylic acid (1.03 g, 3.00 mmol, preparable according to WO 2016 146602 A1, p. 51, Example 3A) in DMF (12 ml), and the mixture was stirred at RT for 15 min. (+/−)-tert-Butyl 6-amino-5-(2-chlorophenyl)hexanoate (893 mg, 3.00 mmol, Example 151A) dissolved in DMF (9 ml) was then added, and the mixture was stirred at 60° C. for 3 h. Subsequently, ethyl acetate and water (100 ml of each) were added to the mixture, which was agitated. After phase separation, the aqueous phase was extracted twice with ethyl acetate (80 ml). The combined organic phases were washed with saturated aqueous sodium chloride solution (100 ml), dried over sodium sulfate, filtered and concentrated, and the residue was taken up in dichloromethane and purified by flash column chromatography (100 g silica gel Biotage Snap-Cartridge Ultra, cyclohexane/ethyl acetate 98:2→8:2, Isolera One). This gave 1.19 g (93% purity, 59% of theory) of the title compound.

LC-MS (Method 1): $R_t$=2.66 min; MS (ESIpos): m/z=621/623 [M+H]$^+$ $^1$H-NMR (400 MHz, DMSO-d6) δ [ppm]: 8.84 (t, 1H), 7.94 (d, 1H), 7.85 (dd, 1H), 7.72 (br. s, 1H), 7.56-7.41 (m, 7H), 7.41-7.17 (m, 2H), 3.70 (br. s, 2H), 3.62-3.52 (m, 1H), 2.25-2.05 (m, 5H), 1.86-1.70 (m, 1H), 1.69-1.55 (m, 1H), 1.54-1.30 (m, 2H), 1.35 (s, 9H).

Separation of the Enantiomers:

The title compound (1.06 g) was dissolved in methanol (50 ml) and separated into the enantiomers by preparative SFC on a chiral phase (see Examples 303A and 304A) [column: Daicel Chiralcel OJ-H, 5 μm, 250 mm×30 mm; flow rate: 100 ml/min; detection: 210 nm; temperature: 38° C.; injection: 1.0 ml; mobile phase: 82% carbon dioxide/18% methanol→67% carbon dioxide/33% methanol, run time 11 min]: The combined target fractions were concentrated, and the respective residue was dried under reduced pressure.

Example 303A tert-Butyl 6-{[(6-bromo-3-methyl-2-phenylquinolin-4-yl)carbonyl]amino}-5-(2-chlorophenyl)hexanoate (Enantiomer 1)

In the enantiomer separation described in Example 302A, 480 mg (100% purity, ee 100%) of the title compound were obtained as the enantiomer that eluted earlier.

$R_t$=0.90 min (chiral analytical HPLC; Daicel Chiralpak OJ-3 3 μm, 100 mm×4.6 mm, mobile phase carbon dioxide/methanol 8:2, isocratic; flow rate 3 ml/min; pressure 130 bar, temperature 40° C.; detection 210 nm)

LC-MS (Method 1): $R_t$=2.67 min; MS (ESIpos): m/z=621/623 [M+H]$^+$ $^1$H-NMR (400 MHz, DMSO-d6) δ [ppm]: −0.149 (0.03), 0.146 (0.03), 1.194 (0.07), 1.320 (0.16), 1.354 (16.00), 1.398 (0.17), 1.421 (0.14), 1.438 (0.18), 1.448 (0.18), 1.463 (0.20), 1.480 (0.15), 1.496 (0.09), 1.511 (0.11), 1.576 (0.08), 1.609 (0.19), 1.622 (0.17), 1.634 (0.20), 1.732 (0.19), 1.745 (0.20), 1.759 (0.20), 1.792 (0.11), 2.145 (0.99), 2.165 (0.66), 2.171 (0.59), 2.183 (0.80), 2.189 (0.76), 2.201 (0.39), 2.207 (0.38), 2.229 (0.08), 2.328 (0.04), 2.366 (0.04), 2.670 (0.04), 2.710 (0.03), 3.581 (0.25), 3.597 (0.22), 3.701 (0.39), 7.236 (0.19), 7.254 (0.40), 7.273 (0.28), 7.298 (0.08), 7.317 (0.06), 7.350 (0.24), 7.369 (0.43), 7.387 (0.23), 7.433 (0.65), 7.453 (0.54), 7.478 (0.65), 7.499 (1.20), 7.507 (0.82), 7.519 (2.58), 7.719 (0.09), 7.833 (0.38), 7.838 (0.36), 7.856 (0.58), 7.860 (0.57), 7.930 (1.03), 7.953 (0.66), 8.832 (0.24), 8.846 (0.48), 8.859 (0.24).

$^1$H-NMR (400 MHz, DMSO-d6) δ [ppm]: 8.85 (t, 1H), 7.94 (d, 1H), 7.85 (dd, 1H), 7.72 (br. s, 1H), 7.56-7.42 (m, 7H), 7.40-7.20 (m, 2H), 3.70 (br. s, 2H), 3.63-3.50 (m, 1H), 2.24-2.08 (m, 5H), 1.88-1.71 (m, 1H), 1.69-1.54 (m, 1H), 1.53-1.30 (m, 2H), 1.35 (s, 9H).

Example 304A tert-Butyl 6-{[(6-bromo-3-methyl-2-phenylquinolin-4-yl)carbonyl]amino}-5-(2-chlorophenyl)hexanoate (Enantiomer 2)

In the enantiomer separation described in Example 302A, 438 mg (100% purity, ee 100%) of the title compound were obtained as the enantiomer that eluted later.

$R_t$=3.05 min (chiral analytical HPLC; Daicel Chiralpak OJ-3 3 μm, 100 mm×4.6 mm, mobile phase carbon dioxide/methanol 8:2, isocratic; flow rate 3 ml/min; pressure 130 bar, temperature 40° C.; detection 210 nm)

LC-MS (Method 1): $R_t$=2.68 min; MS (ESIpos): m/z=621/623 [M+H]$^+$ $^1$H-NMR (400 MHz, DMSO-d6) δ [ppm]: 1.194 (0.07), 1.354 (16.00), 1.420 (0.16), 1.462 (0.21), 1.480 (0.16), 1.510 (0.11), 1.609 (0.19), 1.633 (0.21), 1.731 (0.19), 1.757 (0.21), 2.144 (1.03), 2.164 (0.69), 2.182 (0.84), 2.188 (0.79), 2.200 (0.42), 2.327 (0.06), 2.669 (0.05), 3.580 (0.25), 3.701 (0.42), 7.235 (0.19), 7.254 (0.41), 7.272 (0.29), 7.350 (0.25), 7.368 (0.45), 7.386 (0.25), 7.433 (0.65), 7.452 (0.55), 7.479 (0.68), 7.498 (1.24), 7.507 (0.91), 7.518 (2.62), 7.714 (0.10), 7.833 (0.40), 7.838 (0.38), 7.855 (0.62), 7.860 (0.60), 7.930 (1.04), 7.952 (0.67), 8.829 (0.26), 8.844 (0.49), 8.857 (0.25).

$^1$H-NMR (400 MHz, DMSO-d6) δ [ppm]: 8.84 (t, 1H), 7.94 (d, 1H), 7.85 (dd, 1H), 7.71 (br. s, 1H), 7.57-7.42 (m, 7H), 7.37 (t, 1H), 7.26 (t, 1H), 3.70 (br. s, 2H), 3.63-3.51 (m, 1H), 2.26-2.06 (m, 5H), 1.85-1.70 (m, 1H), 1.69-1.55 (m, 1H), 1.53-1.30 (m, 2H), 1.35 (s, 9H).

Example 305A (+/−)-tert-Butyl 6-{[(6-bromo-3-methyl-2-phenylquinolin-4-yl)carbonyl]amino}-3-(2-chlorophenyl)-5-methylhexanoate (Racemate)

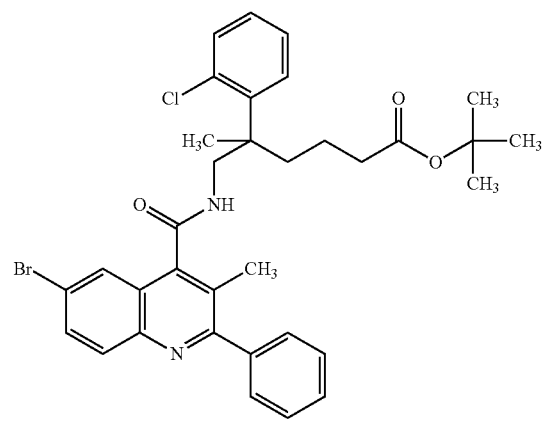 [SMILES: Cc1c(-c2ccccc2)nc2ccc(Br)cc2c1C(=O)NCC(C)(CCCC(=O)OC(C)(C)C)c1ccccc1Cl]

HATU (1.19 g, 3.14 mmol) and DIPEA (1.1 ml, 6.3 mmol) were added to a mixture of 6-bromo-3-methyl-2-phenylquinoline-4-carboxylic acid (895 mg, 2.62 mmol, preparable according to WO 2016 146602 A1, p. 51, Example 3A) in DMF (10 ml), and the mixture was stirred at RT for 15 min. (+/−)-tert-Butyl 6-amino-5-(2-chlorophenyl)-5-methylhexanoate (816 mg, "2.62 mmol", Example 152A, not corrected for purity, as a mixture with (+/−)-tert-butyl 6-amino-5-methyl-5-phenylhexanoate), dissolved in DMF (8 ml) was then added, and the mixture was stirred at 60° C. for 3 h, followed by 18 h at RT. Subsequently, ethyl acetate and water (150 ml of each) were added to the mixture, which was agitated. After phase separation, the aqueous phase was extracted twice with ethyl acetate (80 ml). The combined organic phases were washed with saturated aqueous sodium chloride solution (200 ml), dried over sodium sulfate, filtered and concentrated, and the residue was taken up in dichloromethane and purified by flash column chromatography (100 g of silica gel Biotage Snap-Cartridge KP-Sil, cyclohexane/ethyl acetate 97:3→7:3, Isolera One). Concentration and drying of the residues under reduced pressure gave two mixed fractions each comprising the target compound as a mixture with the dechlorinated product (tert-butyl 6-{[(6-bromo-3-methyl-2-phenylquinolin-4-yl)carbonyl]amino}-5-methyl-5-phenylhexanoate).

The first mixed fraction (866 mg) was used for the relevant subsequent reaction (see Example 240). The second mixed fraction (386 mg) was dissolved in a mixture of DMSO, acetonitrile and THF and purified by preparative HPLC (Method 15). The combined target fractions were concentrated, and the residues were lyophilized. This gave 161 mg (100% purity) of the title compound. Also obtained were 148 mg (97% purity) of the dechlorinated product (tert-butyl 6-{[(6-bromo-3-methyl-2-phenylquinolin-4-yl)carbonyl]amino}-5-methyl-5-phenylhexanoate, see Example 306A).

LC-MS (Method 1): $R_t$=2.76 min; MS (ESIpos): m/z=635/637 [M+H]$^+$ $^1$H-NMR (400 MHz, DMSO-d6) δ [ppm]: 1.074 (0.18), 1.359 (16.00), 1.526 (2.00), 1.618 (0.24), 2.118 (0.75), 2.136

(1.16), 2.154 (0.58), 2.394 (0.20), 3.672 (0.21), 3.693 (0.22), 4.298 (0.36), 4.316 (0.38), 4.332 (0.35), 4.349 (0.32), 7.260 (0.35), 7.279 (0.32), 7.309 (0.41), 7.327 (0.20), 7.411 (0.44), 7.430 (0.78), 7.446 (0.42), 7.498 (0.93), 7.506 (0.92), 7.517 (2.01), 7.828 (0.37), 7.850 (0.53), 7.855 (0.48), 7.924 (0.98), 7.946 (0.60), 8.599 (0.40).

$^1$H-NMR (400 MHz, DMSO-d6) δ [ppm]: 8.60 (t, 1H), 7.93 (d, 1H), 7.84 (dd, 1H), 7.69 (br. s, 1H), 7.56-7.47 (m, 5H), 7.46-7.38 (m, 2H), 7.34-7.23 (m, 2H), 4.32 (dd, 1H), 3.68 (dd, 1H), 2.42-2.32 (m, 1H), 2.22-2.02 (m, 5H), 1.62 (td, 1H), 1.53 (s, 3H), 1.4-1.3 (m, 1H, partially obscured), 1.39 (s, 3H), 1.36 (s, 9H), 1.14-0.99 (m, 1H).

Example 306A (+/−)-tert-Butyl 6-{[(6-bromo-3-methyl-2-phenylquinolin-4-yl)carbonyl]amino}-5-methyl-5-phenylhexanoate (Racemate)

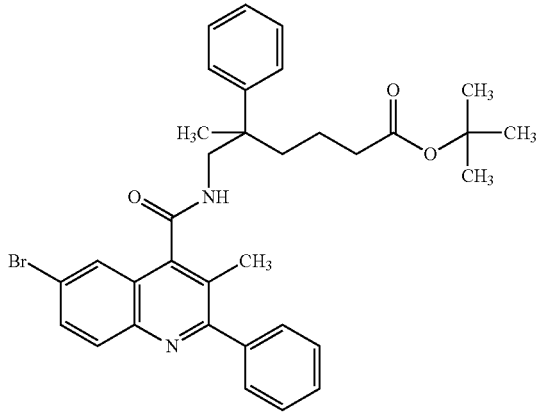 [SMILES: Cc1c(-c2ccccc2)nc2ccc(Br)cc2c1C(=O)NCC(C)(CCCC(=O)OC(C)(C)C)c1ccccc1]

As described in Example 305A, 148 mg (97% purity) of the title compound were obtained.

LC-MS (Method 1): $R_t$=2.70 min; MS (ESIpos): m/z=601/603 [M+H]$^+$ $^1$H-NMR (400 MHz, DMSO-d6) δ [ppm]: 1.162 (0.17), 1.351 (16.00), 1.388 (3.98), 1.599 (0.22), 1.631 (0.15), 1.762 (0.14), 1.784 (0.20), 2.099 (0.70), 2.118 (1.20), 2.136 (0.63), 2.365 (0.12), 3.540 (0.21), 3.562 (0.26), 3.727 (0.45), 3.843 (0.28), 3.860 (0.28), 3.876 (0.23), 3.893 (0.21), 7.215 (0.39), 7.233 (0.26), 7.326 (0.43), 7.345 (0.86), 7.364 (0.54), 7.405 (1.12), 7.424 (0.66), 7.499 (0.78), 7.506 (0.68), 7.517 (1.61), 7.525 (1.49), 7.827 (0.35), 7.850 (0.51), 7.855 (0.50), 7.927 (0.97), 7.950 (0.62), 8.608 (0.38).

$^1$H-NMR (400 MHz, DMSO-d6) δ [ppm]: 8.61 (t, 1H), 7.94 (d, 1H), 7.84 (dd, 1H), 7.67 (br. s, 1H), 7.56-7.46 (m, 5H), 7.44-7.39 (m, 2H), 7.35 (t, 2H), 7.22 (t, 1H), 3.87 (dd, 1H), 3.55 (dd, 1H), 2.22-2.02 (m, 5H), 1.79 (td, 1H), 1.60 (td, 1H), 1.4-1.3 (m, 1H, partially obscured), 1.39 (s, 3H), 1.35 (s, 9H), 1.23-1.07 (m, 1H).

Example 307A 2-(Bromomethyl)-1-(difluoromethoxy)-3-fluorobenzene

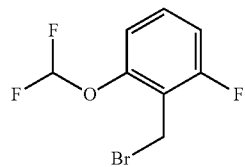

To a solution of [2-(difluoromethoxy)-6-fluorophenyl]methanol (9.90 g, 51.5 mmol, Example 3A) in dichloromethane (60 ml) was added dropwise while stirring, at −15° C., a solution of phosphorus tribromide (1.6 ml, 16 mmol) in dichloromethane (20 ml). Subsequently, the cooling bath was removed and the mixture was stirred at RT for a further 2 h. Thereafter, saturated sodium bicarbonate solution, water and dichloromethane (100 ml each) were added gradually to the mixture, which was agitated. After phase separation, the organic phase was washed with saturated sodium chloride solution (200 ml), dried over sodium sulfate, filtered and concentrated, and the residue was dried briefly under reduced pressure. This gave 9.60 g (95% purity, 69% of theory) of the title compound.

GC-MS (Method 12): $R_t$=3.38 min, MS (EIpos): m/z=254/256 [M]$^+$ $^1$H-NMR (400 MHz, DMSO-d6) δ [ppm]: 1.238 (0.57), 1.255 (1.12), 1.273 (0.58), 4.610 (15.58), 4.614 (16.00), 7.105 (3.32), 7.126 (3.80), 7.161 (2.02), 7.184 (8.39), 7.205 (2.57), 7.366 (8.46), 7.470 (2.03), 7.487 (2.27), 7.491 (3.74), 7.508 (3.68), 7.512 (2.00), 7.529 (1.66), 7.549 (4.14).

$^1$H-NMR (400 MHz, DMSO-d6) δ [ppm]: 7.60-7.03 (m, 4H), 4.61 (d, 2H).

Example 308A

[2-(Difluoromethoxy)-6-fluorophenyl]acetonitrile

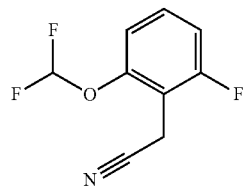

To a solution of 2-(bromomethyl)-1-(difluoromethoxy)-3-fluorobenzene (9.60 g, 37.6 mmol, Example 307A) in dichloromethane (60 ml) were added, while stirring, water (60 ml) and tetrabutylammonium bromide (1.21 g, 3.76 mmol). Subsequently, a solution of potassium cyanide (7.35 g, 113 mmol) in water (120 ml) was added, and the mixture was stirred at RT for 2.5 h. Subsequently, the phases were separated, and the organic phase was washed twice with saturated sodium bicarbonate solution (100 ml each time), dried over sodium sulfate, filtered and concentrated, and the residue was dried briefly under reduced pressure. This gave 7.26 g (98% purity, 94% of theory) of the title compound.

GC-MS (Method 12): $R_t$=3.70 min, MS (EIpos): m/z=201 [M]$^+$

LC-MS (Method 1): R$_t$=1.56 min
$^1$H-NMR (400 MHz, DMSO-d6) δ [ppm]: 0.937 (0.68), 3.164 (0.78), 3.177 (0.77), 3.952 (16.00), 7.152 (3.20), 7.171 (6.16), 7.215 (2.00), 7.237 (3.89), 7.259 (2.35), 7.353 (6.55), 7.489 (1.60), 7.509 (2.98), 7.526 (3.04), 7.531 (1.93), 7.535 (3.48), 7.547 (1.32).
$^1$H-NMR (400 MHz, DMSO-d6) δ [ppm]: 7.58-7.43 (m, 1H), 7.39-7.05 (m, 3H), 3.95 (s, 2H).

Example 309A (+/−)-tert-Butyl 4-cyano-4-[2-(difluoromethoxy)-6-fluorophenyl]butanoate (Racemate)

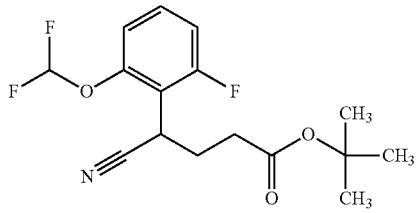 [SMILES: CC(C)(C)OC(=O)CCC(C#N)c1c(F)cccc1OC(F)F]

To a solution of [2-(difluoromethoxy)-6-fluorophenyl]acetonitrile (7.24 g, 36.0 mmol, Example 308A) in THF (30 ml) under argon was added gradually while stirring, at about −70 to −60° C., a 2 M solution of LDA in THF (22 ml, 43 mmol). The mixture was allowed to come to 0° C. and, after 15 min, cooled back down again to −70° C. Subsequently, a solution of tert-butyl 3-bromopropanoate (6.8 ml, 43 mmol) in THF (15 ml) was slowly added dropwise thereto at about −70 to −60° C. while stirring. Stirring of the mixture was continued overnight, in the course of which the cooling bath (dry ice/isopropanol) was allowed to come gradually to RT. Subsequently, water and ethyl acetate (100 ml of each) were gradually added at about 0° C. to the mixture, which was agitated. After phase separation, the aqueous phase was extracted once with ethyl acetate (100 ml). The combined organic phases were washed once with saturated sodium chloride solution (150 ml), dried over sodium sulfate, filtered and concentrated, and the residue was taken up in dichloromethane and purified by flash column chromatography (400 g of silica gel, cyclohexane/ethyl acetate gradient 10:1). The combined target fractions were concentrated, and the residue was dried under reduced pressure. This gave 7.11 g (74% purity, 45% of theory) of the title compound.
LC-MS (Method 2): R$_t$=1.10 min; MS (ESIpos): m/z=330 [M+H]$^+$ Example 310A (+/−)-tert-Butyl 5-amino-4-[2-(difluoromethoxy)-6-fluorophenyl]pentanoate (Racemate)

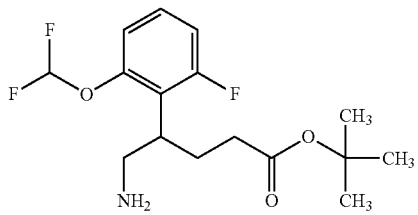 [SMILES: CC(C)(C)OC(=O)CCC(CN)c1c(F)cccc1OC(F)F]

Raney nickel (937 mg, 16.0 mmol) was added to a solution of (+/−)-tert-butyl 4-cyano-4-[2-(difluoromethoxy)-6-fluorophenyl]butanoate (7.07 g, 74% purity, 16.0 mmol, Example 309A) in tert-butanol (97 ml), and the mixture was hydrogenated at atmospheric pressure for three days. Subsequently, the catalyst was filtered off through kieselguhr, which was washed through twice with tert-butanol (30 ml each time). The filtrate was concentrated, and the residue was dried under reduced pressure. This gave 6.21 g (65% purity, 76% of theory) of the title compound.
LC-MS (Method 1): R$_t$=1.16 min; MS (ESIpos): m/z=334 [M+H]$^+$ Example 311A (+/−)-tert-Butyl 5-{[(6-bromo-3-methyl-2-phenylquinolin-4-yl)carbonyl]amino}-4-[2-(difluoromethoxy)-6-fluorophenyl]pentanoate (Racemate)

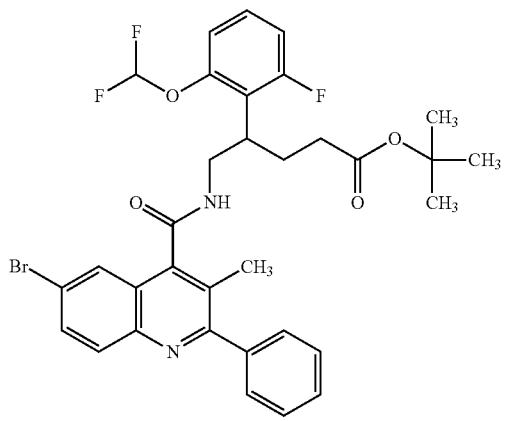 [SMILES: Cc1c(-c2ccccc2)nc2ccc(Br)cc2c1C(=O)NCC(CCC(=O)OC(C)(C)C)c1c(F)cccc1OC(F)F]

HATU (639 mg, 1.68 mmol) and DIPEA (570 µl, 3.3 mmol) were added to a mixture of 6-bromo-3-methyl-2-phenylquinoline-4-carboxylic acid (500 mg, 1.46 mmol, preparable according to WO 2016/146602, Example 3A) in DMF (6 ml), and the mixture was stirred at RT for 15 min. (+/−)-tert-Butyl 5-amino-4-[2-(difluoromethoxy)-6-fluorophenyl]pentanoate (751 mg, 65% purity, 1.46 mmol, Example 310A) dissolved in DMF (3 ml) was then added, and the mixture was stirred at 60° C. for 16 h. After cooling to RT, ethyl acetate and water (100 ml of each) were added to the mixture, which was agitated. After phase separation, the aqueous phase was extracted once with ethyl acetate (80 ml). The combined organic phases were washed with saturated sodium chloride solution (100 ml), dried over sodium sulfate, filtered and concentrated, and the residue was taken up in dichloromethane and purified by flash column chromatography (50 g silica gel Biotage Snap-Cartridge Ultra, cyclohexane/ethyl acetate gradient 97:3→7:3, Isolera One). The combined target fractions were concentrated, and the residue was dried under reduced pressure. This gave 749 mg (88% purity, 69% of theory) of the title compound.
LC-MS (Method 1): R$_t$=2.54 min; MS (ESIpos): m/z=657/659 [M+H]$^+$
$^1$H-NMR (400 MHz, DMSO-d6) δ [ppm]: 8.92 (t, 1H), 7.94 (d, 1H), 7.86 (dd, 1H), 7.70 (br. s, 1H), 7.58-7.45 (m, 5H), 7.45-7.22 (m, 2H), 7.16-6.99 (m, 2H), 3.92-3.67 (m, 2H), 3.60-3.44 (m, 1H), 2.22-1.87 (m, 7H), 1.35 (s, 9H).

Separation of the Enantiomers:

The title compound (640 mg, 88% purity) was dissolved in a warm mixture of acetonitrile (7 ml) and isopropanol (3 ml) and separated into the enantiomers by preparative HPLC on a chiral phase (see Examples 312A and 313A) [column: Daicel Chiralpak IE, 5 µm 250 mm×20 mm; flow rate: 15 ml/min; detection: 210 nm; temperature: 25° C.; injection: 0.50 ml; mobile phase: 70% heptane; 30% isopropanol; run time 19 min, isocratic]. The combined target fractions were concentrated, and the residue was lyophilized in acetonitrile/water.

Example 312A (+)-tert-Butyl 5-{[(6-bromo-3-methyl-2-phenylquinolin-4-yl)carbonyl]amino}-4-[2-(difluoromethoxy)-6-fluorophenyl]pentanoate (Enantiomer 1)

In the enantiomer separation described in Example 311A, three batches of the title compound were obtained as the enantiomer that eluted earlier: 78 mg (batch 1, 76% purity, ee 99%, see optical rotation and LC-MS), 21 mg (batch 2, 75% purity, ee 92%) and 186 mg (batch 3, 88% purity, ee 94%).

$[\alpha]_D^{20}$=+24.6°, 589 nm, c=0.33 g/100 ml, methanol

LC-MS (Method 1): $R_t$=2.56 min; MS (ESIpos): m/z=657/659 [M+H]$^+$

Example 313A (−)-tert-Butyl 5-{[(6-bromo-3-methyl-2-phenylquinolin-4-yl)carbonyl]amino}-4-[2-(difluoromethoxy)-6-fluorophenyl]pentanoate (Enantiomer 2)

In the enantiomer separation described in Example 311A, two batches of the title compound were obtained as the enantiomer that eluted later: 76 mg (batch 1, 97% purity, ee 95%) and 118 mg (batch 2, 97% purity, ee 99%, see optical rotation and LC-MS)

$[\alpha]_D^{20}$=−29.1°, 589 nm, c=0.34 g/100 ml, methanol

LC-MS (Method 1): $R_t$=2.56 min; MS (ESIpos): m/z=657/659 [M+H]$^+$

Example 314A (+/−)-tert-Butyl 4-cyano-4-(2,5-difluorophenyl)butanoate (Racemate)

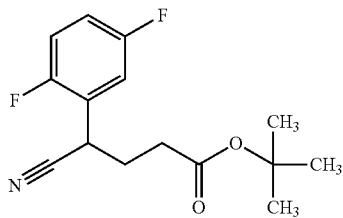 [SMILES: CC(C)(C)OC(=O)CCC(C#N)c1cc(F)ccc1F]

Under an argon atmosphere, an LDA solution was prepared by gradually adding an n-butyllithium solution (1.6 M in hexane, 44 ml, 70 mmol) to an initial charge of diisopropylamine (10 ml, 74 mmol) in THF (44 ml) at −78° C. After the addition had ended, the solution was stirred at 0° C. for a further 10 min. This LDA solution was slowly added dropwise to a solution, cooled to −78° C., of (2,5-difluorophenyl)acetonitrile (8.1 ml, 98% purity, 64 mmol) in THF (120 ml). On completion of addition, the cooling bath was removed, the reaction mixture was allowed to come to 0° C. and, after 15 min, was cooled again to −78° C. Then a solution of tert-butyl 3-bromopropanoate (13 ml, 97% purity, 77 mmol) in 44 ml of THF was added dropwise and the mixture was stirred at −78° C. for a further 1 h, then allowed to warm up to RT and stirred at RT overnight. For workup, ammonium chloride solution (300 ml, 10% in water) was added. The mixture was stirred vigorously for 5 minutes and then extracted twice with ethyl acetate. The combined organic phases were successively washed twice each with 1 M hydrochloric acid, a saturated sodium bicarbonate solution and a saturated sodium chloride solution. The organic phase was then dried over sodium sulfate and concentrated on a rotary evaporator. The residue was dissolved in a little DMSO and purified in 4 portions by means of preparative HPLC (Method 30). The product-containing fractions were combined and concentrated on a rotary evaporator. This gave 8.05 g (100% purity, 45% of theory) of the title compound.

LC-MS (Method 1): $R_t$=2.11 min; MS (ESIpos): m/z=282 [M+H]$^+$ $^1$H-NMR (400 MHz, DMSO-d6) δ [ppm]: 1.381 (16.00), 2.313 (0.86), 2.332 (1.28), 2.350 (0.44), 4.414 (0.63), 7.353 (0.40), 7.366 (0.62), 7.374 (0.51), 7.377 (0.49).

Example 315A (+/−)-tert-Butyl 5-amino-4-(2,5-difluorophenyl)pentanoate (Racemate)

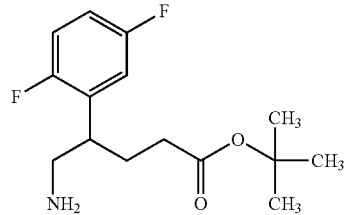 [SMILES: CC(C)(C)OC(=O)CCC(CN)c1cc(F)ccc1F]

(+/−)-tert-Butyl 4-cyano-4-(2,5-difluorophenyl)butanoate (racemate, 8.05 g, 100% purity, 28.6 mmol, Example 314A) was initially charged in tert-butanol (210 ml, 2.2 mol) and methanol (9.3 ml), and Raney nickel (1.68 g, 28.6 mmol) was added. The reaction mixture was stirred under standard hydrogen pressure for 9 days. In spite of incomplete conversion, the reaction was stopped. The catalyst was filtered off through kieselguhr and washed three times with methanol (30 ml each time). The filtrate was concentrated by rotary evaporation and the residue was taken up in ethyl acetate (200 ml). The organic phase was extracted twice with 1 M hydrochloric acid (200 ml each time). The combined aqueous phases were brought to pH 8 by gradual addition of sodium bicarbonate and then extracted twice with dichloromethane (200 ml each time). The combined organic phases were dried over sodium sulfate, filtered and concentrated. This gave 3.84 g (100% purity, 47% of theory) of the title compound.

LC-MS (Method 1): $R_t$=1.12 min; MS (ESIpos): m/z=286 [M+H]$^+$ $^1$H-NMR (400 MHz, DMSO-d$_6$): δ [ppm]=7.29-7.04 (m, 3H), 2.92-2.84 (m, 1H), 2.79-2.67 (m, 2H), 2.05-1.91 (m, 3H), 1.74-1.61 (m, 1H), 1.35 (s, 9H).

¹H-NMR (400 MHz, DMSO-d6) δ [ppm]: 1.111 (0.42), 1.354 (16.00), 2.012 (1.26), 2.025 (0.85), 2.728 (0.47), 2.736 (0.51), 2.747 (0.69), 2.751 (0.69).

Example 316A (+/−)-tert-Butyl 5-{[(6-bromo-3-methyl-2-phenylquinolin-4-yl)carbonyl]amino}-4-(2,5-difluorophenyl)pentanoate (Racemate)

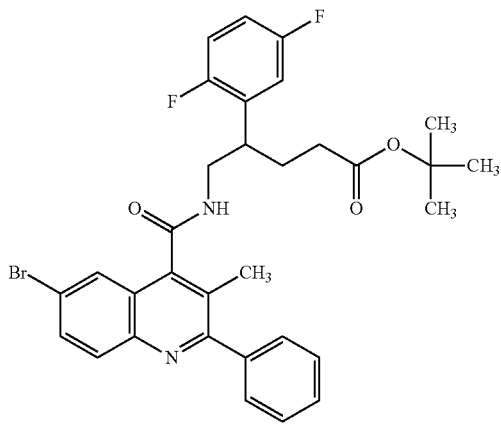 [SMILES: Cc1c(-c2ccccc2)nc2ccc(Br)cc2c1C(=O)NCC(CCC(=O)OC(C)(C)C)c1cc(F)ccc1F]

HATU (1.34 g, 3.53 mmol) and DIPEA (1.2 ml, 7.1 mmol) were added to a solution of 6-bromo-3-methyl-2-phenylquinoline-4-carboxylic acid (1.01 g, 2.94 mmol, preparable according to WO 2016/146602, Example 3A) in DMF (34 ml). The mixture was stirred at RT for 15 min. A solution of (+/−)-tert-butyl 5-amino-4-(2,5-difluorophenyl)pentanoate (840 mg, 2.94 mmol, Example 315A) in a little DMF was added, and the mixture was stirred at 60° C. for 2 h, and then allowed to cool to RT. The mixture was diluted with ethyl acetate and washed successively twice with 1 M hydrochloric acid and twice with a saturated sodium bicarbonate solution. The organic phase was dried over sodium sulfate, filtered and concentrated. The residue was dissolved in a little DMSO and purified by preparative HPLC (Method 30). Suitable fractions were concentrated together and dried under reduced pressure. This gave 1.16 g (100% purity, 65% of theory) of the title compound.

LC-MS (Method 1): $R_t$=2.52 min; MS (ESIpos): m/z=609/611 [M+H]$^+$

¹H-NMR (400 MHz, DMSO-d6) δ [ppm]: 8.88 (t, 1H), 7.94 (d, 1H); 7.85 (dd, 1H), 7.65 (br. s, 1H), 7.55-7.46 (m, 5H), 7.32 (ddd, 1H), 7.23 (dt, 1H), 7.17-7.07 (m, 1H), 3.81-3.63 (m, 2H), 3.43-3.33 (m, 1H), 2.20-1.96 (m. 6H), 1.86-1.74 (m, 1H), 1.37 (m, 9H).

Separation of the Enantiomers:

The title compound (1.09 g) was dissolved in a mixture (12 ml) of acetonitrile, methanol and dichloromethane and separated into the enantiomers by preparative SFC on a chiral phase (see Examples 317A and 318A) [column: Daicel Chiralcel OX-H, 5 μm, 250 mm×30 mm; flow rate: 100 ml/min; detection: 210 nm; temperature: 40° C.; injection: 0.30 ml; mobile phase: 81% carbon dioxide; 19% methanol; run time 9.5 min, isocratic]. The combined target fractions were concentrated, and the residue was lyophilized from acetonitrile/water.

Example 317A tert-Butyl 5-{[(6-bromo-3-methyl-2-phenylquinolin-4-yl)carbonyl]amino}-4-(2,5-difluorophenyl)pentanoate (Enantiomer 1)

In the enantiomer separation described in Example 316A, 432 mg (>99% purity, ee>99%) of the title compound were obtained as the enantiomer that eluted earlier.

LC-MS (Method 1): $R_t$=2.51 min; MS (ESIpos): m/z=609/611 [M+H]$^+$

¹H-NMR (400 MHz, DMSO-d6) δ [ppm]: −0.008 (0.20), 0.008 (0.20), 1.030 (0.22), 1.045 (0.22), 1.369 (16.00), 1.806 (0.17), 2.012 (0.19), 2.029 (0.20), 2.049 (0.19), 2.061 (0.17), 2.087 (0.74), 2.104 (1.03), 2.123 (0.70), 3.368 (0.17), 3.673 (0.18), 3.687 (0.27), 7.117 (0.18), 7.200 (0.20), 7.211 (0.21), 7.223 (0.32), 7.234 (0.32), 7.293 (0.17), 7.300 (0.20), 7.306 (0.21), 7.315 (0.30), 7.324 (0.21), 7.330 (0.20), 7.338 (0.17), 7.489 (0.21), 7.501 (0.68), 7.508 (0.70), 7.519 (2.70), 7.529 (0.88), 7.533 (0.82), 7.833 (0.36), 7.838 (0.33), 7.856 (0.56), 7.861 (0.54), 7.929 (1.06), 7.952 (0.68), 8.860 (0.22), 8.874 (0.39), 8.888 (0.21).

Example 318A tert-Butyl 5-{[(6-bromo-3-methyl-2-phenylquinolin-4-yl)carbonyl]amino}-4-(2,5-difluorophenyl)pentanoate (Enantiomer 2)

In the enantiomer separation described in Example 316A, 366 mg (97% purity, ee 94%) of the title compound were obtained as the enantiomer that eluted later.

LC-MS (Method 1): $R_t$=2.51 min; MS (ESIpos): m/z=609/611 [M+H]$^+$

¹H-NMR (400 MHz, DMSO-d6) δ [ppm]: 1.030 (0.69), 1.046 (0.70), 1.369 (16.00), 1.806 (0.20), 1.814 (0.17), 1.831 (0.17), 1.999 (0.17), 2.012 (0.22), 2.029 (0.23), 2.049 (0.21), 2.061 (0.19), 2.088 (0.84), 2.104 (1.17), 2.124 (0.83), 3.369 (0.20), 3.674 (0.22), 3.688 (0.31), 3.701 (0.18), 3.737 (0.19), 3.752 (0.18), 7.117 (0.22), 7.200 (0.21), 7.211 (0.23), 7.223 (0.35), 7.235 (0.34), 7.246 (0.17), 7.293 (0.19), 7.301 (0.23), 7.307 (0.24), 7.315 (0.34), 7.324 (0.24), 7.330 (0.23), 7.338 (0.18), 7.490 (0.25), 7.501 (0.74), 7.508 (0.77), 7.519 (3.02), 7.833 (0.37), 7.838 (0.35), 7.856 (0.57), 7.861 (0.57), 7.929 (1.08), 7.952 (0.68), 8.860 (0.25), 8.875 (0.45), 8.888 (0.24).

Exemplary Embodiments

Example 1

(+/−)-3-{[(6-Bromo-3-methyl-2-phenylquinolin-4-yl)carbonyl]amino}-2-phenylpropanoic Acid (Racemate)

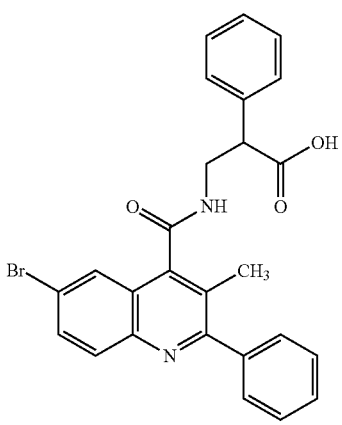

At RT, 1 M aqueous sodium hydroxide solution (1.8 ml, 1.8 mmol) was added to a solution of (+/−)-methyl 3-{[(6-bromo-3-methyl-2-phenylquinolin-4-yl)carbonyl]amino}phenylpropanoate (153 mg, 304 μmol, Example 153A) in THF (3.8 ml) and methanol (750 μl), and the mixture was stirred at RT for 2 h. The mixture was then adjusted to pH 3 by addition of TFA (160 μl, 2.1 mmol) and purified by preparative HPLC (Method 15). The combined target fractions were concentrated and lyophilized. This gave 147 mg (100% purity, 99% of theory) of the title compound.

LC-MS (Method 1): $R_t$=1.84 min; MS (ESIpos): m/z=489/491 [M+H]$^+$ $^1$H-NMR (400 MHz, DMSO-d6) δ [ppm]: −0.008 (1.54), 0.008 (1.39), 2.146 (3.32), 3.839 (1.33), 3.859 (2.67), 3.875 (2.66), 3.890 (1.71), 3.987 (2.43), 4.006 (3.60), 4.025 (1.43), 7.300 (0.95), 7.310 (1.56), 7.322 (1.64), 7.332 (1.06), 7.359 (0.74), 7.383 (13.34), 7.393 (16.00), 7.493 (1.15), 7.497 (1.29), 7.502 (1.24), 7.506 (4.09), 7.514 (3.84), 7.526 (11.82), 7.530 (11.18), 7.534 (7.60), 7.538 (6.08), 7.542 (5.18), 7.550 (1.32), 7.844 (2.39), 7.849 (2.09), 7.866 (3.62), 7.871 (3.43), 7.938 (6.67), 7.961 (4.21), 8.953 (1.27), 8.967 (2.44), 8.981 (1.28).

Separation of the Enantiomers:

The title compound (120 mg) was dissolved in methanol (20 ml) and separated into the enantiomers by preparative SFC on a chiral phase (see Examples 2 and 3) [column: Daicel Chiralcel OJ, 10 μm, 250 mm×20 mm; flow rate: 80 ml/min; detection: 210 nm; temperature: 40° C.; injection: 1.5 ml; mobile phase: 70% carbon dioxide/30% methanol; run time 7 min, isocratic]. The combined target fractions were concentrated and the residue was dried under reduced pressure.

Example 2

(−)-3-{[(6-Bromo-3-methyl-2-phenylquinolin-4-yl)carbonyl]amino}-2-phenylpropanoic Acid (Enantiomer 1)

In the enantiomer separation described in Example 1, 48 mg (99% purity, ee 100%) of the title compound were obtained as the enantiomer that eluted earlier.

$[α]_D^{20}$=−52.4°, 589 nm, c=0.37 g/100 ml, methanol

LC-MS (Method 1): $R_t$=1.87 min; MS (ESIpos): m/z=489/491 [M+H]$^+$ $^1$H-NMR (400 MHz, DMSO-d6) δ [ppm]: −0.008 (1.61), 0.008 (1.51), 2.145 (3.84), 3.390 (2.69), 3.838 (1.45), 3.858 (2.86), 3.873 (2.92), 3.888 (1.79), 3.986 (2.43), 4.005 (3.66), 4.025 (1.42), 5.754 (0.57), 7.300 (1.16), 7.310 (1.79), 7.321 (1.90), 7.331 (1.21), 7.359 (0.97), 7.382 (14.91), 7.392 (16.00), 7.490 (1.45), 7.494 (1.60), 7.503 (4.56), 7.511 (4.16), 7.523 (12.91), 7.527 (12.16), 7.532 (8.26), 7.536 (6.68), 7.539 (5.57), 7.547 (1.36), 7.746 (0.83), 7.838 (2.39), 7.844 (2.10), 7.861 (3.53), 7.866 (3.29), 7.935 (6.47), 7.957 (4.09), 8.950 (1.42), 8.963 (2.65), 8.977 (1.37), 12.636 (0.94).

Example 3

(+)-3-{[(6-Bromo-3-methyl-2-phenylquinolin-4-yl)carbonyl]amino}-2-phenylpropanoic Acid (Enantiomer 2)

In the enantiomer separation described in Example 1, 45 mg (98% purity, ee 97%) of the title compound were obtained as the enantiomer that eluted later.

$[α]_D^{20}$=+53.3°, 589 nm, c=0.36 g/100 ml, methanol

LC-MS (Method 1): $R_t$=1.86 min; MS (ESIpos): m/z=489/491 [M+H]$^+$ $^1$H-NMR (400 MHz, DMSO-d6) δ [ppm]: −0.008 (2.72), 0.008 (2.08), 2.145 (4.80), 3.837 (1.65), 3.857 (3.14), 3.873 (3.24), 3.887 (1.86), 3.983 (2.11), 4.002 (3.05), 4.021 (1.23), 5.754 (1.78), 7.308 (2.12), 7.319 (2.33), 7.329 (1.55), 7.358 (1.70), 7.380 (15.29), 7.391 (16.00), 7.479 (1.30), 7.490 (2.31), 7.493 (2.50), 7.503 (5.97), 7.511 (5.63), 7.523 (15.28), 7.527 (14.25), 7.531 (9.97), 7.535 (8.05), 7.539 (6.55), 7.547 (1.78), 7.743 (1.09), 7.838 (2.93), 7.843 (2.58), 7.860 (4.19), 7.865 (3.87), 7.934 (7.38), 7.957 (4.61), 8.948 (1.54), 8.961 (2.62), 8.975 (1.38).

Example 4

(+/−)-3-{[(6-Bromo-3-methyl-2-phenylquinolin-4-yl)carbonyl]amino}-2-(2-chlorophenyl)propanoic Acid (Racemate)

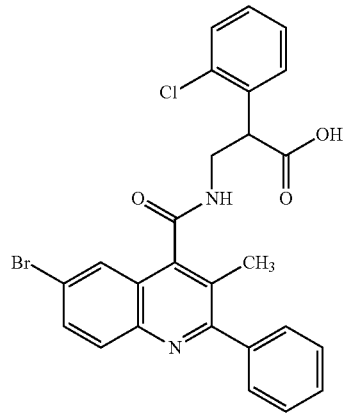 [SMILES: Cc1c(-c2ccccc2)nc2ccc(Br)cc2c1C(=O)NCC(C(=O)O)c1ccccc1Cl]

At RT, 1 M aqueous sodium hydroxide solution (24 ml, 24 mmol) was added to a solution of (+/−)-ethyl 3-{[(6-bromo-3-methyl-2-phenylquinolin-4-yl)carbonyl]amino}-2-(2-chlorophenyl)propanoate (2.20 g, 3.99 mmol, Example 154A) in THF (32 ml) and methanol (6.0 ml), and the mixture was stirred at RT for 2 h. Subsequently, water and ammonium chloride solution (100 ml of each) were added to the mixture, which was agitated. The aqueous phase was extracted once with ethyl acetate (100 ml). The combined organic phases were dried over sodium sulfate, filtered and concentrated, and the residue was dried under reduced pressure. This gave 1.89 g (99% purity, 90% of theory) of the title compound (crude product). About 100 mg of the crude product were repurified by preparative HPLC (Method 23). The combined target fractions were concentrated and the residue was dried under reduced pressure. This gave 91 mg (100% purity) of the repurified title compound (see analysis).

LC-MS (Method 1): $R_t$=1.93 min; MS (ESIpos): m/z=523/525 [M+H]$^+$ $^1$H-NMR (400 MHz, DMSO-d6) δ [ppm]: −0.008 (1.46), 0.008 (1.40), 1.194 (0.46), 1.211 (0.50), 2.164 (12.91), 3.881 (1.03), 3.897 (1.02), 3.984 (0.85), 3.998 (1.39), 4.013 (1.29), 4.032 (0.91), 4.483 (1.81), 4.501 (3.08), 4.520 (1.58), 5.754 (3.50), 7.319 (0.99), 7.338 (2.47), 7.353 (2.26), 7.370 (2.06), 7.388 (2.94), 7.405 (1.31), 7.479 (0.74), 7.492 (5.81), 7.495 (5.88), 7.504 (8.98), 7.511 (8.29), 7.514 (6.53), 7.523 (16.00), 7.528 (13.36), 7.536 (7.86), 7.547 (1.66), 7.748 (0.97), 7.838 (2.95), 7.844 (2.54), 7.860 (4.43), 7.866 (4.14), 7.934 (7.94), 7.956 (4.98), 8.959 (1.61), 8.973 (3.20), 8.987 (1.57), 12.794 (0.56).

Separation of the Enantiomers:

The title compound (1.79 g, crude product) was dissolved in methanol (80 ml), filtered and separated into the enantiomers by preparative SFC on a chiral phase (see Examples 5 and 6) [column: Daicel Chiralcel OJ-H, 5 μm, 250 mm×30 mm; flow rate: 175 ml/min; detection: 210 nm; temperature: 38° C.; injection: 3 ml; mobile phase: 67% carbon dioxide/33% methanol; run time 4.5 min, isocratic]. The combined target fractions were concentrated and the residue was dried under reduced pressure.

Example 5

(−)-3-{[(6-Bromo-3-methyl-2-phenylquinolin-4-yl)carbonyl]amino}-2-(2-chlorophenyl)propanoic Acid (Enantiomer 1)

The prepurified title compound was obtained in the enantiomer separation described in Example 4 and repurified by preparative HPLC (Method 24). The combined target fractions were concentrated and lyophilized. This gave 819 mg (100% purity, ee 95%) of the title compound.

[α]$_D^{20}$=−37.1°, 589 nm, c=0.39 g/100 ml, methanol

LC-MS (Method 1): $R_t$=1.91 min; MS (ESIpos): m/z=523/525 [M+H]$^+$ $^1$H-NMR (400 MHz, DMSO-d6) δ [ppm]: 0.008 (1.48), 2.164 (12.99), 3.897 (1.37), 3.998 (2.04), 4.015 (1.92), 4.033 (1.57), 4.483 (2.11), 4.502 (3.31), 4.521 (1.70), 7.318 (1.23), 7.334 (2.69), 7.353 (2.42), 7.370 (2.04), 7.385 (2.99), 7.404 (1.34), 7.491 (6.69), 7.495 (6.78), 7.504 (9.81), 7.511 (8.77), 7.523 (16.00), 7.529 (12.90), 7.537 (7.20), 7.540 (5.52), 7.548 (1.34), 7.750 (1.01), 7.840 (2.91), 7.845 (2.34), 7.862 (4.23), 7.868 (3.62), 7.935 (7.28), 7.957 (4.47), 8.960 (1.77), 8.974 (3.16), 8.989 (1.52).

Example 6

(+)-3-{[(6-Bromo-3-methyl-2-phenylquinolin-4-yl)carbonyl]amino}-2-(2-chlorophenyl)propanoic Acid (Enantiomer 2)

The prepurified title compound was obtained in the enantiomer separation described in Example 4 and repurified by preparative HPLC (Method 24). The combined target fractions were concentrated and lyophilized. This gave 638 mg (100% purity, ee 100%) of the title compound.

[α]$_D^{20}$=+45.6°, 589 nm, c=0.44 g/100 ml, methanol

LC-MS (Method 1): $R_t$=1.94 min; MS (ESIpos): m/z=523/525 [M+H]$^+$ $^1$H-NMR (400 MHz, DMSO-d6) δ [ppm]: −0.008 (2.12), 0.008 (1.86), 2.164 (13.01), 3.882 (1.00), 3.899 (1.02), 3.983 (0.83), 3.997 (1.35), 4.014 (1.32), 4.033 (0.88), 4.483 (1.84), 4.501 (3.12), 4.520 (1.60), 7.315 (0.92), 7.319 (1.02), 7.334 (2.42), 7.338 (2.53), 7.353 (2.23), 7.357 (2.23), 7.366 (1.90), 7.370 (2.08), 7.385 (2.85), 7.389 (2.95), 7.404 (1.34), 7.478 (0.74), 7.492 (5.61), 7.495 (5.61), 7.504 (8.86), 7.511 (8.04), 7.514 (6.19), 7.523 (16.00), 7.527 (13.18), 7.531 (9.63), 7.536 (7.61), 7.539 (6.12), 7.547 (1.54), 7.748 (0.85), 7.838 (2.88), 7.843 (2.47), 7.860 (4.34), 7.865 (4.05), 7.934 (7.79), 7.956 (4.95), 8.958 (1.67), 8.973 (3.28), 8.987 (1.62), 12.797 (2.25).

Example 7

(+/−)-3-{[(6-Bromo-3-methyl-2-phenylquinolin-4-yl)carbonyl]amino}-2-(2-methoxyphenyl)propanoic Acid (Racemate)

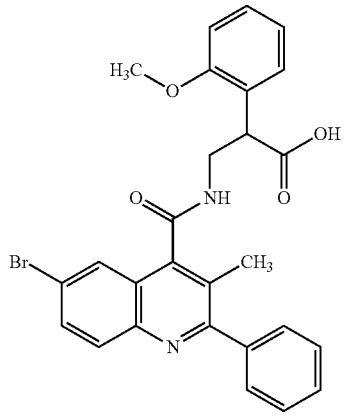 [SMILES: COc1ccccc1C(CNC(=O)c1c(C)c(-c2ccccc2)nc2ccc(Br)cc12)C(=O)O]

At RT, 1 M aqueous sodium hydroxide solution (12 ml, 12 mmol) was added to a solution of (+/−)-methyl 3-{[(6-bromo-3-methyl-2-phenylquinolin-4-yl)carbonyl]amino}-2-(2-methoxyphenyl)propanoate (1.11 g, 2.08 mmol, Example 155A) in THF (18 ml) and methanol (3.6 ml), and the mixture was stirred at RT for 3 h. Water (100 ml) and 1 M hydrochloric acid (15 ml) were then added to the mixture, which was agitated. The aqueous phase was extracted once with ethyl acetate (100 ml). The combined organic phases were dried over sodium sulfate, filtered and concentrated, and the residue was dried under reduced pressure. This gave 1.08 g (100% purity, 100% of theory) of the title compound.

LC-MS (Method 1): $R_t$=1.85 min; MS (ESIpos): m/z=519/521 [M+H]$^+$ $^1$H-NMR (400 MHz, DMSO-d6) δ [ppm]: −0.008 (0.61), 1.181 (0.40), 1.908 (0.42), 2.176 (6.04), 3.162 (0.99), 3.175 (1.01), 3.735 (0.58), 3.750 (0.98), 3.769 (0.95), 3.784 (1.09), 3.797 (16.00), 3.911 (0.54), 3.925 (0.72), 3.929 (0.71), 3.944 (0.99), 3.958 (0.52), 3.962 (0.55), 3.976 (0.48), 4.267 (1.11), 4.286 (2.15), 4.305 (0.88), 6.937 (0.89), 6.955 (1.87), 6.974 (1.09), 7.019 (1.64), 7.039 (1.89), 7.260 (1.06), 7.279 (4.03), 7.298 (2.96), 7.478 (0.47), 7.490 (0.95), 7.504 (2.64), 7.511 (2.38), 7.524 (5.63), 7.530 (5.48), 7.537 (3.68), 7.550 (0.79), 7.774 (0.66), 7.837 (1.35), 7.843 (1.11), 7.860 (2.00), 7.865 (1.77), 7.932 (3.50), 7.955 (2.22), 8.845 (0.81), 8.860 (1.54), 8.873 (0.73), 12.396 (0.79).

Separation of the Enantiomers:

The title compound (1.0 g) was dissolved in 45 ml of a mixture of methanol and acetonitrile and separated into the enantiomers by preparative SFC on a chiral phase (see Examples 8 and 9) [column: Daicel Chiralcel OJ-H, 5 μm, 250 mm×20 mm; flow rate: 80 ml/min; detection: 210 nm; temperature: 40° C.; injection: 0.4 ml; mobile phase: 70% carbon dioxide/30% methanol; run time 4 min, isocratic]. The combined target fractions were concentrated and the residue was dried under reduced pressure.

Example 8

(−)-3-{[(6-Bromo-3-methyl-2-phenylquinolin-4-yl)carbonyl]amino}-2-(2-methoxyphenyl)propanoic Acid (Enantiomer 1)

In the enantiomer separation described in Example 7, 450 mg (100% purity, ee 100%) of the title compound were obtained as the enantiomer that eluted earlier.

$[\alpha]_D^{20}$=−57.5°, 589 nm, c=0.35 g/100 ml, methanol

LC-MS (Method 1): $R_t$=1.84 min; MS (ESIpos): m/z=519/521 [M+H]$^+$ $^1$H-NMR (400 MHz, DMSO-d6) δ [ppm]: −0.008 (0.89), 2.073 (0.62), 2.176 (6.14), 3.750 (1.00), 3.768 (1.06), 3.784 (1.16), 3.797 (16.00), 3.943 (0.98), 4.267 (1.10), 4.286 (2.10), 4.305 (0.86), 6.935 (0.87), 6.938 (0.93), 6.954 (1.81), 6.957 (1.81), 6.973 (1.03), 6.975 (1.06), 7.020 (1.67), 7.039 (1.87), 7.256 (0.87), 7.260 (1.12), 7.279 (4.03), 7.298 (2.95), 7.490 (1.05), 7.493 (1.02), 7.496 (1.01), 7.505 (2.81), 7.512 (2.56), 7.516 (1.71), 7.525 (5.79), 7.530 (5.58), 7.534 (4.52), 7.538 (3.81), 7.542 (2.84), 7.550 (0.83), 7.838 (1.39), 7.843 (1.16), 7.860 (2.02), 7.865 (1.80), 7.933 (3.43), 7.955 (2.18), 8.846 (0.84), 8.860 (1.54).

Example 9

(+)-3-{[(6-Bromo-3-methyl-2-phenylquinolin-4-yl)carbonyl]amino}-2-(2-methoxyphenyl)propanoic Acid (Enantiomer 2)

In the enantiomer separation described in Example 7, 318 mg (99% purity, ee 100%) of the title compound were obtained as the enantiomer that eluted later.

$[\alpha]_D^{20}$=+60.3°, 589 nm, c=0.36 g/100 ml, methanol

LC-MS (Method 1): $R_t$=1.84 min; MS (ESIpos): m/z=519/521 [M+H]$^+$ $^1$H-NMR (400 MHz, DMSO-d6) δ [ppm]: −0.008 (0.62), 0.008 (0.54), 2.073 (1.05), 2.176 (6.09), 2.523 (0.51), 3.735 (0.50), 3.750 (0.84), 3.767 (0.73), 3.784 (0.75), 3.797 (16.00), 3.911 (0.48), 3.925 (0.66), 3.929 (0.67), 3.943 (0.92), 3.962 (0.53), 3.976 (0.46), 4.266 (1.00), 4.285 (2.02), 4.304 (0.83), 6.937 (0.86), 6.956 (1.82), 6.975 (1.04), 7.019 (1.64), 7.039 (1.88), 7.260 (0.98), 7.279 (3.91), 7.298 (2.92), 7.490 (0.78), 7.505 (2.48), 7.511 (2.19), 7.525 (5.43), 7.531 (5.42), 7.537 (3.79), 7.550 (0.84), 7.773 (0.66), 7.838 (1.35), 7.843 (1.13), 7.860 (2.02), 7.865 (1.87), 7.933 (3.53), 7.955 (2.27), 8.847 (0.74), 8.861 (1.48), 8.875 (0.72), 12.407 (0.66).

Example 10

(+/−)-3-{[(6-Bromo-3-methyl-2-phenylquinolin-4-yl)carbonyl]amino}-2-(4-fluorophenyl)propanoic Acid (Racemate)

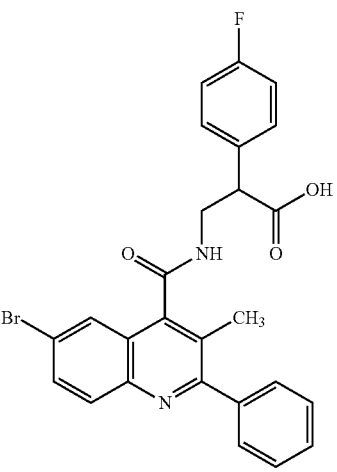 [SMILES: Cc1c(-c2ccccc2)nc2ccc(Br)cc2c1C(=O)NCC(C(=O)O)c1ccc(F)cc1]

At RT, 1 M aqueous sodium hydroxide solution (2.2 ml, 2.2 mmol) was added to a solution of (+/−)-methyl 3-{[(6-bromo-3-methyl-2-phenylquinolin-4-yl)carbonyl]amino}-2-(4-fluorophenyl)propanoate (192 mg, 368 μmol, Example 156A) in THF (3.1 ml) and methanol (630 μl), and the mixture was stirred at RT overnight. The mixture was subsequently adjusted to pH 3 using TFA (198 μl, 2.6 mmol) and concentrated. The residue was taken up in DMSO and purified by preparative HPLC (Method 15). The combined target fractions were concentrated and the residue was dried under reduced pressure. This gave 143 mg (100% purity, 76% of theory) of the title compound.

LC-MS (Method 1): $R_t$=1.88 min; MS (ESIpos): m/z=507/509 [M+H]$^+$ $^1$H-NMR (400 MHz, DMSO-d6) δ [ppm]: 2.086 (1.66), 2.158 (5.56), 3.802 (1.49), 3.854 (3.59), 3.871 (5.34), 3.885 (3.88), 4.000 (2.74), 4.019 (4.23), 4.039 (1.71), 5.754 (1.63), 7.190 (4.07), 7.212 (8.57), 7.234 (4.78), 7.417 (5.22), 7.430 (6.34), 7.437 (5.67), 7.451 (4.32), 7.482 (0.91), 7.493 (2.23), 7.507 (6.82), 7.514 (5.93), 7.526 (16.00), 7.533 (15.50), 7.682 (0.75), 7.838 (2.91), 7.843 (2.58), 7.861 (4.53), 7.865 (4.06), 7.936 (7.11), 7.958 (4.55), 8.939 (2.18), 8.953 (4.25), 8.966 (2.12).

Separation of the Enantiomers:

The title compound (120 mg) was dissolved in 12 ml of a mixture of acetonitrile and methanol and separated into the enantiomers by preparative HPLC on a chiral phase (see Examples 11 and 12) [column: Daicel Chiralpak IA, 5 μm 250 mm×4.6 mm; flow rate: 20 ml/min; detection: 220 nm; temperature: 23° C.; injection: 0.08 ml; mobile phase: 55% heptane/(45% ethanol+0.2% TFA+1% water); isocratic]. The combined target fractions were concentrated and lyophilized.

Example 11

3-{[(6-Bromo-3-methyl-2-phenylquinolin-4-yl)carbonyl]amino}-2-(4-fluorophenyl)propanoic Acid (Enantiomer 1)

In the enantiomer separation described in Example 10, the prepurified title compound was obtained as earlier-eluting enantiomer (ee 100%), then taken up in acetonitrile and repurified by preparative HPLC (Method 15). The combined target fractions were concentrated and lyophilized. This gave 17 mg (100% purity) of the repurified title compound.
LC-MS (Method 1): $R_t$=1.86 min; MS (ESIpos): m/z=507/509 [M+H]$^+$
$^1$H-NMR (400 MHz, DMSO-d6) δ [ppm]: −0.008 (0.75), 0.008 (0.71), 2.157 (5.20), 2.327 (0.46), 2.366 (0.45), 2.523 (2.18), 2.670 (0.40), 3.800 (0.54), 3.853 (3.11), 3.870 (4.71), 3.884 (3.33), 3.998 (2.78), 4.017 (4.32), 4.037 (1.65), 7.189 (4.64), 7.211 (9.47), 7.233 (5.23), 7.407 (1.61), 7.415 (6.21), 7.421 (3.75), 7.429 (7.03), 7.437 (6.30), 7.445 (3.06), 7.451 (5.25), 7.480 (1.60), 7.491 (2.83), 7.496 (2.99), 7.506 (7.45), 7.513 (6.73), 7.525 (16.00), 7.530 (15.37), 7.534 (12.62), 7.538 (9.71), 7.542 (7.43), 7.550 (2.18), 7.682 (0.72), 7.836 (3.05), 7.842 (2.87), 7.859 (4.50), 7.864 (4.25), 7.934 (8.30), 7.956 (5.24), 8.937 (2.32), 8.951 (4.34), 8.965 (2.05), 12.695 (0.72).

Example 12

3-{[(6-Bromo-3-methyl-2-phenylquinolin-4-yl)carbonyl]amino}-2-(4-fluorophenyl)propanoic Acid (Enantiomer 2)

In the enantiomer separation described in Example 10, the prepurified title compound was obtained as later-eluting enantiomer (ee 97%), then taken up in acetonitrile and repurified by preparative HPLC (Method 15). The combined target fractions were concentrated and lyophilized. This gave 18 mg (100% purity) of the repurified title compound.
LC-MS (Method 1): $R_t$=1.86 min; MS (ESIpos): m/z=507/509 [M+H]$^+$
$^1$H-NMR (400 MHz, DMSO-d6) δ [ppm]: 0.008 (0.59), 2.157 (4.91), 2.523 (1.21), 3.852 (2.68), 3.870 (4.44), 3.885 (3.20), 3.999 (2.66), 4.018 (4.37), 4.037 (1.66), 7.189 (4.59), 7.194 (2.01), 7.211 (9.94), 7.216 (2.80), 7.228 (2.29), 7.233 (5.54), 7.241 (0.79), 7.408 (0.93), 7.415 (5.86), 7.421 (3.02), 7.429 (6.70), 7.437 (5.97), 7.446 (2.54), 7.451 (5.00), 7.459 (0.67), 7.480 (0.87), 7.491 (2.04), 7.506 (6.75), 7.513 (5.85), 7.525 (16.00), 7.531 (15.10), 7.534 (12.59), 7.538 (9.63), 7.542 (7.55), 7.550 (2.09), 7.683 (0.64), 7.836 (3.11), 7.842 (2.87), 7.859 (4.78), 7.864 (4.59), 7.934 (9.03), 7.957 (5.79), 8.937 (2.16), 8.951 (4.37), 8.965 (2.06), 12.698 (1.19).

Example 13

(+/−)-3-{[(6-Bromo-3-methyl-2-phenylquinolin-4-yl)carbonyl]amino}-2-methyl-2-phenylpropanoic Acid (Racemate)

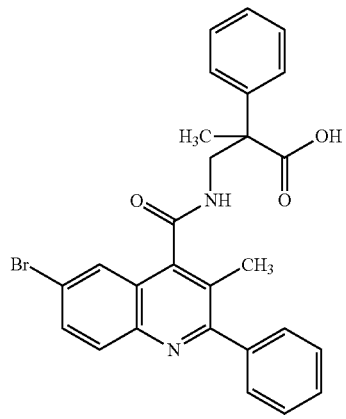

At RT, 1 M aqueous sodium hydroxide solution (2.3 ml, 2.3 mmol) was added to a solution of (+/−)-ethyl 3-{[(6-bromo-3-methyl-2-phenylquinolin-4-yl)carbonyl]amino}-2-methylphenylpropanoate (204 mg, 383 μmol, Example 157A) in THF (3.2 ml) and methanol (1.6 ml), and the mixture was stirred at RT for 20 h. The mixture was then adjusted to pH 3 by addition of TFA (210 μl, 2.7 mmol) and purified by preparative HPLC (Method 20). The combined target fractions were concentrated and lyophilized. This gave 195 mg (100% purity, "100% of theory", contains solvent) of the title compound.
LC-MS (Method 2): $R_t$=1.03 min; MS (ESIpos): m/z=503/505 [M+H]$^+$
$^1$H-NMR (400 MHz, DMSO-d6) δ [ppm]: −0.008 (0.49), 0.008 (0.58), 1.647 (16.00), 2.072 (0.68), 2.116 (2.00), 3.806 (1.36), 3.818 (1.54), 3.840 (1.77), 3.852 (1.63), 4.176 (1.56), 4.194 (1.70), 4.210 (1.46), 4.228 (1.38), 5.754 (1.35), 7.274 (0.78), 7.292 (2.20), 7.310 (1.67), 7.364 (2.52), 7.384 (5.10), 7.402 (3.22), 7.434 (6.71), 7.452 (3.72), 7.477 (0.50), 7.489 (1.51), 7.504 (4.49), 7.510 (3.58), 7.522 (7.48), 7.535 (8.74), 7.552 (1.68), 7.682 (0.67), 7.832 (2.05), 7.837 (1.89), 7.854 (3.10), 7.860 (3.04), 7.931 (5.79), 7.953 (3.72), 8.650 (1.26), 8.663 (1.77), 8.667 (1.79), 8.680 (1.25).

Separation of the Enantiomers:
The title compound (175 mg) was dissolved in methanol (15 ml) and separated into the enantiomers by preparative SFC on a chiral phase (see Examples 14 and 15) [column: Daicel Chiralpak AD-H, 5 μm, 250 mm×20 mm; flow rate: 80 ml/min; detection: 210 nm; temperature: 40° C.; injection: 2.0 ml; mobile phase: 70% carbon dioxide/30% methanol; run time 10 min, isocratic]. The combined target fractions were concentrated and the residue was dried under reduced pressure.

Example 14

(−)-3-{[(6-Bromo-3-methyl-2-phenylquinolin-4-yl)carbonyl]amino}-2-methyl-2-phenylpropanoic Acid (Enantiomer 1)

In the enantiomer separation described in Example 13, 71 mg (95% purity, ee 100%) of the title compound were obtained as the enantiomer that eluted earlier.
$[α]_D^{20}$=−42.9°, 589 nm, c=0.40 g/100 ml, methanol
LC-MS (Method 2): $R_t$=1.05 min; MS (ESIpos): m/z=503/505 [M+H]$^+$
$^1$H-NMR (400 MHz, DMSO-d6) δ [ppm]: −0.008 (0.44), 0.008 (0.44), 1.645 (16.00), 2.116 (2.04), 2.523 (0.51), 3.805 (1.39), 3.817 (1.53), 3.838 (1.78), 3.851 (1.61), 4.174 (1.57), 4.192 (1.69), 4.208 (1.45), 4.226 (1.35), 7.274 (0.81), 7.292 (2.21), 7.310 (1.68), 7.324 (0.46), 7.363 (2.56), 7.383 (5.10), 7.402 (3.25), 7.433 (6.81), 7.451 (3.69), 7.475 (0.57), 7.487 (1.54), 7.502 (4.49), 7.508 (3.60), 7.520 (7.86), 7.533 (8.79), 7.550 (1.62), 7.678 (0.63), 7.828 (1.94), 7.833 (1.79), 7.850 (2.98), 7.856 (2.90), 7.929 (5.51), 7.951 (3.67), 8.648 (1.26), 8.665 (1.77), 8.678 (1.22), 12.658 (1.38).

Example 15

(+)-3-{[(6-Bromo-3-methyl-2-phenylquinolin-4-yl)carbonyl]amino}-2-methyl-2-phenylpropanoic Acid (Enantiomer 2)

In the enantiomer separation described in Example 13, 69 mg (98% purity, ee 100%) of the title compound were obtained as the enantiomer that eluted later.
$[α]_D^{20}$=+42.4°, 589 nm, c=0.37 g/100 ml, methanol LC-MS (Method 2): $R_t$=1.05 min; MS (ESIpos): m/z=503/505 [M+H]$^+$ $^1$H-NMR (400 MHz, DMSO-d6) δ [ppm]: 1.640 (16.00), 2.114 (2.43), 3.804 (1.41), 3.816 (1.55), 3.838 (1.81), 3.850 (1.64), 4.167 (1.52), 4.184 (1.64), 4.200 (1.40), 4.218 (1.31), 7.272 (0.86), 7.290 (2.36), 7.307 (1.81), 7.324 (0.42), 7.361 (2.70), 7.381 (5.38), 7.399 (3.40), 7.431 (7.11), 7.450 (3.85), 7.474 (0.63), 7.487 (1.65), 7.502 (4.79), 7.507 (3.87), 7.520 (8.30), 7.532 (9.51), 7.549 (1.86), 7.678 (0.78), 7.828 (2.05), 7.833 (1.89), 7.850 (3.15), 7.855 (3.08), 7.928 (5.67), 7.950 (3.76), 8.654 (1.26), 8.670 (1.87), 8.684 (1.24).

Example 16

(+/−)-2-({[(6-Bromo-3-methyl-2-phenylquinolin-4-yl)carbonyl]amino}methyl)-2-phenylbutanoic Acid (Racemate)

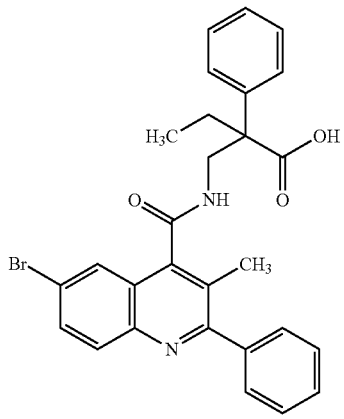

At RT, 1 M aqueous sodium hydroxide solution (6.1 ml, 6.1 mmol) was added to a solution of (+/−)-methyl 2-({[(6-bromo-2-methyl-2-phenylquinolin-4-yl)carbonyl]amino}methyl)-2-phenylbutanoate (540 mg, 1.02 mmol, Example 158A) in THF (8.7 ml) and methanol (1.7 ml), and the mixture was stirred at RT for 16 h. Subsequently, aqueous sodium hydroxide solution (6.1 ml, 6.1 mmol) was added again, and the mixture was stirred at RT for a further 4 h. Subsequently, methanol (5 ml) was added and the mixture was stirred at 40° C. overnight. The mixture was then adjusted to pH 3 by addition of TFA and purified by preparative HPLC (Method 16). The combined target fractions were concentrated and lyophilized. This gave 495 mg (98% purity, 92% of theory) of the title compound.

LC-MS (Method 2): $R_t$=1.07 min; MS (ESIpos): m/z=517/519 [M+H]$^+$ $^1$H-NMR (400 MHz, DMSO-d6) δ [ppm]: 0.883 (5.29), 0.901 (12.03), 0.919 (5.67), 2.085 (2.56), 2.101 (3.71), 2.118 (4.29), 2.138 (4.09), 2.158 (2.91), 2.175 (1.49), 2.193 (0.81), 2.689 (1.35), 2.731 (1.66), 2.890 (1.78), 3.947 (1.70), 3.960 (1.84), 3.981 (2.25), 3.994 (2.15), 4.206 (2.25), 4.223 (2.29), 4.240 (1.89), 4.257 (1.73), 7.274 (2.20), 7.291 (1.79), 7.349 (2.00), 7.370 (6.65), 7.387 (16.00), 7.404 (2.33), 7.475 (0.67), 7.487 (1.79), 7.501 (5.73), 7.507 (4.68), 7.519 (11.55), 7.529 (11.24), 7.546 (1.98), 7.642 (0.69), 7.827 (2.51), 7.832 (2.35), 7.849 (3.86), 7.854 (3.80), 7.923 (7.49), 7.946 (4.75), 8.501 (1.66), 8.516 (2.84), 8.530 (1.64).

Separation of the Enantiomers:

The title compound (450 mg) was dissolved in methanol (25 ml) and separated into the enantiomers by preparative SFC on a chiral phase (see Examples 17 and 18) [column: Daicel Chiralpak AD, 10 μm 250 mm×20 mm; flow rate: 80 ml/min; detection: 210 nm; temperature: 40° C.; injection: 1.0 ml; mobile phase: 78% carbon dioxide/22% isopropanol; run time 10 min, isocratic]. The combined target fractions were concentrated and the residue was dried under reduced pressure.

Example 17

(−)-2-({[(6-Bromo-3-methyl-2-phenylquinolin-4-yl)carbonyl]amino}methyl)-2-phenylbutanoic Acid (Enantiomer 1)

In the enantiomer separation described in Example 16, 156 mg (98% purity, ee 100%) of the title compound were obtained as the enantiomer that eluted earlier.

[α]$_D^{20}$=−10.0°, 436 nm, c=0.32 g/100 ml, chloroform

LC-MS (Method 1): $R_t$=2.02 min; MS (ESIpos): m/z=517/519 [M+H]$^+$ $^1$H-NMR (400 MHz, DMSO-d6) δ [ppm]: 0.882 (5.37), 0.901 (12.17), 0.919 (5.68), 2.084 (2.60), 2.100 (3.68), 2.118 (4.29), 2.137 (4.05), 2.157 (2.89), 2.174 (1.48), 2.193 (0.80), 2.327 (0.48), 2.669 (0.45), 2.890 (0.40), 3.781 (1.39), 3.946 (1.76), 3.958 (1.82), 3.980 (2.11), 3.993 (1.96), 4.205 (1.71), 4.222 (1.83), 4.238 (1.49), 4.256 (1.36), 7.273 (2.16), 7.290 (1.78), 7.349 (1.96), 7.369 (6.67), 7.386 (16.00), 7.403 (2.35), 7.473 (0.68), 7.486 (1.79), 7.500 (5.74), 7.507 (4.75), 7.518 (11.53), 7.528 (11.13), 7.636 (0.69), 7.826 (2.62), 7.831 (2.41), 7.848 (4.00), 7.853 (3.91), 7.923 (7.83), 7.945 (4.94), 8.499 (1.66), 8.515 (2.83), 8.530 (1.61).

Example 18

(+)-2-({[(6-Bromo-3-methyl-2-phenylquinolin-4-yl)carbonyl]amino}methyl)-2-phenylbutanoic Acid (Enantiomer 2)

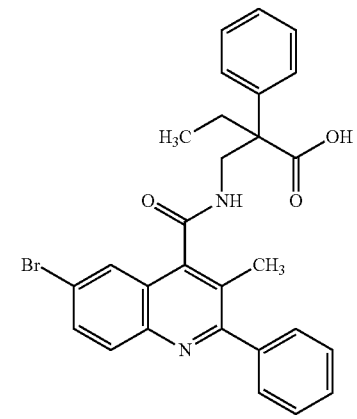 [SMILES: CCC(CNC(=O)c1c(C)c(-c2ccccc2)nc2ccc(Br)cc12)(C(=O)O)c1ccccc1]

In the enantiomer separation described in Example 16, 162 mg (98% purity, ee 100%) of the title compound were obtained as the enantiomer that eluted later.

[α]$_D^{20}$=+11.40, 436 nm, c=0.35 g/100 ml, chloroform

LC-MS (Method 1): $R_t$=2.02 min; MS (ESIpos): m/z=517/519 [M+H]$^+$ $^1$H-NMR (400 MHz, DMSO-d6) δ [ppm]: −0.008 (3.29), 0.008 (3.13), 0.882 (5.46), 0.900 (12.52), 0.918 (5.74), 2.083 (2.56), 2.100 (3.63), 2.117 (4.23), 2.137 (4.00), 2.157 (2.86), 2.174 (1.47), 2.192 (0.78), 2.327 (0.67), 2.366 (0.54), 2.518 (2.78), 2.523 (2.15), 2.669 (0.64), 2.674 (0.48), 2.710 (0.52), 3.555 (5.62), 3.945 (1.41), 3.958 (1.52), 3.980 (1.88), 3.992 (1.71), 4.204 (1.66), 4.221 (1.78), 4.238 (1.44), 4.255 (1.31), 7.258 (0.94), 7.274 (2.11), 7.290 (1.78), 7.348 (2.01), 7.369 (6.76), 7.386 (16.00), 7.403 (2.20), 7.473 (0.73), 7.485 (1.95), 7.499 (5.70), 7.506 (5.02), 7.519 (11.25), 7.526 (10.60), 7.529 (10.35), 7.545 (1.82), 7.638 (0.61), 7.825 (2.75), 7.830 (2.53), 7.847 (4.20), 7.853 (4.05), 7.922 (7.81), 7.944 (4.98), 8.498 (1.69), 8.514 (2.76), 8.528 (1.61), 12.630 (0.48).

Example 19

(+/−)-3-{[(6-Bromo-3-methyl-2-phenylquinolin-4-yl)carbonyl]amino}-2-hydroxy-2-phenylpropanoic Acid (Racemate)

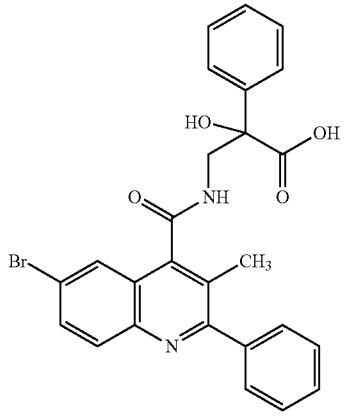

At RT, (+/−)-methyl 3-amino-2-hydroxy-2-phenylpropanoate (602 mg, 3.08 mmol, preparable by addition of 1 M aqueous sodium hydroxide solution to a mixture of (+/−)-methyl 3-amino-2-hydroxy-2-phenylpropanoate hydrochloride (Example 79A) in water to neutral pH, followed by extraction with dichloromethane and concentration of the organic phase) was added to a solution of (6-bromo-3-methyl-2-phenylquinolin-4-yl)(1H-imidazol-1-yl)methanone (1.10 g, 2.80 mmol, preparable according to WO 2016/037954, Example 2A, p. 58) in DMF (15 ml). Slowly and with stirring, a 1 M solution of potassium tert-butoxide (7.0 ml, 7.0 mmol) in THF was then added dropwise, and the reaction mixture was stirred at RT for 2 days. 10% strength citric acid (150 ml) was then added, and the mixture was extracted twice with ethyl acetate (in each case 100 ml). The combined organic phases were washed once with saturated aqueous sodium chloride solution (100 ml) and dried over sodium sulfate, filtered and concentrated. The residue was triturated in a few milliliters of a hot mixture of DMSO, water and acetonitrile, and the solid present was filtered off. The filtrate was purified by means of preparative HPLC (Method 22). The combined target fractions were concentrated and the residue was dried under reduced pressure. This gave 149 mg (100% purity, 11% of theory) of the title compound.

LC-MS (Method 1): $R_t$=1.75 min; MS (ESIpos): m/z=505/507 [M+H]$^+$ $^1$H-NMR (400 MHz, DMSO-d6) δ [ppm]: −0.008 (1.87), 0.008 (1.97), 1.211 (0.43), 2.085 (2.34), 2.366 (0.84), 2.710 (0.84), 3.641 (0.45), 3.964 (4.57), 3.985 (3.50), 3.998 (3.54), 4.019 (3.77), 4.032 (3.54), 4.188 (2.47), 4.205 (2.62), 4.222 (2.06), 4.238 (1.91), 5.753 (6.52), 7.299 (0.99), 7.317 (2.55), 7.335 (2.34), 7.370 (4.53), 7.389 (6.61), 7.407 (2.90), 7.473 (0.88), 7.484 (1.84), 7.488 (1.95), 7.498 (5.68), 7.505 (5.64), 7.518 (16.00), 7.530 (8.94), 7.640 (9.05), 7.658 (8.26), 7.662 (6.09), 7.809 (3.05), 7.814 (2.81), 7.831 (4.48), 7.837 (4.40), 7.907 (9.09), 7.929 (5.81), 8.669 (1.65), 8.683 (2.81), 8.697 (1.59).

Separation of the Enantiomers:

The title compound (140 mg) was dissolved in 17 ml of a mixture of methanol and acetonitrile and separated into the enantiomers by preparative SFC on a chiral phase (see Examples 20 and 21) [column: Daicel Chiralpak AZ-H, 5 μm, 250 mm×20 mm; flow rate: 80 ml/min; detection: 210 nm; temperature: 40° C.; injection: 0.5 ml; mobile phase: 70% carbon dioxide/30% methanol; run time 8 min, isocratic]. The combined target fractions were concentrated and the residue was dried under reduced pressure.

Example 20

(+)-3-{[(6-Bromo-3-methyl-2-phenylquinolin-4-yl)carbonyl]amino}-2-hydroxy-2-phenylpropanoic Acid (Enantiomer 1)

In the enantiomer separation described in Example 19, the prepurified title compound was obtained as earlier-eluting enantiomer (ee 98%) and repurified by preparative HPLC (Method 23). The combined target fractions were concentrated and lyophilized. This gave 19 mg (95% purity) of the title compound.

$[\alpha]_D^{20}$=+22.3°, 589 nm, c=0.16 g/100 ml, methanol

LC-MS (Method 2): $R_t$=0.93 min; MS (ESIpos): m/z=505/507 [M+H]$^+$ $^1$H-NMR (400 MHz, DMSO-d6) δ [ppm]: 2.091 (2.15), 3.987 (1.42), 3.998 (1.50), 4.021 (1.95), 4.032 (1.77), 4.189 (2.04), 4.205 (2.06), 4.223 (1.62), 4.239 (1.51), 4.964 (0.51), 7.317 (2.50), 7.335 (2.35), 7.370 (4.32), 7.389 (6.47), 7.408 (2.86), 7.488 (1.95), 7.499 (5.60), 7.506 (5.19), 7.519 (16.00), 7.641 (8.95), 7.659 (7.59), 7.810 (2.80), 7.833 (4.18), 7.838 (4.16), 7.908 (8.05), 7.930 (5.10), 8.671 (1.74), 8.684 (2.84).

Example 21

(−)-3-{[(6-Bromo-3-methyl-2-phenylquinolin-4-yl)carbonyl]amino}-2-hydroxy-2-phenylpropanoic Acid (Enantiomer 2)

In the enantiomer separation described in Example 19, the prepurified title compound was obtained as later-eluting enantiomer (ee 96%) and repurified by preparative HPLC (Method 23). The combined target fractions were concentrated and lyophilized. This gave 21 mg (96% purity) of the title compound.

$[\alpha]_D^{20}$=−18.9°, 589 nm, c=0.34 g/100 ml, methanol

LC-MS (Method 2): $R_t$=0.93 min; MS (ESIpos): m/z=505/507 [M+H]$^+$ $^1$H-NMR (400 MHz, DMSO-d6) δ [ppm]: 2.096 (2.18), 3.987 (1.37), 3.999 (1.50), 4.021 (1.98), 4.033 (1.83), 4.190 (1.98), 4.207 (2.14), 4.224 (1.65), 4.241 (1.49), 7.300 (1.10), 7.317 (2.65), 7.335 (2.43), 7.370 (4.60), 7.389 (6.63), 7.407 (3.06), 7.476 (0.94), 7.491 (2.08), 7.501 (5.89), 7.508 (5.53), 7.521 (16.00), 7.641 (8.97), 7.660 (7.96), 7.720 (0.57), 7.815 (2.82), 7.820 (2.60), 7.837 (4.27), 7.842 (4.07), 7.911 (7.89), 7.933 (5.02), 8.673 (1.77), 8.687 (3.01), 8.701 (1.71).

Example 22

(+/−)-3-{[(6-Bromo-3-methyl-2-phenylquinolin-4-yl)carbonyl]amino}-2-[3-(trifluoromethyl)phenyl]propanoic Acid (Racemate)

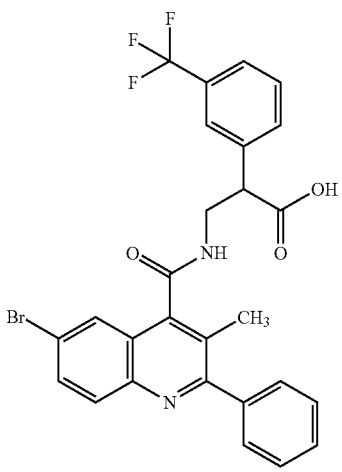 [SMILES: Cc1c(-c2ccccc2)nc2ccc(Br)cc2c1C(=O)NCC(C(=O)O)c1cccc(C(F)(F)F)c1]

At RT, 1 M aqueous sodium hydroxide solution (360 µl, 360 µmol) was added to a solution of (+/−)-ethyl 3-{[(6-bromo-3-methyl-2-phenylquinolin-4-yl)carbonyl]amino}-2-[3-(trifluoromethyl)phenyl]propanoate (35 mg, 59.8 µmol, Example 159A) in THF (510 µl) and methanol (100 µl), and the mixture was stirred at RT for four days. The mixture was subsequently adjusted to pH 3 using TFA (32 µl, 420 µmol) and then concentrated. The residue was taken up in DMSO and purified by preparative HPLC (Method 15). The combined target fractions were concentrated and lyophilized. This gave 147 mg (100% purity, 99% of theory) of the title compound.

LC-MS (Method 2): $R_t$=1.07 min; MS (ESIneg): m/z=557/559 [M−H]⁻

¹H-NMR (400 MHz, DMSO-d6) δ [ppm]: 2.083 (1.10), 3.925 (1.15), 3.938 (1.69), 3.957 (2.04), 3.972 (1.05), 4.125 (1.30), 4.145 (2.27), 4.164 (0.90), 7.517 (16.00), 7.617 (0.69), 7.636 (1.82), 7.655 (1.80), 7.685 (2.15), 7.720 (6.05), 7.738 (1.73), 7.838 (1.37), 7.843 (1.35), 7.861 (2.08), 7.866 (2.10), 7.933 (3.89), 7.955 (2.44), 8.949 (0.93), 8.962 (1.72), 8.975 (0.94).

Example 23

(+/−)-2-(1,3-Benzodioxol-5-yl)-3-{[(6-bromo-3-methyl-2-phenylquinolin-4-yl)carbonyl]amino}propanoic Acid (Racemate)

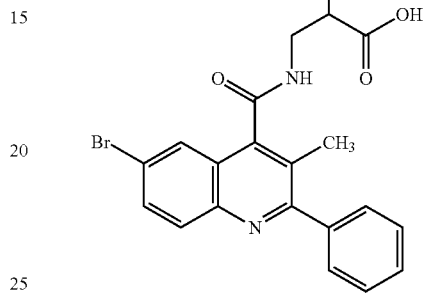

At RT, 1 M aqueous sodium hydroxide solution (1.2 ml, 1.2 mmol) was added to a solution of (+/−)-ethyl 2-(1,3-benzodioxol-5-yl)-3-{[(6-bromo-3-methyl-2-phenylquinolin-4-yl)carbonyl]amino}propanoate (110 mg, 196 µmol, Example 160A) in THF (1.7 ml) and methanol (330 µl), and the mixture was stirred at RT for four days. The mixture was then adjusted to pH 3 by addition of TFA (110 µl, 1.4 mmol) and purified by preparative HPLC (Method 15). The combined target fractions were concentrated and dried under reduced pressure. This gave 84 mg (98% purity, 79% of theory) of the title compound.

LC-MS (Method 2): $R_t$=0.96 min; MS (ESIpos): m/z=533/535 [M+H]⁺

¹H-NMR (400 MHz, DMSO-d6) δ [ppm]: −0.008 (2.23), 0.008 (1.80), 2.185 (7.83), 2.328 (0.82), 2.367 (0.43), 2.523 (2.13), 2.670 (0.77), 3.823 (3.68), 3.906 (3.23), 3.925 (4.20), 3.944 (1.59), 4.869 (0.78), 5.966 (0.46), 6.000 (16.00), 6.830 (3.16), 6.835 (3.38), 6.851 (5.93), 6.855 (6.40), 6.893 (11.41), 6.913 (5.88), 6.935 (8.97), 6.938 (8.35), 7.483 (0.92), 7.495 (2.38), 7.510 (7.43), 7.516 (6.51), 7.529 (14.53), 7.536 (14.85), 7.540 (13.69), 7.556 (2.60), 7.725 (1.16), 7.841 (3.81), 7.846 (3.40), 7.864 (5.64), 7.869 (5.36), 7.938 (10.63), 7.961 (6.64), 8.928 (2.17), 8.941 (4.35), 8.955 (2.07).

Separation of the Enantiomers:

The title compound (60 mg) was dissolved in isopropanol (3 ml) and separated into the enantiomers by preparative HPLC on a chiral phase (see Examples 24 and 25) [column: Chiralpak ID, 5 µm 250 mm×20 mm; flow rate: 9 ml/min; detection: 220 nm; temperature: 50° C.; injection: 0.25 ml; mobile phase: 35% heptane/(65% isopropanol+0.2% acetic acid); run time 15 min, isocratic]. The combined target fractions were concentrated, and the residue was lyophilized in acetonitrile/water.

Example 24

2-(1,3-Benzodioxol-5-yl)-3-{[(6-bromo-3-methyl-2-phenylquinolin-4-yl)carbonyl]amino}propanoic Acid (Enantiomer 1)

In the enantiomer separation described in Example 23, the prepurified title compound was obtained as earlier-eluting enantiomer (ee 99%) and repurified by preparative HPLC (Method 20). The combined target fractions were concentrated, and the residue was lyophilized in acetonitrile/water. This gave 20 mg (98% purity) of the title compound.

LC-MS (Method 2): $R_t$=0.97 min; MS (ESIpos): m/z=533/535 [M+H]$^+$ $^1$H-NMR (400 MHz, DMSO-d6) δ [ppm]: δ [ppm]=8.94 (t, 1H), 7.95 (d, 1H), 7.86 (d, 1H), 7.72 (br. s, 1H), 7.60-7.46 (m, 5H), 6.98-6.81 (m, 3H), 6.00 (s, 2H), 3.98-3.76 (m, 3H), 2.19 (br. s, 3H).

Example 25

2-(1,3-Benzodioxol-5-yl)-3-{[(6-bromo-3-methyl-2-phenylquinolin-4-yl)carbonyl]amino}propanoic Acid (Enantiomer 2)

In the enantiomer separation described in Example 23, the prepurified title compound was obtained as later-eluting enantiomer (ee 94%) and repurified by preparative HPLC (Method 20). The combined target fractions were concentrated, and the residue was lyophilized in acetonitrile/water. This gave 22 mg (98% purity) of the title compound.

LC-MS (Method 2): $R_t$=0.97 min; MS (ESIpos): m/z=533/535 [M+H]$^+$ $^1$H-NMR (400 MHz, DMSO-d6) δ [ppm]: −0.008 (2.29), 0.008 (1.90), 2.185 (7.94), 2.231 (0.87), 2.328 (0.42), 2.523 (1.81), 2.670 (0.47), 3.906 (3.19), 3.925 (4.18), 3.944 (1.62), 5.966 (0.64), 6.000 (16.00), 6.831 (3.05), 6.834 (3.25), 6.851 (5.68), 6.855 (6.08), 6.893 (9.85), 6.913 (5.14), 6.935 (8.46), 6.938 (7.99), 7.484 (0.74), 7.495 (2.17), 7.510 (7.02), 7.517 (6.12), 7.529 (13.81), 7.537 (14.58), 7.540 (13.71), 7.556 (2.98), 7.725 (1.12), 7.842 (3.36), 7.847 (3.10), 7.864 (5.17), 7.869 (5.04), 7.939 (9.15), 7.961 (5.93), 8.928 (2.10), 8.942 (4.33), 8.955 (2.18).

$^1$H-NMR (400 MHz, DMSO-d6) δ [ppm]: 12.63 (br. s, 1H), 8.94 (t, 1H), 7.95 (d, 1H), 7.86 (dd, 1H), 7.73 (br. s, 1H), 7.58-7.44 (m, 5H), 6.98-6.80 (m, 3H), 6.00 (s, 2H), 3.99-3.75 (m, 3H), 2.19 (br. s, 3H).

Example 26

(+/−)-3-{[(6-Bromo-3-methyl-2-phenylquinolin-4-yl)carbonyl]amino}-2-(3-chloropyridin-2-yl)-2-methylpropanoic Acid (Racemate)

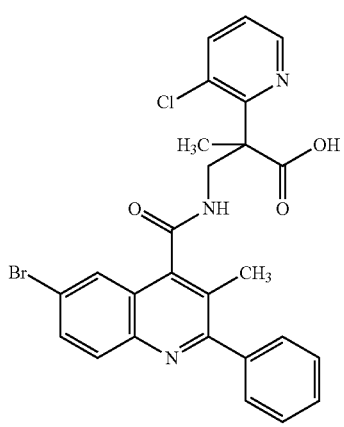

TFA (520 µl, 6.7 mmol) was added to a solution of (+/−)-tert-butyl 3-{[(6-bromo-3-methyl-2-phenylquinolin-4-yl)carbonyl]amino}-2-(3-chloropyridin-2-yl)-2-methylpropanoate (200 mg, 336 µmol, Example 161A) in dichloromethane (2.3 ml), and the mixture was stirred at RT overnight. The mixture was then concentrated and repeatedly, in succession, dichloromethane was added and the mixture was concentrated again. The residue was taken up in dichloromethane and prepurified by flash column chromatography (100 g silica gel Biotage Snap-Cartridge KP-Sil, cyclohexane/ethyl acetate 8:2, Isolera One). The combined target fractions were concentrated and the residue was dried under reduced pressure. The residue was then repurified by preparative HPLC (Method 20). The combined target fractions were concentrated and the residue obtained was dried under reduced pressure. This gave 103 mg (98% purity, 56% of theory) of the title compound.

LC-MS (Method 2): $R_t$=1.01 min; MS (ESIpos): m/z=538/540 [M+H]$^+$ $^1$H-NMR (400 MHz, DMSO-d6) δ [ppm]: 0.008 (0.65), 1.195 (1.04), 1.211 (1.05), 1.261 (0.69), 1.277 (0.68), 1.683 (16.00), 2.190 (5.52), 3.930 (0.60), 3.950 (0.64), 4.471 (0.79), 4.488 (0.91), 4.505 (0.80), 4.523 (0.74), 7.373 (1.45), 7.384 (1.58), 7.392 (1.71), 7.404 (1.68), 7.493 (1.05), 7.508 (3.75), 7.514 (2.97), 7.526 (6.99), 7.538 (8.33), 7.555 (1.93), 7.845 (2.42), 7.849 (1.91), 7.867 (3.42), 7.872 (2.99), 7.899 (2.53), 7.902 (2.70), 7.919 (2.46), 7.922 (2.55), 7.930 (5.60), 7.953 (3.31), 8.527 (2.14), 8.538 (2.19), 8.696 (1.01), 8.712 (2.05), 8.728 (1.14).

Separation of the Enantiomers:

The title compound (70 mg) was dissolved in isopropanol (3 ml) and separated into the enantiomers by preparative HPLC on a chiral phase (see Examples 27 and 28) [column: YMC Chiralart Amylose SA, 5 µm, 250 mm×30 mm; flow rate: 30 ml/min; detection: 220 nm; temperature: 40° C.; injection: 0.40 ml; mobile phase: 50% heptane/(50% isopropanol+0.2% acetic acid); run time 15 min, isocratic]. The combined target fractions were concentrated and the residue was lyophilized.

Example 27

3-{[(6-Bromo-3-methyl-2-phenylquinolin-4-yl)carbonyl]amino}-2-(3-chloropyridin-2-yl)-2-methylpropanoic Acid (Enantiomer 1)

In the enantiomer separation described in Example 26, 21 mg (98% purity, ee 99%) of the title compound were obtained as the enantiomer that eluted earlier.

LC-MS (Method 1): $R_t$=1.89 min; MS (ESIpos): m/z=538/540 [M+H]$^+$ $^1$H-NMR (400 MHz, DMSO-d6) δ [ppm]: 0.008 (0.93), 1.261 (0.44), 1.278 (0.45), 1.682 (16.00), 2.190 (4.78), 3.929 (0.64), 3.949 (0.69), 3.962 (0.61), 4.471 (0.86), 4.488 (0.94), 4.505 (0.85), 4.522 (0.76), 7.373 (1.63), 7.384 (1.74), 7.392 (1.79), 7.404 (1.73), 7.481 (0.56), 7.493 (1.46), 7.507 (4.12), 7.514 (3.34), 7.526 (7.32), 7.535 (7.73), 7.537 (7.88), 7.554 (1.42), 7.844 (2.38), 7.849 (1.82), 7.866 (3.25), 7.871 (2.70), 7.898 (2.33), 7.902 (2.45), 7.919 (2.31), 7.922 (2.43), 7.929 (4.94), 7.952 (2.91), 8.526 (2.14), 8.535 (2.04), 8.694 (1.14), 8.711 (2.11), 8.726 (1.06).

Example 28

3-{[(6-Bromo-3-methyl-2-phenylquinolin-4-yl)carbonyl]amino}-2-(3-chloropyridin-2-yl)-2-methylpropanoic Acid (Enantiomer 2)

In the enantiomer separation described in Example 26, 23 mg (98% purity, ee 99%) of the title compound were obtained as the enantiomer that eluted later.

LC-MS (Method 2): $R_t$=1.00 min; MS (ESIpos): m/z=538/540 [M+H]$^+$ $^1$H-NMR (400 MHz, DMSO-d6) δ [ppm]: 0.008 (0.69), 1.682 (16.00), 2.185 (4.45), 2.189 (4.42), 3.928 (0.63), 3.949 (0.69), 4.470 (0.86), 4.488 (0.93), 4.505 (0.85), 4.522 (0.76), 7.373 (1.62), 7.384 (1.73), 7.392 (1.78), 7.404 (1.73), 7.480 (0.54), 7.493 (1.42), 7.507 (4.03), 7.514 (3.20), 7.525 (7.19), 7.535 (7.70), 7.554 (1.36), 7.844 (2.33), 7.849 (1.76), 7.866 (3.18), 7.871 (2.61), 7.899 (2.36), 7.902 (2.37), 7.919 (2.31), 7.922 (2.36), 7.930 (4.92), 7.952 (2.84), 8.523 (2.07), 8.526 (2.09), 8.535 (2.06), 8.694 (1.13), 8.711 (2.10), 8.727 (1.06).

Example 29

(+/−)-3-{[(6-Bromo-3-methyl-2-phenylquinolin-4-yl)carbonyl]amino}-2-(2-fluorophenyl)-2-methyl-propanoic Acid (Racemate)

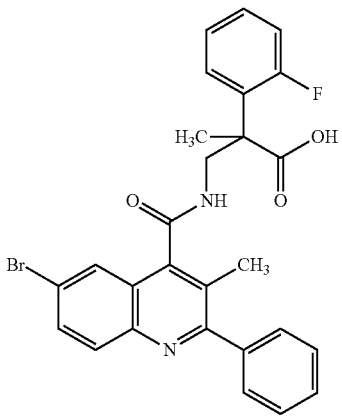 [SMILES: Cc1c(-c2ccccc2)nc2ccc(Br)cc2c1C(=O)NCC(C)(C(=O)O)c1ccccc1F]

At RT, 1 M aqueous sodium hydroxide solution (2.1 ml, 2.1 mmol) was added to a solution of (+/−)-methyl 3-{[(6-bromo-3-methyl-2-phenylquinolin-4-yl)carbonyl]amino}-2-(2-fluorophenyl)-2-methylpropanoate (189 mg, 354 μmol, Example 162A) in THF (3.0 ml) and methanol (1.5 ml), and the mixture was stirred at RT for 24 h. The mixture was then adjusted to pH 3 by addition of TFA (190 μl, 2.5 mmol) and purified by preparative HPLC (Method 20). The combined target fractions were concentrated and the residue was dried under reduced pressure. This gave 154 mg (100% purity, 83% of theory) of the title compound.

LC-MS (Method 2): $R_t$=1.01 min; MS (ESIpos): m/z=521/523 [M+H]$^+$ $^1$H-NMR (400 MHz, DMSO-d6) δ [ppm]: 0.008 (1.16), 1.234 (0.44), 1.637 (16.00), 2.085 (1.65), 3.769 (1.31), 3.781 (1.45), 3.803 (1.60), 3.816 (1.47), 4.251 (1.65), 4.269 (1.82), 4.284 (1.61), 4.304 (1.50), 5.754 (2.61), 7.153 (1.37), 7.173 (1.89), 7.183 (1.90), 7.206 (3.41), 7.226 (1.71), 7.353 (1.43), 7.365 (1.34), 7.389 (2.06), 7.409 (2.94), 7.429 (1.47), 7.477 (0.62), 7.488 (1.54), 7.491 (1.60), 7.501 (5.13), 7.509 (4.63), 7.521 (12.78), 7.525 (11.60), 7.533 (6.95), 7.831 (2.36), 7.836 (2.20), 7.853 (3.67), 7.858 (3.58), 7.922 (7.11), 7.944 (4.32), 8.624 (1.49), 8.638 (2.12), 8.656 (1.47).

Separation of the Enantiomers:

The title compound (137 mg) was dissolved in methanol (17 ml) and separated into the enantiomers by preparative SFC on a chiral phase (see Examples 30 and 31) [column: Daicel Chiralpak AD, 250 mm×20 mm; flow rate: 80 ml/min; detection: 210 nm; temperature: 40° C.; injection: 1.0 ml; mobile phase: 70% carbon dioxide/30% methanol; run time 7 min, isocratic]. The combined target fractions were concentrated and the residue was dried under reduced pressure.

Example 30

(+)-3-{[(6-Bromo-3-methyl-2-phenylquinolin-4-yl)carbonyl]amino}-2-(2-fluorophenyl)-2-methylpropanoic Acid (Enantiomer 1)

In the enantiomer separation described in Example 29, 46 mg (97% purity, ee 100%) of the title compound were obtained as the enantiomer that eluted earlier.

$[α]_D^{20}$=+71.4°, 589 nm, c=0.37 g/100 ml, methanol

LC-MS (Method 2): $R_t$=1.03 min; MS (ESIpos): m/z=521/523 [M+H]$^+$ $^1$H-NMR (400 MHz, DMSO-d6) δ [ppm]: 0.008 (0.62), 1.636 (16.00), 2.093 (1.40), 3.768 (1.33), 3.781 (1.46), 3.801 (1.60), 3.814 (1.48), 4.249 (1.59), 4.268 (1.74), 4.283 (1.54), 4.302 (1.43), 7.153 (1.34), 7.173 (1.85), 7.183 (1.86), 7.205 (3.32), 7.226 (1.68), 7.335 (0.83), 7.352 (1.42), 7.366 (1.32), 7.388 (2.03), 7.409 (2.90), 7.428 (1.48), 7.475 (0.62), 7.490 (1.52), 7.500 (4.83), 7.507 (4.32), 7.519 (12.55), 7.523 (11.56), 7.828 (2.08), 7.833 (2.00), 7.850 (3.30), 7.855 (3.33), 7.920 (6.27), 7.942 (3.91), 8.622 (1.47), 8.639 (2.12), 8.653 (1.46), 12.650 (2.52).

Example 31

(−)-3-{[(6-Bromo-3-methyl-2-phenylquinolin-4-yl)carbonyl]amino}-2-(2-fluorophenyl)-2-methylpropanoic Acid (Enantiomer 2)

In the enantiomer separation described in Example 29, 56 mg (96% purity, ee 100%) of the title compound were obtained as the enantiomer that eluted later.

$[α]_D^{20}$=−70.5°, 589 nm, c=0.39 g/100 ml, methanol

LC-MS (Method 2): $R_t$=1.03 min; MS (ESIpos): m/z=521/523 [M+H]$^+$ $^1$H-NMR (400 MHz, DMSO-d6) δ [ppm]: −0.008 (1.52), 0.008 (1.28), 1.030 (0.98), 1.045 (0.99), 1.283 (0.68), 1.636 (16.00), 2.092 (1.46), 2.522 (0.81), 3.768 (1.38), 3.780 (1.48), 3.801 (1.63), 3.814 (1.48), 4.249 (1.59), 4.267 (1.73), 4.282 (1.55), 4.301 (1.42), 7.152 (1.36), 7.173 (1.90), 7.182 (1.95), 7.205 (3.39), 7.225 (1.73), 7.335 (0.87), 7.350 (1.46), 7.366 (1.37), 7.388 (2.08), 7.408 (2.98), 7.428 (1.53), 7.475 (0.67), 7.486 (1.54), 7.490 (1.62), 7.499 (5.05), 7.507 (4.63), 7.519 (12.83), 7.523 (11.68), 7.531 (7.29), 7.827 (2.24), 7.833 (2.09), 7.850 (3.52), 7.855 (3.45), 7.919 (6.36), 7.942 (3.96), 8.622 (1.51), 8.636 (2.17), 8.653 (1.48), 12.654 (2.75).

Example 32

(+/−)-3-{[(6-Bromo-3-methyl-2-phenylquinolin-4-yl)carbonyl]amino}-2-(2,6-difluorophenyl)-2-methylpropanoic Acid (Racemate)

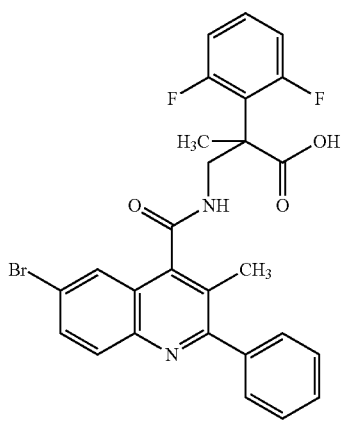 [SMILES: Cc1c(-c2ccccc2)nc2ccc(Br)cc2c1C(=O)NCC(C)(C(=O)O)c1c(F)cccc1F]

TFA (1.6 ml, 21 mmol) was added to a solution of (+/−)-tert-butyl 3-{[(6-bromo-3-methyl-2-phenylquinolin-4-yl)carbonyl]amino}-2-(2,6-difluorophenyl)-2-methylpropanoate (625 mg, 98% purity, 1.03 mmol, Example 163A) in dichloromethane (7.3 ml), and the mixture was stirred at RT overnight. The mixture was then concentrated and repeatedly, in succession, dichloromethane was added and the mixture was concentrated again. The residue was purified by preparative HPLC (Method 20). The combined target fractions were concentrated and the residue obtained was dried under reduced pressure. This gave 492 mg (98% purity, 87% of theory) of the title compound.

LC-MS (Method 2): $R_t$=1.01 min; MS (ESIpos): m/z=539/541 [M+H]$^+$ $^1$H-NMR (400 MHz, DMSO-d6) δ [ppm]: −0.008 (1.84), 0.008 (1.73), 1.761 (12.93), 2.073 (2.77), 2.159 (3.62), 2.327 (0.40), 2.523 (1.15), 3.787 (1.42), 3.800 (1.55), 3.820 (1.75), 3.834 (1.59), 4.196 (1.88), 4.214 (2.04), 4.230 (1.79), 4.248 (1.62), 7.047 (3.11), 7.069 (5.05), 7.094 (3.52), 7.377 (1.49), 7.394 (2.01), 7.410 (1.37), 7.480 (1.03), 7.492 (2.99), 7.507 (8.37), 7.513 (6.86), 7.525 (13.93), 7.538 (16.00), 7.555 (3.11), 7.839 (3.67), 7.845 (3.43), 7.862 (5.71), 7.867 (5.61), 7.933 (10.68), 7.955 (6.66), 8.796 (2.23), 8.812 (3.84), 8.828 (2.16), 12.833 (0.42).

Separation of the Enantiomers:

The title compound (450 mg) was dissolved in isopropanol (5 ml) and separated into the enantiomers by preparative HPLC on a chiral phase (see Examples 33 and 34) [column: Daicel Chiralpak AF, 5 μm 250 mm×20 mm; flow rate: 15 ml/min; detection: 220 nm; temperature: 55° C.; injection: 0.3 ml; mobile phase: 50% heptane/(50% isopropanol+0.2% acetic acid); run time 10 min, isocratic]. The combined target fractions were concentrated and the residue was lyophilized.

Example 33

(+)-3-{[(6-Bromo-3-methyl-2-phenylquinolin-4-yl)carbonyl]amino}-2-(2,6-difluorophenyl)-2-methyl-propanoic Acid (Enantiomer 1)

In the enantiomer separation described in Example 32, 211 mg (98% purity, ee 99%) of the title compound were obtained as the enantiomer that eluted earlier.

$[α]_D^{20}$=+62.7°, 589 nm, c=0.25 g/100 ml, methanol

LC-MS (Method 1): $R_t$=1.92 min; MS (ESIpos): m/z=539/541 [M+H]$^+$ $^1$H-NMR (400 MHz, DMSO-d6) δ [ppm]: 1.762 (13.17), 2.073 (4.25), 2.160 (3.79), 3.788 (1.60), 3.801 (1.75), 3.821 (1.98), 3.835 (1.83), 4.197 (1.96), 4.215 (2.12), 4.231 (1.85), 4.249 (1.66), 7.047 (3.15), 7.070 (5.21), 7.094 (3.51), 7.376 (1.54), 7.393 (2.06), 7.411 (1.42), 7.480 (1.02), 7.492 (2.88), 7.507 (8.19), 7.513 (6.38), 7.525 (13.90), 7.537 (16.00), 7.555 (3.03), 7.629 (0.49), 7.839 (3.36), 7.844 (3.05), 7.861 (5.25), 7.867 (4.98), 7.933 (9.45), 7.955 (5.90), 8.797 (2.25), 8.813 (3.94), 8.829 (2.17), 12.831 (0.43).

Example 34

(−)-3-{[(6-Bromo-3-methyl-2-phenylquinolin-4-yl)carbonyl]amino}-2-(2,6-difluorophenyl)-2-methyl-propanoic Acid (Enantiomer 2)

In the enantiomer separation described in Example 32, 209 mg (98% purity, ee 99%) of the title compound were obtained as the enantiomer that eluted later.

$[α]_D^{20}$=−50.8°, 589 nm, c=0.42 g/100 ml, methanol

LC-MS (Method 1): $R_t$=1.92 min; MS (ESIpos): m/z=539/541 [M+H]$^+$ $^1$H-NMR (400 MHz, DMSO-d6) δ [ppm]: 1.761 (13.10), 2.073 (1.14), 2.159 (3.74), 2.328 (0.45), 2.669 (0.41), 3.787 (1.42), 3.801 (1.54), 3.821 (1.75), 3.835 (1.60), 4.196 (1.84), 4.213 (2.00), 4.230 (1.78), 4.248 (1.62), 7.047 (3.13), 7.069 (5.21), 7.094 (3.54), 7.376 (1.52), 7.393 (2.05), 7.410 (1.40), 7.480 (0.96), 7.493 (2.78), 7.508 (8.25), 7.514 (6.48), 7.526 (14.06), 7.539 (16.00), 7.556 (3.14), 7.841 (3.42), 7.846 (3.18), 7.864 (5.38), 7.869 (5.24), 7.934 (10.00), 7.956 (6.16), 8.797 (2.20), 8.814 (3.90), 8.829 (2.18).

Example 35

(+/−)-3-{[(6-Bromo-3-methyl-2-phenylquinolin-4-yl)carbonyl]amino}-2-(2-chlorophenyl)-2-methyl-propanoic Acid (Racemate)

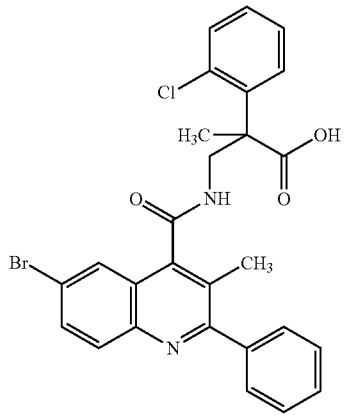 [SMILES: Cc1c(-c2ccccc2)nc2ccc(Br)cc2c1C(=O)NCC(C)(C(=O)O)c1ccccc1Cl]

At RT, 1 M aqueous sodium hydroxide solution (5.9 ml, 5.9 mmol) was added to a solution of (+/−)-methyl 3-{[(6-bromo-3-methyl-2-phenylquinolin-4-yl)carbonyl]amino}-2-(2-chlorophenyl)-2-methylpropanoate (540 mg, 978 μmol, Example 164A) in THF (8.4 ml) and methanol (120 μl), and the mixture was stirred at 40° C. for 8 h. Subsequently, aqueous sodium hydroxide solution (5.9 ml, 5.9 mmol) was added again, and the mixture was stirred at 40° C. for a further 56 h. The mixture was then adjusted to pH 3 by addition of TFA and purified by preparative HPLC (Method 16). The combined target fractions were concentrated, and the residue was lyophilized. This gave 296 mg (98% purity, 55% of theory) of the title compound.

LC-MS (Method 2): $R_t$=1.03 min; MS (ESIpos): m/z=537/539 [M+H]$^+$ $^1$H-NMR (400 MHz, DMSO-d6) δ [ppm]: −0.007 (1.18), 0.008 (0.90), 1.646 (1.14), 1.688 (14.53), 2.073 (1.84), 2.523 (0.85), 2.731 (5.71), 2.890 (7.16), 3.792 (1.39), 3.804 (1.61), 3.825 (1.65), 3.838 (1.60), 4.526 (1.74), 4.545 (1.94), 4.560 (1.78), 4.579 (1.65), 7.323 (1.71), 7.340 (3.30), 7.354 (2.56), 7.372 (1.08), 7.438 (2.79), 7.456 (5.35), 7.460 (4.71), 7.475 (3.07), 7.480 (2.90), 7.491 (1.83), 7.501 (5.16), 7.509 (5.14), 7.520 (16.00), 7.531 (6.71), 7.830 (2.22), 7.835 (2.11), 7.852 (3.59), 7.857 (3.57), 7.918 (6.86), 7.931 (0.60), 7.941 (4.22), 7.952 (1.10), 8.563 (1.62), 8.576 (2.18), 8.581 (2.18), 8.595 (1.59).

Separation of the Enantiomers:

The title compound (275 mg) was dissolved in ethanol (10 ml) and separated into the enantiomers by preparative HPLC on a chiral phase (see Examples 36 and 37) [column: YMC Chiralart Amylose SA, 5 µm, 250 mm×30 mm; flow rate: 30 ml/min; detection: 220 nm; temperature: 40° C.; injection: 0.5 ml; mobile phase: 50% heptane/(50% ethanol+0.2% acetic acid); run time 9.5 min, isocratic]. The combined target fractions were concentrated, and the residue was lyophilized.

Example 36

(−)-3-{[(6-Bromo-3-methyl-2-phenylquinolin-4-yl)carbonyl]amino}-2-(2-chlorophenyl)-2-methylpropanoic Acid (Enantiomer 1)

In the enantiomer separation described in Example 35, the prepurified title compound was obtained as earlier-eluting enantiomer (ee 99%) and repurified by preparative HPLC (Method 15). This gave 68 mg (98% purity) of the title compound.

$[α]_D^{20}$=−94.8°, 589 nm, c=0.40 g/100 ml, chloroform

LC-MS (Method 2): $R_t$=1.03 min; MS (ESIpos): m/z=357/539 [M+H]$^+$ $^1$H-NMR (400 MHz, DMSO-d6) δ [ppm]: −0.008 (3.09), 0.008 (2.81), 1.294 (0.51), 1.645 (0.42), 1.687 (14.26), 2.073 (1.20), 2.328 (0.54), 2.366 (0.43), 2.518 (2.16), 2.523 (1.63), 2.670 (0.50), 3.790 (1.44), 3.803 (1.59), 3.824 (1.70), 3.837 (1.59), 4.395 (0.60), 4.526 (2.20), 4.544 (2.37), 4.559 (2.19), 4.579 (2.04), 7.323 (1.68), 7.340 (3.24), 7.354 (2.51), 7.372 (1.03), 7.437 (2.65), 7.456 (5.25), 7.460 (4.68), 7.474 (3.08), 7.480 (2.87), 7.487 (1.69), 7.490 (1.78), 7.500 (5.04), 7.508 (5.09), 7.519 (16.00), 7.530 (6.41), 7.533 (5.70), 7.828 (2.22), 7.834 (2.09), 7.851 (3.55), 7.856 (3.52), 7.917 (6.88), 7.939 (4.19), 8.561 (1.60), 8.575 (2.13), 8.580 (2.12), 8.593 (1.54).

Example 37

(+)-3-{[(6-Bromo-3-methyl-2-phenylquinolin-4-yl)carbonyl]amino}-2-(2-chlorophenyl)-2-methylpropanoic Acid (Enantiomer 2)

In the enantiomer separation described in Example 35, the prepurified title compound was obtained as later-eluting enantiomer (ee 99%) and repurified by preparative HPLC (Method 15). This gave 99 mg (98% purity) of the title compound.

$[α]_D^{20}$=+96.8°, 589 nm, c=0.33 g/100 ml, chloroform

LC-MS (Method 2): $R_t$=1.03 min; MS (ESIpos): m/z=537/539 [M+H]$^+$ $^1$H-NMR (400 MHz, DMSO-d6) δ [ppm]: −0.008 (2.30), 0.008 (1.81), 1.645 (1.12), 1.687 (14.19), 2.072 (1.44), 2.522 (1.04), 3.790 (1.48), 3.803 (1.68), 3.824 (1.74), 3.837 (1.71), 4.174 (0.72), 4.191 (0.70), 4.207 (0.68), 4.226 (0.65), 4.525 (1.83), 4.544 (1.97), 4.559 (1.83), 4.578 (1.68), 7.322 (1.70), 7.339 (3.25), 7.353 (2.52), 7.371 (1.06), 7.437 (2.76), 7.456 (5.26), 7.459 (4.65), 7.474 (3.03), 7.479 (2.82), 7.489 (1.82), 7.500 (5.03), 7.508 (5.01), 7.518 (16.00), 7.530 (6.62), 7.828 (2.17), 7.833 (2.03), 7.850 (3.52), 7.855 (3.41), 7.917 (6.47), 7.929 (0.56), 7.939 (3.95), 8.561 (1.58), 8.575 (2.15), 8.579 (2.13), 8.593 (1.54).

Example 38

(+/−)-3-{[(6-Bromo-3-methyl-2-phenylquinolin-4-yl)carbonyl]amino}-2-fluoro-2-phenylpropanoic Acid (Racemate)

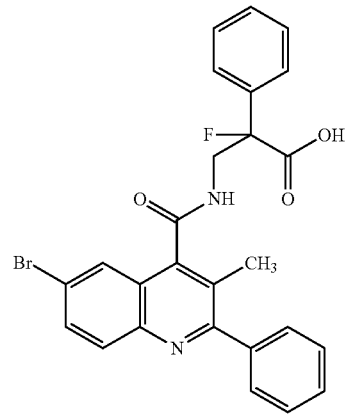 [SMILES: Cc1c(-c2ccccc2)nc2ccc(Br)cc2c1C(=O)NCC(F)(C(=O)O)c1ccccc1]

At RT, 1 M aqueous sodium hydroxide solution (2.2 ml, 2.2 mmol) was added to a solution of (+/−)-ethyl 3-{[(6-bromo-3-methyl-2-phenylquinolin-4-yl)carbonyl]amino}-2-fluorophenylpropanoate (196 mg, 366 µmol, Example 165A) in THF (3.0 ml) and methanol (1.5 ml), and the mixture was stirred at RT for 2.5 h. The mixture was then adjusted to pH 3 by addition of TFA (200 µl, 2.6 mmol) and purified by preparative HPLC (Method 16). The combined target fractions were concentrated, and the residue was dried under reduced pressure. This gave 167 mg (100% purity, 90% of theory) of the title compound.

LC-MS (Method 2): $R_t$=0.95 min; MS (ESIpos): m/z=507/509 [M+H]$^+$ $^1$H-NMR (400 MHz, DMSO-d6) δ [ppm]: 2.085 (1.43), 2.149 (1.02), 2.327 (0.60), 2.347 (0.53), 3.169 (1.97), 3.184 (1.79), 4.255 (1.04), 4.297 (0.88), 4.351 (0.88), 4.369 (0.93), 4.389 (0.69), 4.413 (1.13), 4.430 (0.99), 4.450 (0.65), 4.466 (0.59), 5.754 (0.61), 7.383 (0.77), 7.392 (0.91), 7.460 (4.35), 7.477 (6.02), 7.488 (5.13), 7.502 (8.20), 7.509 (7.36), 7.522 (16.00), 7.583 (9.85), 7.601 (7.29), 7.827 (2.75), 7.849 (4.09), 7.926 (8.71), 7.949 (5.53), 9.118 (2.79), 13.835 (1.53).

Separation of the Enantiomers:

The title compound (140 mg) was dissolved in 15 ml of a methanol/acetonitrile mixture and separated into the enantiomers by preparative SFC on a chiral phase (see Examples 39 and 40) [column: Daicel Chiralpak AD, 250 mm×20 mm; flow rate: 80 ml/min; detection: 210 nm; temperature: 40° C.; injection: 2.0 ml; mobile phase: 75% carbon dioxide/25% isopropanol; run time 8 min, isocratic]. The combined target fractions were concentrated and the residue was dried under reduced pressure.

Example 39

(−)-3-{[(6-Bromo-3-methyl-2-phenylquinolin-4-yl)carbonyl]amino}-2-fluoro-2-phenylpropanoic Acid (Enantiomer 1)

In the enantiomer separation described in Example 38, 58 mg (95% purity, ee 100%) of the title compound were obtained as the enantiomer that eluted earlier.

$[\alpha]_D^{20}$=−27.0°, 589 nm, c=0.38 g/100 ml, methanol

LC-MS (Method 1): $R_t$=1.77 min; MS (ESIpos): m/z=507/509 [M+H]$^+$ $^1$H-NMR (400 MHz, DMSO-d6) δ [ppm]: −0.008 (2.19), 0.008 (1.92), 2.119 (0.93), 2.263 (1.83), 2.327 (0.73), 2.366 (0.41), 2.429 (0.68), 2.669 (0.47), 4.200 (0.52), 4.238 (0.96), 4.280 (0.77), 4.353 (0.80), 4.370 (0.83), 4.389 (0.64), 4.414 (1.03), 4.432 (0.89), 4.451 (0.62), 4.468 (0.55), 7.453 (4.07), 7.472 (5.44), 7.488 (4.67), 7.502 (7.86), 7.509 (6.85), 7.522 (16.00), 7.562 (1.88), 7.580 (9.87), 7.598 (7.25), 7.826 (2.75), 7.830 (2.82), 7.848 (3.96), 7.852 (3.89), 7.863 (0.90), 7.886 (0.77), 7.891 (0.73), 7.924 (8.83), 7.947 (5.69), 7.963 (1.16), 7.985 (0.86), 9.102 (2.47), 9.170 (0.44), 13.870 (0.52).

Example 40

(+)-3-{[(6-Bromo-3-methyl-2-phenylquinolin-4-yl)carbonyl]amino}-2-fluoro-2-phenylpropanoic Acid (Enantiomer 2)

In the enantiomer separation described in Example 38, 41 mg (100% purity, ee 100%) of the title compound were obtained as the enantiomer that eluted later.

$[\alpha]_D^{20}$=+26.2°, 589 nm, c=0.40 g/100 ml, methanol

LC-MS (Method 1): $R_t$=1.77 min; MS (ESIpos): m/z=507/509 [M+H]$^+$ $^1$H-NMR (400 MHz, DMSO-d6) δ [ppm]: 2.148 (1.06), 2.327 (0.82), 2.668 (0.55), 4.238 (1.10), 4.283 (0.84), 4.370 (0.89), 4.414 (1.03), 7.454 (4.26), 7.473 (5.72), 7.488 (4.83), 7.502 (7.38), 7.509 (6.94), 7.522 (16.00), 7.580 (9.88), 7.599 (7.46), 7.826 (2.84), 7.848 (4.32), 7.924 (9.20), 7.947 (5.83), 9.103 (2.71), 13.871 (0.63).

Example 41

(+/−)-3-{[(6-Bromo-3-methyl-2-phenylquinolin-4-yl)carbonyl]amino}-2-methyl-2-[3-(trifluoromethyl)phenyl]propanoic Acid (Racemate)

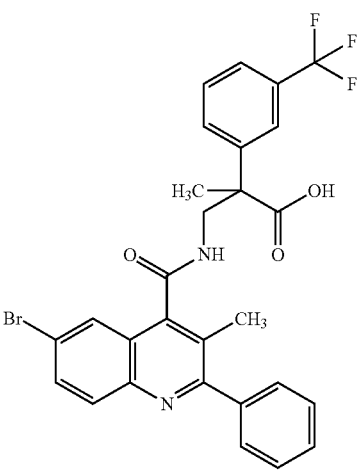 [SMILES: Cc1c(-c2ccccc2)nc2ccc(Br)cc2c1C(=O)NCC(C)(C(=O)O)c1cccc(C(F)(F)F)c1]

At RT, 1 M aqueous sodium hydroxide solution (5.6 ml, 5.6 mmol) was added to a solution of (+/−)-ethyl 3-{[(6-bromo-3-methyl-2-phenylquinolin-4-yl)carbonyl]amino}-2-methyl-2-[3-(trifluoromethyl)phenyl]propanoate (550 mg, 939 μmol, Example 166A) in THF (8.0 ml) and methanol (4.0 ml), and the mixture was stirred at RT for 24 h. The mixture was then adjusted to pH 3 by addition of TFA (510 μl, 6.6 mmol) and purified by preparative HPLC (Method 20). The combined target fractions were concentrated, and the residue was dried under reduced pressure. This gave 480 mg (98% purity, 88% of theory) of the title compound.

LC-MS (Method 1): $R_t$=2.10 min; MS (ESIpos): m/z=571/573 [M+H]$^+$ $^1$H-NMR (400 MHz, DMSO-d6) δ [ppm]: −0.008 (0.47), 0.008 (0.41), 1.693 (15.91), 2.040 (0.83), 2.073 (0.93), 3.652 (0.97), 3.817 (1.22), 3.829 (1.29), 3.851 (1.44), 3.863 (1.30), 4.293 (0.94), 4.311 (1.01), 4.326 (0.92), 4.345 (0.81), 7.486 (1.18), 7.499 (3.81), 7.506 (4.35), 7.516 (16.00), 7.620 (0.98), 7.639 (2.39), 7.658 (2.41), 7.675 (2.77), 7.694 (1.30), 7.727 (4.34), 7.761 (2.69), 7.780 (1.95), 7.826 (1.86), 7.831 (1.75), 7.848 (2.83), 7.853 (2.78), 7.925 (5.80), 7.947 (3.73), 8.700 (1.33), 8.713 (1.87), 8.717 (1.87), 8.730 (1.32).

Separation of the Enantiomers:

The title compound (430 mg) was dissolved in 20 ml of a methanol/acetonitrile mixture and separated into the enantiomers by preparative SFC on a chiral phase (see Examples 42 and 43) [column: Daicel Chiralpak AD, 250 mm×20 mm; flow rate: 80 ml/min; detection: 210 nm; temperature: 40° C.; injection: 0.8 ml; mobile phase: 82% carbon dioxide/18% ethanol; run time 10 min, isocratic]. The combined target fractions were concentrated and the residue was dried under reduced pressure.

Example 42

(−)-3-{[(6-Bromo-3-methyl-2-phenylquinolin-4-yl)carbonyl]amino}-2-methyl-2-[3-(trifluoromethyl)phenyl]propanoic Acid (Enantiomer 1)

In the enantiomer separation described in Example 41, the prepurified title compound was obtained as earlier-eluting enantiomer (ee 100%) and repurified by preparative HPLC (Method 20). The combined target fractions were concentrated and lyophilized. This gave 180 mg (98% purity) of the title compound.

$[\alpha]_D^{20}=-36.7°$, 589 nm, c=0.40 g/100 ml, methanol

LC-MS (Method 1): $R_t$=2.08 min; MS (ESIpos): m/z=571/573 [M+H]$^+$ $^1$H-NMR (400 MHz, DMSO-d6) δ [ppm]: 1.195 (0.51), 1.211 (0.52), 1.694 (15.62), 2.042 (0.84), 2.073 (0.85), 3.819 (1.17), 3.831 (1.22), 3.853 (1.38), 3.865 (1.24), 4.294 (1.09), 4.311 (1.14), 4.327 (1.03), 4.347 (0.92), 7.499 (4.11), 7.507 (4.61), 7.517 (16.00), 7.621 (1.03), 7.640 (2.46), 7.659 (2.45), 7.675 (2.86), 7.695 (1.30), 7.728 (4.32), 7.762 (2.63), 7.781 (1.95), 7.827 (2.02), 7.832 (1.88), 7.849 (3.02), 7.854 (2.93), 7.926 (6.33), 7.948 (3.99), 8.701 (1.33), 8.714 (1.83), 8.732 (1.24).

Example 43

(+)-3-{[(6-Bromo-3-methyl-2-phenylquinolin-4-yl)carbonyl]amino}-2-methyl-2-[3-(trifluoromethyl)phenyl]propanoic Acid (Enantiomer 2)

In the enantiomer separation described in Example 41, the prepurified title compound was obtained as later-eluting enantiomer (ee 99%) and repurified by preparative HPLC (Method 20). The combined target fractions were concentrated and lyophilized. This gave 164 mg (98% purity) of the title compound.

$[\alpha]_D^{20}=+30.4°$, 589 nm, c=0.43 g/100 ml, methanol

LC-MS (Method 1): $R_t$=2.08 min; MS (ESIpos): m/z=571/573 [M+H]$^+$ $^1$H-NMR (400 MHz, DMSO-d6) δ [ppm]: −0.008 (0.61), 0.008 (0.58), 1.693 (16.00), 2.038 (0.80), 2.523 (0.55), 3.818 (1.10), 3.830 (1.19), 3.852 (1.36), 3.864 (1.22), 4.293 (0.93), 4.311 (1.02), 4.327 (0.93), 4.345 (0.81), 7.474 (0.41), 7.488 (1.20), 7.501 (4.00), 7.508 (4.56), 7.518 (15.96), 7.531 (4.11), 7.621 (0.98), 7.639 (2.40), 7.659 (2.40), 7.676 (2.70), 7.695 (1.20), 7.728 (4.31), 7.761 (2.62), 7.780 (1.92), 7.828 (1.90), 7.834 (1.77), 7.851 (2.93), 7.856 (2.84), 7.927 (6.01), 7.949 (3.84), 8.702 (1.33), 8.715 (1.86), 8.719 (1.84), 8.732 (1.29).

Example 44

(+/−)-3-{[(6-Bromo-3-methyl-2-phenylquinolin-4-yl)carbonyl]amino}-2-(3-methoxyphenyl)propanoic Acid (Racemate)

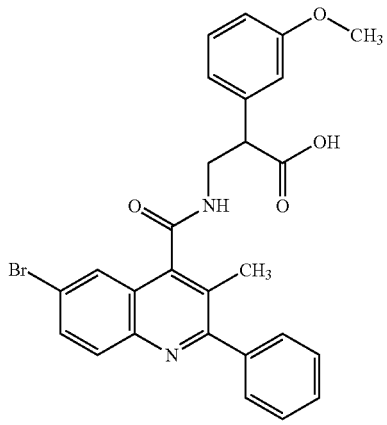 [SMILES: COc1cccc(C(CNC(=O)c2c(C)c(-c3ccccc3)nc3ccc(Br)cc23)C(=O)O)c1]

At RT, TFA (13 ml, 160 mmol) was added to a suspension of (+/−)-tert-butyl 3-{[(6-bromo-4-methyl-2-phenylquinolin-4-yl)carbonyl]amino}-2-(3-methoxyphenyl)propanoate (940 mg, 1.63 mmol, Example 167A) in dichloromethane (26 ml), and the mixture was stirred at RT for 16 h. The mixture was then concentrated and repeatedly, in succession, dichloromethane was added to the residue and the mixture was concentrated again. Subsequently, the residue was dried under reduced pressure. This gave 1.01 g (99% purity, ">100%" of theory, contains TFA and/or solvent) of the title compound.

LC-MS (Method 1): $R_t$=1.85 min; MS (ESIpos): m/z=519/521 [M+H]$^+$ $^1$H-NMR (400 MHz, DMSO-d6) δ [ppm]: −0.149 (0.58), 0.008 (5.19), 0.147 (0.63), 2.160 (5.22), 2.327 (1.01), 2.366 (0.56), 2.670 (1.08), 3.760 (1.54), 3.826 (1.78), 3.845 (3.51), 3.861 (3.56), 3.877 (2.29), 3.958 (2.97), 3.977 (4.16), 3.996 (1.64), 5.176 (0.79), 6.875 (2.53), 6.896 (2.92), 6.924 (5.75), 6.947 (3.63), 6.966 (3.86), 7.278 (3.41), 7.298 (5.40), 7.317 (2.76), 7.509 (5.61), 7.516 (5.28), 7.528 (16.00), 7.757 (1.29), 7.844 (3.11), 7.849 (2.72), 7.867 (4.66), 7.872 (4.38), 7.940 (8.61), 7.963 (5.33), 8.948 (1.73), 8.962 (3.23), 8.977 (1.64).

Separation of the Enantiomers:

The title compound (400 mg) was dissolved in a hot mixture of ethanol, methanol and acetonitrile (5 ml each) and separated into the enantiomers by preparative HPLC on a chiral phase (see Examples 45 and 46) [column: Daicel Chiralpak ID, 5 μm 250 mm×20 mm; flow rate: 15 ml/min; detection: 210 nm; temperature: 25° C.; injection: 0.50 ml; mobile phase: 50% heptane/(50% ethanol+0.2% acetic acid+1% water); run time 18 min, isocratic]. The combined target fractions were concentrated, and the residue was lyophilized in acetonitrile/water.

Example 45

(−)-3-{[(6-Bromo-3-methyl-2-phenylquinolin-4-yl)carbonyl]amino}-2-(3-methoxyphenyl)propanoic Acid (Enantiomer 1)

In the enantiomer separation described in Example 44, 122 mg (95% purity, ee 99%) of the title compound were obtained as the enantiomer that eluted earlier.

$[\alpha]_D^{20}=-39.2°$, 589 nm, c=0.44 g/100 ml, methanol

LC-MS (Method 1): $R_t$=1.86 min; MS (ESIpos): m/z=519/529 [M+H]$^+$ $^1$H-NMR (400 MHz, DMSO-d6) δ [ppm]: 1.030 (1.19), 1.045 (1.18), 1.154 (0.57), 1.375 (0.48), 2.159 (6.15), 2.213 (1.48), 3.313 (8.74), 3.723 (2.36), 3.792 (0.68), 3.812 (1.00), 3.825 (2.18), 3.844 (3.99), 3.860 (4.09), 3.875 (2.49), 3.895 (0.83), 3.908 (0.70), 3.922 (0.42), 3.955 (3.11), 3.974 (4.32), 3.994 (1.63), 6.873 (2.90), 6.893 (3.29), 6.923 (6.09), 6.947 (3.91), 6.966 (4.03), 7.276 (3.32), 7.296 (5.16), 7.315 (2.59), 7.481 (1.36), 7.495 (2.74), 7.506 (6.47), 7.513 (6.14), 7.526 (16.00), 7.529 (15.41), 7.756 (1.44), 7.839 (2.93), 7.844 (2.59), 7.861 (4.27), 7.867 (3.96), 7.937 (7.45), 7.959 (4.74), 8.944 (1.97), 8.958 (3.49), 8.971 (1.77), 12.609 (0.55).

$^1$H-NMR (400 MHz, DMSO-d6) δ [ppm]: 12.61 (br. s, 1H), 8.96 (t, 1H), 7.95 (d, 1H), 7.86 (dd, 1H), 7.76 (br. s, 1H), 7.59-7.40 (m, 5H), 7.30 (t, 1H), 7.01-6.83 (m, 3H), 4.03-3.93 (m, 1H), 3.92-3.77 (m, 2H), 3.74 (s, 3H), 2.16 (br. s, 3H).

Example 46

(+)-3-{[(6-Bromo-3-methyl-2-phenylquinolin-4-yl)carbonyl]amino}-2-(3-methoxyphenyl)propanoic Acid (Enantiomer 1)

In the enantiomer separation described in Example 44, 123 mg (95% purity, ee 98%) of the title compound were obtained as the enantiomer that eluted later.

$[\alpha]_D^{20}$=+49.0°, 589 nm, c=0.37 g/100 ml, methanol
LC-MS (Method 1): $R_t$=1.86 min; MS (ESIpos): m/z=519/521 [M+H]$^+$ $^1$H-NMR (400 MHz, DMSO-d6) δ [ppm]: 0.008 (1.50), 1.030 (3.72), 1.045 (3.75), 1.156 (0.53), 1.283 (0.56), 1.909 (0.81), 2.159 (5.77), 2.213 (1.18), 2.523 (1.58), 3.313 (11.20), 3.650 (0.45), 3.723 (1.63), 3.792 (0.55), 3.812 (0.80), 3.825 (1.95), 3.845 (3.74), 3.861 (3.87), 3.876 (2.36), 3.896 (0.75), 3.909 (0.60), 3.957 (2.87), 3.976 (4.15), 3.995 (1.55), 6.869 (2.25), 6.874 (2.64), 6.889 (2.52), 6.895 (3.00), 6.923 (5.90), 6.947 (3.79), 6.966 (4.00), 7.277 (3.34), 7.296 (5.24), 7.316 (2.69), 7.481 (0.79), 7.493 (1.86), 7.496 (2.08), 7.506 (5.87), 7.514 (5.67), 7.526 (16.00), 7.529 (15.28), 7.538 (8.90), 7.756 (1.29), 7.840 (2.99), 7.845 (2.60), 7.862 (4.46), 7.868 (4.12), 7.938 (7.77), 7.960 (5.00), 8.945 (1.80), 8.958 (3.36), 8.972 (1.72), 12.595 (0.45).

$^1$H-NMR (400 MHz, DMSO-d6) δ [ppm]: 12.59 (br. s, 1H), 8.96 (t, 1H), 7.95 (d, 1H), 7.86 (dd, 1H), 7.76 (br. s, 1H), 7.58-7.47 (m, 5H), 7.30 (t, 1H), 7.00-6.85 (m, 3H), 4.02-3.94 (m, 1H), 3.92-3.78 (m, 2H), 3.75 (s, 3H), 2.16 (br. s, 3H).

Example 47

(+/−)-3-{[(6-Bromo-3-methyl-2-phenylquinolin-4-yl)carbonyl]amino}-2-(3-chlorophenyl)propanoic Acid (Racemate)

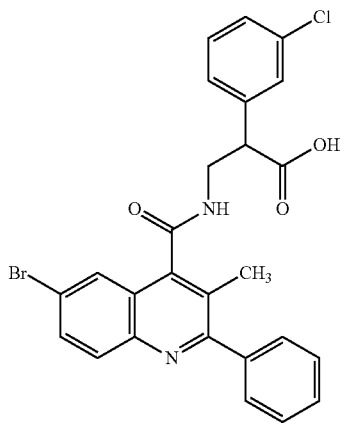 [SMILES: Cc1c(-c2ccccc2)nc2ccc(Br)cc2c1C(=O)NCC(C(=O)O)c1cccc(Cl)c1]

TFA (5.7 ml, 74 mmol) was added to a solution of (+/−)-tert-butyl 3-{[(6-bromo-4-methyl-2-phenylquinolin-4-yl)carbonyl]amino}-2-(3-chlorophenyl)propanoate (430 mg, 741 μmol, Example 168A) in dichloromethane (12 ml), and the mixture was stirred at RT for 16 h. The mixture was then concentrated and repeatedly, in succession, dichloromethane was added and the mixture was concentrated again. The residue was dried under reduced pressure. This gave 420 mg (96% purity, ">100%" of theory, contains TFA and/or solvent) of the title compound.

LC-MS (Method 1): $R_t$=1.97 min; MS (ESIpos): m/z=523/525 [M+H]$^+$ $^1$H-NMR (400 MHz, DMSO-d6) δ [ppm]: −0.008 (2.98), 0.008 (2.34), 2.134 (3.31), 2.328 (0.48), 2.670 (0.49), 3.878 (2.54), 3.896 (4.45), 3.911 (3.63), 4.017 (2.62), 4.036 (3.82), 4.056 (1.58), 5.754 (0.64), 7.358 (2.19), 7.376 (5.07), 7.394 (4.03), 7.406 (5.31), 7.424 (3.24), 7.438 (6.04), 7.483 (0.52), 7.497 (1.49), 7.507 (4.79), 7.515 (4.57), 7.526 (16.00), 7.537 (7.13), 7.703 (0.59), 7.842 (2.44), 7.848 (2.23), 7.865 (3.83), 7.870 (3.74), 7.937 (7.12), 7.959 (4.51), 8.944 (1.58), 8.958 (3.38), 8.972 (1.65).

Separation of the Enantiomers:

The title compound (350 mg) was dissolved in a hot mixture of ethanol, methanol and acetonitrile (5 ml each) and separated into the enantiomers by preparative HPLC on a chiral phase (see Examples 48 and 49) [column: Daicel Chiralpak AD-H, 5 μm, 250 mm×20 mm; flow rate: 15 ml/min; detection: 210 nm; temperature: 25° C.; injection: 0.50 ml; mobile phase: 40% heptane/(60% ethanol+0.2% acetic acid+1% water); run time 25 min, isocratic]. The combined target fractions were concentrated, and the residue was lyophilized in acetonitrile/water.

Example 48

(−)-3-{[(6-Bromo-3-methyl-2-phenylquinolin-4-yl)carbonyl]amino}-2-(3-chlorophenyl)propanoic Acid (Enantiomer 1)

In the enantiomer separation described in Example 47, 124 mg (98% purity, ee 99%) of the title compound were obtained as the enantiomer that eluted earlier.

$[\alpha]_D^{20}$=−47.8°, 589 nm, c=0.35 g/100 ml, methanol
LC-MS (Method 2): $R_t$=1.04 min; MS (ESIpos): m/z=523/525 [M+H]$^+$ $^1$H-NMR (400 MHz, DMSO-d6) δ [ppm]: −0.008 (0.80), 0.008 (0.84), 1.140 (0.42), 1.158 (0.83), 1.177 (0.45), 1.234 (0.68), 1.909 (0.61), 2.135 (3.30), 2.188 (0.80), 2.269 (0.47), 2.523 (1.08), 2.788 (0.47), 3.182 (0.45), 3.878 (2.56), 3.897 (4.40), 3.911 (3.57), 4.018 (2.57), 4.036 (3.71), 4.056 (1.54), 7.358 (2.47), 7.362 (1.62), 7.376 (5.32), 7.380 (4.48), 7.394 (4.20), 7.406 (5.47), 7.424 (3.37), 7.438 (6.11), 7.471 (0.46), 7.482 (0.72), 7.495 (1.84), 7.505 (5.22), 7.513 (5.03), 7.524 (16.00), 7.532 (9.04), 7.536 (7.10), 7.539 (6.31), 7.547 (1.52), 7.701 (0.63), 7.839 (2.61), 7.844 (2.37), 7.861 (4.00), 7.867 (3.82), 7.935 (7.41), 7.957 (4.72), 8.943 (1.63), 8.957 (3.35), 8.971 (1.56), 12.729 (0.57).

$^1$H-NMR (400 MHz, DMSO-d6) δ [ppm]: 12.73 (br. s, 1H), 8.96 (t, 1H), 7.94 (d, 1H), 7.86 (dd, 1H), 7.70 (br. s, 1H), 7.57-7.46 (m, 5H), 7.45-7.33 (m, 4H), 4.03 (t, 1H), 3.90 (t, 2H), 2.14 (br. s, 3H).

Example 49

(+)-3-{[(6-Bromo-3-methyl-2-phenylquinolin-4-yl)carbonyl]amino}-2-(3-chlorophenyl)propanoic Acid (Enantiomer 2)

In the enantiomer separation described in Example 47, 106 mg (98% purity, ee 99%) of the title compound were obtained as the enantiomer that eluted later.

$[\alpha]_D^{20}$=+46.2°, 589 nm, c=0.34 g/100 ml, methanol
LC-MS (Method 2): $R_t$=1.04 min; MS (ESIpos): m/z=523/525 [M+H]$^+$ $^1$H-NMR (400 MHz, DMSO-d6) δ [ppm]: 1.140 (0.54), 1.158 (1.07), 1.176 (0.63), 1.234 (1.23), 2.134 (3.40), 2.188 (0.86), 2.327 (0.41), 2.669 (0.41), 3.877 (2.52), 3.895 (4.35), 3.910 (3.44), 4.016 (2.32), 4.035 (3.40), 4.054 (1.39), 7.357 (2.29), 7.375 (5.14), 7.393 (4.06), 7.405 (5.13), 7.424 (3.26), 7.437 (5.99), 7.481 (0.70), 7.495 (1.75), 7.505 (4.91), 7.512 (4.73), 7.524 (16.00), 7.535 (6.83), 7.700 (0.66), 7.839 (2.38), 7.844 (2.16), 7.861 (3.63), 7.866 (3.43), 7.934 (6.61), 7.957 (4.15), 8.942 (1.59), 8.956 (3.16), 8.969 (1.48), 12.665 (0.42).

$^1$H-NMR (400 MHz, DMSO-d6) δ [ppm]: 12.67 (br. s, 1H), 8.96 (t, 1H), 7.94 (d, 1H), 7.86 (dd, 1H), 7.70 (br. s, 1H), 7.57-7.47 (m, 5H), 7.46-7.33 (m, 4H), 4.03 (t, 1H), 3.90 (t, 2H), 2.13 (br. s, 3H).

Example 50

(+/−)-3-{[(6-Bromo-3-methyl-2-phenylquinolin-4-yl)carbonyl]amino}-2-(3-methylphenyl)propanoic Acid (Racemate)

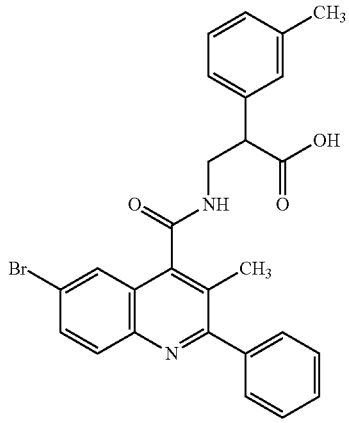 [SMILES: Cc1cccc(C(CNC(=O)c2c(C)c(-c3ccccc3)nc3ccc(Br)cc23)C(=O)O)c1]

TFA (11 ml, 150 mmol) was added to a solution of (+/−)-tert-butyl 3-{[(6-bromo-3-methyl-2-phenylquinolin-4-yl)carbonyl]amino}-2-(3-methylphenyl)propanoate (830 mg, 1.48 mmol, Example 169A) in dichloromethane (24 ml), and the mixture was stirred at RT for 16 h. The mixture was then concentrated and repeatedly, in succession, dichloromethane was added and the mixture was concentrated again. The residue was dried under reduced pressure. This gave 920 mg (92% purity, ">100%" of theory, contains TFA and/or solvent) of the title compound.

LC-MS (Method 2): $R_t$=1.03 min; MS (ESIpos): m/z=503/505 [M+H]$^+$ $^1$H-NMR (400 MHz, DMSO-d6) δ [ppm]: 0.008 (1.20), 2.167 (3.60), 2.303 (16.00), 2.327 (0.50), 2.523 (1.18), 3.782 (0.63), 3.797 (1.15), 3.814 (1.25), 3.831 (0.97), 3.846 (0.81), 3.864 (1.13), 3.878 (1.33), 3.898 (0.70), 3.910 (0.64), 3.940 (2.04), 3.959 (2.94), 3.978 (1.10), 4.359 (1.54), 7.112 (1.44), 7.131 (1.85), 7.161 (1.65), 7.189 (3.89), 7.247 (2.11), 7.265 (3.01), 7.284 (1.15), 7.498 (0.97), 7.508 (3.33), 7.515 (2.94), 7.528 (8.62), 7.532 (8.10), 7.540 (4.93), 7.752 (0.56), 7.846 (1.70), 7.851 (1.50), 7.868 (2.62), 7.873 (2.47), 7.940 (4.71), 7.962 (2.96), 8.943 (1.05), 8.957 (2.00), 8.971 (1.04).

Separation of the Enantiomers:

The title compound (400 mg) was dissolved in a hot mixture of ethanol, methanol and acetonitrile (5 ml each) and separated into the enantiomers by preparative HPLC on a chiral phase (see Examples 51 and 52) [column: Daicel Chiralpak AD-H, 5 μm, 250 mm×20 mm; flow rate: 15 ml/min; detection: 210 nm; temperature: 25° C.; injection: 0.50 ml; mobile phase: 30% heptane/(70% ethanol+0.2% acetic acid+1% water); run time 26 min, isocratic]. The combined target fractions were concentrated, and the residue was lyophilized in acetonitrile/water.

Example 51

(−)-3-{[(6-Bromo-3-methyl-2-phenylquinolin-4-yl)carbonyl]amino}-2-(3-methylphenyl)propanoic Acid (Enantiomer 1)

In the enantiomer separation described in Example 50, 131 mg (98% purity, ee 99%) of the title compound were obtained as the enantiomer that eluted earlier.

$[α]_D^{20}$=−53.2°, 589 nm, c=0.33 g/100 ml, methanol

LC-MS (Method 2): $R_t$=1.03 min; MS (ESIpos): m/z=503/505 [M+H]$^+$ $^1$H-NMR (400 MHz, DMSO-d6) δ [ppm]: 0.008 (0.44), 1.908 (0.56), 2.167 (3.72), 2.222 (0.42), 2.303 (16.00), 2.523 (0.60), 3.782 (0.58), 3.797 (1.07), 3.814 (1.15), 3.831 (0.87), 3.845 (0.72), 3.864 (1.03), 3.877 (1.20), 3.896 (0.58), 3.909 (0.55), 3.938 (1.86), 3.957 (2.71), 3.976 (0.92), 7.111 (1.46), 7.129 (1.89), 7.161 (1.67), 7.189 (3.87), 7.245 (2.14), 7.264 (2.99), 7.283 (1.16), 7.481 (0.44), 7.496 (1.04), 7.506 (3.39), 7.513 (3.00), 7.526 (8.50), 7.531 (7.97), 7.538 (5.11), 7.550 (1.10), 7.751 (0.60), 7.842 (1.66), 7.847 (1.46), 7.864 (2.54), 7.869 (2.37), 7.938 (4.63), 7.960 (2.95), 8.940 (1.05), 8.954 (1.95), 8.968 (1.01).

$^1$H-NMR (400 MHz, DMSO-d6) δ [ppm]: 12.60 (br. s, 1H), 8.95 (t, 1H), 7.95 (d, 1H), 7.86 (dd, 1H), 7.75 (br. s, 1H), 7.58-7.46 (m, 5H), 7.26 (t, 1H), 7.22-7.08 (m, 3H), 4.01-3.73 (m, 3H), 2.30 (s, 3H), 2.17 (br. s, 3H).

Example 52

(+)-3-{[(6-Bromo-3-methyl-2-phenylquinolin-4-yl)carbonyl]amino}-2-(3-methylphenyl)propanoic Acid (Enantiomer 2)

In the enantiomer separation described in Example 50, 119 mg (98% purity, ee 99%) of the title compound were obtained as the enantiomer that eluted later.

$[α]_D^{20}$=+53.0°, 589 nm, c=0.39 g/100 ml, methanol

LC-MS (Method 2): $R_t$=1.04 min; MS (ESIpos): m/z=503/505 [M+H]$^+$ $^1$H-NMR (400 MHz, DMSO-d6) δ [ppm]: −0.008 (0.54), 0.008 (0.51), 1.235 (0.42), 2.166 (3.68), 2.303 (16.00), 2.522 (0.63), 3.782 (0.56), 3.796 (1.05), 3.814 (1.14), 3.830 (0.86), 3.845 (0.71), 3.864 (1.03), 3.877 (1.20), 3.897 (0.57), 3.909 (0.53), 3.939 (1.82), 3.958 (2.69), 3.976 (0.91), 7.111 (1.46), 7.129 (1.86), 7.161 (1.64), 7.188 (3.81), 7.245 (2.14), 7.264 (3.00), 7.283 (1.16), 7.480 (0.47), 7.492 (1.02), 7.495 (1.04), 7.506 (3.33), 7.513 (2.98), 7.525 (8.39), 7.530 (7.87), 7.538 (4.96), 7.550 (0.96), 7.747 (0.57), 7.841 (1.72), 7.846 (1.49), 7.863 (2.61), 7.869 (2.43), 7.937 (4.76), 7.960 (3.01), 8.940 (1.06), 8.953 (1.97), 8.967 (1.00).

$^1$H-NMR (400 MHz, DMSO-d6) δ [ppm]: 12.53 (br. s, 1H), 8.95 (t, 1H), 7.95 (d, 1H), 7.86 (dd, 1H), 7.75 (br. s, 1H), 7.58-7.46 (m, 5H), 7.26 (t, 1H), 7.21-7.08 (m, 3H), 4.01-3.74 (m, 3H), 2.30 (s, 3H), 2.17 (br. s, 3H).

Example 53

(+/−)-3-{[(6-Bromo-3-methyl-2-phenylquinolin-4-yl)carbonyl]amino}-2-hydroxy-2-(2-methoxyphenyl)propanoic Acid (Racemate)

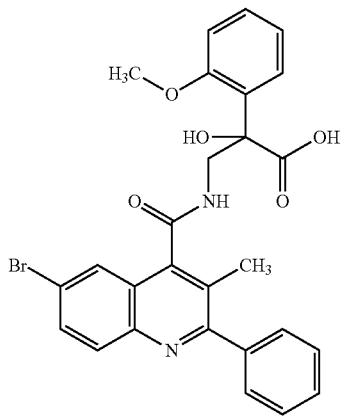

1 M aqueous sodium hydroxide solution (2.4 ml, 2.4 mmol) was added to a solution of (+/−)methyl 3-{[(6-bromo-3-methyl-2-phenylquinolin-4-yl)carbonyl]amino}-2-hydroxy-2-(2-methoxyphenyl)propanoate (220 mg, 400 µmol, Example 170A) in THF (3.4 ml) and methanol (680 µl), and the mixture was stirred at RT for 4.5 h. The mixture was then adjusted to pH 2-3 by addition of TFA (220 µl, 2.8 mmol) and purified by preparative HPLC (Method 15). The combined target fractions were concentrated, and the residue was lyophilized in acetonitrile/water. This gave 202 mg (96% purity, 91% of theory) of the title compound.

LC-MS (Method 2): $R_t$=0.93 min; MS (ESIpos): m/z=535/537 [M+H]$^+$ $^1$H-NMR (400 MHz, DMSO-d6) δ [ppm]: −0.008 (1.70), 0.008 (1.71), 2.072 (3.41), 2.391 (0.68), 2.523 (0.85), 3.952 (0.89), 3.985 (1.08), 4.271 (0.86), 6.925 (1.75), 6.944 (3.55), 6.962 (2.03), 6.987 (2.93), 7.007 (3.32), 7.261 (1.33), 7.280 (2.11), 7.299 (1.08), 7.473 (0.64), 7.483 (1.54), 7.486 (1.71), 7.496 (4.98), 7.504 (4.81), 7.516 (16.00), 7.523 (8.90), 7.527 (7.34), 7.595 (2.60), 7.614 (2.38), 7.816 (2.42), 7.821 (2.23), 7.838 (3.87), 7.843 (3.77), 7.898 (7.48), 7.921 (4.40), 8.410 (1.49), 8.424 (2.08), 8.440 (1.37).

$^1$H-NMR (400 MHz, DMSO-d6) δ [ppm]: 12.40 (br. s, 1H), 8.43 (t, 3H), 7.91 (d, 1H), 7.83 (dd, 1H), 7.69 (br. s, 1H), 7.61 (d, 1H), 7.55-7.46 (m, 5H), 7.28 (t, 1H), 7.06-6.88 (m, 2H), 6.41 (br. s, 1H), 4.35-4.20 (m, 1H), 4.02-3.87 (m, 1H), 3.77 (s, 3H), 2.07 (br. s, 3H).

Example 54

(−)-3-{[(6-Bromo-3-methyl-2-phenylquinolin-4-yl)carbonyl]amino}-2-hydroxy-2-(2-methoxyphenyl)propanoic Acid (Enantiomer 1)

1 M aqueous sodium hydroxide solution (1.4 ml, 1.4 mmol) was added to a solution of (−)-methyl 3-{[(6-bromo-3-methyl-2-phenylquinolin-4-yl)carbonyl]amino}-2-hydroxy-2-(2-methoxyphenyl)propanoate (128 mg, 233 µmol, Example 171A) in THF (2.0 ml) and methanol (500 µl), and the mixture was stirred at RT for 4.5 h. The mixture was then adjusted to pH 2-3 by addition of TFA (130 µl, 1.6 mmol) and purified by preparative HPLC (Method 15). The combined target fractions were concentrated, and the residue was dried under reduced pressure. This gave 120 mg (97% purity, ee 100%, 94% of theory) of the title compound.

$[α]_D^{20}$=−72.0°, 589 nm, c=0.44 g/100 ml, methanol

LC-MS (Method 2): $R_t$=0.93 min; MS (ESIpos): m/z=535/537 [M+H]$^+$ $^1$H-NMR (500 MHz, DMSO-d6) δ [ppm]: −0.007 (0.79), 2.075 (3.30), 2.084 (3.40), 2.392 (0.65), 2.518 (0.53), 3.918 (0.70), 3.954 (0.92), 3.985 (1.11), 4.276 (1.10), 5.752 (1.38), 6.930 (2.20), 6.945 (4.59), 6.960 (2.58), 6.989 (3.67), 7.005 (4.06), 7.266 (1.49), 7.280 (2.47), 7.295 (1.31), 7.475 (0.99), 7.484 (2.53), 7.489 (1.94), 7.496 (5.04), 7.499 (4.90), 7.501 (6.26), 7.515 (16.00), 7.520 (15.75), 7.525 (15.74), 7.600 (3.13), 7.615 (2.99), 7.674 (0.42), 7.818 (3.40), 7.822 (3.23), 7.836 (5.00), 7.840 (4.99), 7.900 (10.21), 7.918 (6.69), 8.414 (1.89), 8.426 (2.86), 8.438 (1.97).

$^1$H-NMR (500 MHz, DMSO-d6) δ [ppm]: 12.40 (br. s, 1H), 8.43 (t, 1H), 7.91 (d, 1H), 7.83 (dd, 1H), 7.67 (br. s, 1H), 7.61 (d, 1H), 7.56-7.44 (m, 5H), 7.28 (t, 1H), 7.03-6.90 (m, 2H), 5.95 (br. s, 1H), 4.33-4.20 (m, 1H), 4.01-3.90 (m, 1H), 3.78 (s, 3H), 2.07 (br. s, 3H).

Example 55

(+)-3-{[(6-Bromo-3-methyl-2-phenylquinolin-4-yl)carbonyl]amino}-2-hydroxy-2-(2-methoxyphenyl)propanoic Acid (Enantiomer 2)

1 M aqueous sodium hydroxide solution (1.3 ml, 1.3 mmol) was added to a solution of (+)-methyl 3-{[(6-bromo-3-methyl-2-phenylquinolin-4-yl)carbonyl]amino}-2-hydroxy-2-(2-methoxyphenyl)propanoate (120 mg, 219 µmol, Example 172A) in THF (1.9 ml) and methanol (470 µl), and the mixture was stirred at RT for 4.5 h. The mixture was then adjusted to pH 2-3 by addition of TFA (120 µl, 1.5 mmol) and purified by preparative HPLC (Method 15). The combined target fractions were concentrated, and the residue was dried under reduced pressure. This gave 111 mg (96% purity, ee 99%, 91% of theory) of the title compound.

$[α]_D^{20}$=+71.7°, 589 nm, c=0.41 g/100 ml, methanol

LC-MS (Method 2): $R_t$=0.93 min; MS (ESIpos): m/z=535/537 [M+H]$^+$ $^1$H-NMR (500 MHz, DMSO-d6) δ [ppm]: −0.006 (0.57), 2.085 (16.00), 2.392 (0.51), 2.518 (0.41), 3.918 (0.50), 3.949 (0.64), 3.985 (0.83), 4.275 (0.78), 5.752 (0.88), 6.931 (1.61), 6.945 (3.28), 6.961 (1.85), 6.989 (2.65), 7.006 (2.89), 7.265 (1.10), 7.280 (1.77), 7.295 (0.95), 7.476 (0.77), 7.485 (1.85), 7.490 (1.46), 7.497 (3.71), 7.500 (3.61), 7.502 (4.50), 7.516 (11.56), 7.521 (11.31), 7.526 (11.01), 7.600 (2.23), 7.614 (2.12), 7.820 (2.41), 7.824 (2.30), 7.838 (3.56), 7.842 (3.54), 7.902 (7.29), 7.920 (4.74), 8.415 (1.36), 8.427 (2.04), 8.439 (1.38).

$^1$H-NMR (500 MHz, DMSO-d6) δ [ppm]: 12.50 (br. s, 1H), 8.43 (t, 1H), 7.91 (d, 1H), 7.83 (dd, 1H), 7.68 (br. s, 1H), 7.61 (d, 1H), 7.55-7.46 (m, 5H), 7.28 (t, 1H), 7.04-6.90 (m, 2H), 5.94 (br. s, 1H), 4.36-4.19 (m, 1H), 4.03-3.88 (m, 1H), 3.78 (s, 3H), 2.08 (s, 3H).

Example 56

(+/−)-3-{[(6-Bromo-3-methyl-2-phenylquinolin-4-yl)carbonyl]amino}-2-(2-fluoro-6-methoxyphenyl)propanoic Acid (Racemate)

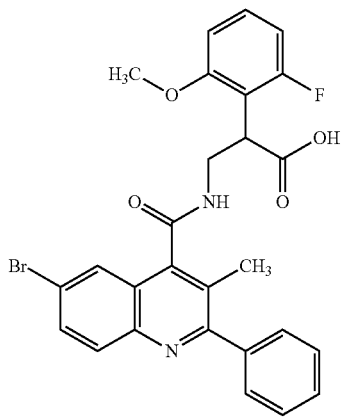

TFA (420 µl, 5.4 mmol) was added to a solution of (+/−)-tert-butyl 3-{[(6-bromo-3-methyl-2-phenylquinolin-4-yl)carbonyl]amino}-2-(2-fluoro-6-methoxyphenyl)propanoate (40 mg, 67 µmol, Example 173A) in dichloromethane (2 ml), and the mixture was allowed to stand at RT for 5 days. The mixture was then concentrated and repeatedly, in succession, dichloromethane was added and the mixture was concentrated again. The residue was taken up in dichloromethane and purified by preparative HPLC (Method 15). The combined target fractions were concentrated, and the residue was lyophilized in acetonitrile/water. This gave 34 mg (100% purity, 93% of theory) of the title compound.

LC-MS (Method 1): $R_t$=1.85 min; MS (ESIpos): m/z=537/539 [M+H]$^+$ $^1$H-NMR (500 MHz, DMSO-d6) δ [ppm]: 1.234 (0.96), 2.173 (16.00), 3.754 (0.79), 4.098 (1.28), 4.109 (2.39), 4.121 (1.80), 4.135 (2.09), 4.147 (1.18), 4.356 (2.32), 4.367 (2.60), 4.373 (2.60), 4.385 (1.98), 6.804 (2.49), 6.822 (4.41), 6.840 (2.56), 6.878 (4.65), 6.895 (4.96), 7.273 (1.25), 7.289 (2.73), 7.303 (2.62), 7.320 (1.09), 7.474 (0.53), 7.477 (0.66), 7.482 (1.13), 7.491 (2.50), 7.493 (2.21), 7.497 (2.17), 7.503 (4.94), 7.505 (4.96), 7.508 (5.85), 7.522 (12.63), 7.528 (14.25), 7.532 (14.52), 7.544 (2.43), 7.753 (0.65), 7.843 (3.64), 7.847 (3.30), 7.860 (5.06), 7.865 (4.82), 7.932 (9.02), 7.949 (6.02), 8.785 (2.08), 8.797 (3.93), 8.809 (2.00).

$^1$H-NMR (500 MHz, DMSO-d6) δ [ppm]: 12.51 (br. s, 1H), 8.80 (t, 1H), 7.94 (d, 1H), 7.85 (dd, 1H), 7.75 (br. s, 1H), 7.57-7.47 (m, 5H), 7.34-7.25 (m, 1H), 6.89 (d, 1H), 6.82 (t, 1H), 4.37 (dd, 1H), 4.19-4.06 (m, 1H), 3.84-3.73 (m, 1H, partially obscured), 3.80 (s, 3H), 2.17 (s, 3H).

Example 57

(−)-3-{[(6-Bromo-3-methyl-2-phenylquinolin-4-yl)carbonyl]amino}-2-(2-fluoro-6-methoxyphenyl)propanoic Acid (Enantiomer 1)

TFA (620 µl, 8.1 mmol) was added to a solution of (−)-tert-butyl 3-{[(6-bromo-3-methyl-2-phenylquinolin-4-yl)carbonyl]amino}-2-(2-fluoro-6-methoxyphenyl)propanoate (60 mg, 101 µmol, Example 174A) in dichloromethane (3 ml), and the mixture was allowed to stand at RT for one day. The mixture was then concentrated and repeatedly, in succession, dichloromethane was added and the mixture was concentrated again. The residue was taken up in dichloromethane and purified by preparative HPLC (Method 15). The combined target fractions were concentrated, and the residue was lyophilized in acetonitrile/water. This gave 55 mg (100% purity, ee>99%, 100% of theory) of the title compound.

$[α]_D^{20}$=−82.2°, 589 nm, c=0.42 g/100 ml, methanol

LC-MS (Method 1): $R_t$=1.86 min; MS (ESIpos): m/z=537/539 [M+H]$^+$ $^1$H-NMR (400 MHz, DMSO-d6) δ [ppm]: 2.171 (16.00), 3.743 (0.65), 3.764 (1.01), 4.088 (1.12), 4.102 (2.09), 4.117 (1.58), 4.136 (1.82), 4.150 (1.08), 4.348 (2.38), 4.363 (2.62), 4.370 (2.64), 4.385 (2.12), 6.799 (1.98), 6.821 (3.50), 6.843 (2.15), 6.876 (3.79), 6.897 (4.17), 7.267 (1.10), 7.288 (2.42), 7.306 (2.34), 7.326 (0.97), 7.479 (0.56), 7.493 (1.54), 7.503 (4.89), 7.511 (4.31), 7.523 (14.02), 7.526 (13.66), 7.535 (7.39), 7.744 (0.75), 7.842 (2.43), 7.846 (2.19), 7.864 (3.90), 7.869 (3.73), 7.930 (6.87), 7.952 (4.18), 8.781 (1.59), 8.796 (3.17), 8.811 (1.58).

$^1$H-NMR (400 MHz, DMSO-d6) δ [ppm]: 12.50 (br. s, 1H), 8.80 (t, 1H), 7.94 (d, 1H), 7.86 (dd, 1H), 7.74 (br. s, 1H), 7.56-7.46 (m, 5H), 7.35-7.25 (m, 1H), 6.89 (d, 1H), 6.82 (t, 1H), 4.37 (dd, 1H), 4.17-4.06 (m, 1H), 3.84-3.73 (m, 1H, partially obscured), 3.80 (s, 3H), 2.17 (s, 3H).

Example 58

(+)-3-{[(6-Bromo-3-methyl-2-phenylquinolin-4-yl)carbonyl]amino}-2-(2-fluoro-6-methoxyphenyl)propanoic Acid (Enantiomer 2)

TFA (730 µl, 9.4 mmol) was added to a solution of (+)-tert-butyl 3-{[(6-bromo-3-methyl-2-phenylquinolin-4-yl)carbonyl]amino}-2-(2-fluoro-6-methoxyphenyl)propanoate (70 mg, 118 µmol, Example 175A) in dichloromethane (3.5 ml), and the mixture was allowed to stand at RT for one day. The mixture was then concentrated and repeatedly, in succession, dichloromethane was added and the mixture was concentrated again. The residue was taken up in dichloromethane and purified by preparative HPLC (Method 15). The combined target fractions were concentrated, and the residue was lyophilized in acetonitrile/water. This initially gave 65 mg ("100% purity", ee>99%, ">100% of theory", contains solvent) of the title compound (see optical rotation).

$[α]_D^{20}$=+80.0°, 589 nm, c=0.40 g/100 ml, methanol

The solvent-containing product was re-lyophilized from acetonitrile/water (cf. analysis). This gave 55 mg (100% pure, 87% of theory) of the title compound.

LC-MS (Method 2): $R_t$=0.99 min; MS (ESIpos): m/z=537/539 [M+H]$^+$ $^1$H-NMR (400 MHz, DMSO-d6) δ [ppm]: −0.149 (0.69), −0.008 (7.09), 0.008 (5.65), 0.146 (0.72), 2.169 (16.00), 2.327 (1.61), 2.366 (1.38), 2.523 (5.32), 2.669 (1.64), 2.710 (1.35), 4.086 (1.44), 4.100 (2.33), 4.115 (1.73), 4.133 (1.97), 4.147 (1.20), 4.347 (1.94), 4.362 (2.18), 4.369 (2.15), 4.383 (1.61), 6.798 (2.06), 6.820 (3.56), 6.842 (2.21), 6.875 (3.83), 6.896 (4.19), 7.267 (1.14), 7.288 (2.39), 7.305 (2.39), 7.326 (0.99), 7.492 (1.61), 7.502 (5.02), 7.510 (4.52), 7.522 (14.71), 7.534 (7.06), 7.741 (0.81), 7.839 (2.60), 7.845 (2.27), 7.862 (4.10), 7.867 (3.83), 7.928 (7.33), 7.951 (4.46), 8.778 (1.59), 8.793 (3.14), 8.807 (1.59).

$^1$H-NMR (400 MHz, DMSO-d6) δ [ppm]: 12.52 (br. s, 1H), 8.79 (t, 1H), 7.94 (d, 1H), 7.86 (dd, 1H), 7.74 (br. s, 1H), 7.56-7.46 (m, 5H), 7.35-7.24 (m, 1H), 6.89 (d, 1H), 6.82 (t, 1H), 4.37 (dd, 1H), 4.18-4.08 (m, 1H), 3.80 (s, 3H), ca. 3.8 (1H, obscured), 2.17 (s, 3H).

Example 59

(−)-3-{[(6-Bromo-3-methyl-2-phenylquinolin-4-yl)carbonyl]amino}-2-(2-methoxyphenyl)-2-methylpropanoic Acid (Enantiomer 1)

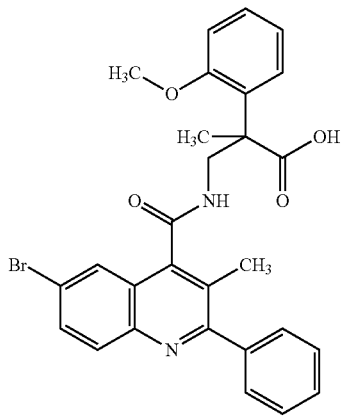

TFA (1.0 ml, 14 mmol) was added to a solution of (−)-tert-butyl 3-{[(6-bromo-3-methyl-2-phenylquinolin-4-yl)carbonyl]amino}-2-(2-methoxyphenyl)-2-methylpropanoate (400 mg, 678 µmol, Example 177A) in dichloromethane (10 ml), and the mixture was stirred at RT overnight. The mixture was then concentrated and repeatedly, in succession, dichloromethane was added and the mixture was concentrated again. The residue was purified by preparative HPLC (Method 16). The combined target fractions were concentrated, and the residue was dried under reduced pressure. This gave 303 mg (98% purity, ee 99%, 82% of theory) of the title compound.

$[α]_D^{20}$=−85.8°, 589 nm, c=0.30 g/100 ml, methanol
LC-MS (Method 2): $R_t$=1.01 min; MS (ESIpos): m/z=533/535 [M+H]$^+$
$^1$H-NMR (500 MHz, DMSO-d6) δ [ppm]: −0.007 (0.46), 1.594 (16.00), 2.071 (2.90), 2.085 (1.42), 3.718 (1.59), 3.728 (1.74), 3.744 (1.87), 3.755 (1.76), 4.314 (1.91), 4.329 (2.11), 4.341 (1.94), 4.356 (1.79), 6.930 (1.35), 6.945 (2.81), 6.960 (1.62), 6.999 (2.72), 7.015 (3.20), 7.251 (5.49), 7.266 (6.00), 7.280 (1.18), 7.480 (0.72), 7.489 (1.76), 7.491 (1.53), 7.493 (1.43), 7.501 (4.35), 7.506 (4.43), 7.518 (11.88), 7.523 (11.44), 7.528 (10.05), 7.539 (1.98), 7.831 (2.65), 7.836 (2.51), 7.849 (3.84), 7.853 (3.79), 7.919 (7.44), 7.936 (5.00), 8.417 (1.69), 8.428 (2.27), 8.432 (2.33), 8.443 (1.73).
$^1$H-NMR (500 MHz, DMSO-d6) δ [ppm]: 12.15 (br. s, 1H), 8.43 (dd, 1H), 7.93 (d, 1H), 7.84 (dd, 1H), 7.64 (br. s, 1H), 7.56-7.45 (m, 5H), 7.31-7.22 (m, 2H), 7.01 (d, 1H), 6.95 (t, 1H), 4.34 (dd, 1H), 3.78 (s, 3H), 3.74 (dd, 1H), 2.08 (br. s, 3H), 1.59 (s, 3H).

Example 60

(+)-3-{[(6-Bromo-3-methyl-2-phenylquinolin-4-yl)carbonyl]amino}-2-(2-methoxyphenyl)-2-methylpropanoic Acid (Enantiomer 2)

TFA (1.0 ml, 14 mmol) was added to a solution of (+)-tert-butyl 3-{[(6-bromo-3-methyl-2-phenylquinolin-4-yl)carbonyl]amino}-2-(2-methoxyphenyl)-2-methylpropanoate (400 mg, 678 µmol, Example 178A) in dichloromethane (10 ml), and the mixture was stirred at RT overnight. The mixture was then concentrated and repeatedly, in succession, dichloromethane was added and the mixture was concentrated again. The residue was purified by preparative HPLC (Method 16). The combined target fractions were concentrated, and the residue was dried under reduced pressure. This gave 133 mg (98% purity, ee 95%, 36% of theory) of the title compound.

$[α]_D^{20}$=+76.7°, 589 nm, c=0.30 g/100 ml, methanol
LC-MS (Method 2): $R_t$=1.01 min; MS (ESIpos): m/z=533/535 [M+H]$^+$
$^1$H-NMR (500 MHz, DMSO-d6) δ [ppm]: −0.007 (0.43), 1.595 (16.00), 2.071 (2.05), 2.086 (1.47), 3.720 (1.58), 3.730 (1.73), 3.746 (1.89), 3.757 (1.78), 4.315 (1.89), 4.330 (2.10), 4.342 (1.94), 4.357 (1.78), 6.931 (1.36), 6.946 (2.83), 6.961 (1.66), 6.999 (2.72), 7.015 (3.24), 7.252 (5.37), 7.267 (5.93), 7.281 (1.28), 7.481 (0.66), 7.490 (1.70), 7.492 (1.49), 7.494 (1.37), 7.502 (4.46), 7.507 (4.51), 7.519 (11.46), 7.524 (11.39), 7.529 (10.46), 7.540 (2.28), 7.593 (0.40), 7.641 (0.41), 7.833 (2.58), 7.837 (2.55), 7.851 (3.77), 7.855 (3.88), 7.920 (7.33), 7.938 (4.95), 8.419 (1.68), 8.430 (2.29), 8.434 (2.40), 8.444 (1.78).
$^1$H-NMR (500 MHz, DMSO-d6) δ [ppm]: 8.43 (dd, 1H), 7.93 (d, 1H), 7.84 (dd, 1H), 7.64 (br. s, 1H), 7.56-7.46 (m, 5H), 7.30-7.22 (m, 2H), 7.01 (d, 1H), 6.95 (t, 1H), 4.34 (dd, 1H), 3.79 (s, 3H), 3.74 (dd, 1H), 2.09 (br. s, 3H), 1.60 (s, 3H).

Example 61

(+)-3-{[(6-Bromo-3-methyl-2-phenylquinolin-4-yl)carbonyl]amino}-2-(2-chloro-6-fluorophenyl)-2-methylpropanoic Acid (Enantiomer 1)

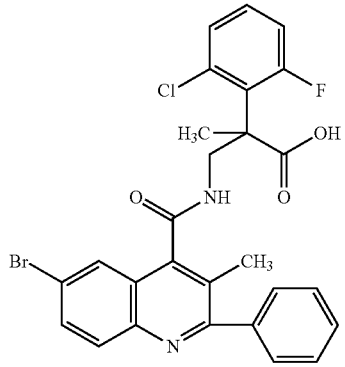 [SMILES: Cc1c(-c2ccccc2)nc2ccc(Br)cc2c1C(=O)NCC(C)(C(=O)O)c1c(F)cccc1Cl]

TFA (380 µl, 4.9 mmol) was added to a solution of (+)-tert-butyl 3-{[(6-bromo-3-methyl-2-phenylquinolin-4-yl)carbonyl]amino}-2-(2-chloro-6-fluorophenyl)-2-methylpropanoate (150 mg, 245 µmol, Example 180A) in dichloromethane (1.7 ml), and the mixture was stirred at RT for 7 h. The mixture was then concentrated and repeatedly, in succession, dichloromethane was added and the mixture was concentrated again. The residue was purified by preparative HPLC (Method 20). The combined target fractions were concentrated, and the residue was dried under reduced pressure. This gave 96 mg (98% purity, ee 99%, 69% of theory) of the title compound.

[α]$_D^{20}$=+68.8°, 589 nm, c=0.38 g/100 ml, methanol

LC-MS (Method 1): R$_t$=1.97 min; MS (ESIpos): m/z=555/557 [M+H]$^+$ $^1$H-NMR (500 MHz, DMSO-d6) δ [ppm]: −0.006 (0.85), 0.006 (0.57), 1.196 (0.41), 1.209 (0.41), 1.838 (8.67), 1.851 (8.44), 2.073 (1.43), 2.167 (1.73), 2.270 (0.45), 2.518 (0.69), 2.522 (0.48), 3.850 (1.19), 4.466 (1.35), 7.168 (1.13), 7.185 (1.55), 7.208 (1.27), 7.314 (1.99), 7.329 (3.87), 7.351 (1.75), 7.482 (1.18), 7.485 (1.27), 7.494 (3.79), 7.501 (3.73), 7.507 (6.74), 7.511 (8.03), 7.525 (12.08), 7.537 (16.00), 7.553 (3.51), 7.843 (3.37), 7.847 (3.18), 7.861 (4.71), 7.865 (4.52), 7.934 (9.34), 7.952 (6.28), 8.769 (2.37), 8.783 (3.82), 8.795 (2.25).

$^1$H-NMR (500 MHz, DMSO-d6) δ [ppm]: 12.85 (br. s, 1H), 8.78 (t, 1H), 7.94 (d, 1H), 7.85 (dd, 1H), 7.68 (br. s, 1H), 7.57-7.47 (m, 5H), 7.41-7.28 (m, 2H), 7.23-7.14 (m, 1H), 4.54-4.39 (m, 1H), 3.91-3.79 (m, 1H), 2.17 (br. s, 3H), 1.84 (d, 3H).

Example 62

(−)-3-{[(6-Bromo-3-methyl-2-phenylquinolin-4-yl)carbonyl]amino}-2-(2-chloro-6-fluorophenyl)-2-methylpropanoic Acid (Enantiomer 2)

TFA (380 μl, 4.9 mmol) was added to a solution of (−)-tert-butyl 3-{[(6-bromo-3-methyl-2-phenylquinolin-4-yl)carbonyl]amino}-2-(2-chloro-6-fluorophenyl)-2-methylpropanoate (150 mg, 245 μmol, Example 181A) in dichloromethane (1.7 ml), and the mixture was stirred at RT for 7 h. The mixture was then concentrated and repeatedly, in succession, dichloromethane was added and the mixture was concentrated again. The residue was purified by preparative HPLC (Method 20). The combined target fractions were concentrated, and the residue was dried under reduced pressure. This gave 112 mg (98% purity, ee 97%, 81% of theory) of the title compound.

[α]$_D^{20}$=−71.7°, 589 nm, c=0.29 g/100 ml, methanol

LC-MS (Method 1): R$_t$=1.97 min; MS (ESIpos): m/z=555/557 [M+H]$^+$ $^1$H-NMR (500 MHz, DMSO-d6) δ [ppm]: −0.007 (0.55), 0.006 (0.41), 1.840 (8.88), 1.853 (8.69), 2.073 (1.64), 2.168 (1.72), 2.271 (0.47), 2.518 (0.46), 3.837 (1.10), 3.851 (1.13), 4.468 (1.32), 4.480 (1.27), 7.168 (1.13), 7.185 (1.52), 7.208 (1.24), 7.315 (1.97), 7.329 (3.96), 7.351 (1.73), 7.477 (0.77), 7.482 (1.15), 7.485 (1.17), 7.494 (3.97), 7.502 (3.56), 7.507 (6.91), 7.511 (8.58), 7.525 (12.45), 7.539 (16.00), 7.554 (3.71), 7.843 (3.54), 7.848 (3.35), 7.861 (4.95), 7.866 (4.81), 7.935 (10.19), 7.953 (6.90), 8.772 (2.46), 8.785 (3.96), 8.798 (2.37).

$^1$H-NMR (500 MHz, DMSO-d6) δ [ppm]: 12.87 (br. s, 1H), 8.79 (t, 1H), 7.94 (d, 1H), 7.85 (dd, 1H), 7.70 (br. s, 1H), 7.59-7.46 (m, 5H), 7.42-7.27 (m, 2H), 7.24-7.12 (m, 1H), 4.53-4.41 (m, 1H), 3.91-3.80 (m, 1H), 2.17 (br. s, 3H), 1.85 (d, 3H).

Example 63

(+/−)-4-{[(6-Bromo-3-methyl-2-phenylquinolin-4-yl)carbonyl]amino}-3-phenylbutanoic Acid (Racemate)

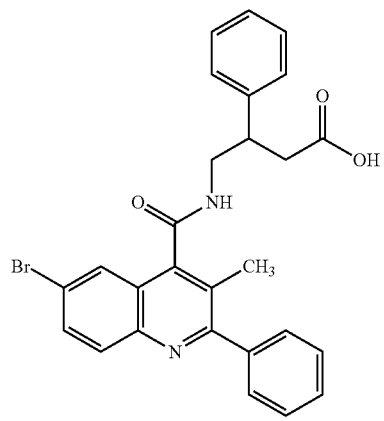 [SMILES: Cc1c(-c2ccccc2)nc2ccc(Br)cc2c1C(=O)NCC(CC(=O)O)c1ccccc1]

HATU (250 mg, 658 μmol) and DIPEA (230 μl, 1.3 mmol) were added to a mixture of 6-bromo-3-methyl-2-phenylquinoline-4-carboxylic Acid (150 mg, 438 μmol, preparable according to WO 2016 146602 A1, p. 51, Example 3A) in DMF (1.5 ml), and the mixture was stirred at RT for 30 min. (+/−)-4-Amino-3-phenylbutanoic acid hydrochloride (142 mg, 658 μmol, CAS-RN 3060-41-1, commercially available), dissolved in DMF (1 ml), was then added, and the mixture was stirred at 60° C. overnight. After cooling to RT, the mixture was purified by preparative HPLC (Method 22). This gave 206 mg (96% purity, 90% of theory) of the title compound.

LC-MS (Method 1): R$_t$=1.85 min; MS (ESIpos): m/z=503/505 (M+H)$^+$ $^1$H-NMR (400 MHz, DMSO-d6) δ [ppm]: 2.065 (1.35), 2.073 (6.33), 2.085 (1.59), 2.573 (1.56), 2.590 (2.18), 2.613 (2.18), 2.724 (2.06), 2.738 (2.28), 2.763 (1.51), 2.778 (1.45), 3.390 (0.91), 3.399 (1.09), 3.405 (0.95), 3.413 (1.61), 3.428 (1.05), 3.436 (0.89), 3.573 (0.84), 3.593 (0.91), 3.607 (1.10), 3.619 (0.64), 3.752 (0.68), 3.770 (0.95), 3.791 (0.87), 3.804 (0.73), 7.224 (1.76), 7.241 (1.64), 7.260 (0.79), 7.278 (1.07), 7.298 (2.13), 7.318 (6.13), 7.337 (12.61), 7.353 (1.88), 7.358 (1.04), 7.490 (1.44), 7.501 (4.52), 7.508 (4.98), 7.519 (16.00), 7.526 (7.90), 7.530 (5.64), 7.534 (4.95), 7.541 (1.29), 7.835 (2.04), 7.840 (1.87), 7.857 (3.22), 7.862 (2.99), 7.929 (6.06), 7.951 (3.77), 8.803 (1.31), 8.820 (1.87), 8.832 (1.28).

Separation of the Enantiomers:

The title compound (200 mg) was separated into the enantiomers by preparative SFC on a chiral phase (see Examples 64 and 65) [column: Daicel Chiralpak AD-H, 5 μm, 250 mm×20 mm; flow rate: 80 ml/min; detection: 210 nm; temperature: 40° C.; injection: 1 ml; mobile phase: 70% carbon dioxide/30% isopropanol; run time 70 min, isocratic].

Example 64

(−)-4-{[(6-Bromo-3-methyl-2-phenylquinolin-4-yl)carbonyl]amino}-3-phenylbutanoic Acid (Enantiomer 1)

In the enantiomer separation described in Example 63, 73 mg (98% purity, ee 100%) of the title compound were obtained as the enantiomer that eluted earlier.

[α]$_D^{20}$=−26.3°, 589 nm, c=0.32 g/100 ml, methanol
LC-MS (Method 1): R$_t$=1.87 min; MS (ESIpos): m/z=503/505 (M+H)$^+$
$^1$H-NMR (400 MHz, DMSO-d6) δ [ppm]: −0.008 (0.76), 0.008 (0.75), 2.084 (1.66), 2.573 (1.59), 2.590 (2.19), 2.613 (2.18), 2.724 (2.14), 2.730 (1.00), 2.738 (2.33), 2.764 (1.55), 2.778 (1.45), 3.392 (0.98), 3.399 (1.13), 3.406 (1.03), 3.414 (1.66), 3.429 (1.09), 3.437 (0.91), 3.561 (0.61), 3.573 (0.90), 3.594 (0.99), 3.607 (1.16), 3.620 (0.66), 3.753 (0.71), 3.772 (1.02), 3.792 (0.90), 3.803 (0.77), 7.208 (1.11), 7.224 (1.97), 7.241 (1.77), 7.260 (0.84), 7.279 (1.22), 7.298 (2.49), 7.318 (6.59), 7.334 (13.17), 7.353 (1.90), 7.359 (1.00), 7.477 (0.79), 7.480 (0.87), 7.489 (1.74), 7.492 (1.94), 7.503 (5.07), 7.510 (5.62), 7.520 (16.00), 7.527 (7.93), 7.532 (5.62), 7.535 (4.55), 7.543 (1.04), 7.837 (2.19), 7.842 (1.93), 7.860 (3.35), 7.865 (2.92), 7.930 (5.95), 7.953 (3.66), 8.806 (1.46), 8.818 (1.95), 8.834 (1.25).

Example 65

(+)-4-{[(6-Bromo-3-methyl-2-phenylquinolin-4-yl)carbonyl]amino}-3-phenylbutanoic Acid (Enantiomer 2)

In the enantiomer separation described in Example 63, the prepurified title compound was obtained as later-eluting enantiomer and repurified by preparative HPLC (Method 21). This gave 65 mg (94% purity, ee 100%) of the title compound.
[α]$_D^{20}$=+26.4°, 589 nm, c=0.35 g/100 ml, methanol
LC-MS (Method 2): R$_t$=0.98 min; MS (ESIpos): m/z=503/505 (M+H)$^+$
$^1$H-NMR (400 MHz, DMSO-d6) δ [ppm]: 2.083 (1.85), 2.572 (1.51), 2.723 (2.01), 2.738 (2.17), 2.763 (1.41), 2.777 (1.34), 3.391 (0.92), 3.399 (1.09), 3.413 (1.64), 3.427 (1.16), 3.436 (0.96), 3.574 (0.97), 3.593 (1.09), 3.606 (1.27), 3.752 (0.72), 3.770 (1.09), 3.791 (1.03), 7.224 (1.64), 7.241 (1.57), 7.298 (1.72), 7.318 (5.68), 7.336 (13.29), 7.352 (2.78), 7.491 (1.18), 7.503 (3.89), 7.510 (4.60), 7.521 (16.00), 7.837 (1.86), 7.842 (1.88), 7.860 (3.04), 7.865 (3.10), 7.930 (5.11), 7.953 (3.46), 8.806 (1.26), 8.822 (2.18), 8.834 (1.62).

Example 66

(+/−)-4-{[(6-Bromo-3-methyl-2-phenylquinolin-4-yl)carbonyl]amino}-3-(4-chlorophenyl)butanoic Acid (Racemate)

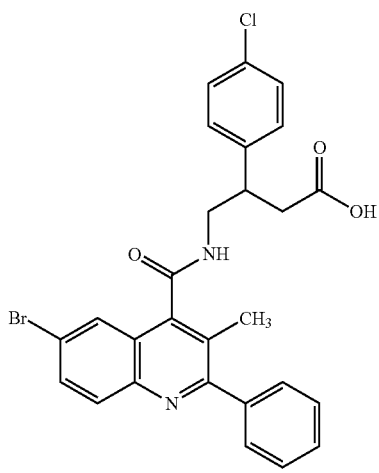 [SMILES: Cc1c(-c2ccccc2)nc2ccc(Br)cc2c1C(=O)NCC(CC(=O)O)c1ccc(Cl)cc1]

HATU (250 mg, 658 µmol) and DIPEA (230 µl, 1.3 mmol) were added to a mixture of 6-bromo-3-methyl-2-phenylquinoline-4-carboxylic Acid (150 mg, 438 µmol, preparable according to WO 2016 146602 A1, p. 51, Example 3A) in DMF (1.5 ml), and the mixture was stirred at RT for 30 min. (+/−)-4-Amino-3-(4-chlorophenyl)butanoic Acid (140 mg, 658 µmol, CAS-RN 1134-47-0, commercially available), dissolved in DMF (2 ml), was then added, and the mixture was stirred at 60° C. for 3 h. After cooling to RT, the mixture was poured into a citric acid solution (50 ml) and agitated. The precipitate formed was filtered off, washed twice with in each case 5 ml of water and purified by preparative HPLC (Method 15). This gave 97 mg (100% purity, 41% of theory) of the title compound.
LC-MS (Method 2): R$_t$=1.09 min; MS (ESIpos): m/z=537/539 [M+H]$^+$
$^1$H-NMR (400 MHz, DMSO-d6) δ [ppm]: 2.086 (5.51), 2.568 (0.68), 2.608 (0.91), 2.725 (0.88), 2.738 (0.98), 2.764 (0.66), 7.380 (16.00), 7.505 (2.07), 7.513 (1.89), 7.524 (5.04), 7.529 (4.78), 7.532 (4.20), 7.536 (3.04), 7.540 (2.40), 7.836 (0.74), 7.841 (0.74), 7.859 (1.17), 7.864 (1.18), 7.932 (2.34), 7.955 (1.50), 8.826 (0.91).
$^1$H-NMR (400 MHz, DMSO-d6): δ [ppm]=12.03 (br. s, 1H), 8.82 (t, 1H), 7.94 (d, 1H), 7.85 (dd, 1H), 7.65-7.46 (m, 6H), 7.38 (s, 4H), 3.79 (br. s, 1H), 3.66-3.52 (m, 1H), 3.47-3.34 (m, 1H), 2.75 (dd, 1H), 2.63-2.55 (m, 1H, partially obscured), 2.20-2.02 (br. m, 3H).
Separation of the Enantiomers:
The title compound (70 mg) was dissolved in a mixture of ethanol (2 ml) and isohexane (3 ml) and separated into the enantiomers by preparative HPLC on a chiral phase (see Examples 67 and 68) [column: Daicel Chiralpak ID, 5 µm 250 mm×20 mm; flow rate: 15 ml/min; temperature: 30° C.; injection: 0.25 ml; mobile phase: 82% isohexane/15% ethanol+0.2% acetic acid; run time 22.5 min, isocratic].

Example 67

(+)-4-{[(6-Bromo-3-methyl-2-phenylquinolin-4-yl)carbonyl]amino}-3-(4-chlorophenyl)butanoic Acid (Enantiomer 1)

In the enantiomer separation described in Example 66, the prepurified title compound was obtained as earlier-eluting enantiomer and repurified by preparative HPLC (Method 15). This gave 28 mg (98% purity, ee 99%) of the title compound.
[α]$_D^{20}$=+40.9°, 589 nm, c=0.33 g/100 ml, chloroform
LC-MS (Method 1): R$_t$=1.95 min; MS (ESIpos): m/z=537/539 [M+H]$^+$
$^1$H-NMR (400 MHz, DMSO-d6) δ [ppm]: 2.583 (0.89), 2.606 (0.88), 2.723 (0.84), 2.737 (0.93), 7.378 (16.00), 7.504 (1.93), 7.512 (1.74), 7.523 (4.86), 7.528 (4.43), 7.532 (3.55), 7.536 (2.58), 7.540 (2.07), 7.836 (0.71), 7.858 (1.10), 7.863 (1.07), 7.931 (2.34), 7.954 (1.48).
$^1$H-NMR (400 MHz, DMSO-d6): δ [ppm]=12.17 (br. s, 1H), 8.82 (t, 1H), 7.94 (d, 1H), 7.85 (dd, 1H), 7.65-7.46 (m, 6H), 7.38 (s, 4H), 3.79 (br. s, 1H), 3.67-3.52 (m, 1H), 3.47-3.32 (m, 1H), 2.75 (dd, 1H), 2.63-2.54 (m, 1H), 2.12 (br. s, 3H).

Example 68

(−)-4-{[(6-Bromo-3-methyl-2-phenylquinolin-4-yl)carbonyl]amino}-3-(4-chlorophenyl)butanoic Acid (Enantiomer 2)

In the enantiomer separation described in Example 66, the prepurified title compound was obtained as later-eluting enantiomer and repurified by preparative HPLC (Method 15). This gave 30 mg (100% purity, ee 94%) of the title compound.

$[\alpha]_D^{20}$=−39.8°, 589 nm, c=0.33 g/100 ml, chloroform

LC-MS (Method 1): $R_t$=1.95 min; MS (ESIpos): m/z=537/539 [M+H]$^+$ $^1$H-NMR (400 MHz, DMSO-d6) δ [ppm]: 2.583 (0.90), 2.607 (0.87), 2.723 (0.84), 2.738 (0.93), 7.379 (16.00), 7.505 (2.05), 7.513 (1.93), 7.524 (5.10), 7.529 (4.75), 7.532 (3.91), 7.536 (2.87), 7.540 (2.25), 7.837 (0.77), 7.842 (0.73), 7.859 (1.19), 7.864 (1.14), 7.932 (2.42), 7.955 (1.51), 8.825 (0.85).

$^1$H-NMR (400 MHz, DMSO-d6): δ [ppm]=8.82 (t, 1H), 7.94 (d, 1H), 7.85 (dd, 1H), 7.69-7.43 (m, 6H), 7.38 (s, 4H), 3.80 (br. s, 1H), 3.65-3.53 (m, 1H), 3.48-3.35 (m, 1H), 2.75 (dd, 1H), 2.63-2.55 (m, 1H), 2.11 (br. s, 3H).

Example 69

(+/−)-4-{[(6-Bromo-3-methyl-2-phenylquinolin-4-yl)carbonyl]amino}-3-(2-chlorophenyl)butanoic Acid

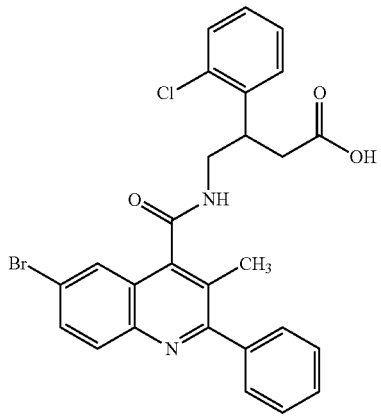 [SMILES: Cc1c(-c2ccccc2)nc2ccc(Br)cc2c1C(=O)NCC(CC(=O)O)c1ccccc1Cl]

TFA (6.8 ml, 89 mmol) was added to a solution of (+/−)-tert-butyl 4-{[(6-bromo-3-methyl-2-phenylquinolin-4-yl)carbonyl]amino}-3-(2-chlorophenyl)butanoate (527 mg, 887 µmol, Example 182A) in dichloromethane (14 ml), and the mixture was stirred at RT for 2 h. The mixture was then concentrated and repeatedly dichloromethane was added and the mixture was concentrated again. The residue was purified by preparative HPLC (Method 22). This gave 340 mg (98% purity, 70% of theory) of the title compound.

LC-MS (Method 2): $R_t$=1.02 min; MS (ESIpos): m/z=537/539 [M+H]$^+$ $^1$H-NMR (400 MHz, DMSO-d6) δ [ppm]: −0.150 (0.40), −0.008 (3.25), 0.008 (3.06), 2.073 (8.11), 2.142 (8.84), 2.192 (0.44), 2.327 (0.65), 2.332 (0.49), 2.523 (1.85), 2.645 (1.30), 2.664 (1.84), 2.674 (0.80), 2.685 (3.47), 2.705 (3.43), 2.723 (3.28), 2.739 (3.51), 2.763 (1.31), 2.779 (1.23), 3.615 (2.15), 3.803 (1.09), 3.932 (1.69), 3.951 (2.09), 3.969 (1.30), 7.246 (1.28), 7.265 (2.98), 7.281 (2.15), 7.334 (1.92), 7.353 (3.15), 7.371 (1.55), 7.428 (4.71), 7.431 (4.62), 7.447 (3.77), 7.451 (3.63), 7.476 (1.01), 7.487 (2.17), 7.501 (6.90), 7.509 (8.95), 7.512 (6.82), 7.521 (14.80), 7.527 (16.00), 7.530 (14.59), 7.534 (10.78), 7.538 (7.36), 7.546 (2.23), 7.648 (0.94), 7.833 (3.21), 7.838 (2.95), 7.855 (4.93), 7.860 (4.75), 7.929 (9.28), 7.952 (5.83), 8.832 (1.79), 8.847 (3.52), 8.862 (1.73).

Separation of the Enantiomers:

The title compound (200 mg) was dissolved in acetonitrile (18 ml) and separated into the enantiomers by preparative SFC on a chiral phase (see Examples 70 and 71) [column: Daicel Chiralpak AD, 5 µm 250 mm×20 mm; flow rate: 80 ml/min; detection: 210 nm; temperature: 40° C.; injection: 0.3 ml; mobile phase: 80% carbon dioxide/20% methanol; run time 12 min, isocratic].

Example 70

(+)-4-{[(6-Bromo-3-methyl-2-phenylquinolin-4-yl)carbonyl]amino}-3-(2-chlorophenyl)butanoic Acid (Enantiomer 1)

In the enantiomer separation described in Example 69, 44 mg (100% purity, ee 100%) of the title compound were obtained as the enantiomer that eluted earlier.

$[\alpha]_D^{20}$=+16.8°, 589 nm, c=0.40 g/100 ml, methanol

LC-MS (Method 1): $R_t$=1.92 min; MS (ESIpos): m/z=537/539 [M+H]$^+$ $^1$H-NMR (400 MHz, DMSO-d6) δ [ppm]: 2.143 (8.97), 2.327 (0.46), 2.631 (0.98), 2.649 (1.09), 2.670 (3.05), 2.689 (2.67), 2.709 (2.71), 2.725 (2.59), 2.749 (1.00), 2.765 (0.95), 3.311 (1.98), 3.711 (1.24), 3.813 (0.94), 3.929 (1.51), 3.945 (1.95), 3.963 (1.23), 7.243 (1.30), 7.261 (3.01), 7.280 (2.15), 7.332 (1.87), 7.350 (3.13), 7.368 (1.51), 7.427 (4.71), 7.447 (3.84), 7.475 (0.85), 7.501 (7.67), 7.508 (8.77), 7.520 (14.62), 7.527 (16.00), 7.656 (1.05), 7.831 (3.10), 7.836 (2.78), 7.853 (4.62), 7.858 (4.42), 7.928 (8.78), 7.950 (5.48), 8.875 (2.67).

Example 71

(−)-4-{[(6-Bromo-3-methyl-2-phenylquinolin-4-yl)carbonyl]amino}-3-(2-chlorophenyl)butanoic Acid (Enantiomer 2)

In the enantiomer separation described in Example 69, 61 mg (98% purity, ee 98%) of the title compound were obtained as the enantiomer that eluted later.

$[\alpha]_D^{20}$=−18.1°, 589 nm, c=0.37 g/100 ml, methanol

LC-MS (Method 1): $R_t$=1.92 min; MS (ESIpos): m/z=537/539 [M+H]$^+$ $^1$H-NMR (400 MHz, DMSO-d6) δ [ppm]: 1.284 (2.85), 2.144 (9.37), 2.193 (0.50), 2.523 (0.75), 2.646 (1.24), 2.665 (1.48), 2.686 (3.35), 2.705 (3.37), 2.723 (3.22), 2.740 (3.43), 2.764 (1.30), 2.780 (1.21), 3.536 (1.08), 3.718 (1.28), 3.815 (0.99), 3.917 (0.65), 3.935 (1.69), 3.953 (2.12), 3.970 (1.36), 3.988 (0.46), 7.246 (1.35), 7.264 (3.13), 7.282 (2.27), 7.334 (2.01), 7.353 (3.31), 7.371 (1.64), 7.429 (4.72), 7.431 (4.62), 7.449 (3.85), 7.475 (0.94), 7.487 (2.24), 7.501 (7.16), 7.508 (8.46), 7.513 (7.20), 7.520 (15.06), 7.527 (16.00), 7.529 (15.63), 7.546 (2.45), 7.663 (0.98), 7.832 (3.10), 7.837 (2.83), 7.854 (4.76), 7.859 (4.58), 7.929 (8.85), 7.952 (5.65), 8.835 (1.83), 8.849 (3.57), 8.864 (1.82), 12.186 (1.34).

Example 72

(+/−)-4-{[(6-Bromo-3-methyl-2-phenylquinolin-4-yl)carbonyl]amino}-3-(3-chlorophenyl)butanoic Acid (Racemate)

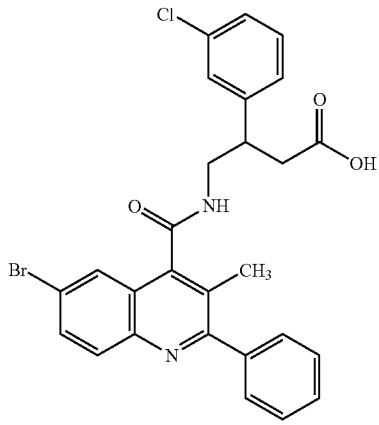 [SMILES: Cc1c(-c2ccccc2)nc2ccc(Br)cc2c1C(=O)NCC(CC(=O)O)c1cccc(Cl)c1]

TFA (2.9 ml, 37 mmol) was added to a solution of (+/−)-tert-butyl 4-{[(6-bromo-3-methyl-2-phenylquinolin-4-yl)carbonyl]amino}-3-(3-chlorophenyl)butanoate (220 mg, 370 µmol, Example 183A) in dichloromethane (6.0 ml), and the mixture was stirred at RT for 2 h. The mixture was then concentrated and repeatedly dichloromethane was added and the mixture was concentrated again. The residue was purified by preparative HPLC (Method 22). This gave 93 mg (96% purity, 45% of theory) of the title compound.

LC-MS (Method 1): $R_t$=1.95 min; MS (ESIpos): m/z=537/539 [M+H]$^+$ $^1$H-NMR (400 MHz, DMSO-d6) δ [ppm]: −0.008 (0.62), 0.008 (0.73), 1.513 (4.18), 2.073 (1.21), 2.592 (1.53), 2.615 (1.62), 2.632 (2.44), 2.655 (2.46), 2.739 (2.29), 2.753 (2.58), 2.779 (1.63), 2.793 (1.51), 3.381 (0.92), 3.390 (1.07), 3.404 (1.69), 3.418 (1.18), 3.427 (1.00), 3.570 (0.82), 3.582 (1.22), 3.595 (0.96), 3.603 (1.23), 3.615 (1.57), 3.628 (0.98), 3.781 (1.47), 3.799 (1.84), 3.805 (1.82), 3.814 (1.83), 3.822 (1.95), 3.832 (1.89), 3.838 (1.86), 3.855 (1.78), 7.280 (1.27), 7.298 (2.12), 7.306 (1.72), 7.311 (2.01), 7.315 (1.69), 7.326 (3.60), 7.330 (5.17), 7.334 (3.33), 7.339 (4.65), 7.357 (3.12), 7.376 (1.02), 7.408 (5.29), 7.412 (3.39), 7.486 (0.77), 7.489 (1.30), 7.492 (1.48), 7.497 (1.47), 7.502 (4.59), 7.510 (4.68), 7.521 (16.00), 7.528 (7.86), 7.532 (5.84), 7.536 (5.32), 7.543 (1.39), 7.836 (1.84), 7.841 (1.74), 7.858 (2.85), 7.864 (2.81), 7.930 (6.11), 7.952 (3.87), 8.805 (1.47), 8.816 (1.89), 8.822 (1.94), 8.833 (1.42).

Separation of the Enantiomers:

The title compound (220 mg) was dissolved in ethanol (2 ml) and separated into the enantiomers by preparative HPLC on a chiral phase (see Examples 73 and 74) [column: Daicel Chiralpak AZ-H, 5 µm, 250 mm×20 mm; flow rate: 20 ml/min; detection: 220 nm; temperature: 23° C.; injection: 0.05 ml; mobile phase: 70% heptane/30% ethanol+0.2% TFA; isocratic].

Example 73

4-{[(6-Bromo-3-methyl-2-phenylquinolin-4-yl)carbonyl]amino}-3-(3-chlorophenyl)butanoic Acid (Enantiomer 1)

In the enantiomer separation described in Example 72, 8 mg (90% purity, ee 81%) of the title compound were obtained as the enantiomer that eluted earlier.

LC-MS (Method 1): $R_t$=1.93 min; MS (ESIpos): m/z=537/539 [M+H]$^+$ $^1$H-NMR (500 MHz, DMSO-d6) δ [ppm]: 0.844 (0.61), 0.858 (0.64), 1.090 (0.69), 1.104 (1.06), 1.118 (0.89), 1.148 (3.99), 1.163 (6.78), 1.177 (3.40), 1.233 (1.25), 1.257 (0.74), 2.067 (1.52), 2.600 (1.45), 2.618 (1.68), 2.632 (2.25), 2.650 (2.00), 2.745 (2.35), 2.756 (2.36), 2.777 (1.59), 2.788 (1.38), 2.906 (1.53), 2.920 (2.35), 2.931 (2.19), 2.945 (1.21), 3.407 (2.39), 3.587 (2.01), 3.612 (2.20), 3.730 (0.92), 3.744 (0.92), 3.790 (1.71), 3.804 (2.25), 3.848 (1.30), 7.298 (2.88), 7.316 (2.92), 7.330 (5.58), 7.341 (4.20), 7.356 (3.37), 7.371 (1.43), 7.408 (6.05), 7.509 (6.59), 7.523 (16.00), 7.842 (2.44), 7.859 (3.28), 7.933 (4.45), 7.951 (3.14), 8.823 (2.93).

Example 74

4-{[(6-Bromo-3-methyl-2-phenylquinolin-4-yl)carbonyl]amino}-3-(3-chlorophenyl)butanoic Acid (Enantiomer 2)

In the enantiomer separation described in Example 72, 8 mg (90% purity, ee 77%) of the title compound were obtained as the enantiomer that eluted later.

LC-MS (Method 1): $R_t$=1.93 min; MS (ESIpos): m/z=537 [M+H]$^+$ $^1$H-NMR (500 MHz, DMSO-d6) δ [ppm]: 0.845 (0.64), 0.859 (0.80), 1.090 (1.19), 1.104 (2.22), 1.118 (1.23), 1.148 (1.87), 1.162 (3.65), 1.177 (1.89), 1.233 (1.16), 1.246 (0.80), 1.258 (0.76), 2.073 (1.36), 2.602 (1.97), 2.620 (2.14), 2.634 (3.02), 2.652 (2.87), 2.746 (2.92), 2.757 (3.08), 2.778 (2.10), 2.790 (1.89), 2.925 (0.79), 2.935 (0.77), 3.380 (0.71), 3.391 (1.40), 3.398 (1.64), 3.409 (2.39), 3.420 (1.66), 3.427 (1.34), 3.439 (0.69), 3.581 (1.16), 3.590 (1.67), 3.601 (1.37), 3.607 (1.59), 3.617 (1.97), 3.626 (1.14), 3.730 (1.14), 3.744 (1.15), 3.792 (1.25), 3.807 (1.66), 3.819 (1.53), 3.825 (1.55), 3.833 (1.39), 3.852 (0.91), 7.284 (1.85), 7.299 (2.56), 7.316 (2.70), 7.331 (6.33), 7.342 (4.73), 7.357 (3.94), 7.373 (1.36), 7.381 (0.69), 7.410 (6.99), 7.489 (1.20), 7.498 (2.45), 7.510 (6.15), 7.515 (5.99), 7.526 (16.00), 7.530 (14.69), 7.536 (11.79), 7.546 (2.42), 7.849 (2.50), 7.853 (2.45), 7.867 (3.55), 7.871 (3.43), 7.940 (6.73), 7.957 (4.55), 8.817 (2.13), 8.826 (2.80), 8.831 (2.86), 8.840 (2.11).

Example 75

(+/−)-4-{[(6-Bromo-3-methyl-2-phenylquinolin-4-yl)carbonyl]amino}-3-(2-methylphenyl)butanoic Acid (Racemate)

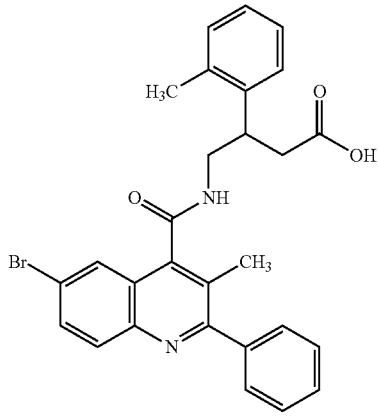 [SMILES: Cc1ccccc1C(CNC(=O)c1c(C)c(-c2ccccc2)nc2ccc(Br)cc12)CC(=O)O]

TFA (10 ml, 130 mmol) was added to a solution of (+/−)-tert-butyl 4-{[(6-bromo-3-methyl-2-phenylquinolin-4-yl)carbonyl]amino}-3-(2-methylphenyl)butanoate (750 mg, 1.31 mmol, Example 184A) in dichloromethane (21 ml), and the mixture was stirred at RT for 2 h. The mixture was then concentrated and repeatedly dichloromethane was added and the mixture was concentrated again. The residue was purified by preparative HPLC (Method 22). This gave 574 mg (98% purity, 83% of theory) of the title compound.

LC-MS (Method 1): $R_t$=1.91 min; MS (ESIpos): m/z=517/519 [M+H]$^+$ $^1$H-NMR (400 MHz, DMSO-d6) δ [ppm]: 1.195 (0.56), 1.211 (0.57), 2.072 (1.53), 2.118 (2.44), 2.398 (16.00), 2.580 (0.92), 2.602 (0.93), 2.620 (1.80), 2.641 (1.77), 2.701 (1.65), 2.715 (1.71), 2.740 (1.10), 2.754 (0.97), 3.475 (0.88), 3.491 (0.99), 3.504 (0.98), 3.714 (0.80), 3.729 (1.18), 3.755 (1.42), 3.771 (1.22), 3.785 (0.96), 3.803 (0.96), 7.087 (0.69), 7.105 (1.83), 7.122 (1.72), 7.151 (3.03), 7.171 (2.05), 7.193 (1.76), 7.210 (0.88), 7.348 (2.62), 7.366 (2.04), 7.490 (1.38), 7.505 (4.13), 7.511 (3.27), 7.516 (2.22), 7.522 (7.34), 7.528 (4.36), 7.533 (8.00), 7.535 (7.96), 7.539 (5.03), 7.543 (3.79), 7.552 (1.44), 7.841 (1.92), 7.846 (1.73), 7.864 (2.88), 7.869 (2.73), 7.940 (5.41), 7.962 (3.45), 8.855 (1.14), 8.871 (1.89), 8.883 (1.04).

Separation of the Enantiomers:

The title compound (750 mg) was separated into the enantiomers by preparative SFC on a chiral phase (see Examples 76 and 77) [column: Daicel Chiralpak AD-H, 5 µm, 250 mm×20 mm; flow rate: 80 ml/min; detection: 210 nm; temperature: 40° C.; injection: 0.2 ml; mobile phase: 85% carbon dioxide/15% ethanol; isocratic].

Example 76

(−)-4-{[(6-Bromo-3-methyl-2-phenylquinolin-4-yl)carbonyl]amino}-3-(2-methylphenyl)butanoic Acid (Enantiomer 1)

In the enantiomer separation described in Example 75, the title compound was obtained as earlier-eluting enantiomer. This gave 188 mg (98% purity, ee 100%) of the title compound.

$[α]_D^{20}$=−23.3°, 589 nm, c=0.29 g/100 ml, methanol

LC-MS (Method 2): $R_t$=1.08 min; MS (ESIpos): m/z=517/519 [M+H]$^+$ $^1$H-NMR (400 MHz, DMSO-d6) δ [ppm]: −0.008 (0.53), 0.008 (0.42), 1.031 (1.36), 1.046 (1.36), 1.285 (0.75), 2.072 (0.86), 2.116 (2.61), 2.396 (16.00), 2.522 (0.65), 2.579 (0.93), 2.600 (0.96), 2.618 (1.83), 2.640 (1.77), 2.700 (1.69), 2.713 (1.75), 2.739 (1.12), 2.753 (0.98), 3.471 (0.96), 3.487 (1.07), 3.502 (1.06), 3.516 (0.67), 3.712 (0.84), 3.727 (1.25), 3.753 (1.51), 3.769 (1.30), 3.783 (1.01), 3.800 (0.98), 3.820 (0.46), 7.085 (0.72), 7.104 (1.90), 7.122 (1.82), 7.150 (3.13), 7.170 (2.15), 7.192 (1.82), 7.210 (0.89), 7.347 (2.72), 7.366 (2.08), 7.475 (0.58), 7.488 (1.59), 7.502 (4.47), 7.508 (3.75), 7.520 (7.82), 7.530 (8.17), 7.532 (8.13), 7.548 (1.47), 7.675 (0.67), 7.837 (2.01), 7.842 (1.81), 7.859 (2.92), 7.864 (2.77), 7.936 (5.33), 7.959 (3.38), 8.849 (1.23), 8.865 (1.95), 8.877 (1.07), 12.073 (1.54).

Example 77

(+)-4-{[(6-Bromo-3-methyl-2-phenylquinolin-4-yl)carbonyl]amino}-3-(2-methylphenyl)butanoic Acid (Enantiomer 2)

In the enantiomer separation described in Example 75, the title compound was obtained as later-eluting enantiomer. This gave 179 mg (98% purity, ee 97%) of the title compound.

$[α]_D^{20}$=+24.8°, 589 nm, c=0.38 g/100 ml, methanol

LC-MS (Method 2): $R_t$=1.08 min; MS (ESIpos): m/z=517/519 [M+H]$^+$ $^1$H-NMR (400 MHz, DMSO-d6) δ [ppm]: −0.008 (0.42), 1.030 (1.22), 1.046 (1.23), 1.284 (0.59), 2.073 (0.85), 2.116 (2.44), 2.396 (16.00), 2.523 (0.47), 2.578 (0.91), 2.599 (0.93), 2.617 (1.82), 2.639 (1.78), 2.699 (1.65), 2.712 (1.74), 2.738 (1.11), 2.752 (0.99), 3.471 (0.90), 3.487 (1.01), 3.501 (1.01), 3.516 (0.66), 3.711 (0.78), 3.726 (1.17), 3.752 (1.41), 3.768 (1.22), 3.782 (0.97), 3.800 (0.96), 3.819 (0.46), 7.086 (0.66), 7.104 (1.82), 7.122 (1.73), 7.150 (2.98), 7.170 (2.01), 7.192 (1.74), 7.210 (0.87), 7.346 (2.67), 7.365 (2.07), 7.475 (0.48), 7.488 (1.38), 7.493 (1.00), 7.502 (4.10), 7.509 (3.35), 7.521 (7.50), 7.529 (7.78), 7.532 (7.90), 7.536 (5.27), 7.548 (1.38), 7.674 (0.60), 7.837 (1.93), 7.843 (1.74), 7.860 (2.90), 7.865 (2.79), 7.936 (5.20), 7.959 (3.34), 8.849 (1.15), 8.865 (1.90), 8.877 (1.05), 12.073 (2.06).

Example 78

(+/−)-4-{[(6-Bromo-3-methyl-2-phenylquinolin-4-yl)carbonyl]amino}-3-(2,6-dichlorophenyl)butanoic Acid (Racemate)

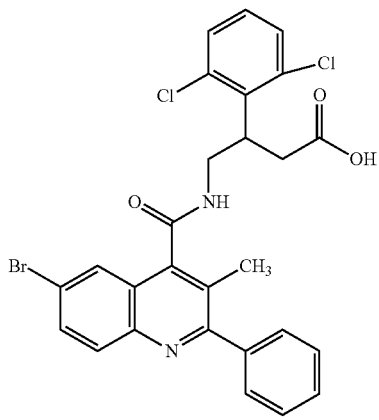 [SMILES: Cc1c(-c2ccccc2)nc2ccc(Br)cc2c1C(=O)NCC(CC(=O)O)c1c(Cl)cccc1Cl]

TFA (1.7 ml, 22 mmol) was added to a solution of (+/−)-tert-butyl 4-{[(6-bromo-3-methyl-2-phenylquinolin-4-yl)carbonyl]amino}-3-(2,6-dichlorophenyl)butanoate (140 mg, 223 μmol, Example 185A) in dichloromethane (3.6 ml), and the mixture was stirred at RT for 2 h. The mixture was then concentrated and repeatedly dichloromethane was added and the mixture was concentrated again. The residue was purified by preparative HPLC (Method 22). This gave 103 mg (97% purity, 78% of theory) of the title compound.

LC-MS (Method 1): $R_t$=1.96 min; MS (ESIpos): m/z=571/573/575 [M+H]$^+$ $^1$H-NMR (400 MHz, DMSO-d6) δ [ppm]: −0.008 (1.34), 0.008 (1.24), 1.194 (0.98), 1.211 (0.93), 1.491 (1.86), 2.073 (1.44), 2.170 (7.32), 2.881 (1.47), 2.898 (1.68), 2.921 (4.94), 2.937 (4.87), 2.948 (4.80), 2.968 (4.74), 2.987 (1.53), 3.008 (1.61), 3.628 (1.72), 3.801 (1.46), 4.118 (1.23), 4.414 (1.41), 4.430 (1.84), 4.450 (1.22), 7.266 (1.46), 7.286 (2.89), 7.307 (1.90), 7.424 (3.69), 7.444 (3.01), 7.464 (4.75), 7.488 (5.02), 7.495 (2.42), 7.504 (8.15), 7.511 (7.06), 7.515 (4.09), 7.523 (15.90), 7.530 (16.00), 7.533 (14.69), 7.537 (10.88), 7.541 (8.23), 7.550 (2.61), 7.838 (4.04), 7.843 (3.56), 7.860 (6.03), 7.866 (5.58), 7.933 (10.89), 7.956 (6.77), 8.914 (1.97), 8.929 (3.71), 8.944 (1.94).

Separation of the Enantiomers:

The title compound (80 mg) was dissolved in 17 ml of a methanol/acetonitrile mixture and separated into the enantiomers by preparative SFC on a chiral phase (see Examples 79 and 80) [column: Daicel Chiralpak AD-H, 5 μm, 250 mm×20 mm; flow rate: 80 ml/min; detection: 210 nm; temperature: 40° C.; injection: 3 ml; mobile phase: 70% carbon dioxide/30% isopropanol; isocratic].

Example 79

4-{[(6-Bromo-3-methyl-2-phenylquinolin-4-yl)carbonyl]amino}-3-(2,6-dichlorophenyl)butanoic Acid (Enantiomer 1)

In the enantiomer separation described in Example 78, the title compound was obtained as earlier-eluting enantiomer and repurified by preparative HPLC (Method 21). This gave 22 mg (98% purity, ee 96%) of the title compound.

LC-MS (Method 2): $R_t$=1.04 min; MS (ESIpos): m/z=571/573/575 [M+H]$^+$ $^1$H-NMR (400 MHz, DMSO-d6) δ [ppm]: 2.073 (0.63), 2.168 (7.87), 2.314 (0.56), 2.327 (0.72), 2.366 (0.53), 2.670 (0.66), 2.710 (0.43), 2.879 (1.34), 2.896 (1.55), 2.919 (4.81), 2.936 (4.87), 2.945 (4.79), 2.966 (4.59), 2.985 (1.43), 3.006 (1.44), 3.814 (1.32), 4.119 (1.35), 4.409 (1.91), 4.428 (2.43), 4.446 (1.78), 4.716 (0.73), 7.267 (1.34), 7.287 (2.87), 7.307 (1.97), 7.424 (3.51), 7.444 (2.89), 7.465 (4.64), 7.485 (4.08), 7.505 (7.47), 7.511 (6.25), 7.524 (16.00), 7.531 (15.93), 7.740 (0.43), 7.840 (3.42), 7.846 (3.16), 7.863 (5.30), 7.868 (5.12), 7.934 (9.44), 7.956 (5.90), 8.914 (2.03), 8.929 (3.94), 8.943 (2.10).

Example 80

4-{[(6-Bromo-3-methyl-2-phenylquinolin-4-yl)carbonyl]amino}-3-(2,6-dichlorophenyl)butanoic Acid (Enantiomer 2)

In the enantiomer separation described in Example 78, the title compound was obtained as later-eluting enantiomer and repurified by preparative HPLC (Method 21). This gave 30 mg (98% purity, ee 95%) of the title compound.

LC-MS (Method 2): $R_t$=1.04 min; MS (ESIpos): m/z=571/573/575 [M+H]$^+$ $^1$H-NMR (400 MHz, DMSO-d6) δ [ppm]: −0.008 (2.08), 0.008 (1.82), 2.168 (7.58), 2.327 (0.87), 2.366 (0.54), 2.669 (0.80), 2.710 (0.55), 2.879 (1.42), 2.896 (1.69), 2.919 (4.96), 2.936 (4.95), 2.945 (4.83), 2.966 (4.71), 2.985 (1.53), 3.006 (1.57), 3.814 (1.27), 4.118 (1.41), 4.411 (2.21), 4.428 (2.71), 7.267 (1.35), 7.286 (2.83), 7.307 (1.96), 7.424 (3.66), 7.444 (2.99), 7.464 (4.84), 7.484 (4.25), 7.504 (7.70), 7.511 (6.69), 7.524 (16.00), 7.530 (15.92), 7.549 (2.71), 7.723 (0.46), 7.839 (3.81), 7.845 (3.49), 7.862 (5.78), 7.867 (5.47), 7.933 (10.51), 7.956 (6.50), 8.913 (2.01), 8.928 (3.84), 8.943 (2.01).

Example 81

(+/−)-4-{[(6-Bromo-3-methyl-2-phenylquinolin-4-yl)carbonyl]amino}-3-(3-methoxyphenyl)butanoic Acid (Racemate)

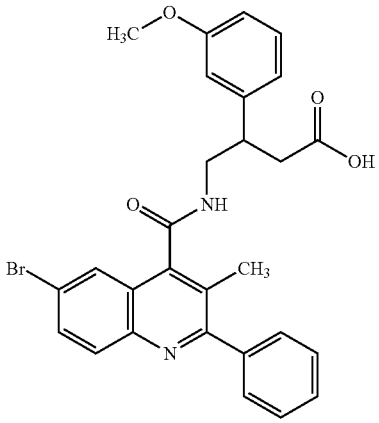 [SMILES: COc1cccc(C(CNC(=O)c2c(C)c(-c3ccccc3)nc3ccc(Br)cc23)CC(=O)O)c1]

TFA (2.9 ml, 37 mmol) was added to a solution of (+/−)-tert-butyl 4-{[(6-bromo-3-methyl-2-phenylquinolin-4-yl)carbonyl]amino}-3-(3-methoxyphenyl)butanoate (220 mg, 373 μmol, Example 186A) in dichloromethane (6.1 ml), and the mixture was stirred at RT for 2 h. The mixture was then concentrated and repeatedly dichloromethane was added and the mixture was concentrated again. The residue was purified by preparative HPLC (Method 22). This gave 145 mg (99% purity, 72% of theory) of the title compound.

LC-MS (Method 1): $R_t$=1.83 min; MS (ESIpos): m/z=533/535 [M+H]$^+$ $^1$H-NMR (400 MHz, DMSO-d6) δ [ppm]: 1.517 (0.61), 2.073 (1.41), 2.100 (1.94), 2.566 (1.54), 2.583 (2.22), 2.606 (2.20), 2.706 (2.11), 2.721 (2.33), 2.746 (1.54), 2.760 (1.42), 3.365 (0.91), 3.372 (1.03), 3.387 (1.66), 3.402 (1.10), 3.409 (0.94), 3.558 (0.75), 3.571 (1.09), 3.585 (0.96), 3.591 (1.18), 3.604 (1.43), 3.618 (0.85), 3.746 (1.11), 3.762 (1.17), 3.778 (1.06), 3.784 (1.09), 3.795 (0.92), 3.817 (0.63), 6.782 (1.71), 6.800 (1.75), 6.805 (1.81), 6.895 (6.74), 6.899 (7.77), 6.917 (3.26), 7.212 (2.22), 7.231 (3.46), 7.251 (1.63), 7.490 (1.27), 7.492 (1.44), 7.503 (4.41), 7.511 (4.41), 7.522 (16.00), 7.529 (8.04), 7.533 (6.09), 7.536 (5.54), 7.544 (1.30), 7.835 (2.08), 7.840 (1.97), 7.857 (3.16), 7.863 (3.14), 7.931 (6.42), 7.954 (4.05), 8.795 (1.39), 8.811 (2.08), 8.823 (1.41).

Separation of the Enantiomers:

The title compound (120 mg) was dissolved in 4 ml of an ethanol/heptane mixture and separated into the enantiomers by preparative HPLC on a chiral phase (see Examples 82 and 83) [column: Daicel Chiralpak AZ-H, 5 µm, 250 mm×20 mm; flow rate: 20 ml/min; detection: 220 nm; temperature: 40° C.; injection: 0.5 ml; mobile phase: 70% heptane/30% ethanol+0.2% TFA, isocratic, run time 8.5 min].

Example 82

(+)-4-{[(6-Bromo-3-methyl-2-phenylquinolin-4-yl)carbonyl]amino}-3-(3-methoxyphenyl)butanoic Acid (Enantiomer 1)

In the enantiomer separation described in Example 81, the title compound was obtained as earlier-eluting enantiomer. This gave 29 mg (98% purity, ee 100%) of the title compound.

$[α]_D^{20}$=+33.7°, 589 nm, c=0.29 g/100 ml, chloroform

LC-MS (Method 1): $R_t$=1.82 min; MS (ESIpos): m/z=533/535 [M+H]$^+$ $^1$H-NMR (400 MHz, DMSO-d6) δ [ppm]: –0.008 (2.93), 0.008 (1.70), 1.038 (0.98), 1.056 (1.91), 1.073 (0.96), 1.207 (1.03), 1.234 (0.68), 2.073 (1.46), 2.101 (1.94), 2.523 (1.89), 2.564 (1.66), 2.581 (2.19), 2.604 (2.10), 2.705 (2.08), 2.719 (2.22), 2.744 (1.47), 2.759 (1.34), 3.362 (0.95), 3.369 (1.04), 3.384 (1.62), 3.400 (1.09), 3.407 (0.99), 3.414 (0.68), 3.432 (1.09), 3.449 (1.04), 3.556 (0.81), 3.568 (1.12), 3.589 (1.22), 3.602 (1.42), 3.615 (0.86), 3.743 (1.21), 3.759 (1.37), 3.782 (1.29), 3.793 (1.15), 3.816 (0.85), 3.996 (1.01), 6.780 (1.72), 6.804 (1.72), 6.894 (6.53), 6.898 (7.12), 6.915 (3.02), 7.210 (2.14), 7.230 (3.25), 7.250 (1.51), 7.489 (1.68), 7.502 (4.67), 7.510 (4.99), 7.521 (16.00), 7.528 (7.49), 7.532 (5.66), 7.535 (4.90), 7.834 (2.12), 7.839 (1.91), 7.856 (3.12), 7.862 (2.88), 7.930 (5.97), 7.952 (3.71), 8.792 (1.44), 8.809 (1.99), 8.821 (1.30).

Example 83

(–)-4-{[(6-Bromo-3-methyl-2-phenylquinolin-4-yl)carbonyl]amino}-3-(3-methoxyphenyl)butanoic Acid (Enantiomer 2)

In the enantiomer separation described in Example 81, the title compound was obtained as later-eluting enantiomer. This gave 35 mg (98% purity, ee 94%) of the title compound.

$[α]_D^{20}$=–25.8°, 589 nm, c=0.32 g/100 ml, chloroform

LC-MS (Method 1): $R_t$=1.82 min; MS (ESIpos): m/z=533/535 [M+H]$^+$ $^1$H-NMR (400 MHz, DMSO-d6) δ [ppm]: –0.008 (1.83), 0.008 (1.04), 0.840 (6.59), 0.858 (16.00), 0.875 (5.02), 1.242 (11.36), 1.247 (11.78), 1.258 (4.11), 1.267 (2.90), 1.279 (2.40), 1.297 (1.03), 2.097 (1.48), 2.564 (1.22), 2.581 (1.75), 2.604 (1.74), 2.705 (1.69), 2.719 (1.84), 2.744 (1.23), 2.759 (1.12), 3.363 (1.03), 3.370 (1.15), 3.385 (1.76), 3.399 (1.49), 3.407 (1.48), 3.422 (1.43), 3.432 (1.64), 3.450 (2.18), 3.467 (2.38), 3.535 (1.05), 3.544 (0.97), 3.556 (1.11), 3.569 (1.26), 3.583 (1.06), 3.589 (1.19), 3.602 (1.33), 3.759 (0.90), 6.781 (1.30), 6.804 (1.36), 6.894 (5.26), 6.898 (5.93), 6.916 (2.49), 7.210 (1.76), 7.230 (2.71), 7.250 (1.26), 7.488 (1.02), 7.491 (1.05), 7.501 (3.41), 7.509 (3.48), 7.520 (12.89), 7.527 (5.81), 7.532 (4.48), 7.535 (3.98), 7.832 (1.68), 7.838 (1.49), 7.855 (2.55), 7.860 (2.38), 7.929 (5.01), 7.952 (3.16), 8.792 (1.07), 8.808 (1.58), 8.820 (1.05).

Example 84

(+/–)-4-{[(6-Bromo-3-methyl-2-phenylquinolin-4-yl)carbonyl]amino}-3-(3-chloropyridin-2-yl)-3-methylbutanoic Acid (Racemate)

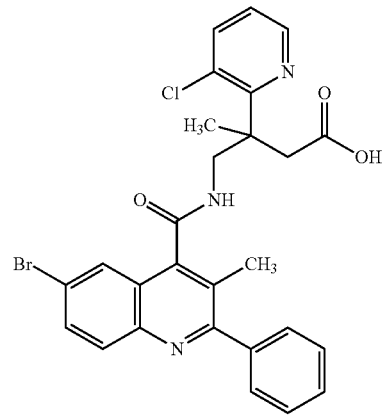 [SMILES: Cc1c(-c2ccccc2)nc2ccc(Br)cc2c1C(=O)NCC(C)(CC(=O)O)c1ncccc1Cl]

TFA (1.6 ml, 21 mmol) was added to a solution of (+/–)-tert-butyl 4-{[(6-bromo-3-methyl-2-phenylquinolin-4-yl)carbonyl]amino}-3-(3-chloropyridin-2-yl)-3-methylbutanoate (650 mg, 1.07 mmol, Example 187A) in dichloromethane (7.2 ml), and the mixture was stirred at RT overnight. The mixture was then concentrated and repeatedly dichloromethane was added and the mixture was concentrated again. The residue was taken up in dichloromethane and purified by flash column chromatography (100 g silica gel Biotage Snap-Cartridge KP-Sil, cyclohexane/ethyl acetate 8:2, Isolera One). This gave 202 mg (98% purity, 34% of theory) of the title compound.

LC-MS (Method 1): $R_t$=1.94 min; MS (ESIpos): m/z=552/554 [M+H]$^+$ $^1$H-NMR (400 MHz, DMSO-d6) δ [ppm]: 1.685 (12.85), 2.073 (1.34), 2.163 (16.00), 2.518 (0.84), 2.523 (0.61), 2.762 (2.25), 2.803 (2.54), 3.285 (2.17), 3.326 (1.94), 4.000 (0.48), 4.016 (0.55), 4.034 (0.81), 4.049 (0.77), 4.110 (0.87), 4.124 (0.93), 4.143 (0.67), 4.158 (0.63), 4.347 (0.43), 7.287 (2.15), 7.298 (2.17), 7.307 (2.26), 7.318 (2.32), 7.490 (1.13), 7.505 (3.27), 7.511 (2.48), 7.517 (1.62), 7.522 (5.09), 7.530 (2.23), 7.536 (6.91), 7.545 (2.41), 7.552 (1.07), 7.555 (1.18), 7.707 (3.35), 7.712 (3.56), 7.830 (2.30), 7.834 (2.42), 7.839

(1.78), 7.844 (1.60), 7.850 (2.27), 7.853 (2.19), 7.861 (2.59), 7.867 (2.41), 7.933 (4.39), 7.955 (2.76), 8.459 (2.26), 8.463 (2.29), 8.471 (2.29), 8.474 (2.11), 8.678 (0.85), 8.693 (1.78), 8.709 (0.84).

Separation of the Enantiomers:

The title compound (175 mg) was dissolved in 5 ml of isopropanol and separated into the enantiomers by preparative HPLC on a chiral phase (see Examples 85 and 86) [column: YMC Chiralart Amylose SA, 5 μm, 250 mm×30 mm; flow rate: 30 ml/min; detection: 220 nm; temperature: 30° C.; injection: 0.35 ml; mobile phase: 70% heptane/30% isopropanol+0.2% TFA, isocratic, run time 14.5 min].

Example 85

(−)-4-{[(6-Bromo-3-methyl-2-phenylquinolin-4-yl)carbonyl]amino}-3-(3-chloropyridin-2-yl)-3-methylbutanoic Acid (Enantiomer 1)

In the enantiomer separation described in Example 84, the prepurified title compound was obtained as earlier-eluting enantiomer and repurified by preparative HPLC (Method 20). This gave 69 mg (98% purity, ee 99%) of the title compound.

$[\alpha]_D^{20}$=−29.1°, 589 nm, c=0.31 g/100 ml, chloroform

LC-MS (Method 2): $R_t$=1.02 min; MS (ESIpos): m/z=552/554 [M+H]$^+$ $^1$H-NMR (400 MHz, DMSO-d6) δ [ppm]: 0.008 (0.71), 1.686 (13.36), 2.164 (16.00), 2.763 (2.29), 2.804 (2.60), 3.286 (2.29), 3.326 (2.03), 4.001 (0.42), 4.017 (0.49), 4.034 (0.77), 4.050 (0.72), 4.111 (0.77), 4.125 (0.81), 4.144 (0.50), 4.159 (0.44), 7.287 (1.99), 7.298 (2.04), 7.307 (2.11), 7.318 (2.13), 7.491 (1.19), 7.506 (3.51), 7.511 (2.65), 7.524 (5.56), 7.536 (7.08), 7.555 (1.24), 7.709 (3.45), 7.714 (3.66), 7.830 (2.18), 7.834 (2.30), 7.840 (1.74), 7.845 (1.64), 7.850 (2.20), 7.854 (2.11), 7.862 (2.53), 7.868 (2.35), 7.934 (4.34), 7.956 (2.71), 8.460 (2.14), 8.463 (2.18), 8.471 (2.15), 8.475 (2.02), 8.679 (0.93), 8.695 (1.93), 8.710 (0.89).

Example 86

(+)-4-{[(6-Bromo-3-methyl-2-phenylquinolin-4-yl)carbonyl]amino}-3-(3-chloropyridin-2-yl)-3-methylbutanoic Acid (Enantiomer 2)

In the enantiomer separation described in Example 84, the prepurified title compound was obtained as later-eluting enantiomer and repurified by preparative HPLC (Method 20). This gave 73 mg (98% purity, ee 99%) of the title compound.

$[\alpha]_D^{20}$=+30.4°, 589 nm, c=0.34 g/100 ml, chloroform

LC-MS (Method 2): $R_t$=1.02 min; MS (ESIpos): m/z=552/554 [M+H]$^+$ $^1$H-NMR (400 MHz, DMSO-d6) δ [ppm]: 1.687 (13.49), 2.165 (16.00), 2.764 (2.32), 2.804 (2.63), 3.286 (2.32), 3.327 (2.05), 4.002 (0.44), 4.017 (0.51), 4.035 (0.80), 4.050 (0.75), 4.112 (0.80), 4.126 (0.85), 4.145 (0.53), 4.160 (0.46), 7.287 (1.94), 7.299 (2.01), 7.307 (2.08), 7.319 (2.11), 7.492 (1.19), 7.506 (3.59), 7.512 (2.74), 7.525 (5.63), 7.537 (7.08), 7.556 (1.33), 7.710 (3.50), 7.715 (3.73), 7.831 (2.13), 7.834 (2.36), 7.841 (1.75), 7.847 (1.73), 7.850 (2.26), 7.854 (2.20), 7.864 (2.53), 7.869 (2.38), 7.935 (4.31), 7.957 (2.71), 8.460 (2.10), 8.464 (2.24), 8.472 (2.13), 8.475 (2.11), 8.681 (0.95), 8.696 (1.97), 8.711 (0.92).

Example 87

(+/−)-4-{[(6-Bromo-3-methyl-2-phenylquinolin-4-yl)carbonyl]amino}-3-(2-chloro-6-fluorophenyl)butanoic Acid (Racemate)

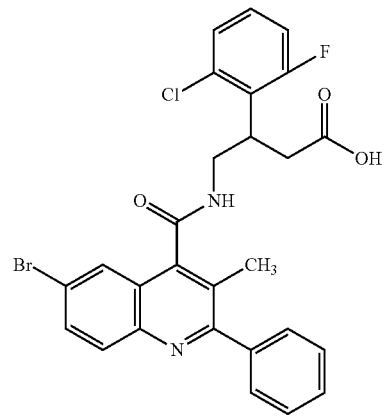 [SMILES: Cc1c(-c2ccccc2)nc2ccc(Br)cc2c1C(=O)NCC(CC(=O)O)c1c(F)cccc1Cl]

TFA (1.4 ml, 21 mmol) was added to a solution of (+/−)-tert-butyl 4-{[(6-bromo-3-methyl-2-phenylquinolin-4-yl)carbonyl]amino}-3-(2-chloro-6-fluorophenyl)butanoate (110 mg, 180 μmol, Example 188A) in dichloromethane (2.9 ml), and the mixture was stirred at RT overnight. The mixture was then concentrated and repeatedly dichloromethane was added and the mixture was concentrated again. The residue was taken up in dichloromethane and purified by preparative HPLC (Method 22). This gave 48 mg (94% purity, 45% of theory) of the title compound.

Separation of the Enantiomers:

The title compound (45 mg) was dissolved in a mixture of 2 ml of isopropanol and 1 ml of heptane and separated into the enantiomers by preparative HPLC on a chiral phase (see Examples 88 and 89) [column: YMC Chiralart Amylose SA, 5 μm, 250 mm×30 mm; flow rate: 30 ml/min; detection: 220 nm; temperature: 35° C.; injection: 1.0 ml; mobile phase: 50% heptane/50% isopropanol+0.2% acetic acid, isocratic, run time 15 min].

LC-MS (Method 1): $R_t$=1.90 min; MS (ESIpos): m/z=555/557 [M+H]$^+$ $^1$H-NMR (600 MHz, DMSO-d6) δ [ppm]: 0.005 (0.97), 2.143 (1.80), 2.614 (0.67), 2.642 (0.71), 2.735 (1.39), 2.747 (1.46), 2.760 (1.05), 2.772 (0.93), 3.715 (1.03), 4.092 (1.28), 7.179 (1.36), 7.189 (1.47), 7.203 (1.20), 7.302 (3.61), 7.476 (0.76), 7.479 (0.91), 7.481 (1.01), 7.484 (1.22), 7.490 (3.37), 7.492 (2.50), 7.496 (3.56), 7.501 (4.86), 7.505 (5.03), 7.506 (5.19), 7.507 (4.18), 7.510 (3.15), 7.515 (3.89), 7.519 (12.20), 7.528 (13.47), 7.530 (16.00), 7.537 (2.27), 7.541 (2.72), 7.545 (1.44), 7.839 (3.12), 7.843 (2.91), 7.854 (4.11), 7.858 (3.81), 7.927 (1.63), 7.930 (8.57), 7.945 (6.15), 9.021 (2.03).

Example 88

(−)-4-{[(6-Bromo-3-methyl-2-phenylquinolin-4-yl)carbonyl]amino}-3-(2-chloro-6-fluorophenyl)butanoic Acid (Enantiomer 1)

Method A:
In the enantiomer separation described in Example 87, the prepurified title compound was obtained as earlier-eluting enantiomer. This gave 17 mg (98% purity, ee 100%) of the title compound.

LC-MS (Method 1): $R_t$=1.91 min; MS (ESIpos): m/z=555 [M+H]$^+$ $^1$H-NMR (400 MHz, DMSO-d6) δ [ppm]: −0.008 (3.47), 0.008 (3.66), 2.154 (5.55), 2.709 (0.71), 2.749 (1.00), 2.799 (1.62), 2.814 (1.64), 2.835 (0.89), 3.314 (3.08), 3.747 (1.19), 3.873 (0.79), 4.109 (1.36), 7.175 (1.30), 7.187 (1.80), 7.199 (1.84), 7.209 (1.55), 7.227 (1.49), 7.318 (5.52), 7.476 (0.85), 7.488 (1.94), 7.491 (2.00), 7.501 (6.32), 7.509 (5.74), 7.521 (16.00), 7.526 (15.04), 7.530 (11.76), 7.534 (9.53), 7.537 (7.36), 7.546 (2.01), 7.837 (3.01), 7.842 (2.69), 7.860 (4.62), 7.865 (4.27), 7.931 (8.32), 7.953 (5.14), 8.940 (1.44), 8.955 (2.61), 8.968 (1.41).

Method B:
TFA (5.1 ml, 66 mmol) was added to a solution of (−)-tert-butyl 4-{[(6-bromo-3-methyl-2-phenylquinolin-4-yl)carbonyl]amino}-3-(2-chloro-6-fluorophenyl)butanoate (1.83 g, 2.99 mmol, Example 189A) in dichloromethane (15 ml), and the mixture was allowed to stand at RT for 4 h. The mixture was then concentrated and repeatedly dichloromethane was added and the mixture was concentrated again. The residue was dissolved in acetonitrile (9 ml) and purified by preparative HPLC (Method 16). This gave 1.55 g (100% purity, ee 99%, 93% of theory) of the title compound.

$[α]_D^{20}$=−40.1°, 589 nm, c=0.48 g/100 ml, methanol

LC-MS (Method 2): $R_t$=1.02 min; MS (ESIpos): m/z=555/557 [M+H]$^+$ $^1$H-NMR (400 MHz, DMSO-d6) δ [ppm]: −0.008 (4.94), 0.008 (2.48), 2.073 (0.51), 2.153 (5.66), 2.327 (0.54), 2.366 (0.42), 2.523 (2.16), 2.669 (0.60), 2.709 (0.68), 2.774 (1.05), 2.804 (2.40), 2.820 (2.36), 2.842 (1.06), 2.859 (0.85), 3.532 (0.98), 3.747 (1.25), 3.877 (0.89), 4.094 (1.31), 4.112 (1.61), 7.178 (1.12), 7.189 (1.95), 7.202 (1.90), 7.211 (1.52), 7.229 (1.52), 7.319 (5.49), 7.477 (1.27), 7.488 (2.48), 7.492 (2.57), 7.502 (6.85), 7.510 (6.25), 7.522 (16.00), 7.526 (14.76), 7.534 (8.66), 7.546 (1.78), 7.839 (3.24), 7.844 (2.82), 7.861 (4.86), 7.866 (4.40), 7.931 (8.73), 7.954 (5.30), 8.928 (1.89), 8.943 (3.44), 8.958 (1.69), 12.223 (0.44).

Example 89

(+)-4-{[(6-Bromo-3-methyl-2-phenylquinolin-4-yl)carbonyl]amino}-3-(2-chloro-6-fluorophenyl)butanoic Acid (Enantiomer 2)

Method A:
In the enantiomer separation described in Example 87, the title compound was obtained as later-eluting enantiomer. This gave 16 mg (98% purity, ee 99%) of the title compound.

LC-MS (Method 1): $R_t$=1.91 min; MS (ESIpos): m/z=555/557 [M+H]$^+$ $^1$H-NMR (400 MHz, DMSO-d6) δ [ppm]: −0.008 (3.94), 0.008 (3.80), 1.234 (0.72), 2.154 (5.67), 2.523 (1.40), 2.669 (0.59), 2.709 (0.81), 2.805 (1.47), 3.312 (3.14), 3.744 (1.07), 3.877 (0.86), 4.108 (1.32), 7.174 (0.95), 7.186 (1.80), 7.199 (1.82), 7.208 (1.52), 7.226 (1.46), 7.317 (5.76), 7.476 (0.85), 7.487 (1.93), 7.491 (2.01), 7.501 (6.44), 7.509 (5.74), 7.521 (16.00), 7.525 (15.01), 7.529 (11.89), 7.533 (9.55), 7.537 (7.67), 7.545 (2.01), 7.837 (3.09), 7.842 (2.90), 7.859 (4.69), 7.864 (4.64), 7.930 (9.07), 7.952 (5.56), 8.962 (2.38).

Method B:
TFA (5.0 ml, 64 mmol) was added to a solution of (+)-tert-butyl 4-{[(6-bromo-3-methyl-2-phenylquinolin-4-yl)carbonyl]amino}-3-(2-chloro-6-fluorophenyl)butanoate (1.79 g, 2.93 mmol, Example 190A) in dichloromethane (15 ml), and the mixture was allowed to stand at RT for 4 h. The mixture was then concentrated and repeatedly dichloromethane was added and the mixture was concentrated again. The residue was dissolved in acetonitrile (9 ml) and purified by preparative HPLC (Method 16). This gave 1.47 g (100% purity, ee 99%, 90% of theory) of the title compound.

$[α]_D^{20}$=+38.0°, 589 nm, c=0.51 g/100 ml, methanol

LC-MS (Method 2): $R_t$=1.02 min; MS (ESIpos): m/z=555/557 [M+H]$^+$ $^1$H-NMR (400 MHz, DMSO-d6) δ [ppm]: 2.065 (0.41), 2.147 (5.69), 2.319 (0.45), 2.661 (0.44), 2.702 (0.53), 2.753 (0.97), 2.797 (2.33), 2.813 (2.38), 2.836 (1.06), 2.852 (0.86), 3.740 (1.43), 3.869 (0.97), 4.086 (1.28), 4.104 (1.61), 5.746 (0.44), 7.170 (1.01), 7.182 (1.87), 7.194 (1.84), 7.204 (1.52), 7.221 (1.56), 7.312 (5.74), 7.469 (0.80), 7.484 (1.96), 7.495 (6.27), 7.502 (5.58), 7.514 (16.00), 7.518 (15.07), 7.526 (9.10), 7.538 (1.91), 7.831 (3.13), 7.836 (2.84), 7.854 (4.76), 7.859 (4.60), 7.924 (8.90), 7.947 (5.47), 8.921 (1.79), 8.936 (3.47), 8.951 (1.73).

Example 90

(+/−)-4-{[(6-Bromo-3-methyl-2-phenylquinolin-4-yl)carbonyl]amino}-3-(4-methylphenyl)butanoic Acid (Racemate)

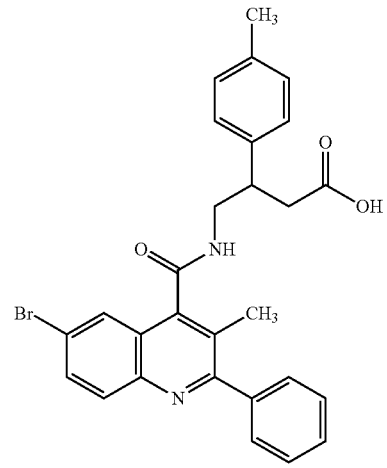 [SMILES: Cc1ccc(C(CNC(=O)c2c(C)c(-c3ccccc3)nc3ccc(Br)cc23)CC(=O)O)cc1]

TFA (1.5 ml, 19 mmol) was added to a solution of (+/−)-tert-butyl 4-{[(6-bromo-3-methyl-2-phenylquinolin-4-yl)carbonyl]amino}-3-(4-methylphenyl)butanoate (110 mg, 192 μmol, Example 191A) in dichloromethane (3.1 ml), and the mixture was stirred at RT for 2 h. The mixture was then concentrated and repeatedly dichloromethane was added and the mixture was concentrated again. The residue was purified by preparative HPLC (Method 22). This gave 98 mg (98% purity, 97% of theory) of the title compound.

LC-MS (Method 1): $R_t$=1.95 min; MS (ESIpos): m/z=517/519 [M+H]$^+$

¹H-NMR (400 MHz, DMSO-d6) δ [ppm]: −0.008 (1.65), 0.008 (1.37), 2.072 (1.21), 2.130 (2.31), 2.259 (16.00), 2.569 (2.41), 2.694 (2.27), 2.708 (2.62), 2.733 (1.79), 2.747 (1.64), 3.354 (1.01), 3.369 (1.50), 3.384 (1.08), 3.588 (1.02), 3.731 (0.99), 3.947 (1.29), 7.115 (5.01), 7.134 (7.42), 7.210 (9.62), 7.230 (6.30), 7.477 (0.60), 7.489 (1.53), 7.492 (1.47), 7.498 (1.78), 7.502 (5.05), 7.511 (4.75), 7.520 (10.92), 7.522 (12.64), 7.527 (11.67), 7.531 (9.46), 7.535 (7.34), 7.539 (5.85), 7.547 (1.72), 7.834 (2.13), 7.839 (2.04), 7.856 (3.30), 7.861 (3.25), 7.929 (7.08), 7.951 (4.47), 8.786 (1.42), 8.800 (2.36), 8.815 (1.44).

Separation of the Enantiomers:

The title compound (70 mg) was dissolved in acetonitrile (2 ml) and ethanol (1 ml) and separated into the enantiomers by preparative HPLC on a chiral phase (see Examples 91 and 92) [column: Daicel Chiralpak IF, 5 μm 250 mm×20 mm; flow rate: 20 ml/min; detection: 220 nm; temperature: 23° C.; injection: 0.08 ml; mobile phase: 70% heptane/30% ethanol+0.2% TFA; isocratic].

Example 91

(+)-4-{[(6-Bromo-3-methyl-2-phenylquinolin-4-yl)carbonyl]amino}-3-(4-methylphenyl)butanoic Acid (Enantiomer 1)

In the enantiomer separation described in Example 90, the title compound was obtained as earlier-eluting enantiomer. This gave 35 mg (98% purity, ee 100%) of the title compound.

$[\alpha]_D^{20}$=+44.9°, 589 nm, c=0.25 g/100 ml, chloroform

LC-MS (Method 1): $R_t$=1.93 min; MS (ESIpos): m/z=517/519 [M+H]⁺

¹H-NMR (400 MHz, DMSO-d6) δ [ppm]: 2.134 (2.36), 2.259 (16.00), 2.569 (2.40), 2.694 (2.27), 2.708 (2.65), 2.734 (1.74), 2.748 (1.62), 2.814 (0.62), 3.354 (0.99), 3.369 (1.51), 3.384 (1.07), 3.589 (0.93), 3.684 (0.89), 3.723 (0.74), 7.115 (4.97), 7.135 (7.41), 7.211 (9.48), 7.231 (6.28), 7.490 (1.38), 7.494 (1.39), 7.499 (1.69), 7.503 (4.96), 7.511 (4.48), 7.523 (12.30), 7.528 (11.39), 7.532 (9.50), 7.536 (7.18), 7.540 (5.79), 7.547 (1.75), 7.835 (2.01), 7.840 (1.94), 7.857 (3.21), 7.863 (3.16), 7.930 (6.63), 7.952 (4.20), 8.787 (1.43), 8.802 (2.41), 8.816 (1.48).

Example 92

(−)-4-{[(6-Bromo-3-methyl-2-phenylquinolin-4-yl)carbonyl]amino}-3-(4-methylphenyl)butanoic Acid (Enantiomer 2)

In the enantiomer separation described in Example 90, the title compound was obtained as later-eluting enantiomer. This gave 32 mg (98% purity, ee 97%) of the title compound.

$[\alpha]_D^{20}$=−39.1°, 589 nm, c=0.27 g/100 ml, chloroform

LC-MS (Method 1): $R_t$=1.93 min; MS (ESIpos): m/z=517/519 [M+H]⁺

¹H-NMR (400 MHz, DMSO-d6) δ [ppm]: −0.008 (0.83), 2.132 (2.34), 2.259 (16.00), 2.569 (2.38), 2.694 (2.21), 2.708 (2.59), 2.733 (1.71), 2.747 (1.62), 3.354 (0.97), 3.368 (1.46), 3.383 (1.04), 3.588 (0.93), 3.683 (0.61), 3.723 (0.76), 7.114 (5.04), 7.134 (7.42), 7.210 (9.44), 7.230 (6.18), 7.489 (1.44), 7.493 (1.47), 7.503 (5.14), 7.511 (4.63), 7.523 (12.42), 7.527 (11.59), 7.531 (9.52), 7.535 (7.23), 7.539 (5.67), 7.547 (1.67), 7.835 (2.11), 7.840 (1.98), 7.857 (3.28), 7.862 (3.18), 7.929 (6.98), 7.952 (4.34), 8.787 (1.42), 8.801 (2.34), 8.815 (1.44).

Example 93

(+/−)-4-{[(6-Bromo-3-methyl-2-phenylquinolin-4-yl)carbonyl]amino}-3-(3-methylphenyl)butanoic Acid (Racemate)

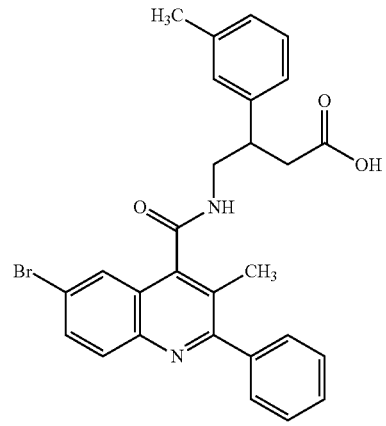 [SMILES: Cc1cccc(C(CNC(=O)c2c(C)c(-c3ccccc3)nc3ccc(Br)cc23)CC(=O)O)c1]

TFA (1.3 ml, 17 mmol) was added to a solution of (+/−)-tert-butyl 4-{[(6-bromo-3-methyl-2-phenylquinolin-4-yl)carbonyl]amino}-3-(3-methylphenyl)butanoate (100 mg, 174 μmol, Example 192A) in dichloromethane (2.8 ml), and the mixture was stirred at RT overnight. The mixture was then concentrated and repeatedly dichloromethane was added and the mixture was concentrated again. The residue was purified by preparative HPLC (Method 22). This gave 90 mg (98% purity, 98% of theory) of the title compound.

LC-MS (Method 1): $R_t$=1.94 min; MS (ESIpos): m/z=517/519 [M+H]⁺

¹H-NMR (400 MHz, DMSO-d6) δ [ppm]: −0.008 (1.53), 0.008 (1.08), 2.073 (0.88), 2.110 (1.56), 2.267 (16.00), 2.572 (1.71), 2.595 (1.70), 2.705 (1.63), 2.719 (1.79), 2.744 (1.20), 2.759 (1.12), 3.356 (0.74), 3.370 (1.19), 3.385 (0.80), 3.393 (0.68), 3.594 (0.83), 3.725 (0.73), 7.025 (1.29), 7.043 (1.52), 7.115 (1.56), 7.138 (4.98), 7.184 (2.01), 7.202 (2.80), 7.221 (1.07), 7.490 (0.94), 7.493 (1.09), 7.503 (3.35), 7.511 (3.25), 7.522 (10.48), 7.525 (9.73), 7.530 (5.87), 7.534 (4.51), 7.537 (3.92), 7.545 (0.98), 7.839 (1.47), 7.844 (1.38), 7.861 (2.28), 7.867 (2.20), 7.932 (4.64), 7.954 (2.89), 8.789 (1.02), 8.804 (1.57), 8.817 (1.00).

Separation of the Enantiomers:

The title compound (70 mg) was dissolved in acetonitrile (1 ml) and ethanol (1 ml) and separated into the enantiomers by preparative HPLC on a chiral phase (see Examples 94 and 95) [column: Daicel Chiralpak IF, 5 μm 250 mm×20 mm; flow rate: 20 ml/min; detection: 220 nm; temperature: 23° C.; injection: 0.05 ml; mobile phase: 70% heptane/30% ethanol+0.2% TFA; isocratic].

Example 94

4-{[(6-Bromo-3-methyl-2-phenylquinolin-4-yl)carbonyl]amino}-3-(3-methylphenyl)butanoic Acid (Enantiomer 1)

In the enantiomer separation described in Example 93, the title compound was obtained as earlier-eluting enantiomer. This gave 13 mg (98% purity, ee 100%) of the title compound.

LC-MS (Method 1): $R_t$=1.93 min; MS (ESIpos): m/z=517/519 [M+H]$^+$ $^1$H-NMR (400 MHz, DMSO-d6) δ [ppm]: 2.109 (1.50), 2.267 (16.00), 2.572 (1.68), 2.595 (1.66), 2.705 (1.59), 2.719 (1.76), 2.745 (1.18), 2.759 (1.11), 3.355 (0.72), 3.370 (1.16), 3.385 (0.79), 3.594 (0.84), 3.724 (0.77), 7.025 (1.25), 7.043 (1.50), 7.115 (1.50), 7.138 (4.89), 7.184 (2.00), 7.202 (2.79), 7.221 (1.06), 7.489 (0.88), 7.492 (1.04), 7.502 (3.30), 7.510 (3.15), 7.521 (10.42), 7.524 (9.62), 7.529 (5.84), 7.533 (4.56), 7.536 (3.97), 7.544 (1.00), 7.837 (1.50), 7.842 (1.40), 7.860 (2.31), 7.865 (2.25), 7.931 (4.75), 7.953 (2.97), 8.787 (0.98), 8.803 (1.52), 8.816 (1.00).

Example 95

4-{[(6-Bromo-3-methyl-2-phenylquinolin-4-yl)carbonyl]amino}-3-(3-methylphenyl)butanoic Acid (Enantiomer 2)

In the enantiomer separation described in Example 93, the title compound was obtained as later-eluting enantiomer. This gave 21 mg (98% purity, ee 98%) of the title compound.

LC-MS (Method 1): $R_t$=1.93 min; MS (ESIpos): m/z=517/519 [M+H]$^+$ $^1$H-NMR (400 MHz, DMSO-d6) δ [ppm]: 2.109 (1.56), 2.268 (16.00), 2.573 (1.67), 2.596 (1.67), 2.705 (1.58), 2.720 (1.76), 2.745 (1.17), 2.759 (1.11), 3.356 (0.73), 3.371 (1.19), 3.385 (0.81), 3.393 (0.69), 3.581 (0.76), 3.595 (0.86), 3.724 (0.78), 3.741 (0.79), 7.025 (1.28), 7.043 (1.55), 7.115 (1.52), 7.138 (5.00), 7.184 (1.98), 7.202 (2.76), 7.221 (1.06), 7.489 (0.87), 7.492 (1.06), 7.502 (3.29), 7.510 (3.10), 7.521 (10.40), 7.524 (10.04), 7.529 (6.10), 7.533 (4.63), 7.536 (4.10), 7.544 (1.01), 7.837 (1.46), 7.843 (1.38), 7.860 (2.24), 7.865 (2.23), 7.931 (4.71), 7.954 (2.93), 8.788 (1.01), 8.803 (1.56), 8.816 (1.01).

Example 96

(+/−)-4-{[(6-Bromo-3-methyl-2-phenylquinolin-4-yl)carbonyl]amino}-3-(2-methoxyphenyl)butanoic Acid (Racemate)

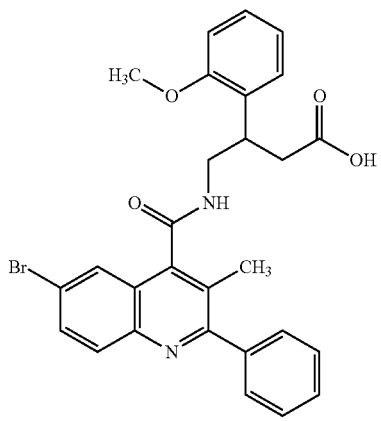 [SMILES: COc1ccccc1C(CNC(=O)c1c(C)c(-c2ccccc2)nc2ccc(Br)cc12)CC(=O)O]

TFA (12 ml, 150 mmol) was added to a solution of (+/−)-tert-butyl 4-{[(6-bromo-3-methyl-2-phenylquinolin-4-yl)carbonyl]amino}-3-(2-methoxyphenyl)butanoate (4.50 g, 7.63 mmol, Example 193A) in dichloromethane (52 ml), and the mixture was stirred at RT overnight. The mixture was then concentrated and repeatedly dichloromethane was added and the mixture was concentrated again. The residue was taken up in dichloromethane and purified by flash column chromatography (100 g silica gel Biotage Snap-Cartridge KP-Sil, cyclohexane/ethyl acetate 8:2, Isolera One). This gave 3.71 g (91% purity, 83% of theory) of the title compound.

LC-MS (Method 1): $R_t$=1.88 min; MS (ESIpos): m/z=533/535 [M+H]$^+$ $^1$H-NMR (400 MHz, DMSO-d6) δ [ppm]: 1.157 (1.09), 1.174 (2.15), 1.192 (1.09), 1.229 (0.95), 1.910 (0.47), 1.988 (4.22), 2.136 (10.90), 2.614 (0.49), 2.632 (0.53), 2.654 (4.30), 2.662 (4.68), 2.673 (5.14), 2.677 (5.09), 2.701 (0.49), 3.171 (16.00), 3.632 (0.75), 3.645 (1.57), 3.660 (1.69), 3.676 (1.97), 3.689 (1.60), 3.714 (1.94), 3.732 (2.38), 3.748 (1.77), 3.765 (0.90), 3.785 (1.99), 3.831 (1.42), 3.849 (0.62), 3.965 (1.62), 4.021 (1.00), 4.039 (1.01), 6.896 (2.08), 6.915 (4.52), 6.933 (2.59), 6.975 (4.42), 6.996 (5.33), 7.196 (2.20), 7.215 (3.50), 7.237 (5.11), 7.256 (3.76), 7.476 (0.67), 7.488 (1.83), 7.501 (6.30), 7.509 (5.32), 7.521 (14.60), 7.526 (14.79), 7.687 (2.41), 7.832 (3.07), 7.837 (2.72), 7.854 (4.66), 7.860 (4.45), 7.928 (8.53), 7.950 (5.31), 8.737 (1.87), 8.751 (3.56), 8.765 (1.87).

Separation of the Enantiomers:

The title compound (705 mg, 100% purity, obtained from another experiment) was dissolved in a mixture of methanol and acetonitrile (25 ml) and separated into the enantiomers by preparative SFC on a chiral phase (see Examples 97 and 98) [column: Daicel Chiralpak AD-H, 5 µm, 250 mm×20 mm; flow rate: 80 ml/min; detection: 210 nm; temperature: 40° C.; injection: 0.50 ml; mobile phase: 70% carbon dioxide/30% isopropanol; isocratic].

Example 97

(−)-4-{[(6-Bromo-3-methyl-2-phenylquinolin-4-yl)carbonyl]amino}-3-(2-methoxyphenyl)butanoic Acid (Enantiomer 1)

In the enantiomer separation described in Example 96, the title compound was obtained as earlier-eluting enantiomer. This gave 269 mg (100% purity, ee 100%) of the title compound.

$[α]_D^{20}$=−16.9°, 589 nm, c=0.35 g/100 ml, methanol

LC-MS (Method 1): $R_t$=1.87 min; MS (ESIpos): m/z=533/535 [M+H]$^+$ $^1$H-NMR (400 MHz, DMSO-d6) δ [ppm]: 1.030 (0.91), 1.045 (0.92), 2.132 (4.61), 2.649 (1.95), 2.657 (2.08), 2.668 (2.36), 2.673 (2.28), 3.640 (0.71), 3.654 (0.75), 3.670 (0.90), 3.709 (0.87), 3.727 (1.06), 3.742 (0.78), 3.779 (0.81), 3.800 (16.00), 3.810 (1.41), 6.893 (0.92), 6.912 (1.98), 6.931 (1.13), 6.974 (1.95), 6.995 (2.36), 7.191 (0.90), 7.195 (0.95), 7.214 (1.50), 7.234 (2.59), 7.252 (1.72), 7.256 (1.33), 7.485 (0.82), 7.489 (0.86), 7.498 (2.75), 7.506 (2.38), 7.518 (6.93), 7.523 (6.62), 7.527 (4.73), 7.531 (3.78), 7.535 (2.89), 7.542 (0.83), 7.680 (0.94), 7.828 (1.30), 7.834 (1.13), 7.850 (2.02), 7.856 (1.84), 7.924 (3.70), 7.946 (2.35), 8.732 (0.81), 8.746 (1.51), 8.760 (0.78), 12.043 (1.22).

Example 98

(+)-4-{[(6-Bromo-3-methyl-2-phenylquinolin-4-yl)carbonyl]amino}-3-(2-methoxyphenyl)butanoic Acid (Enantiomer 2)

In the enantiomer separation described in Example 96, the title compound was obtained as later-eluting enantiomer. This gave 253 mg (100% purity, ee 100%) of the title compound.

[α]$_D^{20}$=+18.1°, 589 nm, c=0.37 g/100 ml, methanol

LC-MS (Method 1): R$_t$=1.87 min; MS (ESIpos): m/z=533/535 [M+H]$^+$ $^1$H-NMR (400 MHz, DMSO-d6) δ [ppm]: 2.073 (1.06), 2.132 (4.23), 2.648 (1.75), 2.657 (1.88), 2.667 (2.13), 2.673 (2.12), 3.670 (0.82), 3.709 (0.79), 3.727 (0.97), 3.800 (16.00), 6.895 (0.85), 6.912 (1.73), 6.914 (1.83), 6.931 (1.02), 6.933 (1.02), 6.976 (1.80), 6.995 (2.17), 7.191 (0.81), 7.195 (0.95), 7.215 (1.42), 7.234 (2.38), 7.237 (1.73), 7.252 (1.59), 7.256 (1.29), 7.485 (0.72), 7.499 (2.50), 7.507 (2.26), 7.519 (6.59), 7.523 (6.36), 7.527 (4.56), 7.531 (3.65), 7.535 (3.04), 7.543 (0.82), 7.680 (0.87), 7.828 (1.33), 7.834 (1.18), 7.851 (2.04), 7.856 (1.96), 7.924 (3.80), 7.946 (2.41), 8.748 (1.34), 12.046 (0.84).

Example 99

(+/−)-4-{[(6-Bromo-3-methyl-2-phenylquinolin-4-yl)carbonyl]amino}-3-[2-(trifluoromethoxy)phenyl] butanoic Acid (Racemate)

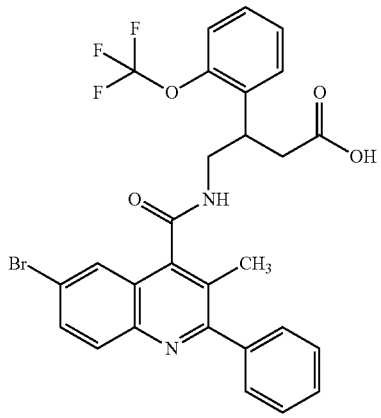 [SMILES: Cc1c(-c2ccccc2)nc2ccc(Br)cc2c1C(=O)NCC(CC(=O)O)c1ccccc1OC(F)(F)F]

TFA (820 µl, 11 mmol) was added to a solution of (+/−)-tert-butyl 4-{[(6-bromo-3-methyl-2-phenylquinolin-4-yl)carbonyl]amino}-3-[2-(trifluoromethoxy)phenyl]butanoate (350 mg, 98% purity, 533 µmol, Example 194A) in dichloromethane (3.8 ml), and the mixture was stirred at RT overnight. The mixture was then concentrated and repeatedly dichloromethane was added and the mixture was concentrated again. The residue was purified by preparative HPLC (Method 16). This gave 241 mg (98% purity, 75% of theory) of the title compound.

LC-MS (Method 2): R$_t$=1.06 min; MS (ESIpos): m/z=587/589 [M+H]$^+$ $^1$H-NMR (400 MHz, DMSO-d6) δ [ppm]: 2.126 (4.63), 2.328 (0.57), 2.585 (1.54), 2.604 (1.66), 2.625 (2.64), 2.643 (2.55), 2.669 (0.52), 2.747 (2.51), 2.762 (2.75), 2.787 (1.77), 2.802 (1.67), 3.643 (1.24), 3.658 (2.05), 3.671 (1.64), 3.808 (4.26), 7.343 (3.31), 7.378 (6.65), 7.387 (5.79), 7.393 (5.65), 7.402 (4.92), 7.477 (0.91), 7.489 (2.29), 7.503 (7.37), 7.510 (6.29), 7.522 (16.00), 7.529 (15.33), 7.589 (3.82), 7.598 (3.69), 7.603 (3.76), 7.612 (3.40), 7.836 (3.22), 7.841 (3.02), 7.858 (4.95), 7.863 (4.80), 7.932 (9.52), 7.955 (5.98), 8.870 (3.68), 8.884 (1.99).

Separation of the Enantiomers:

The title compound (210 mg) was dissolved in ethanol (5 ml) and separated into the enantiomers by preparative HPLC on a chiral phase (see Examples 100 and 101) [column: Daicel Chiralcel OX-H, 5 µm, 250 mm×20 mm; flow rate: 15 ml/min; detection: 220 nm; temperature: 30° C.; injection: 0.15 ml; mobile phase: 85% heptane/15% ethanol; run time 11 min, isocratic]. The later-eluting enantiomer was repurified once more under the same conditions. The combined target fractions were each concentrated, and the residue was then lyophilized.

Example 100

(−)-4-{[(6-Bromo-3-methyl-2-phenylquinolin-4-yl) carbonyl]amino}-3-[2-(trifluoromethoxy)phenyl] butanoic Acid (Enantiomer 1)

In the enantiomer separation described in Example 99, the title compound was obtained as earlier-eluting enantiomer. This gave 87 mg (98% purity, ee 99%) of the title compound.

[α]$_D^{20}$=−20.0°, 589 nm, c=0.25 g/100 ml, methanol

LC-MS (Method 2): R$_t$=1.08 min; MS (ESIpos): m/z=587/589 [M+H]$^+$ $^1$H-NMR (400 MHz, DMSO-d6) δ [ppm]: −0.008 (1.23), 0.008 (1.04), 2.125 (4.52), 2.327 (0.45), 2.523 (1.23), 2.585 (1.75), 2.603 (1.88), 2.625 (2.85), 2.643 (2.74), 2.669 (0.49), 2.689 (3.20), 2.731 (3.78), 2.746 (2.66), 2.762 (2.95), 2.786 (1.95), 2.802 (1.83), 2.890 (4.64), 3.642 (1.26), 3.657 (2.09), 3.672 (1.71), 3.695 (0.78), 3.807 (4.36), 7.323 (1.73), 7.332 (2.60), 7.338 (2.78), 7.343 (3.32), 7.347 (2.98), 7.378 (6.83), 7.387 (5.84), 7.393 (5.69), 7.402 (5.04), 7.478 (0.93), 7.489 (2.33), 7.503 (7.47), 7.511 (6.32), 7.522 (16.00), 7.529 (15.26), 7.548 (2.47), 7.589 (3.95), 7.598 (3.72), 7.603 (3.77), 7.612 (3.43), 7.836 (3.30), 7.842 (3.04), 7.859 (5.11), 7.864 (4.91), 7.933 (9.89), 7.955 (6.62), 8.857 (1.92), 8.870 (3.75), 8.884 (1.99).

Example 101

(+)-4-{[(6-Bromo-3-methyl-2-phenylquinolin-4-yl) carbonyl]amino}-3-[2-(trifluoromethoxy)phenyl] butanoic Acid (Enantiomer 2)

In the enantiomer separation described in Example 99, 82 mg (98% purity, ee 98%) of the title compound were obtained as the enantiomer that eluted later.

[α]$_D^{20}$=+22.8°, 589 nm, c=0.35 g/100 ml, methanol

LC-MS (Method 2): R$_t$=1.08 min; MS (ESIpos): m/z=587/589 [M+H]$^+$ $^1$H-NMR (400 MHz, DMSO-d6) δ [ppm]: −0.008 (1.25), 0.008 (1.39), 1.161 (0.66), 1.177 (0.65), 1.244 (1.05), 1.259 (1.29), 1.275 (0.74), 2.127 (4.52), 2.328 (0.47), 2.564 (0.42), 2.586 (1.73), 2.604 (1.83), 2.626 (2.78), 2.644 (2.70), 2.670 (0.56), 2.690 (4.00), 2.731 (5.60), 2.748 (2.62), 2.763 (2.89), 2.788 (1.91), 2.803 (1.76), 2.890 (6.54), 3.643 (1.24), 3.659 (2.02), 3.673 (1.64), 7.323 (1.84), 7.339 (2.89), 7.343 (3.48), 7.347 (3.09), 7.379 (6.99), 7.387 (5.95), 7.394 (5.83), 7.402 (5.10), 7.478 (1.00), 7.490 (2.52), 7.504 (7.67), 7.511 (6.72), 7.524 (16.00), 7.530 (15.63), 7.533 (14.30), 7.537 (10.49), 7.541 (8.03), 7.549 (2.55), 7.589 (3.94), 7.599 (3.70), 7.604 (3.78), 7.613 (3.42), 7.837 (3.50), 7.843 (3.23), 7.860 (5.31), 7.865 (5.18), 7.934 (10.61), 7.956 (7.03), 8.872 (3.62), 8.886 (1.92).

Example 102

(+/−)-4-{[(6-Bromo-3-methyl-2-phenylquinolin-4-yl)carbonyl]amino}-3-(pyridin-2-yl)butanoic Acid (Racemate)

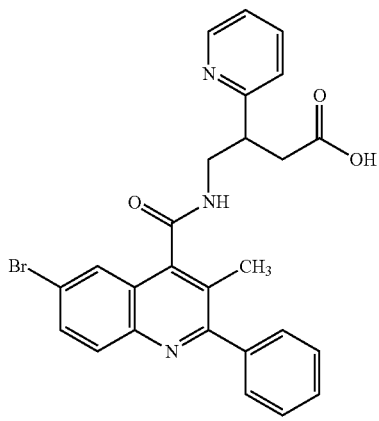 [SMILES: Cc1c(-c2ccccc2)nc2ccc(Br)cc2c1C(=O)NCC(CC(=O)O)c1ccccn1]

TFA (8.2 ml, 110 mmol) was added to a solution of (+/−)-tert-butyl 4-{[(6-bromo-3-methyl-2-phenylquinolin-4-yl)carbonyl]amino}-3-(pyridin-2-yl)butanoate (600 mg, 1.07 mmol, Example 195A) in dichloromethane (17 ml), and the mixture was stirred at RT for 16 h. The mixture was then concentrated and repeatedly dichloromethane was added and the mixture was concentrated again. The residue was purified by preparative HPLC (Method 22). This gave 90 mg (428 mg, 98% purity, 78% of theory) of the title compound.

LC-MS (Method 2): $R_t$=0.80 min; MS (ESIneg): m/z=504/506 [M+H]$^+$ $^1$H-NMR (400 MHz, DMSO-d6) δ [ppm]: −0.008 (2.12), 0.008 (1.81), 2.073 (0.81), 2.130 (5.34), 2.812 (0.58), 2.826 (0.71), 2.854 (2.56), 2.870 (3.13), 2.896 (2.33), 2.916 (0.60), 2.938 (0.66), 3.733 (1.84), 3.746 (1.91), 3.759 (0.84), 3.856 (0.67), 3.881 (1.38), 3.895 (1.37), 3.909 (0.97), 7.481 (0.70), 7.493 (1.88), 7.497 (2.00), 7.502 (2.63), 7.506 (6.48), 7.515 (5.92), 7.523 (15.59), 7.525 (16.00), 7.529 (15.81), 7.533 (11.80), 7.537 (7.95), 7.541 (6.53), 7.549 (2.08), 7.554 (1.06), 7.598 (1.98), 7.750 (1.84), 7.845 (3.15), 7.851 (2.83), 7.868 (4.80), 7.873 (4.55), 7.940 (9.37), 7.962 (5.85), 8.140 (1.50), 8.727 (2.88), 8.740 (2.68), 8.896 (1.70), 8.909 (2.72).

Separation of the Enantiomers:

The title compound (400 mg) was dissolved in methanol (33 ml) and separated into the enantiomers by preparative SFC on a chiral phase (see Examples 103 and 104) [column: Daicel Chiralpak AD, 5 μm 250 mm×20 mm; flow rate: 80 ml/min; detection: 210 nm; temperature: 40° C.; injection: 0.50 ml; mobile phase: 78% carbon dioxide/22% isopropanol; isocratic].

Example 103

(−)-4-{[(6-Bromo-3-methyl-2-phenylquinolin-4-yl)carbonyl]amino}-3-(pyridin-2-yl)butanoic Acid (Enantiomer 1)

In the enantiomer separation described in Example 102, the title compound was obtained as earlier-eluting enantiomer. This gave 116 mg (98% purity, ee 100%) of the title compound.

$[α]_D^{20}$=−26.1°, 589 nm, c=0.38 g/100 ml, methanol

LC-MS (Method 2): $R_t$=0.80 min; MS (ESIneg): m/z=504/506 [M+H]$^+$ $^1$H-NMR (400 MHz, DMSO-d6) δ [ppm]: −0.008 (1.17), 0.008 (1.18), 2.073 (0.99), 2.129 (4.97), 2.524 (1.11), 2.809 (0.67), 2.822 (0.84), 2.851 (2.87), 2.864 (3.16), 2.871 (3.04), 2.893 (2.57), 2.913 (0.72), 2.935 (0.80), 3.185 (2.38), 3.698 (2.11), 3.709 (2.99), 3.730 (1.89), 3.743 (2.02), 3.756 (0.91), 3.878 (1.35), 3.892 (1.30), 3.907 (1.00), 3.928 (0.48), 7.483 (0.61), 7.493 (1.72), 7.496 (1.89), 7.507 (6.03), 7.514 (5.84), 7.525 (16.00), 7.529 (15.78), 7.532 (11.69), 7.536 (7.83), 7.541 (6.61), 7.548 (2.10), 7.590 (1.92), 7.737 (1.76), 7.757 (1.84), 7.846 (3.09), 7.851 (2.89), 7.868 (4.74), 7.873 (4.67), 7.939 (9.18), 7.962 (5.68), 8.131 (1.56), 8.723 (2.98), 8.736 (2.90), 8.892 (1.71), 8.905 (2.63).

Example 104

(+)-4-{[(6-Bromo-3-methyl-2-phenylquinolin-4-yl)carbonyl]amino}-3-(pyridin-2-yl)butanoic Acid (Enantiomer 2)

In the enantiomer separation described in Example 102, the title compound was obtained as later-eluting enantiomer. This gave 122 mg (98% purity, ee 95%) of the title compound.

$[α]_D^{20}$=+23.1°, 589 nm, c=0.33 g/100 ml, methanol

LC-MS (Method 2): $R_t$=0.80 min; MS (ESIneg): m/z=504/506 [M+H]$^+$ $^1$H-NMR (400 MHz, DMSO-d6) δ [ppm]: −0.008 (1.06), 0.008 (1.29), 2.073 (0.85), 2.130 (4.93), 2.329 (0.40), 2.812 (0.71), 2.826 (0.83), 2.855 (2.89), 2.868 (3.23), 2.874 (3.13), 2.896 (2.56), 2.916 (0.72), 2.938 (0.77), 3.713 (3.01), 3.733 (1.91), 3.746 (2.07), 3.759 (0.91), 3.880 (1.32), 3.895 (1.32), 3.909 (0.97), 7.483 (0.78), 7.497 (2.06), 7.507 (6.21), 7.515 (6.03), 7.525 (16.00), 7.529 (15.65), 7.537 (7.59), 7.541 (6.26), 7.599 (1.99), 7.748 (1.90), 7.768 (1.91), 7.846 (3.11), 7.851 (2.82), 7.868 (4.67), 7.874 (4.50), 7.940 (9.06), 7.962 (5.53), 8.143 (1.66), 8.729 (3.09), 8.740 (2.92), 8.895 (1.76), 8.909 (2.62).

Example 105

(+/−)-4-{[(6-Bromo-3-methyl-2-phenylquinolin-4-yl)carbonyl]amino}-3-[2-(trifluoromethyl)phenyl]butanoic Acid (Racemate)

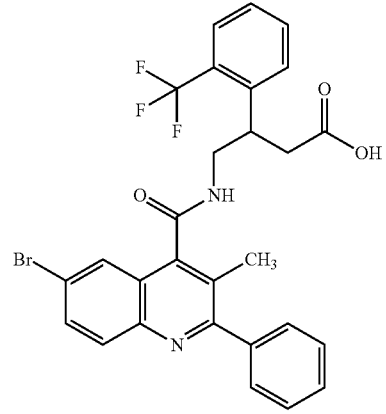 [SMILES: Cc1c(-c2ccccc2)nc2ccc(Br)cc2c1C(=O)NCC(CC(=O)O)c1ccccc1C(F)(F)F]

TFA (2.5 ml, 32 mmol) was added to a solution of (+/−)-tert-butyl 4-{[(6-bromo-3-methyl-2-phenylquinolin- 4-yl)carbonyl]amino}-3-[2-(trifluoromethyl)phenyl]butanoate (1.00 g, 1.59 mmol, Example 196A) in dichloromethane (15 ml), and the mixture was stirred at RT overnight. The mixture was then concentrated and repeatedly, in succession, dichloromethane was added and the mixture was concentrated again. The residue was purified by preparative HPLC (Method 20). The combined target fractions were concentrated and the residue was dried under reduced pressure. This gave 845 mg (98% purity, 91% of theory) of the title compound.

LC-MS (Method 1): $R_t$=1.99 min; MS (ESIpos): m/z=571/573 [M+H]$^+$ $^1$H-NMR (400 MHz, DMSO-d6) δ [ppm]: −0.008 (2.60), 0.008 (2.44), 2.112 (4.45), 2.328 (0.57), 2.606 (1.73), 2.622 (1.84), 2.646 (3.08), 2.662 (3.07), 2.737 (2.87), 2.755 (3.03), 2.777 (1.83), 2.795 (1.75), 3.715 (1.38), 3.787 (1.81), 3.804 (2.48), 3.819 (1.89), 3.898 (1.74), 7.448 (1.64), 7.468 (3.75), 7.487 (4.29), 7.501 (7.41), 7.508 (6.42), 7.520 (16.00), 7.526 (15.35), 7.668 (1.84), 7.686 (3.59), 7.712 (4.92), 7.732 (3.88), 7.776 (3.72), 7.796 (2.64), 7.826 (3.45), 7.832 (3.21), 7.849 (5.09), 7.854 (5.02), 7.926 (9.89), 7.948 (6.33), 8.856 (1.93), 8.871 (3.79), 8.885 (1.87).

$^1$H-NMR (400 MHz, DMSO-d6): δ [ppm]=12.20 (br. s, 1H), 8.87 (t, 2H), 7.93 (d, 1H), 7.84 (dd, 1H), 7.79 (d, 1H), 7.75-7.56 (m, 3H), 7.56-7.44 (m, 6H), 3.93-3.85 (br. m, 1H), 3.84-3.76 (m, 1H), 3.75-3.65 (br. m, 1H), 2.76 (dd, 1H), 2.64 (dd, 1H), 2.11 (br. s, 3H).

Separation of the Enantiomers:

The title compound (750 mg) was dissolved in a 1:1 mixture of acetonitrile and methanol (60 ml) and separated into the enantiomers by preparative SFC on a chiral phase (see Examples 106 and 107) [column: Chiralpak AD-H, 5 μm, 250 mm×30 mm; flow rate: 100 ml/min; detection: 210 nm; temperature: 38° C.; injection: 2.2 ml; mobile phase: 75% carbon dioxide/25% ethanol; run time 15.5 min, isocratic].

Example 106

(+)-4-{[(6-Bromo-3-methyl-2-phenylquinolin-4-yl)carbonyl]amino}-3-[2-(trifluoromethyl)phenyl]butanoic Acid (Enantiomer 1)

In the enantiomer separation described in Example 105, 363 mg (98% purity, ee 100%) of the title compound were obtained as the enantiomer that eluted earlier.

[α]$_D^{20}$=+31.6°, 589 nm, c=0.47 g/100 ml, methanol Residual ethanol was then removed by lyophilization.

LC-MS (Method 1): $R_t$=2.00 min; MS (ESIpos): m/z=571/573 [M+H]$^+$ $^1$H-NMR (400 MHz, DMSO-d6) δ [ppm]: −0.008 (1.38), 0.008 (1.00), 1.234 (0.45), 2.113 (4.47), 2.328 (0.49), 2.607 (1.66), 2.623 (1.82), 2.646 (2.93), 2.663 (2.93), 2.710 (0.52), 2.737 (2.83), 2.755 (2.99), 2.777 (1.82), 2.795 (1.69), 3.710 (1.21), 3.786 (1.68), 3.803 (2.20), 3.819 (1.64), 3.883 (1.19), 7.449 (1.73), 7.469 (3.93), 7.487 (4.52), 7.500 (7.72), 7.508 (6.99), 7.520 (16.00), 7.526 (15.16), 7.533 (10.45), 7.545 (2.74), 7.668 (1.89), 7.687 (3.63), 7.713 (4.86), 7.733 (3.86), 7.776 (3.76), 7.796 (2.57), 7.825 (3.46), 7.830 (3.27), 7.847 (5.01), 7.853 (4.91), 7.925 (9.61), 7.948 (6.13), 8.856 (2.04), 8.871 (3.74), 8.885 (1.85), 12.218 (3.06).

$^1$H-NMR (400 MHz, DMSO-d6): δ [ppm]=12.22 (br. s, 1H), 8.87 (t, 1H), 7.93 (d, 1H), 7.84 (dd, 1H), 7.79 (d, 1H), 7.75-7.56 (m, 3H), 7.56-7.43 (m, 6H), 3.95-3.85 (br. m, 1H), 3.85-3.76 (m, 1H), 3.75-3.65 (br. m, 1H), 2.76 (dd, 1H), 2.64 (dd, 1H), 2.11 (br. s, 3H).

Example 107

(−)-4-{[(6-Bromo-3-methyl-2-phenylquinolin-4-yl)carbonyl]amino}-3-[2-(trifluoromethyl)phenyl]butanoic Acid (Enantiomer 2)

In the enantiomer separation described in Example 105, 357 mg (98% purity, ee 99%) of the title compound were obtained as the enantiomer that eluted later.

[α]$_D^{20}$=−27.3°, 589 nm, c=0.46 g/100 ml, methanol Residual ethanol was then removed by lyophilization.

LC-MS (Method 1): $R_t$=2.00 min; MS (ESIpos): m/z=571/573 [M+H]$^+$ $^1$H-NMR (400 MHz, DMSO-d6) δ [ppm]: −0.149 (0.67), −0.008 (7.44), 0.008 (5.88), 0.146 (0.72), 1.234 (0.59), 2.113 (4.41), 2.327 (0.78), 2.602 (1.69), 2.618 (1.67), 2.642 (2.92), 2.658 (2.90), 2.669 (1.08), 2.734 (2.79), 2.752 (2.96), 2.774 (1.85), 2.792 (1.75), 3.714 (1.21), 3.783 (1.64), 3.801 (2.17), 3.818 (1.64), 3.881 (1.16), 7.449 (1.66), 7.467 (3.70), 7.486 (4.16), 7.500 (7.27), 7.508 (6.39), 7.520 (16.00), 7.525 (15.08), 7.533 (10.41), 7.545 (2.74), 7.667 (1.78), 7.686 (3.55), 7.712 (4.86), 7.732 (3.84), 7.774 (3.71), 7.794 (2.60), 7.825 (3.38), 7.830 (3.12), 7.847 (5.02), 7.852 (4.86), 7.924 (9.40), 7.947 (6.02), 8.867 (1.72), 8.882 (3.06), 12.220 (0.72).

$^1$H-NMR (400 MHz, DMSO-d6): δ [ppm]=12.22 (br. s, 1H), 8.88 (t, 1H), 7.93 (d, 1H), 7.84 (dd, 1H), 7.78 (d, 1H), 7.76-7.58 (m, 3H), 7.56-7.43 (m, 6H), 3.95-3.85 (br. m, 1H), 3.84-3.76 (m, 1H), 3.75-3.64 (br. m, 1H), 2.76 (dd, 1H), 2.64 (dd, 1H), 2.11 (br. s, 3H).

Example 108

(+/−)-4-{[(6-Bromo-3-methyl-2-phenylquinolin-4-yl)carbonyl]amino}-3-(3-methoxypyridin-2-yl)butanoic Acid (Racemate)

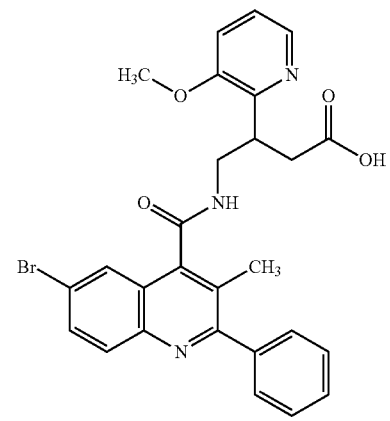 [SMILES: COc1cccnc1C(CNC(=O)c1c(C)c(-c2ccccc2)nc2ccc(Br)cc12)CC(=O)O]

TFA (22 ml, 290 mmol) was added to a solution of (+/−)-tert-butyl 4-{[(6-bromo-3-methyl-2-phenylquinolin-4-yl)carbonyl]amino}-3-(3-methoxypyridin-2-yl)butanoate (1.70 g, 2.88 mmol, Example 197A) in dichloromethane (47 ml), and the mixture was stirred at RT overnight. The mixture was then concentrated and repeatedly, in succession, dichloromethane was added and the mixture was concentrated again. The residue was purified by preparative HPLC (Method 22). This gave 1.28 g (98% purity, 82% of theory) of the title compound.

LC-MS (Method 1): $R_t$=1.61 min; MS (ESIpos): m/z=534/536 [M+H]$^+$ $^1$H-NMR (400 MHz, DMSO-d6) δ [ppm]: −0.008 (0.96), 0.008 (0.66), 2.189 (16.00), 2.607 (1.12), 2.622 (1.19), 2.648 (1.52), 2.662 (1.44), 2.880 (1.29), 2.902 (1.37), 2.921 (1.06), 2.942 (1.03), 3.170 (1.45), 3.342 (0.58), 3.709 (1.46), 3.722 (1.52), 3.957 (0.99), 3.972 (1.05), 3.978 (1.07), 3.994 (0.83), 7.224 (1.46), 7.236 (1.54), 7.245 (1.83), 7.257 (1.81), 7.384 (2.13), 7.403 (1.63), 7.477 (0.46), 7.489 (1.34), 7.504 (3.55), 7.510 (2.87), 7.522 (5.70), 7.536 (6.77), 7.553 (1.24), 7.763 (2.16), 7.836 (1.69), 7.842 (1.42), 7.858 (2.54), 7.864 (2.29), 7.930 (4.36), 7.952 (2.72), 8.116 (2.25), 8.119 (2.29), 8.128 (2.22), 8.130 (2.07), 8.730 (0.98), 8.745 (1.93), 8.760 (0.89), 11.987 (0.59).

Separation of the Enantiomers:

The title compound (1.20 g) was dissolved in 45 ml of a hot mixture of ethanol, heptane and dichloromethane and separated into the enantiomers by preparative HPLC on a chiral phase (see Examples 109 and 110) [column: YMC Chiralart Amylose SA, 5 μm, 250 mm×30 mm; flow rate: 50 ml/min; detection: 210 nm; temperature: 40° C.; injection: 0.60 ml; mobile phase: 60% heptane/40% isopropanol, isocratic; run time 7 min].

Example 109

(−)-4-{[(6-Bromo-3-methyl-2-phenylquinolin-4-yl)carbonyl]amino}-3-(3-methoxypyridin-2-yl)butanoic Acid (Enantiomer 1)

In the enantiomer separation described in Example 108, 526 mg (98% purity, ee 99%) of the title compound were obtained as the enantiomer that eluted earlier.

$[α]_D^{20}$=−14.7°, 589 nm, c=0.50 g/100 ml, chloroform

LC-MS (Method 1): $R_t$=1.60 min; MS (ESIpos): m/z=534/536 [M+H]$^+$ $^1$H-NMR (400 MHz, DMSO-d6) δ [ppm]: 1.031 (2.09), 1.047 (2.10), 2.191 (16.00), 2.606 (1.02), 2.621 (1.09), 2.647 (1.39), 2.661 (1.35), 2.881 (1.17), 2.903 (1.24), 2.921 (0.95), 2.943 (0.95), 3.709 (1.37), 3.723 (1.44), 3.758 (0.43), 3.958 (0.90), 3.973 (1.01), 3.979 (1.04), 3.995 (0.80), 7.219 (1.72), 7.231 (1.77), 7.240 (2.16), 7.252 (2.17), 7.378 (2.43), 7.397 (1.90), 7.489 (1.26), 7.504 (3.55), 7.510 (2.76), 7.523 (5.77), 7.536 (7.05), 7.554 (1.26), 7.765 (2.40), 7.836 (1.75), 7.841 (1.43), 7.858 (2.63), 7.864 (2.36), 7.930 (4.63), 7.952 (2.85), 8.114 (2.39), 8.117 (2.44), 8.126 (2.44), 8.129 (2.34), 8.142 (1.51), 8.731 (0.91), 8.745 (1.87), 8.760 (0.87).

Example 110

(+)-4-{[(6-Bromo-3-methyl-2-phenylquinolin-4-yl)carbonyl]amino}-3-(3-methoxypyridin-2-yl)butanoic Acid (Enantiomer 2)

The enantiomer separation described in Example 108 gave the prepurified title compound (90% purity, ee 98%).

$[α]_D^{20}$=+12.3°, 589 nm, c=0.49 g/100 ml, chloroform

The prepurified title compound was then repurified twice by preparative HPLC (Method 20) and once by preparative HPLC [column: XBridge C18, 5 μm, 100 mm×30 mm; flow rate: 80 ml/min; detection: 210 nm; temperature: 40° C.; injection: 0.25 ml; mobile phase: 85% water/5% (acetonitrile/water 8:2)+2% ammonia solution/5% acetonitrile→75% water/5% (acetonitrile/water 8:2)+2% ammonia solution/20% acetonitrile; run time 5 min]. This gave 240 mg (98% purity) of the title compound.

LC-MS (Method 2): $R_t$=0.84 min; MS (ESIpos): m/z=534/536 [M+H]$^+$ $^1$H-NMR (400 MHz, DMSO-d6) δ [ppm]: 1.754 (7.46), 2.189 (16.00), 2.577 (1.13), 2.592 (1.16), 2.617 (1.47), 2.632 (1.42), 2.836 (1.15), 2.856 (1.20), 2.876 (0.95), 2.897 (0.95), 3.308 (0.85), 3.711 (1.82), 3.947 (1.03), 3.968 (1.21), 3.983 (0.92), 7.215 (1.70), 7.227 (1.79), 7.236 (2.21), 7.248 (2.22), 7.373 (2.57), 7.393 (1.96), 7.488 (1.23), 7.503 (3.63), 7.509 (2.81), 7.522 (5.99), 7.535 (7.46), 7.552 (1.37), 7.761 (2.46), 7.834 (1.63), 7.839 (1.40), 7.857 (2.52), 7.862 (2.31), 7.928 (4.44), 7.950 (2.72), 8.113 (2.53), 8.123 (2.44), 8.804 (1.24).

Example 111

(+/−)-4-{[(6-Bromo-3-methyl-2-phenylquinolin-4-yl)carbonyl]amino}-3-(2-chlorophenyl)-2,2-dimethylbutanoic Acid (Racemate)

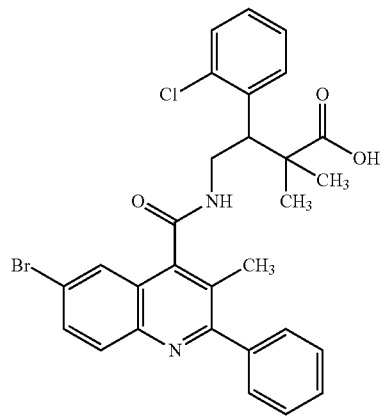 [SMILES: Cc1c(-c2ccccc2)nc2ccc(Br)cc2c1C(=O)NCC(c1ccccc1Cl)C(C)(C)C(=O)O]

TFA (5 ml, 64.9 mmol) was added to a solution of (+/−)-tert-butyl 4-{[(6-bromo-3-methyl-2-phenylquinolin-4-yl)carbonyl]amino}-3-(2-chlorophenyl)-2,2-dimethylbutanoate (330 mg, 531 μmol, Example 198A) in dichloromethane (10 ml), and the mixture was stirred at RT overnight. The mixture was then concentrated and twice, in succession, dichloromethane was added and the mixture was concentrated again. The residue was purified by preparative HPLC (Method: Chromatorex C18, 10 μm, 125×30 mm, acetonitrile/water gradient with 0.01% TFA). This gave 248 mg (99% purity, 82% of theory) of the title compound.

LC-MS (Method 7): $R_t$=1.45 min; MS (ESIpos): m/z=565/567 [M+H]$^+$ $^1$H-NMR (400 MHz, DMSO-d6) δ [ppm]: −0.008 (2.38), 0.008 (2.15), 1.099 (16.00), 1.115 (15.35), 1.919 (0.56), 2.073 (0.42), 2.327 (0.79), 2.366 (0.42), 2.523 (2.16), 2.670 (0.71), 3.661 (1.15), 3.936 (1.92), 4.098 (4.62), 7.270 (1.11), 7.365 (1.10), 7.433 (3.27), 7.453 (3.05), 7.486 (13.79), 7.491 (13.00), 7.504 (3.35), 7.524 (2.60), 7.545 (1.69), 7.798 (1.45), 7.821 (2.24), 7.888 (4.91), 7.911 (2.96), 8.696 (1.97).

1H-NMR (400 MHz, DMSO-d6): δ [ppm]=12.55 (br. s, 1H), 8.75-8.62 (m, 1H), 7.90 (d, 1H), 7.81 (dd, 1H), 7.72-7.18 (m, 10H), 4.14-4.03 (m, 2H, partially obscured), 3.71-3.62 (m, 1H, partially obscured), 1.92 (br. s, 3H), 1.12 (s, 3H), 1.10 (s, 3H).

Separation of the Enantiomers:

The title compound (212 mg) was dissolved in 25 ml of a mixture of methanol and acetonitrile and separated into the

Example 112

4-{[(6-Bromo-3-methyl-2-phenylquinolin-4-yl)carbonyl]amino}-3-(2-chlorophenyl)-2,2-dimethylbutanoic Acid (Enantiomer 1)

In the enantiomer separation described in Example 111, 80 mg (99% purity, ee 100%) of the title compound were obtained as the enantiomer that eluted earlier.

LC-MS (Method 2): $R_t$=1.12 min; MS (ESIpos): m/z=565/567 [M+H]$^+$ $^1$H-NMR (400 MHz, DMSO-d6) δ [ppm]: −0.008 (2.87), 0.008 (3.23), 1.099 (16.00), 1.115 (15.49), 1.937 (0.56), 2.327 (0.54), 2.366 (0.44), 2.523 (1.74), 2.670 (0.55), 2.710 (0.43), 3.663 (0.94), 4.098 (4.16), 7.272 (1.12), 7.366 (1.14), 7.433 (3.29), 7.453 (3.08), 7.485 (14.05), 7.491 (13.77), 7.503 (4.00), 7.515 (1.29), 7.527 (2.52), 7.545 (1.78), 7.797 (1.48), 7.819 (2.29), 7.887 (4.96), 7.909 (3.06), 8.695 (2.05), 12.562 (3.44).

$^1$H-NMR (400 MHz, DMSO-d6): δ [ppm]=12.56 (s, 1H), 8.73-8.64 (m, 1H), 7.90 (d, 1H), 7.81 (dd, 1H), 7.57-7.22 (m, 10H), 4.14-4.06 (m, 2H), 3.71-3.62 (m, 1H), 1.94 (br. s, 3H), 1.11 (s, 3H), 1.10 (s, 3H).

Example 113

4-{[(6-Bromo-3-methyl-2-phenylquinolin-4-yl)carbonyl]amino}-3-(2-chlorophenyl)-2,2-dimethylbutanoic Acid (Enantiomer 2)

In the enantiomer separation described in Example 111, 81 mg (99% purity, ee 99%) of the title compound were obtained as the enantiomer that eluted later.

LC-MS (Method 2): $R_t$=1.12 min; MS (ESIpos): m/z=565/567 [M+H]$^+$ $^1$H-NMR (400 MHz, DMSO-d6) δ [ppm]: −0.008 (2.88), 0.008 (2.30), 1.099 (16.00), 1.114 (15.33), 1.939 (0.59), 2.073 (0.45), 2.327 (0.48), 2.523 (1.54), 2.670 (0.41), 3.662 (0.94), 4.098 (4.20), 7.271 (1.12), 7.364 (1.11), 7.433 (3.21), 7.455 (2.99), 7.486 (14.01), 7.491 (13.51), 7.503 (4.03), 7.515 (1.35), 7.527 (2.61), 7.546 (1.84), 7.797 (1.44), 7.819 (2.27), 7.823 (2.23), 7.887 (4.73), 7.909 (2.96), 8.698 (1.95), 12.563 (1.12).

$^1$H-NMR (400 MHz, DMSO-d6): δ [ppm]=12.56 (br. s, 1H), 8.76-8.64 (m, 1H), 7.90 (d, 1H), 7.81 (dd, 1H), 7.57-7.21 (m, 10H), 4.14-4.04 (m, 2H), 3.72-3.61 (m, 1H), 1.94 (br. s, 3H), 1.11 (s, 3H), 1.10 (s, 3H).

Example 114

(+/−)-4-{[(6-Bromo-3-methyl-2-phenylquinolin-4-yl)carbonyl]amino}-3-(2-chlorophenyl)-3-methylbutanoic Acid (Racemate)

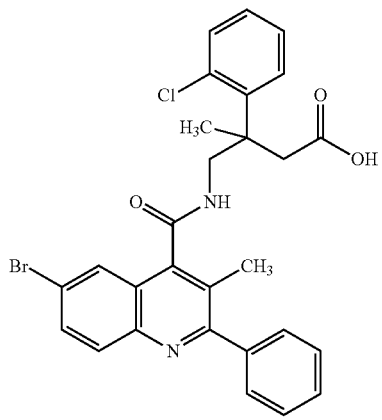 [SMILES: Cc1c(-c2ccccc2)nc2ccc(Br)cc2c1C(=O)NCC(C)(CC(=O)O)c1ccccc1Cl]

TFA (3.7 ml, 49 mmol) was added to a solution of (+/−)-tert-butyl 4-{[(6-bromo-3-methyl-2-phenylquinolin-4-yl)carbonyl]amino}-3-(2-chlorophenyl)-3-methylbutanoate (1.70 g, 87% purity, 2.43 mmol, Example 199A) in dichloromethane (17 ml), and the mixture was stirred at RT overnight. The mixture was then concentrated and repeatedly, in succession, dichloromethane was added and the mixture was concentrated again. The residue was purified by preparative HPLC (Method 15). This gave 1.06 g (98% purity, 77% of theory) of the title compound.

LC-MS (Method 2): $R_t$=1.06 min; MS (ESIpos): m/z=517/519 [M+H]$^+$ $^1$H-NMR (400 MHz, DMSO-d6) δ [ppm]: −0.008 (2.48), 0.008 (1.95), 1.546 (0.42), 1.672 (16.00), 2.072 (1.61), 2.112 (1.69), 2.327 (0.51), 2.523 (1.63), 2.669 (0.51), 2.760 (4.48), 2.798 (5.03), 3.342 (3.72), 3.381 (3.37), 3.777 (1.67), 3.790 (1.85), 3.811 (2.05), 3.824 (1.90), 4.342 (1.91), 4.359 (2.08), 4.375 (1.90), 4.392 (1.78), 7.229 (0.83), 7.248 (2.29), 7.267 (2.18), 7.274 (2.24), 7.278 (2.34), 7.293 (2.82), 7.297 (2.96), 7.312 (1.36), 7.392 (2.60), 7.411 (2.11), 7.459 (3.52), 7.463 (3.53), 7.478 (3.27), 7.482 (3.14), 7.500 (5.81), 7.508 (5.01), 7.519 (12.10), 7.526 (11.50), 7.544 (2.31), 7.654 (0.63), 7.831 (2.64), 7.836 (2.49), 7.853 (4.11), 7.859 (4.10), 7.926 (7.99), 7.949 (5.13), 8.624 (1.72), 8.640 (2.91), 8.655 (1.76).

Example 115

(+)-4-{[(6-Bromo-3-methyl-2-phenylquinolin-4-yl)carbonyl]amino}-3-(2-fluorophenyl)-3-methylbutanoic Acid (Enantiomer 1)

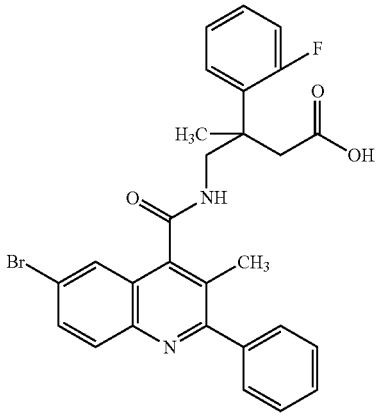 [SMILES: Cc1c(-c2ccccc2)nc2ccc(Br)cc2c1C(=O)NCC(C)(CC(=O)O)c1ccccc1F]

TFA (210 µl, 2.7 mmol) was added to a solution of (+)-tert-butyl 4-{[(6-bromo-3-methyl-2-phenylquinolin-4-yl)carbonyl]amino}-3-(2-fluorophenyl)-3-methylbutanoate (80 mg, 135 µmol, Example 201A) in dichloromethane (2 ml), and the mixture was stirred at RT overnight. The mixture was then concentrated and repeatedly, in succession, dichloromethane was added and the mixture was concentrated again. The residue was purified by preparative HPLC (Method 16). This gave 69 mg (98% purity, ee 100%, 93% of theory) of the title compound.

$[\alpha]_D^{20}$=+31.5°, 589 nm, c=0.31 g/100 ml, methanol

LC-MS (Method 1): $R_t$=1.92 min; MS (ESIpos): m/z=535/537 [M+H]$^+$ $^1$H-NMR (600 MHz, DMSO-d6) δ [ppm]: 1.590 (16.00), 2.076 (1.84), 2.158 (0.55), 2.652 (3.56), 2.677 (4.15), 2.968 (3.73), 2.993 (3.31), 3.668 (1.44), 3.677 (1.57), 3.690 (1.69), 3.699 (1.54), 4.067 (1.93), 4.079 (2.09), 4.089 (1.90), 4.101 (1.75), 7.118 (1.02), 7.140 (2.13), 7.153 (2.82), 7.292 (1.26), 7.350 (1.58), 7.364 (2.78), 7.376 (1.38), 7.486 (0.77), 7.494 (2.62), 7.500 (2.28), 7.505 (4.11), 7.508 (5.56), 7.521 (8.62), 7.533 (10.91), 7.545 (2.64), 7.843 (2.16), 7.847 (2.13), 7.858 (2.94), 7.861 (2.90), 7.936 (5.68), 7.951 (4.15), 8.715 (1.79), 8.726 (3.02), 8.736 (1.77).

$^1$H-NMR (600 MHz, DMSO-d6): δ [ppm]=8.73 (t, 1H), 7.94 (d, 1H), 7.85 (dd, 1H), 7.66 (br. s, 1H), 7.59-7.46 (m, 5H), 7.36 (br. t, 1H), 7.29 (br. s, 1H), 7.19-7.09 (m, 2H), 4.08 (dd, 1H), 3.68 (dd, 1H), 2.98 (d, 1H), 2.66 (d, 1H), 2.08 (br. s, 3H), 1.59 (s, 3H).

Example 116

(−)-4-{[(6-Bromo-3-methyl-2-phenylquinolin-4-yl)carbonyl]amino}-3-(2-fluorophenyl)-3-methylbutanoic Acid (Enantiomer 2)

TFA (210 µl, 2.7 mmol) was added to a solution of (−)-tert-butyl 4-{[(6-bromo-3-methyl-2-phenylquinolin-4-yl)carbonyl]amino}-3-(2-fluorophenyl)-3-methylbutanoate (80 mg, 135 µmol, Example 202A) in dichloromethane (2 ml), and the mixture was stirred at RT overnight. The mixture was then concentrated and repeatedly, in succession, dichloromethane was added and the mixture was concentrated again. The residue was purified by preparative HPLC (Method 16). This gave 60 mg (98% purity, ee 100%, 81% of theory) of the title compound.

$[\alpha]_D^{20}$=−28.9°, 589 nm, c=0.32 g/100 ml, methanol

LC-MS (Method 1): $R_t$=1.92 min; MS (ESIpos): m/z=535/537 [M+H]$^+$ $^1$H-NMR (600 MHz, DMSO-d6) δ [ppm]: 1.587 (16.00), 2.076 (0.93), 2.649 (3.54), 2.674 (4.12), 2.965 (3.72), 2.991 (3.30), 3.664 (2.15), 3.673 (2.30), 3.686 (2.47), 3.696 (2.30), 4.063 (1.95), 4.075 (2.10), 4.086 (1.90), 4.097 (1.75), 7.118 (1.05), 7.139 (2.16), 7.152 (2.84), 7.291 (1.29), 7.348 (1.60), 7.361 (2.79), 7.375 (1.39), 7.484 (0.86), 7.491 (2.60), 7.498 (2.40), 7.503 (4.00), 7.506 (5.30), 7.519 (8.77), 7.530 (11.64), 7.542 (2.44), 7.840 (2.20), 7.855 (2.98), 7.932 (5.50), 7.947 (4.00), 8.710 (1.80), 8.720 (3.02), 8.730 (1.73).

$^1$H-NMR (600 MHz, DMSO-d6): δ [ppm]=12.00 (br. s, 1H), 8.72 (t, 1H), 7.94 (d, 1H), 7.85 (d, 1H), 7.64 (br. s, 1H), 7.56-7.47 (m, 5H), 7.36 (t, 1H), 7.28 (br. s, 1H), 7.19-7.09 (m, 2H), 4.08 (dd, 1H), 3.68 (dd, 1H), 2.98 (d, 1H), 2.66 (d, 1H), 2.10 (br. s, 3H), 1.59 (s, 3H).

Example 117

(+/−)-4-{[(6-Bromo-3-methyl-2-phenylquinolin-4-yl)carbonyl]amino}-3-methyl-3-(pyridin-2-yl)butanoic Acid (Racemate)

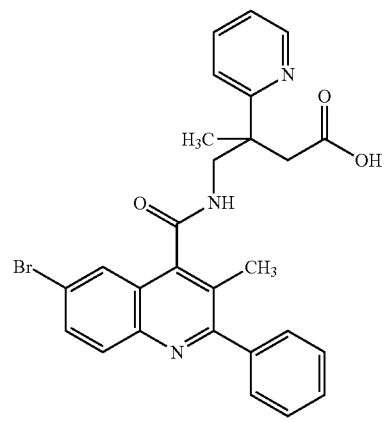 [SMILES: Cc1c(-c2ccccc2)nc2ccc(Br)cc2c1C(=O)NCC(C)(CC(=O)O)c1ccccn1]

TFA (2.4 ml, 31 mmol) was added to a solution of (+/−)-tert-butyl 4-{[(6-bromo-3-methyl-2-phenylquinolin-4-yl)carbonyl]amino}-3-methyl-3-(pyridin-2-yl)butanoate (900 mg, 1.57 mmol, Example 203A) in dichloromethane (20 ml), and the mixture was stirred at RT overnight. The mixture was then concentrated and repeatedly, in succession, dichloromethane was added and the mixture was concentrated again. The residue was purified by preparative HPLC (Method 16). This gave 585 mg (98% purity, 71% of theory) of the title compound.

LC-MS (Method 1): $R_t$=1.67 min; MS (ESIpos): m/z=518/520 [M+H]$^+$ $^1$H-NMR (600 MHz, DMSO-d6) δ [ppm]: 1.199 (0.59), 1.210 (0.60), 1.578 (16.00), 1.686 (0.78), 2.077 (2.22), 2.148 (2.50), 2.172 (1.84), 2.503 (14.98), 2.735 (2.77), 2.762 (3.14), 3.099 (2.31), 3.125 (2.03), 3.765 (1.15), 3.774 (1.28), 3.787 (1.47), 3.797 (1.32), 3.973 (1.15), 3.984 (1.24), 3.995 (1.04), 4.006 (0.93), 7.439 (1.01), 7.487 (0.64), 7.498 (2.33), 7.509 (3.62), 7.512 (4.88), 7.525 (6.71), 7.539 (3.97), 7.543 (7.16), 7.555 (3.07), 7.689 (1.32), 7.701 (1.35), 7.850 (2.35), 7.854 (2.27), 7.865 (3.07), 7.869 (2.96), 7.945 (5.52), 7.960 (4.20), 7.988 (0.95), 7.994 (0.98), 8.007 (0.53), 8.642 (1.83), 8.649 (1.81), 8.753 (1.14), 8.763 (2.10), 8.773 (1.14).

Separation of the Enantiomers:

The title compound (530 mg) was dissolved in methanol (30 ml) and separated into the enantiomers by preparative SFC on a chiral phase (see Examples 118 and 119) [column: Chiralpak AD-H, 5 μm, 250 mm×20 mm; flow rate: 50 ml/min; detection: 210 nm; temperature: 40° C.; injection: 0.40 ml; mobile phase: 78% carbon dioxide/22% isopropanol, isocratic, run time 17 min].

Example 118

(+)-4-{[(6-Bromo-3-methyl-2-phenylquinolin-4-yl)carbonyl]amino}-3-methyl-3-(pyridin-2-yl)butanoic Acid (Enantiomer 1)

In the enantiomer separation described in Example 117, 202 mg (98% purity, ee 100%) of the title compound were obtained as the enantiomer that eluted earlier.

$[\alpha]_D^{20}$=+17.8°, 589 nm, c=0.34 g/100 ml, methanol

LC-MS (Method 1): $R_t$=1.68 min; MS (ESIpos): m/z=518/520 [M+H]$^+$ $^1$H-NMR (400 MHz, DMSO-d6) δ [ppm]: −0.008 (1.63), 0.008 (1.38), 1.030 (2.31), 1.045 (2.33), 1.544 (16.00), 2.170 (15.68), 2.518 (1.12), 2.523 (0.86), 2.672 (3.09), 2.711 (3.64), 3.000 (3.08), 3.039 (2.56), 3.473 (1.48), 3.782 (0.75), 3.797 (0.79), 3.816 (1.38), 3.830 (1.29), 3.873 (1.33), 3.888 (1.41), 3.906 (0.76), 3.921 (0.68), 7.208 (1.60), 7.210 (1.67), 7.220 (1.73), 7.222 (1.90), 7.226 (1.95), 7.228 (1.80), 7.238 (1.78), 7.241 (1.76), 7.477 (0.66), 7.486 (3.63), 7.488 (3.36), 7.499 (3.31), 7.504 (7.89), 7.517 (2.42), 7.522 (6.46), 7.539 (8.25), 7.543 (6.47), 7.548 (3.28), 7.552 (1.58), 7.558 (1.91), 7.564 (1.21), 7.701 (2.51), 7.732 (1.65), 7.736 (1.73), 7.751 (2.38), 7.756 (2.43), 7.771 (1.29), 7.775 (1.27), 7.835 (2.24), 7.841 (1.98), 7.858 (3.38), 7.863 (3.19), 7.934 (5.82), 7.956 (3.76), 8.527 (2.15), 8.529 (2.21), 8.539 (2.09), 8.541 (1.95), 8.628 (1.11), 8.644 (2.31), 8.659 (1.18), 11.953 (4.48).

$^1$H-NMR (400 MHz, DMSO-d6): δ [ppm]=11.95 (s, 1H), 8.64 (t, 1H), 8.53 (dd, 1H), 7.94 (d, 1H), 7.85 (dd, 1H), 7.75 (td, 1H), 7.70 (s, 1H), 7.57-7.46 (m, 6H), 7.22 (ddd, 1H), 3.89 (dd, 1H), 3.81 (dd, 1H), 3.02 (d, 1H), 2.69 (d, 1H), 2.17 (s, 3H), 1.54 (s, 3H).

Example 119

(−)-4-{[(6-Bromo-3-methyl-2-phenylquinolin-4-yl)carbonyl]amino}-3-methyl-3-(pyridin-2-yl)butanoic Acid (Enantiomer 2)

In the enantiomer separation described in Example 117, 72 mg (98% purity, ee 99%) of the title compound were obtained as the enantiomer that eluted later.

$[\alpha]_D^{20}$=−22.1°, 589 nm, c=0.35 g/100 ml, methanol

LC-MS (Method 1): $R_t$=1.68 min; MS (ESIpos): m/z=518/520 [M+H]$^+$ $^1$H-NMR (400 MHz, DMSO-d6) δ [ppm]: −0.008 (1.49), 0.008 (1.29), 1.542 (16.00), 2.171 (15.95), 2.523 (0.88), 2.673 (3.04), 2.712 (3.53), 2.995 (2.98), 3.034 (2.44), 3.786 (0.63), 3.801 (0.73), 3.819 (1.36), 3.834 (1.26), 3.870 (1.31), 3.885 (1.39), 3.903 (0.71), 3.918 (0.62), 7.209 (1.73), 7.221 (1.94), 7.226 (1.93), 7.238 (1.79), 7.485 (3.48), 7.504 (8.08), 7.522 (6.48), 7.539 (8.24), 7.542 (6.57), 7.548 (3.23), 7.558 (1.89), 7.702 (2.74), 7.731 (1.63), 7.735 (1.67), 7.750 (2.44), 7.755 (2.43), 7.770 (1.25), 7.774 (1.23), 7.835 (2.26), 7.840 (2.01), 7.857 (3.39), 7.863 (3.19), 7.934 (6.13), 7.956 (3.87), 8.530 (2.34), 8.539 (2.30), 8.672 (1.37), 11.958 (0.90).

Example 120

(+/−)-4-{[(6-Bromo-3-methyl-2-phenylquinolin-4-yl)carbonyl]amino}-3-(2-methoxyphenyl)-3-methylbutanoic Acid (Racemate)

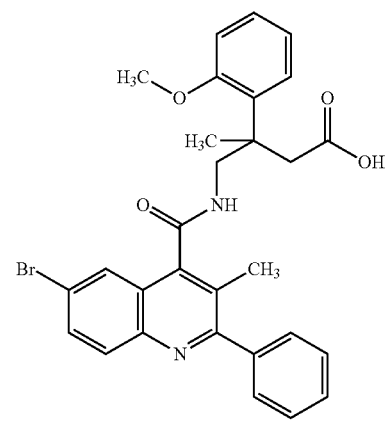 [SMILES: COc1ccccc1C(C)(CNC(=O)c1c(C)c(-c2ccccc2)nc2ccc(Br)cc12)CC(=O)O]

TFA (250 μl, 3.2 mmol) was added to a solution of (+/−)-tert-butyl 4-{[(6-bromo-3-methyl-2-phenylquinolin-4-yl)carbonyl]amino}-3-(2-methoxyphenyl)-3-methylbutanoate (100 mg, 98% purity, 162 μmol, Example 204A) in dichloromethane (1.2 ml), and the mixture was stirred at RT overnight. The mixture was then concentrated and repeatedly, in succession, dichloromethane was added and the mixture was concentrated again. The residue was purified by preparative HPLC (Method 20). This gave 84 mg (98% purity, 92% of theory) of the title compound.

LC-MS (Method 1): $R_t$=1.97 min; MS (ESIpos): m/z=547/549 [M+H]$^+$ $^1$H-NMR (400 MHz, DMSO-d6) δ [ppm]: 1.572 (13.20), 2.072 (2.90), 2.655 (3.43), 2.691 (3.96), 3.072 (3.56), 3.109 (3.10), 3.691 (1.52), 3.704 (1.64), 3.723 (1.81), 3.737 (1.66), 4.205 (1.34), 4.223 (1.47), 4.238 (1.34), 4.255 (1.22), 6.868 (1.38), 6.887 (2.95), 6.905 (1.69), 6.977 (2.51), 6.998 (3.00), 7.188 (1.45), 7.208 (2.41), 7.220 (3.81), 7.239 (3.02), 7.475 (0.44), 7.486 (1.36), 7.497 (4.27), 7.505 (4.46), 7.516 (16.00), 7.660 (0.69), 7.825 (2.17), 7.831 (2.05), 7.848 (3.41), 7.853 (3.40), 7.919 (6.21), 7.941 (3.90), 8.480 (1.38), 8.496 (2.48), 8.511 (1.39).

Example 121

(+)-4-{[(6-Bromo-3-methyl-2-phenylquinolin-4-yl)carbonyl]amino}-3-(2-methoxyphenyl)-3-methylbutanoic Acid (Enantiomer 1)

TFA (1.7 ml, 22 mmol) was added to a solution of (+)-tert-butyl 4-{[(6-bromo-3-methyl-2-phenylquinolin-4-yl)carbonyl]amino}-3-(2-methoxyphenyl)-3-methylbutanoate (650 mg, 1.08 mmol, Example 205A) in dichloromethane (16 ml), and the mixture was stirred at RT overnight. The mixture was then concentrated and repeatedly, in succession, dichloromethane was added and the mixture was concentrated again. The residue was purified by preparative HPLC (Method 16). This gave 398 mg (98% purity, ee 95%, 66% of theory) of the title compound.

$[\alpha]_D^{20}$=+30.0°, 589 nm, c=0.44 g/100 ml, methanol

LC-MS (Method 2): $R_t$=1.04 min; MS (ESIpos): m/z=547/549 [M+H]$^+$ $^1$H-NMR (500 MHz, DMSO-d6) δ [ppm]: −0.007 (0.51), 1.254 (0.43), 1.577 (16.00), 2.071 (4.33), 2.080 (1.58), 2.664 (4.50), 2.693 (5.04), 3.080 (4.33), 3.109 (3.90), 3.702 (1.89), 3.712 (2.07), 3.728 (2.22), 3.739 (1.98), 4.215 (1.45), 4.229 (1.60), 4.241 (1.51), 4.255 (1.33), 6.874 (1.58), 6.889 (3.28), 6.904 (1.84), 6.980 (2.73), 6.996 (3.14), 7.192 (1.44), 7.207 (2.39), 7.226 (4.53), 7.229 (3.80), 7.241 (3.60), 7.244 (3.13), 7.477 (0.76), 7.486 (1.89), 7.488 (1.64), 7.491 (1.52), 7.498 (5.02), 7.503 (4.86), 7.515 (11.97), 7.520 (11.66), 7.525 (10.63), 7.536 (2.01), 7.674 (0.59), 7.828 (3.01), 7.833 (2.86), 7.846 (4.20), 7.851 (4.18), 7.923 (8.09), 7.941 (5.60), 8.487 (1.74), 8.499 (2.97), 8.512 (1.75).

Example 122

(−)-4-{[(6-Bromo-3-methyl-2-phenylquinolin-4-yl)carbonyl]amino}-3-(2-methoxyphenyl)-3-methylbutanoic Acid (Enantiomer 2)

TFA (1.7 ml, 22 mmol) was added to a solution of (−)-tert-butyl 4-{[(6-bromo-3-methyl-2-phenylquinolin-4-yl)carbonyl]amino}-3-(2-methoxyphenyl)-3-methylbutanoate (650 mg, 1.08 mmol, Example 206A) in dichloromethane (16 ml), and the mixture was stirred at RT overnight. The mixture was then concentrated and repeatedly, in succession, dichloromethane was added and the mixture was concentrated again. The residue was purified by preparative HPLC (Method 16). This gave 468 mg (98% purity, ee 99%, 78% of theory) of the title compound.

$[\alpha]_D^{20}$=−35.6°, 589 nm, c=0.43 g/100 ml, methanol

LC-MS (Method 2): $R_t$=1.04 min; MS (ESIpos): m/z=547/549 [M+H]$^+$ $^1$H-NMR (500 MHz, DMSO-d6) δ [ppm]: −0.007 (0.57), 1.575 (16.00), 2.071 (3.31), 2.663 (4.52), 2.692 (5.04), 3.079 (4.34), 3.108 (3.90), 3.700 (1.92), 3.711 (2.10), 3.726 (2.23), 3.737 (1.99), 4.213 (1.45), 4.227 (1.59), 4.239 (1.47), 4.253 (1.30), 6.873 (1.60), 6.888 (3.29), 6.903 (1.83), 6.979 (2.75), 6.995 (3.13), 7.191 (1.48), 7.206 (2.42), 7.225 (4.71), 7.228 (3.78), 7.241 (3.64), 7.243 (3.02), 7.471 (0.43), 7.476 (0.86), 7.485 (1.99), 7.487 (1.72), 7.490 (1.60), 7.497 (4.92), 7.502 (4.85), 7.514 (12.36), 7.519 (11.80), 7.524 (10.39), 7.535 (1.82), 7.673 (0.57), 7.827 (3.06), 7.831 (2.83), 7.845 (4.22), 7.849 (4.10), 7.921 (8.11), 7.939 (5.57), 8.485 (1.76), 8.497 (2.96), 8.510 (1.72).

Example 123

(+/−)-4-{[(6-Bromo-3-methyl-2-phenylquinolin-4-yl)carbonyl]amino}-3-(5-fluoro-2-methoxyphenyl)butanoic Acid (Racemate)

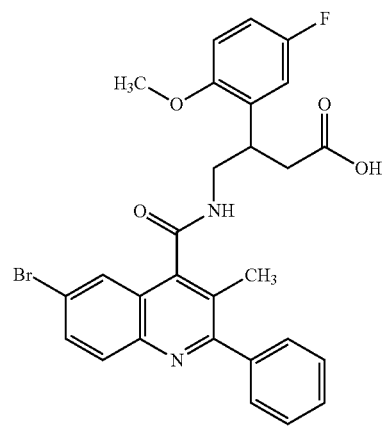 [SMILES: COc1ccc(F)cc1C(CNC(=O)c1c(C)c(-c2ccccc2)nc2ccc(Br)cc12)CC(=O)O]

TFA (250 µl, 3.3 mmol) was added to a solution of (+/−)-tert-butyl 4-{[(6-bromo-3-methyl-2-phenylquinolin-4-yl)carbonyl]amino}-3-(5-fluoro-2-methoxyphenyl)butanoate (100 mg, 165 µmol, Example 207A) in dichloromethane (1.5 ml), and the mixture was stirred at RT for 16 h. The mixture was then concentrated and repeatedly, in succession, dichloromethane was added and the mixture was concentrated again. The residue was purified by preparative HPLC (Method 20). This gave 85 mg (98% purity, 92% of theory) of the title compound.

LC-MS (Method 2): $R_t$=1.01 min; MS (ESIpos): m/z=551/553 [M+H]$^+$ $^1$H-NMR (400 MHz, DMSO-d6) δ [ppm]: 0.008 (1.91), 2.073 (0.62), 2.130 (10.47), 2.328 (0.42), 2.598 (0.87), 2.616 (0.89), 2.637 (3.99), 2.655 (6.87), 2.669 (4.44), 2.693 (0.99), 2.710 (1.01), 3.629 (0.89), 3.641 (1.93), 3.654 (1.67), 3.671 (2.33), 3.684 (1.55), 3.716 (0.77), 3.735 (1.75), 3.753 (2.34), 3.802 (2.87), 3.817 (1.90), 3.833 (1.57), 3.853 (0.85), 4.528 (0.50), 6.972 (1.13), 6.985 (1.67), 6.995 (5.05), 7.008 (6.28), 7.024 (2.40), 7.031 (2.66), 7.046 (0.67), 7.053 (0.86), 7.088 (2.87), 7.094 (2.60), 7.112 (2.95), 7.119 (2.50), 7.309 (0.53), 7.479 (0.71), 7.491 (1.84), 7.494 (1.88), 7.504 (6.38), 7.511 (5.58), 7.523 (16.00), 7.528 (15.38), 7.536 (9.41), 7.638 (1.59), 7.835 (3.16), 7.840 (2.92), 7.857 (4.89), 7.862 (4.72), 7.931 (8.83), 7.953 (5.66), 8.760 (1.91), 8.774 (3.65), 8.788 (1.89).

$^1$H-NMR (400 MHz, DMSO-d6): δ [ppm]=8.77 (t, 1H), 7.94 (d, 1H), 7.85 (dd, 1H), 7.64 (br. s, 1H), 7.56-7.47 (m, 5H), 7.10 (dd, 1H), 7.07-6.95 (m, 2H), 3.86-3.71 (m, 2H), 3.79 (s, 3H), 3.70-3.60 (m, 1H), 2.73-2.58 (m, 2H), 2.13 (br. s, 3H).

Example 124

(+)-4-{[(6-Bromo-3-methyl-2-phenylquinolin-4-yl)carbonyl]amino}-3-(5-fluoro-2-methoxyphenyl)butanoic Acid (Enantiomer 1)

TFA (410 µl, 5.3 mmol) was added to a solution of (+)-tert-butyl 4-{[(6-bromo-3-methyl-2-phenylquinolin-4-yl)carbonyl]amino}-3-(5-fluoro-2-methoxyphenyl)butanoate (165 mg, 98% purity, 266 µmol, Example 209A) in dichloromethane (1.9 ml), and the mixture was stirred at RT for 7 h. The mixture was then concentrated and repeatedly, in succession, dichloromethane was added and the mixture was concentrated again. The residue was purified by preparative HPLC (Method 16). This gave 134 mg (98% purity, 90% of theory, ee 99%) of the title compound.

$[\alpha]_D^{20}$=+17.7°, 589 nm, c=0.42 g/100 ml, methanol

LC-MS (Method 1): $R_t$=1.89 min; MS (ESIpos): m/z=551/553 [M+H]$^+$ $^1$H-NMR (400 MHz, DMSO-d6) δ [ppm]: 0.008 (0.86), 2.073 (0.59), 2.129 (10.14), 2.327 (0.46), 2.519 (2.04), 2.524 (1.96), 2.597 (0.90), 2.615 (1.03), 2.636 (4.25), 2.654 (6.89), 2.669 (4.26), 2.692 (0.91), 2.709 (0.99), 3.628 (1.02), 3.640 (2.04), 3.653 (1.75), 3.670 (2.36), 3.684 (1.54), 3.716 (0.91), 3.734 (2.04), 3.752 (2.78), 3.801 (2.61), 3.816 (1.75), 3.833 (1.43), 3.853 (0.73), 6.972 (1.39), 6.985 (2.06), 6.995 (5.39), 7.008 (6.23), 7.023 (2.42), 7.031 (2.57), 7.046 (0.70), 7.053 (0.91), 7.087 (3.04), 7.094 (2.61), 7.111 (3.00), 7.118 (2.42), 7.478 (1.26), 7.489 (2.54), 7.493 (2.59), 7.503 (7.04), 7.511 (6.33), 7.522 (16.00), 7.527 (14.82), 7.535 (8.46), 7.539 (6.67), 7.547 (1.77), 7.638 (1.44), 7.833 (3.28), 7.838 (2.91), 7.856 (4.92), 7.861 (4.52), 7.930 (8.60), 7.952 (5.46), 8.757 (2.10), 8.772 (3.68), 8.785 (1.80).

$^1$H-NMR (400 MHz, DMSO-d6): δ [ppm]=8.77 (t, 1H), 7.94 (d, 1H), 7.85 (dd, 1H), 7.64 (br. s, 1H), 7.57-7.44 (m, 5H), 7.10 (dd, 1H), 7.07-6.93 (m, 2H), 3.88-3.70 (m, 2H), 3.78 (s, 3H), 3.66 (td, 1H), 2.73-2.57 (m, 2H), 2.13 (br. s, 3H).

Example 125

(−)-4-{[(6-Bromo-3-methyl-2-phenylquinolin-4-yl)carbonyl]amino}-3-(5-fluoro-2-methoxyphenyl)butanoic Acid (Enantiomer 2)

TFA (400 μl, 5.2 mmol) was added to a solution of (−)-tert-butyl 4-{[(6-bromo-3-methyl-2-phenylquinolin-4-yl)carbonyl]amino}-3-(5-fluoro-2-methoxyphenyl)butanoate (160 mg, 98% purity, 258 μmol, Example 208A) in dichloromethane (1.8 ml), and the mixture was stirred at RT for 5 h. The mixture was then concentrated and repeatedly, in succession, dichloromethane was added and the mixture was concentrated again. The residue was purified by preparative HPLC (Method 16). This gave 116 mg (98% purity, 80% of theory, ee 99%) of the title compound.

$[\alpha]_D^{20}$=−17.5°, 589 nm, c=0.36 g/100 ml, methanol

LC-MS (Method 1): $R_t$=1.90 min; MS (ESIpos): m/z=551/553 [M+H]$^+$ $^1$H-NMR (400 MHz, DMSO-d6) δ [ppm]: −0.008 (1.05), 0.008 (0.98), 2.130 (10.36), 2.523 (1.05), 2.598 (0.88), 2.616 (0.89), 2.637 (4.20), 2.655 (7.04), 2.669 (4.51), 2.693 (1.03), 2.709 (1.06), 3.629 (0.86), 3.641 (1.97), 3.654 (1.64), 3.658 (1.64), 3.671 (2.35), 3.685 (1.54), 3.716 (0.68), 3.735 (1.69), 3.753 (2.26), 3.768 (2.21), 3.802 (2.78), 3.817 (1.83), 3.822 (1.40), 3.833 (1.51), 3.853 (0.80), 6.972 (1.20), 6.985 (1.79), 6.995 (5.46), 7.008 (6.55), 7.023 (2.45), 7.031 (2.75), 7.046 (0.67), 7.053 (0.91), 7.088 (3.00), 7.095 (2.67), 7.112 (3.09), 7.119 (2.62), 7.477 (0.74), 7.489 (1.89), 7.492 (1.85), 7.502 (6.44), 7.511 (5.82), 7.522 (16.00), 7.527 (15.40), 7.531 (12.19), 7.535 (9.42), 7.539 (7.62), 7.547 (2.13), 7.637 (1.48), 7.833 (3.40), 7.838 (3.11), 7.855 (5.24), 7.860 (5.04), 7.930 (9.35), 7.952 (6.05), 8.758 (1.97), 8.772 (3.76), 8.786 (1.91).

$^1$H-NMR (400 MHz, DMSO-d6): δ [ppm]=8.77 (t, 1H), 7.94 (d, 1H), 7.85 (dd, 1H), 7.64 (br. s, 1H), 7.56-7.46 (m, 5H), 7.10 (dd, 1H), 7.06-6.95 (m, 2H), 3.88-3.70 (m, 2H), 3.79 (s, 3H), 3.70-3.62 (m, 1H), 2.72-2.59 (m, 2H), 2.13 (br. s, 3H).

Example 126

(+/−)-4-{[(6-Bromo-3-methyl-2-phenylquinolin-4-yl)carbonyl]amino}-3-(2-fluoro-6-methoxyphenyl)butanoic Acid (Racemate)

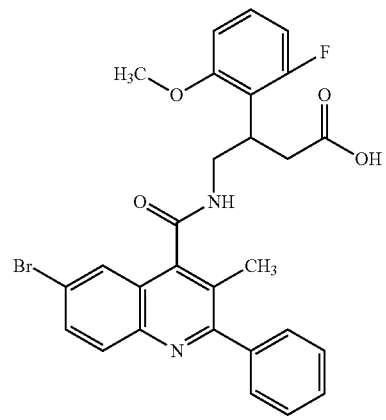 [SMILES: COc1cccc(F)c1C(CNC(=O)c1c(C)c(-c2ccccc2)nc2ccc(Br)cc12)CC(=O)O]

TFA (610 μl, 7.9 mmol) was added to a solution of (+/−)-tert-butyl 4-{[(6-bromo-3-methyl-2-phenylquinolin-4-yl)carbonyl]amino}-3-(2-fluoro-6-methoxyphenyl)butanoate (60 mg, 98.8 μmol, Example 210A) in dichloromethane (3.0 ml), and the mixture was allowed to stand at RT for 2.5 h. The mixture was then concentrated and repeatedly, in succession, dichloromethane was added and the mixture was concentrated again. The residue was purified by preparative HPLC (Method 15). This gave 45 mg (100% purity, 83% of theory) of the title compound.

LC-MS (Method 1): $R_t$=1.88 min; MS (ESIpos): m/z=551/553 [M+H]$^+$ $^1$H-NMR (500 MHz, DMSO-d6) δ [ppm]: −0.007 (0.41), 1.234 (0.69), 2.073 (0.73), 2.148 (5.32), 2.518 (0.50), 2.725 (5.08), 2.728 (5.40), 2.741 (7.14), 2.759 (0.52), 3.686 (1.01), 3.698 (1.78), 3.711 (2.24), 3.723 (2.60), 3.735 (1.48), 3.793 (1.56), 3.802 (3.24), 3.836 (1.69), 3.849 (1.18), 3.944 (0.75), 3.959 (1.78), 3.974 (2.07), 3.989 (1.39), 4.005 (0.54), 6.736 (2.56), 6.754 (3.94), 6.772 (2.67), 6.834 (4.16), 6.851 (4.48), 7.201 (0.98), 7.217 (2.10), 7.231 (2.01), 7.247 (0.83), 7.473 (0.54), 7.476 (0.65), 7.481 (1.15), 7.490 (2.67), 7.492 (2.31), 7.495 (2.26), 7.502 (5.32), 7.504 (5.21), 7.507 (6.24), 7.520 (14.64), 7.526 (16.00), 7.531 (15.46), 7.542 (2.48), 7.683 (0.53), 7.837 (3.88), 7.842 (3.49), 7.855 (5.39), 7.860 (5.01), 7.929 (10.24), 7.947 (6.90), 8.818 (2.17), 8.830 (4.08), 8.842 (2.08).

$^1$H-NMR (500 MHz, DMSO-d6): δ [ppm]=12.05 (br. s, 1H), 8.83 (t, 1H), 7.94 (d, 1H), 7.85 (dd, 1H), 7.68 (br. s, 1H), 7.55-7.46 (m, 5H), 7.27-7.17 (m, 1H), 6.84 (d, 1H), 6.75 (t, 1H), 4.02-3.92 (m, 1H), 3.87-3.77 (m, 1H), 3.82 (s, 3H), 3.75-3.65 (m, 1H), 2.76-2.70 (m, 2H), 2.15 (br. s, 3H).

Example 127

(+)-4-{[(6-Bromo-3-methyl-2-phenylquinolin-4-yl)carbonyl]amino}-3-(2-fluoro-6-methoxyphenyl)butanoic Acid (Enantiomer 1)

TFA (1.6 ml, 21 mmol) was added to a solution of (+)-tert-butyl 4-{[(6-bromo-3-methyl-2-phenylquinolin-4- yl)carbonyl]amino}-3-(2-fluoro-6-methoxyphenyl)butanoate (160 mg, 263 µmol, Example 211A) in dichloromethane (8.0 ml), and the mixture was allowed to stand at RT for 24 h. The mixture was then concentrated and repeatedly, in succession, dichloromethane was added and the mixture was concentrated again. The residue was purified by preparative HPLC (Method 15). This gave 138 mg (100% purity, 95% of theory, ee 99%) of the title compound.

$[\alpha]_D^{20}$=+45.6°, 546 nm, c=0.39 g/100 ml, methanol

LC-MS (Method 1): $R_t$=1.89 min; MS (ESIpos): m/z=551/553 [M+H]$^+$ $^1$H-NMR (400 MHz, DMSO-d6) δ [ppm]: 2.144 (5.94), 2.305 (0.40), 2.721 (5.05), 2.739 (6.25), 3.635 (1.06), 3.674 (1.38), 3.689 (1.90), 3.706 (2.26), 3.722 (2.51), 3.736 (1.55), 3.782 (1.28), 3.853 (0.99), 3.932 (0.61), 3.951 (1.44), 3.970 (1.71), 3.988 (1.13), 6.730 (1.94), 6.752 (3.05), 6.775 (2.11), 6.832 (3.38), 6.853 (3.76), 7.195 (0.82), 7.215 (1.83), 7.233 (1.81), 7.253 (0.71), 7.477 (0.57), 7.491 (1.63), 7.500 (4.91), 7.508 (4.59), 7.520 (16.00), 7.532 (7.41), 7.701 (0.51), 7.834 (2.47), 7.839 (2.22), 7.857 (3.87), 7.862 (3.65), 7.926 (6.94), 7.949 (4.31), 8.811 (1.60), 8.826 (3.15), 8.841 (1.57).

$^1$H-NMR (400 MHz, DMSO-d6): δ [ppm]=12.04 (br. s, 1H), 8.83 (t, 1H), 7.93 (d, 1H), 7.85 (dd, 1H), 7.70 (br. s, 1H), 7.56-7.46 (m, 5H), 7.22 (dd, 1H), 6.84 (d, 1H), 6.75 (t, 1H), 4.03-3.91 (m, 1H), 3.82 (s, 3H), 3.87-3.65 (m, 2H), 2.73 (d, 2H), 2.14 (br. s, 3H).

Example 128

(−)-4-{[(6-Bromo-3-methyl-2-phenylquinolin-4-yl)carbonyl]amino}-3-(2-fluoro-6-methoxyphenyl)butanoic Acid (Enantiomer 2)

TFA (1.8 ml, 24 mmol) was added to a solution of (−)-tert-butyl 4-{[(6-bromo-3-methyl-2-phenylquinolin-4-yl)carbonyl]amino}-3-(2-fluoro-6-methoxyphenyl)butanoate (180 mg, 296 µmol, Example 212A) in dichloromethane (9.0 ml), and the mixture was allowed to stand at RT for 24 h. The mixture was then concentrated and repeatedly, in succession, dichloromethane was added and the mixture was concentrated again. The residue was purified by preparative HPLC (Method 15). This gave 163 mg (100% purity, 100% of theory, ee 99%) of the title compound.

$[\alpha]_D^{20}$=−39.2°, 546 nm, c=0.39 g/100 ml, methanol

LC-MS (Method 1): $R_t$=1.89 min; MS (ESIpos): m/z=551/553 [M+H]$^+$ $^1$H-NMR (400 MHz, DMSO-d6) δ [ppm]: 2.144 (3.40), 2.720 (2.86), 2.739 (3.55), 3.674 (0.45), 3.689 (0.80), 3.706 (1.06), 3.722 (1.25), 3.736 (0.74), 3.781 (0.70), 3.801 (1.84), 3.818 (16.00), 3.853 (0.64), 3.932 (0.53), 3.950 (1.04), 3.969 (1.21), 3.988 (0.90), 4.007 (0.49), 6.730 (1.10), 6.752 (1.70), 6.775 (1.18), 6.832 (1.88), 6.853 (2.09), 7.195 (0.50), 7.215 (1.10), 7.234 (1.13), 7.253 (0.48), 7.491 (0.90), 7.501 (2.80), 7.509 (2.56), 7.521 (9.47), 7.835 (1.37), 7.840 (1.20), 7.858 (2.18), 7.863 (2.00), 7.927 (3.94), 7.949 (2.44), 8.812 (0.91), 8.827 (1.79), 8.841 (0.89).

$^1$H-NMR (400 MHz, DMSO-d6): δ [ppm]=12.12 (br. s, 1H), 8.83 (t, 1H), 7.94 (d, 1H), 7.85 (dd, 1H), 7.69 (br. s, 1H), 7.57-7.46 (m, 5H), 7.22 (dd, 1H), 6.84 (d, 1H), 6.75 (t, 1H), 4.02-3.92 (m, 1H), 3.82 (s, 3H), 3.87-3.66 (m, 2H), 2.73 (d, 2H), 2.14 (br. s, 3H).

Example 129

(+/−)-4-{[(6-Bromo-3-methyl-2-phenylquinolin-4-yl)carbonyl]amino}-3-(2-ethoxyphenyl)butanoic Acid (Racemate)

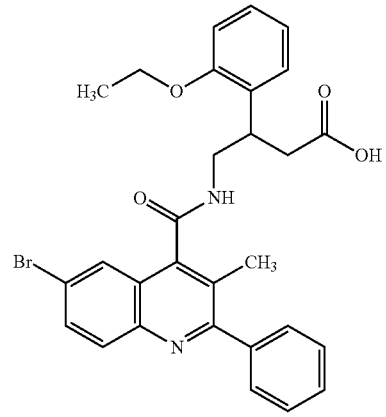 [SMILES: CCOc1ccccc1C(CNC(=O)c1c(C)c(-c2ccccc2)nc2ccc(Br)cc12)CC(=O)O]

TFA (100 µl, 1.3 mmol) was added to a solution of (+/−)-tert-butyl 4-{[(6-bromo-3-methyl-2-phenylquinolin-4-yl)carbonyl]amino}-3-(2-ethoxyphenyl)butanoate (40 mg, 98% purity, 64.9 µmol, Example 213A) in dichloromethane (460 µl), and the mixture was stirred at RT for 3 days. The mixture was then concentrated and repeatedly, in succession, dichloromethane was added and the mixture was concentrated again. The residue was purified by preparative HPLC (Method 16). This gave 32 mg (98% purity, 88% of theory) of the title compound.

LC-MS (Method 1): $R_t$=2.00 min; MS (ESIpos): m/z=547/549 [M+H]$^+$ $^1$H-NMR (400 MHz, DMSO-d6) δ [ppm]: −0.008 (2.15), 0.008 (1.15), 1.357 (7.81), 1.374 (16.00), 1.392 (7.54), 2.131 (7.94), 2.327 (0.46), 2.366 (0.53), 2.523 (2.32), 2.681 (6.13), 2.699 (6.24), 3.612 (0.81), 3.626 (1.44), 3.641 (1.57), 3.658 (1.87), 3.669 (2.00), 3.682 (1.94), 3.700 (2.04), 3.716 (1.35), 3.733 (0.46), 3.838 (1.13), 3.856 (1.63), 3.869 (1.52), 3.885 (1.39), 3.902 (0.63), 4.000 (0.43), 4.017 (1.07), 4.024 (1.46), 4.035 (1.99), 4.041 (3.68), 4.050 (3.25), 4.058 (3.67), 4.068 (2.95), 4.075 (1.71), 4.085 (1.07), 4.584 (0.53), 6.870 (1.82), 6.889 (3.70), 6.906 (2.12), 6.955 (3.54), 6.975 (4.16), 7.166 (1.80), 7.169 (2.03), 7.188 (2.95), 7.209 (4.78), 7.228 (3.16), 7.476 (0.97), 7.488 (1.95), 7.491 (2.08), 7.501 (5.51), 7.509 (5.16), 7.521 (13.33), 7.525 (12.65), 7.529 (9.54), 7.533 (7.34), 7.537 (5.94), 7.544 (1.76), 7.696 (1.94), 7.832 (2.65), 7.838 (2.40), 7.855 (3.99), 7.860 (3.78), 7.928 (7.02), 7.950 (4.45), 8.731 (1.63), 8.745 (2.66), 8.759 (1.55).

Example 130

(−)-4-{[(6-Bromo-3-methyl-2-phenylquinolin-4-yl)carbonyl]amino}-3-(2-ethoxyphenyl)butanoic Acid (Enantiomer 1)

TFA (150 µl, 1.9 mmol) was added to a solution of (−)-tert-butyl 4-{[(6-bromo-3-methyl-2-phenylquinolin-4-yl)carbonyl]amino}-3-(2-ethoxyphenyl)butanoate (60 mg, 98% purity, 97.4 µmol, Example 214A) in dichloromethane (690 µl), and the mixture was stirred at RT overnight. Subsequently, TFA (150 µl, 1.9 mmol) was added again, and the mixture was stirred at RT for a further 4 h. The mixture was then concentrated and repeatedly, in succession, dichloromethane was added and the mixture was concentrated again. The residue was purified by preparative HPLC (Method 16). This gave 51 mg (98% purity, 94% of theory, ee 99%) of the title compound.

$[\alpha]_D^{20}$=−14.2°, 589 nm, c=0.36 g/100 ml, methanol

LC-MS (Method 1): $R_t$=1.99 min; MS (ESIpos): m/z=547/549 [M+H]$^+$ $^1$H-NMR (400 MHz, DMSO-d6) δ [ppm]: 1.357 (7.63), 1.374 (16.00), 1.391 (7.66), 2.131 (8.54), 2.328 (0.54), 2.681 (6.29), 2.699 (6.56), 3.613 (0.64), 3.627 (1.35), 3.641 (1.48), 3.658 (1.79), 3.669 (2.00), 3.682 (1.92), 3.700 (2.09), 3.716 (1.39), 3.734 (0.44), 3.838 (1.12), 3.856 (1.61), 3.869 (1.48), 3.886 (1.40), 3.902 (0.57), 4.024 (1.19), 4.041 (3.49), 4.050 (3.11), 4.058 (3.57), 4.067 (2.94), 4.085 (1.01), 6.869 (1.84), 6.888 (4.01), 6.906 (2.25), 6.955 (3.76), 6.975 (4.49), 7.169 (1.94), 7.188 (3.05), 7.209 (4.91), 7.228 (3.30), 7.477 (0.56), 7.492 (1.58), 7.502 (5.44), 7.509 (4.75), 7.521 (13.88), 7.525 (13.53), 7.533 (7.90), 7.696 (2.14), 7.834 (2.65), 7.839 (2.42), 7.856 (4.12), 7.861 (3.96), 7.928 (7.59), 7.951 (4.75), 8.732 (1.55), 8.746 (2.79), 8.760 (1.62).

Example 131

(+)-4-{[(6-Bromo-3-methyl-2-phenylquinolin-4-yl) carbonyl]amino}-3-(2-ethoxyphenyl)butanoic Acid (Enantiomer 2)

TFA (130 µl, 1.6 mmol) was added to a solution of (+)-tert-butyl 4-{[(6-bromo-3-methyl-2-phenylquinolin-4-yl)carbonyl]amino}-3-(2-ethoxyphenyl)butanoate (50 mg, 98% purity, 81.2 µmol, Example 215A) in dichloromethane (580 µl), and the mixture was stirred at RT overnight. Subsequently, TFA (150 µl, 1.9 mmol) was added again, and the mixture was stirred at RT for a further 4 h. The mixture was then concentrated and repeatedly, in succession, dichloromethane was added and the mixture was concentrated again. The residue was purified by preparative HPLC (Method 16). This gave 43 mg (100% purity, 97% of theory, ee 96%) of the title compound.

$[\alpha]_D^{20}$=+15.00, 546 nm, c=0.37 g/100 ml, methanol

LC-MS (Method 1): $R_t$=1.99 min; MS (ESIpos): m/z=547/549 [M+H]$^+$ $^1$H-NMR (400 MHz, DMSO-d6) δ [ppm]: 0.008 (1.19), 1.357 (7.49), 1.374 (16.00), 1.392 (7.67), 2.132 (7.97), 2.524 (1.23), 2.682 (6.05), 2.699 (6.38), 3.613 (0.64), 3.627 (1.28), 3.641 (1.40), 3.659 (1.71), 3.669 (1.87), 3.683 (1.84), 3.700 (2.00), 3.716 (1.30), 3.734 (0.42), 3.838 (0.99), 3.856 (1.53), 3.870 (1.44), 3.886 (1.34), 3.903 (0.56), 4.018 (0.73), 4.024 (1.13), 4.035 (1.63), 4.042 (3.43), 4.051 (3.00), 4.059 (3.54), 4.068 (2.85), 4.075 (1.64), 4.085 (0.97), 6.870 (1.76), 6.889 (3.86), 6.907 (2.19), 6.956 (3.66), 6.976 (4.33), 7.170 (1.87), 7.189 (2.88), 7.209 (4.73), 7.228 (3.18), 7.477 (0.46), 7.492 (1.38), 7.502 (4.96), 7.510 (4.35), 7.522 (12.96), 7.526 (12.44), 7.534 (7.29), 7.537 (6.06), 7.545 (1.75), 7.697 (1.92), 7.834 (2.42), 7.839 (2.25), 7.856 (3.82), 7.861 (3.77), 7.929 (7.09), 7.951 (4.49), 8.733 (1.45), 8.747 (2.65), 8.760 (1.58).

Example 132

(+/−)-4-{[(6-Bromo-3-methyl-2-phenylquinolin-4-yl)carbonyl]amino}-3-(5-fluoro-2-methoxyphenyl)-3-methylbutanoic Acid (Racemate)

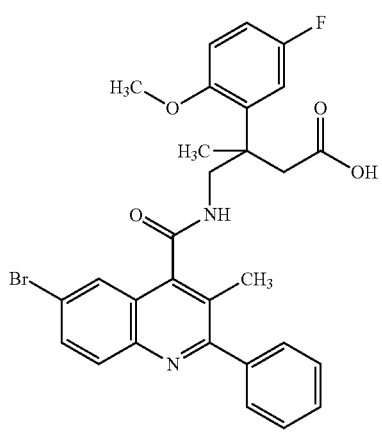 [SMILES: COc1ccc(F)cc1C(C)(CNC(=O)c1c(C)c(-c2ccccc2)nc2ccc(Br)cc12)CC(=O)O]

TFA (190 µl, 2.5 mmol) was added to a solution of (+/−)-tert-butyl 4-{[(6-bromo-3-methyl-2-phenylquinolin-4-yl)carbonyl]amino}-3-(5-fluoro-2-methoxyphenyl)-3-methylbutanoate (80 mg, 98% purity, 126 µmol, Example 216A) in dichloromethane (890 µl), and the mixture was stirred at RT for 3 h. The mixture was then concentrated and repeatedly, in succession, dichloromethane was added and the mixture was concentrated again. The residue was purified by preparative HPLC (Method 16). This gave 63 mg (98% purity, 87% of theory) of the title compound.

LC-MS (Method 1): $R_t$=1.96 min; MS (ESIpos): m/z=565/567 [M+H]$^+$ $^1$H-NMR (500 MHz, DMSO-d6) δ [ppm]: 1.545 (16.00), 2.072 (1.45), 2.630 (4.20), 2.660 (4.55), 3.118 (3.18), 3.148 (2.85), 3.645 (1.16), 3.662 (1.21), 3.787 (0.43), 3.991 (0.88), 4.262 (1.15), 6.980 (2.89), 6.985 (3.88), 7.001 (4.11), 7.006 (5.59), 7.025 (1.87), 7.480 (0.98), 7.489 (2.17), 7.502 (4.86), 7.506 (5.01), 7.519 (11.64), 7.525 (10.85), 7.529 (10.71), 7.832 (2.53), 7.836 (2.44), 7.850 (3.51), 7.854 (3.44), 7.928 (6.72), 7.946 (4.63), 8.529 (1.69), 8.542 (2.64), 8.554 (1.59).

$^1$H-NMR (500 MHz, DMSO-d6): δ [ppm]=11.80 (br. s, 1H), 8.54 (t, 1H), 7.94 (d, 1H), 7.84 (dd, 1H), 7.66 (br. s, 1H), 7.56-7.46 (m, 5H), 7.06-6.94 (m, 3H), 4.33-4.21 (m, 1H), 3.85 (s, 3H), 3.69-3.59 (m, 1H), 3.13 (d, 1H), 2.64 (d, 1H), 2.09 (br. s, 3H), 1.55 (s, 3H).

Example 133

(+)-4-{[(6-Bromo-3-methyl-2-phenylquinolin-4-yl) carbonyl]amino}-3-(5-fluoro-2-methoxyphenyl)-3-methylbutanoic Acid (Enantiomer 1)

TFA (850 µl, 11 mmol) was added to a solution of (+)-tert-butyl 4-{[(6-bromo-3-methyl-2-phenylquinolin-4-yl)carbonyl]amino}-3-(5-fluoro-2-methoxyphenyl)-3-methylbutanoate (350 mg, 98% purity, 552 µmol, Example 217A) in dichloromethane (3.9 ml), and the mixture was stirred at RT overnight. The mixture was then concentrated and repeatedly, in succession, dichloromethane was added and the mixture was concentrated again. The residue was purified by preparative HPLC (Method 16). This gave 256 mg (98% purity, 80% of theory, ee 98%) of the title compound.

[α]$_D^{20}$=+14.2°, 589 nm, c=0.35 g/100 ml, methanol

LC-MS (Method 2): R$_t$=1.04 min; MS (ESIpos): m/z=565/567 [M+H]$^+$ $^1$H-NMR (400 MHz, DMSO-d6) δ [ppm]: −0.008 (2.29), 0.008 (1.82), 1.544 (16.00), 2.073 (1.83), 2.288 (0.43), 2.523 (1.02), 2.624 (4.25), 2.661 (4.92), 3.113 (3.61), 3.151 (3.22), 3.642 (2.21), 3.664 (2.55), 4.260 (1.06), 4.274 (1.01), 6.981 (3.74), 7.008 (7.08), 7.025 (2.13), 7.475 (0.68), 7.487 (1.66), 7.490 (1.82), 7.499 (5.60), 7.508 (5.27), 7.519 (15.60), 7.531 (7.16), 7.643 (0.46), 7.828 (2.57), 7.833 (2.30), 7.850 (3.95), 7.855 (3.70), 7.925 (7.40), 7.947 (4.69), 8.525 (1.67), 8.540 (2.68), 8.555 (1.57).

$^1$H-NMR (400 MHz, DMSO-d6): δ [ppm]=11.84 (br. s, 1H), 8.54 (t, 1H), 7.93 (d, 1H), 7.84 (dd, 1H), 7.64 (br. s, 1H), 7.56-7.45 (m, 5H), 7.07-6.94 (m, 3H), 4.27 (br. dd, 1H), 3.85 (s, 3H), 3.65 (br. dd, 2H), 3.13 (d, 1H), 2.64 (d, 1H), 2.09 (br. s, 3H), 1.54 (s, 3H).

Example 134

(−)-4-{[(6-Bromo-3-methyl-2-phenylquinolin-4-yl)carbonyl]amino}-3-(5-fluoro-2-methoxyphenyl)-3-methylbutanoic Acid (Enantiomer 2)

TFA (610 μl, 7.9 mmol) was added to a solution of (−)-tert-butyl 4-{[(6-bromo-3-methyl-2-phenylquinolin-4-yl)carbonyl]amino}-3-(5-fluoro-2-methoxyphenyl)-3-methylbutanoate (250 mg, 98% purity, 394 μmol, Example 218A) in dichloromethane (2.8 ml), and the mixture was stirred at RT overnight. The mixture was then concentrated and repeatedly, in succession, dichloromethane was added and the mixture was concentrated again. The residue was purified by preparative HPLC (Method 16). This gave 181 mg (98% purity, 80% of theory, ee 98%) of the title compound.

[α]$_D^{20}$=−28.5°, 589 nm, c=0.35 g/100 ml, methanol

LC-MS (Method 2): R$_t$=1.04 min; MS (ESIpos): m/z=565/567 [M+H]$^+$ $^1$H-NMR (400 MHz, DMSO-d6) δ [ppm]: 1.544 (15.55), 2.073 (2.25), 2.327 (0.51), 2.624 (3.82), 2.661 (4.55), 3.113 (3.45), 3.151 (3.03), 3.641 (1.26), 3.665 (1.41), 3.787 (0.56), 4.028 (0.86), 4.259 (1.46), 6.981 (3.61), 7.008 (6.97), 7.024 (2.23), 7.500 (5.47), 7.508 (5.24), 7.519 (16.00), 7.639 (0.53), 7.829 (2.44), 7.834 (2.28), 7.851 (3.80), 7.856 (3.62), 7.925 (6.86), 7.948 (4.33), 8.525 (1.60), 8.541 (2.69), 8.556 (1.58).

$^1$H-NMR (400 MHz, DMSO-d6): δ [ppm]=11.86 (br. s, 1H), 8.54 (t, 1H), 7.93 (d, 1H), 7.84 (dd, 1H), 7.64 (br. s, 1H), 7.56-7.46 (m, 5H), 7.06-6.96 (m, 3H), 4.31-4.22 (m, 1H), 3.85 (s, 3H), 3.70-3.60 (m, 1H), 3.13 (d, 1H), 2.64 (d, 1H), 2.09 (br. s, 3H), 1.54 (s, 3H).

Example 135

(+/−)-4-{[(6-Bromo-3-methyl-2-phenylquinolin-4-yl)carbonyl]amino}-3-(3,5-difluoro-2-methoxyphenyl)-3-methylbutanoic Acid (Racemate)

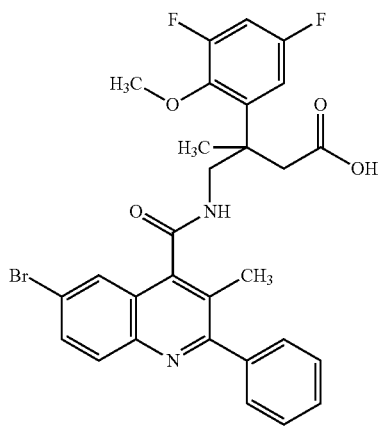 [SMILES: COc1c(F)cc(F)cc1C(C)(CNC(=O)c1c(C)c(-c2ccccc2)nc2ccc(Br)cc12)CC(=O)O]

TFA (190 μl, 2.5 mmol) was added to a solution of (+/−)-tert-butyl 4-{[(6-bromo-3-methyl-2-phenylquinolin-4-yl)carbonyl]amino}-3-(3,5-difluoro-2-methoxyphenyl)-3-methylbutanoate (80 mg, 98% purity, 123 μmol, Example 219A) in dichloromethane (870 μl), and the mixture was stirred at RT overnight. The mixture was then concentrated and repeatedly, in succession, dichloromethane was added and the mixture was concentrated again. The residue was purified by preparative HPLC (Method 16). This gave 57 mg (98% purity, 79% of theory) of the title compound.

LC-MS (Method 2): R$_t$=1.09 min; MS (ESIpos): m/z=583/585 [M+H]$^+$ $^1$H-NMR (400 MHz, DMSO-d6) δ [ppm]: −0.008 (3.94), 0.008 (2.23), 1.159 (0.80), 1.175 (0.84), 1.194 (1.22), 1.205 (0.77), 1.211 (1.25), 1.222 (0.63), 1.433 (1.93), 1.546 (12.64), 2.073 (0.51), 2.159 (1.37), 2.327 (0.41), 2.518 (1.94), 2.523 (1.75), 2.637 (3.40), 2.675 (4.00), 3.121 (2.77), 3.159 (2.42), 3.663 (1.46), 3.677 (1.53), 3.696 (1.70), 3.710 (1.52), 3.964 (16.00), 3.969 (15.16), 4.055 (1.34), 4.072 (1.44), 4.087 (1.26), 4.105 (1.11), 6.885 (1.74), 6.911 (1.64), 7.188 (0.80), 7.194 (0.85), 7.215 (1.30), 7.237 (0.78), 7.480 (0.73), 7.491 (2.15), 7.506 (5.60), 7.512 (4.41), 7.524 (8.54), 7.537 (10.22), 7.556 (1.87), 7.840 (2.15), 7.846 (1.92), 7.863 (3.18), 7.868 (2.92), 7.938 (6.09), 7.961 (3.88), 8.619 (1.48), 8.634 (2.53), 8.649 (1.32).

$^1$H-NMR (400 MHz, DMSO-d6): δ [ppm]=11.99 (br. s, 1H), 8.63 (t, 1H), 7.95 (d, 1H), 7.86 (dd, 1H), 7.63 (br. s, 1H), 7.57-7.45 (m, 5H), 7.27-7.14 (m, 1H), 6.93-6.86 (m, 1H), 4.08 (dd, 1H), 3.97 (d, 3H), 3.69 (dd, 1H), 3.14 (d, 1H), 2.66 (d, 1H), 2.16 (br. s, 3H), 1.55 (s, 3H).

Example 136

(+)-4-{[(6-Bromo-3-methyl-2-phenylquinolin-4-yl)carbonyl]amino}-3-(3,5-difluoro-2-methoxyphenyl)-3-methylbutanoic Acid (Enantiomer 1)

TFA (530 μl, 6.9 mmol) was added to a solution of (+)-tert-butyl 4-{[(6-bromo-3-methyl-2-phenylquinolin-4-yl)carbonyl]amino}-3-(3,5-difluoro-2-methoxyphenyl)-3-methylbutanoate (225 mg, 98% purity, 345 μmol, Example 220A) in dichloromethane (2.4 ml), and the mixture was stirred at RT overnight. The mixture was then concentrated and repeatedly, in succession, dichloromethane was added and the mixture was concentrated again. The residue was purified by preparative HPLC (Method 16). This gave 158 mg (98% purity, 77% of theory, ee 93%) of the title compound.

$[\alpha]_D^{20}=+28.7°$, 589 nm, c=0.35 g/100 ml, methanol

LC-MS (Method 1): $R_t$=2.05 min; MS (ESIpos): m/z=583/585 [M+H]$^+$ $^1$H-NMR (400 MHz, DMSO-d6) δ [ppm]: −0.008 (1.74), 0.007 (1.33), 1.547 (13.49), 2.073 (1.33), 2.159 (1.39), 2.637 (3.51), 2.676 (4.10), 3.121 (2.91), 3.159 (2.57), 3.663 (1.56), 3.677 (1.62), 3.696 (1.81), 3.710 (1.65), 3.964 (16.00), 3.969 (15.76), 4.055 (1.36), 4.072 (1.48), 4.088 (1.30), 4.105 (1.18), 6.885 (1.76), 6.912 (1.74), 7.193 (0.83), 7.215 (1.36), 7.237 (0.81), 7.479 (0.52), 7.492 (1.78), 7.506 (5.43), 7.512 (4.18), 7.524 (8.81), 7.537 (10.58), 7.555 (2.06), 7.841 (2.07), 7.846 (1.91), 7.863 (3.18), 7.868 (3.05), 7.939 (6.26), 7.961 (4.00), 8.619 (1.42), 8.635 (2.66), 8.650 (1.40).

$^1$H-NMR (400 MHz, DMSO-d6): δ [ppm]=12.00 (br. s, 1H), 8.63 (t, 1H), 7.95 (d, 1H), 7.86 (dd, 1H), 7.68 (br. s, 1H), 7.57-7.46 (m, 5H), 7.27-7.17 (m, 1H), 6.90 (d, 1H), 4.08 (dd, 1H), 3.97 (d, 3H), 3.69 (dd, 1H), 3.14 (d, 1H), 2.66 (d, 1H), 2.16 (br. s, 3H), 1.55 (s, 3H).

Example 137

(−)-4-{[(6-Bromo-3-methyl-2-phenylquinolin-4-yl)carbonyl]amino}-3-(3,5-difluoro-2-methoxyphenyl)-3-methylbutanoic Acid (Enantiomer 2)

TFA (530 µl, 6.9 mmol) was added to a solution of (−)-tert-butyl 4-{[(6-bromo-3-methyl-2-phenylquinolin-4-yl)carbonyl]amino}-3-(3,5-difluoro-2-methoxyphenyl)-3-methylbutanoate (225 mg, 98% purity, 345 µmol, Example 221A) in dichloromethane (2.4 ml), and the mixture was stirred at RT overnight. The mixture was then concentrated and repeatedly, in succession, dichloromethane was added and the mixture was concentrated again. The residue was purified by preparative HPLC (Method 16). This gave 159 mg (98% purity, 78% of theory, ee 98%) of the title compound.

$[\alpha]_D^{20}=-31.6°$, 589 nm, c=0.45 g/100 ml, methanol

LC-MS (Method 1): $R_t$=2.05 min; MS (ESIpos): m/z=583/585 [M+H]$^+$ $^1$H-NMR (400 MHz, DMSO-d6) δ [ppm]: −0.008 (0.48), 1.547 (12.71), 2.073 (0.80), 2.160 (1.28), 2.519 (0.84), 2.524 (0.68), 2.638 (3.41), 2.676 (3.97), 3.122 (2.77), 3.160 (2.46), 3.663 (1.63), 3.677 (1.66), 3.696 (1.80), 3.711 (1.64), 3.965 (16.00), 3.970 (15.57), 4.056 (1.31), 4.073 (1.41), 4.089 (1.25), 4.106 (1.13), 6.886 (1.66), 6.913 (1.63), 7.187 (0.69), 7.194 (0.75), 7.216 (1.25), 7.237 (0.75), 7.244 (0.69), 7.480 (0.49), 7.492 (1.79), 7.507 (5.17), 7.513 (3.97), 7.525 (8.15), 7.538 (10.19), 7.557 (1.89), 7.841 (2.06), 7.847 (1.86), 7.864 (3.15), 7.869 (2.99), 7.940 (6.19), 7.962 (3.98), 8.620 (1.35), 8.636 (2.51), 8.651 (1.33).

$^1$H-NMR (400 MHz, DMSO-d6): δ [ppm]=11.99 (br. s, 1H), 8.64 (t, 1H), 7.95 (d, 1H), 7.86 (dd, 1H), 7.67 (br. s, 1H), 7.57-7.46 (m, 5H), 7.26-7.17 (m, 1H), 6.90 (d, 1H), 4.08 (dd, 1H), 3.97 (d, 3H), 3.69 (dd, 1H), 3.14 (d, 1H), 2.66 (d, 1H), 2.16 (br. s, 3H), 1.55 (s, 3H).

Example 138

(+/−)-4-{[(6-Bromo-3-methyl-2-phenylquinolin-4-yl)carbonyl]amino}-3-(4-fluoro-2-methoxyphenyl)-3-methylbutanoic Acid (Racemate)

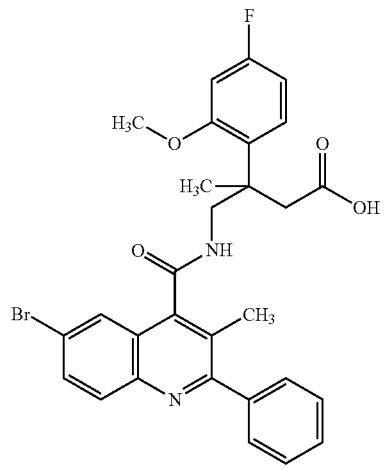 [SMILES: COc1cc(F)ccc1C(C)(CNC(=O)c1c(C)c(-c2ccccc2)nc2ccc(Br)cc12)CC(=O)O]

TFA (190 µl, 2.5 mmol) was added to a solution of (+/−)-tert-butyl 4-{[(6-bromo-3-methyl-2-phenylquinolin-4-yl)carbonyl]amino}-3-(4-fluoro-2-methoxyphenyl)-3-methylbutanoate (80 mg, 98% purity, 126 µmol, Example 222A) in dichloromethane (890 µl), and the mixture was stirred at RT overnight. The mixture was then concentrated and repeatedly, in succession, dichloromethane was added and the mixture was concentrated again. The residue was purified by preparative HPLC (Method 16). This gave 43 mg (98% purity, 59% of theory) of the title compound.

LC-MS (Method 2): $R_t$=1.06 min; MS (ESIpo): m/z=565/567 [M+H]$^+$ $^1$H-NMR (400 MHz, DMSO-d6) δ [ppm]: −0.008 (2.84), 0.008 (2.39), 1.549 (14.23), 2.092 (1.63), 2.286 (0.61), 2.327 (0.44), 2.523 (1.26), 2.594 (4.23), 2.631 (4.77), 2.669 (0.42), 2.853 (0.52), 3.060 (4.14), 3.097 (3.69), 3.603 (3.87), 3.617 (4.23), 3.636 (4.36), 3.649 (4.02), 4.229 (1.86), 4.246 (2.03), 4.261 (1.86), 4.279 (1.71), 6.666 (1.05), 6.672 (1.20), 6.687 (2.07), 6.693 (2.22), 6.708 (1.18), 6.714 (1.17), 6.857 (2.08), 6.863 (2.11), 6.886 (2.19), 6.891 (2.05), 7.192 (2.56), 7.209 (3.14), 7.213 (3.09), 7.231 (2.42), 7.474 (0.64), 7.488 (1.81), 7.498 (5.53), 7.506 (5.27), 7.516 (16.00), 7.528 (7.27), 7.532 (6.20), 7.618 (0.43), 7.645 (0.44), 7.825 (2.60), 7.831 (2.39), 7.848 (4.02), 7.853 (3.90), 7.920 (7.70), 7.943 (4.84), 8.497 (1.71), 8.513 (2.89), 8.528 (1.62).

$^1$H-NMR (400 MHz, DMSO-d6): δ [ppm]=11.81 (br. s, 1H), 8.51 (t, 1H), 7.93 (d, 1H), 7.84 (dd, 1H), 7.66 (br. s, 1H), 7.56-7.45 (m, 5H), 7.21 (dd, 1H), 6.87 (dd, 1H), 6.69 (td, 1H), 4.25 (dd, 1H), 3.86 (s, 3H), 3.63 (dd, 1H, partially obscured), 3.08 (d, 1H), 2.61 (d, 1H), 2.09 (br. s, 3H), 1.55 (s, 3H).

Example 139

(+)-4-{[(6-Bromo-3-methyl-2-phenylquinolin-4-yl)carbonyl]amino}-3-(4-fluoro-2-methoxyphenyl)-3-methylbutanoic Acid (Enantiomer 1)

TFA (1.6 ml, 20 mmol) was added to a solution of (+)-tert-butyl 4-{[(6-bromo-3-methyl-2-phenylquinolin-4- yl)carbonyl]amino}-3-(4-fluoro-2-methoxyphenyl)-3-methylbutanoate (650 mg, 98% purity, 1.02 mmol, Example 223A) in dichloromethane (7.3 ml), and the mixture was stirred at RT overnight. The mixture was then concentrated and repeatedly, in succession, dichloromethane was added and the mixture was concentrated again. The residue was purified by preparative HPLC (Method 16). This gave 553 mg (98% purity, 94% of theory, ee 98%) of the title compound.

$[\alpha]_D^{20}$=+27.5°, 589 nm, c=0.36 g/100 ml, methanol
LC-MS (Method 1): $R_t$=1.98 min; MS (ESIpos): m/z=565/567 [M+H]$^+$ $^1$H-NMR (400 MHz, DMSO-d6) δ [ppm]: −0.008 (1.57), 0.008 (1.42), 1.550 (14.64), 2.030 (0.71), 2.072 (4.01), 2.097 (1.69), 2.286 (0.55), 2.523 (0.91), 2.595 (4.29), 2.632 (4.86), 2.854 (0.49), 3.061 (4.19), 3.097 (3.74), 3.604 (2.68), 3.617 (3.05), 3.636 (3.50), 3.650 (3.52), 3.680 (2.03), 4.230 (1.90), 4.247 (2.09), 4.262 (1.92), 4.280 (1.77), 6.666 (1.07), 6.672 (1.23), 6.688 (2.13), 6.693 (2.28), 6.708 (1.21), 6.714 (1.21), 6.858 (2.13), 6.863 (2.17), 6.886 (2.19), 6.891 (2.11), 7.192 (2.56), 7.210 (3.18), 7.214 (3.14), 7.231 (2.45), 7.475 (0.59), 7.488 (1.77), 7.498 (5.58), 7.506 (5.27), 7.517 (16.00), 7.529 (7.63), 7.613 (0.45), 7.648 (0.45), 7.826 (2.59), 7.831 (2.43), 7.849 (4.03), 7.854 (3.96), 7.921 (7.64), 7.944 (4.84), 8.498 (1.71), 8.513 (2.95), 8.529 (1.67).

$^1$H-NMR (400 MHz, DMSO-d6): δ [ppm]=11.78 (br. s, 1H), 8.51 (t, 1H), 7.93 (d, 1H), 7.84 (dd, 1H), 7.65 (br. s, 1H), 7.55-7.47 (m, 5H), 7.21 (dd, 1H), 6.87 (dd, 1H), 6.69 (td, 1H), 4.25 (dd, 1H), 3.86 (s, 3H), 3.63 (dd, 1H, partially obscured), 3.08 (d, 1H), 2.61 (d, 1H), 2.10 (br. s, 3H), 1.55 (s, 3H).

Example 140

(−)-4-{[(6-Bromo-3-methyl-2-phenylquinolin-4-yl)carbonyl]amino}-3-(4-fluoro-2-methoxyphenyl)-3-methylbutanoic Acid (Enantiomer 2)

TFA (1.7 ml, 21 mmol) was added to a solution of (−)-tert-butyl 4-{[(6-bromo-3-methyl-2-phenylquinolin-4-yl)carbonyl]amino}-3-(4-fluoro-2-methoxyphenyl)-3-methylbutanoate (680 mg, 98% purity, 1.07 mmol, Example 224A) in dichloromethane (7.6 ml), and the mixture was stirred at RT overnight. The mixture was then concentrated and repeatedly, in succession, dichloromethane was added and the mixture was concentrated again. The residue was purified by preparative HPLC (Method 16). This gave 568 mg (98% purity, 92% of theory, ee 98%) of the title compound.

$[\alpha]_D^{20}$=−27.0°, 589 nm, c=0.46 g/100 ml, methanol
LC-MS (Method 1): $R_t$=1.98 min; MS (ESIpos): m/z=565/567 [M+H]$^+$ $^1$H-NMR (400 MHz, DMSO-d6) δ [ppm]: 0.008 (1.45), 1.549 (14.11), 2.073 (1.75), 2.094 (1.73), 2.287 (0.48), 2.523 (1.72), 2.595 (4.05), 2.632 (4.55), 2.854 (0.41), 3.061 (4.00), 3.097 (3.53), 3.604 (1.78), 3.617 (1.92), 3.636 (2.06), 3.650 (1.85), 4.043 (0.45), 4.230 (2.75), 4.248 (2.96), 4.263 (2.80), 4.280 (2.63), 6.672 (1.25), 6.688 (2.10), 6.693 (2.21), 6.708 (1.18), 6.714 (1.15), 6.858 (2.08), 6.863 (2.13), 6.886 (2.16), 6.891 (2.01), 7.192 (2.48), 7.210 (3.10), 7.213 (3.05), 7.231 (2.29), 7.477 (0.75), 7.489 (2.14), 7.500 (5.94), 7.508 (5.81), 7.518 (16.00), 7.618 (0.47), 7.646 (0.47), 7.828 (2.57), 7.833 (2.38), 7.851 (3.89), 7.856 (3.74), 7.923 (7.25), 7.945 (4.55), 8.499 (1.80), 8.515 (2.91), 8.530 (1.64).

$^1$H-NMR (400 MHz, DMSO-d6): δ [ppm]=11.78 (br. s, 1H), 8.51 (t, 1H), 7.93 (d, 1H), 7.84 (dd, 1H), 7.65 (br. s, 1H), 7.56-7.46 (m, 5H), 7.21 (dd, 1H), 6.87 (dd, 1H), 6.69 (td, 1H), 4.26 (dd, 1H), 3.86 (s, 3H), 3.63 (dd, 1H, partially obscured), 3.08 (d, 1H), 2.61 (d, 1H), 2.09 (br. s, 3H), 1.55 (s, 3H).

Example 141

(+/−)-4-{[(6-Bromo-3-methyl-2-phenylquinolin-4-yl)carbonyl]amino}-2,2-difluoro-3-(2-methoxyphenyl)butanoic Acid (Racemate)

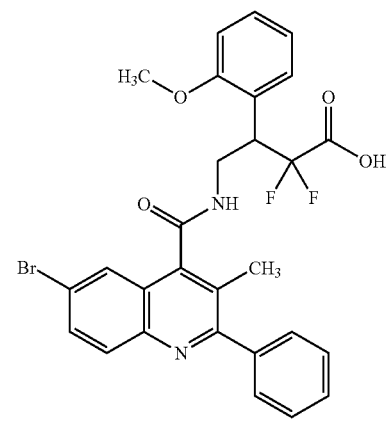 [SMILES: COc1ccccc1C(CNC(=O)c1c(C)c(-c2ccccc2)nc2ccc(Br)cc12)C(F)(F)C(=O)O]

Water (70 μl) and lithium hydroxide (3.2 mg, 134 μM) were added to a mixture of (+/−)-ethyl 4-{[(6-bromo-3-methyl-2-phenylquinolin-4-yl)carbonyl]amino}-2,2-difluoro-3-(2-methoxyphenyl)butanoate and (+/−)-methyl 4-{[(6-bromo-3-methyl-2-phenylquinolin-4-yl)carbonyl] amino}-2,2-difluoro-3-(2-methoxyphenyl)butanoate (40 mg, about 67 μmol, Example 225A) in THF (1 ml), and the mixture was stirred at RT for 1 h. More lithium hydroxide (4.8 mg, 200 μM) was added, and the mixture was stirred at RT for another hour. 1 M hydrochloric acid (350 μl, 330 μmol) was then added, and the mixture was prepurified by preparative HPLC (Chromatorex C18, 10 μm, 125×30 mm, acetonitrile/water gradient with 0.01% TFA). The combined target fractions were concentrated and the residue was lyophilized and then repurified by preparative HPLC (Chromatorex C18, 10 μm, 125×30 mm, acetonitrile/water gradient with 0.01% TFA). The combined target fractions were concentrated and the residue was lyophilized. This gave 13 mg (95% purity, 31% of theory) of the title compound.

LC-MS (Method 1): $R_t$=1.77 min; MS (ESIpos): m/z=569/571 [M+H]$^+$ $^1$H-NMR (600 MHz, DMSO-d6) δ [ppm]: 0.005 (1.53), 1.112 (0.69), 1.162 (0.52), 1.174 (0.86), 1.186 (0.42), 1.383 (0.49), 1.468 (1.69), 2.019 (1.58), 2.386 (0.55), 2.517 (1.58), 2.520 (1.52), 2.523 (1.23), 2.614 (0.58), 3.967 (2.73), 3.976 (1.98), 4.452 (0.53), 4.465 (0.65), 4.479 (0.96), 4.491 (0.98), 4.504 (0.95), 6.976 (0.78), 6.988 (1.48), 7.001 (0.92), 7.016 (2.53), 7.030 (2.72), 7.287 (0.81), 7.300 (1.34), 7.373 (2.30), 7.385 (2.12), 7.473 (0.59), 7.483 (2.04), 7.490 (3.04), 7.500 (15.67), 7.502 (16.00), 7.509 (3.34), 7.514 (2.23), 7.524 (0.92), 7.824 (1.91), 7.828 (1.84), 7.839 (2.64), 7.842 (2.58), 7.910 (5.19), 7.925 (3.69), 8.872 (1.42), 8.882 (2.72), 8.891 (1.42).

$^1$H-NMR (600 MHz, DMSO-d6): δ [ppm]=14.69 (br. s, 1H), 8.88 (t, 1H), 7.92 (d, 1H), 7.83 (dd, 1H), 7.63 (br. s, 1H), 7.54-7.46 (m, 5H), 7.38 (d, 1H), 7.30 (t, 1H), 7.02 (d, 1H), 6.99 (t, 1H), 4.54-4.45 (m, 1H), 4.01-3.91 (m, 2H), 3.75 (s, 3H), 2.02 (br. s, 3H).

Example 142

(+/−)-4-{[(6-Bromo-3-methyl-2-phenylquinolin-4-yl)carbonyl]amino}-3-(2-fluoro-6-methoxyphenyl)-3-methylbutanoic Acid (Racemate)

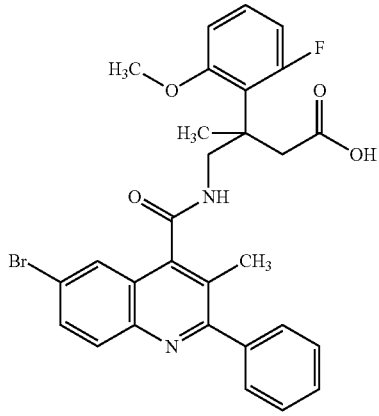 [SMILES: COc1cccc(F)c1C(C)(CNC(=O)c1c(C)c(-c2ccccc2)nc2ccc(Br)cc12)CC(=O)O]

TFA (83 µl, 1.1 mmol) was added to a solution of (+/−)-tert-butyl 4-{[(6-bromo-3-methyl-2-phenylquinolin-4-yl)carbonyl]amino}-3-(2-fluoro-6-methoxyphenyl)-3-methylbutanoate (40 mg, 84% purity, 54 µmol, Example 226A) in dichloromethane (800 µl), and the mixture was allowed to stand at RT overnight. The mixture was then concentrated and repeatedly, in succession, dichloromethane was added and the mixture was concentrated again. The residue was purified by preparative HPLC (Method 15). The combined target fractions were concentrated and the residue was dried under reduced pressure. This gave 30 mg (90% purity, 90% of theory) of the title compound.

LC-MS (Method 1): $R_t$=1.96 min; MS (ESIpos): m/z=565/567 [M+H]$^+$ $^1$H-NMR (400 MHz, DMSO-d6): δ [ppm]=11.67 (br. s, 1H), 8.68 (t, 1H), 7.94 (d, 1H), 7.85 (dd, 1H), 7.64 (br. s, 1H), 7.56-7.46 (m, 5H), 7.26-7.14 (m, 1H), 6.83 (d, 1H), 6.67 (dd, 1H), 4.17 (dd, 1H), 3.83 (s, 3H), 3.67 (dd, 1H), 3.33 (d, 1H), 2.48 (d, 1H, partially obscured), 2.12 (s, 3H), 1.69 (d, 3H).

Example 143

(+)-4-{[(6-Bromo-3-methyl-2-phenylquinolin-4-yl)carbonyl]amino}-3-(2-fluoro-6-methoxyphenyl)-3-methylbutanoic Acid (Enantiomer 1)

TFA (140 µl, 1.8 mmol) was added to a solution of (+)-tert-butyl 4-{[(6-bromo-3-methyl-2-phenylquinolin-4-yl)carbonyl]amino}-3-(2-fluoro-6-methoxyphenyl)-3-methylbutanoate (66 mg, 87% purity, 91.8 µmol, Example 228A) in dichloromethane (1.4 ml), and the mixture was allowed to stand at RT for 3 days. The mixture was then concentrated and repeatedly, in succession, dichloromethane was added and the mixture was concentrated again. The residue was purified by preparative HPLC (Method 15). This gave 56 mg (85% purity, 92% of theory, ee>99%) of the title compound.

$[α]_D^{20}$=+13.8°, 589 nm, c=0.39 g/100 ml, methanol
LC-MS (Method 1): $R_t$=2.07 min; MS (ESIpos): m/z=565/567 [M+H]$^+$ $^1$H-NMR (400 MHz, DMSO-d6): δ [ppm]=8.67 (t, 1H), 7.94 (d, 1H), 7.85 (dd, 1H), 7.64 (br. s, 1H), 7.56-7.47 (m, 5H), 7.25-7.15 (m, 1H), 6.83 (d, 1H), 6.67 (dd, 1H), 4.17 (br. dd, 1H), 3.83 (s, 3H), 3.67 (br. dd, 1H), 3.33 (d, 1H), 2.50 (d, 1H, partially obscured), 2.12 (br. s, 3H), 1.69 (d, 3H).

Example 144

(−)-4-{[(6-Bromo-3-methyl-2-phenylquinolin-4-yl)carbonyl]amino}-3-(2-fluoro-6-methoxyphenyl)-3-methylbutanoic Acid (Enantiomer 2)

TFA (130 µl, 1.6 mmol) was added to a solution of (−)-tert-butyl 4-{[(6-bromo-3-methyl-2-phenylquinolin-4-yl)carbonyl]amino}-3-(2-fluoro-6-methoxyphenyl)-3-methylbutanoate (51 mg, 82.1 µmol, Example 227A) in dichloromethane (1.2 ml), and the mixture was allowed to stand at RT overnight. The mixture was then concentrated and repeatedly, in succession, dichloromethane was added and the mixture was concentrated again. The residue was purified by preparative HPLC (Method 15). This gave 45 mg (100% purity, 96% of theory, ee 96%) of the title compound.

$[α]_D^{20}$=−13.4°, 589 nm, c=0.37 g/100 ml, methanol
LC-MS (Method 1): $R_t$=2.07 min; MS (ESIpos): m/z=565/567 [M+H]$^+$ $^1$H-NMR (400 MHz, DMSO-d6): δ [ppm]=8.68 (t, 1H), 7.94 (d, 1H), 7.85 (dd, 1H), 7.64 (br. s, 1H), 7.57-7.47 (m, 5H), 7.24-7.15 (m, 1H), 6.83 (d, 1H), 6.67 (dd, 1H), 4.17 (dd, 1H), 3.83 (s, 3H), 3.67 (dd, 1H), 3.33 (d, 1H), 2.50 (d, 1H, partially obscured), 2.12 (br. s, 3H), 1.69 (d, 3H).

Example 145

(+/−)-4-{[(6-Bromo-3-methyl-2-phenylquinolin-4-yl)carbonyl]amino}-3-(2-chlorophenyl)pentanoic Acid (Racemate 1)

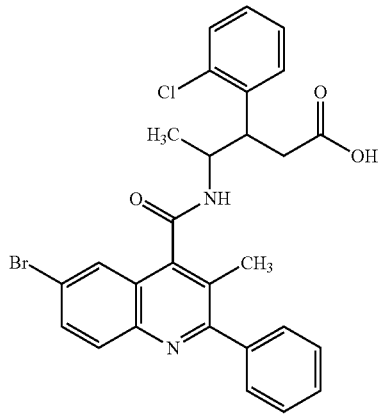 [SMILES: Cc1c(-c2ccccc2)nc2ccc(Br)cc2c1C(=O)NC(C)C(CC(=O)O)c1ccccc1Cl]

TFA (410 µl, 5.4 mmol) was added to a solution of (+/−)-tert-butyl 4-{[(6-bromo-3-methyl-2-phenylquinolin-4-yl)carbonyl]amino}-3-(2-chlorophenyl)pentanoate (109 mg, 179 µmol, Example 230A, racemate 1) in dichloromethane (4.1 ml), and the mixture was allowed to stand at RT for 16 h. The mixture was then concentrated and repeatedly, in succession, dichloromethane was added and the mixture was concentrated again. The residue was purified by preparative HPLC (Method 17). The combined target fractions were concentrated and the residue was lyophilized from acetonitrile/water. This gave 82 mg (100% purity, 83% of theory) of the title compound.

LC-MS (Method 1): R$_t$=1.98 min; MS (ESIpos): m/z=551/553 [M+H]$^+$ $^1$H-NMR (400 MHz, DMSO-d6) δ [ppm]: 0.008 (1.20), 1.237 (13.23), 1.254 (13.14), 1.908 (0.66), 2.073 (0.72), 2.273 (1.13), 2.311 (0.99), 2.327 (0.85), 2.366 (0.56), 2.698 (1.30), 2.710 (0.55), 2.720 (1.29), 2.739 (3.98), 2.761 (4.71), 2.769 (4.90), 2.782 (4.83), 2.809 (1.55), 2.823 (1.22), 3.762 (1.29), 3.783 (2.61), 3.796 (2.76), 3.817 (1.23), 4.656 (1.22), 4.676 (2.24), 4.694 (2.21), 4.713 (1.15), 7.298 (1.38), 7.353 (2.08), 7.422 (2.40), 7.469 (0.98), 7.477 (1.37), 7.490 (3.23), 7.506 (9.56), 7.511 (11.16), 7.524 (16.00), 7.536 (13.89), 7.831 (2.32), 7.853 (3.43), 7.929 (5.38), 7.952 (3.55), 8.767 (1.35).

$^1$H-NMR (400 MHz, DMSO-d6) δ [ppm]: 12.06 (br. s, 1H), 8.77 (br. s, 1H), 7.94 (d, 1H), 7.84 (d, 1H), 7.67-7.15 (m, 10H), 4.78-4.54 (m, 1H), 3.86-3.69 (m, 1H), 2.87-2.63 (m, 2H), 2.44-1.69 (br. m, 3H), 1.25 (d, 3H).

Separation of the Enantiomers:

The title compound (75 mg) was separated into the enantiomers by preparative HPLC on a chiral phase (see Examples 146 and 147) [column: Daicel Chiralpak AD-H, 5 μm, 250 mm×20 mm; flow rate: 40 ml/min; detection: 220 nm; injection: 0.25 ml; mobile phase: 70% heptane/30% ethanol; isocratic]. The combined target fractions were concentrated and the residue was lyophilized from acetonitrile/water.

Example 146

(−)-4-{[(6-Bromo-3-methyl-2-phenylquinolin-4-yl)carbonyl]amino}-3-(2-chlorophenyl)pentanoic Acid (Enantiomer 1)

In the enantiomer separation described in Example 145, 38 mg (100% purity, ee 99%) of the title compound were obtained as the enantiomer that eluted earlier.

[α]$_D^{20}$=−8.3°, 589 nm, c=0.32 g/100 ml, methanol

LC-MS (Method 1): R$_t$=1.97 min; MS (ESIpos): m/z=551/553 [M+H]$^+$ $^1$H-NMR (400 MHz, DMSO-d6) δ [ppm]: −0.008 (2.19), 0.008 (2.01), 1.240 (12.95), 1.256 (12.80), 1.897 (0.65), 2.274 (1.13), 2.312 (0.98), 2.328 (1.02), 2.366 (0.61), 2.670 (0.51), 2.707 (1.20), 2.728 (1.12), 2.747 (3.94), 2.772 (6.13), 2.786 (4.84), 2.813 (1.43), 2.827 (1.08), 3.762 (1.30), 3.783 (2.58), 3.796 (2.77), 3.818 (1.28), 4.501 (1.14), 4.662 (2.03), 4.681 (2.98), 4.699 (2.91), 4.719 (1.83), 7.351 (2.03), 7.423 (2.35), 7.480 (1.28), 7.492 (2.99), 7.508 (9.17), 7.514 (10.79), 7.525 (16.00), 7.538 (13.75), 7.835 (2.31), 7.857 (3.40), 7.931 (5.43), 7.954 (3.52), 8.741 (1.31).

$^1$H-NMR (400 MHz, DMSO-d6) δ [ppm]: 8.74 (br. s, 1H), 7.94 (d, 1H), 7.85 (d, 1H), 7.77-7.13 (m, 10H), 4.76-4.62 (m, 1H), 3.85-3.72 (m, 1H), 2.88-2.64 (m, 2H), 2.39-1.74 (br. m, 3H), 1.25 (d, 3H).

Example 147

(+)-4-{[(6-Bromo-3-methyl-2-phenylquinolin-4-yl)carbonyl]amino}-3-(2-chlorophenyl)pentanoic Acid (Enantiomer 2)

In the enantiomer separation described in Example 145, 38 mg (100% purity, ee 99%) of the title compound were obtained as the enantiomer that eluted later.

[α]$_D^{20}$=+12.0°, 589 nm, c=0.33 g/100 ml, methanol

LC-MS (Method 1): R$_t$=1.97 min; MS (ESIpos): m/z=551/553 [M+H]$^+$ $^1$H-NMR (400 MHz, DMSO-d6) δ [ppm]: −0.008 (2.22), 0.008 (1.95), 1.239 (13.31), 1.256 (13.07), 1.901 (0.65), 2.272 (1.16), 2.311 (0.98), 2.328 (1.06), 2.366 (0.64), 2.670 (0.56), 2.706 (1.25), 2.728 (1.14), 2.747 (4.02), 2.772 (6.21), 2.786 (4.89), 2.813 (1.47), 2.826 (1.10), 3.762 (1.35), 3.783 (2.64), 3.796 (2.83), 3.817 (1.32), 4.370 (1.38), 4.661 (1.70), 4.681 (2.69), 4.698 (2.64), 4.719 (1.54), 7.352 (1.99), 7.422 (2.29), 7.480 (1.20), 7.492 (2.87), 7.508 (9.04), 7.514 (10.65), 7.525 (16.00), 7.538 (13.81), 7.835 (2.29), 7.857 (3.41), 7.931 (5.41), 7.953 (3.58), 8.743 (1.32).

$^1$H-NMR (400 MHz, DMSO-d6) δ [ppm]: 8.74 (br. s, 1H), 7.94 (d, 1H), 7.85 (d, 1H), 7.78-7.11 (m, 10H), 4.76-4.62 (m, 1H), 3.86-3.69 (m, 1H), 2.87-2.61 (m, 2H), 2.39-1.71 (br. m, 3H), 1.25 (d, 3H).

Example 148

(+/−)-4-{[(6-Bromo-3-methyl-2-phenylquinolin-4-yl)carbonyl]amino}-3-(2-chlorophenyl)pentanoic Acid (Racemate 2)

TFA (550 μl, 7.1 mmol) was added to a solution of (+/−)-tert-butyl 4-{[(6-bromo-3-methyl-2-phenylquinolin-4-yl)carbonyl]amino}-3-(2-chlorophenyl)pentanoate (143 mg, 236 μmol, Example 231A, racemate 2, not corrected for purity) in dichloromethane (5.4 ml), and the mixture was allowed to stand at RT for 16 h. The mixture was then concentrated and repeatedly, in succession, dichloromethane was added and the mixture was concentrated again. The residue was purified by preparative HPLC (Method 17). The combined target fractions were concentrated and the residue was lyophilized from acetonitrile/water. This gave 111 mg (100% purity, 86% of theory) of the title compound.

LC-MS (Method 1): R$_t$=2.08 min; MS (ESIpos): m/z=551/553 [M+H]$^+$ $^1$H-NMR (400 MHz, DMSO-d6) δ [ppm]: 0.008 (2.38), 1.120 (15.15), 1.136 (15.18), 2.287 (11.03), 2.366 (0.80), 2.523 (1.59), 2.670 (0.67), 2.710 (0.58), 2.794 (0.75), 2.835 (2.56), 2.863 (6.52), 2.875 (5.06), 2.903 (1.42), 2.915 (0.86), 3.755 (1.32), 3.774 (2.51), 3.791 (2.41), 3.812 (1.29), 4.481 (2.28), 4.500 (2.25), 7.285 (2.60), 7.342 (2.37), 7.361 (3.86), 7.379 (2.19), 7.443 (7.20), 7.458 (8.84), 7.476 (4.56), 7.488 (1.67), 7.507 (4.27), 7.523 (16.00), 7.542 (14.10), 7.557 (5.25), 7.563 (3.96), 7.582 (13.25), 7.585 (13.78), 7.601 (7.42), 7.605 (6.11), 7.712 (1.08), 7.871 (5.30), 7.876 (4.76), 7.893 (7.73), 7.898 (7.35), 7.976 (12.07), 7.998 (7.91), 8.918 (0.82), 12.022 (0.72).

$^1$H-NMR (400 MHz, DMSO-d6) δ [ppm]: 12.02 (br. s, 1H), 8.92 (br. s, 1H), 7.98 (d, 1H), 7.89 (dd, 1H), 7.71 (br. s, 1H), 7.62-7.41 (m, 7H), 7.41-7.23 (m, 2H), 4.58-4.34 (m, 1H), 3.90-3.69 (m, 1H), 2.95-2.74 (m, 2H), 2.29 (br. s, 3H), 1.13 (d, 3H).

Separation of the Enantiomers:

The title compound (100 mg) was dissolved in ethanol (5 ml) and separated into the enantiomers by preparative HPLC on a chiral phase (see Examples 149 and 150) [column: YMC Chiralart Amylose SA, 5 μm, 250 mm×30 mm; flow rate: 30 ml/min; detection: 220 nm; temperature: 50° C.; injection: 0.4 ml; mobile phase: 50% heptane/50% ethanol; run time 9 min, isocratic]. The combined target fractions were concentrated and the residue was lyophilized from acetonitrile/water.

Example 149

(−)-4-{[(6-Bromo-3-methyl-2-phenylquinolin-4-yl)carbonyl]amino}-3-(2-chlorophenyl)pentanoic Acid (Enantiomer 3)

In the enantiomer separation described in Example 148, 51 mg (98% purity, ee 99%) of the title compound were obtained as the enantiomer that eluted earlier.

$[\alpha]_D^{20}$=−43.1°, 589 nm, c=0.31 g/100 ml, methanol

LC-MS (Method 1): $R_t$=2.09 min; MS (ESIpos): m/z=551/553 $[M+H]^+$ $^1$H-NMR (400 MHz, DMSO-d6) δ [ppm]: 1.120 (15.75), 1.136 (16.00), 1.234 (1.04), 1.906 (5.70), 2.287 (11.95), 2.366 (0.59), 2.670 (0.51), 2.709 (0.50), 2.796 (0.79), 2.836 (2.62), 2.863 (6.36), 2.875 (5.02), 2.903 (1.40), 3.757 (1.40), 3.775 (2.72), 3.791 (2.60), 4.482 (2.49), 4.501 (2.48), 7.285 (2.88), 7.342 (2.62), 7.360 (4.13), 7.377 (2.37), 7.442 (7.42), 7.458 (9.11), 7.475 (5.06), 7.506 (4.47), 7.522 (15.99), 7.541 (14.31), 7.556 (5.31), 7.584 (14.44), 7.600 (7.51), 7.708 (1.13), 7.870 (4.75), 7.875 (4.52), 7.893 (6.97), 7.897 (6.98), 7.975 (11.38), 7.997 (7.40), 8.915 (0.92), 12.023 (0.72).

$^1$H-NMR (400 MHz, DMSO-d6) δ [ppm]: 12.02 (br. s, 1H), 8.92 (br. s, 1H), 7.98 (d, 1H), 7.88 (dd, 1H), 7.71 (br. s, 1H), 7.62-7.42 (m, 7H), 7.41-7.23 (m, 2H), 4.56-4.43 (m, 1H), 3.84-3.73 (m, 1H), 2.94-2.75 (m, 2H), 2.29 (br. s, 3H), 1.13 (d, 3H).

Example 150

(+)-4-{[(6-Bromo-3-methyl-2-phenylquinolin-4-yl)carbonyl]amino}-3-(2-chlorophenyl)pentanoic Acid (Enantiomer 4)

In the enantiomer separation described in Example 148, 50 mg (100% purity, ee 99%) of the title compound were obtained as the enantiomer that eluted later.

$[\alpha]_D^{20}$=+44.8°, 589 nm, c=0.34 g/100 ml, methanol

LC-MS (Method 1): $R_t$=2.09 min; MS (ESIpos): m/z=551/553 $[M+H]^+$ $^1$H-NMR (400 MHz, DMSO-d6) δ [ppm]: 1.121 (15.53), 1.137 (15.76), 1.234 (0.98), 1.911 (3.31), 2.288 (11.97), 2.366 (0.64), 2.670 (0.42), 2.710 (0.50), 2.805 (0.74), 2.845 (2.61), 2.869 (6.06), 2.908 (1.29), 3.779 (2.66), 3.795 (2.57), 4.487 (2.46), 4.505 (2.45), 7.287 (2.85), 7.344 (2.57), 7.362 (4.10), 7.379 (2.37), 7.444 (6.97), 7.459 (8.99), 7.476 (5.05), 7.488 (1.97), 7.507 (4.50), 7.523 (16.00), 7.543 (14.48), 7.557 (5.51), 7.563 (4.31), 7.583 (13.32), 7.585 (14.36), 7.601 (7.69), 7.605 (6.62), 7.707 (1.19), 7.871 (5.03), 7.876 (4.79), 7.894 (7.43), 7.899 (7.37), 7.976 (11.53), 7.999 (7.62), 8.896 (1.08), 12.013 (1.09).

$^1$H-NMR (400 MHz, DMSO-d6) δ [ppm]: 12.01 (br. s, 1H), 8.90 (br. s, 1H), 7.99 (d, 1H), 7.89 (dd, 1H), 7.71 (br. s, 1H), 7.63-7.42 (m, 7H), 7.40-7.22 (m, 2H), 4.57-4.41 (m, 1H), 3.85-3.72 (m, 1H), 2.96-2.74 (m, 2H), 2.29 (br. s, 3H), 1.13 (d, 3H).

Example 151

(+/−)-5-{[(6-Bromo-3-methyl-2-phenylquinolin-4-yl)carbonyl]amino}-4-(2-chlorophenyl)pentanoic Acid (Racemate)

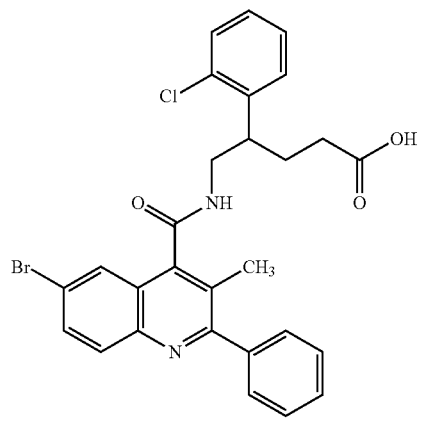 [SMILES: Cc1c(-c2ccccc2)nc2ccc(Br)cc2c1C(=O)NCC(CCC(=O)O)c1ccccc1Cl]

TFA (3.5 ml, 46 mmol) was added to a solution of (+/−)-tert-butyl 5-{[(6-bromo-3-methyl-2-phenylquinolin-4-yl)carbonyl]amino}-4-(2-chlorophenyl)pentanoate (1.40 g, 2.30 mmol, Example 232A) in dichloromethane (16 ml), and the mixture was stirred at RT for 7 h. The mixture was then concentrated and repeatedly dichloromethane was added and the mixture was concentrated again. The residue was purified by preparative HPLC (Method 19). This gave 1.17 g (98% purity, 90% of theory) of the title compound.

LC-MS (Method 1): $R_t$=1.97 min; MS (ESIpos): m/z=551/553 $[M+H]^+$ $^1$H-NMR (400 MHz, DMSO-d6) δ [ppm]: −0.008 (0.75), 1.805 (0.47), 1.824 (0.99), 1.847 (1.30), 1.870 (0.70), 2.034 (0.64), 2.054 (2.58), 2.073 (10.29), 2.089 (2.87), 2.100 (2.84), 2.141 (4.96), 2.170 (1.18), 3.688 (1.28), 3.707 (1.72), 3.720 (2.05), 7.249 (0.90), 7.267 (1.95), 7.286 (1.35), 7.358 (1.18), 7.376 (2.11), 7.394 (1.10), 7.438 (3.36), 7.440 (3.41), 7.458 (2.79), 7.460 (2.78), 7.500 (6.51), 7.508 (4.47), 7.520 (16.00), 7.531 (5.82), 7.694 (0.48), 7.830 (2.13), 7.835 (1.98), 7.853 (3.18), 7.858 (3.14), 7.928 (5.99), 7.950 (3.77), 8.841 (1.29), 8.855 (2.54), 8.870 (1.23).

$^1$H-NMR (400 MHz, DMSO-d6) δ [ppm]: 11.99 (br. s, 1H), 8.86 (t, 1H), 7.94 (d, 1H), 7.85 (dd, 1H), 7.69 (br. s, 1H), 7.56-7.48 (m, 6H), 7.45 (dd, 1H), 7.38 (br. t, 1H), 7.27 (br. t, 1H), 3.87-3.49 (m, 3H), 2.22-2.02 (m, 6H), 1.92-1.71 (m, 1H).

Separation of the Enantiomers:

The title compound (1.0 g) was dissolved in a 1:1 mixture of acetonitrile and methanol (100 ml) and separated into the enantiomers by preparative SFC on a chiral phase (see Examples 152 and 153) [column: Daicel Chiralpak AD-H, 5 μm, 250 mm×30 mm; flow rate: 100 ml/min; detection: 210 nm; temperature: 38° C.; injection: 0.6 ml; mobile phase: 68% carbon dioxide/32% methanol; run time 14 min, isocratic]. The combined target fractions were concentrated and the residue was dried under reduced pressure.

Example 152

(−)-5-{[(6-Bromo-3-methyl-2-phenylquinolin-4-yl)carbonyl]amino}-4-(2-chlorophenyl)pentanoic Acid (Enantiomer 1)

In the enantiomer separation described in Example 151, 518 mg (98% purity, ee 98%) of the title compound were obtained as the enantiomer that eluted earlier. The substance was subsequently lyophilized.

$[\alpha]_D^{20}$=−11.1°, 589 nm, c=0.37 g/100 ml, methanol

LC-MS (Method 1): $R_t$=1.98 min; MS (ESIpos): m/z=551/553 [M+H]$^+$ $^1$H-NMR (400 MHz, DMSO-d6) δ [ppm]: −0.008 (1.55), 0.008 (1.55), 1.031 (0.68), 1.046 (0.70), 1.234 (0.66), 1.284 (1.07), 1.804 (0.44), 1.823 (0.94), 1.846 (1.23), 1.869 (0.68), 2.033 (0.59), 2.053 (2.43), 2.088 (2.71), 2.099 (2.69), 2.140 (4.66), 2.170 (1.18), 2.366 (0.81), 2.710 (0.85), 3.536 (0.42), 3.619 (1.01), 3.719 (1.42), 7.248 (0.88), 7.267 (1.86), 7.286 (1.34), 7.358 (1.16), 7.375 (2.06), 7.394 (1.09), 7.437 (3.50), 7.440 (3.33), 7.457 (2.89), 7.499 (6.46), 7.507 (4.44), 7.519 (16.00), 7.530 (5.52), 7.693 (0.46), 7.829 (2.23), 7.834 (1.99), 7.851 (3.31), 7.856 (3.20), 7.927 (6.22), 7.949 (3.92), 8.839 (1.23), 8.854 (2.39), 8.868 (1.16), 12.043 (1.79).

$^1$H-NMR (400 MHz, DMSO-d6) δ [ppm]: 12.05 (br. s, 1H), 8.85 (t, 1H), 7.94 (d, 1H), 7.84 (dd, 1H), 7.69 (br. s, 1H), 7.56-7.47 (m, 6H), 7.45 (dd, 1H), 7.38 (br. t, 1H), 7.27 (br. t, 1H), 3.83-3.53 (m, 3H), 2.22-2.00 (m, 6H), 1.92-1.74 (m, 1H).

Example 153

(+)-5-{[(6-Bromo-3-methyl-2-phenylquinolin-4-yl)carbonyl]amino}-4-(2-chlorophenyl)pentanoic Acid (Enantiomer 2)

In the enantiomer separation described in Example 151, 496 mg (98% purity, ee 97%) of the title compound were obtained as the enantiomer that eluted later. The substance was subsequently lyophilized.

$[\alpha]_D^{20}$=+16.5°, 589 nm, c=0.44 g/100 ml, methanol

LC-MS (Method 1): $R_t$=1.98 min; MS (ESIpos): m/z=551/553 [M+H]$^+$ $^1$H-NMR (400 MHz, DMSO-d6) δ [ppm]: −0.008 (0.95), 0.008 (0.81), 1.234 (0.60), 1.285 (0.86), 1.805 (0.48), 1.824 (1.03), 1.847 (1.34), 1.870 (0.74), 2.034 (0.66), 2.044 (0.81), 2.054 (2.62), 2.074 (2.15), 2.089 (2.92), 2.100 (2.92), 2.141 (5.04), 2.171 (1.25), 2.523 (0.48), 3.621 (1.09), 3.687 (0.58), 3.707 (1.13), 3.721 (1.56), 3.732 (1.34), 7.248 (0.92), 7.267 (1.98), 7.285 (1.39), 7.357 (1.22), 7.376 (2.16), 7.394 (1.15), 7.437 (3.50), 7.440 (3.25), 7.457 (2.93), 7.460 (2.67), 7.477 (0.67), 7.489 (1.92), 7.499 (6.75), 7.507 (4.65), 7.519 (16.00), 7.530 (5.84), 7.692 (0.46), 7.828 (2.25), 7.834 (1.98), 7.851 (3.36), 7.856 (3.13), 7.927 (6.00), 7.949 (3.83), 8.840 (1.33), 8.855 (2.61), 8.869 (1.26), 12.045 (1.75).

$^1$H-NMR (400 MHz, DMSO-d6) δ [ppm]: 12.05 (br. s, 1H), 8.85 (t, 1H), 7.94 (d, 1H), 7.84 (dd, 1H), 7.69 (br. s, 1H), 7.55-7.48 (m, 6H), 7.45 (dd, 1H), 7.38 (br. t, 1H), 7.27 (br. t, 1H), 3.83-3.55 (m, 3H), 2.22-2.01 (m, 6H), 1.91-1.77 (m, 1H).

Example 154

(+/−)-5-{[(6-Bromo-3-methyl-2-phenylquinolin-4-yl)carbonyl]amino}-4-(2-chlorophenyl)-4-methylpentanoic Acid (Racemate)

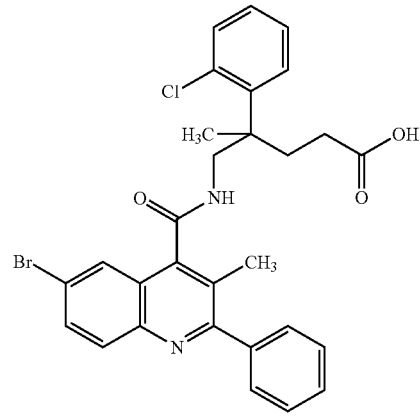 [SMILES: Cc1c(-c2ccccc2)nc2ccc(Br)cc2c1C(=O)NCC(C)(CCC(=O)O)c1ccccc1Cl]

TFA (198 μl, 2.57 mmol) was added to a solution of (+/−)-tert-butyl 5-{[(6-bromo-3-methyl-2-phenylquinolin-4-yl)carbonyl]amino}-4-(2-chlorophenyl)-4-methylpentanoate (80 mg, 129 μmol, Example 233A) in dichloromethane (911 μl), and the mixture was stirred at RT for 7 h. The mixture was then concentrated and repeatedly dichloromethane was added and the mixture was concentrated again. The residue was purified by preparative HPLC (Method 16). The combined target fractions were concentrated and the residue was dried under reduced pressure. This gave 68 mg (98% purity, 92% of theory) of the title compound.

LC-MS (Method 2): $R_t$=1.07 min; MS (ESIpos): m/z=565/567 [M+H]$^+$ $^1$H-NMR (400 MHz, DMSO-d6) δ [ppm]: 0.008 (1.35), 1.382 (0.70), 1.521 (16.00), 1.725 (0.83), 1.737 (0.96), 1.754 (1.30), 1.765 (1.99), 1.776 (1.15), 1.793 (1.58), 1.805 (1.47), 1.889 (1.36), 1.901 (1.55), 1.923 (1.80), 1.934 (1.86), 1.952 (0.95), 1.964 (1.39), 2.006 (1.79), 2.018 (1.52), 2.036 (2.12), 2.046 (2.66), 2.056 (1.85), 2.074 (2.33), 2.086 (2.02), 2.312 (0.43), 2.327 (0.54), 2.366 (0.43), 2.523 (1.26), 2.648 (0.89), 2.660 (1.12), 2.679 (1.55), 2.690 (1.43), 2.710 (1.15), 2.722 (0.71), 3.670 (1.74), 3.683 (1.89), 3.704 (2.07), 3.717 (1.88), 4.342 (2.29), 4.359 (2.49), 4.375 (2.34), 4.393 (2.19), 7.261 (0.91), 7.278 (2.37), 7.302 (2.68), 7.325 (3.06), 7.341 (1.52), 7.414 (4.36), 7.417 (4.44), 7.432 (4.91), 7.446 (2.34), 7.473 (0.77), 7.489 (1.89), 7.499 (6.18), 7.506 (5.65), 7.518 (14.98), 7.522 (13.05), 7.665 (0.52), 7.828 (2.74), 7.833 (2.49), 7.850 (4.25), 7.855 (4.03), 7.924 (7.73), 7.946 (4.92), 8.623 (1.86), 8.638 (3.12), 8.653 (1.90).

Separation of the Enantiomers:

The title compound (55 mg) was dissolved in methanol (10 ml) and separated into the enantiomers by preparative SFC on a chiral phase (see Examples 155 and 156) [column: Daicel Chiralpak AD SFC, 5 μm, 250 mm×20 mm; flow rate: 80 ml/min; detection: 210 nm; temperature: 40° C.; injection: 0.5 ml; mobile phase: 80% carbon dioxide/20% ethanol; run time 18 min, isocratic]. The combined target fractions were concentrated and the residue was dried under reduced pressure.

Example 155

(−)-5-{[(6-Bromo-3-methyl-2-phenylquinolin-4-yl)carbonyl]amino}-4-(2-chlorophenyl)-4-methylpentanoic Acid (Enantiomer 1)

In the enantiomer separation described in Example 154, 17 mg (98% purity, ee 100%) of the title compound were obtained as the enantiomer that eluted earlier.

$[\alpha]_D^{20}$=−38.2°, 589 nm, c=0.27 g/100 ml, methanol

LC-MS (Method 1): $R_t$=2.01 min; MS (ESIpos): m/z=565/567 [M+H]$^+$ $^1$H-NMR (400 MHz, DMSO-d6) δ [ppm]: 1.234 (1.04), 1.520 (16.00), 1.721 (0.73), 1.732 (0.85), 1.750 (1.20), 1.760 (1.83), 1.770 (1.10), 1.788 (1.39), 1.800 (1.29), 1.889 (1.23), 1.901 (1.42), 1.923 (1.74), 1.933 (1.83), 1.952 (0.95), 1.964 (1.36), 2.001 (1.61), 2.013 (1.39), 2.031 (1.96), 2.040 (2.43), 2.069 (1.99), 2.080 (1.89), 2.310 (0.50), 2.328 (0.54), 2.366 (1.55), 2.643 (0.85), 2.655 (1.01), 2.675 (1.74), 2.709 (2.15), 3.313 (12.37), 3.670 (1.67), 3.682 (1.83), 3.703 (1.96), 3.716 (1.80), 4.341 (1.89), 4.358 (2.08), 4.374 (1.89), 4.392 (1.74), 7.259 (1.01), 7.277 (2.52), 7.301 (2.81), 7.324 (3.22), 7.340 (1.48), 7.417 (4.42), 7.432 (4.70), 7.446 (2.56), 7.473 (0.88), 7.488 (2.02), 7.498 (6.28), 7.505 (5.78), 7.516 (14.93), 7.521 (13.32), 7.654 (0.54), 7.825 (2.65), 7.830 (2.52), 7.848 (4.07), 7.853 (4.04), 7.922 (7.57), 7.945 (4.83), 8.631 (1.77), 8.646 (3.00), 8.661 (1.70).

Example 156

(+)-5-{[(6-Bromo-3-methyl-2-phenylquinolin-4-yl)carbonyl]amino}-4-(2-chlorophenyl)-4-methylpentanoic Acid (Enantiomer 2)

In the enantiomer separation described in Example 154, 17 mg (98% purity, ee 100%) of the title compound were obtained as the enantiomer that eluted later.

$[\alpha]_D^{20}$=+40.0°, 589 nm, c=0.27 g/100 ml, methanol

LC-MS (Method 1): $R_t$=2.01 min; MS (ESIpos): m/z=565/567 [M+H]$^+$ $^1$H-NMR (400 MHz, DMSO-d6) δ [ppm]: 1.235 (0.76), 1.520 (16.00), 1.719 (0.74), 1.730 (0.82), 1.758 (1.74), 1.786 (1.33), 1.797 (1.22), 1.889 (1.19), 1.900 (1.38), 1.931 (1.86), 1.963 (1.32), 1.999 (1.58), 2.011 (1.36), 2.039 (2.39), 2.067 (1.93), 2.078 (1.94), 2.309 (0.52), 2.327 (0.73), 2.653 (1.00), 2.672 (1.91), 2.709 (0.93), 3.669 (1.69), 3.682 (1.82), 3.702 (1.98), 3.715 (1.82), 4.341 (1.87), 4.357 (2.07), 4.374 (1.90), 4.391 (1.75), 7.260 (1.10), 7.277 (2.64), 7.300 (2.91), 7.324 (3.28), 7.340 (1.53), 7.417 (4.54), 7.432 (4.81), 7.472 (0.95), 7.497 (6.67), 7.505 (6.14), 7.516 (15.64), 7.670 (0.59), 7.825 (2.88), 7.830 (2.70), 7.847 (4.40), 7.852 (4.24), 7.922 (8.20), 7.945 (5.18), 8.635 (1.78), 8.649 (3.02), 8.664 (1.67).

Example 157

(+/−)-5-{[(6-Bromo-3-methyl-2-phenylquinolin-4-yl)carbonyl]amino}-4-(2-chloro-6-fluorophenyl)pentanoic Acid (Racemate)

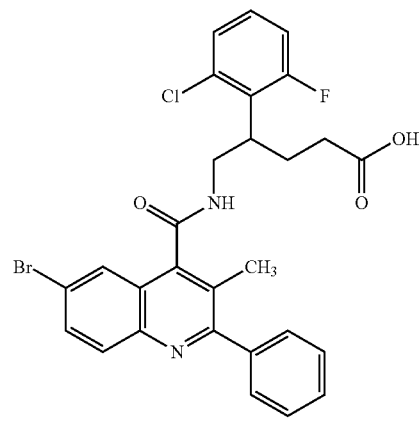 [SMILES: Cc1c(-c2ccccc2)nc2ccc(Br)cc2c1C(=O)NCC(CCC(=O)O)c1c(F)cccc1Cl]

TFA (1.4 ml, 18 mmol) was added to a solution of (+/−)-tert-butyl 5-{[(6-bromo-3-methyl-2-phenylquinolin-4-yl)carbonyl]amino}-4-(2-chloro-6-fluorophenyl)pentanoate (550 mg, 879 μmol, Example 236A) in dichloromethane (8.3 ml), and the mixture was stirred at RT for 16 h. The mixture was then concentrated and repeatedly dichloromethane was added and the mixture was concentrated again. The residue was purified by preparative HPLC (Method 16). The combined target fractions were concentrated and the residue was dried under reduced pressure. This gave 499 mg (98% purity, 98% of theory) of the title compound.

LC-MS (Method 2): $R_t$=1.04 min; MS (ESIpos): m/z=569/571 [M+H]$^+$ $^1$H-NMR (400 MHz, DMSO-d6) δ [ppm]: 0.008 (1.37), 1.965 (0.62), 2.073 (2.03), 2.085 (2.50), 2.110 (2.88), 2.121 (2.94), 2.159 (8.08), 3.749 (1.78), 4.366 (0.42), 7.191 (0.74), 7.205 (1.11), 7.215 (1.29), 7.227 (1.07), 7.242 (1.01), 7.332 (4.41), 7.480 (0.49), 7.492 (1.47), 7.503 (4.44), 7.511 (4.26), 7.522 (16.00), 7.533 (6.25), 7.838 (2.44), 7.844 (2.21), 7.861 (3.71), 7.866 (3.56), 7.933 (6.68), 7.955 (4.19), 8.928 (1.23), 8.942 (2.23).

$^1$H-NMR (400 MHz, DMSO-d6) δ [ppm]: 8.94 (t, 1H), 7.94 (d, 1H), 7.85 (dd, 1H), 7.72 (br. s, 1H), 7.56-7.47 (m, 5H), 7.38-7.28 (m, 2H), 7.26-7.16 (m, 1H), 3.91-3.68 (m, 3H), 2.25-1.88 (m, 7H).

Separation of the Enantiomers:

The title compound (440 mg) was dissolved in 40 ml of a 1:1 mixture of methanol and acetonitrile and separated into the enantiomers by preparative SFC on a chiral phase (see Examples 158 and 159) [column: Daicel Chiralpak AD-H, 5 μm, 250 mm×30 mm; flow rate: 100 ml/min; detection: 210 nm; temperature: 38° C.; injection: 1.2 ml; mobile phase: 68% carbon dioxide/32% isopropanol; run time 16 min, isocratic]. The combined target fractions were concentrated and the residue was dried under reduced pressure.

Example 158

(−)-5-{[(6-Bromo-3-methyl-2-phenylquinolin-4-yl)carbonyl]amino}-4-(2-chloro-6-fluorophenyl)pentanoic Acid (Enantiomer 1)

In the enantiomer separation described in Example 157, 221 mg (98% purity, ee 94%) of the title compound were obtained as the enantiomer that eluted earlier. The substance was subsequently lyophilized.

[α]$_D^{20}$=−28.1°, 589 nm, c=0.35 g/100 ml, methanol

LC-MS (Method 2): R$_t$=1.04 min; MS (ESIpos): m/z=569/571 [M+H]$^+$ $^1$H-NMR (400 MHz, DMSO-d6) δ [ppm]: −0.008 (1.87), 0.008 (1.61), 1.030 (0.60), 1.046 (0.64), 1.966 (0.58), 2.084 (2.34), 2.109 (2.76), 2.119 (2.78), 2.158 (7.85), 2.524 (1.21), 3.748 (1.70), 7.190 (0.73), 7.204 (1.10), 7.214 (1.26), 7.227 (1.07), 7.242 (1.02), 7.331 (4.34), 7.478 (0.51), 7.491 (1.46), 7.501 (4.44), 7.509 (4.32), 7.521 (16.00), 7.527 (7.90), 7.532 (6.22), 7.535 (5.69), 7.836 (2.58), 7.841 (2.27), 7.858 (3.86), 7.864 (3.65), 7.931 (6.90), 7.953 (4.31), 8.926 (1.23), 8.940 (2.16), 12.075 (0.53).

$^1$H-NMR (400 MHz, DMSO-d6) δ [ppm]: 12.08 (br. s, 1H), 8.94 (t, 1H), 7.94 (d, 1H), 7.85 (dd, 1H), 7.72 (br. s, 1H), 7.56-7.46 (m, 5H), 7.37-7.28 (m, 2H), 7.27-7.17 (m, 1H), 3.94-3.66 (m, 3H), 2.23-1.89 (m, 7H).

Example 159

(+)-5-{[(6-Bromo-3-methyl-2-phenylquinolin-4-yl)carbonyl]amino}-4-(2-chloro-6-fluorophenyl)pentanoic Acid (Enantiomer 2)

In the enantiomer separation described in Example 157, 192 mg (98% purity, ee 94%) of the title compound were obtained as the enantiomer that eluted later. The substance was subsequently lyophilized.

[α]$_D^{20}$=+38.2°, 589 nm, c=0.36 g/100 ml, methanol

LC-MS (Method 2): R$_t$=1.04 min; MS (ESIpos): m/z=569/571 [M+H]$^+$ $^1$H-NMR (400 MHz, DMSO-d6) δ [ppm]: 0.008 (1.41), 1.030 (0.64), 1.045 (0.68), 1.235 (0.53), 1.974 (0.64), 2.083 (2.36), 2.108 (2.73), 2.120 (2.76), 2.157 (7.76), 2.328 (0.54), 2.670 (0.42), 3.749 (1.71), 7.214 (1.20), 7.227 (1.08), 7.242 (1.01), 7.331 (4.31), 7.491 (1.41), 7.501 (4.31), 7.509 (4.22), 7.521 (16.00), 7.532 (6.07), 7.836 (2.45), 7.841 (2.22), 7.858 (3.75), 7.863 (3.52), 7.930 (6.91), 7.953 (4.26), 8.940 (2.16), 12.061 (0.45).

$^1$H-NMR (400 MHz, DMSO-d6) δ [ppm]: 12.06 (br. s, 1H), 8.94 (t, 1H), 7.94 (d, 1H), 7.85 (dd, 1H), 7.70 (br. s, 1H), 7.56-7.46 (m, 5H), 7.38-7.29 (m, 2H), 7.27-7.17 (m, 1H), 3.93-3.66 (m, 3H), 2.22-1.91 (m, 7H).

Example 160

(+/−)-5-{[(6-Bromo-3-methyl-2-phenylquinolin-4-yl)carbonyl]amino}-4-(2-methylphenyl)pentanoic Acid (Racemate)

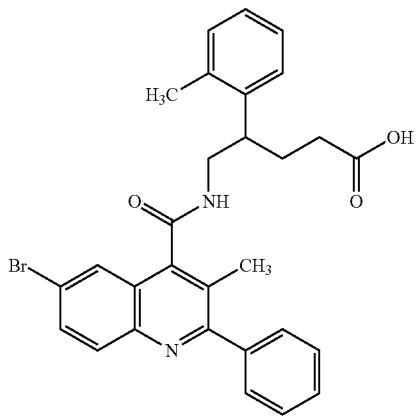 [SMILES: Cc1ccccc1C(CCC(=O)O)CNC(=O)c1c(C)c(-c2ccccc2)nc2ccc(Br)cc12]

TFA (190 μl, 2.5 mmol) was added to a solution of (+/−)-tert-butyl 5-{[(6-bromo-3-methyl-2-phenylquinolin-4-yl)carbonyl]amino}-4-(2-methylphenyl)pentanoate (75 mg, 98% purity, 125 μmol, Example 237A) in dichloromethane (890 μl), and the mixture was stirred at RT overnight. The mixture was then concentrated and repeatedly dichloromethane was added and the mixture was concentrated again. The residue was purified by preparative HPLC (Method 16). The combined target fractions were concentrated and the residue was dried under reduced pressure. This gave 53 mg (98% purity, 77% of theory) of the title compound.

LC-MS (Method 1): R$_t$=2.00 min; MS (ESIpos): m/z=531/533 [M+H]$^+$ $^1$H-NMR (400 MHz, DMSO-d6) δ [ppm]: −0.008 (2.21), 0.008 (1.47), 1.777 (0.46), 1.793 (0.92), 1.818 (1.16), 1.837 (0.65), 2.026 (0.86), 2.044 (1.56), 2.053 (1.38), 2.073 (7.16), 2.082 (4.15), 2.107 (3.35), 2.331 (16.00), 2.523 (0.68), 3.320 (1.12), 3.338 (1.22), 3.367 (0.50), 3.478 (1.02), 3.490 (1.29), 3.510 (1.62), 3.524 (1.69), 3.540 (1.39), 3.714 (2.22), 3.733 (2.42), 3.749 (2.03), 3.765 (1.75), 3.784 (1.14), 3.864 (0.50), 7.095 (0.75), 7.113 (2.01), 7.131 (1.76), 7.167 (3.35), 7.184 (1.90), 7.194 (1.17), 7.214 (1.95), 7.232 (1.07), 7.304 (3.11), 7.323 (2.15), 7.477 (0.44), 7.491 (1.29), 7.501 (4.06), 7.509 (3.74), 7.521 (12.71), 7.533 (5.68), 7.685 (0.58), 7.834 (2.00), 7.839 (1.81), 7.857 (3.08), 7.862 (2.94), 7.933 (5.59), 7.955 (3.59), 8.827 (1.27), 8.842 (1.97), 8.856 (1.25).

Example 161

(−)-5-{[(6-Bromo-3-methyl-2-phenylquinolin-4-yl)carbonyl]amino}-4-(2-methylphenyl)pentanoic Acid (Enantiomer 1)

TFA (290 μl, 3.7 mmol) was added to a solution of (−)-tert-butyl 5-{[(6-bromo-3-methyl-2-phenylquinolin-4-yl)carbonyl]amino}-4-(2-methylphenyl)pentanoate (110 mg, 187 μmol, Example 238A) in dichloromethane (1.3 ml), and the mixture was stirred at RT overnight. The mixture was then concentrated and repeatedly dichloromethane was added and the mixture was concentrated again. The residue was purified by preparative HPLC (Method 16). The combined target fractions were concentrated and the residue was dried under reduced pressure. This gave 85 mg (98% purity, ee 99%, 84% of theory) of the title compound.

[α]$_D^{20}$=−14.4°, 589 nm, c=0.36 g/100 ml, methanol

LC-MS (Method 2): R$_t$=1.05 min; MS (ESIpos): m/z=531/533 [M+H]$^+$ $^1$H-NMR (400 MHz, DMSO-d6) δ [ppm]: 0.008 (0.72), 1.762 (0.40), 1.778 (0.57), 1.793 (1.03), 1.817 (1.22), 1.837 (0.68), 2.026 (1.10), 2.045 (1.96), 2.054 (1.92), 2.073 (7.90), 2.082 (4.58), 2.100 (3.49), 2.107 (3.68), 2.283 (0.50), 2.299 (0.90), 2.331 (16.00), 2.523 (1.16), 3.320 (1.18), 3.338 (1.22), 3.367 (0.40), 3.478 (0.84), 3.490 (1.08), 3.510 (1.29), 3.524 (1.25), 3.539 (0.76), 3.715 (0.95), 3.733 (1.43), 3.750 (1.25), 3.766 (1.11), 3.785 (0.63), 7.095 (0.90), 7.113 (2.15), 7.131 (1.88), 7.167 (3.49), 7.184 (2.07), 7.194 (1.30), 7.213 (2.03), 7.231 (1.10), 7.304 (3.20), 7.323 (2.18), 7.478 (0.88), 7.491 (2.00), 7.501 (4.88), 7.509 (4.69), 7.521 (13.16), 7.533 (5.93), 7.686 (0.65), 7.834 (2.17), 7.840 (1.93), 7.857 (3.18), 7.862 (2.93), 7.933 (5.55), 7.955 (3.53), 8.827 (1.43), 8.841 (2.07), 8.855 (1.26).

¹H-NMR (400 MHz, DMSO-d6) δ [ppm]: 11.98 (br. s, 1H), 8.84 (t, 1H), 7.94 (d, 1H), 7.85 (dd, 1H), 7.69 (br. s, 1H), 7.56-7.45 (m, 5H), 7.34-7.28 (m, 1H), 7.26-7.06 (m, 3H), 3.81-3.69 (m, 1H), 3.56-3.46 (m, 1H), 3.39-3.26 (m, 1H), 2.33 (s, 3H), 2.18-1.98 (m, 6H), 1.87-1.74 (m, 1H).

Example 162

(+)-5-{[(6-Bromo-3-methyl-2-phenylquinolin-4-yl)carbonyl]amino}-4-(2-methylphenyl)pentanoic Acid (Enantiomer 2)

TFA (290 µl, 3.7 mmol) was added to a solution of (+)-tert-butyl 5-{[(6-bromo-3-methyl-2-phenylquinolin-4-yl)carbonyl]amino}-4-(2-methylphenyl)pentanoate (110 mg, 187 µmol, Example 239A) in dichloromethane (1.3 ml), and the mixture was stirred at RT overnight. Subsequently, TFA (140 µl, 1.9 mmol) was added again, and the mixture was stirred at RT for a further night.

This was followed by concentration of the mixture, and repeated additions of dichloromethane followed by concentration again. The residue was purified by preparative HPLC (Method 16). The combined target fractions were concentrated and the residue was dried under reduced pressure. This gave 88 mg (98% purity, ee 99%, 86% of theory) of the title compound.

$[\alpha]_D^{20}$=+15.5°, 589 nm, c=0.37 g/100 ml, methanol

LC-MS (Method 2): $R_t$=1.05 min; MS (ESIpos): m/z=531/533 [M+H]⁺

¹H-NMR (400 MHz, DMSO-d6) δ [ppm]: 0.008 (0.97), 1.778 (0.45), 1.793 (0.92), 1.818 (1.14), 1.837 (0.65), 2.026 (0.83), 2.044 (1.53), 2.053 (1.37), 2.073 (7.18), 2.082 (4.17), 2.107 (3.40), 2.331 (16.00), 2.523 (0.69), 3.320 (1.07), 3.338 (1.15), 3.366 (0.40), 3.478 (0.74), 3.490 (1.00), 3.510 (1.23), 3.524 (1.22), 3.539 (0.77), 3.714 (0.92), 3.733 (1.43), 3.750 (1.28), 3.766 (1.19), 3.785 (0.75), 7.095 (0.76), 7.113 (2.03), 7.131 (1.77), 7.167 (3.35), 7.184 (1.93), 7.194 (1.17), 7.214 (1.92), 7.231 (1.05), 7.304 (3.11), 7.323 (2.14), 7.478 (0.50), 7.488 (1.24), 7.491 (1.42), 7.501 (4.18), 7.509 (3.98), 7.521 (12.74), 7.532 (5.63), 7.535 (4.82), 7.543 (1.04), 7.685 (0.58), 7.834 (2.12), 7.839 (1.87), 7.857 (3.22), 7.862 (3.01), 7.933 (5.66), 7.955 (3.64), 8.827 (1.30), 8.841 (1.98), 8.855 (1.22).

¹H-NMR (400 MHz, DMSO-d6) δ [ppm]: 12.01 (br. s, 1H), 8.84 (t, 1H), 7.94 (d, 1H), 7.85 (dd, 1H), 7.69 (br. s, 1H), 7.55-7.47 (m, 5H), 7.35-7.28 (m, 1H), 7.25-7.08 (m, 3H), 3.80-3.69 (m, 1H), 3.56-3.45 (m, 1H), 3.39-3.27 (m, 1H), 2.33 (s, 3H), 2.19-2.00 (m, 6H), 1.86-1.74 (m, 1H).

Example 163

(+/−)-5-{[(6-Bromo-3-methyl-2-phenylquinolin-4-yl)carbonyl]amino}-4-(2-chloro-5-fluorophenyl)pentanoic Acid (Racemate)

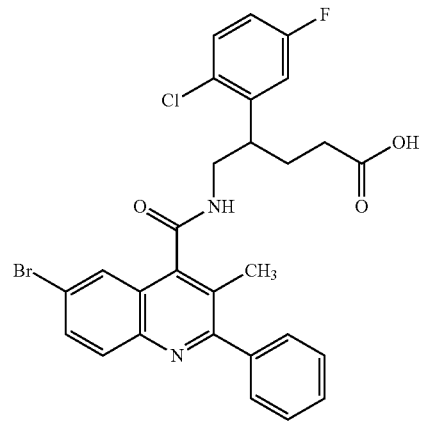 [SMILES: Cc1c(-c2ccccc2)nc2ccc(Br)cc2c1C(=O)NCC(CCC(=O)O)c1cc(F)ccc1Cl]

TFA (150 µl, 1.9 mmol) was added to a solution of (+/−)-tert-butyl 5-{[(6-bromo-3-methyl-2-phenylquinolin-4-yl)carbonyl]amino}-4-(2-chloro-5-fluorophenyl)pentanoate (60 mg, 95.9 µmol, Example 240A) in dichloromethane (680 µl), and the mixture was stirred at RT overnight. Subsequently, TFA (150 µl, 1.9 mmol) was added again, and the mixture was stirred at RT for a further 24 h. This was followed by concentration of the mixture, and repeated additions of dichloromethane followed by concentration again. The residue was purified by preparative HPLC (Method 16). The combined target fractions were concentrated and the residue was dried under reduced pressure. This gave 48 mg (98% purity, 86% of theory) of the title compound.

LC-MS (Method 1): $R_t$=2.00 min; MS (ESIpos): m/z=569/571 [M+H]⁺

¹H-NMR (400 MHz, DMSO-d6) δ [ppm]: 1.819 (1.01), 1.839 (1.23), 2.031 (0.98), 2.062 (2.52), 2.088 (2.22), 2.101 (2.02), 2.110 (2.52), 2.140 (8.20), 2.158 (2.61), 2.181 (0.91), 3.612 (1.09), 3.739 (2.47), 4.055 (1.13), 7.119 (0.79), 7.139 (1.42), 7.409 (1.76), 7.416 (1.87), 7.434 (1.85), 7.442 (1.75), 7.481 (2.77), 7.494 (3.57), 7.502 (5.96), 7.509 (4.48), 7.520 (16.00), 7.531 (5.82), 7.663 (0.43), 7.833 (2.34), 7.838 (2.11), 7.855 (3.52), 7.860 (3.44), 7.930 (6.44), 7.952 (4.06), 8.847 (1.27), 8.862 (2.54), 8.876 (1.24).

¹H-NMR (400 MHz, DMSO-d6) δ [ppm]: 8.86 (t, 1H), 7.94 (d, 1H), 7.85 (dd, 1H), 7.66 (br. s, 1H), 7.56-7.47 (m, 6H), 7.43 (dd, 1H), 7.18-7.09 (m, 1H), 3.79-3.55 (m, 3H), 2.22-1.99 (m, 6H), 1.88-1.76 (m, 1H).

Example 164

(−)-5-{[(6-Bromo-3-methyl-2-phenylquinolin-4-yl)carbonyl]amino}-4-(2-chloro-5-fluorophenyl)pentanoic Acid (Enantiomer 1)

TFA (3.3 ml, 43 mmol) was added to a solution of (−)-tert-butyl 5-{[(6-bromo-3-methyl-2-phenylquinolin-4-yl)carbonyl]amino}-4-(2-chloro-5-fluorophenyl)pentanoate (1.56 g, 86% purity, 2.14 mmol, Example 241A) in dichloromethane (15 ml), and the mixture was stirred at RT overnight. The mixture was then concentrated and repeatedly dichloromethane was added and the mixture was concentrated again. The residue was twice purified by preparative HPLC (Method 16). The combined target fractions were concentrated and the residue was dried under reduced pressure. This gave 949 mg (98% purity, ee 99%, 76% of theory) of the title compound.

$[\alpha]_D^{20}$=−22.2°, 589 nm, c=0.42 g/100 ml, methanol

LC-MS (Method 1): $R_t$=1.97 min; MS (ESIpos): m/z=569/571 [M+H]$^+$ $^1$H-NMR (400 MHz, DMSO-d6) δ [ppm]: −0.008 (2.07), 1.797 (0.50), 1.819 (1.05), 1.840 (1.25), 1.861 (0.74), 2.018 (0.76), 2.031 (1.01), 2.050 (1.19), 2.061 (2.61), 2.073 (0.72), 2.088 (2.28), 2.101 (2.05), 2.110 (2.52), 2.140 (8.45), 2.158 (2.74), 2.181 (0.93), 2.198 (0.44), 3.615 (1.02), 3.738 (2.40), 7.119 (0.79), 7.139 (1.41), 7.154 (0.82), 7.408 (1.88), 7.416 (1.91), 7.434 (1.91), 7.441 (1.83), 7.480 (2.72), 7.494 (3.60), 7.502 (5.20), 7.508 (4.41), 7.519 (16.00), 7.529 (5.73), 7.830 (2.18), 7.835 (2.03), 7.853 (3.29), 7.858 (3.25), 7.928 (5.99), 7.950 (3.83), 8.845 (1.32), 8.860 (2.66), 8.874 (1.26), 12.066 (1.15).

$^1$H-NMR (400 MHz, DMSO-d6) δ [ppm]: 12.07 (br. s, 1H), 8.86 (t, 1H), 7.94 (d, 1H), 7.85 (dd, 1H), 7.66 (br. s, 1H), 7.55-7.47 (m, 6H), 7.42 (dd, 1H), 7.18-7.09 (m, 1H), 3.82-3.55 (m, 3H), 2.21-1.98 (m, 6H), 1.91-1.76 (m, 1H).

Example 165

(+)-5-{[(6-Bromo-3-methyl-2-phenylquinolin-4-yl)carbonyl]amino}-4-(2-chloro-5-fluorophenyl)pentanoic Acid (Enantiomer 2)

TFA (3.0 ml, 39 mmol) was added to a solution of (+)-tert-butyl 5-{[(6-bromo-3-methyl-2-phenylquinolin-4-yl)carbonyl]amino}-4-(2-chloro-5-fluorophenyl)pentanoate (1.26 g, 98% purity, 1.97 mmol, Example 242A) in dichloromethane (14 ml), and the mixture was stirred at RT overnight. The mixture was then concentrated and repeatedly dichloromethane was added and the mixture was concentrated again. The residue was purified by preparative HPLC (Method 16). The combined target fractions were concentrated and the residue was dried under reduced pressure. This gave 1.03 g (98% purity, ee 95%, 89% of theory) of the title compound.

$[\alpha]_D^{20}$=+20.1°, 589 nm, c=0.38 g/100 ml, methanol

LC-MS (Method 1): $R_t$=1.97 min; MS (ESIpos): m/z=569/571 [M+H]$^+$ $^1$H-NMR (400 MHz, DMSO-d6) δ [ppm]: −0.008 (2.01), 0.008 (1.76), 1.796 (0.49), 1.819 (1.03), 1.828 (0.64), 1.840 (1.24), 1.861 (0.71), 2.018 (0.76), 2.031 (1.00), 2.049 (1.19), 2.061 (2.63), 2.073 (0.82), 2.088 (2.31), 2.101 (2.07), 2.110 (2.51), 2.140 (8.28), 2.158 (2.73), 2.181 (0.94), 2.198 (0.45), 2.523 (0.64), 3.616 (1.00), 3.738 (2.38), 7.119 (0.77), 7.139 (1.37), 7.154 (0.82), 7.408 (1.85), 7.416 (1.90), 7.434 (1.90), 7.441 (1.82), 7.480 (2.76), 7.494 (3.67), 7.500 (5.17), 7.508 (4.41), 7.519 (16.00), 7.530 (5.70), 7.830 (2.31), 7.835 (2.07), 7.853 (3.49), 7.858 (3.30), 7.928 (6.23), 7.950 (3.98), 8.845 (1.30), 8.860 (2.64), 8.874 (1.26), 12.067 (1.03).

$^1$H-NMR (400 MHz, DMSO-d6) δ [ppm]: 12.07 (br. s, 1H), 8.86 (t, 1H), 7.94 (d, 1H), 7.85 (dd, 1H), 7.66 (br. s, 1H), 7.56-7.47 (m, 6H), 7.42 (dd, 1H), 7.18-7.10 (m, 1H), 3.83-3.54 (m, 3H), 2.22-1.99 (m, 6H), 1.90-1.76 (m, 1H).

Example 166

(+/−)-5-{[(6-Bromo-3-methyl-2-phenylquinolin-4-yl)carbonyl]amino}-4-(2-methoxyphenyl)pentanoic Acid (Racemate)

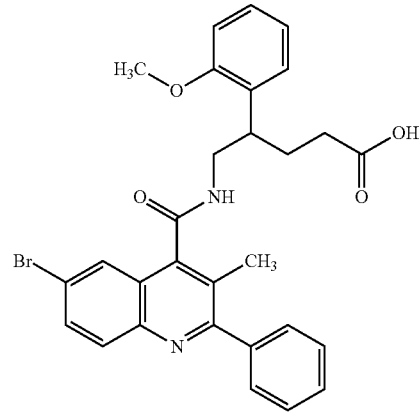 [SMILES: COc1ccccc1C(CCC(=O)O)CNC(=O)c1c(C)c(-c2ccccc2)nc2ccc(Br)cc12]

TFA (100 μl, 1.3 mmol) was added to a solution of (+/−)-tert-butyl 5-{[(6-bromo-3-methyl-2-phenylquinolin-4-yl)carbonyl]amino}-4-(2-methoxyphenyl)pentanoate (40 mg, 98% purity, 64.9 μmol, Example 243A) in dichloromethane (460 μl), and the mixture was stirred at RT overnight. The mixture was then concentrated and repeatedly dichloromethane was added and the mixture was concentrated again. The residue was purified by preparative HPLC (Method 16). The combined target fractions were concentrated and the residue was dried under reduced pressure. This gave 35 mg (98% purity, 96% of theory) of the title compound.

LC-MS (Method 1): $R_t$=1.96 min; MS (ESIpos): m/z=547/549 [M+H]$^+$ $^1$H-NMR (400 MHz, DMSO-d6) δ [ppm]: 1.195 (0.72), 1.212 (0.73), 1.776 (0.74), 1.802 (1.20), 1.816 (1.27), 1.853 (0.50), 1.985 (1.24), 2.004 (1.49), 2.016 (2.88), 2.049 (4.81), 2.075 (3.56), 2.092 (1.80), 2.146 (7.88), 2.328 (0.67), 2.367 (0.76), 2.670 (0.44), 2.731 (1.81), 2.890 (2.22), 3.401 (1.49), 3.620 (0.86), 3.636 (1.30), 3.653 (1.88), 3.668 (2.28), 3.683 (1.42), 3.704 (1.55), 3.721 (2.03), 3.740 (2.03), 4.988 (0.72), 6.927 (1.69), 6.946 (3.49), 6.964 (2.23), 6.979 (3.61), 6.999 (4.03), 7.200 (1.99), 7.220 (3.32), 7.228 (4.01), 7.246 (3.29), 7.492 (2.11), 7.502 (5.02), 7.510 (5.09), 7.522 (16.00), 7.707 (1.77), 7.832 (2.38), 7.838 (2.30), 7.855 (3.59), 7.860 (3.61), 7.928 (6.05), 7.950 (4.12), 8.757 (1.62), 8.772 (2.96), 8.786 (1.60).

$^1$H-NMR (400 MHz, DMSO-d6) δ [ppm]: 8.77 (br. t, 1H), 7.94 (d, 1H), 7.85 (dd, 1H), 7.71 (br. s, 1H), 7.57-7.46 (m, 5H), 7.27-7.18 (m, 2H), 7.02-6.89 (m, 2H), 3.78 (s, 3H), 3.77-3.60 (m, 2H), 3.46-3.34 (m, 1H), 2.19-1.94 (m, 6H), 1.88-1.73 (m, 1H).

Example 167

(−)-5-{[(6-Bromo-3-methyl-2-phenylquinolin-4-yl)carbonyl]amino}-4-(2-methoxyphenyl)pentanoic Acid (Enantiomer 1)

TFA (150 μl, 1.9 mmol) was added to a solution of (−)-tert-butyl 5-{[(6-bromo-3-methyl-2-phenylquinolin-4-yl)carbonyl]amino}-4-(2-methoxyphenyl)pentanoate (60 mg, 98% purity, 97.4 µmol, Example 244A) in dichloromethane (690 µl), and the mixture was stirred at RT overnight. Subsequently, TFA (150 µl, 1.9 mmol) was added again, and the mixture was stirred at RT for a further 3 h. This was followed by concentration of the mixture, and repeated additions of dichloromethane followed by concentration again. The residue was purified by preparative HPLC (Method 16). The combined target fractions were concentrated and the residue was lyophilized. This gave 51 mg (98% purity, ee 97%, 93% of theory) of the title compound.

$[\alpha]_D^{20}$=−12.6°, 589 nm, c=0.37 g/100 ml, methanol

LC-MS (Method 2): $R_t$=1.05 min; MS (ESIpos): m/z=547/549 [M+H]$^+$ $^1$H-NMR (400 MHz, DMSO-d6) δ [ppm]: −0.008 (1.92), 0.008 (1.56), 1.776 (0.63), 1.801 (1.03), 1.815 (1.14), 1.829 (0.88), 1.839 (0.64), 1.853 (0.42), 1.984 (0.94), 1.997 (1.05), 2.004 (1.10), 2.016 (2.66), 2.043 (3.49), 2.048 (4.43), 2.074 (3.42), 2.092 (1.49), 2.114 (0.98), 2.145 (7.48), 2.523 (1.02), 3.399 (1.46), 3.599 (0.77), 3.620 (1.26), 3.634 (1.77), 3.652 (2.54), 3.667 (3.10), 3.682 (2.34), 3.703 (2.65), 3.719 (3.18), 3.739 (3.19), 3.756 (2.77), 3.953 (0.59), 6.927 (1.56), 6.945 (3.49), 6.964 (2.06), 6.979 (3.60), 6.998 (4.19), 7.200 (1.81), 7.219 (3.06), 7.227 (3.89), 7.239 (1.91), 7.246 (3.28), 7.477 (0.49), 7.490 (1.47), 7.500 (4.51), 7.508 (4.29), 7.520 (16.00), 7.531 (6.55), 7.705 (1.50), 7.829 (2.44), 7.834 (2.20), 7.851 (3.77), 7.856 (3.62), 7.926 (6.85), 7.948 (4.37), 8.755 (1.48), 8.770 (2.95), 8.784 (1.47).

$^1$H-NMR (400 MHz, DMSO-d6) δ [ppm]: 12.00 (br. s, 1H), 8.77 (t, 1H), 7.93 (d, 1H), 7.85 (dd, 1H), 7.71 (br. s, 1H), 7.55-7.46 (m, 5H), 7.27-7.18 (m, 2H), 7.01-6.91 (m, 2H), 3.78 (s, 3H), 3.77-3.61 (m, 2H), 3.46-3.33 (m, 1H), 2.19-1.95 (m, 6H), 1.87-1.74 (m, 1H).

Example 168

(+)-5-{[(6-Bromo-3-methyl-2-phenylquinolin-4-yl)carbonyl]amino}-4-(2-methoxyphenyl)pentanoic Acid (Enantiomer 2)

TFA (140 µl, 1.8 mmol) was added to a solution of (+)-tert-butyl 5-{[(6-bromo-3-methyl-2-phenylquinolin-4-yl)carbonyl]amino}-4-(2-methoxyphenyl)pentanoate (55 mg, 98% purity, 89.3 µmol, Example 245A) in dichloromethane (630 µl), and the mixture was stirred at RT overnight. Subsequently, TFA (140 µl, 1.8 mmol) was added again, and the mixture was stirred at RT for a further 4 h. This was followed by concentration of the mixture, and repeated additions of dichloromethane followed by concentration again. The residue was purified by preparative HPLC (Method 16). The combined target fractions were concentrated and the residue was lyophilized. This gave 46 mg (98% purity, ee 99%, 92% of theory) of the title compound.

$[\alpha]_D^{20}$=+14.1°, 589 nm, c=0.35 g/100 ml, methanol

LC-MS (Method 2): $R_t$=1.05 min; MS (ESIpos): m/z=547/549 [M+H]$^+$ $^1$H-NMR (400 MHz, DMSO-d6) δ [ppm]: −0.008 (0.42), 1.802 (0.63), 1.815 (0.70), 1.828 (0.53), 1.984 (0.57), 1.997 (0.64), 2.004 (0.65), 2.016 (1.63), 2.043 (2.14), 2.048 (2.70), 2.074 (2.10), 2.092 (0.92), 2.114 (0.59), 2.145 (4.55), 2.524 (0.53), 3.400 (1.05), 3.431 (0.60), 3.619 (2.56), 3.633 (2.25), 3.652 (2.13), 3.667 (2.07), 3.682 (1.32), 3.703 (1.21), 3.719 (1.35), 3.739 (1.22), 3.756 (0.91), 3.776 (16.00), 6.927 (0.96), 6.946 (2.13), 6.964 (1.26), 6.979 (2.22), 6.998 (2.60), 7.200 (1.12), 7.219 (1.89), 7.227 (2.40), 7.239 (1.18), 7.246 (2.03), 7.490 (0.90), 7.500 (2.81), 7.508 (2.70), 7.520 (9.88), 7.527 (5.03), 7.531 (4.00), 7.534 (3.68), 7.704 (0.90), 7.829 (1.57), 7.834 (1.40), 7.851 (2.41), 7.856 (2.30), 7.926 (4.33), 7.948 (2.78), 8.755 (0.91), 8.770 (1.80), 8.784 (0.90).

$^1$H-NMR (400 MHz, DMSO-d6) δ [ppm]: 11.97 (br. s, 1H), 8.77 (t, 1H), 7.93 (d, 1H), 7.85 (dd, 1H), 7.70 (br. s, 1H), 7.56-7.44 (m, 5H), 7.26-7.18 (m, 2H), 7.02-6.91 (m, 2H), 3.78 (s, 3H), 3.76-3.61 (m, 2H), 3.45-3.35 (m, 1H), 2.20-1.94 (m, 6H), 1.87-1.73 (m, 1H).

Example 169

(+/−)-5-{[(6-Bromo-3-methyl-2-phenylquinolin-4-yl)carbonyl]amino}-4-(2-chloro-5-fluorophenyl)-4-methylpentanoic Acid (Racemate)

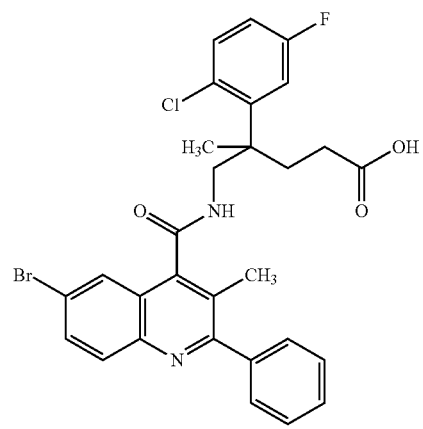 [SMILES: Cc1c(-c2ccccc2)nc2ccc(Br)cc2c1C(=O)NCC(C)(CCC(=O)O)c1cc(F)ccc1Cl]

TFA (69 µl, 900 µmol) was added to a solution of (+/−)-tert-butyl 5-{[(6-bromo-3-methyl-2-phenylquinolin-4-yl)carbonyl]amino}-4-(2-chloro-5-fluorophenyl)-4-methylpentanoate (40 mg, 72% purity, 45.0 µmol, Example 246A) in dichloromethane (320 µl), and the mixture was stirred at RT for 48 h. Subsequently, TFA (69 µl, 900 µmol) was added again, and the mixture was stirred at RT for a further 24 h. This was followed by concentration of the mixture, and repeated additions of dichloromethane followed by concentration again. The residue was purified by preparative HPLC (Method 15). The combined target fractions were concentrated and ethyl acetate and saturated sodium bicarbonate solution (10 ml each) were added to the residue which was agitated. After phase separation, the aqueous phase was extracted twice with ethyl acetate (10 ml each time). The combined organic phases were dried over sodium sulfate, filtered and concentrated, and the residue was dried under reduced pressure. This gave 25 mg (98% purity, 93% of theory) of the title compound.

LC-MS (Method 2): $R_t$=1.09 min; MS (ESIpos): m/z=583/585 [M+H]$^+$ $^1$H-NMR (400 MHz, DMSO-d6) δ [ppm]: 1.233 (0.75), 1.334 (0.50), 1.475 (16.00), 1.555 (0.62), 1.592 (1.31), 1.617 (0.98), 1.853 (0.95), 1.877 (1.37), 1.914 (1.56), 1.951 (1.24), 2.146 (2.24), 2.259 (0.40), 2.327 (0.62), 2.366 (0.44), 2.669 (0.59), 2.710 (0.42), 3.327 (4.51), 3.698 (1.25), 4.301 (1.03), 7.119 (1.15), 7.139 (2.08), 7.160 (1.25), 7.217 (2.04), 7.246 (2.10), 7.445 (1.49), 7.468 (1.99), 7.484 (2.99), 7.499 (6.68), 7.504 (5.17), 7.518 (9.57), 7.532 (11.52), 7.644 (0.86), 7.820 (2.62), 7.825 (2.41), 7.842 (3.95), 7.847 (3.88), 7.921 (7.11), 7.943 (4.62), 9.110 (0.51).

$^1$H-NMR (400 MHz, DMSO-d6) δ [ppm]: 9.11 (br. s, 1H), 7.93 (d, 1H), 7.84 (dd, 1H), 7.64 (br. s, 1H), 7.57-7.42 (m, 6H), 7.23 (br. d, 1H), 7.18-7.07 (m, 1H), 4.39-4.25 (m, 1H), 3.77-3.62 (m, 1H), 2.49-2.40 (m, 1H, partially obscured), 2.15 (br. s, 3H), 2.02-1.79 (m, 2H), 1.67-1.52 (m, 1H), 1.47 (s, 3H).

Example 170

(−)-5-{[(6-Bromo-3-methyl-2-phenylquinolin-4-yl) carbonyl]amino}-4-(2-chloro-5-fluorophenyl)-4-methylpentanoic Acid (Enantiomer 1)

TFA (72 µl, 940 µmol) was added to a solution of (−)-tert-butyl 5-{[(6-bromo-3-methyl-2-phenylquinolin-4-yl)carbonyl]amino}-4-(2-chloro-5-fluorophenyl)-4-methylpentanoate (60 mg, 93.8 µmol, Example 247A) in dichloromethane (690 µl), and the mixture was allowed to stand at RT overnight. The mixture was then concentrated and repeatedly dichloromethane was added and the mixture was concentrated again. The residue was purified by preparative HPLC (Method 16). The combined target fractions were concentrated and ethyl acetate and saturated sodium bicarbonate solution (10 ml each) were added to the residue which was agitated. After phase separation, the aqueous phase was extracted twice with ethyl acetate (10 ml each time). The combined organic phases were dried over sodium sulfate, filtered and concentrated, and the residue was lyophilized. This gave 48 mg (98% purity, 86% of theory) of the title compound.

$[\alpha]_D^{20}$=−10.4°, 589 nm, c=0.25 g/100 ml, methanol

LC-MS (Method 1): $R_t$=2.05 min; MS (ESIpos): m/z=583/585 [M+H]$^+$ $^1$H-NMR (400 MHz, DMSO-d6) δ [ppm]: 1.463 (16.00), 1.744 (1.05), 1.761 (1.23), 1.776 (0.90), 1.998 (1.25), 2.016 (1.10), 2.165 (5.53), 2.332 (1.41), 2.353 (1.27), 2.366 (1.37), 2.670 (0.74), 2.710 (0.64), 3.736 (0.94), 4.244 (0.86), 7.101 (1.05), 7.108 (1.30), 7.127 (2.15), 7.141 (1.37), 7.149 (1.42), 7.256 (1.82), 7.281 (1.92), 7.435 (1.75), 7.450 (2.12), 7.457 (2.03), 7.471 (2.15), 7.485 (2.13), 7.500 (7.01), 7.518 (8.09), 7.538 (9.99), 7.556 (2.99), 7.655 (3.04), 7.816 (2.46), 7.821 (2.31), 7.839 (3.72), 7.844 (3.66), 7.919 (6.26), 7.942 (4.16).

$^1$H-NMR (400 MHz, DMSO-d6) δ [ppm]: 9.45 (br. s, 1H), 7.93 (d, 1H), 7.83 (dd, 1H), 7.65 (br. s, 1H), 7.58-7.41 (m, 6H), 7.27 (br. d, 1H), 7.16-7.08 (m, 1H), 4.24 (br. s, 1H), 3.74 (br. s, 1H), 2.42-2.29 (m, 1H), 2.17 (br. s, 3H), 2.07-1.93 (m, 1H), 1.83-1.68 (m, 1H), 1.46 (s, 3H), 1.55-1.43 (m, 1H).

Example 171

(+)-5-{[(6-Bromo-3-methyl-2-phenylquinolin-4-yl) carbonyl]amino}-4-(2-chloro-5-fluorophenyl)-4-methylpentanoic Acid (Enantiomer 2)

TFA (96 µl, 1.3 mmol) was added to a solution of (+)-tert-butyl 5-{[(6-bromo-3-methyl-2-phenylquinolin-4-yl)carbonyl]amino}-4-(2-chloro-5-fluorophenyl)-4-methylpentanoate (80 mg, 125 µmol, Example 248A) in dichloromethane (920 µl), and the mixture was allowed to stand at RT overnight. The mixture was then concentrated and repeatedly dichloromethane was added and the mixture was concentrated again. The residue was purified by preparative HPLC (Method 16). The combined target fractions were concentrated and ethyl acetate and saturated sodium bicarbonate solution (10 ml each) were added to the residue which was agitated. After phase separation, the aqueous phase was extracted twice with ethyl acetate (10 ml each time). The combined organic phases were dried over sodium sulfate, filtered and concentrated, and the residue was lyophilized. This gave 68 mg (98% purity, 91% of theory) of the title compound.

$[\alpha]_D^{20}$=+14.5°, 589 nm, c=0.25 g/100 ml, methanol

LC-MS (Method 1): $R_t$=2.05 min; MS (ESIpos): m/z=583/585 [M+H]$^+$ $^1$H-NMR (400 MHz, DMSO-d6) δ [ppm]: −0.149 (0.46), 0.147 (0.46), 1.462 (16.00), 1.743 (1.16), 1.761 (1.28), 2.007 (1.21), 2.168 (6.38), 2.327 (1.98), 2.366 (1.39), 2.669 (1.02), 2.689 (2.41), 2.710 (0.78), 2.731 (0.91), 2.890 (0.88), 3.731 (0.89), 4.213 (0.83), 7.109 (1.31), 7.128 (2.20), 7.142 (1.34), 7.148 (1.37), 7.261 (1.83), 7.286 (1.85), 7.435 (1.90), 7.450 (2.20), 7.457 (2.12), 7.472 (2.30), 7.485 (2.25), 7.500 (7.08), 7.518 (7.99), 7.539 (9.68), 7.558 (2.92), 7.656 (3.56), 7.816 (2.46), 7.821 (2.36), 7.838 (3.76), 7.843 (3.65), 7.919 (6.25), 7.941 (4.07), 9.524 (0.41).

$^1$H-NMR (400 MHz, DMSO-d6) δ [ppm]: 9.52 (br. s, 1H), 7.93 (d, 1H), 7.83 (dd, 1H), 7.66 (br. s, 1H), 7.57-7.42 (m, 6H), 7.27 (br. d, 1H), 7.16-7.09 (m, 1H), 4.22 (br. s, 1H), 3.73 (br. s, 1H), 2.40-2.27 (m, 1H), 2.17 (br. s, 3H), 2.07-1.95 (m, 1H), 1.83-1.70 (m, 1H), 1.49 (m, 1H), 1.46 (s, 3H).

Example 172

(+/−)-5-{[(6-Bromo-3-methyl-2-phenylquinolin-4-yl)carbonyl]amino}-4-(2-chloro-3,6-difluorophenyl) pentanoic Acid (Racemate)

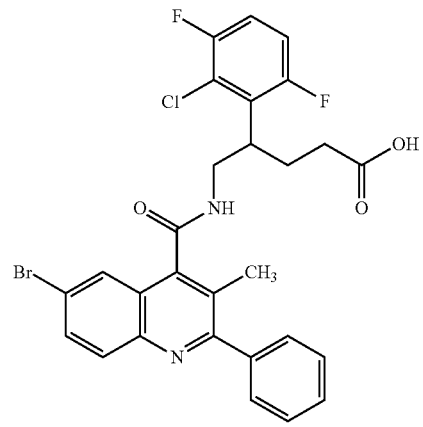 [SMILES: Cc1c(-c2ccccc2)nc2ccc(Br)cc2c1C(=O)NCC(CCC(=O)O)c1c(F)ccc(F)c1Cl]

TFA (120 µl, 1.6 mmol) was added to a solution of (+/−)-tert-butyl 5-{[(6-bromo-3-methyl-2-phenylquinolin-4-yl)carbonyl]amino}-4-(2-chloro-3,6-difluorophenyl)pentanoate (100 mg, 155 µmol, Example 249A) in dichloromethane (1.1 ml), and the mixture was allowed to stand at RT for 5 days. The mixture was then concentrated and repeatedly dichloromethane was added and the mixture was concentrated again. The residue was purified by preparative HPLC (Method 16). The combined target fractions were concentrated and the residue was lyophilized. This gave 81 mg (96% purity, 85% of theory) of the title compound.

LC-MS (Method 2): $R_t$=1.07 min; MS (ESIpos): m/z=587/589 [M+H]$^+$ $^1$H-NMR (400 MHz, DMSO-d6) δ [ppm]: −0.008 (2.48), 0.008 (2.23), 1.366 (1.46), 1.374 (1.01), 1.989 (0.64), 2.077 (1.02), 2.090 (1.26), 2.096 (1.29), 2.111 (2.28), 2.153 (8.77), 2.187 (1.59), 2.209 (0.60), 2.225 (0.43), 2.524 (0.98), 3.761 (1.41), 3.801 (1.14), 7.270 (0.60), 7.281 (0.72), 7.294 (1.33), 7.304 (1.38), 7.318 (1.03), 7.329 (0.90), 7.406 (1.25), 7.415 (1.25), 7.482 (0.54), 7.495 (1.55), 7.505 (4.63), 7.513 (4.55), 7.524 (16.00), 7.535 (6.42), 7.538 (5.67), 7.844 (2.39), 7.849 (2.16), 7.866 (3.69), 7.871 (3.52), 7.938 (6.67), 7.960 (4.19), 8.942 (1.21), 8.956 (2.17).

¹H-NMR (400 MHz, DMSO-d6) δ [ppm]: 8.96 (t, 1H), 7.95 (d, 1H), 7.86 (dd, 1H), 7.72 (br. s, 1H), 7.56-7.48 (m, 5H), 7.45-7.37 (m, 1H), 7.35-7.25 (m, 1H), 3.95-3.68 (m, 3H), 2.26-1.92 (m, 7H).

Example 173

(−)-5-{[(6-Bromo-3-methyl-2-phenylquinolin-4-yl)carbonyl]amino}-4-(2-chloro-3,6-difluorophenyl)pentanoic Acid (Enantiomer 1)

TFA (290 μl, 3.7 mmol) was added to a solution of (−)-tert-butyl 5-{[(6-bromo-3-methyl-2-phenylquinolin-4-yl)carbonyl]amino}-4-(2-chloro-3,6-difluorophenyl)pentanoate (240 mg, 373 μmol, Example 250A) in dichloromethane (2.7 ml), and the mixture was allowed to stand at RT for 2 days. The mixture was then concentrated and repeatedly dichloromethane was added and the mixture was concentrated again. The residue was taken up in acetonitrile and purified by preparative HPLC (Method 15). The combined target fractions were concentrated and the residue was lyophilized. This gave 212 mg (100% purity, ee>95%, 97% of theory) of the title compound.

[α]$_D^{20}$=−39.2°, 589 nm, c=0.34 g/100 ml, methanol
LC-MS (Method 1): R$_t$=1.99 min; MS (ESIpos): m/z=587/589 [M+H]⁺

¹H-NMR (400 MHz, DMSO-d6) δ [ppm]: 0.008 (1.93), 1.990 (0.67), 2.073 (3.12), 2.097 (1.31), 2.112 (2.29), 2.154 (9.13), 2.187 (1.62), 2.210 (0.58), 2.524 (0.76), 3.762 (1.50), 3.803 (1.22), 4.388 (0.53), 7.270 (0.59), 7.281 (0.72), 7.294 (1.36), 7.304 (1.41), 7.319 (1.05), 7.330 (0.90), 7.405 (1.27), 7.415 (1.22), 7.482 (0.54), 7.495 (1.55), 7.505 (4.66), 7.513 (4.50), 7.524 (16.00), 7.535 (6.51), 7.843 (2.34), 7.849 (2.11), 7.866 (3.63), 7.871 (3.44), 7.938 (6.46), 7.960 (4.05), 8.942 (1.26), 8.957 (2.25).

¹H-NMR (400 MHz, DMSO-d6) δ [ppm]: 11.97 (br. s, 1H), 8.96 (t, 1H), 7.95 (d, 1H), 7.86 (dd, 1H), 7.72 (br. s, 1H), 7.57-7.47 (m, 5H), 7.45-7.37 (m, 1H), 7.35-7.24 (m, 1H), 3.94-3.67 (m, 3H), 2.25-1.90 (m, 7H).

Example 174

(+)-5-{[(6-Bromo-3-methyl-2-phenylquinolin-4-yl)carbonyl]amino}-4-(2-chloro-3,6-difluorophenyl)pentanoic Acid (Enantiomer 2)

TFA (300 μl, 3.9 mmol) was added to a solution of (+)-tert-butyl 5-{[(6-bromo-3-methyl-2-phenylquinolin-4-yl)carbonyl]amino}-4-(2-chloro-3,6-difluorophenyl)pentanoate (250 mg, 388 μmol, Example 251A) in dichloromethane (2.9 ml), and the mixture was allowed to stand at RT for 2 days. The mixture was then concentrated and repeatedly dichloromethane was added and the mixture was concentrated again. The residue was taken up in acetonitrile and purified by preparative HPLC (Method 15). The combined target fractions were concentrated and the residue was lyophilized. This gave 217 mg (100% purity, ee 98%, 95% of theory) of the title compound.

[α]$_D^{20}$=+37.4°, 589 nm, c=0.36 g/100 ml, methanol
LC-MS (Method 1): R$_t$=1.99 min; MS (ESIpos): m/z=587/589 [M+H]⁺

¹H-NMR (400 MHz, DMSO-d6) δ [ppm]: −0.008 (3.25), 0.008 (2.24), 1.990 (0.66), 2.073 (2.48), 2.097 (1.28), 2.111 (2.23), 2.153 (8.83), 2.186 (1.54), 2.209 (0.55), 2.524 (1.02), 3.740 (2.63), 7.270 (0.59), 7.281 (0.71), 7.294 (1.32), 7.304 (1.37), 7.319 (1.03), 7.329 (0.88), 7.405 (1.24), 7.415 (1.20), 7.494 (1.50), 7.504 (4.49), 7.512 (4.34), 7.523 (16.00), 7.535 (6.16), 7.842 (2.29), 7.847 (2.09), 7.864 (3.52), 7.870 (3.33), 7.936 (6.38), 7.959 (3.98), 8.940 (1.22), 8.955 (2.16).

¹H-NMR (400 MHz, DMSO-d6) δ [ppm]: 12.10 (br. s, 1H), 8.95 (t, 1H), 7.94 (d, 1H), 7.86 (dd, 1H), 7.72 (br. s, 1H), 7.56-7.47 (m, 5H), 7.46-7.36 (m, 1H), 7.34-7.26 (m, 1H), 3.83-3.62 (m, 3H), 2.24-1.90 (m, 7H).

Example 175

(+/−)-5-{[(6-Bromo-3-methyl-2-phenylquinolin-4-yl)carbonyl]amino}-4-(2-fluorophenyl)pentanoic Acid (Racemate)

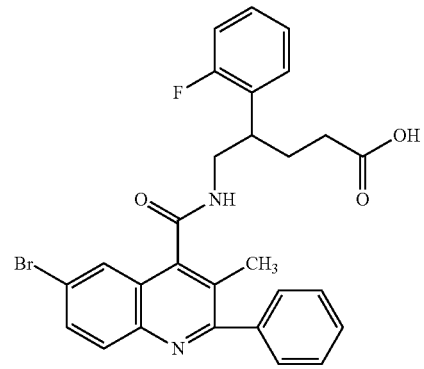 [SMILES: Cc1c(-c2ccccc2)nc2ccc(Br)cc2c1C(=O)NCC(CCC(=O)O)c1ccccc1F]

TFA (650 μl, 8.5 mmol) was added to a solution of (+/−)-tert-butyl 5-{[(6-bromo-3-methyl-2-phenylquinolin-4-yl)carbonyl]amino}-4-(2-fluorophenyl)pentanoate (500 mg, 845 μmol, Example 252A) in dichloromethane (6.2 ml), and the mixture was allowed to stand at RT overnight. The mixture was then concentrated and repeatedly dichloromethane was added and the mixture was concentrated again. The residue was taken up in acetonitrile and purified by preparative HPLC (Method 16). The combined target fractions were concentrated and the residue was lyophilized. Ethyl acetate and saturated sodium bicarbonate solution (10 ml each) were added to the lyophilizate, which was then agitated. After phase separation, the aqueous phase was extracted twice with ethyl acetate (10 ml each time). The combined organic phases were dried over sodium sulfate, filtered and concentrated, and the residue was lyophilized. This gave 449 mg (98% purity, 97% of theory) of the title compound.

LC-MS (Method 1): R$_t$=1.90 min; MS (ESIpos): m/z=535/537 [M+H]⁺

¹H-NMR (400 MHz, DMSO-d6) δ [ppm]: 1.788 (0.55), 1.805 (0.74), 1.814 (0.87), 1.828 (0.96), 1.839 (0.68), 1.850 (0.52), 2.033 (0.88), 2.045 (1.01), 2.060 (2.26), 2.069 (1.20), 2.086 (3.57), 2.094 (4.79), 2.117 (4.38), 2.134 (2.79), 2.155 (1.10), 3.347 (0.85), 3.359 (0.89), 3.368 (0.87), 3.637 (0.46), 3.651 (0.80), 3.670 (1.01), 3.684 (1.39), 3.697 (0.75), 3.735 (0.60), 3.753 (0.87), 3.771 (0.75), 7.144 (1.24), 7.166 (1.93), 7.191 (2.44), 7.208 (2.20), 7.226 (1.54), 7.271 (0.78), 7.286 (1.30), 7.302 (1.25), 7.324 (0.53), 7.401 (1.30), 7.404 (1.30), 7.419 (2.25), 7.438 (1.13), 7.490 (1.36), 7.502 (3.61), 7.510

(4.01), 7.520 (16.00), 7.834 (1.78), 7.839 (1.57), 7.857 (2.72), 7.861 (2.48), 7.929 (5.01), 7.951 (3.11), 8.853 (1.26), 8.868 (2.06), 8.882 (1.09).

$^1$H-NMR (400 MHz, DMSO-d6) δ [ppm]: 8.87 (t, 1H), 7.94 (d, 1H), 7.85 (dd, 1H), 7.68 (br. s, 1H), 7.55-7.46 (m, 5H), 7.45-7.38 (m, 1H), 7.36-7.25 (m, 1H), 7.25-7.13 (m, 2H), 3.83-3.72 (m, 1H), 3.71-3.62 (m, 1H), 3.41-3.30 (m, 1H), 2.20-1.99 (m, 6H), 1.88-1.75 (m, 1H).

Separation of the Enantiomers:

The title compound (400 mg) was dissolved in methanol (20 ml) and separated into the enantiomers by preparative SFC on a chiral phase (see Examples 176 and 177) [column: Daicel Chiralpak AD, 5 µm 250 mm×20 mm; flow rate: 80 ml/min; detection: 210 nm; temperature: 40° C.; injection: 1.0 ml; mobile phase: 21% acetonitrile/79% carbon dioxide; run time 13 min, isocratic]. The combined target fractions were concentrated and the residue was dried under reduced pressure.

Example 176

(−)-5-{[(6-Bromo-3-methyl-2-phenylquinolin-4-yl)carbonyl]amino}-4-(2-fluorophenyl)pentanoic Acid (Enantiomer 1)

In the enantiomer separation described in Example 175, 128 mg (98% purity, ee 96%) of the title compound were obtained as the enantiomer that eluted earlier.

$[α]_D^{20}$=−32.2°, 589 nm, c=0.34 g/100 ml, methanol

LC-MS (Method 2): $R_t$=1.00 min; MS (ESIpos): m/z=535/537 [M+H]$^+$ $^1$H-NMR (400 MHz, DMSO-d6) δ [ppm]: −0.008 (2.76), 0.008 (1.82), 1.785 (0.53), 1.812 (0.78), 1.826 (0.88), 1.847 (0.53), 2.030 (1.00), 2.056 (2.16), 2.073 (2.12), 2.083 (3.51), 2.092 (4.44), 2.114 (4.01), 2.131 (2.68), 2.523 (1.54), 3.530 (2.19), 3.634 (0.52), 3.648 (0.83), 3.667 (1.03), 3.681 (1.32), 3.695 (0.75), 3.732 (0.63), 3.750 (0.85), 7.144 (1.22), 7.165 (1.92), 7.189 (2.26), 7.206 (2.10), 7.225 (1.45), 7.285 (1.19), 7.302 (1.04), 7.399 (1.28), 7.418 (2.19), 7.436 (1.19), 7.486 (1.67), 7.499 (3.86), 7.506 (4.36), 7.517 (16.00), 7.527 (4.36), 7.828 (1.83), 7.833 (1.66), 7.850 (2.65), 7.855 (2.51), 7.924 (5.15), 7.946 (3.20), 8.848 (1.13), 8.863 (1.83), 8.877 (1.05), 12.048 (0.45).

$^1$H-NMR (400 MHz, DMSO-d6) δ [ppm]: 12.05 (br. s, 1H), 8.86 (t, 1H), 7.93 (d, 1H), 7.84 (dd, 1H), 7.67 (br. s, 1H), 7.55-7.47 (m, 5H), 7.45-7.39 (m, 1H), 7.35-7.25 (m, 1H), 7.24-7.13 (m, 2H), 3.83-3.71 (m, 1H), 3.71-3.61 (m, 1H), 3.41-3.33 (m, 1H, partially obscured), 2.20-1.99 (m, 6H), 1.88-1.75 (m, 1H).

Example 177

(+)-5-{[(6-Bromo-3-methyl-2-phenylquinolin-4-yl)carbonyl]amino}-4-(2-fluorophenyl)pentanoic Acid (Enantiomer 2)

In the enantiomer separation described in Example 175, 130 mg (98% purity, ee 99%) of the title compound were obtained as the enantiomer that eluted later.

$[α]_D^{20}$=+36.9°, 589 nm, c=0.25 g/100 ml, methanol

LC-MS (Method 2): $R_t$=1.00 min; MS (ESIpos): m/z=535/537 [M+H]$^+$ $^1$H-NMR (400 MHz, DMSO-d6) δ [ppm]: −0.008 (1.11), 0.008 (1.01), 1.786 (0.50), 1.803 (0.70), 1.813 (0.78), 1.825 (0.90), 1.836 (0.61), 1.848 (0.49), 2.031 (0.80), 2.043 (0.93), 2.056 (1.99), 2.067 (1.12), 2.073 (1.31), 2.084 (3.28), 2.092 (4.41), 2.115 (3.90), 2.131 (2.64), 2.152 (1.05), 2.523 (0.46), 3.635 (0.44), 3.648 (0.75), 3.667 (0.96), 3.681 (1.32), 3.695 (0.72), 3.733 (0.56), 3.752 (0.80), 3.769 (0.71), 7.144 (1.09), 7.165 (1.77), 7.190 (2.21), 7.206 (2.04), 7.225 (1.44), 7.271 (0.66), 7.285 (1.15), 7.301 (1.12), 7.322 (0.46), 7.399 (1.13), 7.403 (1.14), 7.418 (2.04), 7.421 (1.92), 7.436 (1.02), 7.480 (0.55), 7.486 (1.15), 7.499 (3.30), 7.506 (3.66), 7.517 (16.00), 7.523 (5.91), 7.528 (4.35), 7.828 (1.76), 7.833 (1.58), 7.850 (2.67), 7.855 (2.52), 7.924 (5.27), 7.947 (3.33), 8.849 (1.12), 8.864 (1.90), 8.878 (1.07).

$^1$H-NMR (400 MHz, DMSO-d6) δ [ppm]: 12.05 (br. s, 1H), 8.86 (t, 1H), 7.93 (d, 1H), 7.84 (dd, 1H), 7.67 (br. s, 1H), 7.54-7.48 (m, 5H), 7.45-7.39 (m, 1H), 7.36-7.26 (m, 1H), 7.24-7.12 (m, 2H), 3.82-3.71 (m, 1H), 3.71-3.61 (m, 1H), 3.42-3.33 (m, 1H, partially obscured), 2.22-1.98 (m, 6H), 1.89-1.75 (m, 1H).

Example 178

(+/−)-5-{[(6-Bromo-3-methyl-2-phenylquinolin-4-yl)carbonyl]amino}-4-[2-(difluoromethoxy)phenyl]pentanoic Acid (Racemate)

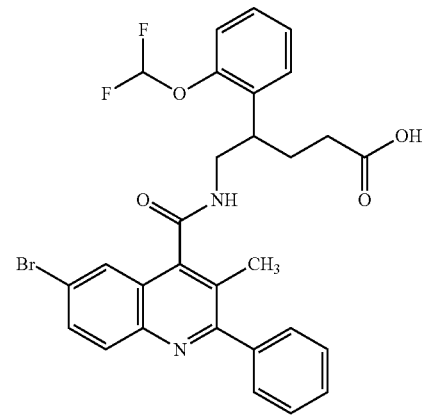 [SMILES: Cc1c(-c2ccccc2)nc2ccc(Br)cc2c1C(=O)NCC(CCC(=O)O)c1ccccc1OC(F)F]

TFA (600 µl, 7.8 mmol) was added to a solution of (+/−)-tert-butyl 5-{[(6-bromo-3-methyl-2-phenylquinolin-4-yl)carbonyl]amino}-4-[2-(difluoromethoxy)phenyl]pentanoate (500 mg, 782 µmol, Example 253A) in dichloromethane (5.7 ml), and the mixture was allowed to stand at RT overnight. The mixture was then concentrated and repeatedly dichloromethane was added and the mixture was concentrated again. The residue was taken up in acetonitrile and purified by preparative HPLC (Method 16). The combined target fractions were concentrated and the residue was lyophilized. Ethyl acetate and saturated sodium bicarbonate solution (10 ml each) were added to the lyophilizate, which was then agitated. After phase separation, the aqueous phase was extracted twice with ethyl acetate (10 ml each time). The combined organic phases were dried over sodium sulfate, filtered and concentrated, and the residue was lyophilized. This gave 238 mg (98% purity, 51% of theory) of the title compound.

LC-MS (Method 1): $R_t$=2.00 min; MS (ESIpos): m/z=583/585 [M+H]$^+$ $^1$H-NMR (400 MHz, DMSO-d6) δ [ppm]: 1.821 (0.58), 1.841 (1.12), 1.862 (1.43), 1.886 (0.90), 2.000 (0.42), 2.022 (1.00), 2.037 (3.07), 2.067 (3.02), 2.077 (4.34), 2.095 (2.55), 2.124 (4.67), 2.146 (2.22), 3.378 (1.23), 3.397 (1.28), 3.636 (0.63), 3.651 (1.02), 3.669 (1.45), 3.684 (1.78), 3.698 (0.98), 3.733 (1.04), 3.751 (1.49), 3.768 (1.39), 3.783 (0.87), 3.803

(0.56), 4.624 (1.03), 6.992 (2.69), 7.158 (3.03), 7.178 (9.00), 7.245 (1.19), 7.263 (3.01), 7.281 (2.28), 7.311 (2.07), 7.330 (2.45), 7.346 (0.98), 7.363 (2.70), 7.430 (3.02), 7.433 (3.12), 7.448 (2.55), 7.452 (2.49), 7.481 (0.55), 7.494 (1.58), 7.504 (4.68), 7.512 (4.55), 7.523 (15.91), 7.525 (16.00), 7.534 (6.68), 7.538 (5.96), 7.680 (0.71), 7.838 (2.34), 7.843 (2.22), 7.860 (3.62), 7.865 (3.62), 7.934 (6.72), 7.956 (4.28), 8.832 (1.55), 8.847 (2.98), 8.861 (1.52).

$^1$H-NMR (400 MHz, DMSO-d6) δ [ppm]: 8.85 (t, 1H), 7.94 (d, 1H), 7.85 (dd, 1H), 7.68 (br. s, 1H), 7.56-7.48 (m, 5H), 7.44 (dd, 1H), 7.38-7.23 (m, 2H), 7.21-6.97 (m, 2H), 3.82-3.72 (m, 1H), 3.71-3.60 (m, 1H), 3.45-3.32 (m, 1H), 2.21-1.98 (m, 6H), 1.94-1.78 (m, 1H).

Separation of the Enantiomers:

The title compound (230 mg) was dissolved in methanol (20 ml) and separated into the enantiomers by preparative SFC on a chiral phase (see Examples 179 and 180) [column: Daicel Chiralpak AD-H, 5 μm, 250 mm×20 mm; flow rate: 80 ml/min; detection: 210 nm; temperature: 40° C.; injection: 1.0 ml; mobile phase: 25% isopropanol/75% carbon dioxide; run time 7 min, isocratic]. The combined target fractions were concentrated and the residue was dried under reduced pressure.

Example 179

(−)-5-{[(6-Bromo-3-methyl-2-phenylquinolin-4-yl)carbonyl]amino}-4-[2-(difluoromethoxy)phenyl]pentanoic Acid (Enantiomer 1)

In the enantiomer separation described in Example 178, 60 mg (98% purity, ee 99%) of the title compound were obtained as the enantiomer that eluted earlier.

$[α]_D^{20}$=−17.7°, 589 nm, c=0.30 g/100 ml, methanol

LC-MS (Method 2): $R_t$=1.03 min; MS (ESIpos): m/z=583/585 [M+H]$^+$ $^1$H-NMR (400 MHz, DMSO-d6) δ [ppm]: −0.008 (1.52), 0.008 (1.39), 1.030 (4.20), 1.045 (4.27), 1.819 (0.56), 1.840 (1.09), 1.860 (1.40), 1.884 (0.90), 1.999 (0.40), 2.020 (0.94), 2.035 (3.03), 2.065 (2.88), 2.075 (4.17), 2.094 (2.50), 2.123 (4.63), 2.145 (2.12), 3.375 (1.26), 3.394 (1.29), 3.523 (0.73), 3.634 (0.59), 3.648 (0.97), 3.666 (1.40), 3.682 (1.74), 3.696 (0.94), 3.731 (1.00), 3.747 (1.42), 3.766 (1.36), 3.782 (0.83), 3.800 (0.53), 6.991 (2.74), 7.157 (2.98), 7.177 (9.10), 7.243 (1.17), 7.261 (2.98), 7.279 (2.29), 7.310 (2.02), 7.329 (2.40), 7.345 (0.97), 7.363 (2.73), 7.428 (3.01), 7.432 (3.03), 7.447 (2.55), 7.451 (2.44), 7.477 (0.57), 7.490 (1.52), 7.500 (4.55), 7.508 (4.30), 7.520 (16.00), 7.530 (6.42), 7.677 (0.70), 7.831 (2.27), 7.836 (2.11), 7.853 (3.48), 7.859 (3.41), 7.929 (6.63), 7.951 (4.24), 8.826 (1.52), 8.841 (2.91), 8.855 (1.50), 12.015 (2.69).

$^1$H-NMR (400 MHz, DMSO-d6) δ [ppm]: 12.02 (s, 1H), 8.84 (t, 1H), 7.94 (d, 1H), 7.85 (dd, 1H), 7.68 (br. s, 1H), 7.56-7.48 (m, 5H), 7.44 (dd, 1H), 7.38-7.23 (m, 2H), 7.19-6.98 (m, 2H), 3.82-3.72 (m, 1H), 3.71-3.61 (m, 1H), 3.43-3.34 (m, 1H), 2.20-1.97 (m, 6H), 1.92-1.76 (m, 1H).

Example 180

(+)-5-{[(6-Bromo-3-methyl-2-phenylquinolin-4-yl)carbonyl]amino}-4-[2-(difluoromethoxy)phenyl]pentanoic Acid (Enantiomer 2)

In the enantiomer separation described in Example 178, 67 mg (98% purity, ee 99%) of the title compound were obtained as the enantiomer that eluted later.

$[α]_D^{20}$=+16.8°, 589 nm, c=0.33 g/100 ml, methanol

LC-MS (Method 2): $R_t$=1.03 min; MS (ESIpos): m/z=583/585 [M+H]$^+$ $^1$H-NMR (400 MHz, DMSO-d6) δ [ppm]: −0.008 (2.17), 0.008 (1.84), 1.030 (4.30), 1.045 (4.35), 1.819 (0.54), 1.839 (1.03), 1.859 (1.36), 1.883 (0.86), 2.020 (0.90), 2.035 (2.94), 2.075 (4.00), 2.093 (2.37), 2.122 (4.45), 3.374 (1.21), 3.394 (1.22), 3.633 (0.56), 3.648 (0.95), 3.666 (1.33), 3.681 (1.65), 3.696 (0.90), 3.730 (0.95), 3.747 (1.42), 3.766 (1.37), 3.779 (0.89), 3.800 (0.51), 4.325 (0.54), 4.336 (0.52), 6.991 (2.66), 7.156 (2.92), 7.177 (8.88), 7.243 (1.12), 7.260 (2.91), 7.278 (2.22), 7.310 (1.94), 7.328 (2.30), 7.344 (0.94), 7.362 (2.66), 7.428 (2.91), 7.431 (2.87), 7.447 (2.49), 7.477 (0.50), 7.490 (1.46), 7.500 (4.46), 7.508 (4.24), 7.520 (16.00), 7.531 (6.21), 7.677 (0.71), 7.831 (2.33), 7.836 (2.11), 7.853 (3.53), 7.859 (3.38), 7.928 (6.72), 7.951 (4.28), 8.826 (1.45), 8.841 (2.79), 8.855 (1.41), 12.014 (2.07).

$^1$H-NMR (400 MHz, DMSO-d6) δ [ppm]: 12.01 (s, 1H), 8.84 (t, 1H), 7.94 (d, 1H), 7.85 (dd, 1H), 7.68 (br. s, 1H), 7.56-7.48 (m, 5H), 7.44 (dd, 1H), 7.38-7.22 (m, 2H), 7.20-6.96 (m, 2H), 3.83-3.71 (m, 1H), 3.71-3.60 (m, 1H), 3.44-3.34 (m, 1H), 2.20-1.96 (m, 6H), 1.94-1.77 (m, 1H).

Example 181

(+/−)-5-{[(6-Bromo-3-methyl-2-phenylquinolin-4-yl)carbonyl]amino}-4-(2,6-difluorophenyl)pentanoic Acid (Racemate)

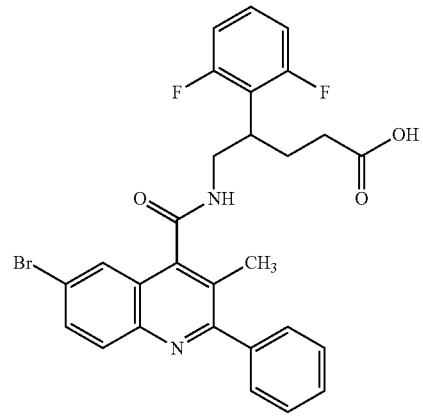 [SMILES: Cc1c(-c2ccccc2)nc2ccc(Br)cc2c1C(=O)NCC(CCC(=O)O)c1c(F)cccc1F]

TFA (630 μl, 8.2 mmol) was added to a solution of (+/−)-tert-butyl 5-{[(6-bromo-3-methyl-2-phenylquinolin-4-yl)carbonyl]amino}-4-(2,6-difluorophenyl)pentanoate (500 mg, 820 μmol, Example 254A) in dichloromethane (6.0 ml), and the mixture was allowed to stand at RT overnight. The mixture was then concentrated and repeatedly dichloromethane was added and the mixture was concentrated again. The residue was taken up in acetonitrile and purified by preparative HPLC (Method 16). The combined target fractions were concentrated and the residue was lyophilized. Ethyl acetate and saturated sodium bicarbonate solution (10 ml each) were added to the lyophilizate, which was then agitated. After phase separation, the aqueous phase was extracted twice with ethyl acetate (10 ml each time). The combined organic phases were dried over sodium sulfate, filtered and concentrated, and the residue was lyophilized. This gave 442 mg (98% purity, 95% of theory) of the title compound.

LC-MS (Method 1): $R_t$=1.92 min; MS (ESIpos): m/z=553/555 [M+H]$^+$

¹H-NMR (400 MHz, DMSO-d6) δ [ppm]: −0.008 (0.64), 0.008 (0.51), 1.886 (0.55), 1.901 (0.72), 1.916 (0.93), 1.927 (0.87), 1.958 (0.42), 2.061 (0.90), 2.074 (1.15), 2.092 (1.18), 2.112 (1.59), 2.127 (5.66), 2.144 (7.80), 3.521 (0.88), 3.721 (0.74), 3.740 (1.31), 3.754 (1.85), 3.769 (1.54), 3.788 (1.01), 3.809 (0.81), 7.056 (2.54), 7.078 (4.69), 7.101 (3.00), 7.333 (0.88), 7.352 (1.17), 7.369 (0.79), 7.483 (0.41), 7.493 (1.23), 7.505 (3.76), 7.512 (3.82), 7.523 (16.00), 7.534 (5.28), 7.842 (2.02), 7.847 (1.84), 7.864 (3.16), 7.869 (3.07), 7.934 (5.90), 7.956 (3.70), 8.942 (1.26), 8.957 (2.42), 8.971 (1.26).

¹H-NMR (400 MHz, DMSO-d6) δ [ppm]: 8.96 (t, 1H), 7.94 (d, 1H), 7.86 (dd, 1H), 7.71 (br. s, 1H), 7.56-7.46 (m, 5H), 7.40-7.29 (m, 1H), 7.08 (t, 2H), 3.86-3.68 (m, 2H), 3.58-3.46 (m, 1H), 2.22-2.03 (m, 6H), 1.98-1.85 (m, 1H).

Separation of the Enantiomers:

The title compound (380 mg) was dissolved in methanol (20 ml) and separated into the enantiomers by preparative SFC on a chiral phase (see Examples 182 and 183) [column: Daicel Chiralpak AD, 5 μm 250 mm×20 mm; flow rate: 80 ml/min; detection: 210 nm; temperature: 40° C.; injection: 1.0 ml; mobile phase: 25% isopropanol/75% carbon dioxide; run time 10 min, isocratic]. The combined target fractions were concentrated and the residue was dried under reduced pressure.

Example 182

(−)-5-{[(6-Bromo-3-methyl-2-phenylquinolin-4-yl)carbonyl]amino}-4-(2,6-difluorophenyl)pentanoic Acid (Enantiomer 1)

In the enantiomer separation described in Example 181, the prepurified title compound was obtained as the enantiomer that eluted earlier (ee 99%). This was followed by purification by preparative HPLC (Method 14). The combined target fractions were concentrated, and the residue was dried under reduced pressure. The residue was then repurified again by preparative HPLC (Method 18). This gave 27 mg (98% purity) of the repurified title compound.

$[α]_D^{20}$=−47.5°, 589 nm, c=0.31 g/100 ml, methanol

LC-MS (Method 1): $R_t$=1.92 min; MS (ESIpos): m/z=553/555 [M+H]⁺

¹H-NMR (400 MHz, DMSO-d6) δ [ppm]: −0.008 (3.36), 0.008 (3.27), 1.909 (0.80), 2.054 (0.74), 2.067 (0.89), 2.088 (1.10), 2.114 (4.71), 2.130 (4.70), 2.144 (4.68), 2.327 (0.54), 2.670 (0.59), 3.514 (0.89), 3.714 (0.65), 3.733 (1.16), 3.748 (1.58), 3.762 (1.27), 3.782 (0.91), 7.054 (2.15), 7.076 (4.00), 7.099 (2.52), 7.332 (0.78), 7.348 (1.00), 7.488 (1.07), 7.501 (3.22), 7.508 (3.48), 7.519 (16.00), 7.835 (1.80), 7.840 (1.66), 7.857 (2.81), 7.863 (2.74), 7.928 (5.21), 7.951 (3.25), 8.939 (1.07), 8.954 (1.99), 8.969 (1.07).

¹H-NMR (400 MHz, DMSO-d6) δ [ppm]: 12.00 (br. s, 1H), 8.95 (t, 1H), 7.94 (d, 1H), 7.85 (dd, 1H), 7.70 (br. s, 1H), 7.56-7.45 (m, 5H), 7.41-7.25 (m, 1H), 7.08 (t, 2H), 3.88-3.67 (m, 2H), 3.51 (br. s, 1H), 2.24-2.01 (m, 6H), 1.99-1.82 (m, 1H).

Example 183

(+)-5-{[(6-Bromo-3-methyl-2-phenylquinolin-4-yl)carbonyl]amino}-4-(2,6-difluorophenyl)pentanoic Acid (Enantiomer 2)

In the enantiomer separation described in Example 181, the prepurified title compound was obtained as the enantiomer that eluted later (ee 99%). This was followed by repurification by preparative HPLC (Method 14). The combined target fractions were concentrated, and the residue was dried under reduced pressure. This gave 56 mg (98% purity) of the repurified title compound.

$[α]_D^{20}$=+56.2°, 589 nm, c=0.38 g/100 ml, methanol

LC-MS (Method 2): $R_t$=0.99 min; MS (ESIpos): m/z=553/555 [M+H]⁺

¹H-NMR (400 MHz, DMSO-d6) δ [ppm]: 1.882 (0.61), 1.897 (0.80), 1.912 (1.00), 1.952 (0.41), 2.058 (1.06), 2.073 (2.93), 2.089 (1.45), 2.124 (5.99), 2.140 (7.91), 3.517 (0.98), 3.703 (0.47), 3.717 (0.82), 3.735 (1.41), 3.750 (1.92), 3.764 (1.59), 3.784 (1.10), 3.804 (0.85), 7.055 (2.46), 7.077 (4.38), 7.100 (2.65), 7.332 (0.99), 7.350 (1.19), 7.367 (0.78), 7.489 (1.84), 7.501 (4.01), 7.509 (4.54), 7.519 (16.00), 7.836 (1.87), 7.841 (1.61), 7.858 (2.80), 7.863 (2.43), 7.929 (4.66), 7.951 (2.85), 8.935 (1.35), 8.950 (2.28), 8.964 (1.15), 12.082 (1.35).

¹H-NMR (400 MHz, DMSO-d6) δ [ppm]: 12.08 (br. s, 1H), 8.95 (t, 1H), 7.94 (d, 1H), 7.85 (dd, 1H), 7.70 (br. s, 1H), 7.56-7.46 (m, 5H), 7.41-7.29 (m, 1H), 7.08 (t, 2H), 3.87-3.67 (m, 2H), 3.52 (br. s, 1H), 2.21-2.02 (m, 6H), 1.98-1.83 (m, 1H).

Example 184

(+/−)-5-{[(6-Bromo-3-methyl-2-phenylquinolin-4-yl)carbonyl]amino}-4-(2-chloro-3-fluorophenyl)pentanoic Acid (Racemate)

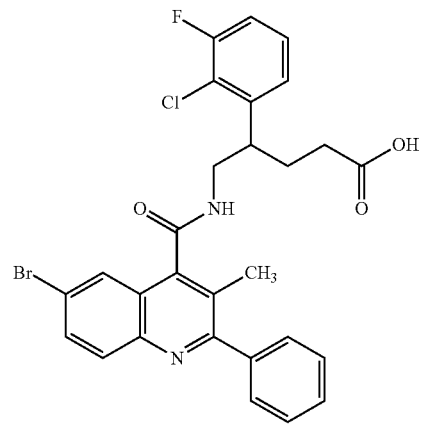 [SMILES: Cc1c(-c2ccccc2)nc2ccc(Br)cc2c1C(=O)NCC(CCC(=O)O)c1cccc(F)c1Cl]

TFA (120 μl, 1.6 mmol) was added to a solution of (+/−)-tert-butyl 5-{[(6-bromo-3-methyl-2-phenylquinolin-4-yl)carbonyl]amino}-4-(2-chloro-3-fluorophenyl)pentanoate (100 mg, 160 μmol, Example 255A) in dichloromethane (1.2 ml), and the mixture was allowed to stand at RT for three days. The mixture was then concentrated and repeatedly dichloromethane was added and the mixture was concentrated again. The residue was taken up in acetonitrile and purified by preparative HPLC (Method 15). The combined target fractions were concentrated and the residue was lyophilized. This gave 78 mg (100% purity, 86% of theory) of the title compound.

LC-MS (Method 1): $R_t$=1.96 min; MS (ESIpos): m/z=569/571 [M+H]⁺

¹H-NMR (400 MHz, DMSO-d6) δ [ppm]: 1.818 (0.64), 1.838 (1.05), 1.858 (1.38), 1.880 (0.81), 2.028 (0.44), 2.049 (0.90), 2.073 (2.99), 2.085 (1.48), 2.098 (3.43), 2.110 (5.48), 2.140 (5.75), 2.176 (1.34), 3.631 (1.74), 3.746 (1.83), 7.283 (0.98), 7.304 (2.11), 7.325 (1.39), 7.364 (1.57), 7.382 (3.21), 7.401 (1.38), 7.419 (1.64), 7.434 (1.44), 7.454 (0.55), 7.479

(0.61), 7.492 (1.67), 7.502 (4.92), 7.510 (4.75), 7.522 (16.00), 7.533 (6.95), 7.651 (0.43), 7.832 (2.36), 7.837 (2.13), 7.854 (3.59), 7.859 (3.37), 7.930 (6.74), 7.953 (4.29), 8.854 (1.51), 8.869 (2.99), 8.883 (1.46).

¹H-NMR (400 MHz, DMSO-d6) δ [ppm]: 12.09 (br. s, 1H), 8.87 (t, 1H), 7.94 (d, 1H), 7.85 (dd, 1H), 7.65 (br. s, 1H), 7.56-7.47 (m, 5H), 7.46-7.35 (m, 2H), 7.34-7.26 (m, 1H), 3.87-3.35 (m, 3H, partially obscured), 2.23-2.00 (m, 6H), 1.93-1.75 (m, 1H).

Example 185

(−)-5-{[(6-Bromo-3-methyl-2-phenylquinolin-4-yl)carbonyl]amino}-4-(2-chloro-3-fluorophenyl)pentanoic Acid (Enantiomer 1)

TFA (740 µl, 9.7 mmol) was added to a solution of (−)-tert-butyl 5-{[(6-bromo-3-methyl-2-phenylquinolin-4-yl)carbonyl]amino}-4-(2-chloro-3-fluorophenyl)pentanoate (275 mg, 439 µmol, Example 256A) in dichloromethane (3.7 ml), and the mixture was allowed to stand at RT for 16 h. The mixture was then concentrated and repeatedly dichloromethane was added and the mixture was concentrated again. The residue was taken up in acetonitrile and purified by preparative HPLC (Method 16). The combined target fractions were concentrated and the residue was lyophilized. This gave 204 mg (100% purity, ee 96%, 81% of theory) of the title compound.

$[\alpha]_D^{20}$=−18.3°, 589 nm, c=0.38 g/100 ml, methanol
LC-MS (Method 1): $R_t$=1.96 min; MS (ESIpos): m/z=569/571 [M+H]⁺

¹H-NMR (400 MHz, DMSO-d6) δ [ppm]: 1.818 (0.61), 1.837 (1.07), 1.857 (1.36), 1.879 (0.84), 2.070 (2.64), 2.084 (1.42), 2.097 (3.39), 2.109 (5.38), 2.140 (5.93), 3.640 (1.33), 3.745 (1.77), 7.283 (1.02), 7.304 (2.13), 7.326 (1.43), 7.364 (1.63), 7.382 (3.24), 7.400 (1.44), 7.419 (1.73), 7.434 (1.48), 7.454 (0.60), 7.491 (1.75), 7.502 (4.64), 7.509 (4.71), 7.522 (16.00), 7.643 (0.42), 7.831 (2.09), 7.836 (2.04), 7.853 (3.22), 7.858 (3.21), 7.929 (5.64), 7.952 (3.62), 8.853 (1.50), 8.868 (2.89), 8.881 (1.45), 12.068 (0.80).

¹H-NMR (400 MHz, DMSO-d6) δ [ppm]: 12.07 (br. s, 1H), 8.87 (t, 1H), 7.94 (d, 1H), 7.84 (dd, 1H), 7.64 (br. s, 1H), 7.56-7.47 (m, 5H), 7.46-7.35 (m, 2H), 7.34-7.25 (m, 1H), 3.87-3.55 (m, 3H), 2.22-1.99 (m, 6H), 1.92-1.76 (m, 1H).

Example 186

(+)-5-{[(6-Bromo-3-methyl-2-phenylquinolin-4-yl)carbonyl]amino}-4-(2-chloro-3-fluorophenyl)pentanoic Acid (Enantiomer 2)

TFA (790 µl, 10 mmol) was added to a solution of (+)-tert-butyl 5-{[(6-bromo-3-methyl-2-phenylquinolin-4-yl)carbonyl]amino}-4-(2-chloro-3-fluorophenyl)pentanoate (290 mg, 463 µmol, Example 257A) in dichloromethane (3.9 ml), and the mixture was allowed to stand at RT for 16 h. The mixture was then concentrated and repeatedly dichloromethane was added and the mixture was concentrated again. The residue was taken up in acetonitrile and purified by preparative HPLC (Method 16). The combined target fractions were concentrated and the residue was lyophilized. This gave 266 mg (100% purity, ee 98%, 100% of theory) of the title compound.

$[\alpha]_D^{20}$=+18.0°, 589 nm, c=0.37 g/100 ml, methanol
LC-MS (Method 1): $R_t$=1.96 min; MS (ESIpos): m/z=569/571 [M+H]⁺

¹H-NMR (400 MHz, DMSO-d6) δ [ppm]: 1.818 (0.65), 1.838 (1.11), 1.858 (1.42), 1.880 (0.84), 2.029 (0.40), 2.049 (0.92), 2.071 (2.77), 2.085 (1.40), 2.099 (3.51), 2.110 (5.62), 2.141 (6.00), 2.176 (1.41), 3.518 (2.35), 3.640 (1.85), 7.283 (1.02), 7.304 (2.17), 7.325 (1.44), 7.364 (1.67), 7.382 (3.38), 7.401 (1.44), 7.419 (1.73), 7.434 (1.50), 7.454 (0.57), 7.479 (0.64), 7.492 (1.68), 7.503 (4.84), 7.510 (4.62), 7.522 (16.00), 7.533 (7.15), 7.646 (0.41), 7.832 (2.25), 7.837 (2.05), 7.855 (3.46), 7.860 (3.27), 7.930 (6.14), 7.953 (3.94), 8.855 (1.57), 8.870 (3.08), 8.884 (1.51).

¹H-NMR (400 MHz, DMSO-d6) δ [ppm]: 12.10 (br. s, 1H), 8.87 (t, 1H), 7.94 (d, 1H), 7.85 (dd, 1H), 7.65 (br. s, 1H), 7.56-7.47 (m, 5H), 7.46-7.34 (m, 2H), 7.34-7.26 (m, 1H), 3.87-3.58 (m, 3H, partially obscured), 2.22-2.00 (m, 6H), 1.93-1.76 (m, 1H).

Example 187

(+/−)-N-[2-{[(6-Bromo-3-methyl-2-phenylquinolin-4-yl)carbonyl]amino}-1-(2-chlorophenyl)ethyl]-N-methylglycine (Racemate)

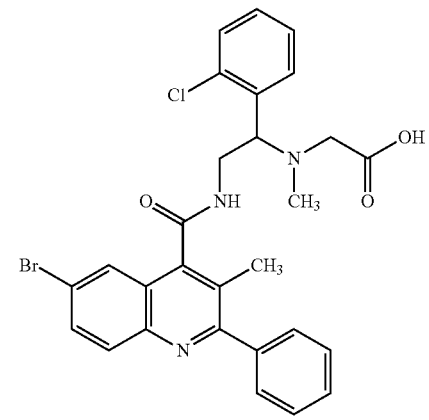 [SMILES: Cc1c(-c2ccccc2)nc2ccc(Br)cc2c1C(=O)NCC(c1ccccc1Cl)N(C)CC(=O)O]

TFA (190 µl, 2.4 mmol) was added to a solution of (+/−)-tert-butyl N-[2-{[(6-bromo-3-methyl-2-phenylquinolin-4-yl)carbonyl]amino}-1-(2-chlorophenyl)ethyl]-N-methylglycinate (150 mg, 241 µmol, Example 258A) in dichloromethane (1.8 ml), and the mixture was allowed to stand at RT for 16 h. The mixture was then concentrated and repeatedly dichloromethane was added and the mixture was concentrated again. The residue was taken up in acetonitrile and purified by preparative HPLC (Method 16). The combined target fractions were concentrated and the residue was lyophilized. Ethyl acetate and saturated sodium bicarbonate solution (10 ml each) were then added to the residue, the mixture was shaken and after phase separation the aqueous phase was extracted twice with ethyl acetate (10 ml). The combined organic phases were dried over sodium sulfate, filtered and concentrated, and the residue was lyophilized. This gave 106 mg (98% purity, 76% of theory) of the title compound.

LC-MS (Method 1): $R_t$=1.54 min; MS (ESIpos): m/z=566/568 [M+H]⁺

¹H-NMR (400 MHz, DMSO-d6) δ [ppm]: 2.089 (7.35), 2.644 (1.80), 4.062 (0.43), 4.161 (0.56), 5.018 (0.45), 7.434 (1.06), 7.454 (1.84), 7.473 (1.43), 7.513 (16.00), 7.552 (1.61), 7.572 (1.18), 7.676 (0.54), 7.761 (0.86), 7.778 (0.78), 7.834 (1.30), 7.839 (1.23), 7.856 (2.01), 7.861 (2.01), 7.926 (3.68), 7.948 (2.25), 8.881 (1.00).

¹H-NMR (400 MHz, DMSO-d6) δ [ppm]: 8.88 (br. s, 1H), 7.93 (d, 1H), 7.85 (dd, 1H), 7.81-7.73 (m, 1H), 7.68 (br. s, 1H), 7.56 (br. d, 1H), 7.53-7.40 (m, 7H), 5.02 (br. s, 1H), 4.12 (br. d, 2H), 3.70 (br. d, 2H), 2.64 (br. s, 3H), 2.09 (s, 3H).

Separation of the Enantiomers:

The title compound (70 mg) was dissolved in methanol (10 ml) and separated into the enantiomers by preparative SFC on a chiral phase (see Examples 188 and 189) [column: Daicel Chiralpak AD, 5 μm 250 mm×20 mm; flow rate: 80 ml/min; detection: 210 nm; temperature: 40° C.; injection: 1.0 ml; mobile phase: 25% isopropanol/75% carbon dioxide; run time 9 min, isocratic]. The combined target fractions were concentrated and the residue was dried under reduced pressure.

Example 188

(−)-N-[2-{[(6-Bromo-3-methyl-2-phenylquinolin-4-yl)carbonyl]amino}-1-(2-chlorophenyl)ethyl]-N-methylglycine (Enantiomer 1)

In the enantiomer separation described in Example 187, 22 mg (98% purity, ee 99%) of the title compound were obtained as the enantiomer that eluted earlier.

$[\alpha]_D^{20}$=−27.9°, 589 nm, c=0.25 g/100 ml, methanol

LC-MS (Method 2): $R_t$=0.81 min; MS (ESIpos): m/z=566/568 [M+H]⁺

¹H-NMR (400 MHz, DMSO-d6) δ [ppm]: −0.008 (1.35), 0.008 (1.09), 2.152 (14.46), 2.327 (0.41), 2.362 (16.00), 2.523 (1.06), 3.149 (1.90), 3.191 (2.75), 3.353 (4.75), 3.396 (2.42), 3.827 (0.54), 3.979 (0.65), 4.631 (1.23), 4.648 (1.83), 4.665 (1.11), 7.306 (0.72), 7.310 (0.81), 7.325 (1.95), 7.329 (1.97), 7.344 (1.76), 7.348 (1.69), 7.366 (1.51), 7.384 (2.16), 7.400 (0.94), 7.465 (2.88), 7.468 (2.88), 7.485 (3.05), 7.488 (3.02), 7.500 (3.68), 7.507 (3.24), 7.519 (8.83), 7.524 (8.36), 7.532 (5.29), 7.544 (1.15), 7.577 (2.10), 7.581 (2.12), 7.596 (1.80), 7.600 (1.70), 7.742 (1.68), 7.827 (1.80), 7.832 (1.58), 7.849 (2.77), 7.854 (2.62), 7.923 (4.87), 7.945 (3.12), 8.726 (1.02), 8.741 (2.04), 8.755 (0.99).

¹H-NMR (400 MHz, DMSO-d6) δ [ppm]: 12.19 (br. s, 1H), 8.74 (t, 1H), 7.93 (d, 1H), 7.84 (dd, 1H), 7.74 (br. s, 1H), 7.59 (dd, 1H), 7.56-7.49 (m, 5H), 7.48 (dd, 1H), 7.38 (td, 1H), 7.33 (td, 1H), 4.65 (t, 1H), 3.98 (br. s, 1H), 3.83 (br. s, 1H), 3.37 (d, 1H, partially obscured), 3.17 (d, 2H), 2.36 (s, 3H), 2.15 (s, 3H).

Example 189

(+)-N-[2-{[(6-Bromo-3-methyl-2-phenylquinolin-4-yl)carbonyl]amino}-1-(2-chlorophenyl)ethyl]-N-methylglycine (Enantiomer 2)

In the enantiomer separation described in Example 187, 19 mg (98% purity, ee 99%) of the title compound were obtained as the enantiomer that eluted later.

$[\alpha]_D^{20}$=+27.1°, 589 nm, c=0.25 g/100 ml, methanol

LC-MS (Method 2): $R_t$=0.81 min; MS (ESIpos): m/z=566/568 [M+H]⁺

¹H-NMR (400 MHz, DMSO-d6) δ [ppm]: 0.008 (1.13), 2.152 (14.59), 2.327 (0.43), 2.362 (16.00), 3.149 (1.93), 3.191 (2.73), 3.353 (4.74), 3.396 (2.45), 3.823 (0.54), 3.979 (0.64), 4.631 (1.21), 4.648 (1.81), 4.666 (1.16), 7.310 (0.79), 7.325 (1.94), 7.329 (1.97), 7.344 (1.73), 7.348 (1.72), 7.366 (1.55), 7.385 (2.19), 7.399 (0.90), 7.465 (3.00), 7.468 (3.11), 7.485 (3.09), 7.488 (3.18), 7.500 (3.65), 7.507 (3.20), 7.519 (8.85), 7.524 (8.42), 7.532 (5.37), 7.580 (2.11), 7.596 (1.77), 7.742 (1.80), 7.827 (1.91), 7.832 (1.64), 7.849 (2.86), 7.854 (2.70), 7.923 (5.10), 7.945 (3.24), 8.727 (1.00), 8.741 (2.02), 8.756 (0.97).

¹H-NMR (400 MHz, DMSO-d6) δ [ppm]: 12.15 (br. s, 1H), 8.74 (t, 1H), 7.93 (d, 1H), 7.84 (dd, 1H), 7.74 (br. s, 1H), 7.59 (dd, 1H), 7.55-7.49 (m, 5H), 7.48 (dd, 1H), 7.38 (td, 1H), 7.33 (td, 1H), 4.65 (t, 1H), 3.98 (br. s, 1H), 3.82 (br. s, 1H), 3.37 (d, 1H, partially obscured), 3.17 (d, 1H), 2.36 (s, 3H), 2.15 (s, 3H).

Example 190

(+/−)-N-[2-{[(6-Bromo-3-methyl-2-phenylquinolin-4-yl)carbonyl]amino}-1-(2-chlorophenyl)ethyl]glycine (Racemate)

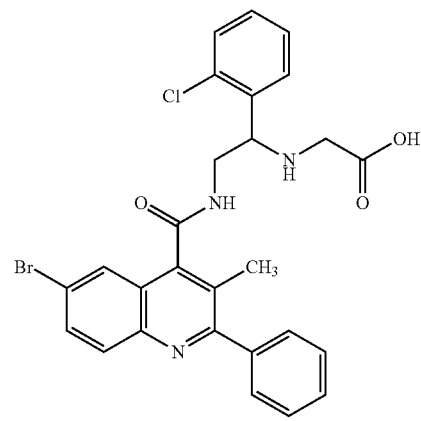

TFA (190 μl, 2.5 mmol) was added to a solution of (+/−)-tert-butyl N-[2-{[(6-bromo-3-methyl-2-phenylquinolin-4-yl)carbonyl]amino}-1-(2-chlorophenyl)ethyl]glycinate (150 mg, 246 μmol, Example 259A) in dichloromethane (1.8 ml), and the mixture was allowed to stand at RT for 16 h. The mixture was then concentrated and repeatedly dichloromethane was added and the mixture was concentrated again. The residue was taken up in acetonitrile and purified by preparative HPLC (Method 16). The combined target fractions were concentrated and the residue was lyophilized. Ethyl acetate and saturated sodium bicarbonate solution (10 ml each) were then added to the residue, the mixture was shaken and after phase separation the aqueous phase was extracted twice with ethyl acetate (10 ml). The combined organic phases were dried over sodium sulfate, filtered and concentrated, and the residue was lyophilized. This gave 52 mg (98% purity, 37% of theory) of the title compound.

LC-MS (Method 1): $R_t$=1.47 min; MS (ESIpos): m/z=552/554 [M+H]⁺

¹H-NMR (400 MHz, DMSO-d6) δ [ppm]: −0.150 (0.75), 0.146 (0.72), 1.235 (1.11), 1.365 (0.81), 1.876 (0.72), 2.283 (16.00), 2.327 (2.01), 2.366 (1.42), 2.670 (1.90), 2.690 (1.92), 2.709 (1.64), 2.731 (2.26), 2.761 (2.70), 2.802 (2.51), 2.890 (2.01), 3.569 (1.62), 3.667 (1.39), 4.302 (2.31), 7.289 (2.79), 7.306 (2.34), 7.345 (2.23), 7.362 (3.21), 7.419 (4.13), 7.438 (3.99), 7.510 (6.94), 7.529 (5.97), 7.567 (7.41), 7.672 (2.59), 7.690 (2.51), 7.842 (2.51), 7.865 (3.43), 7.903 (3.51), 7.939 (4.32), 7.960 (2.70), 9.456 (1.23).

$^1$H-NMR (400 MHz, DMSO-d6) δ [ppm]: 9.46 (br. s, 1H), 7.99-7.81 (m, 3H), 7.68 (br. d, 1H), 7.61-7.25 (m, 9H), 4.30 (br. s, 1H), 3.67 (br. s, 1H), 3.54 (br. s, 1H), 2.84-2.60 (m, 2H), 2.28 (s, 3H).

Example 191

(+/−)-[2-{[(6-Bromo-3-methyl-2-phenylquinolin-4-yl)carbonyl]amino}-1-(2-chlorophenyl)ethoxy]acetic Acid (Racemate)

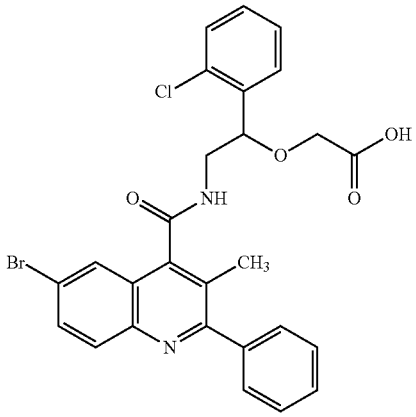 [SMILES: Cc1c(-c2ccccc2)nc2ccc(Br)cc2c1C(=O)NCC(OCC(=O)O)c1ccccc1Cl]

With stirring, 1 M aqueous sodium hydroxide solution (1.2 ml, 1.2 mmol) was added to a solution of (+/−)-ethyl [2-{[(6-bromo-3-methyl-2-phenylquinolin-4-yl)carbonyl]amino}-1-(2-chlorophenyl)ethoxy]acetate (179 mg, 307 μmol, Example 260A) in a mixture of THF (3 ml) and methanol (1 ml), and the mixture was allowed to stand at RT for 1.5 h. TFA (97 μl, 1.3 mmol) was then added, and the mixture was purified directly (without further work-up) by preparative HPLC (Method 15). The combined target fractions were concentrated, and the residue was lyophilized. This gave 164 mg (100% purity, 96% of theory) of the title compound.

LC-MS (Method 1): $R_t$=1.97 min; MS (ESIpos): m/z=553/555 [M+H]$^+$ $^1$H-NMR (400 MHz, DMSO-d6) δ [ppm]: 2.217 (0.41), 2.263 (16.00), 3.910 (3.67), 3.951 (5.90), 4.039 (6.43), 4.080 (4.00), 5.166 (1.86), 5.180 (3.39), 5.194 (1.77), 7.376 (1.03), 7.391 (2.46), 7.395 (2.47), 7.409 (2.68), 7.414 (2.90), 7.421 (2.41), 7.437 (2.78), 7.455 (1.35), 7.493 (4.12), 7.496 (4.26), 7.516 (8.14), 7.536 (6.88), 7.558 (7.92), 7.579 (5.24), 7.599 (2.67), 7.824 (2.67), 7.851 (2.45), 7.856 (1.90), 7.874 (3.42), 7.879 (2.91), 7.949 (4.95), 7.971 (3.19), 8.946 (1.54), 8.960 (2.80), 8.974 (1.44).

$^1$H-NMR (400 MHz, DMSO-d6) δ [ppm]: 12.66 (br. s, 1H), 8.96 (t, 1H), 7.96 (d, 1H), 7.87 (dd, 1H), 7.82 (br. s, 1H), 7.63-7.48 (m, 7H), 7.47-7.35 (m, 2H), 5.18 (t, 1H), 4.06 (d, 1H), 3.94 (d, 1H), 3.79 (br. s, 2H), 2.26 (s, 3H).

Example 192

(+)-[2-{[(6-Bromo-3-methyl-2-phenylquinolin-4-yl)carbonyl]amino}-1-(2-chlorophenyl)ethoxy]acetic Acid (Enantiomer 1)

With stirring, 1 M aqueous sodium hydroxide solution (2.9 ml, 2.9 mmol) was added to a solution of (+)-ethyl [2-{[(6-bromo-3-methyl-2-phenylquinolin-4-yl)carbonyl]amino}-1-(2-chlorophenyl)ethoxy]acetate (415 mg, 713 μmol, Example 261A) in THF (7.0 ml) and methanol (2.3 ml), and the mixture was allowed to stand at RT for 1.5 h. Trifluoroacetic Acid (230 μl, 2.9 mmol) was then added, and the mixture was purified directly (without further work-up) by preparative HPLC (Method 17). The combined target fractions were concentrated, and the residue was lyophilized. This gave 308 mg (100% purity, ee 99%, 78% of theory) of the title compound.

$[α]_D^{20}$=+53.0°, 589 nm, c=0.46 g/100 ml, methanol

LC-MS (Method 2): $R_t$=1.05 min; MS (ESIpos): m/z=553/555 [M+H]$^+$ $^1$H-NMR (400 MHz, DMSO-d6) δ [ppm]: −0.008 (1.47), 2.263 (16.00), 3.783 (2.00), 3.904 (2.71), 3.945 (4.66), 4.035 (5.37), 4.076 (3.05), 5.163 (1.64), 5.177 (3.23), 5.191 (1.60), 7.371 (0.76), 7.375 (0.85), 7.390 (2.20), 7.394 (2.26), 7.408 (2.32), 7.413 (2.47), 7.421 (2.04), 7.437 (2.44), 7.440 (2.62), 7.455 (1.11), 7.492 (3.62), 7.496 (4.22), 7.514 (7.64), 7.533 (6.13), 7.556 (6.82), 7.560 (5.89), 7.580 (4.34), 7.599 (2.27), 7.603 (2.04), 7.822 (2.29), 7.847 (2.38), 7.853 (1.67), 7.870 (3.34), 7.875 (2.84), 7.946 (5.43), 7.968 (3.50), 8.977 (1.70), 12.693 (2.36).

$^1$H-NMR (400 MHz, DMSO-d6) δ [ppm]: 12.69 (s, 1H), 8.98 (t, 1H), 7.95 (d, 1H), 7.86 (dd, 1H), 7.82 (br. s, 1H), 7.62-7.47 (m, 7H), 7.47-7.36 (m, 2H), 5.18 (t, 1H), 4.05 (d, 1H), 3.93 (d, 1H), 3.78 (br. s, 2H), 2.26 (s, 3H).

Example 193

(−)-[2-{[(6-Bromo-3-methyl-2-phenylquinolin-4-yl)carbonyl]amino}-1-(2-chlorophenyl)ethoxy]acetic Acid (Enantiomer 2)

With stirring, 1 M aqueous sodium hydroxide solution (2.7 ml, 2.7 mmol) was added to a solution of (−)-ethyl [2-{[(6-bromo-3-methyl-2-phenylquinolin-4-yl)carbonyl]amino}-1-(2-chlorophenyl)ethoxy]acetate (390 mg, 670 μmol, Example 262A) in THF (6.5 ml) and methanol (2.2 ml), and the mixture was allowed to stand at RT for 1.5 h. Trifluoroacetic Acid (210 μl, 2.7 mmol) was then added, and the mixture was purified directly (without further work-up) by preparative HPLC (Method 17). The combined target fractions were concentrated, and the residue was lyophilized. This gave 307 mg (100% purity, ee 99%, 83% of theory) of the title compound.

$[α]_D^{20}$=−54.3°, 589 nm, c=0.44 g/100 ml, methanol

LC-MS (Method 2): $R_t$=1.05 min; MS (ESIpos): m/z=553/555 [M+H]$^+$ $^1$H-NMR (400 MHz, DMSO-d6) δ [ppm]: 0.008 (1.08), 2.263 (16.00), 3.783 (1.96), 3.905 (2.66), 3.946 (4.56), 4.036 (5.22), 4.077 (2.98), 5.163 (1.60), 5.177 (3.16), 5.191 (1.54), 7.371 (0.78), 7.376 (0.89), 7.390 (2.23), 7.395 (2.31), 7.409 (2.37), 7.414 (2.54), 7.422 (2.07), 7.437 (2.40), 7.440 (2.66), 7.455 (1.10), 7.492 (3.75), 7.496 (4.41), 7.514 (7.86), 7.534 (6.17), 7.556 (7.02), 7.560 (6.04), 7.580 (4.26), 7.599 (2.27), 7.603 (2.05), 7.822 (2.33), 7.848 (2.53), 7.853 (1.75), 7.870 (3.52), 7.875 (2.97), 7.946 (5.67), 7.968 (3.63), 8.961 (1.03), 8.975 (1.90), 8.989 (0.98), 12.693 (2.11).

$^1$H-NMR (400 MHz, DMSO-d6) δ [ppm]: 12.69 (br. s, 1H), 8.97 (t, 1H), 7.95 (d, 1H), 7.86 (dd, 1H), 7.82 (br. s, 1H), 7.62-7.48 (m, 7H), 7.47-7.36 (m, 2H), 5.18 (t, 1H), 4.05 (d, 1H), 3.93 (d, 1H), 3.78 (br. s, 2H), 2.26 (s, 3H).

Example 194

(+/−)-{[2-{[(6-Bromo-3-methyl-2-phenylquinolin-4-yl)carbonyl]amino}-1-(2-chlorophenyl)ethyl]sulfanyl}acetic Acid (Racemate)

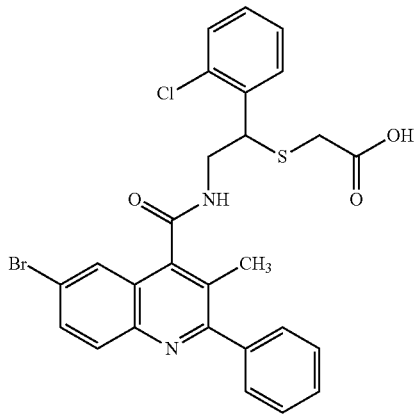

With stirring, 1 M aqueous sodium hydroxide solution (3.5 ml, 3.5 mmol) was added to a solution of (+/−)-methyl {[2-{[(6-bromo-3-methyl-2-phenylquinolin-4-yl)carbonyl]amino}-1-(2-chlorophenyl)ethyl]sulfanyl}acetate (388 mg, 87% purity, 578 μmol, Example 263A) in THF (4.9 ml) and methanol (2.5 ml), and the mixture was stirred at RT for 16 h. Subsequently, the mixture was purified directly (without further work-up) by preparative HPLC (Method 19). The combined target fractions were concentrated and the residue was lyophilized. This gave 310 mg (98% purity, 92% of theory) of the title compound.

LC-MS (Method 2): $R_t$=1.06 min; MS (ESIpos): m/z=569/571 [M+H]$^+$ $^1$H-NMR (400 MHz, DMSO-d6) δ [ppm]: 2.073 (0.84), 2.147 (8.51), 3.201 (3.59), 3.239 (5.50), 3.357 (5.53), 3.395 (3.63), 3.986 (2.19), 4.816 (1.34), 4.835 (2.38), 4.854 (1.22), 7.306 (0.88), 7.324 (2.07), 7.342 (1.55), 7.385 (1.44), 7.404 (2.33), 7.421 (1.11), 7.473 (3.71), 7.476 (3.66), 7.493 (3.82), 7.496 (4.49), 7.500 (4.38), 7.508 (4.14), 7.518 (16.00), 7.529 (5.23), 7.532 (4.74), 7.609 (2.61), 7.625 (2.21), 7.777 (0.53), 7.831 (2.28), 7.836 (1.94), 7.853 (3.32), 7.859 (3.04), 7.928 (5.63), 7.951 (3.58), 9.024 (1.27), 9.039 (2.50), 9.053 (1.20).

$^1$H-NMR (400 MHz, DMSO-d6) δ [ppm]: 12.65 (br. s, 1H), 9.04 (t, 1H), 7.94 (d, 1H), 7.84 (dd, 1H), 7.78 (br. s, 1H), 7.62 (dd, 1H), 7.55-7.46 (m, 6H), 7.40 (t, 1H), 7.33 (t, 1H), 4.84 (t, 1H), 3.99 (br. s, 2H), 3.37 (d, 1H), 3.22 (d, 1H), 2.15 (s, 3H).

Separation of the Enantiomers:

The title compound (250 mg) was dissolved in methanol (15 ml) and separated into the enantiomers by preparative SFC on a chiral phase (see Examples 195 and 196) [column: Daicel AD-H, 5 μm, 250 mm×20 mm; flow rate: 80 ml/min; detection: 210 nm; temperature: 40° C.; injection: 0.5 ml; mobile phase: 25% isopropanol/75% carbon dioxide; run time 13.2 min, isocratic]. The combined target fractions were concentrated and the residue was lyophilized.

Example 195

(+)-{[2-{[(6-Bromo-3-methyl-2-phenylquinolin-4-yl)carbonyl]amino}-1-(2-chlorophenyl)ethyl]sulfanyl}acetic Acid (Enantiomer 1)

In the enantiomer separation described in Example 194, 110 mg (98% purity, ee 99%) of the title compound were obtained as the enantiomer that eluted earlier.

[α]$_D^{20}$=+22.8°, 589 nm, c=0.25 g/100 ml, methanol

LC-MS (Method 1): $R_t$=1.97 min; MS (ESIpos): m/z=569/571 [M+H]$^+$ $^1$H-NMR (400 MHz, DMSO-d6) δ [ppm]: −0.008 (0.70), 1.030 (0.60), 1.046 (0.60), 2.059 (0.59), 2.073 (0.43), 2.145 (8.31), 2.523 (0.40), 3.199 (3.42), 3.236 (5.29), 3.353 (5.58), 3.391 (3.45), 3.582 (0.55), 3.983 (1.61), 4.812 (1.30), 4.831 (2.31), 4.850 (1.17), 7.305 (0.86), 7.322 (2.04), 7.341 (1.53), 7.384 (1.42), 7.402 (2.32), 7.420 (1.13), 7.472 (3.68), 7.475 (3.49), 7.495 (4.93), 7.506 (4.01), 7.516 (16.00), 7.527 (5.22), 7.606 (2.57), 7.624 (2.17), 7.773 (0.52), 7.828 (2.15), 7.833 (1.84), 7.850 (3.13), 7.856 (2.89), 7.926 (5.32), 7.948 (3.38), 9.025 (1.18), 9.040 (2.35), 9.054 (1.21).

$^1$H-NMR (400 MHz, DMSO-d6) δ [ppm]: 12.65 (br. s, 1H), 9.04 (t, 1H), 7.93 (d, 1H), 7.84 (dd, 1H), 7.77 (br. s, 1H), 7.62 (d, 1H), 7.55-7.45 (m, 6H), 7.40 (t, 1H), 7.33 (t, 1H), 4.83 (t, 1H), 3.98 (br. s, 2H), 3.37 (d, 1H), 3.22 (d, 1H), 2.15 (s, 3H).

Example 196

(−)-{[2-{[(6-Bromo-3-methyl-2-phenylquinolin-4-yl)carbonyl]amino}-1-(2-chlorophenyl)ethyl]sulfanyl}acetic Acid (Enantiomer 2)

In the enantiomer separation described in Example 194, 70 mg (98% purity, ee 99%) of the title compound were obtained as the enantiomer that eluted later.

[α]$_D^{20}$=−25.4°, 589 nm, c=0.28 g/100 ml, methanol

LC-MS (Method 1): $R_t$=1.97 min; MS (ESIpos): m/z=569/571 [M+H]$^+$ $^1$H-NMR (400 MHz, DMSO-d6) δ [ppm]: −0.008 (1.20), 0.008 (0.96), 1.151 (0.48), 2.058 (0.42), 2.146 (8.57), 2.523 (0.60), 3.194 (3.65), 3.232 (5.76), 3.344 (6.61), 3.382 (3.69), 3.980 (1.60), 4.806 (1.31), 4.825 (2.35), 4.844 (1.18), 7.304 (0.87), 7.322 (2.08), 7.340 (1.56), 7.383 (1.46), 7.402 (2.36), 7.419 (1.13), 7.471 (3.88), 7.474 (3.73), 7.491 (3.92), 7.495 (4.69), 7.498 (4.45), 7.506 (4.11), 7.517 (16.00), 7.527 (5.22), 7.530 (4.79), 7.605 (2.60), 7.622 (2.20), 7.776 (0.56), 7.828 (2.40), 7.833 (1.99), 7.850 (3.49), 7.856 (3.13), 7.925 (5.97), 7.948 (3.77), 9.041 (1.14), 9.055 (2.19), 9.069 (1.09).

$^1$H-NMR (400 MHz, DMSO-d6) δ [ppm]: 12.69 (br. s, 1H), 9.06 (t, 1H), 7.93 (d, 1H), 7.84 (dd, 1H), 7.78 (br. s, 1H), 7.61 (dd, 1H), 7.56-7.45 (m, 6H), 7.40 (t, 1H), 7.32 (t, 1H), 4.83 (t, 1H), 3.98 (br. s, 2H), 3.36 (d, 1H), 3.22 (d, 1H), 2.15 (s, 3H).

Example 197

(+/−)-{[2-{[(6-Bromo-3-methyl-2-phenylquinolin-4-yl)carbonyl]amino}-1-(2-chlorophenyl)ethyl]sulfonyl}acetic Acid (Racemate)

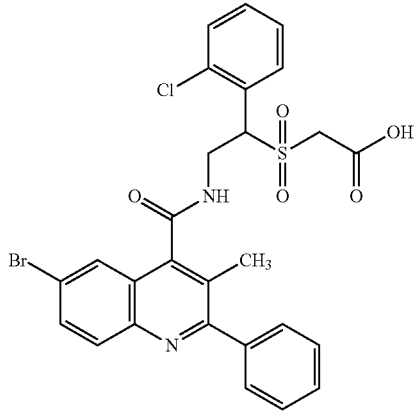 [SMILES: Cc1c(-c2ccccc2)nc2ccc(Br)cc2c1C(=O)NCC(c1ccccc1Cl)S(=O)(=O)CC(=O)O]

1 M aqueous sodium hydroxide solution (300 µl, 300 µmol) was added to a solution of (+/−)methyl {[2-{[(6-bromo-3-methyl-2-phenylquinolin-4-yl)carbonyl]amino}-1-(2-chlorophenyl)ethyl]sulfonyl}acetate (50 mg, 93% purity, 75.5 µmol, Example 264A) in THF (740 µl) and methanol (250 µl), and the mixture was allowed to stand at RT for 16 h. Subsequently, the mixture was purified directly (without further work-up) by preparative HPLC (Method 17). The combined target fractions were concentrated, and the residue was lyophilized. This gave 40 mg (98% purity, 86% of theory) of the title compound.

LC-MS (Method 1): $R_t$=1.86 min; MS (ESIpos): m/z=601/603 [M+H]$^+$ $^1$H-NMR (400 MHz, DMSO-d6) δ [ppm]: 9.23 (br. s, 1H), 7.92 (d, 1H), 7.83 (dd, 1H), 7.76-7.57 (m, 2H), 7.56-7.38 (m, 8H), 5.87 (t, 1H), 4.42-4.18 (m, 3H), 4.00-3.83 (m, 1H), 2.01 (br. s, 3H).

Separation of the Enantiomers:

The title compound (35 mg) was dissolved in a mixture of ethanol (1 ml) and dichloromethane (2 ml) and separated into the enantiomers by preparative HPLC on a chiral phase (see Examples 198 and 199) [column: Daicel Chiralpak IF, 5 µm 250 mm×20 mm; flow rate: 15 ml/min; detection: 220 nm; temperature: 35° C.; injection: 0.50 ml; mobile phase: 60% heptane/40% (ethanol+0.2% TFA), run time 12 min, isocratic]. The combined target fractions were concentrated and the residue was lyophilized.

Example 198

(+/−)-{[2-{[(6-Bromo-3-methyl-2-phenylquinolin-4-yl)carbonyl]amino}-1-(2-chlorophenyl)ethyl]sulfonyl}acetic Acid (Enantiomer 1)

In the enantiomer separation described in Example 197, the prepurified title compound was obtained as the enantiomer that eluted earlier (ee 99%). This was followed by repurification by preparative HPLC (Method 18). The combined target fractions were concentrated, and the residue was dried under reduced pressure. 23 mg (95% purity, contains solvent according to $^1$H NMR) of the repurified title compound were obtained.

$[\alpha]_D^{20}$=+17.2°, 589 nm, c=0.25 g/100 ml, methanol
LC-MS (Method 1): $R_t$=1.78 min; MS (ESIpos): m/z=601/603 [M+H]$^+$ $^1$H-NMR (400 MHz, DMSO-d6) δ [ppm]: 9.32 (s, 1H), 7.91 (d, 1H), 7.83 (dd, 1H), 7.75 (d, 1H), 7.56-7.37 (m, 9H), 6.02-5.93 (m, 1H), 4.41-4.15 (m, 2H), 3.91 (d, 1H), 3.56 (d, 1H), 2.03 (br. s, 3H).

Example 199

{[2-{[(6-Bromo-3-methyl-2-phenylquinolin-4-yl)carbonyl]amino}-1-(2-chlorophenyl)ethyl]sulfonyl}acetic Acid (Enantiomer 2)

In the enantiomer separation described in Example 197, the prepurified title compound was obtained as the enantiomer that eluted later (ee 99%). This was followed by repurification by preparative HPLC (Method 18). The combined target fractions were concentrated, and the residue was dried under reduced pressure. This gave 23 mg (95% purity) of the repurified title compound.

LC-MS (Method 1): $R_t$=1.78 min; MS (ESIpos): m/z=601/603 [M+H]$^+$ $^1$H-NMR (400 MHz, DMSO-d6) δ [ppm]: 9.42-9.32 (m, 1H), 7.91 (d, 1H), 7.82 (dd, 1H), 7.75 (d, 1H), 7.56-7.31 (m, 9H), 5.98 (dd, 1H), 4.44-4.28 (m, 1H), 4.26-4.14 (m, 1H), 3.87 (d, 1H), 3.52 (d, 1H), 2.04 (br. s, 3H).

Example 200

(+/−)-5-{[(6-Bromo-3-methyl-2-phenylquinolin-4-yl)carbonyl]amino}-4-(6-chloro-2,3-difluorophenyl)pentanoic Acid (Racemate)

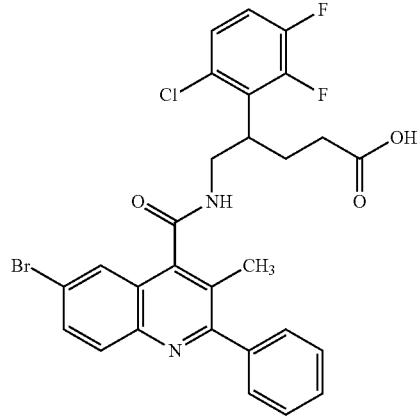 [SMILES: Cc1c(-c2ccccc2)nc2ccc(Br)cc2c1C(=O)NCC(CCC(=O)O)c1c(Cl)ccc(F)c1F]

TFA (320 µl, 4.1 mmol) was added to a solution of (+/−)-tert-butyl 5-{[(6-bromo-3-methyl-2-phenylquinolin-4-yl)carbonyl]amino}-4-(6-chloro-2,3-difluorophenyl)pentanoate (121 mg, 188 µmol, Example 265A) in dichloromethane (1.6 ml), and the mixture was allowed to stand at RT for 16 h. The mixture was then concentrated and repeatedly dichloromethane was added and the mixture was concentrated again. The residue was taken up in acetonitrile and purified by preparative HPLC (Method 15). The combined target fractions were concentrated and the residue was lyophilized. This gave 81 mg (100% purity, 73% of theory) of the title compound.

LC-MS (Method 2): $R_t$=1.05 min; MS (ESIpos): m/z=587/589 [M+H]$^+$

¹H-NMR (400 MHz, DMSO-d6) δ [ppm]: 0.008 (0.62), 1.988 (0.64), 2.073 (0.98), 2.084 (1.18), 2.103 (1.23), 2.121 (2.06), 2.156 (10.15), 2.183 (2.38), 2.206 (0.95), 2.524 (0.67), 3.730 (1.05), 3.766 (0.80), 3.814 (1.72), 7.350 (0.69), 7.373 (2.16), 7.384 (2.42), 7.406 (1.29), 7.426 (1.00), 7.491 (1.49), 7.502 (4.34), 7.510 (4.30), 7.521 (16.00), 7.532 (5.94), 7.838 (2.39), 7.844 (2.04), 7.861 (3.68), 7.866 (3.33), 7.933 (6.34), 7.955 (3.93), 8.940 (1.24), 8.954 (2.38), 8.968 (1.16).

¹H-NMR (400 MHz, DMSO-d6) δ [ppm]: 12.10 (br. s, 1H), 8.95 (br. t, 1H), 7.94 (d, 1H), 7.86 (dd, 1H), 7.72 (br. s, 1H), 7.57-7.46 (m, 5H), 7.46-7.32 (m, 2H), 3.96-3.61 (m, 3H), 2.27-1.85 (m, 7H).

Example 201

(−)-5-{[(6-Bromo-3-methyl-2-phenylquinolin-4-yl)carbonyl]amino}-4-(6-chloro-2,3-difluorophenyl)pentanoic Acid (Enantiomer 1)

TFA (170 μl, 2.2 mmol) was added to a solution of (−)-tert-butyl 5-{[(6-bromo-3-methyl-2-phenylquinolin-4-yl)carbonyl]amino}-4-(6-chloro-2,3-difluorophenyl)pentanoate (140 mg, 217 μmol, Example 266A) in dichloromethane (3.8 ml), and the mixture was stirred at RT overnight. The mixture was then concentrated and repeatedly dichloromethane was added and the mixture was concentrated again. The residue was taken up in acetonitrile and purified by preparative HPLC (Method 14). The combined target fractions were concentrated, and the residue was lyophilized. This gave 93 mg (98% purity, ee 99%, 71% of theory) of the title compound.

$[\alpha]_D^{20}$=−31.6°, 589 nm, c=0.25 g/100 ml, methanol
LC-MS (Method 1): $R_t$=2.08 min; MS (ESIpos): m/z=587/569 [M+H]$^+$ ¹H-NMR (400 MHz, DMSO-d6) δ [ppm]: 1.991 (0.63), 2.071 (0.93), 2.083 (1.12), 2.102 (1.18), 2.118 (1.94), 2.156 (10.24), 2.179 (2.39), 3.730 (1.04), 3.766 (0.82), 3.813 (1.70), 7.372 (2.13), 7.384 (2.40), 7.405 (1.29), 7.426 (1.00), 7.491 (1.42), 7.502 (4.04), 7.509 (3.99), 7.521 (16.00), 7.838 (2.18), 7.843 (2.00), 7.861 (3.31), 7.866 (3.21), 7.932 (5.89), 7.955 (3.64), 8.940 (1.16), 8.955 (2.24), 8.969 (1.13).

¹H-NMR (400 MHz, DMSO-d6) δ [ppm]: 12.11 (br. s, 1H), 8.96 (t, 1H), 7.94 (d, 1H), 7.85 (dd, 1H), 7.72 (br. s, 1H), 7.55-7.46 (m, 5H), 7.46-7.33 (m, 2H), 3.92-3.63 (m, 3H), 2.28-1.82 (m, 7H).

Example 202

(+)-5-{[(6-Bromo-3-methyl-2-phenylquinolin-4-yl)carbonyl]amino}-4-(6-chloro-2,3-difluorophenyl)pentanoic Acid (Enantiomer 2)

TFA (170 μl, 2.3 mmol) was added to a solution of (+)-tert-butyl 5-{[(6-bromo-3-methyl-2-phenylquinolin-4-yl)carbonyl]amino}-4-(6-chloro-2,3-difluorophenyl)pentanoate (145 mg, 225 μmol, Example 267A) in dichloromethane (4.0 ml), and the mixture was stirred at RT overnight. The mixture was then concentrated and repeatedly dichloromethane was added and the mixture was concentrated again. The residue was taken up in acetonitrile and purified by preparative HPLC (Method 14). The combined target fractions were concentrated, and the residue was lyophilized. This gave 94 mg (98% purity, ee 93%, 70% of theory) of the title compound.

$[\alpha]_D^{20}$=+34.9°, 589 nm, c=0.28 g/100 ml, methanol
LC-MS (Method 1): $R_t$=2.08 min; MS (ESIpos): m/z=587/589 [M+H]$^+$ ¹H-NMR (400 MHz, DMSO-d6) δ [ppm]: 1.153 (0.91), 1.180 (0.64), 1.992 (0.63), 2.074 (0.95), 2.087 (1.14), 2.105 (1.16), 2.125 (1.89), 2.156 (10.43), 2.188 (2.43), 2.210 (0.95), 3.731 (1.05), 3.768 (0.82), 3.815 (1.72), 7.373 (2.18), 7.385 (2.46), 7.406 (1.30), 7.428 (1.04), 7.492 (1.55), 7.503 (4.33), 7.510 (4.32), 7.522 (16.00), 7.532 (6.01), 7.840 (2.40), 7.845 (2.15), 7.862 (3.65), 7.867 (3.48), 7.934 (6.44), 7.956 (3.98), 8.940 (1.22), 8.955 (2.34), 8.969 (1.15).

¹H-NMR (400 MHz, DMSO-d6) δ [ppm]: 12.08 (br. s, 1H), 8.95 (t, 1H), 7.94 (d, 1H), 7.86 (dd, 1H), 7.72 (br. s, 1H), 7.55-7.47 (m, 5H), 7.45-7.33 (m, 2H), 3.93-3.62 (m, 3H), 2.28-1.87 (m, 7H).

Example 203

(+/−)-5-{[(6-Bromo-3-methyl-2-phenylquinolin-4-yl)carbonyl]amino}-4-[2-(trifluoromethyl)phenyl]pentanoic Acid (Racemate)

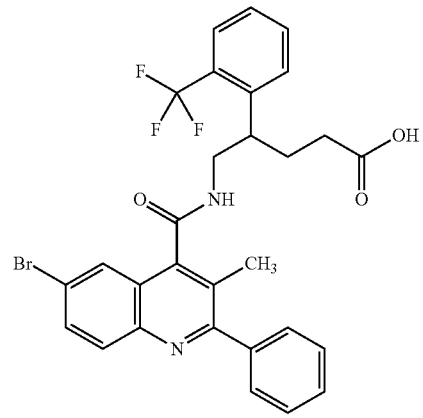 [SMILES: Cc1c(-c2ccccc2)nc2ccc(Br)cc2c1C(=O)NCC(CCC(=O)O)c1ccccc1C(F)(F)F]

1 M aqueous sodium hydroxide solution (3.2 ml, 3.2 mmol) was added to a solution of (+/−)methyl 5-{[(6-bromo-3-methyl-2-phenylquinolin-4-yl)carbonyl]amino}-4-[2-(trifluoromethyl)phenyl]pentanoate (500 mg, 96% purity, 801 μmol, Example 268A) in THF (7.8 ml) and methanol (2.6 ml), and the mixture was allowed to stand at RT for 16 h. Subsequently, the mixture was purified directly (without further work-up) by preparative HPLC (Method 17). The combined target fractions were concentrated, and the residue was lyophilized. This gave 415 mg (98% purity, 87% of theory) of the title compound.

LC-MS (Method 2): $R_t$=1.09 min; MS (ESIpos): m/z=585/587 [M+H]$^+$

¹H-NMR (400 MHz, DMSO-d6) δ [ppm]: −0.008 (3.38), 0.008 (2.76), 1.667 (1.46), 1.681 (1.85), 1.691 (2.53), 1.714 (2.17), 1.725 (1.83), 1.758 (0.78), 1.780 (1.28), 1.820 (5.23), 1.832 (2.78), 1.844 (2.63), 1.856 (1.82), 1.879 (0.92), 1.968 (1.06), 1.982 (1.59), 1.996 (1.85), 2.014 (1.74), 2.026 (2.03), 2.179 (5.86), 2.258 (0.88), 2.328 (0.58), 2.366 (0.51), 2.670 (0.56), 2.710 (0.46), 3.606 (1.44), 3.622 (1.90), 3.638 (2.00), 3.719 (1.35), 3.735 (2.21), 3.751 (2.00), 3.767 (1.50), 7.426 (1.77), 7.440 (3.06), 7.458 (2.01), 7.472 (1.21), 7.476 (1.17), 7.488 (3.64), 7.499 (5.24), 7.504 (11.48), 7.509 (8.35), 7.523 (13.20), 7.542 (16.00), 7.561 (4.59), 7.661 (1.58), 7.681 (7.35), 7.694 (15.24), 7.710 (6.12), 7.826 (4.03), 7.831 (3.77), 7.849 (6.03), 7.854 (5.92), 7.929 (10.87), 7.952 (7.22), 9.401 (2.02).

¹H-NMR (400 MHz, DMSO-d6) δ [ppm]: 9.40 (br. s, 1H), 7.94 (d, 1H), 7.84 (dd, 1H), 7.80-7.58 (m, 4H), 7.57-7.39 (m, 6H), 3.81-3.69 (m, 1H), 3.68-3.55 (m, 1H), 3.37-3.24 (m, 1H, obscured), 2.18 (br. s, 3H), 2.06-1.94 (m, 1H), 1.91-1.75 (m, 2H), 1.74-1.60 (m, 1H).

Separation of the Enantiomers:

The title compound (380 mg) was taken up in methanol (30 ml), filtered and separated into the enantiomers by preparative SFC on a chiral phase (see Examples 204 and 205) [column: Daicel Chiralcel AD-H, 5 μm, 250 mm×20 mm; flow rate: 80 ml/min; injection: 0.50 ml; mobile phase: 25% isopropanol/75% carbon dioxide; run time 6 min, isocratic]. The combined target fractions were concentrated and the residue was lyophilized.

Example 204

(−)-5-{[(6-Bromo-3-methyl-2-phenylquinolin-4-yl)carbonyl]amino}-4-[2-(trifluoromethyl)phenyl]pentanoic Acid (Enantiomer 1)

In the enantiomer separation described in Example 203, 122 mg (98% purity, ee 99%) of the title compound were obtained as the enantiomer that eluted earlier.

$[\alpha]_D^{20}$=−21.3°, 589 nm, c=0.29 g/100 ml, methanol

LC-MS (Method 1): $R_t$=2.11 min; MS (ESIpos): m/z=585/587 [M+H]⁺

¹H-NMR (400 MHz, DMSO-d6) δ [ppm]: −0.008 (1.59), 0.008 (1.00), 1.030 (1.73), 1.046 (1.73), 1.876 (2.12), 1.889 (2.92), 1.904 (2.98), 1.926 (2.60), 1.983 (1.27), 2.004 (2.14), 2.027 (2.52), 2.042 (1.42), 2.063 (2.62), 2.084 (1.71), 2.097 (1.99), 2.105 (2.02), 2.164 (4.49), 2.248 (0.63), 2.328 (0.41), 2.524 (1.71), 2.670 (0.40), 3.625 (1.75), 3.643 (2.03), 3.657 (2.01), 3.762 (2.00), 3.778 (1.81), 3.794 (1.41), 7.446 (1.79), 7.465 (3.56), 7.488 (4.35), 7.499 (5.24), 7.504 (8.90), 7.510 (7.19), 7.523 (13.11), 7.536 (16.00), 7.555 (3.03), 7.624 (0.60), 7.678 (2.04), 7.698 (4.60), 7.711 (6.35), 7.729 (8.88), 7.748 (2.18), 7.830 (3.68), 7.836 (3.32), 7.853 (5.27), 7.858 (4.94), 7.934 (9.75), 7.956 (6.33), 8.991 (2.64).

¹H-NMR (400 MHz, DMSO-d6) δ [ppm]: 8.99 (br. t, 1H), 7.94 (d, 1H), 7.84 (dd, 1H), 7.78-7.57 (m, 4H), 7.57-7.42 (m, 6H), 3.85-3.72 (m, 1H), 3.70-3.59 (m, 1H), 3.37-3.27 (m, 1H, partially obscured), 2.23-1.96 (m, 5H), 1.95-1.83 (m, 2H).

Example 205

(+)-5-{[(6-Bromo-3-methyl-2-phenylquinolin-4-yl)carbonyl]amino}-4-[2-(trifluoromethyl)phenyl]pentanoic Acid (Enantiomer 2)

In the enantiomer separation described in Example 203, 109 mg (98% purity, ee 98%) of the title compound were obtained as the enantiomer that eluted later.

$[\alpha]_D^{20}$=+22.7°, 589 nm, c=0.37 g/100 ml, methanol

LC-MS (Method 1): $R_t$=2.11 min; MS (ESIpos): m/z=585/587 [M+H]⁺

¹H-NMR (400 MHz, DMSO-d6) δ [ppm]: −0.008 (0.81), 1.031 (3.90), 1.046 (3.97), 1.858 (0.66), 1.889 (1.78), 1.909 (2.85), 1.926 (2.61), 1.938 (1.68), 1.949 (2.14), 2.004 (1.36), 2.023 (2.06), 2.046 (2.38), 2.062 (1.51), 2.080 (2.49), 2.109 (1.99), 2.118 (2.20), 2.166 (4.52), 2.250 (0.57), 3.631 (1.49), 3.648 (1.82), 3.664 (1.87), 3.766 (1.88), 3.774 (1.80), 3.782 (1.72), 3.799 (1.33), 7.450 (1.66), 7.469 (3.74), 7.489 (4.62), 7.505 (8.38), 7.511 (6.77), 7.524 (12.77), 7.537 (16.00), 7.555 (3.12), 7.629 (0.55), 7.682 (1.86), 7.701 (4.31), 7.715 (6.05), 7.734 (8.49), 7.755 (2.27), 7.832 (3.52), 7.837 (3.31), 7.854 (5.18), 7.859 (5.12), 7.935 (9.70), 7.957 (6.31), 8.942 (1.72), 8.955 (3.21), 8.969 (1.68).

¹H-NMR (400 MHz, DMSO-d6) δ [ppm]: 8.96 (t, 1H), 7.94 (d, 1H), 7.85 (dd, 1H), 7.78-7.58 (m, 4H), 7.57-7.43 (m, 6H), 3.85-3.72 (m, 1H), 3.71-3.59 (m, 1H), 3.38-3.29 (m, 1H), 2.23-1.99 (m, 5H), 1.98-1.82 (m, 2H).

Example 206

(+/−)-5-{[(6-Bromo-3-methyl-2-phenylquinolin-4-yl)carbonyl]amino}-4-(5-fluoro-2-methylphenyl)pentanoic Acid (Racemate)

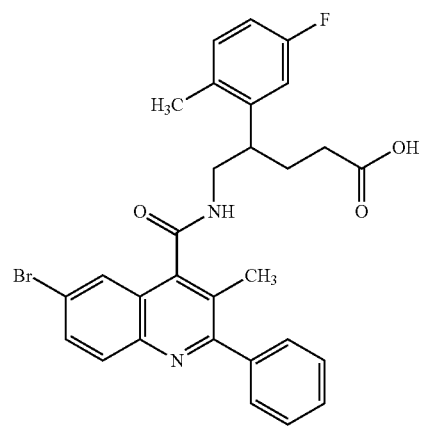

TFA (340 μl, 4.4 mmol) was added to a solution of (+/−)-tert-butyl 5-{[(6-bromo-3-methyl-2-phenylquinolin-4-yl)carbonyl]amino}-4-(5-fluoro-2-methylphenyl)pentanoate (122 mg, 202 μmol, Example 269A) in dichloromethane (1.7 ml), and the mixture was allowed to stand at RT for 16 h. The mixture was then concentrated and repeatedly dichloromethane was added and the mixture was concentrated again. The residue was taken up in acetonitrile and purified by preparative HPLC (Method 15). The combined target fractions were concentrated and the residue was lyophilized. This gave 91 mg (100% purity, 82% of theory) of the title compound.

LC-MS (Method 2): $R_t$=1.05 min; MS (ESIpos): m/z=549/551 [M+H]⁺

¹H-NMR (400 MHz, DMSO-d6) δ [ppm]: −0.008 (0.76), 0.969 (0.40), 1.773 (0.79), 1.788 (0.99), 1.796 (1.02), 1.807 (1.15), 1.812 (1.15), 1.830 (0.89), 1.845 (0.48), 1.981 (0.45), 2.001 (1.09), 2.013 (1.39), 2.032 (1.49), 2.051 (1.65), 2.080 (5.67), 2.096 (8.09), 2.112 (4.66), 2.295 (14.18), 2.524 (0.71), 3.505 (0.93), 3.518 (1.31), 3.538 (1.41), 3.552 (1.61), 3.565 (0.95), 3.724 (0.98), 3.743 (1.45), 3.762 (1.27), 3.776 (1.15), 3.796 (0.69), 6.920 (0.96), 6.941 (1.82), 6.957 (1.03), 7.156 (2.15), 7.162 (2.21), 7.183 (2.42), 7.190 (4.02), 7.207 (2.52), 7.211 (2.39), 7.227 (1.87), 7.478 (0.56), 7.491 (1.66), 7.501 (4.98), 7.509 (4.71), 7.520 (16.00), 7.531 (7.07), 7.648 (0.56), 7.833 (2.49), 7.838 (2.35), 7.855 (3.81), 7.860 (3.73), 7.932 (6.89), 7.954 (4.42), 8.836 (1.61), 8.852 (2.38), 8.865 (1.56).

¹H-NMR (400 MHz, DMSO-d6) δ [ppm]: 12.06 (br. s, 1H), 8.85 (t, 1H), 7.94 (d, 1H), 7.85 (dd, 1H), 7.65 (br. s, 1H), 7.56-7.45 (m, 5H), 7.24-7.13 (m, 2H), 6.94 (td, 1H), 3.76 (td, 1H), 3.54 (td, 1H), 3.42-3.30 (1H, obscured), 2.30 (s, 3H), 2.16-1.96 (m, 6H), 1.87-1.73 (m, 1H).

Example 207

(−)-5-{[(6-Bromo-3-methyl-2-phenylquinolin-4-yl)carbonyl]amino}-4-(5-fluoro-2-methylphenyl)pentanoic Acid (Enantiomer 1)

TFA (310 µl, 4.1 mmol) was added to a solution of (−)-tert-butyl 5-{[(6-bromo-3-methyl-2-phenylquinolin-4-yl)carbonyl]amino}-4-(5-fluoro-2-methylphenyl)pentanoate (112 mg, 185 µmol, Example 270A) in dichloromethane (1.6 ml), and the mixture was allowed to stand at RT overnight. The mixture was then concentrated and repeatedly dichloromethane was added and the mixture was concentrated again. The residue was purified by preparative HPLC (Method 17). The combined target fractions were concentrated, and the residue was lyophilized. This gave 95 mg (100% purity, ee 99%, 93% of theory) of the title compound.

$[\alpha]_D^{20}$=−20.0°, 589 nm, c=0.34 g/100 ml, methanol

LC-MS (Method 1): $R_t$=1.98 min; MS (ESIpos): m/z=549/551 [M+H]$^+$ $^1$H-NMR (400 MHz, DMSO-d6) δ [ppm]: 0.008 (1.08), 1.769 (0.75), 1.784 (1.00), 1.792 (1.01), 1.807 (1.16), 1.822 (0.89), 1.841 (0.49), 1.976 (0.49), 1.996 (1.09), 2.009 (1.38), 2.028 (1.46), 2.036 (1.15), 2.046 (1.73), 2.073 (5.26), 2.089 (7.14), 2.105 (5.18), 2.294 (14.25), 3.503 (0.90), 3.516 (1.28), 3.537 (1.37), 3.550 (1.61), 3.564 (0.94), 3.724 (0.98), 3.742 (1.45), 3.762 (1.25), 3.775 (1.14), 3.796 (0.69), 6.918 (0.95), 6.939 (1.84), 6.954 (1.05), 7.154 (2.15), 7.160 (2.16), 7.181 (2.40), 7.188 (3.89), 7.205 (2.56), 7.209 (2.38), 7.226 (1.89), 7.477 (0.54), 7.490 (1.62), 7.500 (4.98), 7.508 (4.63), 7.520 (16.00), 7.531 (7.15), 7.647 (0.58), 7.832 (2.54), 7.837 (2.31), 7.854 (3.87), 7.859 (3.68), 7.931 (6.92), 7.953 (4.45), 8.838 (1.58), 8.853 (2.39), 8.866 (1.54).

$^1$H-NMR (400 MHz, DMSO-d6) δ [ppm]: 12.11 (br. s, 1H), 8.85 (t, 1H), 7.94 (d, 1H), 7.85 (dd, 1H), 7.65 (br. s, 1H), 7.56-7.44 (m, 5H), 7.25-7.11 (m, 2H), 6.94 (td, 1H), 3.82-3.69 (m, 1H), 3.59-3.48 (m, 1H), 3.4-3.3 (1H, obscured), 2.29 (s, 3H), 2.18-1.95 (m, 6H), 1.86-1.73 (m, 1H).

Example 208

(+)-5-{[(6-Bromo-3-methyl-2-phenylquinolin-4-yl)carbonyl]amino}-4-(5-fluoro-2-methylphenyl)pentanoic Acid (Enantiomer 2)

TFA (310 µl, 4.0 mmol) was added to a solution of (+)-tert-butyl 5-{[(6-bromo-3-methyl-2-phenylquinolin-4-yl)carbonyl]amino}-4-(5-fluoro-2-methylphenyl)pentanoate (110 mg, 182 µmol, Example 271A) in dichloromethane (1.5 ml), and the mixture was allowed to stand at RT overnight. The mixture was then concentrated and repeatedly dichloromethane was added and the mixture was concentrated again. The residue was purified by preparative HPLC (Method 17). The combined target fractions were concentrated, and the residue was lyophilized. This gave 93 mg (100% purity, ee 97%, 93% of theory) of the title compound.

$[\alpha]_D^{20}$=+16.3°, 589 nm, c=0.37 g/100 ml, methanol

LC-MS (Method 1): $R_t$=1.98 min; MS (ESIpos): m/z=549/551 [M+H]$^+$ $^1$H-NMR (400 MHz, DMSO-d6) δ [ppm]: 0.069 (0.42), 1.771 (0.79), 1.787 (1.01), 1.794 (1.04), 1.805 (1.19), 1.825 (0.92), 1.843 (0.50), 1.979 (0.49), 1.998 (1.12), 2.012 (1.42), 2.030 (1.52), 2.049 (1.74), 2.077 (5.56), 2.093 (7.82), 2.109 (5.15), 2.294 (14.31), 3.504 (0.87), 3.517 (1.27), 3.537 (1.36), 3.551 (1.60), 3.565 (0.93), 3.724 (0.97), 3.742 (1.47), 3.761 (1.28), 3.775 (1.15), 3.796 (0.67), 6.919 (1.00), 6.939 (1.89), 6.956 (1.07), 7.155 (2.18), 7.161 (2.23), 7.189 (4.00), 7.206 (2.58), 7.226 (1.83), 7.476 (0.63), 7.490 (1.71), 7.500 (5.00), 7.508 (4.64), 7.520 (16.00), 7.647 (0.60), 7.832 (2.38), 7.837 (2.20), 7.854 (3.59), 7.859 (3.49), 7.931 (6.51), 7.953 (4.17), 8.837 (1.60), 8.851 (2.45), 8.865 (1.55).

$^1$H-NMR (400 MHz, DMSO-d6) δ [ppm]: 12.08 (br. s, 1H), 8.85 (t, 1H), 7.94 (d, 1H), 7.85 (dd, 1H), 7.65 (br. s, 1H), 7.56-7.45 (m, 5H), 7.25-7.13 (m, 2H), 6.94 (td, 1H), 3.82-3.68 (m, 1H), 3.60-3.48 (m, 1H), 3.4-3.3 (1H, obscured), 2.29 (s, 3H), 2.19-1.95 (m, 6H), 1.86-1.71 (m, 1H).

Example 209

(+/−)-5-{[(6-Bromo-3-methyl-2-phenylquinolin-4-yl)carbonyl]amino}-4-[2-(trifluoromethoxy)phenyl]pentanoic Acid (Racemate)

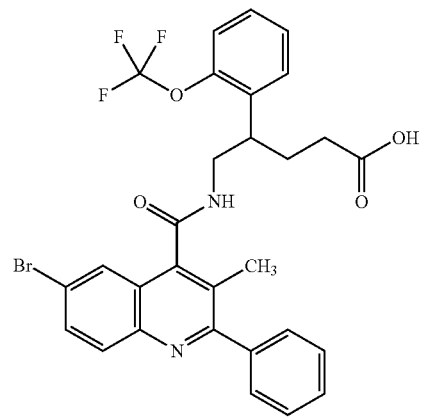 [SMILES: Cc1c(-c2ccccc2)nc2ccc(Br)cc2c1C(=O)NCC(CCC(=O)O)c1ccccc1OC(F)(F)F]

TFA (290 µl, 3.8 mmol) was added to a solution of (+/−)-tert-butyl 5-{[(6-bromo-3-methyl-2-phenylquinolin-4-yl)carbonyl]amino}-4-[2-(trifluoromethoxy)phenyl]pentanoate (250 mg, 380 µmol, Example 272A) in dichloromethane (5.0 ml), and the mixture was stirred at RT overnight. The mixture was then concentrated and repeatedly dichloromethane was added and the mixture was concentrated again. The residue was taken up in acetonitrile and purified by preparative HPLC (Method 14). The combined target fractions were concentrated, and the residue was lyophilized. This gave 192 mg (98% purity, 82% of theory) of the title compound.

LC-MS (Method 1): $R_t$=2.15 min; MS (ESIpos): m/z=601/603 [M+H]$^+$ $^1$H-NMR (400 MHz, DMSO-d6) δ [ppm]: 1.826 (1.37), 1.836 (1.46), 1.847 (1.91), 1.870 (1.28), 2.054 (2.96), 2.062 (2.63), 2.082 (10.68), 2.109 (2.89), 2.146 (4.05), 2.525 (1.39), 3.412 (2.61), 3.627 (0.95), 3.642 (1.39), 3.660 (2.20), 3.676 (2.63), 3.691 (1.67), 3.703 (1.63), 3.720 (2.17), 3.738 (1.79), 3.754 (1.04), 3.772 (0.61), 7.341 (2.05), 7.359 (3.90), 7.381 (1.83), 7.400 (5.00), 7.409 (4.18), 7.418 (4.79), 7.437 (1.32), 7.478 (1.54), 7.490 (2.82), 7.494 (2.85), 7.504 (7.28), 7.511 (6.65), 7.523 (16.00), 7.529 (14.55), 7.536 (9.55), 7.548 (2.33), 7.565 (3.86), 7.581 (2.94), 7.588 (2.71), 7.655 (0.64), 7.835 (3.21), 7.841 (2.87), 7.858 (4.67), 7.863 (4.30), 7.934 (8.58), 7.957 (5.43), 8.864 (2.03), 8.879 (3.53), 8.893 (1.77).

$^1$H-NMR (400 MHz, DMSO-d6) δ [ppm]: 12.07 (br. s, 1H), 8.88 (t, 1H), 7.94 (d, 1H), 7.85 (dd, 1H), 7.66 (br. s, 1H), 7.60-7.46 (m, 6H), 7.45-7.31 (m, 3H), 3.86-3.56 (m, 2H), 3.48-3.33 (m, 1H, partially obscured), 2.25-1.97 (m, 6H), 1.91-1.76 (m, 1H).

Example 210

(+)-5-{[(6-Bromo-3-methyl-2-phenylquinolin-4-yl)carbonyl]amino}-4-[2-(trifluoromethoxy)phenyl]pentanoic Acid (Enantiomer 1)

TFA (1.2 ml, 15 mmol) was added to a solution of (+)-tert-butyl 5-{[(6-bromo-3-methyl-2-phenylquinolin-4-yl)carbonyl]amino}-4-[2-(trifluoromethoxy)phenyl]pentanoate (1.00 g, 1.52 mmol, Example 273A) in dichloromethane (10 ml), and the mixture was allowed to stand at RT overnight. The mixture was then concentrated and repeatedly dichloromethane was added and the mixture was concentrated again. The residue was purified by preparative HPLC (Method 19). The combined target fractions were concentrated, and the residue was lyophilized. This gave 782 mg (98% purity, 94% of theory) of the title compound.

$[\alpha]_D^{20}$=+20.8°, 589 nm, c=0.30 g/100 ml, methanol
LC-MS (Method 1): $R_t$=2.08 min; MS (ESIpos): m/z=601/603 [M+H]$^+$
$^1$H-NMR (400 MHz, DMSO-d6) δ [ppm]: -0.008 (1.23), 0.008 (1.09), 1.827 (1.38), 1.838 (1.41), 1.849 (1.97), 1.872 (1.34), 2.058 (2.52), 2.074 (4.27), 2.086 (11.66), 2.112 (2.61), 2.146 (3.88), 2.333 (0.49), 3.415 (1.70), 3.429 (1.69), 3.628 (1.61), 3.643 (2.22), 3.661 (3.30), 3.677 (3.96), 3.692 (3.02), 3.703 (3.03), 3.720 (3.62), 3.738 (3.22), 3.754 (2.28), 3.772 (1.71), 7.341 (1.76), 7.360 (3.77), 7.381 (1.51), 7.400 (4.95), 7.410 (4.07), 7.419 (4.86), 7.437 (1.15), 7.479 (0.88), 7.490 (2.03), 7.504 (6.72), 7.511 (5.87), 7.524 (16.00), 7.529 (14.91), 7.536 (9.93), 7.548 (2.26), 7.566 (3.87), 7.582 (3.03), 7.589 (2.94), 7.658 (0.62), 7.837 (3.15), 7.842 (2.93), 7.859 (4.76), 7.864 (4.68), 7.935 (9.45), 7.958 (6.02), 8.862 (1.93), 8.877 (3.73), 8.891 (1.94).
$^1$H-NMR (400 MHz, DMSO-d6) δ [ppm]: 12.11 (br. s, 1H), 8.88 (t, 1H), 7.94 (d, 1H), 7.85 (dd, 1H), 7.66 (br. s, 1H), 7.60-7.47 (m, 6H), 7.45-7.31 (m, 3H), 3.79-3.61 (m, 2H), 3.47-3.37 (m, 1H), 2.24-1.99 (m, 6H), 1.92-1.75 (m, 1H).

Example 211

(-)-5-{[(6-Bromo-3-methyl-2-phenylquinolin-4-yl)carbonyl]amino}-4-[2-(trifluoromethoxy)phenyl]pentanoic Acid (Enantiomer 2)

TFA (1.2 ml, 15 mmol) was added to a solution of (-)-tert-butyl 5-{[(6-bromo-3-methyl-2-phenylquinolin-4-yl)carbonyl]amino}-4-[2-(trifluoromethoxy)phenyl]pentanoate (1.00 g, 1.52 mmol, Example 274A) in dichloromethane (9.4 ml), and the mixture was allowed to stand at RT overnight. The mixture was then concentrated and repeatedly dichloromethane was added and the mixture was concentrated again. The residue was purified by preparative HPLC (Method 19). The combined target fractions were concentrated, and the residue was lyophilized. This gave 726 mg (98% purity, 78% of theory) of the title compound.

$[\alpha]_D^{20}$=-18.6°, 589 nm, c=0.34 g/100 ml, methanol
LC-MS (Method 2): $R_t$=1.10 min; MS (ESIpos): m/z=601/603 [M+H]$^+$
$^1$H-NMR (400 MHz, DMSO-d6) δ [ppm]: -0.008 (2.09), 0.008 (1.21), 1.814 (0.89), 1.825 (1.42), 1.837 (1.47), 1.848 (1.95), 1.871 (1.29), 2.019 (0.40), 2.058 (2.85), 2.063 (2.58), 2.085 (11.46), 2.112 (2.86), 2.145 (3.97), 3.627 (0.89), 3.642 (1.34), 3.661 (2.18), 3.676 (2.64), 3.691 (1.66), 3.702 (1.64), 3.719 (2.17), 3.737 (1.80), 3.752 (1.00), 3.771 (0.61), 7.341 (1.92), 7.356 (3.21), 7.360 (3.85), 7.363 (3.12), 7.381 (1.75), 7.400 (4.97), 7.409 (4.13), 7.419 (4.77), 7.437 (1.16), 7.478 (1.32), 7.490 (2.64), 7.493 (2.63), 7.504 (7.12), 7.511 (6.61), 7.523 (16.00), 7.528 (14.76), 7.536 (9.48), 7.548 (2.27), 7.565 (3.91), 7.582 (2.98), 7.589 (2.80), 7.652 (0.61), 7.836 (3.23), 7.841 (2.90), 7.858 (4.74), 7.864 (4.41), 7.934 (8.93), 7.957 (5.65), 8.861 (2.07), 8.875 (3.64), 8.889 (1.81).
$^1$H-NMR (400 MHz, DMSO-d6) δ [ppm]: 12.06 (br. s, 1H), 8.88 (t, 1H), 7.94 (d, 1H), 7.85 (dd, 1H), 7.65 (br. s, 1H), 7.61-7.47 (m, 6H), 7.45-7.31 (m, 3H), 3.80-3.60 (m, 2H), 3.5-3.4 (1H, obscured), 2.24-2.00 (m, 6H), 1.91-1.76 (m, 1H).

Example 212

(+/-)-5-{[(6-Bromo-3-chloro-2-phenylquinolin-4-yl)carbonyl]amino}-4-(2-chlorophenyl)pentanoic Acid (Racemate)

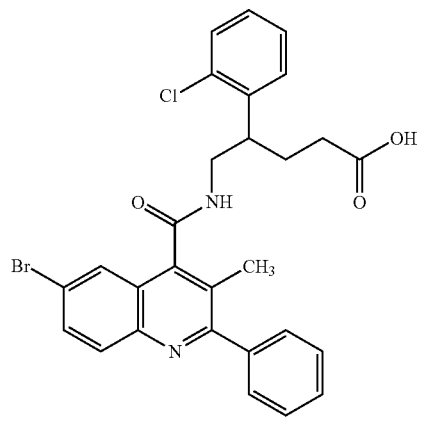

TFA (370 μl, 4.8 mmol) was added to a solution of (+/-)-tert-butyl 5-{[(6-bromo-3-chloro-2-phenylquinolin-4-yl)carbonyl]amino}-4-(2-chlorophenyl)pentanoate (150 mg, 239 μmol, Example 275A) in dichloromethane (2.0 ml), and the mixture was stirred at RT overnight. The mixture was then concentrated and repeatedly dichloromethane was added and the mixture was concentrated again. The residue was purified by preparative HPLC (Method 14). The combined target fractions were concentrated, and the residue was lyophilized. This gave 100 mg (100% purity, 73% of theory) of the title compound.

LC-MS (Method 1): $R_t$=2.08 min; MS (ESIpos): m/z=571/573/575 [M+H]$^+$
$^1$H-NMR (400 MHz, DMSO-d6) δ [ppm]: 9.13 (br. s, 1H), 8.01 (d, 1H), 7.96 (dd, 1H), 7.70-7.63 (m, 3H), 7.58-7.52 (m, 3H), 7.47 (dd, 2H), 7.37 (t, 1H), 7.31-7.20 (m, 1H), 3.80-3.52 (m, 3H), 2.15-1.92 (m, 3H), 1.90-1.77 (m, 1H).

Example 213

(-)-5-{[(6-Bromo-3-chloro-2-phenylquinolin-4-yl)carbonyl]amino}-4-(2-chlorophenyl)pentanoic Acid (Enantiomer 1)

TFA (1.9 ml, 25 mmol) was added to a solution of (-)-tert-butyl 5-{[(6-bromo-3-chloro-2-phenylquinolin-4-yl)carbonyl]amino}-4-(2-chlorophenyl)pentanoate (715 mg, 1.14 mmol, Example 276A) in dichloromethane (8.8 ml), and the mixture was allowed to stand at RT for 22 h. The mixture was then concentrated and repeatedly dichloromethane was added and the mixture was concentrated again. The residue was dissolved in 6 ml of acetonitrile. 2 ml of this resulting crude product solution were purified by preparative HPLC (Method 17), and the combined target fractions were concentrated, and the residue was lyophilized. This gave 337 mg (100% purity, 52% of theory, see analysis) of a first fraction of the title compound. From the crude product solution that remained (4 ml) a solid precipitated which even after addition of a further 2 ml of acetonitrile did not redissolve. Accordingly, after 3 h of standing at RT, the solid was filtered off, washed once with acetonitrile (1 ml) and dried under reduced pressure. This gave 197 mg (100% purity, 30% of theory) of a second batch of the title compound.

$[\alpha]_D^{20}=-10.6°$, 589 nm, c=0.36 g/100 ml, methanol

LC-MS (Method 2): $R_t$=1.09 min; MS (ESIpos): m/z=571/573/575 $[M+H]^+$ $^1$H-NMR (400 MHz, DMSO-d6) δ [ppm]: 1.365 (0.80), 1.832 (1.80), 1.857 (2.81), 1.880 (1.60), 1.901 (0.60), 2.050 (1.74), 2.063 (3.99), 2.074 (3.56), 2.090 (7.57), 2.114 (4.60), 2.123 (3.87), 2.149 (2.58), 2.171 (1.21), 3.615 (2.49), 3.714 (4.45), 3.726 (5.85), 7.257 (2.21), 7.275 (5.13), 7.293 (3.66), 7.360 (3.07), 7.379 (5.51), 7.397 (2.83), 7.450 (6.62), 7.470 (5.52), 7.498 (5.87), 7.520 (5.94), 7.530 (14.76), 7.536 (16.00), 7.545 (12.64), 7.662 (9.54), 7.667 (11.41), 7.676 (12.92), 7.942 (3.25), 7.947 (3.02), 7.965 (6.62), 7.969 (6.33), 8.006 (10.46), 8.028 (5.08), 8.991 (2.69), 9.005 (5.23), 9.019 (2.56), 12.041 (0.92).

$^1$H-NMR (400 MHz, DMSO-d6) δ [ppm]: 12.04 (br. s, 1H), 9.00 (t, 1H), 8.01 (d, 1H), 7.96 (dd, 1H), 7.71-7.64 (m, 3H), 7.59-7.43 (m, 5H), 7.38 (t, 1H), 7.28 (t, 1H), 3.81-3.66 (m, 2H), 3.65-3.54 (m, 1H), 2.22-1.99 (m, 3H), 1.93-1.75 (m, 1H).

Example 214

(+)-5-{[(6-Bromo-3-chloro-2-phenylquinolin-4-yl)carbonyl]amino}-4-(2-chlorophenyl)pentanoic Acid (Enantiomer 2)

TFA (2.0 ml, 26 mmol) was added to a solution of (+)-tert-butyl 5-{[(6-bromo-3-chloro-2-phenylquinolin-4-yl)carbonyl]amino}-4-(2-chlorophenyl)pentanoate (735 mg, 1.17 mmol, Example 277A) in dichloromethane (9.0 ml), and the mixture was allowed to stand at RT for 22 h. The mixture was then concentrated and repeatedly dichloromethane was added and the mixture was concentrated again. The residue was taken up in 8 ml of acetonitrile. This mixture was sonicated with heating and then left to stand at RT for 3 h. The solid present was filtered off, washed with twice acetonitrile (1 ml each) and dried under reduced pressure. This gave 522 mg (100% purity, 78% of theory) of the title compound.

$[\alpha]_D^{20}=+11.7°$, 589 nm, c=0.53 g/100 ml, methanol

LC-MS (Method 2): $R_t$=1.09 min; MS (ESIpos): m/z=571/573/575 $[M+H]^+$ $^1$H-NMR (400 MHz, DMSO-d6) δ [ppm]: 1.365 (0.85), 1.832 (1.62), 1.847 (1.64), 1.858 (2.62), 1.880 (1.50), 1.901 (0.55), 2.050 (1.57), 2.063 (3.64), 2.074 (2.95), 2.080 (2.51), 2.090 (6.93), 2.100 (4.42), 2.114 (4.05), 2.123 (3.57), 2.149 (2.48), 2.159 (1.28), 2.171 (1.18), 3.616 (2.16), 3.713 (3.90), 3.726 (5.23), 7.255 (1.92), 7.258 (2.17), 7.277 (4.93), 7.293 (3.39), 7.296 (3.52), 7.361 (2.97), 7.380 (5.38), 7.398 (2.68), 7.449 (6.16), 7.452 (6.60), 7.469 (5.16), 7.472 (5.38), 7.500 (5.52), 7.520 (5.31), 7.530 (14.83), 7.536 (16.00), 7.547 (12.13), 7.555 (3.66), 7.571 (0.74), 7.653 (1.69), 7.661 (8.93), 7.667 (10.86), 7.676 (12.18), 7.685 (7.49), 7.942 (3.44), 7.947 (3.32), 7.965 (6.91), 7.970 (7.12), 8.006 (11.94), 8.028 (5.78), 8.990 (2.47), 9.005 (5.10), 9.019 (2.45), 12.042 (2.44).

$^1$H-NMR (400 MHz, DMSO-d6) δ [ppm]: 12.04 (br. s, 1H), 9.00 (t, 1H), 8.01 (d, 1H), 7.96 (dd, 1H), 7.72-7.63 (m, 3H), 7.58-7.43 (m, 5H), 7.38 (t, 1H), 7.31-7.23 (m, 1H), 3.80-3.67 (m, 2H), 3.66-3.56 (m, 1H), 2.20-1.98 (m, 3H), 1.92-1.78 (m, 1H).

Example 215

(+/−)-5-{[(6-Bromo-3-chloro-2-phenylquinolin-4-yl)carbonyl]amino}-4-[2-(trifluoromethyl)phenyl]pentanoic Acid (Racemate)

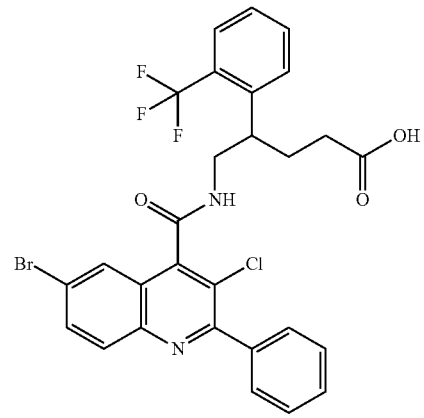 [SMILES: O=C(O)CCC(CNC(=O)c1c(Cl)c(-c2ccccc2)nc2ccc(Br)cc12)c1ccccc1C(F)(F)F]

TFA (200 μl, 2.7 mmol) was added to a solution of (+/−)-tert-butyl 5-{[(6-bromo-3-chloro-2-phenylquinolin-4-yl)carbonyl]amino}-4-[2-(trifluoromethyl)phenyl]pentanoate (80 mg, 121 μmol, Example 280A) in dichloromethane (1.0 ml), and the mixture was allowed to stand at RT for 3.5 h. The mixture was then concentrated and repeatedly dichloromethane was added and the mixture was concentrated again. The residue was purified by preparative HPLC (Method 17). The combined target fractions were concentrated, and the residue was lyophilized. This gave 57 mg (100% purity, 78% of theory) of the title compound.

LC-MS (Method 1): $R_t$=2.13 min; MS (ESIpos): m/z=605/607 $[M+H]^+$ $^1$H-NMR (400 MHz, DMSO-d6) δ [ppm]: 1.917 (1.64), 1.926 (1.70), 1.939 (3.77), 1.953 (2.29), 1.970 (3.17), 1.982 (1.57), 1.994 (2.62), 2.006 (1.90), 2.038 (1.64), 2.057 (2.56), 2.065 (1.57), 2.081 (2.75), 2.097 (1.35), 2.121 (1.21), 2.144 (1.04), 2.156 (1.46), 2.168 (1.72), 2.181 (1.71), 2.190 (1.70), 2.229 (0.47), 3.640 (0.79), 3.656 (1.32), 3.673 (2.34), 3.689 (2.73), 3.706 (1.75), 3.718 (1.78), 3.734 (2.68), 3.751 (2.16), 3.768 (1.32), 3.783 (0.71), 7.466 (2.15), 7.484 (4.72), 7.503 (2.97), 7.537 (14.63), 7.542 (16.00), 7.551 (11.33), 7.553 (11.19), 7.574 (0.99), 7.623 (3.21), 7.679 (8.09), 7.684 (9.17), 7.692 (9.95), 7.703 (6.72), 7.712 (5.60), 7.732 (9.29), 7.753 (11.58), 7.772 (3.08), 7.951 (3.64), 7.956 (3.38), 7.973 (6.89), 7.978 (6.87), 8.018 (11.35), 8.040 (5.77), 9.055 (2.33), 9.069 (4.61), 9.084 (2.26).

¹H-NMR (400 MHz, DMSO-d6) δ [ppm]: 12.06 (br. s, 1H), 9.07 (t, 1H), 8.03 (d, 1H), 7.97 (dd, 1H), 7.81-7.43 (m, 10H), 3.87-3.56 (m, 2H), 3.4-3.3 (1H, obscured), 2.26-1.82 (m, 4H).

Example 216

(−)-5-{[(6-Bromo-3-chloro-2-phenylquinolin-4-yl)carbonyl]amino}-4-[2-(trifluoromethyl)phenyl]pentanoic Acid (Enantiomer 1)

TFA (220 µl, 2.8 mmol) was added to a solution of (−)-tert-butyl 5-{[(6-bromo-3-chloro-2-phenylquinolin-4-yl)carbonyl]amino}-4-[2-(trifluoromethyl)phenyl]pentanoate (85 mg, 128 µmol, Example 281A) in dichloromethane (1.1 ml), and the mixture was allowed to stand at RT overnight. The mixture was then concentrated and repeatedly dichloromethane was added and the mixture was concentrated again. The residue was purified by preparative HPLC (Method 17). The combined target fractions were concentrated, and the residue was lyophilized. This gave 62 mg (100% purity, 80% of theory) of the title compound.

$[α]_D^{20}$=−15.0°, 589 nm, c=0.22 g/100 ml, methanol
LC-MS (Method 1): $R_t$=2.13 min; MS (ESIpos): m/z=605/607 [M+H]⁺

¹H-NMR (400 MHz, DMSO-d6) δ [ppm]: 1.236 (1.00), 1.917 (1.50), 1.943 (3.67), 1.957 (2.00), 1.974 (3.20), 1.987 (1.36), 1.998 (2.60), 2.010 (1.91), 2.041 (1.57), 2.060 (2.55), 2.068 (1.50), 2.084 (2.74), 2.100 (1.29), 2.123 (1.22), 2.146 (0.98), 2.158 (1.36), 2.170 (1.63), 2.182 (1.54), 2.192 (1.54), 2.231 (0.45), 2.328 (0.46), 2.670 (0.50), 3.641 (0.73), 3.657 (1.19), 3.674 (2.22), 3.690 (2.57), 3.706 (1.64), 3.718 (1.67), 3.733 (2.53), 3.750 (2.02), 3.767 (1.19), 3.783 (0.62), 7.467 (2.09), 7.485 (4.66), 7.504 (2.87), 7.536 (14.83), 7.542 (16.00), 7.550 (10.71), 7.553 (11.29), 7.562 (3.32), 7.577 (0.86), 7.623 (3.10), 7.669 (1.40), 7.678 (8.29), 7.683 (9.37), 7.692 (9.37), 7.702 (6.59), 7.713 (5.25), 7.733 (9.14), 7.754 (11.35), 7.773 (2.88), 7.951 (3.80), 7.956 (3.60), 7.973 (7.06), 7.978 (7.33), 8.018 (12.32), 8.040 (6.20), 9.049 (2.26), 9.064 (4.63), 9.079 (2.22), 12.023 (2.74).

¹H-NMR (400 MHz, DMSO-d6) δ [ppm]: 12.02 (br. s, 1H), 9.06 (t, 1H), 8.03 (d, 1H), 7.97 (dd, 1H), 7.81-7.44 (m, 10H), 3.82-3.60 (m, 2H), 3.4-3.3 (m, 1H, partially obscured), 2.26-1.85 (m, 4H).

Example 217

(+)-5-{[(6-Bromo-3-chloro-2-phenylquinolin-4-yl)carbonyl]amino}-4-[2-(trifluoromethyl)phenyl]pentanoic Acid (Enantiomer 2)

TFA (220 µl, 2.8 mmol) was added to a solution of (+)-tert-butyl 5-{[(6-bromo-3-chloro-2-phenylquinolin-4-yl)carbonyl]amino}-4-[2-(trifluoromethyl)phenyl]pentanoate (85 mg, 128 µmol, Example 282A) in dichloromethane (1.1 ml), and the mixture was allowed to stand at RT overnight. The mixture was then concentrated and repeatedly dichloromethane was added and the mixture was concentrated again. The residue was purified by preparative HPLC (Method 17). The combined target fractions were concentrated, and the residue was lyophilized. This gave 62 mg (100% purity, 80% of theory) of the title compound.

$[α]_D^{20}$=+14.3°, 589 nm, c=0.43 g/100 ml, methanol
LC-MS (Method 1): $R_t$=2.13 min; MS (ESIpos): m/z=605/607 [M+H]⁺

¹H-NMR (400 MHz, DMSO-d6) δ [ppm]: 1.235 (0.71), 1.917 (1.81), 1.941 (3.98), 1.955 (2.36), 1.972 (3.30), 1.984 (1.60), 1.995 (2.69), 2.007 (1.95), 2.039 (1.80), 2.058 (2.66), 2.082 (2.81), 2.098 (1.37), 2.122 (1.27), 2.145 (1.18), 2.158 (1.55), 2.169 (1.82), 2.181 (1.75), 2.191 (1.71), 2.328 (0.42), 3.640 (0.93), 3.655 (1.46), 3.673 (2.46), 3.689 (2.81), 3.706 (1.88), 3.718 (1.89), 3.734 (2.72), 3.750 (2.15), 3.767 (1.29), 7.466 (2.34), 7.485 (4.91), 7.503 (3.34), 7.536 (15.16), 7.542 (16.00), 7.550 (11.28), 7.553 (11.15), 7.562 (3.43), 7.575 (1.00), 7.623 (3.41), 7.678 (8.94), 7.684 (9.79), 7.692 (10.30), 7.702 (7.12), 7.712 (5.76), 7.732 (9.48), 7.753 (11.47), 7.772 (2.96), 7.950 (3.82), 7.956 (3.60), 7.973 (6.94), 7.978 (6.88), 8.018 (11.31), 8.040 (5.66), 9.052 (2.48), 9.067 (4.61), 9.081 (2.21), 12.038 (0.76).

¹H-NMR (400 MHz, DMSO-d6) δ [ppm]: 12.04 (br. s, 1H), 9.07 (t, 1H), 8.03 (d, 1H), 7.97 (dd, 1H), 7.80-7.43 (m, 10H), 3.81-3.60 (m, 2H), 3.4-3.3 (m, 1H, partially obscured), 2.26-1.86 (m, 4H).

Example 218

(+/−)-4-(2-Chlorophenyl)-5-{[(6-ethynyl-3-methyl-2-phenylquinolin-4-yl)carbonyl]amino}pentanoic Acid (Racemate)

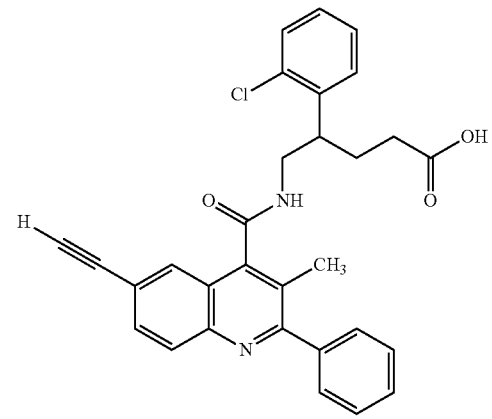 [SMILES: C#Cc1ccc2nc(-c3ccccc3)c(C)c(C(=O)NCC(CCC(=O)O)c3ccccc3Cl)c2c1]

TFA (400 µl, 5.2 mmol) was added to a solution of (+/−)-tert-butyl 4-(2-chlorophenyl)-5-{[(6-ethynyl-3-methyl-2-phenylquinolin-4-yl)carbonyl]amino}pentanoate (130 mg, 235 µmol, Example 283A) in dichloromethane (2.0 ml), and the mixture was allowed to stand at RT for 3.5 h. The mixture was then concentrated and repeatedly dichloromethane was added and the mixture was concentrated again. The residue was purified by preparative HPLC (Method 17). The combined target fractions were concentrated, and the residue was lyophilized. This gave 69 mg (100% purity, 59% of theory) of the title compound.

LC-MS (Method 1): $R_t$=1.88 min; MS (ESIpos): m/z=497 [M+H]⁺

¹H-NMR (400 MHz, DMSO-d6) δ [ppm]: 1.801 (0.56), 1.822 (1.23), 1.844 (1.55), 1.867 (0.84), 2.028 (0.84), 2.048 (3.24), 2.082 (3.52), 2.098 (3.73), 2.126 (4.59), 2.144 (3.85), 2.168 (1.41), 3.611 (1.29), 3.670 (0.59), 3.683 (0.89), 3.703 (1.37), 3.716 (1.78), 3.729 (1.06), 3.767 (1.15), 3.782 (0.98), 4.414 (6.20), 7.239 (1.05), 7.258 (2.20), 7.277 (1.56), 7.353 (1.29), 7.371 (2.26), 7.389 (1.23), 7.429 (3.77), 7.449 (3.09), 7.497 (6.68), 7.507 (4.98), 7.519 (16.00), 7.706 (2.76), 7.728 (3.22), 7.956 (4.41), 7.977 (3.77), 8.822 (1.51), 8.837 (2.81), 8.850 (1.42).

¹H-NMR (400 MHz, DMSO-d6) δ [ppm]: 12.06 (br. s, 1H), 8.84 (t, 1H), 7.97 (d, 1H), 7.72 (d, 1H), 7.7-7.4 (br. m, 1H), 7.56-7.47 (m, 6H), 7.44 (d, 1H), 7.37 (t, 1H), 7.26 (t, 1H), 4.41 (s, 1H), 3.90-3.47 (m, 3H), 2.31-1.99 (m, 6H), 1.94-1.61 (m, 1H).

Example 219

(−)-4-(2-Chlorophenyl)-5-{[(6-ethynyl-3-methyl-2-phenylquinolin-4-yl)carbonyl]amino}pentanoic Acid (Enantiomer 1)

TFA (570 µl, 7.4 mmol) was added to a solution of (−)-tert-butyl 4-(2-chlorophenyl)-5-{[(6-ethynyl-3-methyl-2-phenylquinolin-4-yl)carbonyl]amino}pentanoate (185 mg, 334 µmol, Example 284A) in dichloromethane (2.8 ml), and the mixture was allowed to stand at RT overnight. The mixture was then concentrated and repeatedly dichloromethane was added and the mixture was concentrated again. The residue was purified by preparative HPLC (Method 17). The combined target fractions were concentrated, and the residue was lyophilized. This gave 126 mg (100% purity, 76% of theory) of the title compound.

$[\alpha]_D^{20}$=−20.3°, 589 nm, c=0.41 g/100 ml, methanol

LC-MS (Method 1): $R_t$=1.88 min; MS (ESIpos): m/z=497 [M+H]$^+$ $^1$H-NMR (400 MHz, DMSO-d6) δ [ppm]: 1.802 (0.53), 1.823 (1.17), 1.845 (1.47), 1.867 (0.80), 2.050 (3.23), 2.085 (3.29), 2.100 (3.72), 2.128 (4.42), 2.147 (3.44), 2.171 (1.30), 3.612 (1.21), 3.671 (0.55), 3.684 (0.83), 3.703 (1.29), 3.717 (1.70), 3.730 (1.00), 3.766 (1.09), 4.414 (7.46), 7.238 (0.99), 7.258 (2.14), 7.277 (1.51), 7.353 (1.23), 7.371 (2.17), 7.389 (1.18), 7.429 (3.88), 7.449 (3.19), 7.498 (6.54), 7.507 (4.77), 7.519 (16.00), 7.706 (3.04), 7.728 (3.50), 7.956 (4.48), 7.978 (3.78), 8.821 (1.46), 8.835 (2.75), 8.849 (1.39), 12.049 (0.97).

$^1$H-NMR (400 MHz, DMSO-d6) δ [ppm]: 12.05 (br. s, 1H), 8.84 (t, 1H), 7.97 (d, 1H), 7.72 (d, 1H), 7.7-7.4 (br. m, 1H), 7.56-7.47 (m, 6H), 7.44 (d, 1H), 7.37 (t, 1H), 7.26 (t, 1H), 4.41 (s, 1H), 3.87-3.48 (m, 3H), 2.27-1.95 (m, 6H), 1.92-1.70 (m, 1H).

Example 220

(+)-4-(2-Chlorophenyl)-5-{[(6-ethynyl-3-methyl-2-phenylquinolin-4-yl)carbonyl]amino}pentanoic Acid (Enantiomer 2)

TFA (570 µl, 7.4 mmol) was added to a solution of (+)-tert-butyl 4-(2-chlorophenyl)-5-{[(6-ethynyl-3-methyl-2-phenylquinolin-4-yl)carbonyl]amino}pentanoate (185 mg, 334 µmol, Example 285A) in dichloromethane (2.8 ml), and the mixture was allowed to stand at RT overnight. The mixture was then concentrated and repeatedly dichloromethane was added and the mixture was concentrated again. The residue was purified by preparative HPLC (Method 17). The combined target fractions were concentrated, and the residue was lyophilized. This gave 152 mg (100% purity, 91% of theory) of the title compound.

$[\alpha]_D^{20}$=+20.2°, 589 nm, c=0.32 g/100 ml, methanol

LC-MS (Method 1): $R_t$=1.88 min; MS (ESIpos): m/z=497 [M+H]$^+$ $^1$H-NMR (400 MHz, DMSO-d6) δ [ppm]: 1.802 (0.55), 1.823 (1.21), 1.845 (1.53), 1.868 (0.84), 2.030 (0.81), 2.038 (0.93), 2.051 (3.31), 2.086 (3.46), 2.101 (3.94), 2.128 (4.59), 2.148 (3.59), 2.171 (1.36), 3.613 (1.28), 3.670 (0.59), 3.684 (0.90), 3.703 (1.37), 3.717 (1.79), 3.730 (1.07), 3.750 (0.88), 3.766 (1.13), 3.782 (0.97), 4.414 (6.81), 7.239 (1.01), 7.258 (2.19), 7.277 (1.54), 7.353 (1.26), 7.372 (2.24), 7.390 (1.22), 7.429 (3.97), 7.449 (3.25), 7.498 (6.77), 7.507 (4.77), 7.519 (16.00), 7.706 (2.80), 7.728 (3.25), 7.956 (4.78), 7.978 (4.08), 8.820 (1.55), 8.835 (2.96), 8.849 (1.51).

$^1$H-NMR (400 MHz, DMSO-d6) δ [ppm]: 12.04 (br. s, 1H), 8.83 (t, 1H), 7.97 (d, 1H), 7.72 (d, 1H), 7.7-7.4 (br. m, 1H), 7.57-7.47 (m, 6H), 7.44 (d, 1H), 7.37 (t, 1H), 7.26 (t, 1H), 4.41 (s, 1H), 3.88-3.53 (m, 3H), 2.25-1.96 (m, 6H), 1.93-1.71 (m, 1H).

Example 221

(+/−)-5-{[(6-Bromo-3-chloro-2-phenylquinolin-4-yl)carbonyl]amino}-4-(2-chloro-3,6-difluorophenyl)pentanoic Acid (Racemate)

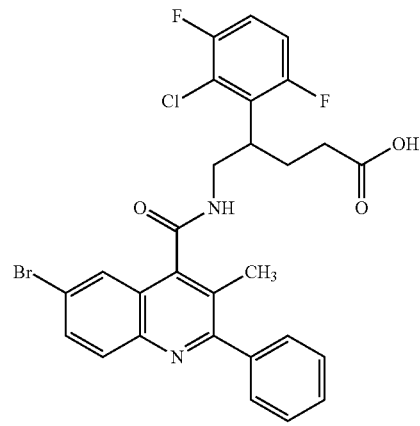 [SMILES: Cc1c(-c2ccccc2)nc2ccc(Br)cc2c1C(=O)NCC(CCC(=O)O)c1c(F)ccc(F)c1Cl]

TFA (170 µl, 2.2 mmol) was added to a solution of (+/−)-tert-butyl 5-{[(6-bromo-3-chloro-2-phenylquinolin-4-yl)carbonyl]amino}-4-(2-chloro-3,6-difluorophenyl)pentanoate (65 mg, 98 µmol, Example 286A) in dichloromethane (830 µl), and the mixture was allowed to stand at RT for 18 h. The mixture was then concentrated and repeatedly dichloromethane was added and the mixture was concentrated again. The residue was purified by preparative HPLC (Method 17). The combined target fractions were concentrated, and the residue was lyophilized. This gave 34 mg (100% purity, 56% of theory) of the title compound.

LC-MS (Method 1): $R_t$=2.08 min; MS (ESIpos): m/z=607/609/611 [M+H]$^+$ $^1$H-NMR (400 MHz, DMSO-d6) δ [ppm]: 1.981 (1.03), 2.074 (1.54), 2.093 (1.50), 2.109 (3.76), 2.146 (8.52), 2.174 (2.16), 2.189 (1.98), 2.212 (0.70), 2.695 (0.74), 3.755 (2.13), 3.774 (2.01), 3.819 (2.95), 7.268 (1.40), 7.279 (1.57), 7.291 (2.84), 7.302 (2.94), 7.317 (2.27), 7.328 (2.13), 7.382 (1.83), 7.393 (2.11), 7.404 (2.97), 7.415 (2.88), 7.425 (1.53), 7.437 (1.31), 7.531 (14.68), 7.537 (16.00), 7.547 (12.47), 7.569 (0.76), 7.657 (8.52), 7.663 (9.38), 7.672 (8.91), 7.681 (6.87), 7.694 (3.13), 7.956 (3.51), 7.961 (3.33), 7.978 (7.36), 7.983 (7.60), 8.015 (12.42), 8.037 (5.55), 9.088 (2.21), 9.102 (4.20), 9.115 (2.13), 12.096 (8.00).

$^1$H-NMR (400 MHz, DMSO-d6) δ [ppm]: 12.10 (s, 1H), 9.10 (t, 1H), 8.02 (d, 1H), 7.97 (dd, 1H), 7.73-7.63 (m, 3H), 7.57-7.51 (m, 3H), 7.41 (td, 1H), 7.30 (td, 1H), 3.95-3.67 (m, 3H), 2.27-2.05 (m, 3H), 2.04-1.89 (m, 1H).

Example 222

(−)-5-{[(6-Bromo-3-chloro-2-phenylquinolin-4-yl)carbonyl]amino}-4-(2-chloro-3,6-difluorophenyl)pentanoic Acid (Enantiomer 1)

TFA (110 µl, 1.5 mmol) was added to a solution of (−)-tert-butyl 5-{[(6-bromo-3-chloro-2-phenylquinolin-4-yl)carbonyl]amino}-4-(2-chloro-3,6-difluorophenyl)pentanoate (45 mg, 68 µmol, Example 287A) in dichloromethane (520 µl), and the mixture was allowed to stand at RT for 22 h. The mixture was then concentrated and repeatedly dichloromethane was added and the mixture was concentrated again. The residue was purified by preparative HPLC (Method 17). The combined target fractions were concentrated, and the residue was lyophilized. This gave 34 mg (100% purity, 82% of theory) of the title compound.

$[\alpha]_D^{20}$=−33.3°, 589 nm, c=0.38 g/100 ml, methanol

LC-MS (Method 1): $R_t$=2.08 min; MS (ESIpos): m/z=607/609/611 [M+H]$^+$ $^1$H-NMR (400 MHz, DMSO-d6) δ [ppm]: 1.235 (0.82), 1.980 (1.02), 2.093 (1.51), 2.109 (3.71), 2.146 (8.29), 2.189 (1.92), 2.212 (0.68), 3.753 (2.12), 3.775 (2.01), 3.819 (2.95), 7.268 (1.36), 7.279 (1.56), 7.292 (2.78), 7.303 (2.89), 7.317 (2.23), 7.329 (2.09), 7.382 (1.79), 7.393 (2.05), 7.404 (2.89), 7.415 (2.80), 7.426 (1.49), 7.437 (1.25), 7.522 (1.82), 7.531 (14.85), 7.538 (16.00), 7.546 (11.67), 7.548 (12.40), 7.569 (0.72), 7.649 (1.59), 7.658 (8.50), 7.663 (9.30), 7.672 (8.78), 7.681 (6.87), 7.694 (3.02), 7.956 (3.50), 7.961 (3.35), 7.978 (7.36), 7.984 (7.66), 8.015 (12.07), 8.037 (5.42), 9.088 (2.19), 9.102 (4.15), 9.116 (2.11), 12.097 (2.42).

$^1$H-NMR (400 MHz, DMSO-d6) δ [ppm]: 12.10 (s, 1H), 9.10 (t, 1H), 8.02 (d, 1H), 7.97 (dd, 1H), 7.74-7.63 (m, 3H), 7.58-7.51 (m, 3H), 7.41 (td, 1H), 7.30 (td, 1H), 3.94-3.67 (m, 3H), 2.26-2.06 (m, 3H), 1.98 (br. s, 1H).

Example 223

(+)-5-{[(6-Bromo-3-chloro-2-phenylquinolin-4-yl)carbonyl]amino}-4-(2-chloro-3,6-difluorophenyl)pentanoic Acid (Enantiomer 2)

TFA (110 µl, 1.5 mmol) was added to a solution of (+)-tert-butyl 5-{[(6-bromo-3-chloro-2-phenylquinolin-4-yl)carbonyl]amino}-4-(2-chloro-3,6-difluorophenyl)pentanoate (45 mg, 68 µmol, Example 288A) in dichloromethane (520 µl), and the mixture was allowed to stand at RT for 22 h. The mixture was then concentrated and repeatedly dichloromethane was added and the mixture was concentrated again. The residue was purified by preparative HPLC (Method 17). The combined target fractions were concentrated, and the residue was lyophilized. This gave 29 mg (100% purity, 69% of theory) of the title compound.

$[\alpha]_D^{20}$=+35.3°, 589 nm, c=0.36 g/100 ml, methanol

LC-MS (Method 1): $R_t$=2.08 min; MS (ESIpos): m/z=607/609/611 [M+H]$^+$ $^1$H-NMR (400 MHz, DMSO-d6) δ [ppm]: −0.008 (0.62), 1.235 (0.56), 1.977 (0.97), 2.108 (3.49), 2.142 (8.02), 2.186 (1.89), 2.209 (0.65), 3.750 (2.03), 3.774 (1.91), 3.817 (2.76), 7.267 (1.37), 7.278 (1.54), 7.291 (2.80), 7.302 (2.88), 7.317 (2.23), 7.328 (2.12), 7.381 (1.76), 7.393 (2.01), 7.403 (2.88), 7.414 (2.78), 7.425 (1.49), 7.436 (1.23), 7.522 (1.67), 7.531 (15.31), 7.537 (16.00), 7.547 (12.27), 7.555 (3.68), 7.569 (0.74), 7.648 (1.53), 7.657 (8.76), 7.662 (9.30), 7.672 (8.81), 7.681 (6.84), 7.693 (3.00), 7.956 (3.75), 7.961 (3.45), 7.978 (7.82), 7.983 (7.97), 8.015 (12.92), 8.037 (5.78), 9.088 (2.12), 9.102 (4.02), 9.116 (2.04), 12.106 (0.55).

$^1$H-NMR (400 MHz, DMSO-d6) δ [ppm]: 12.11 (br. s, 1H), 9.10 (t, 1H), 8.02 (d, 1H), 7.97 (dd, 1H), 7.74-7.63 (m, 3H), 7.58-7.50 (m, 3H), 7.41 (td, 1H), 7.30 (td, 1H), 3.94-3.67 (m, 3H), 2.25-2.06 (m, 3H), 1.98 (br. s, 1H).

Example 224

(+/−)-5-{[(6-Bromo-3-methyl-2-phenylquinolin-4-yl)carbonyl]amino}-4-(pyridin-2-yl)pentanoic Acid (Racemate)

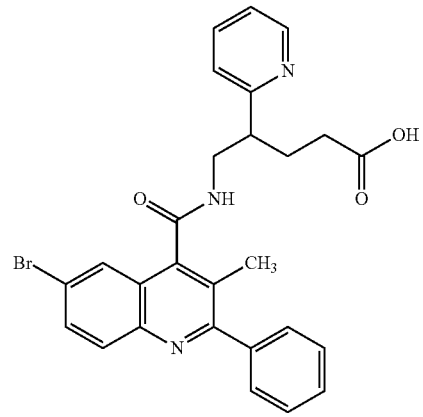 [SMILES: Cc1c(-c2ccccc2)nc2ccc(Br)cc2c1C(=O)NCC(CCC(=O)O)c1ccccn1]

TFA (270 µl, 3.5 mmol) was added to a solution of (+/−)-tert-butyl 5-{[(6-bromo-3-methyl-2-phenylquinolin-4-yl)carbonyl]amino}-4-(pyridin-2-yl)pentanoate (100 mg, 174 µmol, Example 289A, not corrected for purity) in dichloromethane (750 µl), and the mixture was stirred at RT for 7 h. The mixture was then concentrated and repeatedly dichloromethane was added and the mixture was concentrated again. The residue was purified by preparative HPLC (column Chromatorex C18, 10 µm, 125×30 mm; gradient 20%-60% acetonitrile in 0.1% aqueous ammonia solution). The combined target fractions were concentrated, and the residue was lyophilized. This gave 46 mg (92% purity, 49% of theory) of the title compound.

LC-MS (Method 5): $R_t$=0.99 min; MS (ESIpos): m/z=518/520 [M+H]$^+$ $^1$H-NMR (400 MHz, DMSO-d6) δ [ppm]: 1.107 (12.82), 1.737 (0.48), 1.882 (0.41), 1.905 (0.87), 1.914 (0.67), 1.924 (1.29), 1.938 (0.95), 1.945 (0.81), 1.967 (0.78), 1.982 (0.86), 1.988 (1.35), 1.995 (1.12), 2.000 (1.11), 2.011 (1.20), 2.021 (2.54), 2.047 (2.18), 2.059 (1.78), 2.067 (1.57), 2.079 (2.19), 2.102 (2.39), 2.108 (2.79), 2.125 (4.18), 2.147 (2.08), 2.518 (2.49), 2.523 (1.57), 2.539 (1.37), 3.202 (0.98), 3.619 (0.83), 3.638 (0.87), 3.652 (1.11), 3.794 (0.70), 7.247 (1.05), 7.263 (1.42), 7.276 (1.14), 7.312 (1.73), 7.331 (1.84), 7.472 (0.45), 7.475 (0.48), 7.481 (0.73), 7.485 (1.28), 7.487 (1.44), 7.498 (4.79), 7.506 (4.67), 7.516 (16.00), 7.518 (15.39), 7.523 (7.66), 7.528 (5.83), 7.532 (5.46), 7.539 (1.18), 7.737 (1.28), 7.752 (1.95), 7.772 (1.02), 7.829 (2.64), 7.834 (2.35), 7.851 (3.81), 7.856 (3.77), 7.922 (7.82), 7.944 (4.82), 8.579 (2.37), 8.589 (2.35), 8.796 (1.37), 8.811 (2.19), 8.825 (1.33), 12.041 (1.59).

$^1$H-NMR (400 MHz, DMSO-d6) δ [ppm]: 12.04 (br. s, 1H), 8.81 (t, 1H), 8.58 (d, 1H), 7.93 (d, 1H), 7.84 (dd, 1H), 7.75 (t, 1H), 7.67 (br. s, 1H), 7.55-7.45 (m, 5H), 7.32 (d, 1H), 7.26 (t, 1H), 3.88-3.73 (m, 1H), 3.71-3.55 (m, 1H), 3.27-3.13 (m, 1H), 2.23-1.86 (m, 7H).

Example 225

(+/−)-5-{[(6-Bromo-3-methyl-2-phenylquinolin-4-yl)carbonyl]amino}-4-[2-fluoro-6-(trifluoromethyl)phenyl]pentanoic Acid (Racemate)

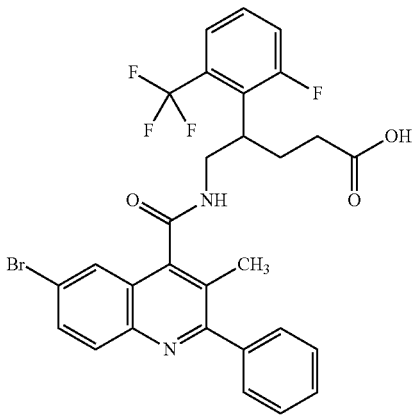 [SMILES: Cc1c(-c2ccccc2)nc2ccc(Br)cc2c1C(=O)NCC(CCC(=O)O)c1c(F)cccc1C(F)(F)F]

tert-Butyl 5-{[(6-bromo-3-methyl-2-phenylquinolin-4-yl)carbonyl]amino}-4-[2-fluoro-6-(trifluoromethyl)phenyl]pentanoate (80 mg, 93% purity, 113 µmol, Example 290A) was dissolved in dichloromethane (1.5 ml). At RT, TFA (850 µl, 11.28 mmol) was added and the mixture was stirred at RT for 1 h. The volatile components were then removed on a rotary evaporator. Three times, some toluene was added to the residue and the mixture was re-concentrated on a rotary evaporator. The residue was dissolved in a little DMSO and purified by preparative HPLC (Method 28). The suitable fractions were combined and concentrated under reduced pressure. The residue was dried under reduced pressure. This gave 63 mg (100% purity, 93% of theory) of the title compound.

LC-MS (Method 1): $R_t$=2.03 min; MS (ESIpos): m/z=603/605 [M+H]$^+$ $^1$H-NMR (400 MHz, DMSO-d6) δ [ppm]: 12.11 (br. s, 1H), 8.96 (t, 1H), 7.95 (d, 1H), 7.85 (dd, 1H), 7.75-7.46 (m, 9H), 3.95 (br. s, 1H), 3.72 (br. s, 1H), 3.31 (1H, obscured, tentative), 2.25-1.98 (m, 7H).

Example 226

(+)-5-{[(6-Bromo-3-methyl-2-phenylquinolin-4-yl)carbonyl]amino}-4-[2-fluoro-6-(trifluoromethyl)phenyl]pentanoic Acid (Enantiomer 1)

tert-Butyl 5-{[(6-bromo-3-methyl-2-phenylquinolin-4-yl)carbonyl]amino}-4-[2-fluoro-6-(trifluoromethyl)phenyl]pentanoate (440 mg, 667 µmol, Example 291A, enantiomer 1) was dissolved in dichloromethane (8.9 ml). At RT, TFA (5 ml, 66.7 mmol) was added and the mixture was stirred at RT for 1 h. The volatile components were then removed on a rotary evaporator. The residue was dissolved in a little DMSO and purified by preparative HPLC (Method 29). The suitable fractions were combined and concentrated under reduced pressure. The residue was dried under reduced pressure. This gave 356 mg (98% purity, 87% of theory) of the title compound.

LC-MS (Method 1): $R_t$=2.01 min; MS (ESIpos): m/z=603/605 [M+H]$^+$ $^1$H-NMR (400 MHz, DMSO-d6) δ [ppm]: 12.06 (br. s, 1H), 8.95 (t, 1H), 7.95 (d, 1H), 7.85 (dd, 1H), 7.78-7.44 (m, 9H), 3.96 (br. s, 1H), 3.73 (br. s, 1H), 3.32 (1H, obscured, tentative), 2.24-2.00 (m, 7H).

$[α]_D^{20}$=+45.6°, 589 nm, c=0.415 g/100 ml, methanol

Example 227 (−)-5-{[(6-Bromo-3-methyl-2-phenylquinolin-4-yl)carbonyl]amino}-4-[2-fluoro-6-(trifluoromethyl)phenyl]pentanoic Acid (Enantiomer 2)

tert-Butyl 5-{[(6-bromo-3-methyl-2-phenylquinolin-4-yl)carbonyl]amino}-4-[2-fluoro-6-(trifluoromethyl)phenyl]pentanoate (412 mg, 625 µmol, Example 292A, enantiomer 2) was dissolved in dichloromethane (8.3 ml). At RT, TFA (4.6 ml, 62.5 mmol) was added and the mixture was stirred at RT for 1 h. The volatile components were then removed on a rotary evaporator. The residue was dissolved in a little DMSO and purified by preparative HPLC (Method 29). The suitable fractions were combined and concentrated under reduced pressure. The residue was dried under reduced pressure. 344 mg (98% purity, 89% of theory) of the title compound were obtained.

LC-MS (Method 1): $R_t$=2.01 min; MS (ESIpos): m/z=603/605 [M+H]$^+$ $^1$H-NMR (400 MHz, DMSO-d6) δ [ppm]: 12.06 (br. s, 1H), 8.95 (t, 1H), 7.95 (d, 1H), 7.85 (dd, 1H), 7.80-7.44 (m, 9H), 3.96 (br. s, 1H), 3.73 (br. s, 1H), 3.33 (1H, partially obscured, tentative), 2.24-2.00 (m, 7H).

$[α]_D^{20}$=−45.6°, 589 nm, c=0.38 g/100 ml, methanol

Example 228 (+/−)-5-{[(6-Bromo-3-methyl-2-phenylquinolin-4-yl)carbonyl]amino}-4-(2,3,5,6-tetrafluorophenyl)pentanoic Acid (Racemate)

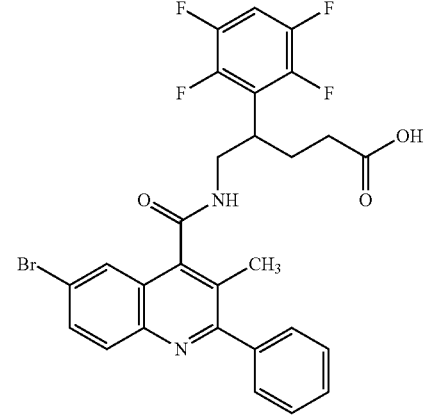 [SMILES: Cc1c(-c2ccccc2)nc2ccc(Br)cc2c1C(=O)NCC(CCC(=O)O)c1c(F)c(F)cc(F)c1F]

(+/−)-tert-Butyl 5-{[(6-bromo-3-methyl-2-phenylquinolin-4-yl)carbonyl]amino}-4-(2,3,5,6-tetrafluorophenyl)pentanoate (25 mg, 38.7 µmol, Example 293A) was dissolved in dichloromethane (520 µl). At RT, TFA (290 µl, 3.8 mmol) was added and the mixture was stirred at RT overnight. The volatile components were then removed on a rotary evaporator. Repeatedly, some toluene was added to the residue and the mixture was re-concentrated on a rotary evaporator. The residue was dissolved in a little DMSO and purified by preparative HPLC (Method 28). The combined target fractions were concentrated, and the residue was dried under reduced pressure. 17 mg (100% purity, 74% of theory) of the title compound were obtained.

LC-MS (Method 2): $R_t$=1.04 min; MS (ESIpos): m/z=589/591 [M+H]$^+$ $^1$H-NMR (400 MHz, DMSO-d$_6$): δ [ppm]=12.13 (br. s, 1H), 8.98 (t, 1H), 7.95 (d, 1H), 7.86 (dd, 1H), 7.8-7.6 (m, 2H), 7.58-7.46 (m, 5H), 3.87-3.77 (m, 2H), 3.61-3.51 (m, 1H), 2.27-2.04 (m, 6H), 2.00-1.90 (m, 1H).

Example 229

(−)-5-{[(6-Bromo-3-methyl-2-phenylquinolin-4-yl)carbonyl]amino}-4-(2,3,5,6-tetrafluorophenyl)pentanoic Acid (Enantiomer 1)

tert-Butyl 5-{[(6-bromo-3-methyl-2-phenylquinolin-4-yl)carbonyl]amino}-4-(2,3,5,6-tetrafluorophenyl)pentanoate (265 mg, 410 μmol, Example 294A, enantiomer 1) was dissolved in dichloromethane (5.5 ml). At RT, TFA (3.1 ml, 41.0 mmol) was added and the mixture was stirred at RT overnight. The volatile components were then removed on a rotary evaporator. Repeatedly, some toluene was added to the residue and the mixture was re-concentrated on a rotary evaporator. The residue was dissolved in a little DMSO and purified by preparative HPLC (Method 28). The suitable fractions were combined and concentrated under reduced pressure. The residue was dried under reduced pressure. 237 mg (98% purity, 96% of theory) of the title compound were obtained.

$[α]_D^{20}$=−50.9°, 589 nm, c=0.45 g/100 ml, methanol

LC-MS (Method 1): $R_t$=1.99 min; MS (ESIpos): m/z=589/591 [M+H]$^+$ $^1$H-NMR (400 MHz, DMSO-d6) δ [ppm]: −0.008 (2.12), 0.008 (1.97), 1.922 (0.60), 1.956 (1.02), 1.981 (0.92), 1.997 (0.53), 2.074 (1.06), 2.088 (1.41), 2.107 (1.34), 2.128 (1.19), 2.158 (6.34), 2.202 (3.94), 2.219 (5.66), 2.238 (2.23), 2.328 (0.54), 2.366 (0.44), 2.669 (0.47), 2.710 (0.41), 3.167 (0.95), 3.558 (1.10), 3.794 (2.43), 3.810 (3.34), 7.495 (1.52), 7.506 (4.54), 7.514 (4.40), 7.525 (16.00), 7.536 (6.45), 7.539 (5.76), 7.800 (1.00), 7.848 (2.66), 7.853 (2.35), 7.870 (3.85), 7.875 (3.72), 7.940 (7.13), 7.963 (4.44), 8.155 (0.67), 8.969 (1.31), 8.984 (2.59), 8.998 (1.30).

Example 230

(+)-5-{[(6-Bromo-3-methyl-2-phenylquinolin-4-yl)carbonyl]amino}-4-(2,3,5,6-tetrafluorophenyl)pentanoic Acid (Enantiomer 2)

tert-Butyl 5-{[(6-bromo-3-methyl-2-phenylquinolin-4-yl)carbonyl]amino}-4-(2,3,5,6-tetrafluorophenyl)pentanoate (274 mg, 99% pure, 420 μmol, Example 295A, enantiomer 2) was dissolved in dichloromethane (5.6 ml). At RT, TFA (3.2 ml, 42.0 mmol) was added and the mixture was stirred at RT overnight. The volatile components were then removed on a rotary evaporator. Repeatedly, some toluene was added to the residue and the mixture was re-concentrated on a rotary evaporator. The residue was dissolved in a little DMSO and purified by preparative HPLC (Method 28). The suitable fractions were combined and concentrated under reduced pressure. The residue was dried under reduced pressure. 235 mg (99% purity, 94% of theory) of the title compound were obtained.

$[α]_D^{20}$=+47.2°, 589 nm, c=0,445 g/100 ml, methanol

LC-MS (Method 1): $R_t$=2.00 min; MS (ESIpos): m/z=589/591 [M+H]$^+$ $^1$H-NMR (400 MHz, DMSO-d6) δ [ppm]: −0.008 (1.64), 0.008 (1.47), 1.923 (0.61), 1.957 (1.04), 1.981 (0.93), 1.998 (0.52), 2.056 (0.44), 2.075 (1.06), 2.089 (1.38), 2.107 (1.35), 2.126 (1.21), 2.159 (6.40), 2.202 (3.92), 2.219 (5.62), 2.238 (2.22), 2.329 (0.43), 3.559 (1.10), 3.794 (2.44), 3.809 (3.34), 7.495 (1.49), 7.506 (4.49), 7.514 (4.34), 7.525 (16.00), 7.536 (6.42), 7.539 (5.68), 7.799 (1.00), 7.848 (2.55), 7.853 (2.31), 7.870 (3.72), 7.875 (3.60), 7.941 (6.90), 7.963 (4.29), 8.969 (1.33), 8.984 (2.61), 8.998 (1.28), 12.153 (0.46).

Example 231

(+/−)-5-{[(6-Bromo-3-methyl-2-phenylquinolin-4-yl)carbonyl]amino}-4-(2,3,5-trifluorophenyl)pentanoic Acid (Racemate)

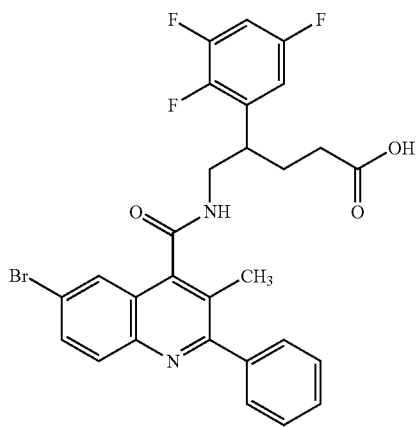 [SMILES: Cc1c(-c2ccccc2)nc2ccc(Br)cc2c1C(=O)NCC(CCC(=O)O)c1cc(F)cc(F)c1F]

(+/−)-tert-Butyl 5-{[(6-bromo-3-methyl-2-phenylquinolin-4-yl)carbonyl]amino}-4-(2,3,5-trifluorophenyl)pentanoate (25 mg, 39.8 μmol, Example 296A) was dissolved in dichloromethane (530 μl). At RT, TFA (40 μl, 3.1 mmol) was added and the mixture was stirred at RT for 1 h. Since the conversion was incomplete (HPLC control), additional portions of trifluoroacetic acid (230 μl in total) were added. Stirring was continued until no more starting material could be detected by HPLC (4 h). The volatile components were then removed on a rotary evaporator. Repeatedly, some toluene was added to the residue and the mixture was re-concentrated on a rotary evaporator. The residue was dissolved in a little DMSO and purified by preparative HPLC (Method 28). The combined target fractions were concentrated, and the residue was dried under reduced pressure. This gave 20 mg (100% purity, 88% of theory) of the title compound.

LC-MS (Method 2): $R_t$=1.02 min; MS (ESIpos): m/z=571/573 [M+H]$^+$ $^1$H-NMR (400 MHz, DMSO-d$_6$): δ [ppm]=12.10 (br. s, 1H), 8.89 (t, 1H), 7.94 (d, 1H), 7.85 (dd, 1H), 7.81-7.56 (br. s, 1H), 7.56-7.46 (m, 5H), 7.46-7.35 (m, 1H), 7.27-7.20 (m, 1H), 3.84-3.66 (m, 2H), 3.50-3.37 (m, 1H), 2.24-1.98 (m, 6H), 1.88-1.77 (m, 1H).

Example 232

5-{[(6-Bromo-3-methyl-2-phenylquinolin-4-yl)carbonyl]amino}-4-(2,3,5-trifluorophenyl)pentanoic Acid (Enantiomer 1)

tert-Butyl 5-{[(6-bromo-3-methyl-2-phenylquinolin-4-yl)carbonyl]amino}-4-(2,3,5-trifluorophenyl)pentanoate (38 mg, 60.2 µmol, Example 297A, enantiomer 1) was dissolved in dichloromethane (800 µl). At RT, TFA (450 µl) was added and the mixture was stirred at RT overnight. The volatile components were then removed on a rotary evaporator. Repeatedly, some toluene was added to the residue and the mixture was re-concentrated on a rotary evaporator. The residue was dissolved in a little DMSO and purified by preparative HPLC (Method 28). The combined target fractions were concentrated under reduced pressure, and the residue was dried under reduced pressure. This gave 29 mg (100% purity, 84% of theory) of the title compound.

LC-MS (Method 2): $R_t$=1.04 min; MS (ESIpos): m/z=571/573 [M+H]$^+$ $^1$H-NMR (400 MHz, DMSO-d6) δ [ppm]: 0.008 (2.16), 1.798 (0.71), 1.834 (1.03), 1.849 (0.83), 1.872 (0.53), 2.018 (1.07), 2.031 (1.34), 2.051 (1.41), 2.073 (9.44), 2.082 (1.24), 2.124 (4.71), 2.145 (7.02), 2.327 (0.68), 2.366 (0.51), 2.670 (0.61), 2.709 (0.50), 3.428 (1.17), 3.682 (0.83), 3.703 (1.26), 3.716 (1.82), 3.729 (1.15), 3.763 (0.91), 7.223 (1.35), 7.411 (1.03), 7.494 (1.56), 7.504 (4.57), 7.512 (4.41), 7.523 (16.00), 7.534 (6.76), 7.837 (2.19), 7.842 (2.04), 7.859 (3.36), 7.864 (3.29), 7.933 (6.54), 7.956 (4.15), 8.875 (1.32), 8.890 (2.48), 8.903 (1.37), 12.092 (0.68).

Example 233

5-{[(6-Bromo-3-methyl-2-phenylquinolin-4-yl)carbonyl]amino}-4-(2,3,5-trifluorophenyl)pentanoic Acid (Enantiomer 2)

tert-Butyl 5-{[(6-bromo-3-methyl-2-phenylquinolin-4-yl)carbonyl]amino}-4-(2,3,5-trifluorophenyl)pentanoate (40 mg, 62.8 µmol, Example 298A, enantiomer 2) was dissolved in dichloromethane (840 µl). At RT, trifluoroacetic Acid (470 µl) was added and the mixture was stirred at RT overnight. The volatile components were then removed on a rotary evaporator. Repeatedly, some toluene was added to the residue and the mixture was re-concentrated on a rotary evaporator. The residue was dissolved in a little DMSO and purified by preparative HPLC (Method 28). The combined target fractions were concentrated under reduced pressure, and the residue was dried under reduced pressure. 25 mg (100% purity, 70% of theory) of the title compound were obtained.

LC-MS (Method 1): $R_t$=1.97 min; MS (ESIpos): m/z=571/573 [M+H]$^+$ $^1$H-NMR (400 MHz, DMSO-d6) δ [ppm]: −0.149 (1.73), −0.008 (16.00), 0.008 (15.95), 0.146 (1.73), 1.825 (0.98), 2.022 (1.21), 2.041 (1.17), 2.060 (1.31), 2.117 (3.50), 2.140 (3.50), 2.327 (1.77), 2.366 (1.82), 2.670 (1.96), 2.710 (2.01), 3.411 (1.35), 3.713 (1.63), 7.225 (1.35), 7.395 (1.07), 7.503 (4.34), 7.511 (4.10), 7.523 (14.23), 7.836 (2.19), 7.841 (2.01), 7.859 (3.17), 7.864 (3.08), 7.932 (6.30), 7.955 (4.10), 8.908 (2.10).

Example 234

(+/−)-5-{[(6-Bromo-3-methyl-2-phenylquinolin-4-yl)carbonyl]amino}-4-(2,3,6-trichlorophenyl)pentanoic Acid (Racemate)

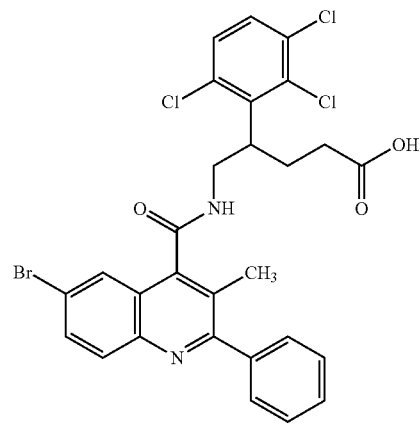 [SMILES: Cc1c(-c2ccccc2)nc2ccc(Br)cc2c1C(=O)NCC(CCC(=O)O)c1c(Cl)ccc(Cl)c1Cl]

(+/−)-tert-Butyl 5-{[(6-bromo-3-methyl-2-phenylquinolin-4-yl)carbonyl]amino}-4-(2,3,6-trichlorophenyl)pentanoate (80 mg, 118 µmol, Example 299A) was dissolved in dichloromethane (1.6 ml). At RT, TFA (880 µl, 11.8 mmol) was added and the mixture was stirred at RT for 2 h. The volatile components were removed on a rotary evaporator, and the residue was dried under reduced pressure. The crude product was then dissolved in a little DMSO and purified by preparative HPLC (Method 29). The combined target fractions were concentrated under reduced pressure, and the residue was dried under reduced pressure. 66 mg (100% purity, 90% of theory) of the title compound were obtained.

LC-MS (Method 1): $R_t$=2.14 min; MS (ESIpos): m/z=619/621/623 [M+H]$^+$ $^1$H-NMR (400 MHz, DMSO-d$_6$): δ [ppm]=12.11 (br. s, 1H), 8.99-8.87 (m, 1H), 7.95 (dd, 1H), 7.89-7.83 (m, 1H), 7.82-7.64 (m, 1H), 7.64-7.57 (m, 1H), 7.56-7.46 (m, 6H), 4.20-4.00 (m, 2H), 3.94-3.79 (m, 1H), 2.35-2.03 (m, 7H).

Example 235

(+)-5-{[(6-Bromo-3-methyl-2-phenylquinolin-4-yl)carbonyl]amino}-4-(2,3,6-trichlorophenyl)pentanoic Acid (Enantiomer 1)

tert-Butyl 5-{[(6-bromo-3-methyl-2-phenylquinolin-4-yl)carbonyl]amino}-4-(2,3,6-trichlorophenyl)pentanoate (227 mg, 95% pure, 319 µmol, Example 300A, enantiomer 1) was dissolved in dichloromethane (2.7 ml). At RT, TFA (2.4 ml) was added and the mixture was stirred at RT for 2 h. The volatile components were then removed on a rotary evaporator. Twice, some toluene was added to the residue and the mixture was re-concentrated on a rotary evaporator. The residue was dissolved in a little DMSO and purified by preparative HPLC (Method 30). The combined target fractions were concentrated under reduced pressure, and the residue was dried under reduced pressure. This gave 148 mg (96% purity, 73% of theory) of the title compound.

$[α]_D^{20}$=+34.1°, 589 nm, c=0.44 g/100 ml, methanol

LC-MS (Method 2): $R_t$=1.11 min; MS (ESIpos): m/z=619/621/623 [M+H]$^+$

¹H-NMR (400 MHz, DMSO-d6) δ [ppm]: 2.073 (8.70), 2.095 (2.02), 2.108 (2.74), 2.128 (3.53), 2.153 (5.13), 2.164 (4.58), 2.180 (9.66), 2.212 (1.42), 2.237 (0.76), 2.283 (1.22), 2.311 (1.53), 2.328 (1.16), 2.670 (0.67), 3.832 (0.83), 3.850 (1.05), 3.863 (1.16), 3.876 (1.10), 4.087 (1.55), 4.111 (1.70), 4.141 (0.81), 7.476 (1.72), 7.504 (5.34), 7.509 (4.33), 7.513 (4.34), 7.528 (16.00), 7.551 (5.39), 7.586 (2.11), 7.593 (2.25), 7.607 (1.58), 7.695 (0.45), 7.741 (0.47), 7.840 (1.67), 7.846 (2.40), 7.863 (2.55), 7.868 (3.83), 7.874 (2.07), 7.935 (4.34), 7.940 (3.94), 7.957 (2.78), 7.963 (2.48), 8.927 (1.77), 8.940 (2.09), 12.107 (1.53).

Example 236

(−)-5-{[(6-Bromo-3-methyl-2-phenylquinolin-4-yl)carbonyl]amino}-4-(2,3,6-trichlorophenyl)pentanoic Acid (Enantiomer 2)

tert-Butyl 5-{[(6-bromo-3-methyl-2-phenylquinolin-4-yl)carbonyl]amino}-4-(2,3,6-trichlorophenyl)pentanoate (280 mg, 99% pure, 410 μmol, Example 301A, enantiomer 2) was dissolved in dichloromethane (3.5 ml). At RT, TFA (3.1 ml) was added and the mixture was stirred at RT for 2 h. The volatile components were then removed on a rotary evaporator. Twice, some toluene was added to the residue and the mixture was re-concentrated on a rotary evaporator. The residue was dissolved in a little DMSO and purified by preparative HPLC (Method 31). The combined target fractions were concentrated under reduced pressure, and the residue was dried under reduced pressure. 214 mg (100% purity, 84% of theory) of the title compound were obtained.

$[\alpha]_D^{20}$=−33.9°, 589 nm, c=0.19 g/100 ml, methanol

LC-MS (Method 2): $R_t$=1.11 min; MS (ESIpos): m/z=619/621/623 [M+H]⁺

¹H-NMR (400 MHz, DMSO-d6) δ [ppm]: −0.149 (0.76), −0.008 (6.72), 0.008 (7.91), 0.146 (0.78), 2.073 (5.46), 2.082 (1.42), 2.095 (2.02), 2.108 (2.66), 2.128 (3.53), 2.153 (5.18), 2.164 (4.61), 2.180 (9.99), 2.212 (1.38), 2.237 (0.78), 2.284 (1.19), 2.310 (1.54), 2.327 (1.49), 2.366 (0.71), 2.670 (1.10), 2.710 (0.64), 3.832 (0.80), 3.863 (1.17), 4.088 (1.56), 4.111 (1.77), 4.140 (0.85), 7.476 (1.77), 7.504 (5.32), 7.510 (4.24), 7.513 (4.22), 7.528 (16.00), 7.551 (5.89), 7.593 (2.27), 7.607 (1.58), 7.746 (0.46), 7.840 (1.83), 7.846 (2.52), 7.852 (1.40), 7.863 (2.73), 7.869 (4.03), 7.875 (2.13), 7.935 (4.52), 7.940 (4.06), 7.957 (2.87), 7.963 (2.48), 8.926 (1.83), 8.940 (2.27), 12.111 (1.05).

Example 237

(+/−)-6-{[(6-Bromo-3-methyl-2-phenylquinolin-4-yl)carbonyl]amino}-5-(2-chlorophenyl)hexanoic Acid (Racemate)

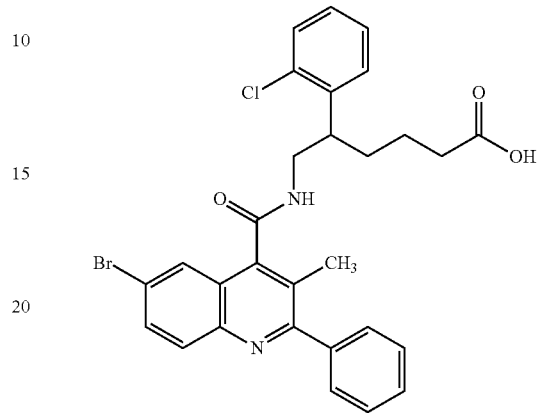

TFA (120 μl, 1.6 mmol) was added to a solution of (+/−)-tert-butyl 6-{[(6-bromo-3-methyl-2-phenylquinolin-4-yl)carbonyl]amino}-5-(2-chlorophenyl)hexanoate (100 mg, 161 μmol, Example 302A) in dichloromethane (1.2 ml), and the mixture was allowed to stand at RT for three days. The mixture was then concentrated and repeatedly dichloromethane was added and the mixture was concentrated again. The residue was dissolved in acetonitrile and purified by preparative HPLC (Method 15). The combined target fractions were concentrated, and the residue was lyophilized. This gave 73 mg (100% purity, 80% of theory) of the title compound.

LC-MS (Method 1): $R_t$=2.02 min; MS (ESIpos): m/z=565/567 [M+H]⁺

¹H-NMR (400 MHz, DMSO-d6) δ [ppm]: 11.97 (br. s, 1H), 8.85 (t, 1H), 7.94 (d, 1H), 7.85 (dd, 1H), 7.72 (br. s, 1H), 7.56-7.42 (m, 7H), 7.37 (t, 1H), 7.26 (t, 1H), 3.80-3.35 (m, 3H, partially obscured), 2.27-2.06 (m, 5H), 1.87-1.72 (m, 1H), 1.70-1.57 (m, 1H), 1.53-1.25 (m, 2H).

Example 238

(−)-6-{[(6-Bromo-3-methyl-2-phenylquinolin-4-yl)carbonyl]amino}-5-(2-chlorophenyl)hexanoic Acid (Enantiomer 1)

TFA (1.3 ml, 16 mmol) was added to a solution of tert-butyl 6-{[(6-bromo-3-methyl-2-phenylquinolin-4-yl)carbonyl]amino}-5-(2-chlorophenyl)hexanoate (460 mg, 740 μmol, Example 303A, enantiomer 1) in dichloromethane (6.2 ml), and the mixture was allowed to stand at RT for 16 h. The mixture was then concentrated and repeatedly dichloromethane was added and the mixture was concentrated again. The residue was purified by preparative HPLC (Method 16). The combined target fractions were concentrated, and the residue was lyophilized. This gave 367 mg (100% purity, 88% of theory) of the title compound.

$[\alpha]_D^{20}$=−12.4°, 589 nm, c=0.37 g/100 ml, methanol

LC-MS (Method 1): $R_t$=2.03 min; MS (ESIpos): m/z=565/567 [M+H]⁺

¹H-NMR (400 MHz, DMSO-d6) δ [ppm]: 1.326 (0.41), 1.339 (0.80), 1.358 (1.09), 1.370 (1.18), 1.384 (1.22), 1.398

(0.94), 1.422 (0.87), 1.438 (1.19), 1.449 (1.18), 1.457 (1.11), 1.464 (1.30), 1.481 (1.04), 1.497 (0.61), 1.594 (0.46), 1.628 (1.23), 1.640 (1.09), 1.652 (1.32), 1.664 (1.00), 1.675 (0.67), 1.687 (0.47), 1.742 (0.66), 1.755 (1.22), 1.769 (1.35), 1.782 (1.33), 1.802 (0.95), 1.815 (0.72), 2.150 (6.24), 2.187 (4.80), 2.205 (8.14), 2.224 (3.74), 2.248 (0.42), 3.170 (9.01), 3.548 (1.70), 3.587 (3.08), 3.601 (3.03), 3.965 (0.54), 7.235 (1.26), 7.254 (2.76), 7.273 (1.90), 7.349 (1.67), 7.368 (3.04), 7.386 (1.62), 7.432 (4.96), 7.452 (4.08), 7.486 (5.02), 7.502 (8.76), 7.508 (6.18), 7.521 (16.00), 7.525 (15.01), 7.723 (0.62), 7.835 (2.89), 7.840 (2.55), 7.857 (4.35), 7.862 (4.06), 7.932 (8.15), 7.954 (5.11), 8.834 (1.76), 8.849 (3.52), 8.863 (1.67).

$^1$H-NMR (400 MHz, DMSO-d6) δ [ppm]: 11.95 (br. s, 1H), 8.85 (t, 1H), 7.94 (d, 1H), 7.85 (dd, 1H), 7.72 (br. s, 1H), 7.56-7.42 (m, 7H), 7.37 (t, 1H), 7.26 (t, 1H), 3.77-3.51 (m, 3H, partially obscured), 2.25-2.09 (m, 5H), 1.85-1.73 (m, 1H), 1.71-1.56 (m, 1H), 1.53-1.25 (m, 2H).

Example 239

(+)-6-{[(6-Bromo-3-methyl-2-phenylquinolin-4-yl)carbonyl]amino}-5-(2-chlorophenyl)hexanoic Acid (Enantiomer 2)

TFA (11.1 ml, 15 mmol) was added to a solution of tert-butyl 6-{[(6-bromo-3-methyl-2-phenylquinolin-4-yl)carbonyl]amino}-5-(2-chlorophenyl)hexanoate (415 mg, 667 μmol, Example 304A, enantiomer 2) in dichloromethane (5.6 ml), and the mixture was allowed to stand at RT for 16 h. The mixture was then concentrated and repeatedly dichloromethane was added and the mixture was concentrated again. The residue was purified by preparative HPLC (Method 16). The combined target fractions were concentrated, and the residue was lyophilized. This gave 367 mg (100% purity, 88% of theory) of the title compound.

$[α]_D^{20}$=+13.6°, 589 nm, c=0.44 g/100 ml, methanol

LC-MS (Method 1): $R_t$=2.03 min; MS (ESIpos): m/z=565/567 [M+H]$^+$ $^1$H-NMR (400 MHz, DMSO-d6) δ [ppm]: 0.008 (1.03), 1.337 (0.89), 1.356 (1.15), 1.369 (1.22), 1.382 (1.24), 1.396 (0.97), 1.421 (0.94), 1.436 (1.25), 1.447 (1.20), 1.455 (1.14), 1.462 (1.28), 1.480 (1.00), 1.495 (0.57), 1.592 (0.56), 1.626 (1.26), 1.640 (1.11), 1.650 (1.31), 1.662 (0.99), 1.687 (0.45), 1.741 (0.75), 1.754 (1.29), 1.768 (1.40), 1.780 (1.32), 1.814 (0.72), 2.149 (6.09), 2.185 (4.76), 2.204 (7.72), 2.222 (3.48), 2.248 (0.41), 3.547 (0.97), 3.584 (1.69), 3.698 (2.95), 7.234 (1.33), 7.253 (2.63), 7.272 (1.78), 7.349 (1.71), 7.368 (2.91), 7.386 (1.57), 7.431 (4.72), 7.451 (3.97), 7.485 (5.40), 7.501 (8.92), 7.508 (6.68), 7.520 (16.00), 7.532 (7.56), 7.699 (0.61), 7.834 (2.92), 7.839 (2.51), 7.856 (4.20), 7.861 (3.76), 7.930 (7.74), 7.952 (4.78), 8.832 (1.79), 8.847 (3.30), 8.860 (1.53).

$^1$H-NMR (400 MHz, DMSO-d6) δ [ppm]: 11.95 (br. s, 1H), 8.85 (t, 2H), 7.94 (d, 1H), 7.85 (dd, 1H), 7.72 (br. s, 1H), 7.56-7.42 (m, 7H), 7.37 (t, 1H), 7.25 (t, 1H), 3.78-3.50 (m, 3H), 2.24-2.09 (m, 5H), 1.85-1.71 (m, 1H), 1.70-1.57 (m, 1H), 1.54-1.27 (m, 2H).

Example 240

(+/−)-6-{[(6-Bromo-3-methyl-2-phenylquinolin-4-yl)carbonyl]amino}-5-(2-chlorophenyl)-5-methyl-hexanoic Acid (Racemate)

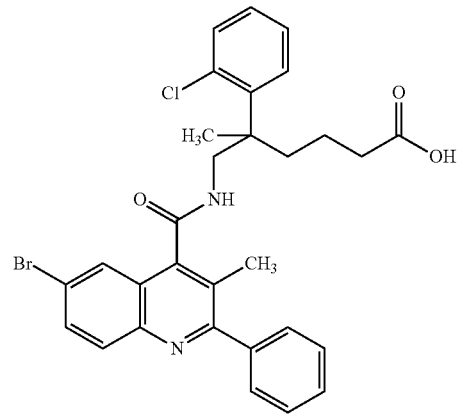 [SMILES: Cc1c(-c2ccccc2)nc2ccc(Br)cc2c1C(=O)NCC(C)(CCCC(=O)O)c1ccccc1Cl]

TFA (1.0 ml, 14 mmol) was added to a solution of (+/−)-tert-butyl 6-{[(6-bromo-3-methyl-2-phenylquinolin-4-yl)carbonyl]amino}-5-(2-chlorophenyl)-5-methylhexanoate (866 mg, "1.36 mmol", not corrected for purity, first mixed fraction of Example 305A) in dichloromethane (10 ml), and the mixture was allowed to stand at RT for two days. The mixture was then concentrated and repeatedly dichloromethane was added and the mixture was concentrated again. The residue was dissolved in acetonitrile and purified by preparative HPLC (Method 16). Three fractions were concentrated. After drying under reduced pressure, the first fraction gave 189 mg (100% purity) of a first batch of the dechlorinated product ((+/−)-6-{[(6-bromo-3-methyl-2-phenylquinolin-4-yl)carbonyl]amino}-5-methyl-5-phenyl-hexanoic acid, see Example 243). The third fraction gave 282 mg (96% purity) of a first batch of the title compound. The middle fraction was repurified by preparative HPLC (Method 26). Concentration of the respective target fractions and drying under reduced pressure gave 61 mg (100% purity) of a second batch of the dechlorinated product ((+/−)-6-{[(6-bromo-3-methyl-2-phenylquinolin-4-yl)carbonyl]amino}-5-methyl-5-phenylhexanoic acid, see Example 243). Also obtained were 67 mg (100% purity, see analysis) of a second batch of the title compound.

LC-MS (Method 1): $R_t$=2.12 min; MS (ESIpos): m/z=579/581 [M+H]$^+$ $^1$H-NMR (400 MHz, DMSO-d6) δ [ppm]: 0.008 (2.57), 1.047 (0.92), 1.066 (1.29), 1.079 (1.36), 1.098 (1.09), 1.110 (0.75), 1.315 (1.08), 1.335 (1.35), 1.347 (1.37), 1.366 (1.11), 1.391 (1.30), 1.529 (16.00), 1.600 (1.04), 1.611 (1.11), 1.633 (1.91), 1.644 (1.75), 1.666 (1.15), 1.676 (0.94), 2.085 (10.08), 2.138 (5.60), 2.156 (9.00), 2.175 (4.42), 2.282 (0.46), 2.327 (0.47), 2.366 (0.42), 2.397 (0.92), 2.418 (1.50), 2.450 (0.85), 3.666 (1.69), 3.678 (1.84), 3.698 (2.02), 3.712 (1.97), 3.852 (1.49), 4.292 (1.78), 4.309 (1.97), 4.326 (1.79), 4.343 (1.64), 5.754 (8.27), 7.242 (1.04), 7.260 (2.63), 7.279 (2.41), 7.292 (2.38), 7.310 (3.20), 7.327 (1.59), 7.413 (3.43), 7.432 (6.46), 7.451 (3.16), 7.474 (0.83), 7.486 (2.00), 7.500 (6.53), 7.507 (5.67), 7.518 (14.80), 7.524 (13.14), 7.680 (0.60), 7.829 (2.76), 7.833 (2.56), 7.851 (4.25), 7.856 (4.03), 7.925 (7.72), 7.947 (4.86), 8.590 (1.85), 8.605 (3.26), 8.619 (1.86).

¹H-NMR (400 MHz, DMSO-d6) δ [ppm]: 12.01 (br. s, 1H), 8.62 (t, 1H), 7.93 (d, 1H), 7.84 (dd, 1H), 7.67 (br. s, 1H), 7.56-7.39 (m, 7H), 7.35-7.21 (m, 2H), 4.31 (dd, 1H), 3.69 (dd, 1H), 2.47-2.35 (m, 1H), 2.24-2.02 (m, 5H), 1.64 (td, 1H), 1.53 (s, 3H), 1.43-1.25 (m, 1H), 1.15-0.99 (m, 1H).

Separation of the Enantiomers:

The title compound (247 mg) was dissolved in methanol (15 ml) and separated into the enantiomers by preparative SFC on a chiral phase (see Examples 241 and 242) [column: Daicel Chiralcel IC, 5 μm, 250 mm×20 mm; flow rate: 80 ml/min; injection: 0.30 ml; mobile phase: 25% acetonitrile/75% carbon dioxide; run time 19 min, isocratic]. The combined target fractions were concentrated, and the respective residue was dried under reduced pressure.

Example 241

(−)-6-{[(6-Bromo-3-methyl-2-phenylquinolin-4-yl)carbonyl]amino}-5-(2-chlorophenyl)-5-methyl-hexanoic Acid (Enantiomer 1)

In the enantiomer separation described in Example 240, 66 mg (95% purity, ee>99%) of the title compound were obtained as the enantiomer that eluted earlier.

$[\alpha]_D^{20}$=−27.7°, 589 nm, c=0.35 g/100 ml, methanol

LC-MS (Method 1): $R_t$=2.13 min; MS (ESIpos): m/z=579/581 [M+H]⁺

¹H-NMR (400 MHz, DMSO-d6) δ [ppm]: 1.048 (0.93), 1.065 (1.23), 1.077 (1.29), 1.095 (1.07), 1.233 (0.55), 1.314 (1.06), 1.332 (1.34), 1.345 (1.33), 1.363 (1.09), 1.390 (1.60), 1.527 (16.00), 1.601 (1.01), 1.610 (1.08), 1.633 (1.83), 1.642 (1.71), 1.665 (1.04), 2.133 (4.41), 2.151 (5.76), 2.278 (0.54), 2.391 (1.00), 2.414 (1.60), 2.422 (1.59), 2.447 (0.93), 3.667 (1.35), 3.679 (1.46), 3.700 (1.57), 3.712 (1.44), 4.289 (1.68), 4.306 (1.85), 4.322 (1.69), 4.340 (1.55), 7.241 (1.11), 7.259 (2.75), 7.278 (2.56), 7.290 (2.48), 7.309 (3.37), 7.326 (1.71), 7.343 (0.60), 7.411 (3.64), 7.431 (6.51), 7.451 (3.18), 7.472 (0.93), 7.498 (6.58), 7.505 (5.67), 7.517 (14.29), 7.523 (13.42), 7.672 (0.63), 7.826 (2.64), 7.848 (4.09), 7.923 (6.70), 7.945 (4.28), 8.596 (1.73), 8.610 (3.12), 8.624 (1.78).

Example 242

(+)-6-{[(6-Bromo-3-methyl-2-phenylquinolin-4-yl)carbonyl]amino}-5-(2-chlorophenyl)-5-methyl-hexanoic Acid (Enantiomer 2)

In the enantiomer separation described in Example 240, 60 mg (100% purity, ee>99%) of the title compound were obtained as the enantiomer that eluted later.

$[\alpha]_D^{20}$=+25.7°, 589 nm, c=0.35 g/100 ml, methanol

LC-MS (Method 1): $R_t$=2.12 min; MS (ESIpos): m/z=579/581 [M+H]⁺

¹H-NMR (400 MHz, DMSO-d6) δ [ppm]: −0.008 (2.05), 0.008 (1.72), 1.077 (1.24), 1.113 (0.92), 1.232 (0.71), 1.332 (1.25), 1.527 (16.00), 1.611 (1.06), 1.633 (1.68), 1.664 (0.94), 2.149 (4.91), 2.277 (0.62), 2.327 (0.64), 2.387 (1.03), 2.414 (1.57), 2.443 (0.98), 2.670 (0.47), 3.540 (1.21), 3.668 (1.34), 3.680 (1.37), 3.701 (1.51), 4.288 (1.61), 4.305 (1.81), 4.322 (1.67), 4.338 (1.52), 7.241 (1.12), 7.259 (2.88), 7.278 (2.66), 7.291 (2.48), 7.308 (3.45), 7.326 (1.62), 7.411 (3.37), 7.431 (6.32), 7.451 (3.15), 7.472 (1.00), 7.484 (2.24), 7.498 (6.98), 7.505 (5.98), 7.516 (14.63), 7.523 (13.31), 7.667 (0.64), 7.825 (3.06), 7.830 (2.78), 7.848 (4.56), 7.853 (4.27), 7.923 (8.71), 7.945 (5.48), 8.600 (1.77), 8.615 (2.99), 8.630 (1.66).

Example 243

(+/−)-6-{[(6-Bromo-3-methyl-2-phenylquinolin-4-yl)carbonyl]amino}-5-methyl-5-phenylhexanoic Acid (Racemate)

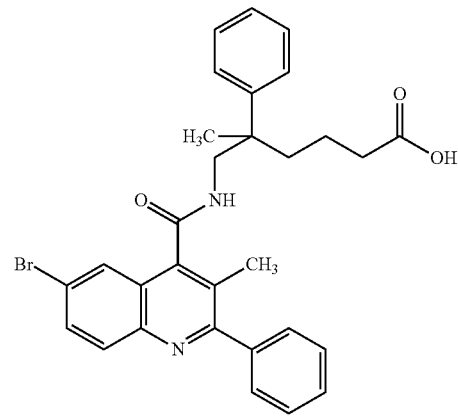 [SMILES: Cc1c(-c2ccccc2)nc2ccc(Br)cc2c1C(=O)NCC(C)(CCCC(=O)O)c1ccccc1]

As described in Example 240, 189 mg (100% purity, see analysis) of a first batch of the title compound and 61 mg (100% purity) of a second batch of the title compound were obtained.

LC-MS (Method 1): $R_t$=2.07 min; MS (ESIpos): m/z=545/547 [M+H]⁺

¹H-NMR (400 MHz, DMSO-d6) δ [ppm]: −0.150 (0.16), 0.007 (1.24), 0.146 (0.16), 1.141 (0.62), 1.160 (0.85), 1.173 (0.93), 1.192 (0.80), 1.204 (0.51), 1.334 (0.82), 1.353 (1.06), 1.366 (1.17), 1.391 (16.00), 1.529 (0.36), 1.586 (0.62), 1.597 (0.70), 1.619 (1.29), 1.629 (1.23), 1.651 (0.85), 1.661 (0.68), 1.774 (0.75), 1.784 (0.82), 1.806 (1.18), 1.816 (1.12), 1.838 (0.58), 2.085 (1.70), 2.118 (4.12), 2.136 (6.68), 2.155 (3.41), 2.331 (0.27), 2.346 (0.24), 2.365 (0.43), 2.669 (0.18), 2.709 (0.18), 3.169 (2.40), 3.538 (1.47), 3.551 (1.61), 3.571 (1.97), 3.584 (1.97), 3.655 (1.18), 3.833 (1.50), 3.850 (1.59), 3.866 (1.33), 3.883 (1.21), 3.964 (0.23), 4.527 (0.14), 5.753 (0.28), 7.196 (0.88), 7.213 (2.20), 7.231 (1.49), 7.325 (2.43), 7.344 (4.84), 7.363 (2.95), 7.412 (6.54), 7.431 (4.28), 7.473 (0.54), 7.485 (1.44), 7.500 (4.46), 7.507 (3.68), 7.518 (8.57), 7.528 (8.40), 7.570 (0.34), 7.588 (0.28), 7.667 (0.57), 7.827 (1.92), 7.833 (1.76), 7.850 (2.94), 7.855 (2.81), 7.928 (5.42), 7.950 (3.54), 8.598 (1.29), 8.613 (2.28), 8.628 (1.26).

¹H-NMR (400 MHz, DMSO-d6) δ [ppm]: 11.97 (br. s, 1H), 8.61 (t, 1H), 7.94 (d, 1H), 7.84 (dd, 1H), 7.67 (br. s, 1H), 7.59-7.46 (m, 5H), 7.45-7.39 (m, 2H), 7.34 (t, 2H), 7.22 (t, 1H), 3.86 (dd, 1H), 3.56 (dd, 1H), 2.25-1.98 (m, 5H), 1.81 (td, 1H), 1.62 (td, 1H), 1.45-1.29 (m, 1H), 1.39 (s, 3H), 1.25-1.09 (m, 1H).

Separation of the Enantiomers:

The title compound (160 mg) was dissolved in methanol (20 ml) and separated into the enantiomers by preparative SFC on a chiral phase (see Examples 244 and 245) [column: Daicel Chiralpak AD, 250 mm×20 mm; flow rate: 80 ml/min; injection: 0.50 ml; mobile phase: 12% acetonitrile/88% carbon dioxide; run time 22 min, isocratic]. The combined target fractions were concentrated, and the respective residue was dried under reduced pressure.

Example 244

(−)-6-{[(6-Bromo-3-methyl-2-phenylquinolin-4-yl)carbonyl]amino}-5-methyl-5-phenylhexanoic Acid (Enantiomer 1)

In the enantiomer separation described in Example 243, 56 mg (100% purity, ee 99%) of the title compound were obtained as the enantiomer that eluted earlier.

$[\alpha]_D^{20}$=−18.7°, 589 nm, c=0.40 g/100 ml, methanol

LC-MS (Method 1): $R_t$=2.07 min; MS (ESIpos): m/z=545/547 [M+H]$^+$ $^1$H-NMR (400 MHz, DMSO-d6) δ [ppm]: −0.008 (1.29), 0.008 (1.06), 1.030 (0.82), 1.045 (0.85), 1.140 (0.68), 1.160 (0.92), 1.172 (1.00), 1.191 (0.83), 1.333 (0.83), 1.352 (1.07), 1.390 (16.00), 1.585 (0.67), 1.597 (0.76), 1.618 (1.35), 1.629 (1.28), 1.650 (0.90), 1.661 (0.71), 1.773 (0.78), 1.782 (0.87), 1.805 (1.23), 1.814 (1.18), 1.837 (0.61), 1.846 (0.52), 2.072 (1.18), 2.115 (4.26), 2.133 (6.73), 2.152 (3.32), 2.730 (1.67), 2.889 (1.91), 3.538 (1.13), 3.551 (1.24), 3.572 (1.45), 3.585 (1.34), 3.833 (1.37), 3.850 (1.52), 3.866 (1.24), 3.883 (1.12), 7.196 (1.02), 7.213 (2.47), 7.231 (1.65), 7.324 (2.71), 7.344 (5.30), 7.363 (3.21), 7.412 (6.82), 7.431 (4.23), 7.472 (0.60), 7.484 (1.69), 7.499 (5.05), 7.506 (4.13), 7.517 (9.35), 7.527 (9.32), 7.545 (1.74), 7.669 (0.66), 7.826 (2.19), 7.831 (1.97), 7.848 (3.28), 7.853 (3.08), 7.927 (6.46), 7.949 (4.33), 8.602 (1.35), 8.617 (2.32), 8.632 (1.27).

Example 245

(+)-6-{[(6-Bromo-3-methyl-2-phenylquinolin-4-yl)carbonyl]amino}-5-methyl-5-phenylhexanoic Acid (Enantiomer 2)

In the enantiomer separation described in Example 243, 35 mg (100% purity, ee 94%) of the title compound were obtained as the enantiomer that eluted later.

$[\alpha]_D^{20}$=+18.0°, 589 nm, c=0.35 g/100 ml, methanol

LC-MS (Method 1): $R_t$=2.07 min; MS (ESIpos): m/z=545/547 [M+H]$^+$ $^1$H-NMR (400 MHz, DMSO-d6) δ [ppm]: 1.141 (0.68), 1.161 (0.94), 1.173 (1.04), 1.192 (0.85), 1.334 (0.85), 1.353 (1.12), 1.391 (16.00), 1.587 (0.64), 1.597 (0.75), 1.619 (1.37), 1.629 (1.29), 1.651 (0.91), 1.662 (0.72), 1.784 (0.88), 1.806 (1.25), 1.816 (1.20), 1.839 (0.64), 2.118 (4.31), 2.137 (6.84), 2.155 (3.37), 2.731 (0.94), 2.890 (1.03), 3.537 (1.19), 3.551 (1.22), 3.571 (1.40), 3.585 (1.31), 3.833 (1.37), 3.850 (1.49), 3.866 (1.25), 3.883 (1.15), 7.196 (1.01), 7.214 (2.46), 7.232 (1.68), 7.325 (2.70), 7.344 (5.36), 7.363 (3.26), 7.412 (6.97), 7.432 (4.22), 7.473 (0.59), 7.485 (1.59), 7.500 (4.92), 7.506 (4.04), 7.518 (9.53), 7.528 (9.42), 7.667 (0.68), 7.827 (2.12), 7.831 (1.97), 7.849 (3.18), 7.854 (3.09), 7.927 (6.17), 7.949 (4.02), 8.598 (1.37), 8.613 (2.42), 8.628 (1.31), 11.939 (1.52).

Example 246

1-[2-{[(6-Bromo-3-methyl-2-phenylquinolin-4-yl)carbonyl]amino}-1-(2-methoxyphenyl)ethyl]pyrrolidine-3-carboxylic Acid

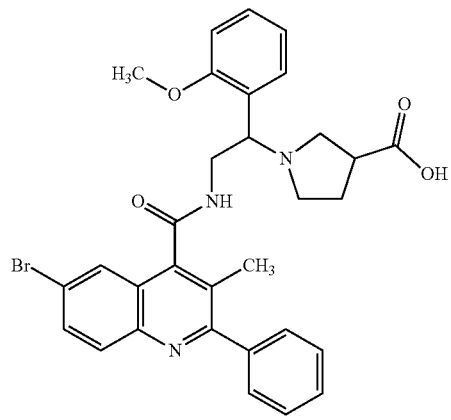 [SMILES: COc1ccccc1C(CNC(=O)c1c(C)c(-c2ccccc2)nc2ccc(Br)cc12)N1CCC(C(=O)O)C1]

HATU (125 mg, 329 μmol) and DIPEA (110 μl, 660 μmol) were added to a mixture of 6-bromo-3-methyl-2-phenylquinoline-4-carboxylic Acid (75 mg, 219 μmol, preparable according to WO 2016 146602 A1, p. 51, Example 3A) in DMF (2 ml), and the mixture was stirred at RT for 30 min. 1-[2-Amino-1-(2-methoxyphenyl)ethyl]pyrrolidine-3-carboxylic Acid (102 mg, 85% purity, 329 μmol, CAS-RN 886363-84-4, commercially available), dissolved in DMF (1 ml), was then added, and the mixture was stirred at 60° C. for 3 h. Subsequently, ethyl acetate and water (20 ml of each) were added to the mixture, which was agitated. After phase separation, the aqueous phase was extracted twice with ethyl acetate (20 ml). The combined organic phases were washed with saturated aqueous sodium chloride solution, dried over sodium sulfate, filtered and concentrated. On concentration, a solid precipitated, which was filtered off. The filtrate was concentrated and the residue was taken up in dichloromethane and prepurified by flash column chromatography (50 g silica gel Biotage Snap-Cartridge KP-Sil, cyclohexane/ethyl acetate 85:15, Isolera One). The combined target fractions were concentrated and the residue was repurified by preparative HPLC (Method 16). This was followed by another repurification by preparative HPLC (Method 22). This was followed by another repurification by preparative HPLC (Method 25). 4 mg (90% purity, 3% of theory) of the title compound were obtained.

LC-MS (Method 2): $R_t$=0.80 & 0.82 min; MS (ESIpos): m/z=588/590 [M+H]$^+$ $^1$H-NMR (400 MHz, DMSO-d6) δ [ppm]: 1.236 (0.85), 1.886 (1.62), 1.899 (1.67), 2.167 (12.14), 2.183 (2.43), 2.256 (0.64), 2.328 (0.71), 2.366 (0.76), 2.403 (0.48), 2.421 (0.53), 2.451 (0.74), 2.569 (2.03), 2.589 (1.30), 2.637 (0.52), 2.670 (0.72), 2.710 (0.41), 2.765 (2.17), 2.774 (4.88), 2.834 (1.19), 2.872 (0.89), 2.905 (1.19), 2.939 (2.25), 2.958 (5.33), 3.724 (0.92), 3.783 (16.00), 3.910 (0.82), 4.181 (1.03), 4.195 (1.76), 4.208 (0.91), 4.256 (0.68), 6.928 (1.16), 6.947 (2.36), 6.965 (1.35), 7.003 (2.11), 7.023 (2.44), 7.232 (1.32), 7.250 (2.08), 7.270 (0.95), 7.337 (0.85), 7.354 (1.91), 7.370 (1.78), 7.385 (0.70), 7.474 (0.63), 7.487 (1.71), 7.501 (4.65), 7.506 (4.14), 7.520 (8.73), 7.531 (9.03), 7.795 (1.46), 7.836 (2.96), 7.860 (3.31), 7.926 (4.22), 7.948 (2.61), 8.584 (1.09), 8.599 (1.48), 8.614 (0.99).

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

Abbreviations and Acronyms

CRTH2 chemoattractant receptor-homologous molecule expressed on T helper type 2 cells
DMEM Dulbecco's modified Eagle's medium
DMSO dimethyl sulfoxide
DP PGD2 receptor
$EC_{50}$ half-maximum effective concentration
em. emission
EP PGE2 receptor
ex. excitation
from Company (source)
FCS fetal calf serum
FP PGF2α receptor
HEPES 2-[4-(2-hydroxyethyl)piperazin-1-yl]ethanesulfonic acid
$IC_{50}$ half-maximum inhibitory concentration
IP PGI2 receptor
lit. literature (reference)
MES 2-(N-morpholino)ethanesulfonic acid
Pen/Strep penicillin/streptomycin
PGD2 prostaglandin D2
PGE2 prostaglandin E2
PGF2α prostaglandin F2a
(PGI2) prostaglandin I2
TC tissue culture
TP thromboxane A2 receptor
Tris tris(hydroxymethyl)aminomethane
v/v volume to volume ratio (of a solution)
w/w weight to weight ratio (of a solution)

B-1. In Vitro Test of Inhibition of Human FP Receptor Activity

For the characterization of test substances in respect of FP antagonism, PGF2α-induced calcium flux in FP-expressing CHEM1 cells (Millipore, HTS093C) was used.

3000 cells in 30 µl of full medium [DMEM F12, 10% FCS, 1.35 mM sodium pyruvate, 20 mM HEPES, 4 mM GlutaMAX™, 2% sodium bicarbonate, 1% Pen/Strep, 1% 100× non-essential amino acids] are sown per well of a 384 multititre plate (from Greiner, TC plate, black with clear base) and incubated at 33° C., 5% $CO_2$ for 24 hours. Prior to the measurement, the medium is replaced by 30 µl of Fluo-8 AM loading buffer [calcium-free Tyrode (130 mM NaCl, 5 mM KCl, 20 mM HEPES, 1 mM $MgCl_2$, 4.8 mM $NaHCO_3$, pH 7.4), 2 mM $CaCl_2$, 6.3 mM Probenecid, 5 µM Fluo-8 AM, 0.0112% Pluronic®] and incubated at 37° C., 5% $CO_2$ for 30 minutes. The test substance is prepared in DMSO in various concentrations as a dose-response curve (starting concentration 10 mM, dilution factor 3.16) and prediluted 1:50 with calcium-free Tyrode, 2 mM $CaCl_2$, 0.002% SmartBlock (from CANDOR Bioscience GmbH). 10 µl of the prediluted substance solution are added to the Fluo-8-laden cells and incubated at 37° C., 5% $CO_2$ for 10 minutes. The FP receptor is activated by adding 40 µl of 2 nM (final concentration) PGF2α in calcium-free Tyrode, 2 mM $CaCl_2$, 0.002% SmartBlock, and the calcium flux is determined by measuring the fluorescence at ex. 470 nm/em. 525 nm in a fluorescence measuring instrument (FLIPR Tetra®, Molecular Devices) for 120 seconds.

Table 1 below lists the $IC_{50}$ values from this assay for individual working examples of the invention (some as mean values from multiple independent individual determinations):

TABLE 1

| Ex. No. | FP receptor activity $IC_{50}$ [µmol/l] |
|---|---|
| 1 | 0.13 |
| 2 | 0.16 |
| 3 | 0.27 |
| 4 | 0.031 |
| 5 | 0.037 |
| 6 | 0.032 |
| 7 | 0.024 |
| 8 | 0.13 |
| 9 | 0.0072 |
| 10 | 0.32 |
| 11 | 0.47 |
| 12 | 0.18 |
| 13 | 0.094 |
| 14 | 0.053 |
| 15 | 0.19 |
| 16 | 0.17 |
| 17 | 0.26 |
| 18 | 0.12 |
| 19 | 0.15 |
| 20 | 0.097 |
| 21 | 0.17 |
| 22 | 0.076 |
| 23 | 0.53 |
| 24 | 0.58 |
| 25 | >1.0 |
| 26 | 0.044 |
| 27 | 0.053 |
| 28 | 0.10 |
| 29 | 0.14 |
| 30 | 0.34 |
| 31 | 0.068 |
| 32 | 0.15 |
| 33 | 0.19 |
| 34 | 0.13 |
| 35 | 0.19 |
| 36 | 0.81 |
| 37 | 0.16 |
| 38 | 0.047 |
| 39 | 0.14 |
| 40 | 0.034 |
| 41 | 0.13 |
| 42 | 0.12 |
| 43 | 0.14 |
| 44 | 0.19 |
| 45 | 0.60 |
| 46 | 0.23 |
| 47 | 0.043 |
| 48 | 0.033 |
| 49 | 0.069 |
| 50 | 0.079 |
| 51 | 0.042 |
| 52 | 0.071 |
| 53 | 0.18 |
| 54 | 0.50 |
| 55 | 0.078 |
| 56 | 0.021 |
| 57 | 0.21 |
| 58 | 0.0097 |
| 59 | 0.39 |
| 60 | 0.12 |
| 61 | 0.23 |
| 62 | 0.043 |
| 63 | 0.34 |
| 64 | 0.34 |
| 65 | 0.22 |
| 66 | 0.50 |
| 67 | 0.37 |

TABLE 1-continued

| Ex. No. | FP receptor activity IC$_{50}$ [μmol/l] |
|---|---|
| 68 | >1.0 |
| 69 | 0.048 |
| 70 | 0.032 |
| 71 | 0.036 |
| 72 | 0.045 |
| 73 | 0.086 |
| 74 | 0.079 |
| 75 | 0.069 |
| 76 | 0.023 |
| 77 | 0.085 |
| 78 | 0.10 |
| 79 | 0.14 |
| 80 | 0.051 |
| 81 | 0.19 |
| 82 | 0.22 |
| 83 | 0.28 |
| 84 | 0.016 |
| 85 | 0.016 |
| 86 | 0.24 |
| 87 | 0.023 |
| 88 | 0.019 |
| 89 | 0.027 |
| 90 | 0.47 |
| 91 | 0.46 |
| 92 | 0.32 |
| 93 | 0.080 |
| 94 | 0.096 |
| 95 | 0.084 |
| 96 | 0.023 |
| 97 | 0.12 |
| 98 | 0.0090 |
| 99 | 0.028 |
| 100 | 0.020 |
| 101 | 0.032 |
| 102 | 0.46 |
| 103 | 0.29 |
| 104 | >1.0 |
| 105 | 0.092 |
| 106 | 0.28 |
| 107 | 0.051 |
| 108 | 0.078 |
| 109 | 0.075 |
| 110 | 0.075 |
| 111 | 0.089 |
| 112 | 0.092 |
| 113 | 0.062 |
| 114 | 0.018 |
| 115 | 0.031 |
| 116 | 0.074 |
| 117 | 0.24 |
| 118 | 0.28 |
| 119 | 0.15 |
| 120 | 0.030 |
| 121 | 0.010 |
| 122 | 0.46 |
| 123 | 0.011 |
| 124 | 0.0053 |
| 125 | 0.097 |
| 126 | 0.039 |
| 127 | 0.025 |
| 128 | 0.11 |
| 129 | 0.13 |
| 130 | 0.32 |
| 131 | 0.099 |
| 132 | 0.032 |
| 133 | 0.047 |
| 134 | 0.80 |
| 135 | 0.013 |
| 136 | 0.013 |
| 137 | 0.44 |
| 138 | 0.042 |
| 139 | 0.028 |
| 140 | >1.0 |
| 141 | 0.024 |
| 142 | 0.015 |
| 143 | 0.0068 |

TABLE 1-continued

| Ex. No. | FP receptor activity IC$_{50}$ [μmol/l] |
|---|---|
| 144 | 0.13 |
| 145 | 0.049 |
| 146 | >1.0 |
| 147 | >1.0 |
| 148 | 0.042 |
| 149 | >1.0 |
| 150 | 0.96 |
| 151 | 0.0078 |
| 152 | 0.0079 |
| 153 | 0.0090 |
| 154 | 0.015 |
| 155 | 0.060 |
| 156 | 0.0080 |
| 157 | 0.0037 |
| 158 | 0.0035 |
| 159 | 0.024 |
| 160 | 0.013 |
| 161 | 0.0082 |
| 162 | 0.033 |
| 163 | 0.0087 |
| 164 | 0.015 |
| 165 | 0.0066 |
| 166 | 0.0061 |
| 167 | 0.026 |
| 168 | 0.0036 |
| 169 | 0.026 |
| 170 | 0.11 |
| 171 | 0.011 |
| 172 | 0.0032 |
| 173 | 0.0011 |
| 174 | 0.019 |
| 175 | 0.015 |
| 176 | 0.012 |
| 177 | 0.019 |
| 178 | 0.0065 |
| 179 | 0.0041 |
| 180 | 0.0082 |
| 181 | 0.0092 |
| 182 | 0.0072 |
| 183 | 0.023 |
| 184 | 0.0077 |
| 185 | 0.0039 |
| 186 | 0.017 |
| 187 | 0.036 |
| 188 | 0.054 |
| 189 | 0.062 |
| 190 | 0.067 |
| 191 | 0.10 |
| 192 | 0.042 |
| 193 | 0.15 |
| 194 | 0.0079 |
| 195 | 0.0080 |
| 196 | 0.012 |
| 197 | 0.021 |
| 198 | 0.40 |
| 199 | 0.025 |
| 200 | 0.0036 |
| 201 | 0.0012 |
| 202 | 0.0062 |
| 203 | 0.0076 |
| 204 | 0.0037 |
| 205 | 0.022 |
| 206 | 0.013 |
| 207 | 0.010 |
| 208 | 0.011 |
| 209 | 0.0018 |
| 210 | 0.0061 |
| 211 | 0.0017 |
| 212 | 0.0066 |
| 213 | 0.0028 |
| 214 | 0.0044 |
| 215 | 0.0054 |
| 216 | 0.0050 |
| 217 | 0.019 |
| 218 | 0.013 |
| 219 | 0.010 |

TABLE 1-continued

| Ex. No. | FP receptor activity IC$_{50}$ [µmol/l] |
|---|---|
| 220 | 0.0080 |
| 221 | 0.0024 |
| 222 | 0.00096 |
| 223 | 0.012 |
| 224 | 0.10 |
| 225 | 0.0047 |
| 226 | 0.10 |
| 227 | 0.0016 |
| 228 | 0.0042 |
| 229 | 0.0027 |
| 230 | 0.049 |
| 231 | 0.022 |
| 232 | 0.0088 |
| 233 | 0.025 |
| 234 | 0.0072 |
| 235 | 0.032 |
| 236 | 0.0020 |
| 237 | 0.0052 |
| 238 | 0.0043 |
| 239 | 0.010 |
| 240 | 0.024 |
| 241 | 0.068 |
| 242 | 0.016 |
| 243 | 0.031 |
| 244 | 0.020 |
| 245 | 0.063 |
| 246 | 0.094 |
| 247 | 0.0072 |
| 248 | 0.013 |
| 249 | 0.0028 |
| 250 | 0.017 |
| 251 | 0.015 |
| 252 | 0.014 |

B-2. In Vitro FP Receptor Binding Inhibition Test

For the FP receptor binding test, human recombinant prostanoid FP receptors, expressed in HEK293 cells, in modified MES buffer, pH 6.0, are used. This test is conducted commercially (at Eurofins Panlabs, catalog #268510). 80 µg of membrane are incubated with 1 nM [$^3$H]-PGF2α at 25° C. for 60 minutes. The amount of membrane protein can vary from batch to batch and is adjusted if required. Unspecific binding is determined in the presence of 1 µM cloprostenol. The membranes are filtered, washed and then analyzed in order to determine the specific binding of [$^3$H]-PGF2α. Substances are tested for inhibitory activity at a concentration of 10 µM or in the form of a dose-response curve [lit.: Abramovitz et al., *J. Biol. Chem.* 1994, 269 (4): 2632].

B-3. In Vitro CRTH2 Receptor Binding Inhibition Test

For this test, human recombinant prostanoid CRTH2 receptors, expressed in CHO-K1 cells, in modified Tris-HCl buffer, pH 7.4, are used. This test is conducted commercially (at Eurofins Panlabs, catalog #268030). 4 µg of membrane are incubated with 1 nM [$^3$H]-PGD2 at 25° C. for 120 minutes. The amount of membrane protein can vary from batch to batch and is adjusted if required.

Unspecific binding is determined in the presence of 1 µM PGD2. The membranes are filtered, washed and then analyzed in order to determine the specific binding of [$^3$H]-PGD2. Substances are tested for inhibitory activity at a concentration of 10 µM or in the form of a dose-response curve [lit.: Sugimoto et al., *J. Pharmacol. Exp. Ther.* 2003, 305 (1): 347].

B-4. In Vitro DP Receptor Binding Inhibition Test

For this test, human recombinant prostanoid DP receptors, expressed in Chem-1 cells, in modified HEPES buffer, pH 7.4, are used. This test is conducted commercially (at Eurofins Panlabs, catalog #268060). 10 µg of membrane are incubated with 2 nM [$^3$H]-PGD2 at 25° C. for 120 minutes. The amount of membrane protein can vary from batch to batch and is adjusted if required. Unspecific binding is determined in the presence of 1 µM PGD2. The membranes are filtered, washed and then analyzed in order to determine the specific binding of [$^3$H]-PGD2. Substances are tested for inhibitory activity at a concentration of 10 µM or in the form of a dose-response curve [lit.: Wright et al., *Br. J. Pharmacol.* 1998, 123 (7): 1317; Sharif et al., *Br. J. Pharmacol.* 2000, 131 (6): 1025].

B-5. In Vitro EP1 Receptor Binding Inhibition Test

For this test, human recombinant prostanoid EP1 receptors, expressed in HEK293 cells, in modified MES buffer, pH 6.0, are used. This test is conducted commercially (at Eurofins Panlabs, catalog #268110). 14 µg of membrane are incubated with 1 nM [$^3$H]-PGE2 at 25° C. for 60 minutes.

The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Abramovitz et al., *Biochim. Biophys. Acta* 2000, 1483 (2): 285; Funk et al., *J. Biol. Chem.* 1993, 268 (35): 26767].

B-6. In Vitro EP2 Receptor Binding Inhibition Test

For this test, human recombinant prostanoid EP2 receptors, expressed in HEK293 cells, in modified MES/KOH buffer, pH 6.0, are used. This test is conducted commercially (at Eurofins Panlabs, catalog #268200). 25 mg/ml of membrane are incubated with 4 nM [$^3$H]-PGE2 at 25° C. for 120 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Bastien et al., *J. Biol. Chem.* 1994, 269 (16): 11873; Boie et al., *Eur. J. Pharmacol.* 1997, 340 (2-3): 227].

B-7. In Vitro EP3 Receptor Binding Inhibition Test

For this test, human recombinant prostanoid EP3 receptors, expressed in HEK293 cells, in modified MES buffer, pH 6.0, are used. This test is conducted commercially (at Eurofins Panlabs, catalog #268310). 3 µg of membrane are incubated with 0.5 nM [$^3$H]-PGE2 at 25° C. for 120 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Schmidt et al., *Eur. J. Biochem.* 1995, 228 (1): 23].

B-8. In Vitro EP4 Receptor Binding Inhibition Test

For this test, human recombinant prostanoid EP4 receptors, expressed in Chem-1 cells, in modified MES buffer, pH 6.0, are used. This test is conducted commercially (at Eurofins Panlabs, catalog #268420). 3 µg of membrane are incubated with 1 nM [$^3$H]-PGE2 at 25° C. for 120 minutes. The amount of membrane protein can vary from batch to batch and is adjusted if required. Unspecific binding is determined in the presence of 10 µM PGE2. The membranes are filtered, washed and then analyzed in order to determine the specific binding of [$^3$H]-PGE2. Substances are tested for inhibitory activity at a concentration of 10 µM or in the form of a dose-response curve [lit.: Davis et al., *Br. J. Pharmacol.* 2000, 130 (8): 1919].

B-9. In Vitro IP Receptor Binding Inhibition Test

For this test, human recombinant prostanoid IP receptors, expressed in HEK293 cells, in modified HEPES buffer, pH 6.0, are used. This test is conducted commercially (at Eurofins Panlabs, catalog #268600). 15 µg of membrane are incubated with 5 nM [$^3$H]-iloprost at 25° C. for 60 minutes. The amount of membrane protein can vary from batch to batch and is adjusted if required. Unspecific binding is determined in the presence of 10 µM iloprost. The membranes are filtered, washed and then analyzed in order to determine the specific binding of [$^3$H]-iloprost. Substances are tested for inhibitory activity at a concentration of 10 µM or in the form of a dose-response curve [lit.: Armstrong et al., *Br. J. Pharmacol.* 1989, 97 (3): 657; Boie et al., *J. Biol. Chem.* 1994, 269 (16): 12173].

B-10. In Vitro TP Receptor Binding Inhibition Test

For this test, human recombinant prostanoid TP receptors, expressed in HEK-293 EBNA cells, in modified Tris/HCl buffer, pH 7.4, are used. This test is conducted commercially (at Eurofins Panlabs, catalog #285510). 18.4 µg of membrane are incubated with 5 nM [$^3$H]-SQ-29 548 at 25'C for 30 minutes. The amount of membrane protein can vary from batch to batch and is adjusted if required. Unspecific binding is determined in the presence of 1 µM SQ-29 548. The membranes are filtered, washed and then analyzed in order to determine the specific binding of [$^3$H]-SQ-29 548. Substances are tested for inhibitory activity at a concentration of 10 µM or in the form of a dose-response curve [lit.: Saussy Jr. et al., *J. Biol. Chem.* 1986, 261: 3025; Hedberg et al., *J. Pharmacol. Exp. Ther.* 1988, 245: 786].

B-11. In Vitro Test for DP Agonism and Antagonism

For the characterization of test substances in respect of DP agonism and antagonism, PGD2-induced calcium flux in DP-expressing CHEM1 cells (Millipore, HTS091C) was used: 3000 cells in 25 µl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of DP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of DP antagonism, the DP receptor is activated in the FLIPR Tetra® by adding 20 µl of −76 nM (2×$EC_{50}$, final concentration) PGD2 in, for example, calcium-free Tyrode/2 mM $CaCl_2$, and the calcium flux is determined by measuring the fluorescence at ex. 470 nm/em. 525 nm for 120 seconds [lit.: T. Matsuoka et al. (2000) *Science* 287: 2013-2017; S. Narumiya and G. A. Fitzgerald (2001) *J. Clin. Invest.* 108: 25-30].

B-12. In Vitro Test for EP1 Agonism and Antagonism

For the characterization of test substances in respect of EP1 agonism and antagonism, PGE2-induced calcium flux in EP1-expressing CHEM1 cells (Millipore, HTS099C) was used: 3000 cells in 25 µl of full medium [DMEM, 4.5 g/l glucose, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP1 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP1 antagonism, the EP1 receptor is activated in the FLIPR Tetra® by adding 20 µl of −6 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: Y. Matsuoka et al. (2005) *Proc. Natl. Acad. Sci. USA* 102: 16066-16071; S. Narumiya and G. A. Fitzgerald (2001) *J. Clin. Invest.* 108: 25-30; K. Watanabe et al. (1999) *Cancer Res.* 59: 5093-5096].

B-13. In Vitro Test for EP2 Agonism and Antagonism

For the characterization of test substances in respect of EP2 agonism and antagonism, PGE2-induced calcium flux in EP2-expressing CHEM9 cells (Millipore, HTS185C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP2 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP2 antagonism, the EP2 receptor is activated in the FLIPR Tetra® by adding 20 µl of −22 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: C. R. Kennedy et al. (1999) *Nat. Med.* 5: 217-220; S. Narumiya and G. A. Fitzgerald (2001) *J. Clin. Invest.* 108: 25-30; N. Yang et al. (2003) *J. Clin. Invest.* 111: 727-735].

B-14. In Vitro Test for EP3 Agonism and Antagonism

For the characterization of test substances in respect of EP3 agonism and antagonism, PGE2-induced calcium flux in EP3 (splice variant 6)-expressing CHEM1 cells (Millipore, HTS092C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP3 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP3 antagonism, the EP3 receptor is activated in the FLIPR Tetra® by adding 20 µl of –2 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: M. Kotani et al. (1995) Mol. Pharmacol. 48: 869-879; M. Kotani et al. (1997) Genomics 40: 425-434; T. Kunikata et al. (2005) Nat. Immunol. 6: 524-531; S. Narumiya and G. A. Fitzgerald (2001) J. Clin. Invest. 108: 25-30; F. Ushikubi et al. (1998) Nature 395: 281-284].

B-15. In Vitro Test for EP4 Agonism and Antagonism

For the characterization of test substances in respect of EP4 agonism and antagonism, PGE2-induced calcium flux in EP4-expressing CHEM1 cells (Millipore, HTS142C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of EP4 agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of EP4 antagonism, the EP4 receptor is activated in the FLIPR Tetra® by adding 20 µl of –26 nM (2×$EC_{50}$, final concentration) PGE2 in, for example, calcium-free Tyrode/2 mM $CaCl_2$, and the calcium flux is determined by measuring the fluorescence at ex. 470 nm/em. 525 nm for 120 seconds [lit.: S. Narumiya and G. A. Fitzgerald (2001) J. Clin. Invest. 108: 25-30; M. Nguyen et al. (1997) Nature 390: 78-81; K. Yoshida et al. (2002) Proc. Natl. Acad. Sci. USA 99: 4580-4585].

B-16. In Vitro Test for IP Agonism and Antagonism

For the characterization of test substances in respect of IP agonism and antagonism, iloprost-induced calcium flux in IP-expressing CHEM1 cells (Millipore, HTS131C) was used: 3000 cells in 25 µl of plating medium [DMEM, 4.5 g/l glucose, 4 mM glutamine, 10% heat-inactivated FCS, 1% 100× non-essential amino acids, 10 mM HEPES, 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of IP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of IP antagonism, the IP receptor is activated in the FLIPR Tetra® by adding 20 µl of –106 nM (2×$EC_{50}$, final concentration) iloprost in, for example, calcium-free Tyrode/2 mM $CaCl_2$, and the calcium flux is determined by measuring the fluorescence at ex. 470 nm/em. 525 nm for 120 seconds [lit.: S. Narumiya et al. (1999) Physiol. Rev. 79: 1193-1226; T. Murata et al. (1997) Nature 388: 678-682; Y. Cheng et al. (2002) Science 296: 539-541; C. H. Xiao et al. (2001) Circulation 104: 2210-2215; G. A. Fitzgerald (2004) N. Engl. J. Med. 351: 1709-1711].

B-17. In Vitro Test for TP Agonism and Antagonism

For the characterization of test substances in respect of TP agonism and antagonism, U46619-induced calcium flux in TP-expressing CHEM1 cells (Millipore, HTS081C) was used: 3000 cells in 25 µl of plating medium [DMEM, 10% heat-inactivated FCS, 1% 100× non-essential amino acids, 10 mM HEPES, 0.25 mg/ml Geneticin (G418), 100 U/ml penicillin and streptomycin] are sown per well of a 384 multititer plate (from Greiner, TC plate, black with clear base) and incubated at 37° C./5% $CO_2$ for 24 hours. Prior to the measurement, the medium is replaced by 30 µl of calcium dye loading buffer (FLIPR Calcium Assay, Molecular Devices) and incubated at 37° C./5% $CO_2$ for 60 minutes. The test substance is prepared in DMSO in various concentrations as a dose-response curve (starting concentration 10 mM, dilution factor 3.16) and prediluted 1:50 with, for example, calcium-free Tyrode (130 mM NaCl, 5 mM KCl, 20 mM HEPES, 1 mM $MgCl_2$, 4.8 mM $NaHCO_3$, pH 7.4)/2 mM $CaCl_2$. For the measurement of TP agonism, in a fluorescence measuring instrument (FLIPR Tetra®, Molecular Devices), 10 µl of the prediluted substance solution are added to the calcium dye-laden cells, and the calcium flux is determined by measuring the fluorescence at ex. 470 nm/em. 525 nm for 120 seconds. Thereafter, the cells are incubated at 37° C./5% $CO_2$ for 10 minutes. For the measurement of TP antagonism, the TP receptor is activated in the FLIPR Tetra® by adding 20 µl of –88 nM (2×$EC_{50}$, final concentration) U46619 in, for example, calcium-free Tyrode/2 mM $CaCl_2$, and the calcium flux is determined by measuring the fluorescence at ex. 470 nm/em. 525 nm for 120 seconds [lit.: S. Ali et al. (1993) *J. Biol. Chem.* 268: 17397-17403; K. Hanasaki et al. (1989) *Biochem. Pharmacol.* 38: 2967-2976; M. Hirata et al. (1991) *Nature* 349: 617-620].

B-18. Animal Model of Bleomycin-Induced Pulmonary Fibrosis

Bleomycin-induced pulmonary fibrosis in the mouse or rat is a widely used animal model of pulmonary fibrosis. Bleomycin is a glycopeptide antibiotic employed in oncology for the therapy of testicular tumors and Hodgkin- and Non-Hodgkin tumors. It is eliminated renally, has a half-life of about 3 hours and, as cytostatic, influences various phases of the division cycle [Lazo et al., *Cancer Chemother. Biol. Response Modif.* 15, 44-50 (1994)]. Its anti-neoplastic effect is based on an oxidatively damaging action on DNA [Hay et al., *Arch. Toxicol.* 65, 81-94 (1991)]. Lung tissue is at a particular risk when exposed to bleomycin since it contains only a small number of cysteine hydrolases which, in other tissues, lead to inactivation of bleomycin. Following administration of bleomycin, the animals suffer an acute respiratory distress syndrome (ARDS) with subsequent development of pulmonary fibrosis.

Administration of bleomycin may be by single or repeat intratracheal, inhalative, intravenous or intraperitoneal administration. Treatment of the animals with the test substance (by gavage, by addition to the feed or drinking water, using an osmotic minipump, by subcutaneous or intraperitoneal injection or by inhalation) starts at the day of the first bleomycin administration or therapeutically 3-14 days later and extends over a period of 2-6 weeks. At the end of the study, a bronchio-alveolar lavage to determine the cell content and the pro-inflammatory and pro-fibrotic markers and measurements of lung function and a histological assessment of pulmonary fibrosis are carried out.

B-19. Animal Model of DQ12 Quartz-Induced Pulmonary Fibrosis

DQ12 quartz-induced pulmonary fibrosis in the mouse or rat is a widely used animal model of pulmonary fibrosis [Shimbori et al., *Exp. Lung Res.* 36, 292-301 (2010)]. DQ12 quartz is quartz which is highly active owing to breaking or grinding. In mice and rats, intratracheal or inhalative administration of DQ12 quartz leads to alveolar proteinosis followed by interstitial pulmonary fibrosis. The animals receive a single or repeat intratracheal or inhalative instillation of DQ12 quartz. Treatment of the animals with the test substance (by gavage, by addition to the feed or drinking water, using an osmotic minipump, by subcutaneous or intraperitoneal injection or by inhalation) starts at the day of the first silicate instillation or therapeutically 3-14 days later and extends over a period of 3-12 weeks. At the end of the study, a bronchio-alveolar lavage to determine the cell content and the pro-inflammatory and pro-fibrotic markers and measurements of lung function and a histological assessment of pulmonary fibrosis are carried out.

B-20. Animal Model of DQ12 Quartz-Induced Pulmonary Inflammation

In the mouse and the rat, intratracheal administration of DQ12 quartz leads to an inflammation in the lung [Shimbori et al., *Exp. Lung Res.* 36, 292-301 (2010)]. On the day of the instillation of DQ12 quartz or a day later the animals are treated with the test substance for a duration of 24 h up to 7 days (by gavage, by addition to the feed or drinking water, using an osmotic minipump, by subcutaneous or intraperitoneal injection or by inhalation). At the end of the experiment, a bronchio-alveolar lavage to determine the cell content and the pro-inflammatory and pro-fibrotic markers is carried out.

B-21. Carbon Tetrachloride ($CCl_4$)-Induced Hepatic Fibrosis in Mice

Sixty C57BL/6J mice (Charles River, male, 8 weeks old) are randomized and divided equally into 4 groups (15 mice per group). Group 1 serve as the untreated healthy control group, whereas groups 2-4 serve as mice suffering from hepatic fibrosis. Hepatic fibrosis is induced by intraperitoneal injection of 50 µl $CCl_4$/olive oil suspension ($CCl_4$+olive oil, 1+9 v/v) three times per week (Monday, Wednesday and Friday) over the entire study period. $CCl_4$ is the oldest and most widely used substance for triggering toxically induced hepatic fibrosis (Starkel and Leclercq, *Best Pract. Res. Clin. Gastroenterol.* 2011, 25, 319-333). The $CCl_4$-treated mice of group 2 serve as disease control and do not receive any further treatments, whereas the $CCl_4$-treated mice of group 3 are additionally treated with vehicle and hence serve as vehicle control. The $CCl_4$-treated mice of group 4 serve as group treated with a compound of the formula (I). The oral treatment of group 3 with the vehicle solution and of group 4 with a compound of the formula (I) starts on day 1 and is continued twice daily (in the morning and evening) over the complete study period of two weeks. At the end of the study, all animals are sacrificed under anesthetic, and the livers are removed and fixed in 4% buffered formaldehyde solution for the subsequent histological processing and analysis. For this purpose, liver samples for all animals are embedded in paraffin and 3 µm-thick paraffin sections are produced. Thereafter, all the liver sections are deparaffinized and stained with Picro-Sirius Red (Waldeck, Germany) to determine the liver fibrosis. Picro-Sirius Red staining is a histological technique for staining of collagen in tissue and hence of fibrosis. A Carl Zeiss microscope (Axio Observer) connected to a computer is used to scan the Picro-Sirius Red-stained liver sections for production of corresponding images. The sections are scanned with 20× enlargement and a light intensity of 4.8 V. The images thus produced are then converted to JPG format, and the red-stained area is quantified by means of ImageJ software (National Institute of Health, USA). The results are reported in % Sirius Red per unit area.

B-22. Animal Model of Unilateral Ureteral Obstruction (UUO) in Mice (Renal Fibrosis)

Unilateral ureteral obstruction in mice and rats is a widely used animal model for interstitial renal fibrosis (Chevalier et al., *Kidney Int.* 2009, 75, 1145-1152). Permanent occlusion of the ureter leads, as a result of the sustained accumulation of the urine, to increased inflammatory cell infiltration into the interstitium, to tubular cell death and to irreversible loss of the renal parenchyma. After 5 to 7 days, owing to the elevated deposition of extracellular matrix proteins, interstitial fibrosis arises. Adult male C57Bl6J mice (Charles River Laboratories, Sulzfeld, Germany) having a weight of 20-22 g are anesthetized with isoflurane, then, after opening up the abdominal cavity, a ureter is ligated and severed beneath the ligature. In the sham-operated control mice (SHAM), the abdominal cavity is merely opened up, but the ureter is not ligated. The treatment of the animals in the substance groups is started after the operation and continued for 10 days. 10 days after the UUO, the animals are anesthetized and sacrificed by exsanguination. Thereafter, the kidneys are removed and renal fibrosis is assessed on the basis of the expression of pro-inflammatory and pro-fibrotic markers, and a histological assessment of the renal tissue.

B-23. Silica-Induced Pulmonary Fibrosis in Mice: Therapeutic Chronic 30-Day Study with FP Antagonists Adult female C57Bl6J mice (Charles River Laboratories, Sulzfeld, Germany) having a weight of 18-20 g are anesthetized in a chamber with isoflurane (3% v/v) and treated intratracheally with 2.5 mg of crystalline DQ12 silica dissolved in 70 μL of sterile phosphate-buffered saline. Untreated control mice receive the same volume of phosphate-buffered saline. On day 10 after the silica treatment, the animals in the substance groups are treated for 20 days. 30 days after the installation of silica, the animals are anesthetized with an intraperitoneal injection of ketamine/medetomidine (50 mg/kg and 0.33 mg/kg) combined with a subcutaneous injection of Temgesic (0.06 mg/kg) and sacrificed by exsanguination. Thereafter, the trachea is cannulated, and the animals' lungs are lavaged three times with 0.5 ml of ice-cold phosphate-buffered saline. Thereafter, the lungs are removed, weighed and shock-frozen in dry ice. After homogenization of the lung tissue, hydroxyproline is determined by HPLC [Paroni et al., *Clin. Chem.* 1992, 38, 407-411; column: Phenomenex Synergi Hydro RP 4 μm 80A, 75×4.6 mm; gradient: eluent A: water (6 ml/l triethylamine, 3 ml/l acetic acid) pH 4.3; solvent B: acetonitrile; flow rate: 1.3 ml/min). The data are recorded as mean values±SEM of 8-12 animals per group. The statistical analysis is conducted with the unpaired Student's t test. P values <0.05 are considered to be significant.

B-24. Effects of FP Antagonists on Mechanical Sensitivity (Peripheral, Mouse)

Mechanical allodynia was examined using the von Frey test on the injected and uninjected rear paws several times after the injection.

Mechanical allodynia was measured with 8 Semmes-Weinstein filaments (Stölting©; Wood Dale, Ill., USA) having different stiffness (0.04; 0.07; 0.16; 0.4; 1.0. 4.0 and 8.0 g) by the up-down method (Chaplan et al., *J. Neurosci. Meth.* 1994, 53, 56-63). Intact male ND4 mice (30 g, 10 animals per group) were placed in individual acrylic chambers on a metal grid surface, and were allowed to get used to their environment for at least 15 minutes before the testing. Each filament was pressed with sufficient force at right angles to the underside of the paw, in order to cause slight bending against the paw, and was held for about 6 seconds or until a positive response was registered (paw quickly withdrawn). The testing was commenced with the 0.4 g filament. If the paw was not withdrawn, the next strongest stimulus was used. In the case that the paw was withdrawn, the next weakest stimulus was used. This process was repeated until up to 4 responses had been obtained after the initial change in response (no response after positive response or positive response after no response). If the animal did not react after the strongest filament had been reached or the animal reacted after the weakest filament had been reached, the test was stopped for this time point. The 50% paw response threshold was calculated using the following formula:

$$50\% \text{ Paw Response Threshold } (g) = \frac{10^{(Xf+k\delta)}}{10\,000}$$

Xf=value (in logarithmic units) of the last von Frey filament used k=table value for the pattern of positive/negative responses (see Chaplan et al., *J. Neurosci. Meth.* 1994, 53, 56-63, Annex 1, page 62)

δ=average difference (in logarithmic units) between the stimuli

The mean and standard deviation of the mean (SEM) was determined for each paw for each treatment group at each time point.

Group Design

| No. | Treatment | Dose (mg/kg) | Dose volume | Vehicle | Ad-min. | Day of treatment/ frequency |
|---|---|---|---|---|---|---|
| 1 | fluprostenol | ~0.15 | 20 μL | 10% DMSO in PBS | IPL | day 0, T = 0 |
|   | vehicle | / | 5 mL/kg | DMSO/ PEG400/ H₂O (10/60/30) | PO | 3x, T = -2, 8, 22 h |
| 2 | fluprostenol | ~0.15 | 20 μL | 10% DMSO in PBS | IPL | day 0, T = 0 |
|   | Ex. 153 | 90 | 5 mL/kg | DMSO/ PEG400/ H2O (10/60/30) | PO | 3x, T = -2, 8, 22 h |
| 3 | fluprostenol | ~1.5 | 20 μL | 10% DMSO in PBS | IPL | day 0, T = 0 |
|   | vehicle | / | 5 mL/kg | DMSO/ PEG400/ H₂O (10/60/30) | PO | 3x, T = -2, 8, 22 h |
| 4 | fluprostenol | ~1.5 | 20 μL | 10% DMSO in PBS | IPL | day 0, T = 0 |
|   | Ex. 153 | 90 | 5 mL/kg | DMSO/ PEG400/ H2O (10/60/30) | PO | 3x, T = -2, 8, 22 h |

IPL: intraplantary;
PO: per os

In order to assess the analgesic effect of an FP antagonist on fluprostenol-induced mechanical sensitivity, the test substance from Ex. 153 (90 mg/kg) was administered 2 hours before and 8 and 22 hours after the injection of fluprostenol. Ipsilateral and contralateral 50% paw response thresholds were examined prior to the administration of fluprostenol and 0.5, 2, 6 and 24 h after the administration. In the group treated with 1.5 mg/kg fluprostenol, oral administration of Ex. 153 (90 mg/kg) increased the "50% Paw Response Thresholds" 0.5 hours after the fluprostenol injection significantly compared to vehicle-treated animals. In the group treated with 0.15 mg/kg fluprostenol, oral administration of Ex. 153 (90 mg/kg) increased the "50% Paw Response Thresholds" 24 hours after the fluprostenol injection significantly compared to vehicle-treated animals (see Table 2).

TABLE 2

50% Paw Response Thresholds (g)

| Time (h) | Group 1 | | Group 2 | | Group 3 | | Group 4 | |
|---|---|---|---|---|---|---|---|---|
| | mean | SEM | mean | SEM | mean | SEM | mean | SEM |
| BL (baseline) | 4.674 | 0.9985 | 4.421 | 0.9326 | 4.35 | 0.9245 | 4.215 | 0.9664 |
| 0.5 | 0.975 | 0.2096 | 2.65 | 0.8343 | 0.229 | 0.1135 | 0.728 | 0.2598 |
| 2 | 1.164 | 0.3284 | 2.403 | 0.8626 | 0.536 | 0.2116 | 0.716 | 0.2451 |
| 6 | 0.732 | 0.1917 | 1.89 | 0.8388 | 0.936 | 0.2443 | 1.57 | 0.5395 |
| 24 | 0.816 | 0.17 | 3.245 | 0.8173 | 1.225 | 0.3563 | 1.683 | 0.7927 |

C. WORKING EXAMPLES OF PHARMACEUTICAL COMPOSITIONS

The compounds of the invention can be converted to pharmaceutical preparations as follows:

Tablet:
Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:
Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:
Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. Solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

The invention claimed is:
1. A compound of formula (I)

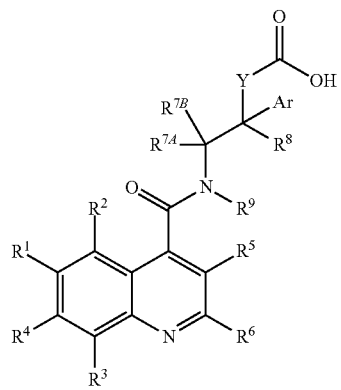

in which
Ar represents phenyl or represents pyridyl,
where phenyl may be up to tetrasubstituted and pyridyl up to disubstituted, in each case identically or differently, by fluorine, chlorine, by up to tri-fluorine-substituted $(C_1$-$C_4)$-alkyl, up to tetra-fluorine-substituted $(C_3$-$C_4)$-cycloalkyl, up to tri-fluorine-substituted $(C_1$-$C_2)$-alkoxy, or up to tri-fluorine-substituted $(C_1$-$C_2)$-alkylsulfanyl, or where two substituents of the phenyl or pyridyl group, if they are attached to adjacent ring atoms, are optionally attached to one another in such a way that they together form a methylenedioxy or ethylenedioxy group,
or
where phenyl may be up to pentasubstituted by fluorine,
Y represents a bond or a group of the formula

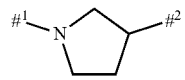

where
$\#^1$ represents the attachment site to the carbon atom,
$\#^2$ represents the attachment site to the carboxyl group,
X represents a bond, —$CH_2$—, —O—, —$S(=O)_m$— or —$N(R^{11})$—, in which
m represents 0, 1 or 2 and
$R^{11}$ represents hydrogen or methyl,
$R^{10A}$ and $R^{10B}$ independently of one another represent hydrogen, fluorine or methyl,
or
$R^{10A}$ and $R^{10B}$ together with the carbon atom to which they are attached form a cyclopropyl group,
k represents 1, 2, 3 or 4,
$R^1$ represents halogen, up to penta-fluorine-substituted $(C_1$-$C_4)$-alkyl, up to tri-fluorine-substituted methoxy, (trifluoromethyl)sulfanyl, pentafluorosulfanyl, trimethylsilyl, ethynyl, cyclopropyl or cyclobutyl,
where cyclopropyl and cyclobutyl may be up to tetrasubstituted by fluorine,
$R^2$, $R^3$ and $R^4$ independently of one another represent hydrogen, halogen or up to tri-fluorine-substituted methyl,
$R^5$ represents halogen, up to penta-fluorine-substituted $(C_1$-$C_4)$-alkyl, up to tri-fluorine-substituted methoxy, hydroxyl, methylsulfanyl, (trifluoromethyl)sulfanyl, cyano, ethenyl, cyclopropyl or cyclobutyl,
where cyclopropyl and cyclobutyl may be up to tetrasubstituted by fluorine,
$R^6$ represents phenyl which may be up to trisubstituted by identical or different substituents from the group consisting of fluorine, chlorine,
methyl, which is up to trisubstituted by fluorine, and methoxy, which is up to trisubstituted by fluorine, or
represents thienyl which may be mono- or disubstituted by methyl or monosubstituted by chlorine or bromine, or represents thiazolyl or pyridyl,
$R^{7A}$ and $R^{7B}$ independently of one another represent hydrogen or methyl,
or
$R^{7A}$ and $R^{7B}$ together with the carbon atom to which they are attached form a cyclopropyl group,
$R^8$ represents hydrogen, fluorine, methyl, trifluoromethyl, ethyl or hydroxyl,
$R^9$ represents hydrogen or methyl,
and/or an N-oxide, salt, solvate, salt of an N-oxide and solvate of an N-oxide and/or salt thereof.

2. The compound of formula (I) as claimed in claim 1, in which
Ar represents phenyl or represents 2-pyridyl,
where phenyl may be up to tetrasubstituted by fluorine or up to trisubstituted by identical or different fluorine, chlorine, methyl, trifluoromethyl, difluoromethyl, methoxy, difluoromethoxy, trifluoromethoxy or ethoxy substituents, or where two substituents of the phenyl group, if they are attached to adjacent ring atoms, are optionally attached to one another in such a way that they together form a methylenedioxy group, and
where 2-pyridyl may be up to disubstituted by identical or different substituents from the group consisting of chlorine and methoxy,
Y is a bond or a group of the formula $\#^1$—X—$(CR^{10A}R^{10B})_k$—$\#^2$ where
$\#^1$ represents the attachment site to the carbon atom,
$\#^2$ represents the attachment site to the carboxyl group,
X represents a bond, —CH$_2$—, —O—, —S(=O)$_m$— or —N(R$^{11}$)—, in which
m represents 0 or 2 and
R$^{11}$ represents hydrogen or methyl,
$R^{10A}$ and $R^{10B}$ are independently hydrogen, fluorine or methyl,
k represents 1, 2 or 3,
$R^1$ represents chlorine, bromine, iodine, methyl, isopropyl, tert-butyl, difluoromethyl, trifluoromethyl, trifluoromethoxy, (trifluoromethyl)sulfanyl, trimethylsilyl, ethynyl, cyclopropyl or cyclobutyl,
$R^2$ represents hydrogen,
$R^3$ and $R^4$ independently of one another represent hydrogen, chlorine or methyl,
$R^5$ represents fluorine, chlorine, bromine, iodine, methyl, ethyl, propyl, monofluoromethyl, difluoromethyl, trifluoromethyl, methoxy, trifluoromethoxy, hydroxy, methylsulfanyl or cyclopropyl,
and
$R^6$ represents phenyl which may be mono- or disubstituted by identical or different fluorine or chlorine substituents or monosubstituted by methyl, trifluoromethyl, methoxy or trifluoromethoxy, or represents thienyl which may be mono- or disubstituted by methyl or monosubstituted by chlorine or bromine,
$R^{7A}$ represents hydrogen or methyl,
$R^{7B}$ represents hydrogen,
$R^8$ represents hydrogen, fluorine, methyl, ethyl or hydroxy,
$R^9$ represents hydrogen,
and/or a salt, solvate and/or solvate of a salt thereof.

3. The compound of formula (I) as claimed in claim 1, in which
Ar represents phenyl,
where phenyl may be up to tetrasubstituted by fluorine or up to trisubstituted by identical or different fluorine, chlorine, methyl, trifluoromethyl, difluoromethyl, methoxy, difluoromethoxy or trifluoromethoxy substituents, Y represents a group of the formula $\#^1$—$(CH_2)_n$—$\#^2$ where
$\#^1$ represents the attachment site to the carbon atom,
$\#^2$ represents the attachment site to the carboxyl group,
n represents 1, 2 or 3,
$R^1$ represents bromine or ethynyl,
$R^2$, $R^3$ and $R^4$ each represent hydrogen,
$R^5$ represents chlorine or methyl,
and
$R^6$ represents phenyl which may be monosubstituted by fluorine,
$R^{7A}$ and $R^{7B}$ each represent hydrogen,
$R^8$ represents hydrogen or methyl,
$R^9$ represents hydrogen,
and/or a salt, solvate and/or solvate of a salt thereof.

4. The compound of formula (I) as claimed in claim 1, in which
Ar represents phenyl,
where phenyl may be up to tetrasubstituted by fluorine or up to trisubstituted by identical or different fluorine, chlorine, methyl, trifluoromethyl, difluoromethoxy or trifluoromethoxy substituents,
Y represents a group of the formula $\#^1$—CH$_2$CH$_2$—$\#^2$ where
$\#^1$ represents the attachment site to the carbon atom,
$\#^2$ represents the attachment site to the carboxyl group,
$R^1$ represents bromine or ethynyl,
$R^2$, $R^3$, $R^4$ each represent hydrogen,
$R^5$ represents methyl or chlorine,
$R^6$ represents phenyl,
$R^{7A}$, $R^{7B}$, $R^8$ and $R^9$ are each hydrogen,
and/or a salt, solvate and/or solvate of a salt thereof.

5. A process for preparing a compound of formula (I) as defined in claim 1, comprising:
[A] reacting a compound of formula (II)

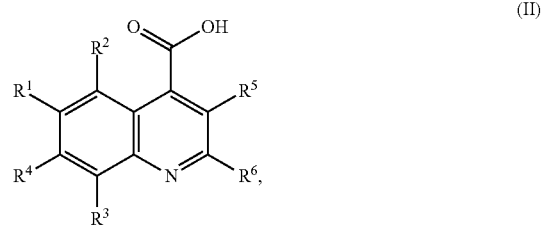

with activation of the carboxylic acid function, with an amine compound of formula (III-A)

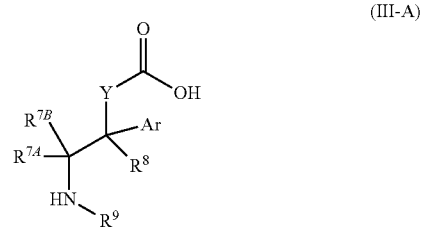

to obtain a compound of formula (I)

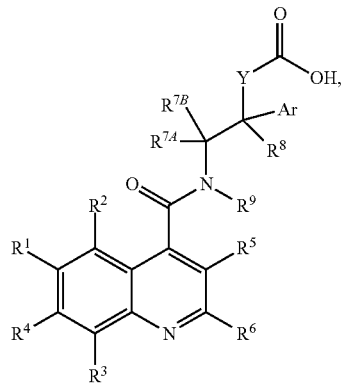

or with an amine compound of formula (III-B)

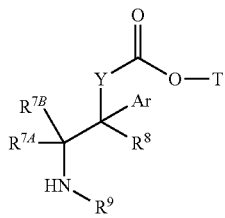

in which
T represents an ester protecting group,
to obtain a compound of formula (IV)

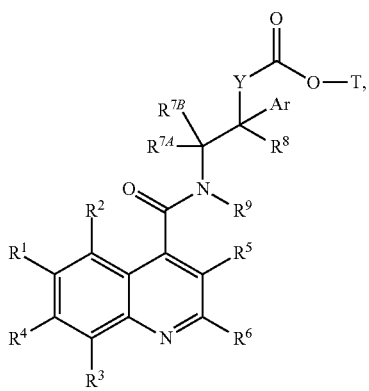

and in a subsequent step
[B] detaching the ester radical T of the compound of the formula (IV)

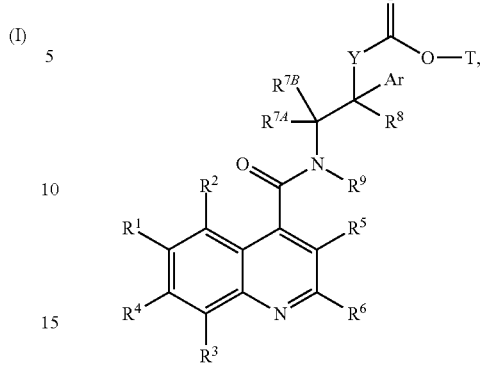

in which
T represents an ester protecting group,
to obtain the compound of formula (I)

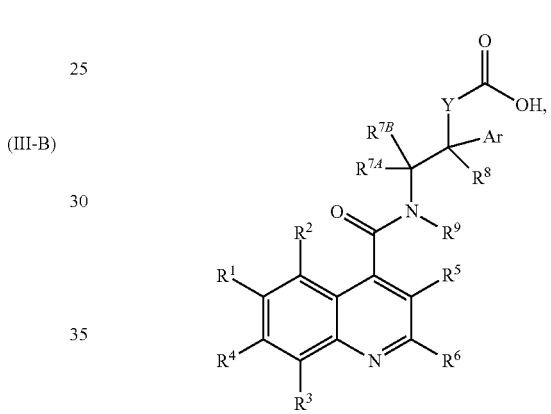

wherein the compound of formula (I) is optionally separated into enantiomers and/or diastereomers and/or converted with one or more appropriate (i) solvents and/or (ii) bases or acids to a solvate, salt and/or solvate of the salt thereof.

6. The compound as defined in claim 1 for treatment and/or prevention of disease.

7. The compound as defined in claim 1 for use in a method for treatment and/or prevention of idiopathic pulmonary fibrosis, pulmonary hypertension, bronchiolitis obliterans syndrome, inflammatory and fibrotic skin and eye disorders and fibrotic disorders of the internal organs.

8. A product comprising a compound as defined in claim 1 for production of a medicament for treatment and/or prevention of idiopathic pulmonary fibrosis, pulmonary hypertension, bronchiolitis obliterans syndrome, inflammatory and fibrotic skin and eye disorders and fibrotic disorders of the internal organs.

9. A medicament comprising a compound as defined in claim 1 in combination with one or more inert, nontoxic, pharmaceutically suitable excipients.

10. A medicament comprising a compound as defined in claim 1 in combination with one or more further active ingredients selected from the group consisting of PDE 5 inhibitors, sGC activators, sGC stimulators, prostacyclin analogues, IP receptor agonists, endothelin antagonists, compounds that inhibit the signal transduction cascade and pirfenidone.

11. The medicament as claimed in claim 9 for treatment and/or prevention of idiopathic pulmonary fibrosis, pulmonary hypertension, bronchiolitis obliterans syndrome, inflammatory and fibrotic skin and eye disorders and fibrotic disorders of the internal organs.

12. A method for treatment and/or prevention of idiopathic pulmonary fibrosis, pulmonary hypertension, bronchiolitis obliterans syndrome, inflammatory and fibrotic skin and eye disorders and fibrotic disorders of the internal organs in humans and animals by administration of an effective amount of at least one compound as defined in claim 1, or of a medicament as defined thereof.

13. The process according to claim 5, wherein
T represents $(C_1-C_4)$-alkyl.

* * * * *